US009096646B2

(12) United States Patent
McMurry et al.

(10) Patent No.: US 9,096,646 B2
(45) Date of Patent: Aug. 4, 2015

(54) CXCR4 RECEPTOR COMPOUNDS

(75) Inventors: Thomas J. McMurry, Winchester, MA (US); Athan Kuliopulos, Winchester, MA (US); Lidija Covic, Boston, MA (US); Boris Tchernychev, Chestnut Hill, MA (US)

(73) Assignee: Anchor Therapeutics, Inc., Cambridge, MA (US)

( * ) Notice: Subject to any disclaimer, the term of this patent is extended or adjusted under 35 U.S.C. 154(b) by 665 days.

(21) Appl. No.: 13/127,443

(22) PCT Filed: Nov. 4, 2009

(86) PCT No.: PCT/US2009/005979
§ 371 (c)(1),
(2), (4) Date: Aug. 17, 2011

(87) PCT Pub. No.: WO2010/053550
PCT Pub. Date: May 14, 2010

(65) Prior Publication Data
US 2013/0210709 A1    Aug. 15, 2013

Related U.S. Application Data

(60) Provisional application No. 61/198,254, filed on Nov. 4, 2008, provisional application No. 61/240,176, filed on Sep. 4, 2009.

(51) Int. Cl.
*C07K 7/08* (2006.01)
*C07K 14/715* (2006.01)
*C07K 7/06* (2006.01)
*A61K 38/00* (2006.01)

(52) U.S. Cl.
CPC ... *C07K 7/08* (2013.01); *C07K 7/06* (2013.01); *C07K 14/7158* (2013.01); *A61K 38/00* (2013.01)

(58) Field of Classification Search
CPC ......... C07K 14/7158; C07K 7/06; C07K 7/08
See application file for complete search history.

(56) References Cited

U.S. PATENT DOCUMENTS

| | | | |
|---|---|---|---|
| 6,864,229 | B2 | 3/2005 | Kuliopulos et al. |
| 7,166,702 | B1 | 1/2007 | McDonald et al. |
| 7,214,384 | B2 | 5/2007 | Zuckermann et al. |
| 7,304,127 | B2 | 12/2007 | Saxinger |
| 7,423,007 | B2 | 9/2008 | Fujii et al. |
| 7,696,168 | B2 | 4/2010 | Kuliopulos et al. |
| 2005/0202019 | A1 | 9/2005 | Murphy et al. |
| 2006/0166274 | A1 | 7/2006 | Kuliopulos et al. |
| 2006/0257869 | A1 | 11/2006 | Ben-Sasson et al. |
| 2007/0003558 | A1 | 1/2007 | von Andrian et al. |
| 2007/0179090 | A1 | 8/2007 | Kuliopulos et al. |
| 2007/0258893 | A1 | 11/2007 | Shim et al. |
| 2008/0214451 | A1 | 9/2008 | Kuliopulos et al. |
| 2008/0214648 | A1 | 9/2008 | De Kock et al. |
| 2008/0312178 | A1 | 12/2008 | Soppet et al. |
| 2009/0175877 | A1 | 7/2009 | Mueller et al. |
| 2009/0270322 | A1 | 10/2009 | Kuliopulos et al. |
| 2010/0062003 | A1 | 3/2010 | Murphy et al. |
| 2010/0137207 | A1 | 6/2010 | Kuliopulos et al. |
| 2011/0070244 | A1 | 3/2011 | von Andrian et al. |
| 2013/0005944 | A1 | 1/2013 | Looby et al. |

FOREIGN PATENT DOCUMENTS

| | | |
|---|---|---|
| CN | 101094866 A | 12/2007 |
| WO | WO 01/16182 A2 | 3/2001 |
| WO | WO 2004/087068 A2 | 10/2004 |
| WO | WO 2004/110341 A2 | 12/2004 |
| WO | WO 2006/052723 A2 | 5/2006 |
| WO | WO 2009/148947 A1 | 12/2009 |
| WO | WO 2010/053550 A2 | 5/2010 |
| WO | WO 2011/106703 A2 | 9/2011 |

OTHER PUBLICATIONS

Covic et al. Activation and inhibition of G protein-coupled receptors by cell-penetrating membrane-tethered peptides. Proc Natl Acad Sci U S A. Jan. 22, 2002; 99(2):643-8.*
Roland et al. Role of the intracellular domains of CXCR4 in SDF-1-mediated signaling. Blood. Jan. 15, 2003;101(2):399-406.*
Brinckerhoff et al. Terminal Modifications Inhibit Proteolytic Degradation of an Immunogenic Mart-127-35 Peptide: Implications for Peptide Vaccines. Int. J. Cancer. (1999) 83, 326-334.*
Transmittal of International Search Report and the Written Opinion of the International Searching Authority for PCT/US2009/005979. Date mailed: May 20, 2010.
Kaneider, N.C., et al., "Reversing Systemic Inflammatory Response Syndrome with Chemokine Receptor Pepducins,"*Nature Medicine*, 11(6):661-665 (2005).
Tchernychev, B., et al., "Discovery of a CXCR4 agonist pepducin that mobilizes bone marrow hematopoietic cells,"*PNAS*, 107(51): 22255-22259 (2010).
Notification Concerning Transmittal of Copy of International Preliminary Report on Patentability (Chapter I of the Patent Cooperation Treaty) for International Application No: PCT/US2009/005979, Titled: "CXCR4 Receptor Compounds," Date of Mailing: May 19, 2011.
Notification of Transmittal of the International Search Report and the Written Opinion of the International Searching Authority, or the Declaration for International Application No: PCT/US11/26322, Titled: "CXCR4 Receptor Compounds," Date of Mailing: Aug. 29, 2011.

(Continued)

*Primary Examiner* — Satyanarayana R Gudibande
*Assistant Examiner* — Jia-Hai Lee
(74) *Attorney, Agent, or Firm* — Hamilton, Brook, Smith & Reynolds, P.C.

(57) ABSTRACT

The invention relates generally to compounds which are allosteric modulators (e.g., positive and negative allosteric modulators, and allosteric agonists) of the G protein coupled receptor for stromal derived factor 1 (SDF-I), also known as the CXCR4 receptor. The CXCR4 receptor compounds are derived from the intracellular loops and domains of the CXCR4 receptor. The invention also relates to the use of these CXCR4 receptor compounds and pharmaceutical compositions comprising the CXCR4 receptor compounds in the treatment of diseases and conditions associated with CXCR4 modulation such as bone marrow transplantation, chemosensitization, cancer, metastatic disease, inflammatory diseases, HIV infection and stem cell-based regenerative medicine.

17 Claims, 49 Drawing Sheets

(56) References Cited

OTHER PUBLICATIONS

Notification Concerning Transmittal of Copy of International Preliminary Report on Patentability (Chapter I of the Patent Cooperation Treaty) for International Application No: PCT/US2011/026322, Titled: "CXCR4 Receptor Compounds," Date of Mailing: Sep. 7, 2012.

Office Action, U.S. Appl. No. 13/580,775, Dated: Oct. 4, 2013.
European Search Report for EP Application No. 11748182.0 "CXCR4 Receptor Compounds" dated Apr. 15, 2014.
Final Office Action for U.S. Appl. No. 13/580,775, "CXCR4 Receptor Compounds" dated Sep. 9, 2014.
Struyf, S., et al., "Citrullination of CXCL12 Differentially Reduces CXCR4 and CXCR7 Binding with Loss of Inflammatory and Anti-HIV-1 Activity via CXCR4", *J. Immunol*, 182: 666-674 (2009).

\* cited by examiner

CXCR4 i1 loop CHTX data

CEM and Sup-B-15 cells

Comp. #

Sequence

33

MGYQKKLR
SMTD

Chemotaxis data

37
SUP B-15

MGYQKKLR
SMTDKY

37
CEM

MGYQKKLR
SMTDKY

38

MGYQKKLR
SMTDKYRL

38

MGYQKKLR
SMTDKYRL

39
SUP B-15

MGYQKKLR
SMTDKYRL
HL

39
CEM

MGYQKKLR
SMTDKYRL
HL

41
SUP B-15

KKLRSMTD
KYRLHLSV

41
CEM

KKLRSMTD
KYRLHLSV

42
SUP B-15

KKLRSMTD
KYRLHL

42
CEM

KKLRSMTD
KYRLHL

44

KKLRSMTD
KYRL

45

KKLRSMTD
KYR

46

KKLRSMTD
KY

50

SGYQKKLR
SSTD

50

SGYQKKLR
SSTD

52

QKKLRSMT
DKYRI

53

MGYQKKLR
SMTDKYRL
HL

53

MGYQKKLR
SMTDKYRL
HL

54

MGYQKKLR
SMTDKYRL
HL

54

MGYQKKLR
SMTDKYRL
HL

55

MGYQKKLR
SMTDKYRL
HLSV

55

MGYQKKLR
SMTDKYRL
HLSV

59

MGYQKKLR
SMTDK

59

MGYQKKLR
SMTDK

81
HATNSQRPRKLLAE

80
HATNSQRPRKLLA

79
HATNSQRPRKL

78
VHATNSQRPRKLLA

77
DRYLAIVHATNSQRPRKLL

76
DRYLAIVHATNSQRPRKLL

CXCR4 i3 loop Chemotaxis data
CEM cells

Comp. #
Sequence

Chemotaxis data

88
SKLSHSKGHQ
KRKALKTTVIL

89
KLSHSKGHQK
RKALKTTVIL

90
KLSHSKGHQK
RKALKTTV

90
KLSHSKGHQK
RKALKTTV

92
KLSHSKGHQK
RKALK

92
KLSHSKGHQK
RKALK

95
LSHSKGHQKR
KALK

96
SHSKGHQKRK
ALK

97
HSKGHQKRKA
LKT

99
HSKGHQKRKA
LKTTV

CXCR4 i4loop (CEM)
Comp. #
Sequence

Chemotaxis

116

GAKFKTSAQHALTSV
R

115
GAKFKTSAQHALTSV
SRGSSLK

114

GAKFKTSAQHALTS
VSRGSSLKILSK

112

GAKFKTSAQHALTS
VSRGSSLKILSGGK

110
GAKFKTSAQHALTS
VSRGSSLKILSKGKR
GGSCFH

109
GAKFKTSAQHALTS
VSRGSSLKILSKGKR
GGHSSVST

108
GAKFKTSAQHALTS
VSRGSSLKILSKGKR
G

107
GAKFKTSAQHALTS
VSRGSSLKILSKGKR
GGHSSVST

BFUE

CFU-GM

CXCR4 RECEPTOR COMPOUNDS

RELATED APPLICATIONS

This application is the U.S. National Stage of International Application No. PCT/US2009/005979, filed Nov. 4, 2009, which designates the U.S., published in English, and claims the benefit of U.S. Provisional Application No. 61/198,254, filed Nov. 4, 2008 and U.S. Provisional Application No. 61/240,176, filed Sep. 4, 2009. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:
a) File name: 42771009003revisedsequence.txt; created Apr. 17, 2013, 91 KB in size.

BACKGROUND OF THE INVENTION

G protein coupled receptors (GPCRs) constitute one of the largest families of genes in the human genome. GPCRs are integral membrane signaling proteins. Hydrophobicity mapping of the amino acid sequences of G-protein coupled receptors has led to a model of the typical G-protein-coupled receptor as containing seven hydrophobic membrane-spanning regions with the amino terminal on the extracellular side of the membrane and the carboxyl terminal on the intracellular side of the membrane.

GPCRs mediate the transmission of intracellular signals ("signal transduction") by activating guanine nucleotide-binding proteins (G proteins) to which the receptor is coupled. GPCRs are activated by a wide range of endogenous stimuli, including peptides, amino acids. hormones, light, and metal ions. The following reviews are incorporated by reference: Hill, British J. Pharm 147: s27 (2006); Palczeski, Ann Rev Biochemistry 75: 743-767 (2006); Dorsham & Gutkind, Nature Reviews 7: 79-94 (2007); Kobilka & Schertler, Trends Pharmacol Sci. 2: 79-83 (2008).

GPCRs are important targets for drug discovery as they are involved in a wide range of cellular signaling pathways and are implicated in many pathological conditions (e.g., cardiovascular and mental disorders, cancer, AIDS). In fact, GPCRs are targeted by 40-50% of approved drugs, illustrating the critical importance of this class of pharmaceutical targets. Interestingly, this number represents only about 30 GPCRs, a small fraction of the total number of GPCRs thought to be relevant to human disease. Over 1000 GPCRs are known in the human genome, and GPCRs remain challenging targets from a research and development perspective in part because these amembrane bound receptors with complex pharmacology.

There remains a need for the development of new pharmaceuticals that are allosteric modulators of GPCRs (e.g., negative and positive allosteric modulators, allosteric agonists, and ago-allosteric modulators).

SUMMARY OF THE INVENTION

The invention relates generally to compounds which are allosteric modulators (e.g., negative and positive allosteric modulators, allosteric agonists, and ago-allosteric modulators) of the G protein coupled receptor for stromal derived factor 1 (SDF-1, CXCL12), also known as the CXCR4 receptor. The CXCR4 receptor compounds are derived from the intracellular loops and domains of the CXCR4 receptor. The invention also relates to the use of these CXCR4 receptor compounds and pharmaceutical compositions comprising the CXCR4 receptor compounds in the treatment of diseases and conditions associated with CXCR4 receptor modulation such as bone marrow transplantation, chemosensitization, cancer, metastatic disease, inflammatory diseases, HIV infection and stem cell-based regenerative medicine.

More specifically, the invention relates to compounds represented by $$TLP, \qquad \text{Formula I:}$$

or a pharmaceutically acceptable salt thereof, wherein:
P is a peptide comprising at least three contiguous amino-acid residues of an intracellular i1, i2, i3 loop or an intracellular i4 domain of the CXCR4 receptor;
L is a linking moiety represented by C(O) and bonded to P at an N terminal nitrogen of an N-terminal amino-acid residue;
and T is a lipophilic tether moiety bonded to L, wherein the C-terminal amino acid residue of P is optionally functionalized.

The invention also relates to pharmaceutical compositions comprising one or more compounds of the invention and a carrier, and the use of the disclosed compounds and compositions in methods of treating diseases and conditions responsive to modulation (inhibition or activation) of the CXCR4 receptor.

BRIEF DESCRIPTION OF. THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1A:
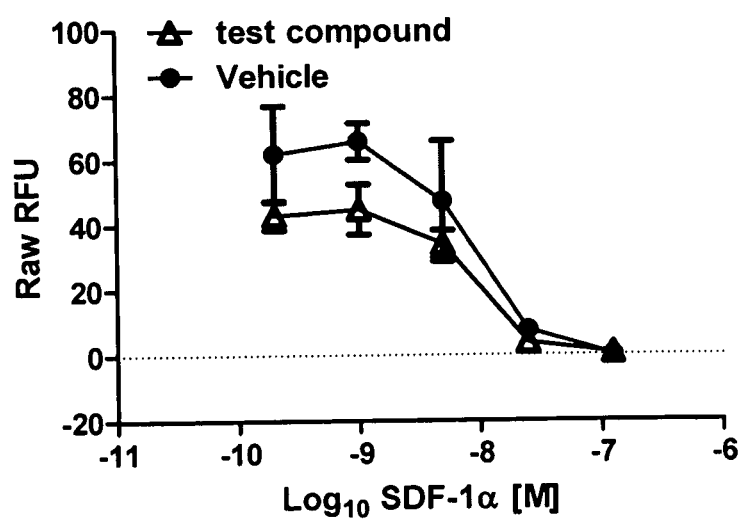
FIGS. 1A-1V are a series of graphical representations of compounds of the invention derived from the i1 loop in a chemotaxis assay as compared with vehicle.
Figure 1B:
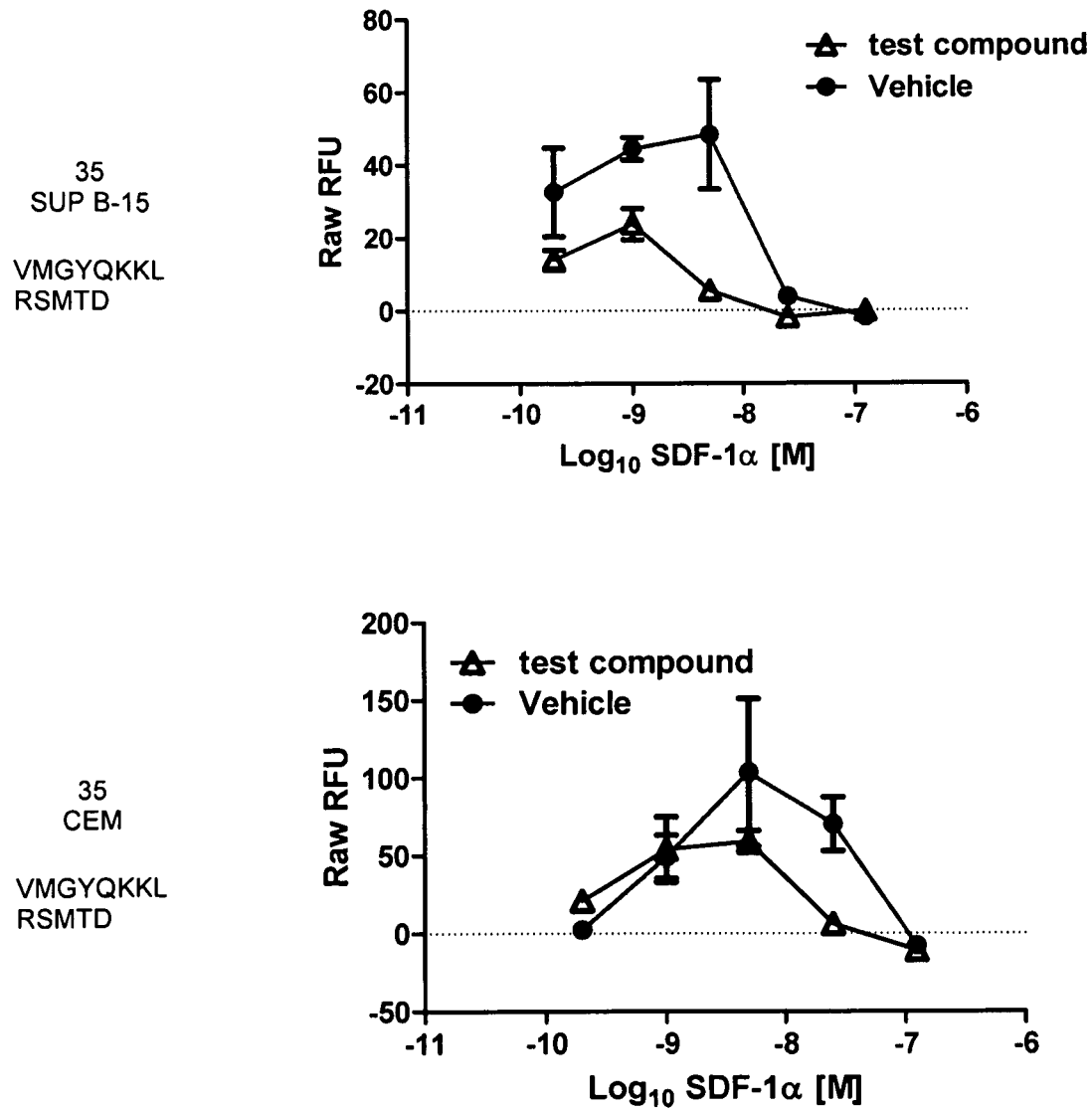
Figure 1C:
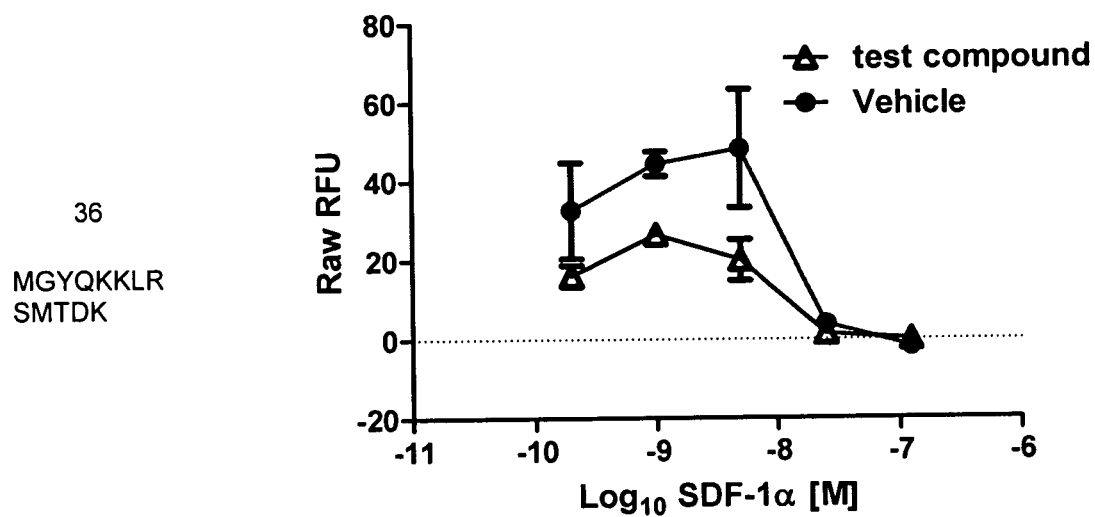
Figure 1D:
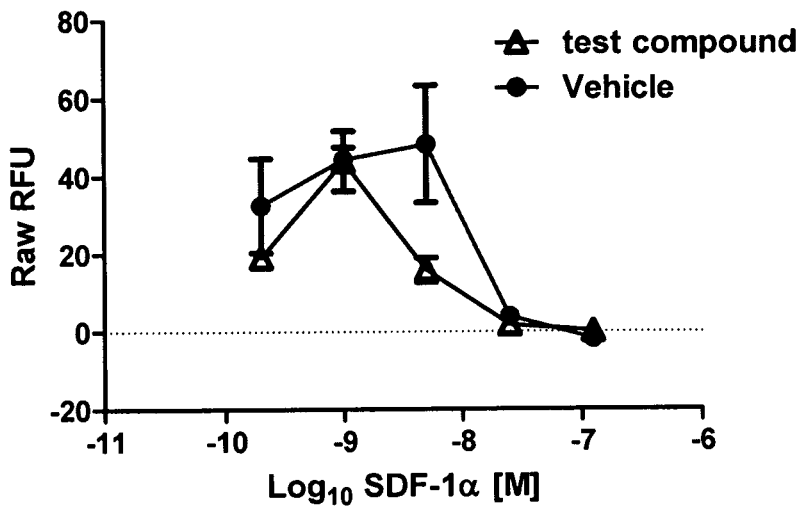
Figure 1D:
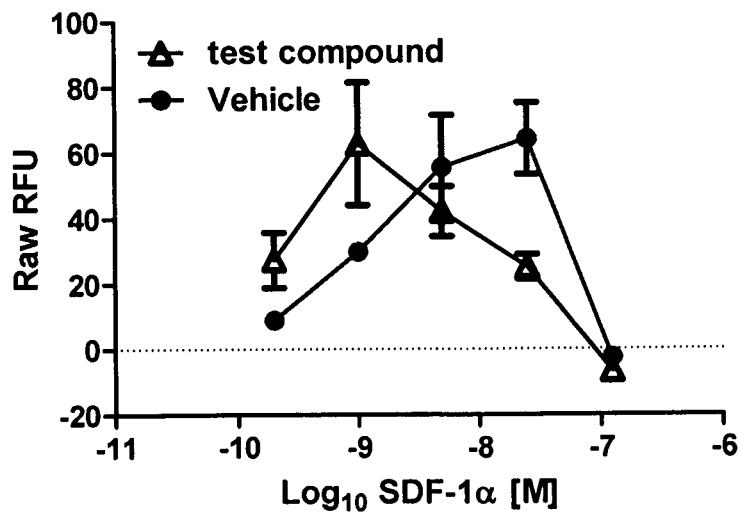
Figure 1E:
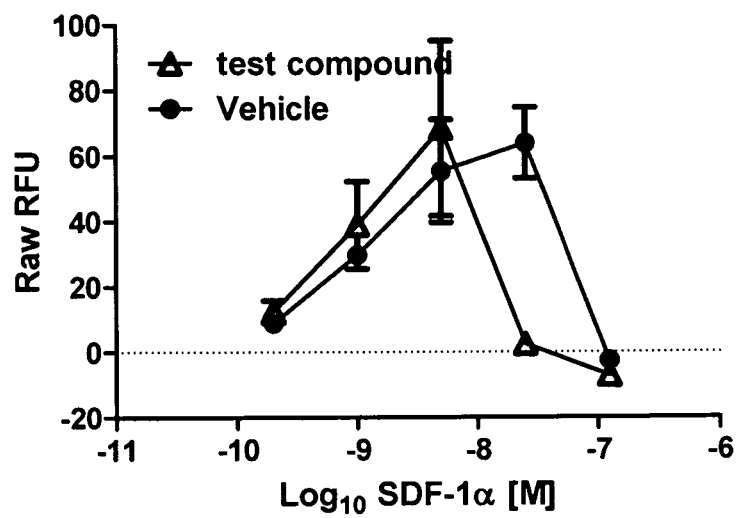
Figure 1E:
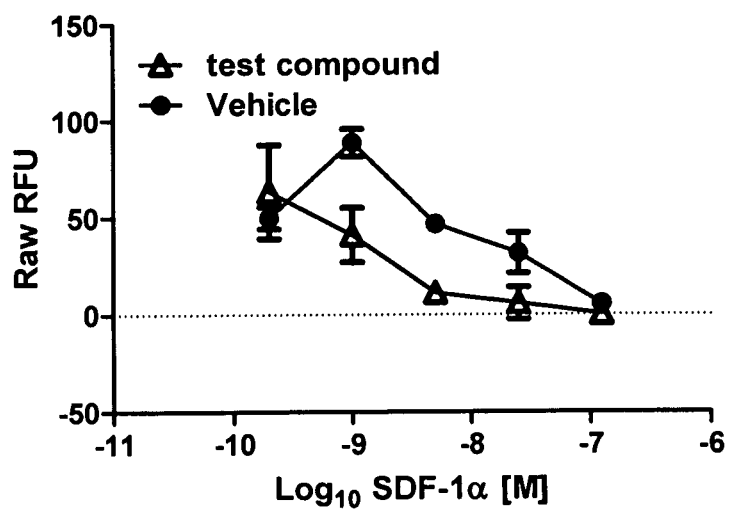
Figure 1F:
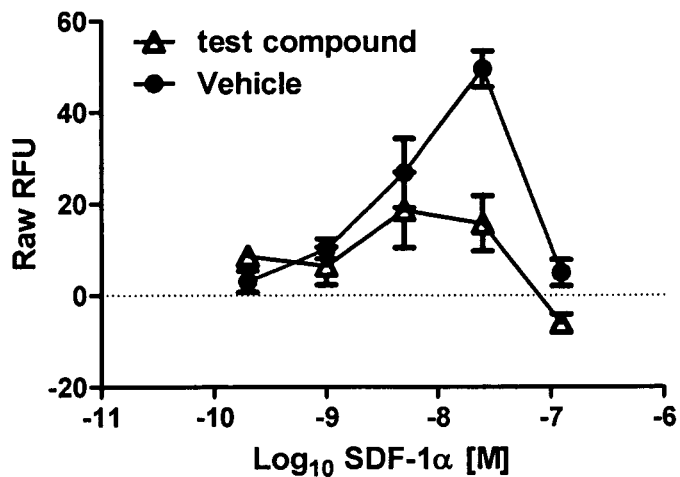
Figure 1F:
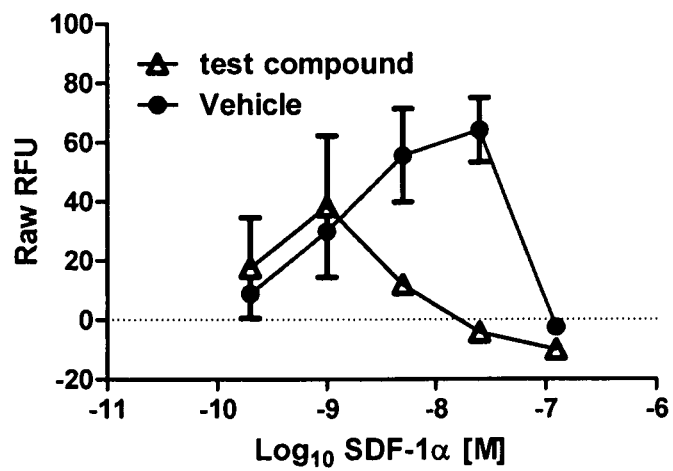
Figure 1G:
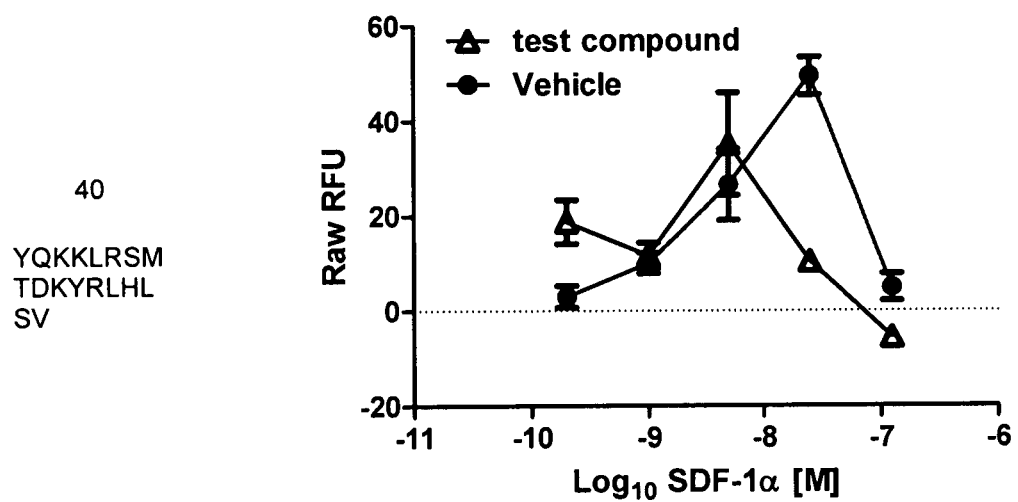
Figure 1H:
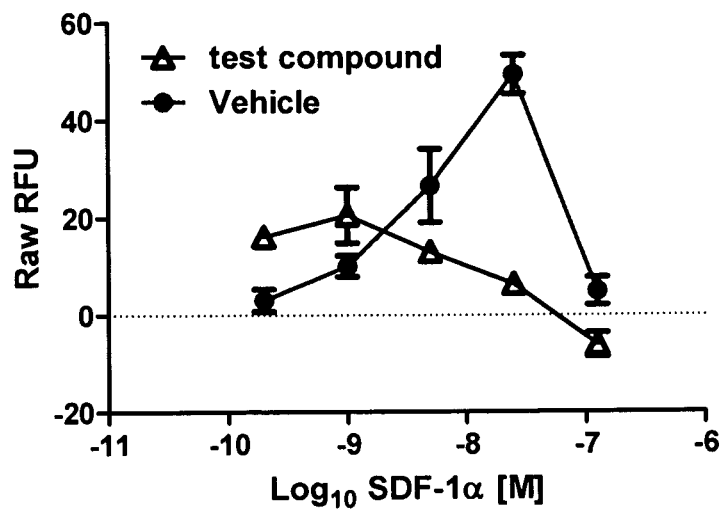
Figure 1H:
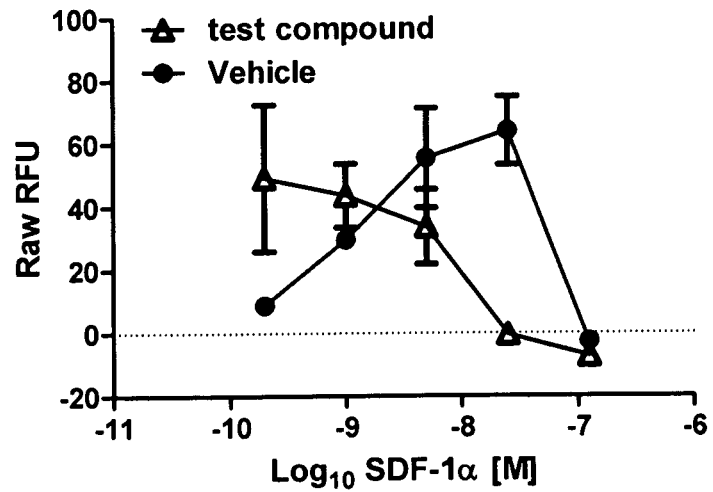
Figure 1I:
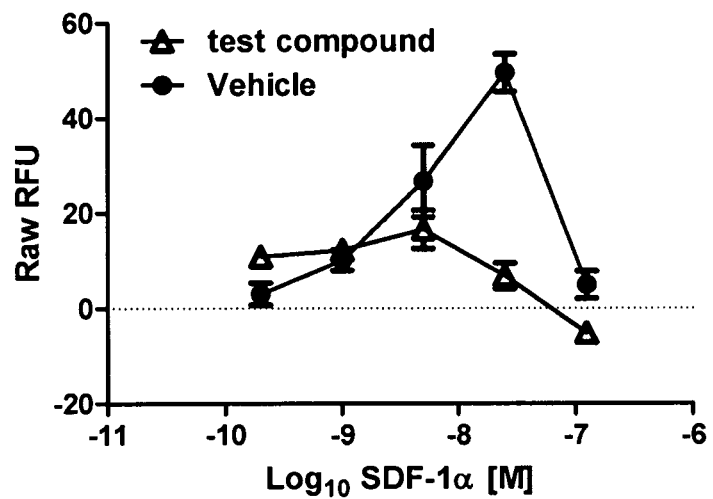
Figure 1I:
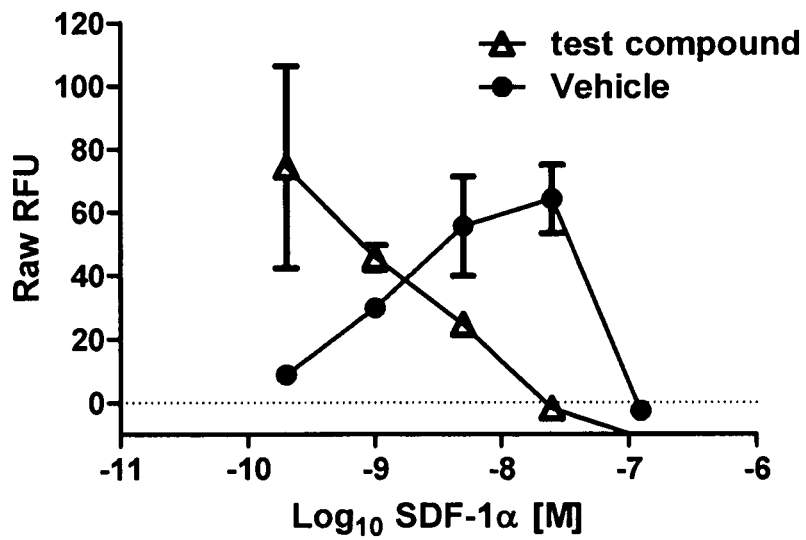
Figure 1J:
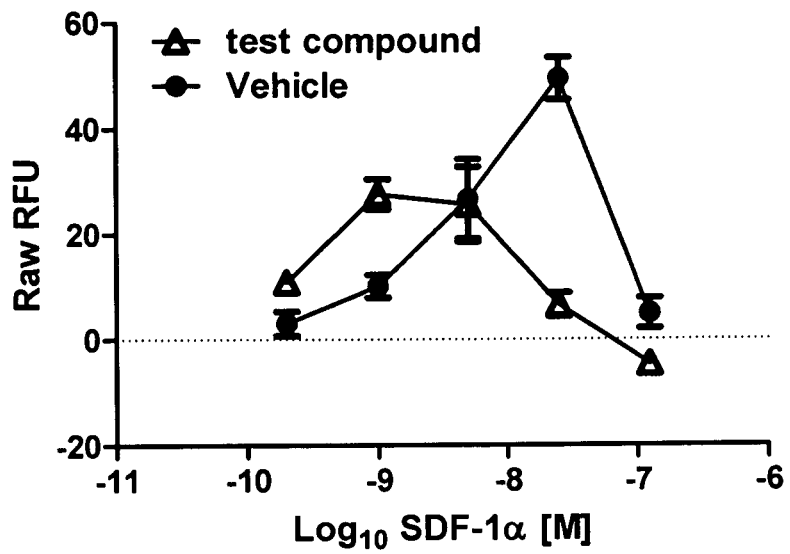
Figure 1J:
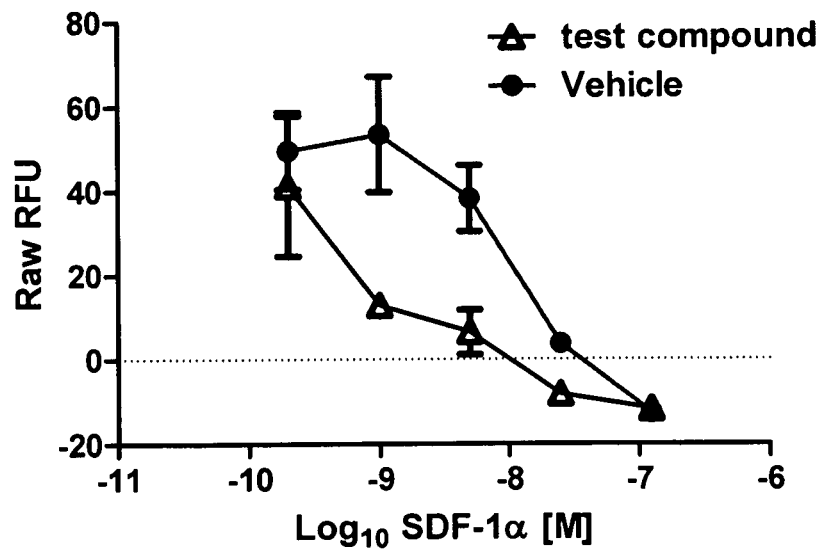
Figure 1K:
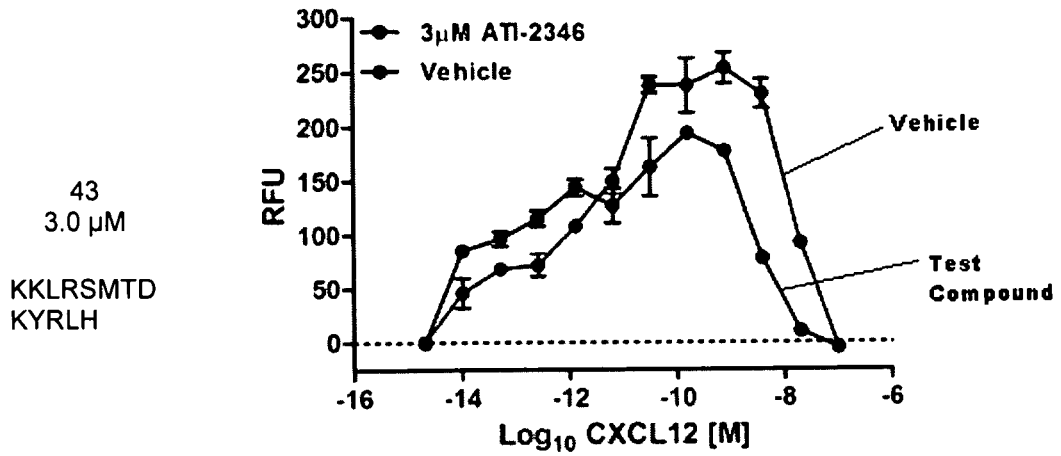
Figure 1K:
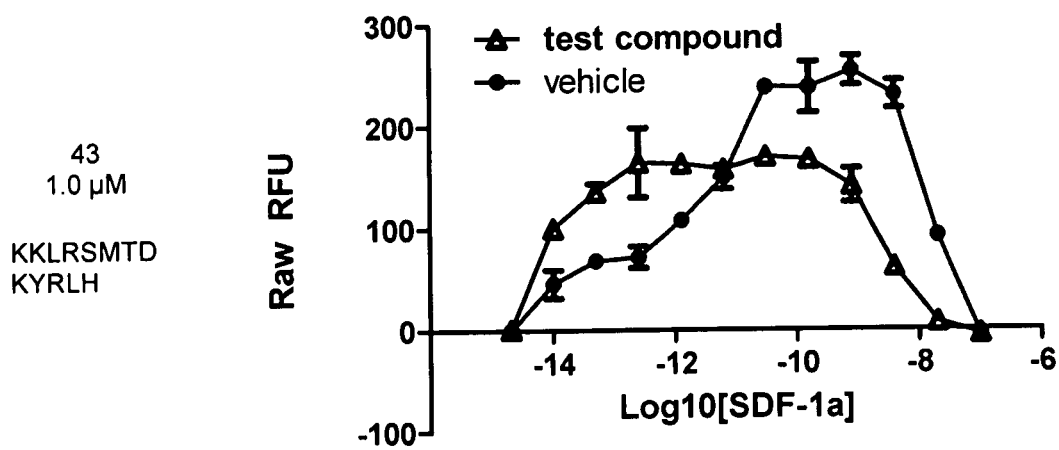
Figure 1L:
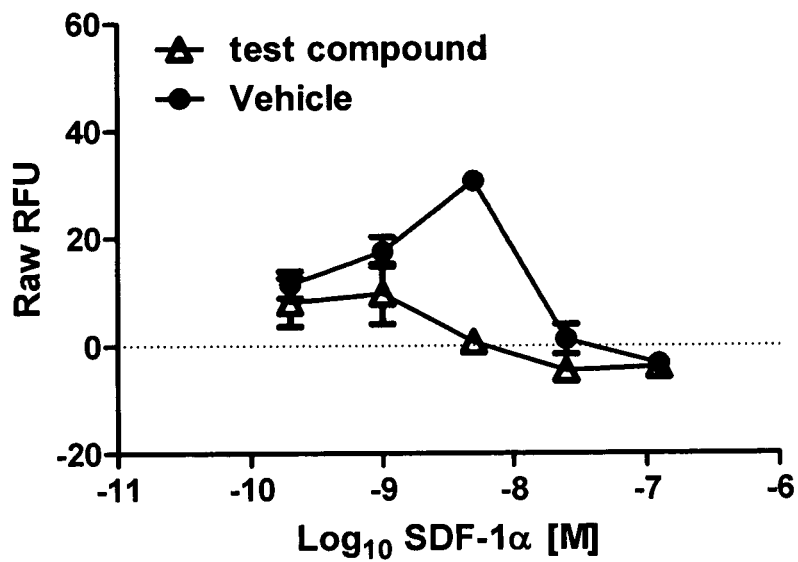
Figure 1L:
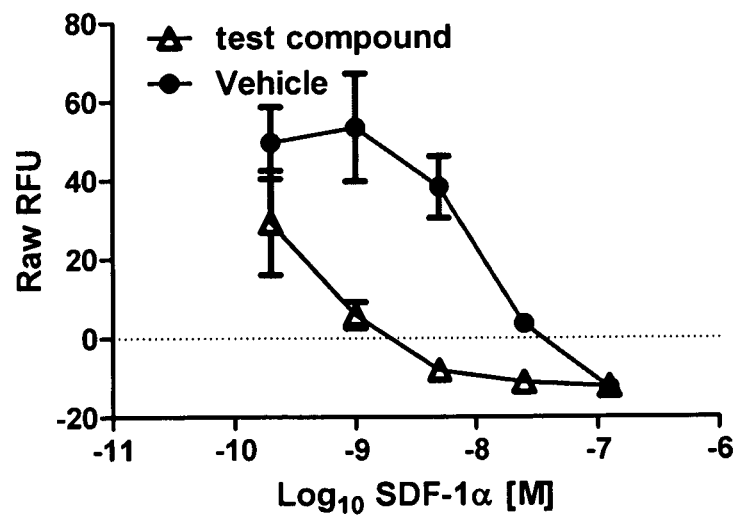
Figure 1M:
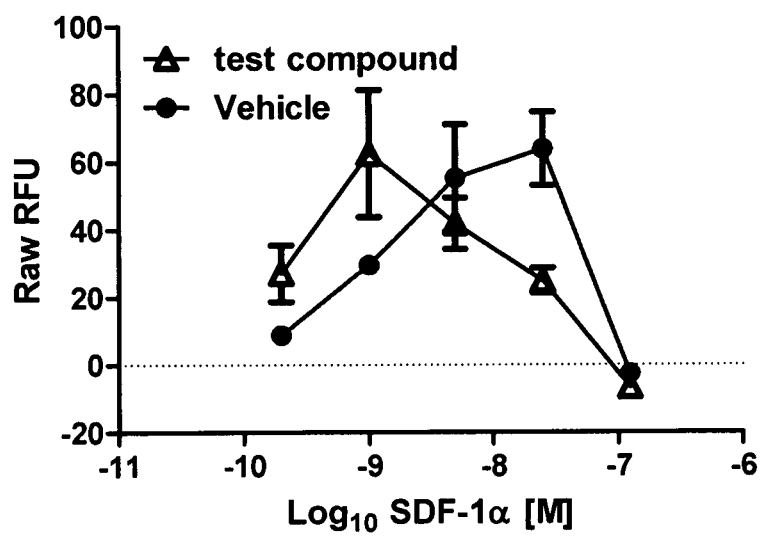
Figure 1N:
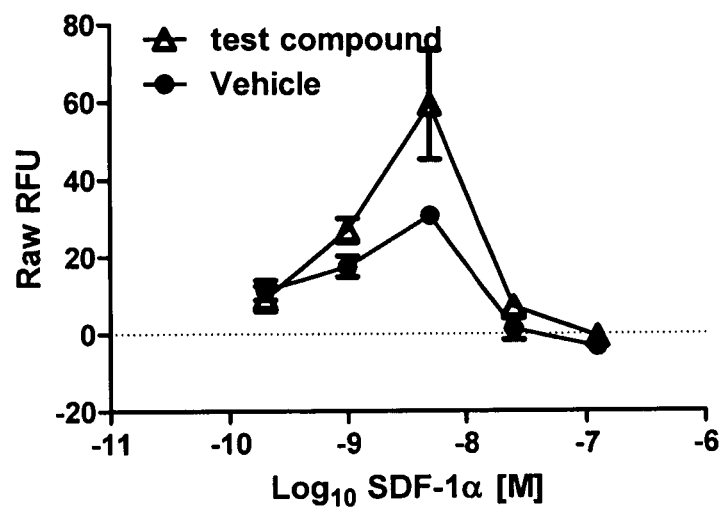
Figure 1N:
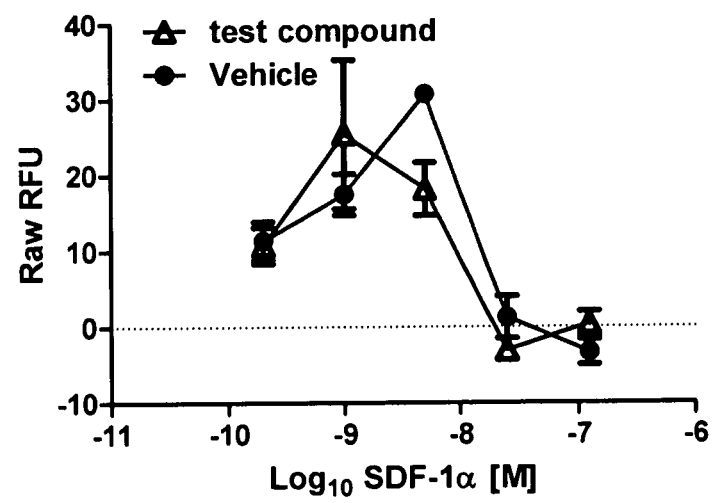
Figure 1O:
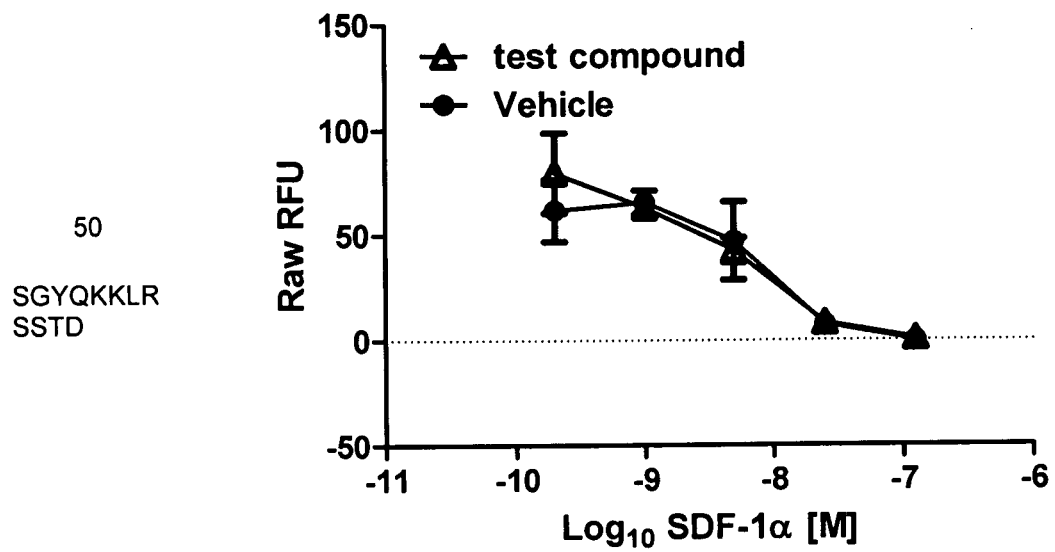
Figure 1O:
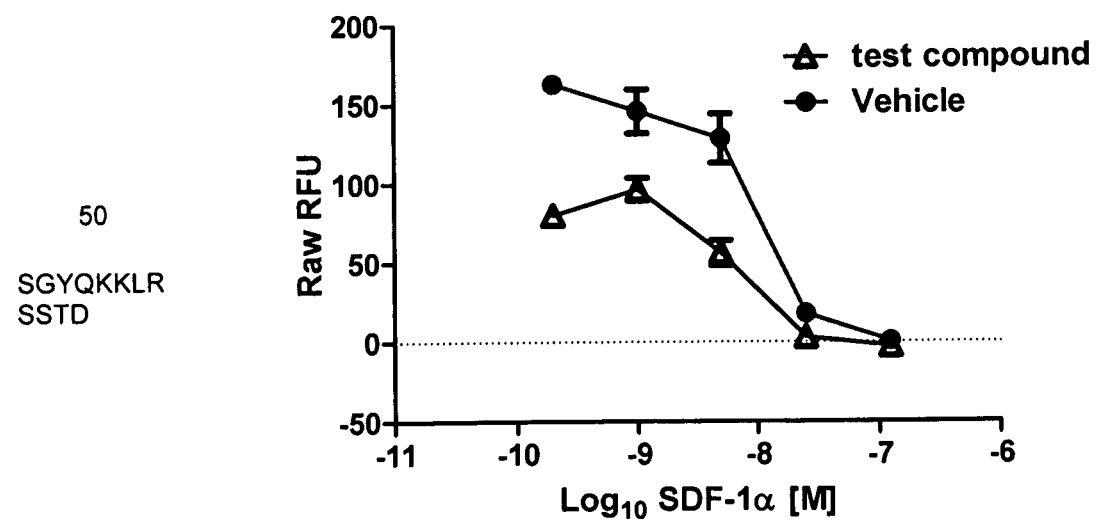
Figure 1P:
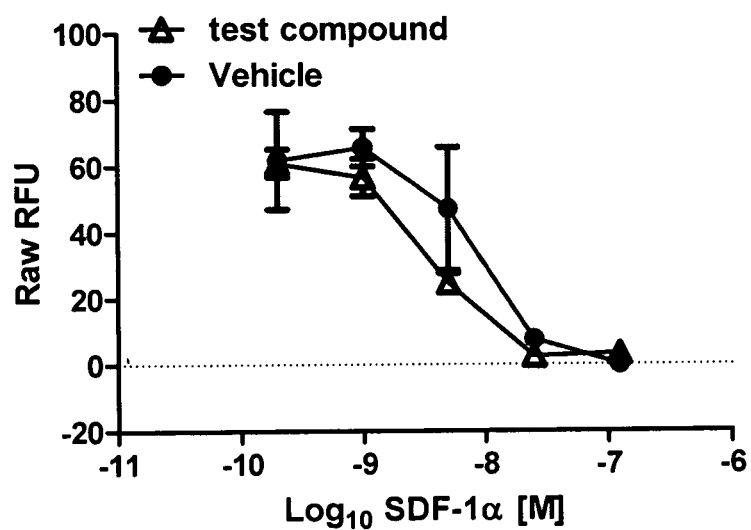
Figure 1Q:
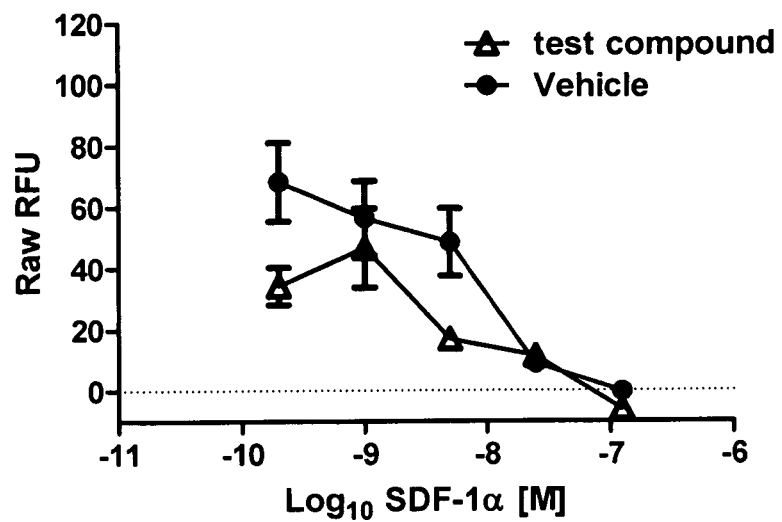
Figure 1Q:
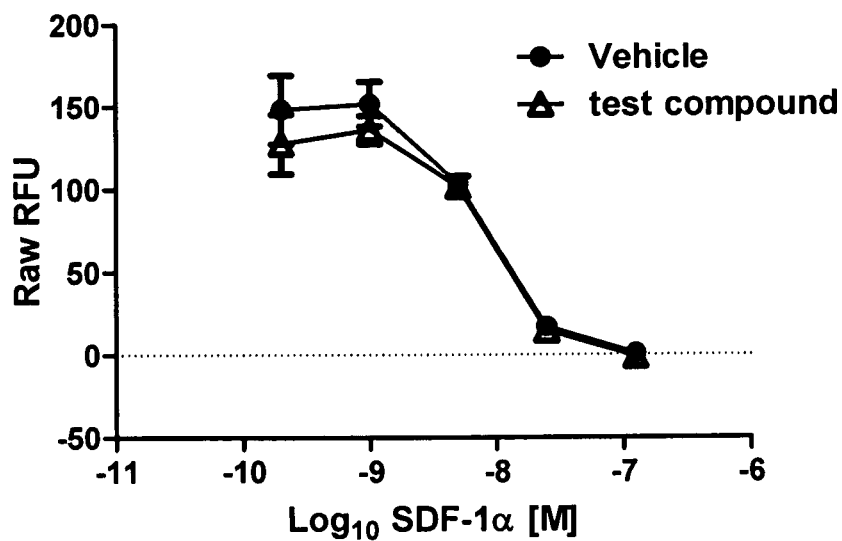
Figure 1R:
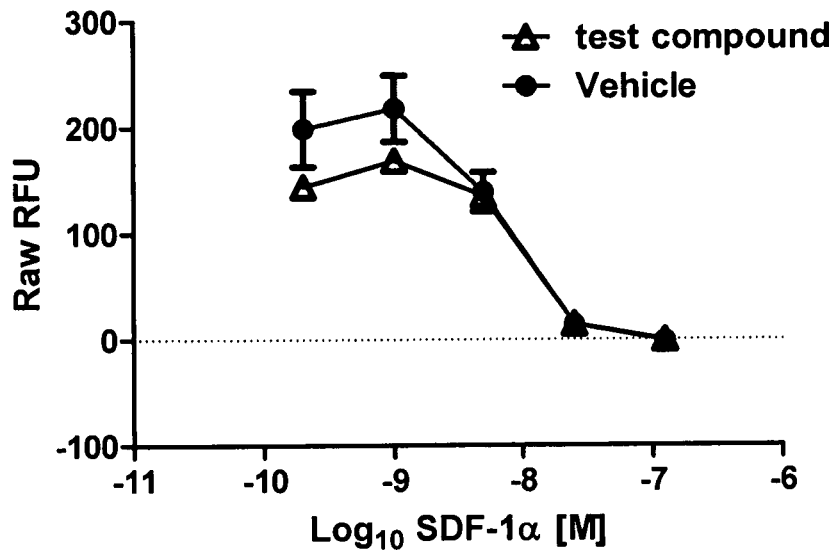
Figure 1R:
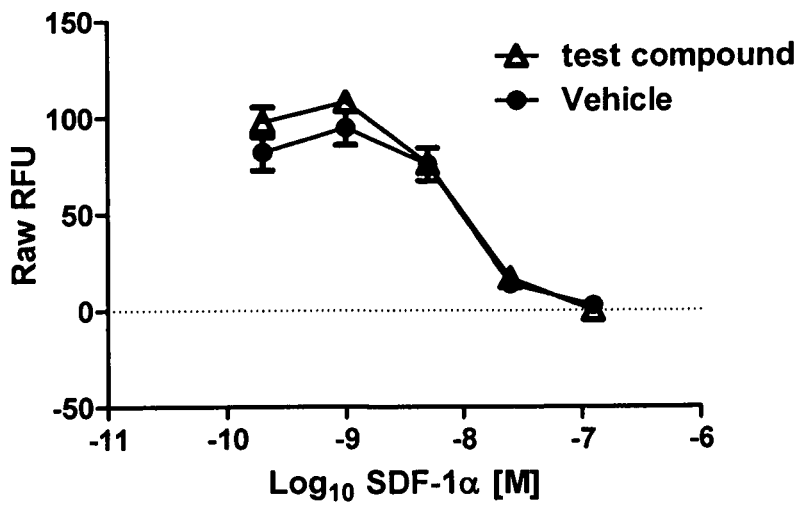
Figure 1S:
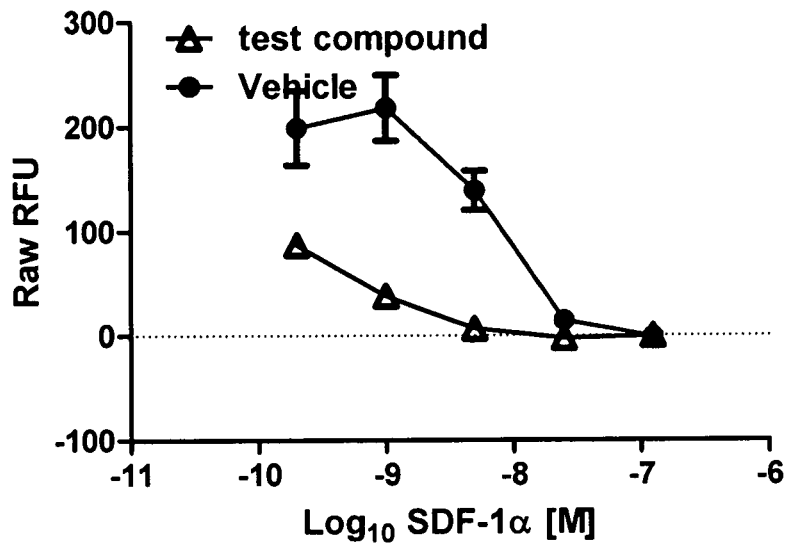
Figure 1S:
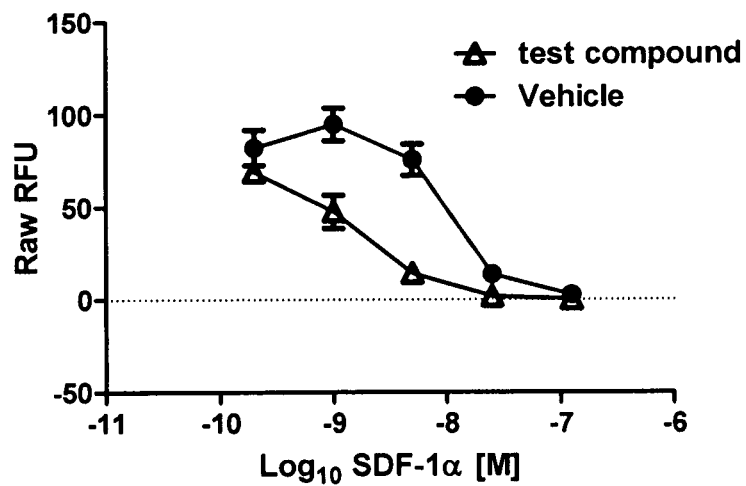
Figure 1T:
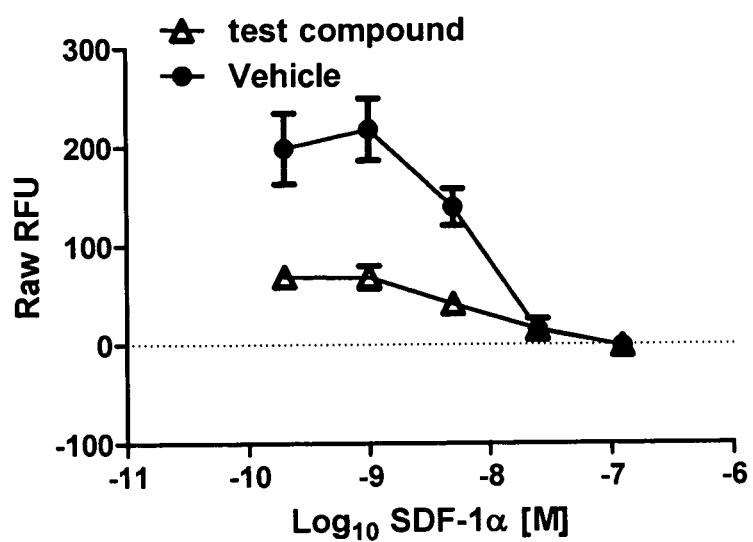
Figure 1U:
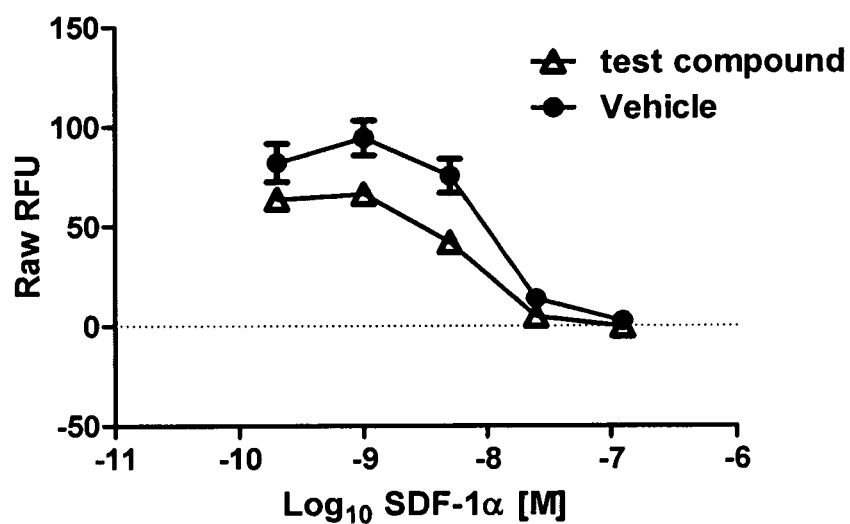
Figure 1V:
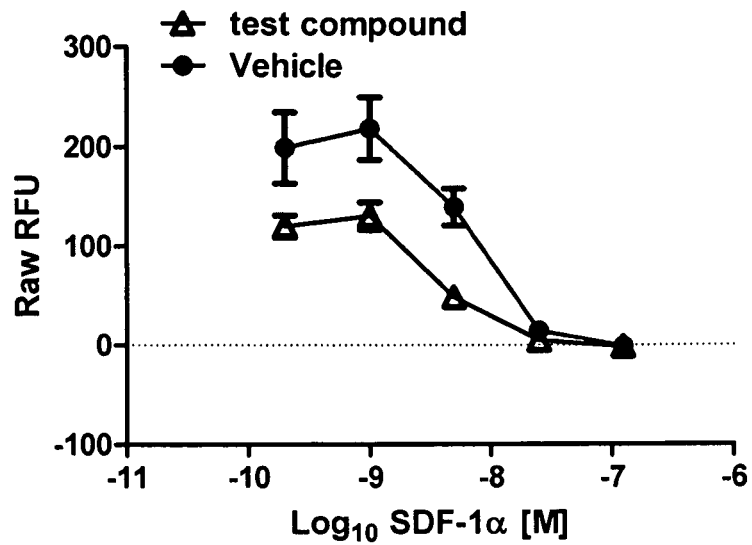
Figure 1V:
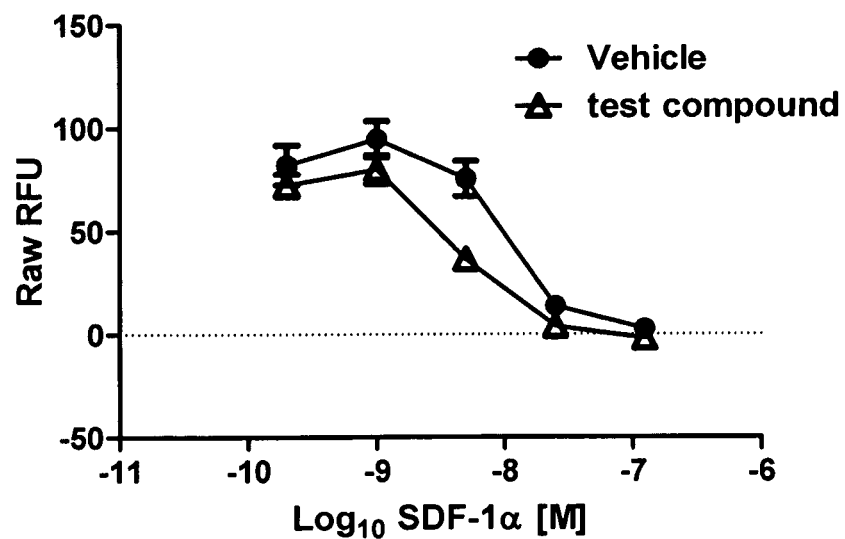
Figure 2A:
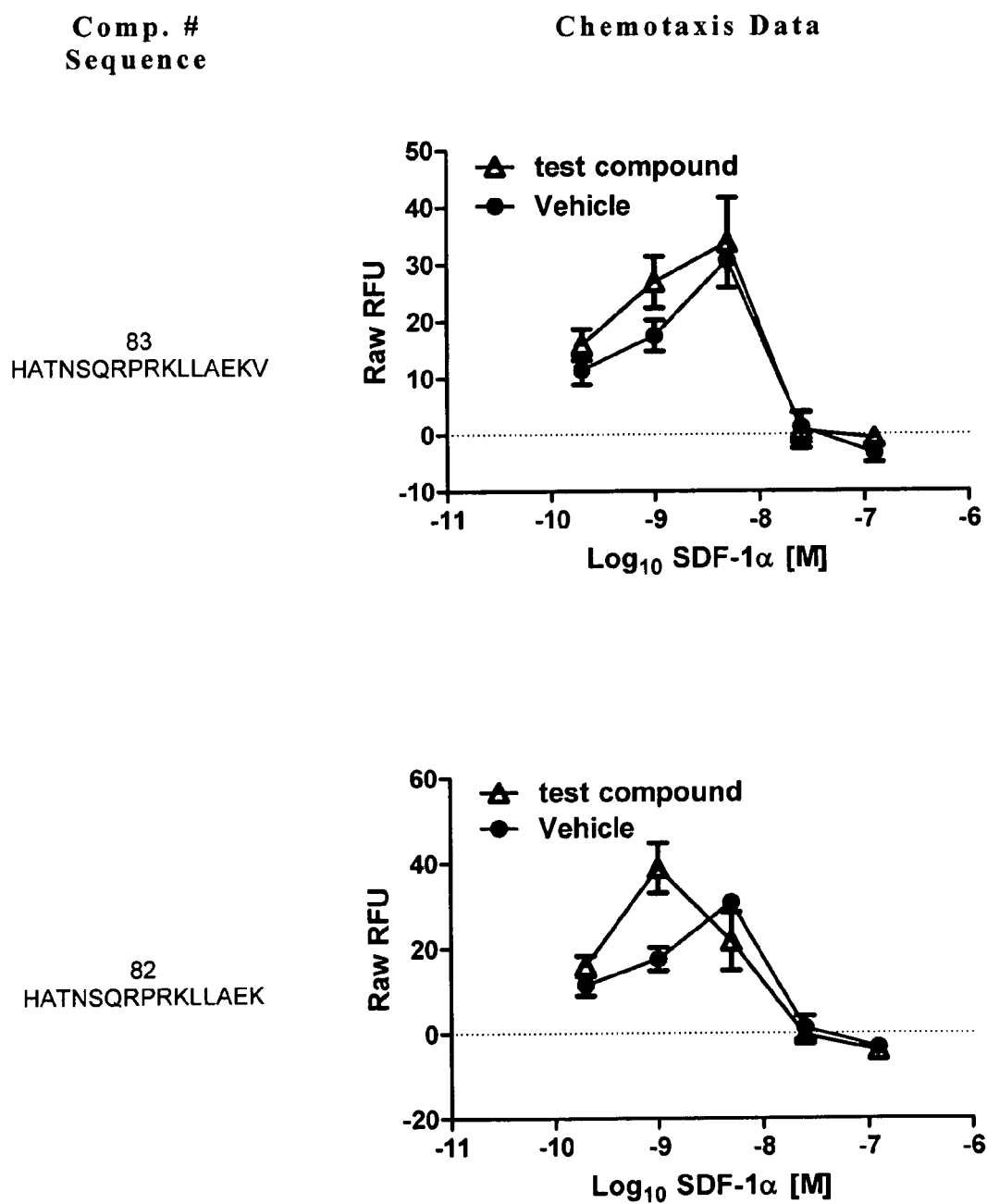
FIGS. 2A-2D are a series of graphical representations of compounds of the invention derived from the i2 loop in a chemotaxis assay as compared with vehicle.
Figure 2B:
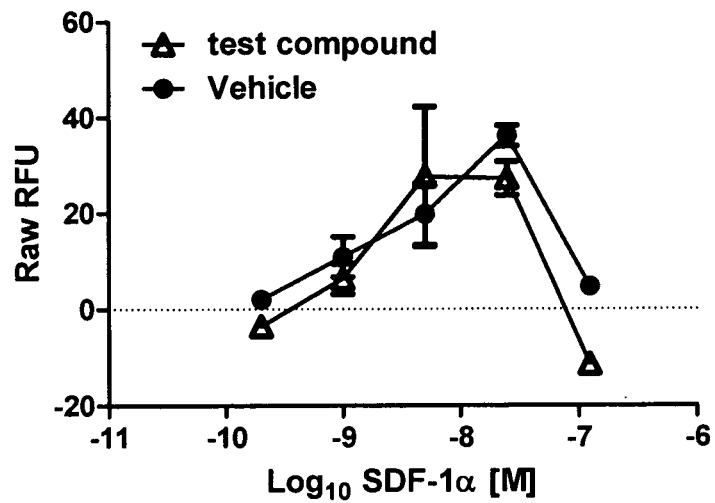
Figure 2B:
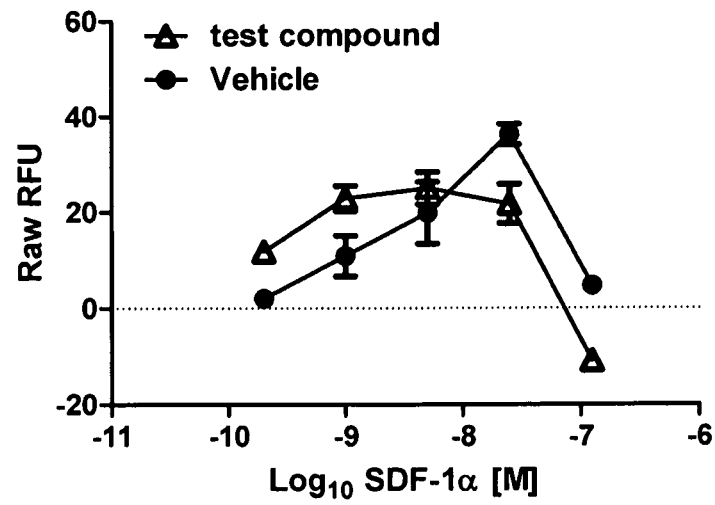
Figure 2C:
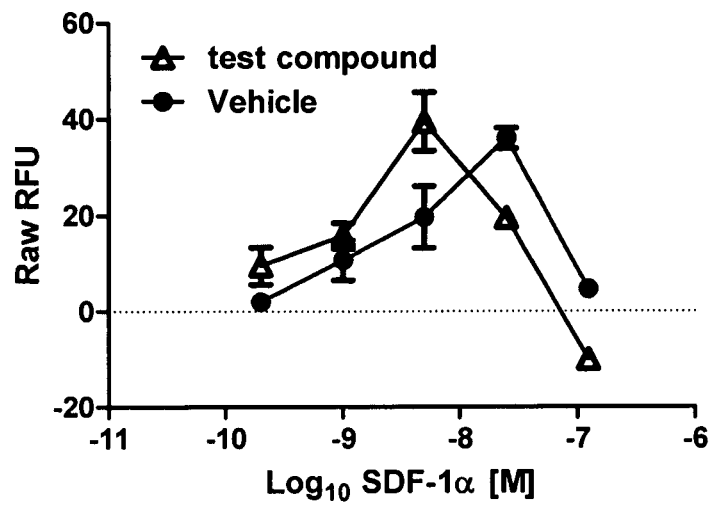
Figure 2C:
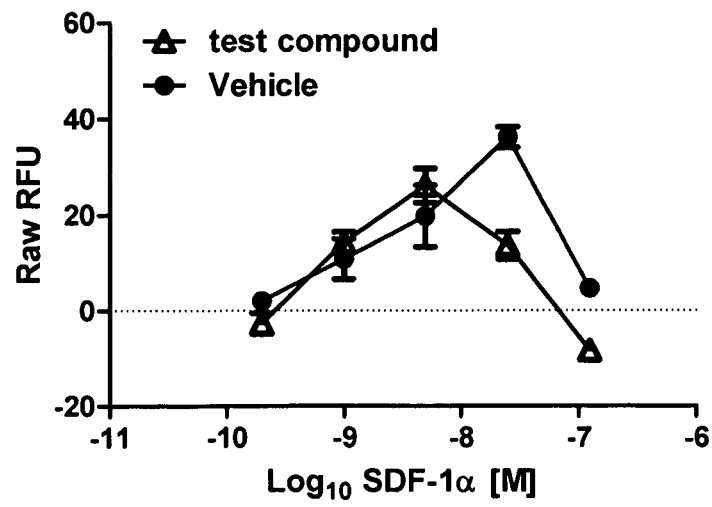
Figure 2D:
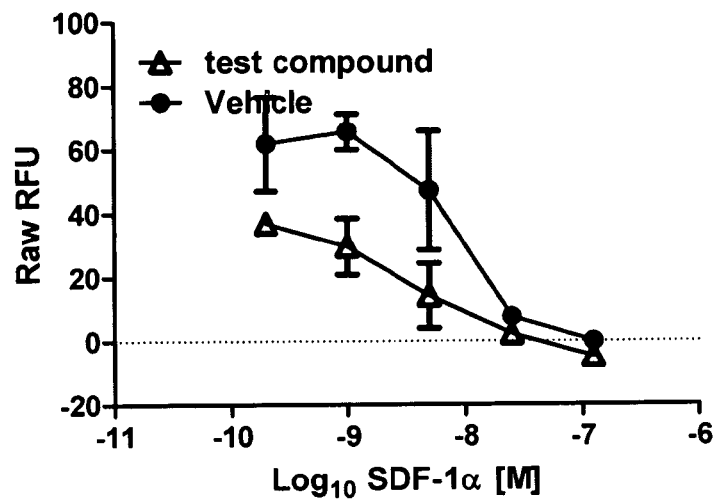
Figure 2D:
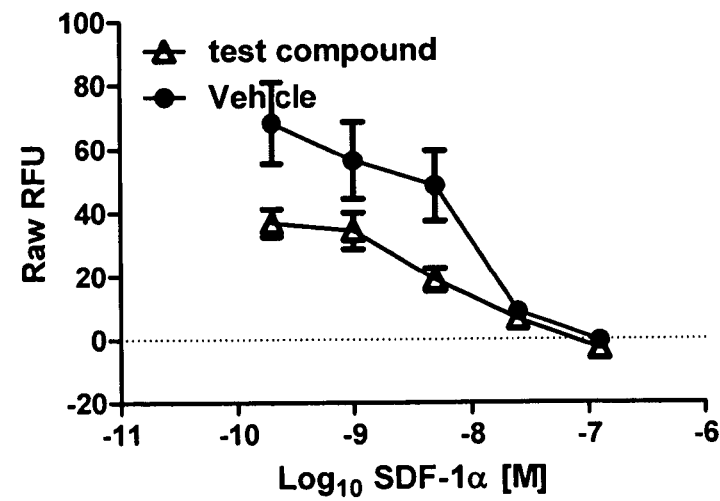
Figure 3A:
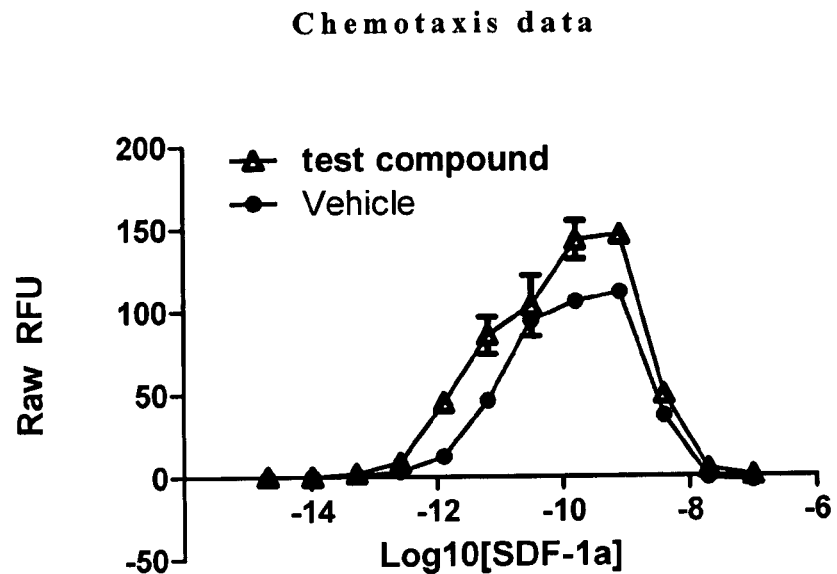
FIGS. 3A-3G are a series of graphical representations of compounds of the invention derived from the i3 loop in a chemotaxis assay as compared with vehicle.
Figure 3A:
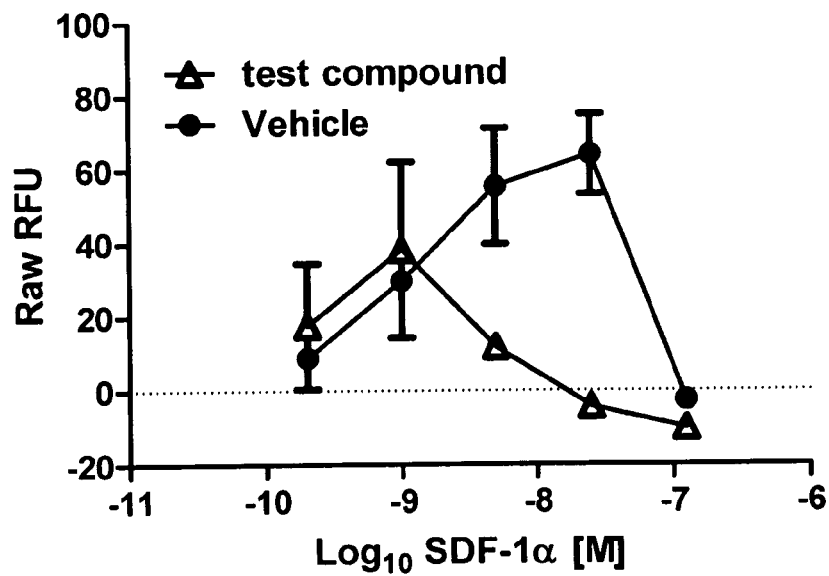
Figure 3B:
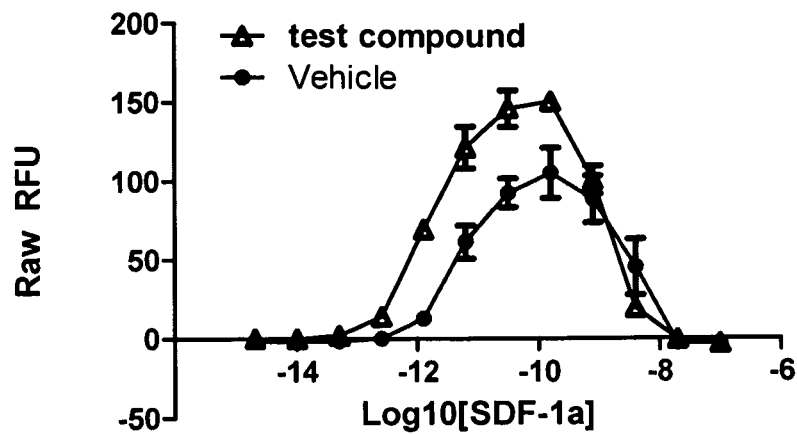
Figure 3B:
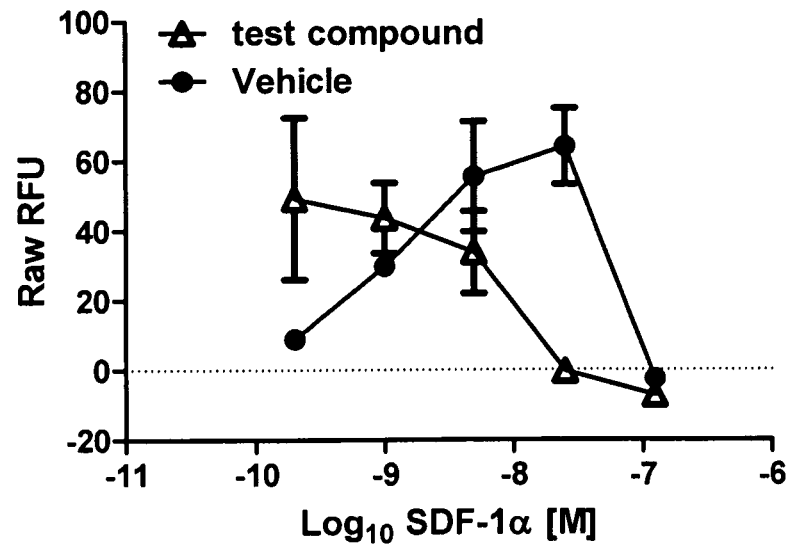
Figure 3C:
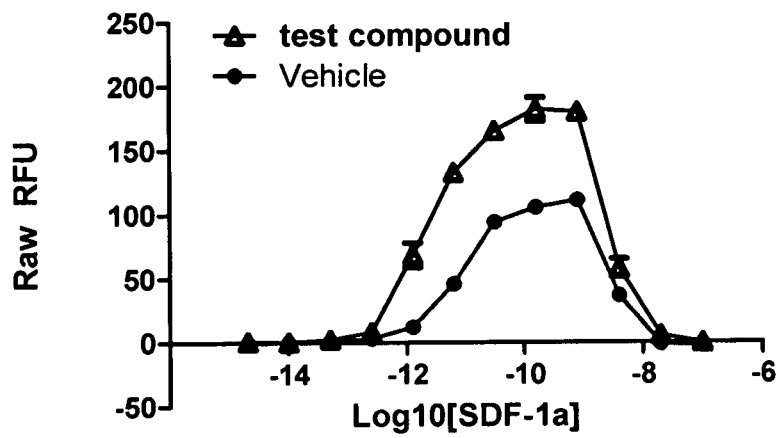
Figure 3C:
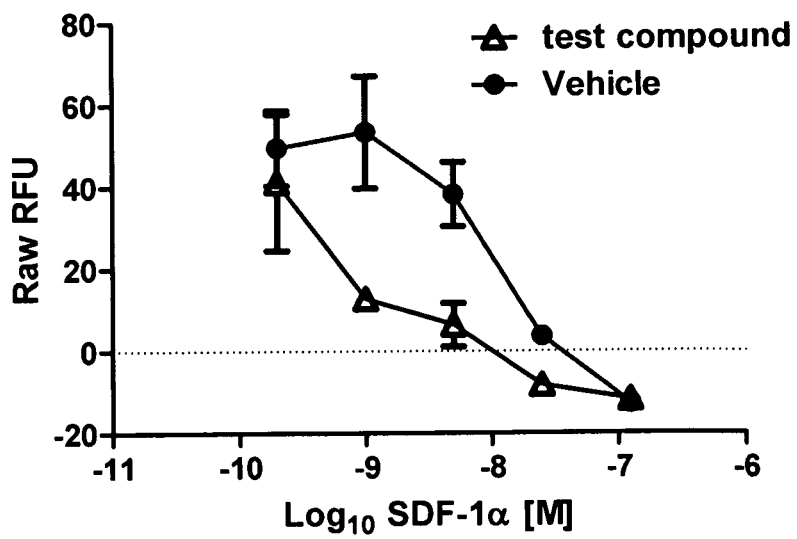
Figure 3D:
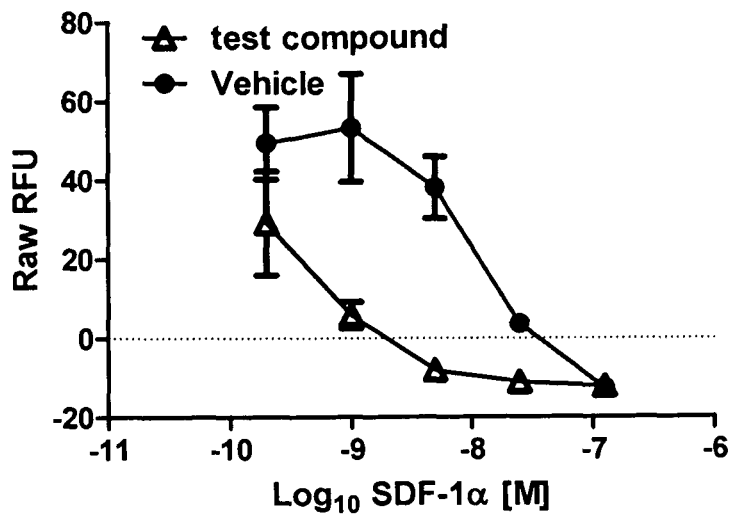
Figure 3D:
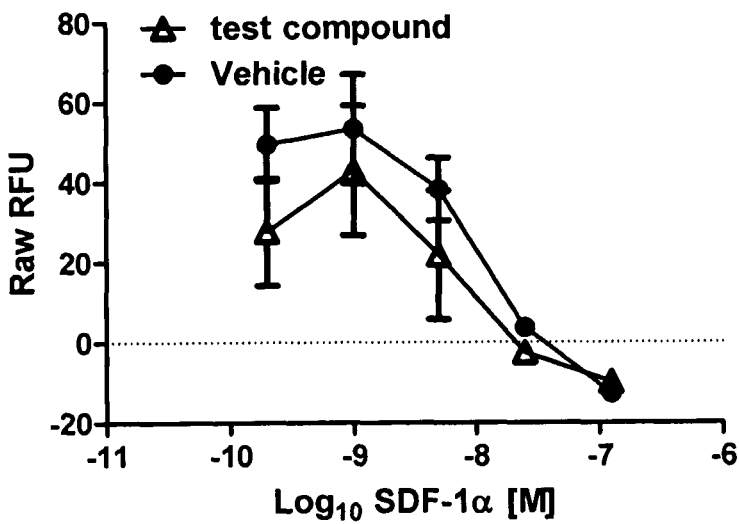
Figure 3E:
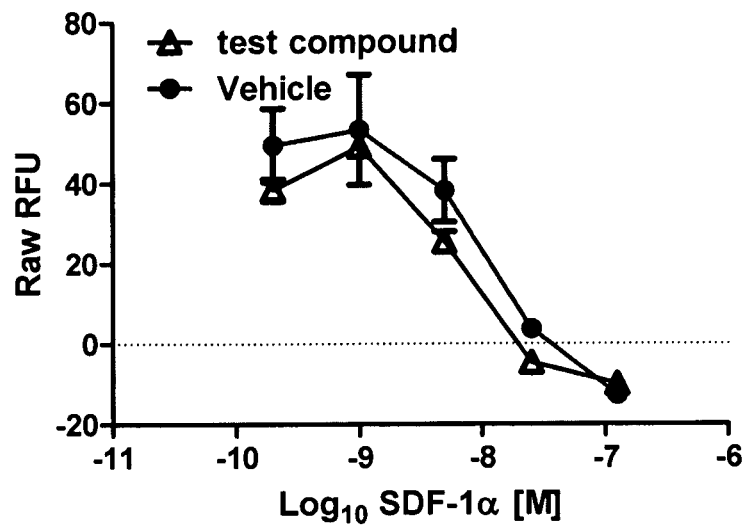
Figure 3E:
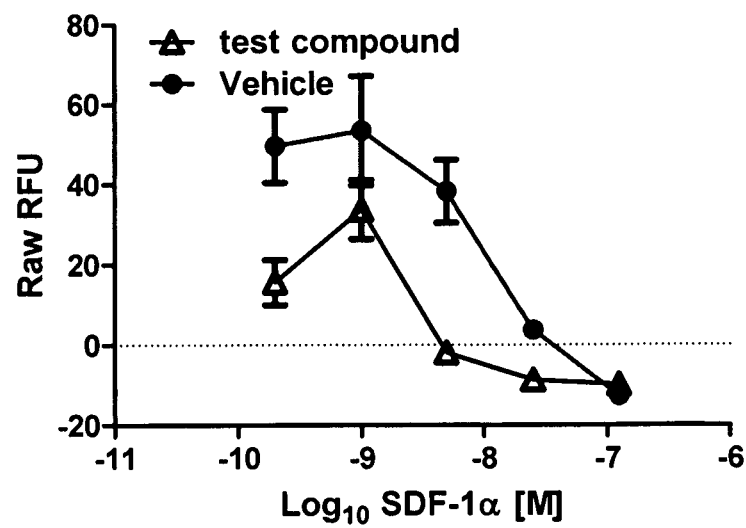
Figure 3F:
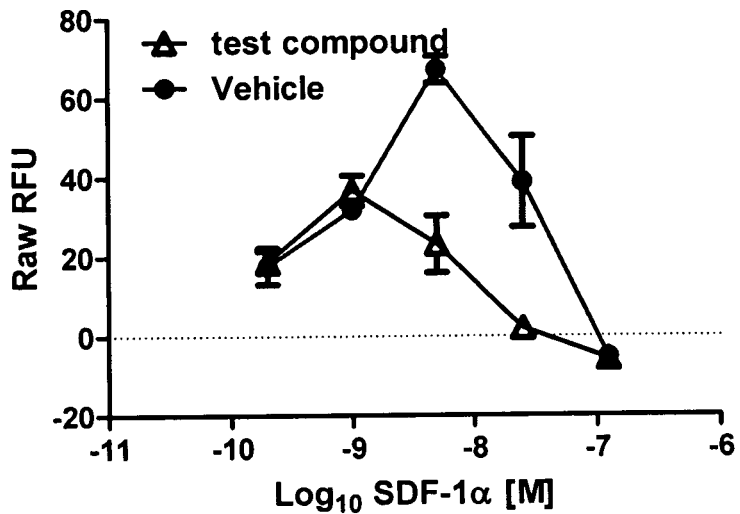
Figure 3F:
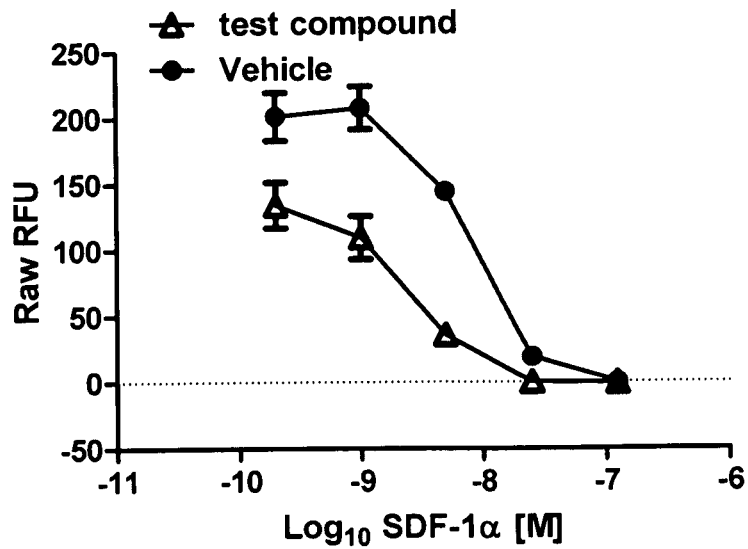
Figure 3G:
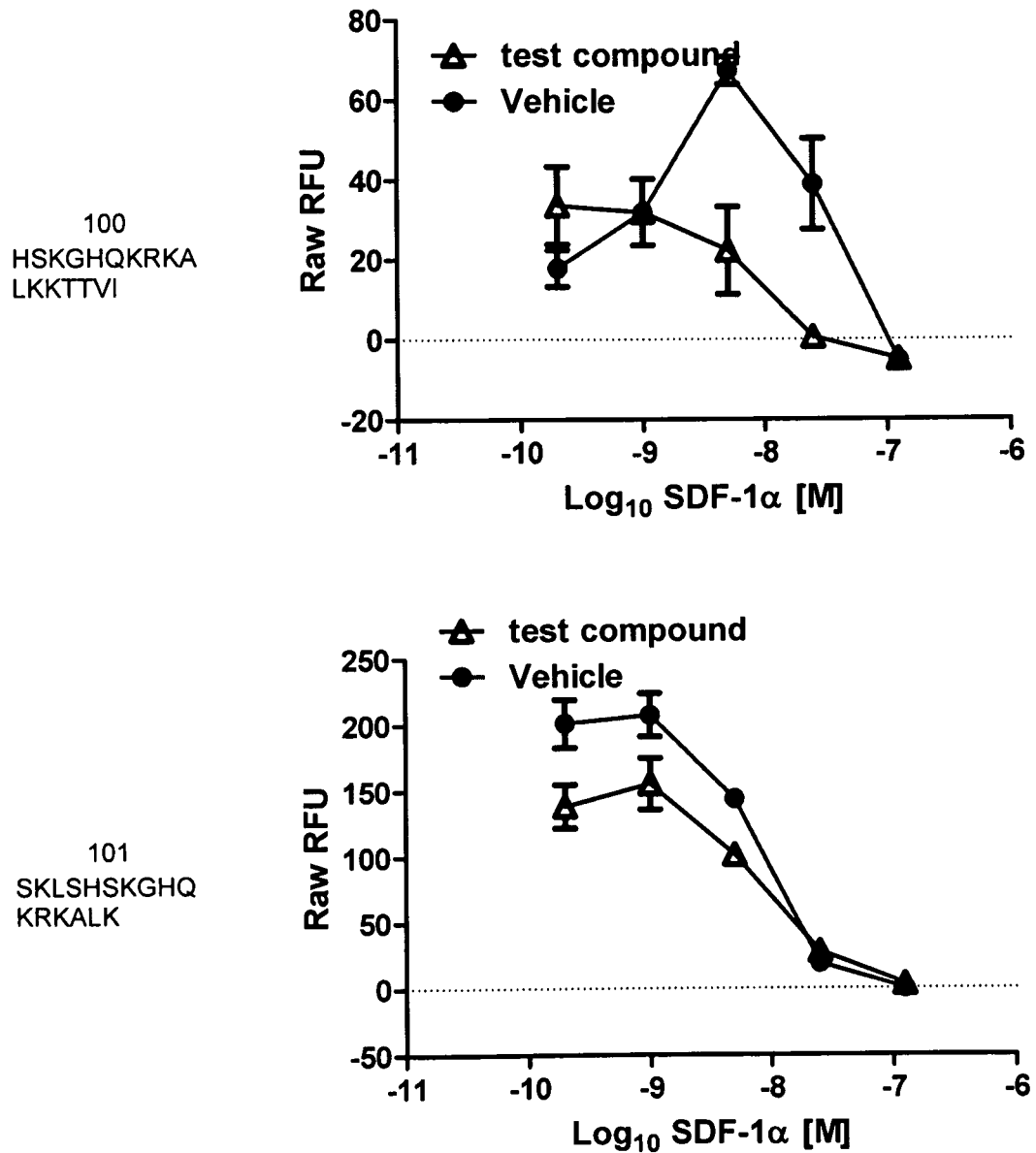
Figure 4A:
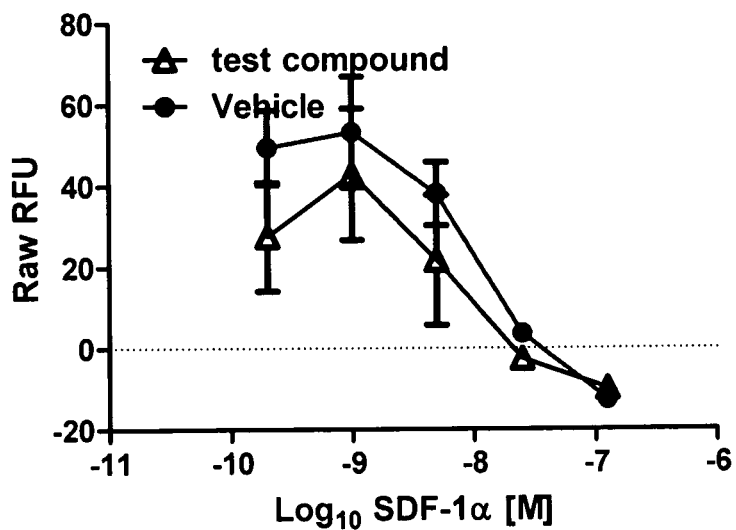
FIGS. 4A-4D are a series of graphical representations of compounds of the invention derived from the i4 domain in a chemotaxis assay as compared with vehicle.
Figure 4A:
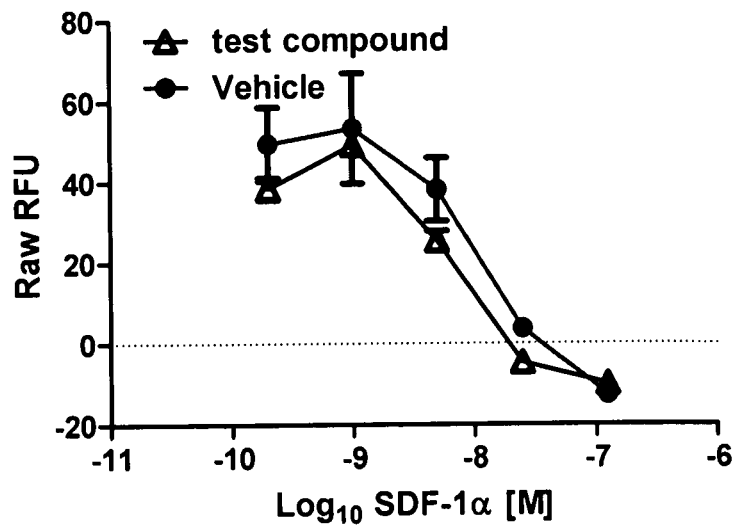
Figure 4B:
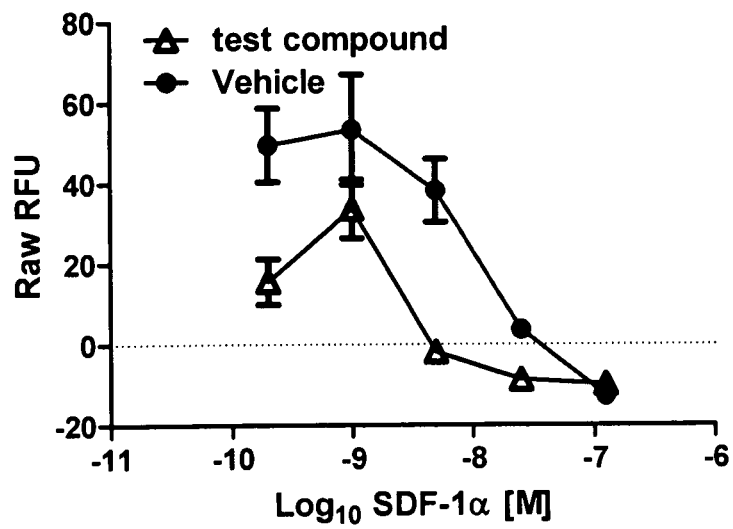
Figure 4B:
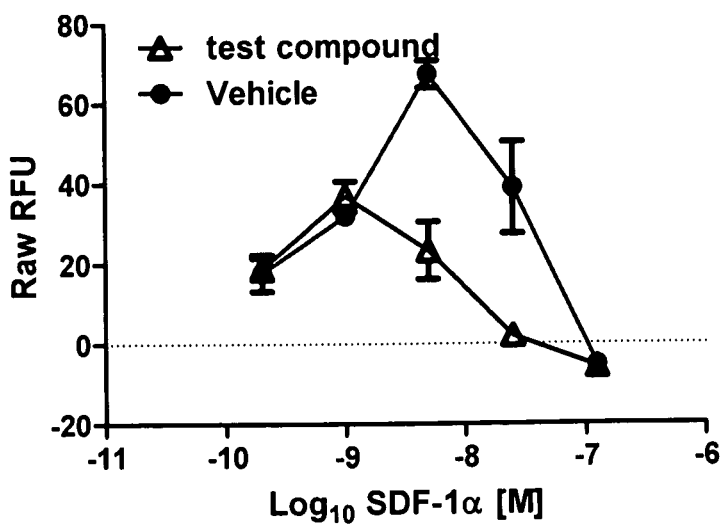
Figure 4C:
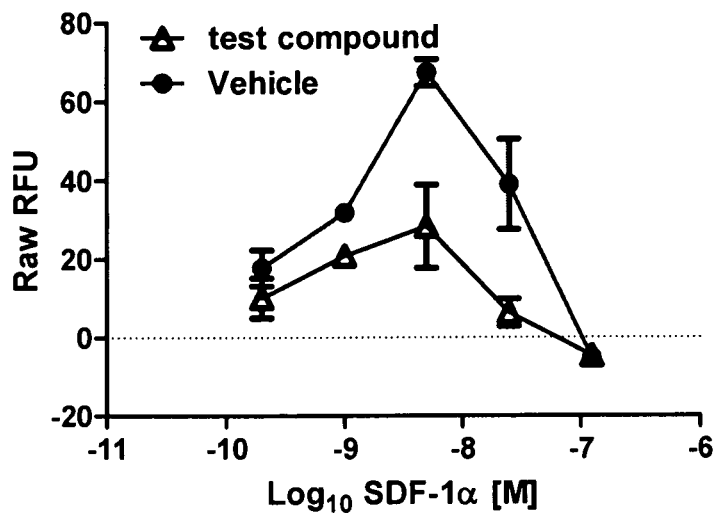
Figure 4C:
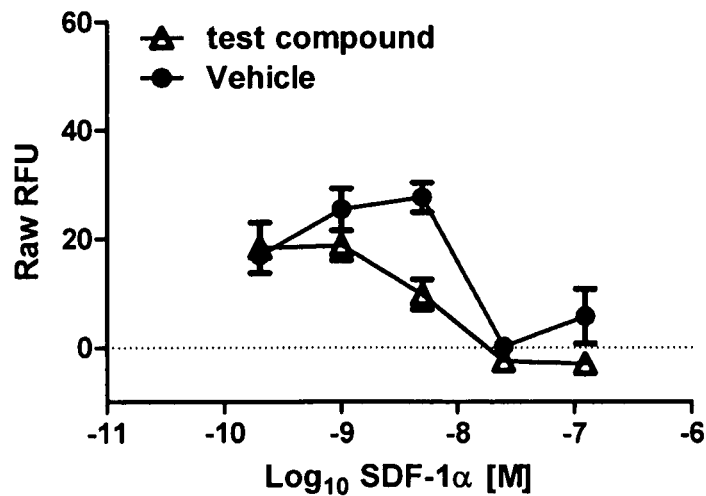
Figure 4D:
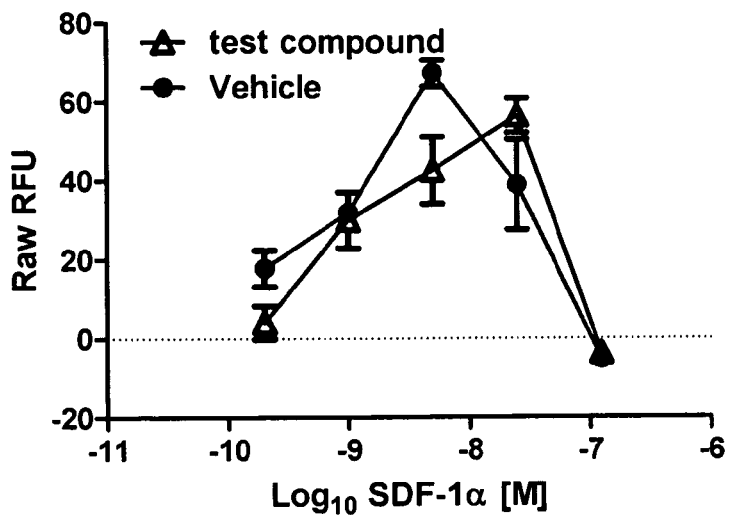
Figure 4D:
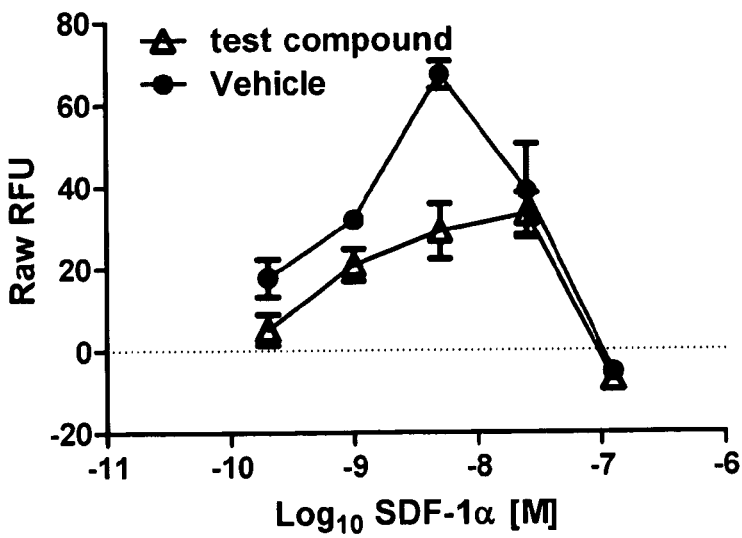

A description of example embodiments of the invention follows.

G Protein Coupled Receptors (GPCRs)

G protein coupled receptors (GPCRs) constitute one of the largest superfamilies of genes in the human genome; these transmembrane proteins enable the cell the respond to its environment by sensing extracellular stimuli and initiating intracellular signal transduction cascades. GPCRs mediate signal transduction through the binding and activation of guanine nucleotide-binding proteins (G proteins) to which the receptor is coupled. Wide arrays of ligands bind to these receptors, which in turn orchestrate signaling networks integral to many cellular functions. Diverse GPCR ligands include small proteins, peptides, amino acids, biogenic amines, lipids, ions, odorants and even photons of light. The following reviews are incorporated by reference: Hill, British J. Pharm 147: s27 (2006); Dorsham & Gutkind, *Nature Reviews* 7: 79-94 (2007).

In addition to modulating a diverse array of homeostatic processes, GPCR signaling pathways are integral components of many pathological conditions (e.g., cardiovascular and mental disorders, cancer, AIDS). In fact, GPCRs are targeted by 40-50% of approved drugs illustrating the critical importance of this class of pharmaceutical targets. Interestingly, this number represents only about 30 GPCRs, a small fraction of the total number of GPCRs thought to be relevant to human disease. GPCRs are membrane bound receptors that exhibit complex pharmacological properties and remain challenging targets from a research and development perspective. Given their importance in human health combined with their prevalence (over 1000 known GPCRs in the human genome) GPCRs represent an important target receptor class for drug discovery and design.

GPCRs are integral membrane proteins that mediate diverse signaling cascades through an evolutionarily conserved structural motif. All GPCRs are thought to consist of seven hydrophobic transmembrane spanning α-helices with the amino terminus on the extracellular side of the membrane and the carboxyl terminus on the intracellular side of the membrane. The transmembrane helices are linked together sequentially by extracellular (e1, e2, e3) and intracellular (cytoplasmic) loops (i1, i2, i3). The intracellular loops or domains are intimately involved in the coupling and turnover of G proteins and include: i1, which connects TM1-TM2; i2, connecting TM3-TM4; i3, connecting TM5-TM6; and a portion of the C-terminal cytoplasmic tail (domain 4). Due in part to the topological homology of the 7TM domains and the recent high resolution crystal structures of several GPCRs (Palczewski et al., *Science* 289, 739-45 (2000), Rasmussen, S. G. et al., *Nature* 450, 383-7 (2007)) skilled modelers are now able to predict the general boundaries of GPCR loop domains through the alignment of several related receptors. These predictions are aided in part by a number of programs used by computational biologists, including EMBOSS, ClustalW2, Kalign, and MAFFT (Multiple Alignment using Fast Fourier Transform). Importantly, many of these programs are publically available (see, for example, The European Bioinformatics Institute (EMBL-EBI) web site http://www.ebi.ac.uk/Tools/) and most have web-based interfaces.

GPCR mediated signal transduction is initiated by the binding of a ligand to its cognate receptor. In many instances GPCR ligand binding is believed to take place in a hydrophilic pocket generated by a cluster of helices near the extracellular domain. However, other ligands, such as large peptides, are thought to bind to the extracellular region of protein and hydrophobic ligands are postulated to intercalate into a receptor binding pocket through the membrane between gaps in the helices. The process of ligand binding induces conformational changes within the receptor. These changes involve the outward movement of helix 6, which in turn alters the conformations of the intracellular loops and ultimately results in a receptor form that is able to bind and activate a heterotrimeric G protein (Farrens, D., et al. *Science* 274, 768-770 (1996), Gether, U. and Kobilka, B., *J. Biol. Chem.* 273, 17979-17982 (1998)). Upon binding the receptor catalyzes the exchange of GTP for GDP in the alpha subunit of the heterotrimeric G protein, which results in a separation of the G protein from the receptor as well a dissociation of the alpha and beta/gamma subunits of the G protein itself. Notably, this process is catalytic and results in signal amplification in that activation of one receptor may elicit the activation and turnover of numerous G proteins, which in turn may regulate multiple second messenger systems. Signaling diversity is further achieved through the existence of numerous G protein types as well as differing isoforms of alpha, beta and gamma subunits. Typically, GPCRs interact with G proteins to regulate the synthesis or inhibition of intracellular second messengers such as cyclic AMP, inositol phosphates, diacylglycerol and calcium ions, thereby triggering a cascade of intracellular events that eventually leads to a biological response.

GPCR signaling may be modulated and attenuated through cellular machinery as well as pharmacological intervention. Signal transduction may be 'switched off' with relatively fast kinetics (seconds to minutes) by a process called rapid desensitization. For GPCRs, this is caused by a functional uncoupling of receptors from heterotrimeric G proteins, without a detectable change in the total number of receptors present in cells or tissues. This process involves the phosphorylation of the receptor C terminus, which enables the protein arrestin to bind to the receptor and occlude further G protein coupling. Once bound by arrestin the receptor may be internalized into the cell and either recycled back to the cell surface or degraded. The alpha subunit of the G protein possesses intrisic GTPase activity, which attenuates signaling and promotes re-association with the beta/gamma subunits and a return to the basal state. GPCR signaling may also be modulated pharmacologically. Agonist drugs act directly to activate the receptors, whereas antagonist drugs act indirectly to block receptor signaling by preventing agonist activity through their associating with the receptor. GPCR binding and signaling can also be modified through allosteric modulation, that is by ligands that bind not at the orthosteric binding site but through binding at an allosteric site elsewhere in the receptors. Allosteric modulators can include both positive and negative modulators of orthosteric ligand mediated activity, allosteric agonists (that act in the absence of the orthosteric ligand), and ago-allosteric modulators (ligands that have agonist activity on their own but that can also modulate the activity of the orthosteric ligand).

The large superfamily of GPCRs may be divided into subclasses based on structural and functional similarities. GPCR families include Class A Rhodopsin like, Class B Secretin like, Class C Metabotropic glutamate/pheromone, Class D Fungal pheromone, Class E cAMP receptors (Dictyostelium), the Frizzled/Smoothened family, and various orphan GPCRs. In addition, putative families include Ocular albinism proteins, Insect odorant receptors, Plant Mlo receptors, Nematode chemoreceptors, Vomeronasal receptors (VIR & V3R) and taste receptors.

Class A GPCRs, also called family A or rhodopsin-like, are the largest class of receptors and characteristically have relatively small extracellular loops that form the basis for selectivity vs. endogenous agonists and small-molecule drugs. In addition, Class A receptors also have relatively small intracellular loops. Class A receptors include amine family members such as dopamine and serotonin, peptide members such as chemokine and opioid, the visual opsins, odorant receptors and an array of hormone receptors.

The CXCR4 receptor (SDF-1) is a Class A receptor that has been implicated in conditions such as cancer, metastatic disease, leukocyte homeostasis, hematopoietic stem cell homing to the bone marrow, hematopoietic cell engraftment, inflammatory diseases and HIV tropism.

Peptides

As defined herein, P is a peptide comprising at least three contiguous amino-acid residues (e.g., at least 3, 4, 5, 6, 7, 8, 9, 10, 11, 12, 13, 14, 15, or 16) of an intracellular i1, i2 or i3 loop or intracellular i4 domain of the CXCR4 receptor. It is understood that, the N-terminal nitrogen of the N-terminal amino acid residue of P to which the linking moiety C(O) is bonded can be one of the at least three contiguous amino acid residues or it can be an amino acid residue distinct from the at least three contiguous amino acid residues.

Intracellular i1 loop as used herein refers to the loop which connects TM1 to TM2 and the corresponding transmembrane junctional residues.

Intracellular i2 loop as used herein refers to the loop which connects TM3 to TM4 and the corresponding transmembrane junctional residues.

Intracellular i3 loop as used herein refers to the loop which connects TM5 to TM6 and the corresponding transmembrane junctional residues.

Intracellular i4 domain as used herein refers to the C-terminal cytoplasmic tail and the transmembrane junctional residue.

In a specific embodiment, P comprises at least three, at least four, at least five, at least six, at least seven, at least eight, at least nine, at least ten, at least eleven, at least twelve, at least thirteen, at least fourteen, at least fifteen, at least sixteen contiguous amino acid residues of the intracellular i1, i2 or i3 loop or intracellular i4 domain of the CXCR4 receptor.

In certain embodiment, P is cyclized. The amino acids can be cyclized via their side chains or end to end.

In a more specific embodiment, the at least three contiguous amino acids of P (e.g., at least 3, 4, 5, 6, 7, 8, 9, 10, 11, 12, 13, 14, 15, or 16) are derived from the intracellular i1, i2 or i3 loop or intracellular i4 domain of the CXCR4 receptor, wherein the amino acid sequence of each loop and the i4 domain is as described in Table 1.

TABLE 1

| Intracellular Loop or Domain | CXCR4 Receptor |
|---|---|
| i1 | MGYQKKLRSMTDKYRLH (SEQ ID NO: 370) |

TABLE 1-continued

| Intracellular Loop or Domain | CXCR4 Receptor |
|---|---|
| i2 | DRYLAIVHATNSQRPRKLLAEK (SEQ ID NO: 371) |
| i3 | IIISKLSHSKGHQKRKALKTTVI (SEQ ID NO: 372) |
| i4 | GAKFKTSAQHALTSVSRGSSLKILSKGKRGGH SSVSTESESSSFHSS (SEQ ID NO: 373) |

It is understood that in addition to the amino acids listed in the sequences in Table 1, the intracellular loop for the i1 loop, i2 loop, i3 loop and i4 domain can also include the transmembrane junctional residues. For example, the i1 loop can include SEQ ID NO: 4370 where one or more residues from the transmembrane junctional residues are included on either the C-terminus, the N-terminus or both. For example, SEQ ID NO: 370 can include either a Serine residue, or a Serine-Alanine residue at the C-terminus, SEQ ID NOS: 374 and 375 respectively. Similarly, the N-teminus of the i1 loop sequence described in Table 1 can also be extended to include a Valine residue (SEQ ID NO: 377) or Valine-Leucine residues (SEQ ID NO: 378), or by -Valine-Leucine-Isoleucine residues (SEQ ID NO: 379) or by -Valine-Leucine-Isoleucine-Valine residues (SEQ ID NO: 380).

In another embodiment, P comprises at least three, at least four, at least five, at least six, at least seven, at least eight, at least nine, at least ten, at least eleven, at least twelve, at least thirteen, at least fourteen, at least fifteen, or at least sixteen contiguous amino acid residues of the i1 intracellular loop of the CXCR4 receptor.

In an even more specific embodiment, P is selected from the group consisting of SEQ ID NOS:1-148 as listed in Table 2 below. Amino acids designated as lower case letters indicate D-amino acids.

TABLE 2

| CXCR4 i-Loop | Sequence | SEQ ID NO: |
|---|---|---|
| i1 | SGYQKKLRSSTD | 1 |
| i1 | MGYQKKLRSATD | 2 |
| i1 | SGYQKKLRSMTD | 3 |
| i1 | JGYQKKLRSJTD | 4 |
| i1 | LGYQKKLRSLTD | 5 |
| i1 | IGYQKKLRSITD | 6 |
| i1 | JGYQKKLRSSTD | 7 |
| i1 | JGYQKKLRSMTD | 8 |
| i1 | LGYQKKLRSMTD | 9 |
| i1 | IGYQKKLRSMTD | 10 |
| i1 | AGYQKKLRSMTD | 11 |
| i1 | MAYQKKLRSMTD | 12 |
| i1 | MGAQKKLRSMTD | 13 |
| i1 | MGYAKKLRSMTD | 14 |

TABLE 2 -continued

| CXCR4 i-Loop | Sequence | SEQ ID NO: |
|---|---|---|
| i1 | MGYQKKLRAMTD | 15 |
| i1 | MGYQKKLRSATD | 16 |
| i1 | MGYQKKLRSMAD | 17 |
| i1 | MGYQKKLRSMTA | 18 |
| i1 | MGYQAKLRSMTD | 19 |
| i1 | MGYQKKLASMTD | 20 |
| i1 | MGYQKALRSMTD | 21 |
| i1 | MGYQKKARSMTD | 22 |
| i1 | mGYQKKLRSMTD | 23 |
| i1 | MGyQKKLRSMTD | 24 |
| i1 | MGYqKKLRSMTD | 25 |
| i1 | MGYQkKLRSMTD | 26 |
| i1 | MGYQKkLRSMTD | 27 |
| i1 | MGYQKKlRSMTD | 28 |
| i1 | MGYQKKLrSMTD | 29 |
| i1 | MGYQKKLRsMTD | 30 |
| i1 | MGYQKKLRSmTD | 31 |
| i1 | MGYQKKLRSMtD | 32 |
| i1 | MGYQKKLRSMTd | 33 |
| i1 | GSHYQKKLRSSTD | 34 |
| i1 | GSGYQKKLRSSTD | 35 |
| i1 | YQKKLRSSTD | 36 |
| i1 | GYQKKLRSJTD | 37 |
| i1 | GYQKKLRSLTD | 38 |
| i1 | GYQKKLRSMTDKYRLH | 39 |
| i1 | YQKKLRSMTDKYRLH | 40 |
| i1 | QKKLRSMTDKYRLH | 41 |
| i1 | KKLRSMTDKYRLH | 42 |
| i1 | KLRSMTDKYRLH | 43 |
| i1 | LRSMTDKYRLH | 44 |
| i1 | RSMTDKYRLH | 45 |
| i1 | SMTDKYRLH | 46 |
| i1 | MTDKYRLH | 47 |
| i1 | TDKYRLH | 48 |
| i1 | GYQKKLRSMTDKYRL | 49 |
| i1 | GYQKKLRSMTDKYR | 50 |
| i1 | GYQKKLRSMTDKY | 51 |
| i1 | GYQKKLRSMTDK | 52 |
| i1 | GYQKKLRSMTD | 53 |
| i1 | GYQKKLRSITD- | 54 |
| i1 | GYQKKLRSMT | 55 |
| i1 | GYQKKLRSM | 56 |
| i1 | GYQKKLRS | 57 |
| i1 | GYQKKLR | 58 |
| i1 | YQKKLRS | 59 |
| i1 | QKKLRSM | 60 |
| i1 | KKLRSMT | 61 |
| i1 | KLRSMTD | 62 |
| i1 | LRSMTDK | 63 |
| i1 | RSMTDKY | 64 |
| i1 | SMTDKYR | 65 |
| i1 | MTDKYRL | 66 |
| i1 | KRMKTSLYDGRMQYLK | 67 |
| i1 | sGYQKKLRSSTD | 68 |
| i1 | KKLRSMTDKY | 69 |
| i1 | KKLRSMTDKYR | 70 |
| i1 | KKLRSMTDKYRL | 71 |
| i1 | KKLRSXTDKYRLH (X = Norluceine (Nle)) | 72 |
| i1 | KKLRSMTDKYRLHL | 73 |
| i1 | KKLRSMTDKYRLHLSV | 74 |
| i1 | QKKLRSMTDKYRI | 75 |
| i1 | QKKLRSMTDKYRLHL | 76 |
| i1 | YQKKLRSMTDKYRLHLSV | 77 |
| i1 | LVMGYQKKLRSMTD | 78 |
| i1 | MGYQKKLRSMTDK | 79 |
| i1 | MGYQKKLRSMTDKY | 80 |
| i1 | MGYQKKLRSMTDKYRI | 81 |
| i1 | MGYQKKLRSMTDKYRL | 82 |
| i1 | MGYQKKLRSMTDKYRLHL | 83 |
| i1 | MGYQKKLRSMTDKYRLHLSV | 84 |
| i1 | YTKRLDSHRKLKM | 85 |
| i1 | VMGYQKKLRSMTD | 86 |
| i1 | KKLCRSMTDKCYRL | 87 |
| i1 | KKLRCSMTDCKYRL | 88 |
| i1 | kKLRSMTDKYRLH | 89 |
| i1 | KkLRSMTDKYRLH | 90 |
| i1 | KKlRSMTDKYRLH | 91 |

TABLE 2 -continued

| CXCR4 i-Loop | Sequence | SEQ ID NO: |
|---|---|---|
| i1 | KKLrSMTDKYRLH | 92 |
| i1 | KKLRsMTDKYRLH | 93 |
| i1 | KKLRSmTDKYRLH | 94 |
| i1 | AKLRSMTDKYRLH | 95 |
| i1 | KALRSMTDKYRLH | 96 |
| i1 | KKARSMTDKYRLH | 97 |
| i1 | KKLASMTDKYRLH | 98 |
| i1 | KKLRAMTDKYRLH | 99 |
| i1 | KKLRSATDKYRLH | 100 |
| i1 | AGYQKKLRSMTDKYRL | 101 |
| i1 | MAYQKKLRSMTDKYRL | 102 |
| i1 | MGAQKKLRSMTDKYRL | 103 |
| i1 | MGYAKKLRSMTDKYRL | 104 |
| i1 | MGYQAKLRSMTDKYRL | 105 |
| i1 | MGYQKALRSMTDKYRL | 106 |
| i1 | MGYQKKARSMTDKYRL | 107 |
| i1 | MGYQKKLASMTDKYRL | 108 |
| i1 | KKLRSMADKYRLH | 109 |
| i1 | KKLRSMTAKYRLH | 110 |
| i1 | KKLRSMTDAYRLH | 111 |
| i1 | KKLRSMTDKARLH | 112 |
| i1 | KKLRSMTDKYALH | 113 |
| i1 | KKLRSMTDKYRAH | 114 |
| i1 | KKLRSMTDKYRLA | 115 |
| i1 | MGYQKKLRAMTDKYRL | 116 |
| i1 | MGYQKKLRSATDKYRL | 117 |
| i1 | MGYQKKLRSMADKYRL | 118 |
| i1 | MGYQKKLRSMTAKYRL | 119 |
| i1 | MGYQKKLRSMTDAYRL | 120 |
| i1 | MGYQKKLRSMTDKARL | 121 |
| i1 | MGYQKKLRSMTDKYAL | 122 |
| i1 | MGYQKKLRSMTDKYRA | 123 |
| i1 | KKLRSMtDKYRLH | 124 |
| i1 | KKLRSMTdKYRLH | 125 |
| i1 | KKLRSMTDKYrLH | 126 |
| i1 | KKLRSMTDKYRlH | 127 |
| i1 | KKLRSMTDKYRLh | 128 |
| i1 | MGYQKKLRSMTDKYrL | 129 |
| i1 | MGYQKKLRSMTDKyRL | 130 |
| i1 | MGYQICKLRSMTDkYRL | 131 |
| i1 | MGYQKKLRSMTdKYRL | 132 |
| i1 | MGYQKKLRSMtDKYRL | 133 |
| i1 | mGYQKKLRSMTDKYRL | 134 |
| i1 | MGyQKKLRSMTDKYRL | 135 |
| i1 | MGYqCKLRSMTDKYRL | 136 |
| i1 | MGYQkKLRSMTDKYRL | 137 |
| i1 | MGYQKkLRSMTDKYRL | 138 |
| i1 | MGYQKKlRSMTDKYRL | 139 |
| i1 | MGYQKKLrSMTDKYRL | 140 |
| i1 | MGYQKKLRsMTDKYRL | 141 |
| i1 | MGYQKKLRSmTDKYRL | 142 |
| i1 | KKLRSMTDKYRlS | 143 |
| i1 | MGYQKKLRSpTDKYRL | 144 |
| i1 | MGYQKKLRpMTDKYRL | 145 |
| i1 | MGYQKKLpSMTDKYRL | 146 |
| i1 | MGYQKKpRSMTDKYRL | 147 |
| i1 | MGYQKKLRSMPDKYRL | 148 |

In another specific embodiment, the at least three contiguous amino acids of P (e.g., at least 3, 4, 5, 6, 7, 8, 9, 10, 11, 12, 13, 14, 15, or 16) are derived from the i2 intracellular loop of the CXCR4 receptor.

In a more specific embodiment, P is selected from the group consisting of SEQ ID NOS: 149-199 as listed in Table 3 below.

TABLE 3

| CXCR4 i-Loop | Sequence | SEQ ID NO: |
|---|---|---|
| i2 | DRYLAIVHATNSQRPRKLLAEK | 149 |
| i2 | DRYLAIVHATNSQRPRKLLAE | 150 |
| i2 | DRYLAIVHATNSQRPRKLLA | 151 |
| i2 | DRYLAIVHATNSQRPRKLL | 152 |
| i2 | DRYLAIVHATNSQRPRKL | 153 |
| i2 | DRYLAIVHATNSQRPRK | 154 |
| i2 | DRYLAIVHATNSQRPR | 155 |
| i2 | DRYLAIVHATNSQRP | 156 |
| i2 | DRYLAIVHATNSQR | 157 |
| i2 | DRYLAIVHATNSQ | 158 |
| i2 | DRYLAIVHATNS | 159 |
| i2 | DRYLAIVHATN | 160 |

TABLE 3 -continued

| CXCR4 i-Loop | Sequence | SEQ ID NO: |
|---|---|---|
| i2 | DRYLAIVHAT | 161 |
| i2 | DRYLAIVHA | 162 |
| i2 | DRYLAIVH | 163 |
| i2 | DRYLAIV | 164 |
| i2 | RYLAIVHATNSQRPRKLLAEK | 165 |
| i2 | YLAIVHATNSQRPRKLLAEK | 166 |
| i2 | LAIVHATNSQRPRKLLAEK | 167 |
| i2 | AIVHATNSQRPRKLLAEK | 168 |
| i2 | IVHATNSQRPRKLLAEK | 169 |
| i2 | VHATNSQRPRKLLAEK | 170 |
| i2 | HATNSQRPRKLLAEK- | 171 |
| i2 | ATNSQRPRKLLAEK | 172 |
| i2 | TNSQRPRKLLAEK | 173 |
| i2 | NSQRPRKLLAEK | 174 |
| i2 | SQRPRKLLAEK | 175 |
| i2 | QRPRKLLAEK | 176 |
| i2 | RPRKLLAEK | 177 |
| i2 | PRKLLAEK | 178 |
| i2 | RKLLAEK | 179 |
| i2 | RYLAIVH- | 180 |
| i2 | YLAIVHA | 181 |
| i2 | LAIVHAT | 182 |
| i2 | AIVHATN- | 183 |
| i2 | IVHATNS- | 184 |
| i2 | VHATNSQ | 185 |
| i2 | HATNSQR | 186 |
| i2 | ATNSQRP | 187 |
| i2 | TNSQRPR- | 188 |
| i2 | NSQRPRK | 189 |
| i2 | SQRPRKL | 190 |
| i2 | QRPRKLL | 191 |
| i2 | RPRKLLA | 192 |
| i2 | PRKLLAE | 193 |
| i2 | VHATNSQRPRKLLAEKVVY | 194 |
| i2 | VHATNSQRPRKLLA | 195 |
| i2 | HATNSQRPRKL | 196 |
| i2 | HATNSQRPRKLLA | 197 |
| i2 | HATNSQRPRKLLAE | 198 |
| i2 | HATNSQRPRKLLAEKV | 199 |

In yet another specific embodiment, P comprises at least three contiguous amino (e.g., at least 3, 4, 5, 6, 7, 8, 9, 10, 11, 12, 13, 14, 15, or 16) of the i3 intracellular loop of the CXCR4 receptor.

In a more specific embodiment, P is selected from the group consisting of SEQ ID NOS:200-254 as listed in Table 4 below.

TABLE 4

| CXCR4 i-Loop | Sequence | SEQ ID: |
|---|---|---|
| i3 | HSKKGHQKRKALK | 200 |
| i3 | JGYQKKLRSJTD | 201 |
| i3 | IIISKLSHSKGHQKRKALKT | 202 |
| i3 | IIISKLSHSKGHQKRKALK | 203 |
| i3 | IIISKLSHSKGHQKRKAL | 204 |
| i3 | IIISKLSHSKGHQKRKA | 205 |
| i3 | IIISKLSHSKGHQKRK | 206 |
| i3 | IIISKLSHSKGHQKR | 207 |
| i3 | IIISKLSHSKGHQK | 208 |
| i3 | IIISKLSHSKGHQ | 209 |
| i3 | IIISKLSHSKGH | 210 |
| i3 | IIISKLSHSKG | 211 |
| i3 | IIISKLSHSK | 212 |
| i3 | IIISKLSHS | 213 |
| i3 | IIISKLSH | 214 |
| i3 | IIISKLS | 215 |
| i3 | IISKLSHSKGHQKRKALKT | 216 |
| i3 | ISKLSHSKGHQKRKALKT | 217 |
| i3 | SKLSHSKGHQKRKALKT | 218 |
| i3 | KLSHSKGHQKRKALKT | 219 |
| i3 | LSHSKGHQKRKALKT | 220 |
| i3 | SHSKGHQKRKALKT | 221 |
| i3 | HSKGHQKRKALKT | 222 |
| i3 | SKGHQKRKALKT | 223 |
| i3 | KGHQKRKALKT | 224 |
| i3 | GHQKRKALKT | 225 |
| i3 | HQKRKALKT | 226 |
| i3 | QKRKALKT | 227 |

TABLE 4-continued

| CXCR4 i-Loop | Sequence | SEQ ID: |
|---|---|---|
| i3 | KRKALKT | 228 |
| i3 | IISKLSH | 229 |
| i3 | ISKLSHS | 230 |
| i3 | SKLSHSK | 231 |
| i3 | KLSHSKG | 232 |
| i3 | LSHSKGH | 233 |
| i3 | SHSKGHQ | 234 |
| i3 | HSKGHQK | 235 |
| i3 | SKGHQKR | 236 |
| i3 | KGHQKRK | 237 |
| i3 | GHQKRKA | 238 |
| i3 | HQKRKAL | 239 |
| i3 | QKRKALK | 240 |
| i3 | HSKGHQKRKALKTT | 241 |
| i3 | HSKGHQKRKALKTTV | 242 |
| i3 | HSKGHQKRKALKTTVI | 243 |
| i3 | HSKGHQKRKQALK | 244 |
| i3 | KLSHSKGHQKRKA | 245 |
| i3 | KLSHSKGHQKRKAL | 246 |
| i3 | KLSHSKGHQKRKALK | 247 |
| i3 | KLSHSKGHQKRKALKTTV | 248 |
| i3 | KLSHSKGHQKRKALKTTVIL | 249 |
| i3 | LSHSKGHQKRKALK | 250 |
| i3 | SHSKGHQKRKALK | 251 |
| i3 | SKLSHSKGHQKRKALK | 252 |
| i3 | SKLSHSKGHQKRKALKTTVIL | 253 |
| i3 | QHLHIALKKSTSRKVKSGTLK | 254 |

In further specific embodiment, P comprises at least three contiguous amino (e.g., at least 3, 4, 5, 6, 7, 8, 9, 10, 11, 12, 13, 14, 15 or 16) of the i4 intracellular domain of the CXCR4 receptor.

In a more specific embodiment, P is selected from the group consisting of SEQ ID NOS: 255-368 as listed in Table 5 below.

TABLE 5

| CXCR4 i-Loop | Sequence | SEQ ID NO: |
|---|---|---|
| i4 | GAKFKTSAQHALTSVSRGSSLKILSKGKRGGHSSVSTESESSSFH | 255 |
| i4 | GAKFKTSAQHALTSVSRGSSLKILSKGKRGGHSSVSTESESSSF | 256 |
| i4 | GAKFKTSAQHALTSVSRGSSLKILSKGKRGGHSSVSTESESSS | 257 |
| i4 | GAKFKTSAQHALTSVSRGSSLKILSKGKRGGHSSVSTESESS | 258 |
| i4 | GAKFKTSAQHALTSVSRGSSLKILSKGKRGGHSSVSTESES | 259 |
| i4 | GAKFKTSAQHALTSVSRGSSLKILSKGKRGGHSSVSTESE | 260 |
| i4 | GAKFKTSAQHALTSVSRGSSLKILSKGKRGGHSSVSTES | 261 |
| i4 | GAKFKTSAQHALTSVSRGSSLKILSKGKRGGHSSVSTE | 262 |
| i4 | GAKFKTSAQHALTSVSRGSSLKILSKGKRGGHSSVST | 263 |
| i4 | GAKFKTSAQHALTSVSRGSSLKILSKGKRGGHSSVS | 264 |
| i4 | GAKFKTSAQHALTSVSRGSSLKILSKGKRGGHSSV | 265 |
| i4 | GAKFKTSAQHALTSVSRGSSLKILSKGKRGGHSS | 266 |
| i4 | GAKFKTSAQHALTSVSRGSSLKILSKGKRGGHS | 267 |
| i4 | GAKFKTSAQHALTSVSRGSSLKILSKGKRGGH | 268 |
| i4 | GAKFKTSAQHALTSVSRGSSLKILSKGKRGG | 269 |
| i4 | GAKFKTSAQHALTSVSRGSSLKILSKGKRG | 270 |
| i4 | GAKFKTSAQHALTSVSRGSSLKILSKGKR | 271 |
| i4 | GAKFKTSAQHALTSVSRGSSLKILSKGK | 272 |
| i4 | GAKFKTSAQHALTSVSRGSSLKILSKG | 273 |

TABLE 5-continued

| CXCR4 i-Loop | Sequence | SEQ ID NO: |
|---|---|---|
| i4 | GAKFKTSAQHALTSVSRGSSLKILSK | 274 |
| i4 | GAKFKTSAQHALTSVSRGSSLKILS | 275 |
| i4 | GAKFKTSAQHALTSVSRGSSLKIL | 276 |
| i4 | GAKFKTSAQHALTSVSRGSSLKI | 277 |
| i4 | GAKFKTSAQHALTSVSRGSSLK | 278 |
| i4 | GAKFKTSAQHALTSVSRGSSL | 279 |
| i4 | GAKFKTSAQHALTSVSRGSS | 280 |
| i4 | GAKFKTSAQHALTSVSRGS | 281 |
| i4 | GAKFKTSAQHALTSVSRG | 282 |
| i4 | GAKFKTSAQHALTSVSR | 283 |
| i4 | GAKFKTSAQHALTSVS | 284 |
| i4 | GAKFKTSAQHALTSV | 285 |
| i4 | GAKFKTSAQHALTS | 286 |
| i4 | GAKFKTSAQHALT | 287 |
| i4 | GAKFKTSAQHAL | 288 |
| i4 | GAKFKTSAQHA | 289 |
| i4 | GAKFKTSAQH | 290 |
| i4 | AKFKTSAQHALTSVSRGSSLKILSKGKRGGHSSVSTESESSSFHSS | 291 |
| i4 | KFKTSAQHALTSVSRGSSLKILSKGKRGGHSSVSTESESSSFHSS | 292 |
| i4 | FKTSAQHALTSVSRGSSLKILSKGKRGGHSSVSTESESSSFHSS | 293 |
| i4 | KTSAQHALTSVSRGSSLKILSKGKRGGHSSVSTESESSSFHSS | 294 |
| i4 | TSAQHALTSVSRGSSLKILSKGKRGGHSSVSTESESSSFHSS | 295 |
| i4 | SAQHALTSVSRGSSLKILSKGKRGGHSSVSTESESSSFHSS | 296 |
| i4 | AQHALTSVSRGSSLKILSKGKRGGHSSVSTESESSSFHSS | 297 |
| i4 | QHALTSVSRGSSLKILSKGKRGGHSSVSTESESSSFHSS | 298 |
| i4 | HALTS VSRGSSLKILSKGKRGGHSSVSTESESSSFHSS | 299 |
| i4 | ALTSVSRGSSLKILSKGKRGGHSSVSTESESSSFHSS | 300 |
| i4 | LTSVSRGSSLKILSKGKRGGHSSVSTESESSSFHSS | 301 |
| i4 | TSVSRGSSLKILSKGKRGGHSSVSTESESSSFHSS | 302 |
| i4 | SVSRGSSLKILSKGKRGGHSSVSTESESSSFHSS | 303 |
| i4 | VSRGSSLKILSKGKRGGHSSVSTESESSSFHSS | 304 |
| i4 | SRGSSLKILSKGKRGGHSSVSTESESSSFHSS | 305 |
| i4 | RGSSLKILSKGKRGGHSSVSTESESSSFHSS | 306 |
| i4 | GSSLKILSKGKRGGHSSVSTESESSSFHSS | 307 |
| i4 | SSLKILSKGKRGGHSSVSTESESSSFHSS | 308 |
| i4 | SLKILSKGKRGGHSSVSTESESSSFHSS | 309 |
| i4 | LKILSKGKRGGHSSVSTESESSSFHSS | 310 |
| i4 | KILSKGKRGGHSSVSTESESSSFHSS | 311 |
| i4 | ILSKGKRGGHSSVSTESESSSFHSS | 312 |

TABLE 5-continued

| CXCR4 i-Loop | Sequence | SEQ ID NO: |
|---|---|---|
| i4 | LSKGKRGGHSSVSTESESSSFHSS | 313 |
| i4 | SKGKRGGHSSVSTESESSSFHSS | 314 |
| i4 | KGKRGGHSSVSTESESSSFHSS | 315 |
| i4 | GKRGGHSSVSTESESSSFHSS | 316 |
| i4 | KRGGHSSVSTESESSSFHSS | 317 |
| i4 | RGGHSSVSTESESSSFHSS | 318 |
| i4 | GGHSSVSTESESSSFHSS | 320 |
| i4 | GHSSVSTESESSSFHSS | 321 |
| i4 | HSSVSTESESSSFHSS | 322 |
| i4 | SSVSTESESSSFHSS | 323 |
| i4 | SVSTESESSSFHSS | 324 |
| i4 | VSTESESSSFHSS | 325 |
| i4 | STESESSSFHSS | 326 |
| i4 | TESESSSFHSS | 327 |
| i4 | ESESSSFHSS | 328 |
| i4 | AKFKTSAQHA | 329 |
| i4 | KFKTSAQHAL | 330 |
| i4 | FKTSAQHALT | 331 |
| i4 | KTSAQHALTS | 332 |
| i4 | TSAQHALTSV | 333 |
| i4 | SAQHALTSVS | 334 |
| i4 | AQHALTSVSR | 335 |
| i4 | QHALTSVSRG | 336 |
| i4 | HALTSVSRGS | 337 |
| i4 | ALTSVSRGSS | 338 |
| i4 | LTSVSRGSSL | 339 |
| i4 | TSVSRGSSLK | 340 |
| i4 | SVSRGSSLKI | 341 |
| i4 | VSRGSSLKIL | 342 |
| i4 | SRGSSLKILS | 343 |
| i4 | RGSSLKILSK | 345 |
| i4 | GSSLKILSKG | 346 |
| i4 | SSLKILSKGK | 347 |
| i4 | SLKILSKGKR | 348 |
| i4 | LKILSKGKRG | 349 |
| i4 | KILSKGKRGG | 350 |
| i4 | ELSKGKRGGH | 351 |
| i4 | LSKGKRGGHS | 352 |

TABLE 5-continued

| CXCR4 i-Loop | Sequence | SEQ ID NO: |
|---|---|---|
| i4 | SKGKRGGHSS | 353 |
| i4 | KGKRGGHSSV | 354 |
| i4 | GKRGGHSSVS | 355 |
| i4 | KRGGHSSVST | 356 |
| i4 | RGGHSSVSTE | 357 |
| i4 | GGHSSVSTES | 358 |
| i4 | GHSSVSTESE | 359 |
| i4 | HSSVSTESES | 360 |
| i4 | SSVSTESESS | 361 |
| i4 | SVSTESESSS | 362 |
| i4 | VSTESESSSF | 363 |
| i4 | STESESSSFH | 364 |
| i4 | TESESSSFHS | 365 |
| i4 | ESESSSFHSS | 366 |
| i4 | GAKFKTSAQHALTSVSRGSSLKILSKGKRGGHSSVSTESESSSFHS | 367 |
| i4 | GAKFKTSAQHALTSVSRGSSLKILSKGKRGGHSCFH | 368 |

It is understood that the sequences presented in Tables 2-5 can be optionally functionalized at the C-terminus. Functionalized at the C-terminus means that the acid moiety present at the C-terminus is replaced by some other functional group. Suitable functional groups include —C(O)N($R_2$)$_2$, —C(O)O$R_3$, or C(O)NHC(O)O$R_2$, where $R_2$ is hydrogen or a an alkyl group, for example a ($C_1$-$C_{10}$) alkyl group and $R_3$ is an alkyl group, for example, a ($C_1$-$C_{10}$) alkyl group.

In another embodiment, the C-terminus of P has a lipophilic tether moiety. In certain embodiments, the lipophilic tether moiety is attached to a NH capped C-terminus of P.

It is understood that as long as P comprises the indicated number of contiguous amino acids residues from the CXCR4 intracellular loop (i1, i2 or i3) or domain (i4) from which it is derived, the remainder of the peptide, if present, can be selected from:

(a) any natural amino acid residue, unnatural amino acid residue or a combination thereof;

(b) a peptide sequence comprising natural amino acid residues, non-natural amino acid residues and combinations thereof;

(c) a peptide sequence according to (b) comprising one or more peptide backbone modifications;

(d) a peptide sequence according to (c) comprising one or more retro-inverso peptide linkages;

(e) a peptide sequence according to (c) wherein one or more peptide bonds are replaced by

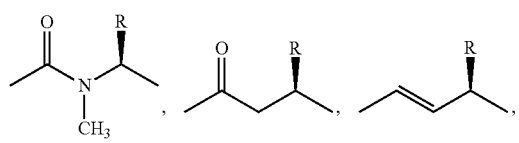

-continued

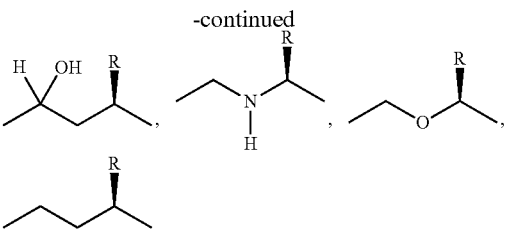

or a combination thereof;

(f) a peptide sequence according to (c) comprising one or more depsipeptide linkages, wherein the amide linkage is replaced with an ester linkage; and (g) a peptide sequence according to (c) comprising one or more conformational restrictions; and (h) a peptide sequence according to (c) comprising one or more of (d)-(g).

Furthermore, it is understood that even within the indicated number of contiguous amino acid residues derived from the GPCR intracellular loop (i1, i2 or i3) or domain (i4), there can be: peptide backbone modifications such as, but not limited to, those described in (e) above; retro-inverso peptide linkages; despsipeptide linkages; conformational restrictions; or a combination thereof.

It is noted that P of Formula I can optionally functionalized at the C-terminus. Functionalized at the C-terminus means that the acid moiety present at the C-terminus is replaced by some other functional group. Suitable functional groups include —C(O)N($R_2$)$_2$, —C(O)O$R_3$, or C(O)NHC(O)O$R_2$, where $R_2$ is hydrogen or an alkyl group, for example a ($C_1$-$C_{10}$) alkyl group and $R_3$ is an alkyl group, for example a ($C_1$-$C_{10}$) alkyl group. Functionalization of the C-terminus can result from the methods used to prepare.

Peptidomimetic as used herein refers to a compound comprising non-peptidic structural elements in place of a peptide sequence.

As used herein, the term "amino acid" includes both a naturally occurring amino acid and a non-natural amino acid.

As used herein, the term "naturally occurring amino acid" means a compound represented by the formula $NH_2$—CHR—COOH, wherein R is the side chain of a naturally occurring amino acids such as lysine, arginine, serine, tyrosine etc. as shown in the Table below.

| Table of Common Naturally Occurring Amino Acids | | | |
|---|---|---|---|
| | Amino acid | Three letter code | One letter code |
| Non-polar; neutral at pH 7.4 | alanine | Ala | A |
| | isoleucine | Ile | I |
| | leucine | Leu | L |
| | methionine | Met | M |
| | phenylalanine | Phe | F |
| | proline | Pro | P |
| | tryptophan | Trp | W |
| | valine | Val | V |
| Polar, uncharged at pH 7.0 | asparagine | Asn | N |
| | cysteine | Cys | C |
| | glycine | Gly | G |
| | glutamine | Gln | Q |
| | serine | Ser | S |
| | threonine | Thr | T |
| | tyrosine | Tyr | Y |
| Polar; charged at pH 7 | glutamic acid | Glu | E |
| | arginine | Arg | R |
| | aspartic acid | Asp | D |
| | histidine | His | H |
| | lysine | Lys | K |

"Non-natural amino acid" means an amino acid for which there is no nucleic acid codon. Examples of non-natural amino acids include, for example, the D-isomers of the natural α-amino acids such as D-proline (D-P, D-Pro) as indicated above; natural α-amino acids with non-natural side chains

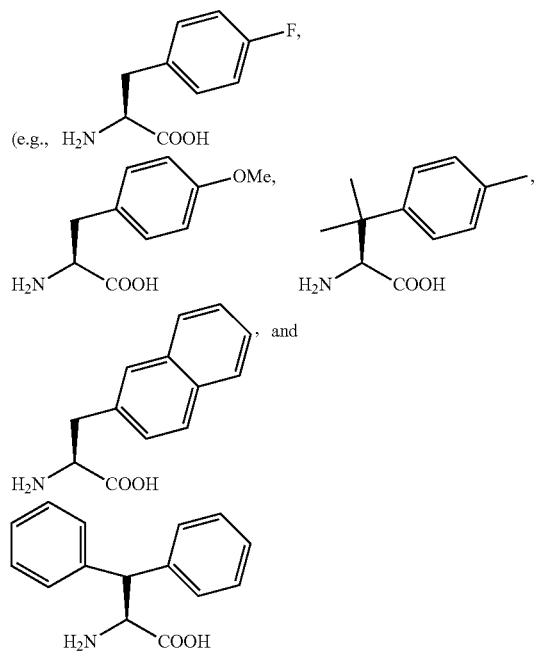

related to phenylalanine); Aib (aminobutyric acid), bAib (3-aminoisobutyric acid), Nva (norvaline), β-Ala, Aad (2-aminoadipic acid), bAad (3-aminoadipic acid), Abu (2-aminobutyric acid), Gaba (γ-aminobutyric acid), Acp (6-aminocaproic acid), Dbu (2,4-diaminobutryic acid), α-aminopimelic acid, TMSA (trimethylsilyl-Ala), aIle (allo-isoleucine), Nle (norleucine), tert-Leu, Cit (citrulline), Orn (ornithine, O), Dpm (2,2'-diaminopimelic acid), Dpr (2,3-diaminopropionic acid), α or β-Nal, Cha (cyclohexyl-Ala), hydroxyproline, Sar (sarcosine), and the like.

Unnatural amino acids also include cyclic amino acids; and amino acid analogs, for example, $N^\alpha$-alkylated amino acids such as MeGly ($N^\alpha$-methylglycine), EtGly ($N^\alpha$-ethylglycine) and EtAsn ($N^\alpha$-ethylasparagine); and amino acids in which the α-carbon bears two side-chain substituents. As with the natural amino acids, the residues of the unnatural amino acids are what are left behind when the unnatural amino acid becomes part of a peptide sequence as described herein.

Amino acid residues are amino acid structures as described above that lack a hydrogen atom of the amino group or the hydroxyl moiety of the carboxyl group or both resulting in the units of a peptide chain being amino-acid residues.

The D-isomers of the natural amino acids are designated herein with a lower case letter of the corresponding naturally occurring amino acid. For example, d-proline is designated "p" rather than "P" as is used for naturally occurring proline.

Tethers (T)

T of Formula I is a lipohilic tether moiety which imparts lipophilicity to the CXCR4 receptor compounds of the invention. The lipophilicity which T imparts, can promote penetration of the CXCR4 receptor compounds into the cell membrane and tethering of the CXCR4 receptor compounds to the cell membrane. As such, the lipophilicity imparted by T can facilitate interaction between the CXCR4 receptor compounds of the invention and the cognate receptor.

The relative lipophilicity of compounds suitable for use as the lipophilic tether moiety of Formula I can be quantified by measuring the amount of the compound that partitions into an organic solvent layer (membrane-like) vs. an aqueous solvent layer (analogous to the extracellular or cytoplasmic environment). The partition coefficient in a mixed solvent composition, such as octanol/water or octanol/PBS, is the ratio of compound found at equilibrium in the octanol vs. the aqueous solvent (Partition coeff P=[compound]$_{octanol}$/[compound]$_{aqueous}$). Frequently, the partition coefficient is expressed in logarithmic form, as the log P. Compounds with greater lipophilicity have a more positive log P than more hydrophilic compounds and tend to interact more strongly with membrane bilayers.

Computational programs are also available for calculating the partition coefficient for compounds suitable for use as the lipophilic tether moiety (T). In situations where the chemical structure is being varied in a systematic manner, for example by adding additional methylene units (—$CH_2$—) onto to an existing alkyl group, the trend in log P can be calculated using, for example, ChemDraw (CambridgeSoft, Inc).

In one embodiment, T is an optionally substituted ($C_6$-$C_{30}$) alkyl, ($C_6$-$C_{30}$)alkenyl, ($C_6$-$C_{30}$)alkynyl wherein 0-3 carbon atoms are replaced with oxygen, sulfur, nitrogen or a combination thereof.

In a specific embodiment, the ($C_6$-$C_{30}$)alkyl, ($C_6$-$C_{30}$)alkenyl, ($C_6$-$C_{30}$)alkynyl are substituted at one or more substitutable carbon atoms with halogen, —CN, —OH, —$NH_2$, $NO_2$, —NH($C_1$-$C_6$)alkyl, —N(($C_1$-$C_6$)alkyl)$_2$, ($C_1$-$C_6$)alkyl, ($C_1$-$C_6$)haloalkyl, ($C_1$-$C_6$)alkoxy, ($C_1$-$C_6$)haloalkoxy, aryloxy, ($C_1$-$C_6$)alkoxycarbonyl, —$CONH_2$, —$OCONH_2$, —$NHCONH_2$, —N($C_1$-$C_6$)alkylCONH$_2$, —N($C_1$-$C_6$)alkyl- CONH(C$_1$-C$_6$)alkyl, —NHCONH(C$_1$-C$_6$)alkyl, —NHCON((C$_1$-C$_6$)alkyl)$_2$, —N(C$_1$-C$_6$)alkylCON((C$_1$-C$_6$)alkyl)$_2$, —NHC(S)NH$_2$, —N(C$_1$-C$_6$)alkylC(S)NH$_2$, —N(C$_1$-C$_6$)alkylC(S)NH(C$_1$-C$_6$)alkyl, —NHC(S)NH(C$_1$-C$_6$)alkyl, —NHC(S)N((C$_1$-C$_6$)alkyl)$_2$, —N(C$_1$-C$_6$)alkylC(S)N((C$_1$-C$_6$)alkyl)$_2$, —CONH(C$_1$-C$_6$)alkyl, —OCONH(C$_1$-C$_6$)alkyl —CON((C$_1$-C$_6$)alkyl)$_2$, —C(S)(C$_1$-C$_6$)alkyl, —S(O)$_p$(C$_1$-C$_6$)alkyl, —S(O)$_p$NH$_2$, —S(O)$_p$NH(C$_1$-C$_6$)alkyl, —S(O)$_p$N((C$_1$-C$_6$)alkyl)$_2$, —CO(C$_1$-C$_6$)alkyl, —OCO(C$_1$-C$_6$)alkyl, —C(O)O(C$_1$-C$_6$)alkyl, —OC(O)O(C$_1$-C$_6$)alkyl, —C(O)H or —CO$_2$H; and p is 1 or 2.

In a specific embodiment, T is selected from the group consisting of: CH$_3$(CH$_2$)$_9$OPh-, CH$_3$(CH$_2$)$_6$C=C(CH$_2$)$_6$, CH$_3$(CH$_2$)$_{11}$O(CH$_2$)$_3$, CH$_3$(CH$_2$)$_9$O(CH$_2$)$_2$ and CH$_3$(CH$_2$)$_{13}$.

In a specific embodiment, T is selected from the group consisting of: CH$_3$(CH$_2$)$_{16}$, CH$_3$(CH$_2$)$_{15}$, CH$_3$(CH$_2$)$_{14}$, CH$_3$(CH$_2$)$_{13}$, CH$_3$(CH$_2$)$_{12}$, CH$_3$(CH$_2$)$_{11}$, CH$_3$(CH$_2$)$_{10}$, CH$_3$(CH$_2$)$_9$, CH$_3$(CH$_2$)$_8$, CH$_3$(CH$_2$)$_9$OPh-, CH$_3$(CH$_2$)$_6$C↑C(CH$_2$)$_6$, CH$_3$(CH$_2$)$_{11}$O(CH$_2$)$_3$, and CH$_3$(CH$_2$)$_9$O(CH$_2$)$_2$ and CH$_3$(CH$_2$)$_{13}$.

It is understood that the lipophilic moiety (T) of Formula I can be derived from precursor liphophilic compounds (e.g., fatty acids and bile acids). As used herein, "derived from" with regard to T, means that T is derived from a precursor lipophilic compound and that reaction of the precursor lipophilic compound in preparing the APJ receptor compounds of Formula I, results in a lipophilic tether moiety represented by T in Formula I that is structurally modified in comparison to the precursor lipophilic compound.

For example, the lipophilic tether moiety, T of Formula I, can be derived from a fatty acid or a bile acid. It is understood that in accordance with Formula I, when T is derived from a fatty acid (i.e., a fatty acid derivative) it is attached to L-P at the carbon atom alpha to the carbonyl carbon of the acid functional group in the fatty acid from which it is derived. For example, when T is derived from palmitic acid

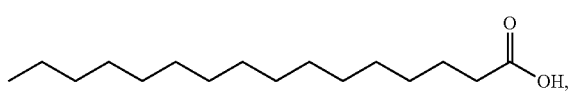 [SMILES: CCCCCCCCCCCCCCCC(=O)O]

T of Formula I has the following structure:

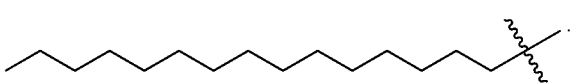 [SMILES: "." ; *CCCCCCCCCCCCCCC]

Similarly, when T is derived from stearic acid,

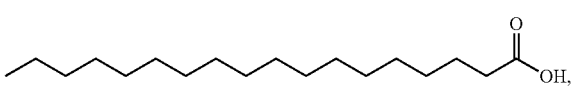

T of Formula I has the following structure:

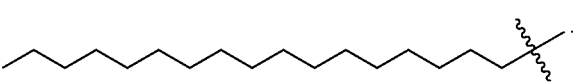 [SMILES: "." ; *CCCCCCCCCCCCCCCCC]

Similarly when T is derived from 3-(dodecyloxy)propanoic acid,

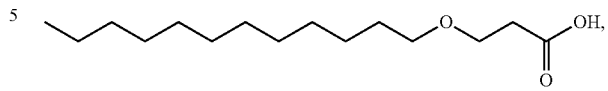

T of Formula I has the following structure:

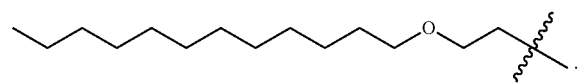 [SMILES: *CCOCCCCCCCCCCCC ; "."]

Similarly, when T is derived from 4-(undecyloxy)butanoic acid,

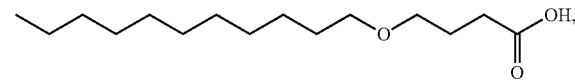 [SMILES: CCCCCCCCCCCOCCCC(=O)O]

T of Formula I has the following structure:

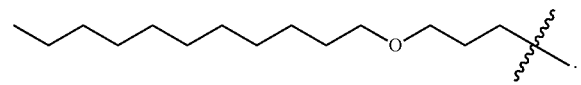 [SMILES: *CCCOCCCCCCCCCCC]

Similarly, when T is derived from elaidic acid,

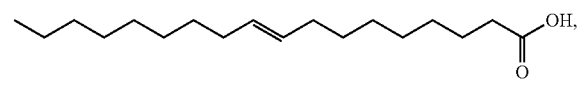 [SMILES: CCCCCCCC/C=C/CCCCCCCC(=O)O]

T of Formula I has the following structure:

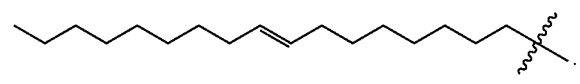 [SMILES: *CCCCCCC/C=C/CCCCCCCC]

Similarly, when T is derived from oleic acid,

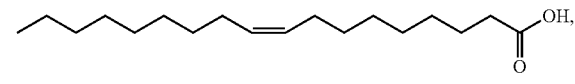 [SMILES: CCCCCCCC/C=C\CCCCCCCC(=O)O]

T of Formula I has the following structure:

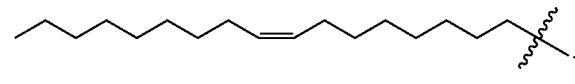 [SMILES: *CCCCCCC/C=C\CCCCCCCC]

Similarly, when T is derived from 16-hydroxypalmitic acid,

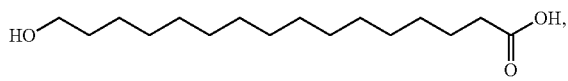 [SMILES: O=C(O)CCCCCCCCCCCCCCCO]

T of Formula I has the following structure:

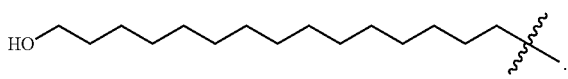 [SMILES: *CCCCCCCCCCCCCCCO]

Similarly, when T is derived from 2-aminooctadecanoic acid

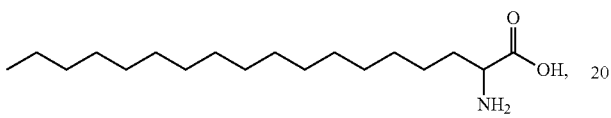

T of Formula I has the following structure:

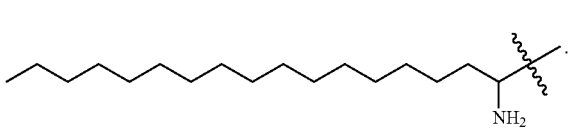 [SMILES: *C(N)CCCCCCCCCCCCCCCC]

Similarly, when T is derived from 2-amino-4-(dodecyloxy) butanoic acid

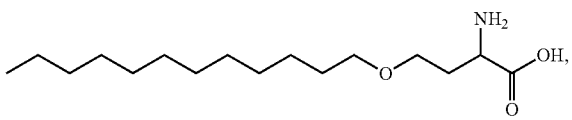 [SMILES: CCCCCCCCCCCCOCCC(N)C(=O)O]

T of Formula I has the following structure:

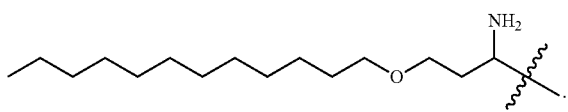 [SMILES: *C(N)CCOCCCCCCCCCCCC]

In a further embodiment, T is derived from a fatty acid. In a specific embodiment, T is derived from a fatty acid selected from the group consisting of: butyric acid, caproic acid, caprylic acid, capric acid, lauric acid, myristic acid, palmitic acid, stearic acid, arachidic acid, behenic acid, and lignoceric acid.

In another specific embodiment, T is derived from a fatty acid selected from the group consisting of: myristoleic acid, palmitoleic acid, oleic acid, linoleic acid, α-linolenic acid, arachidonic acid, eicosapentaenoic acid, erucic acid, docosahexaenoic acid.

In another embodiment, T of Formula I can be derived from a bile acid. Similar to the embodiment where T is a fatty acid derivative, it is understood that in accordance with Formula I, when T is derived from a bile acid (i.e., a bile acid derivative) it is attached to L-P at the carbon atom alpha to the carbonyl carbon of the acid functional group in the bile acid from which it is derived. For example, when T is derived from lithocholic acid,

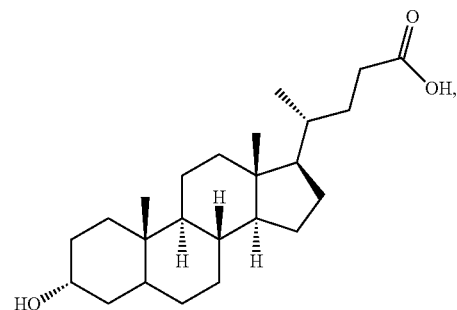

T of Formula I has the following structure:

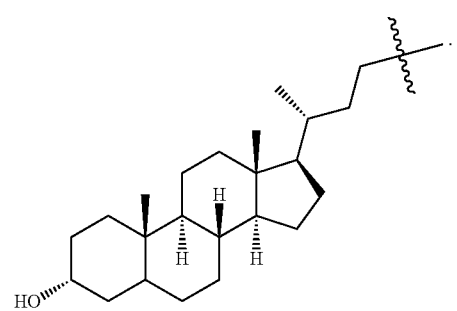

In a further embodiment, T is derived from a bile acid. In a specific embodiment, T is derived from a bile acid selected from the group consisting of: lithocholic acid, chenodeoxycholic acid, deoxycholic acid, cholanic acid, cholic acid, ursocholic acid, ursodeoxycholic acid, isoursodeoxycholic acid, lagodeoxycholic acid, dehydrocholic acid, hyocholic acid, hyodeoxycholic acid and the like.

For example, T is selected from:

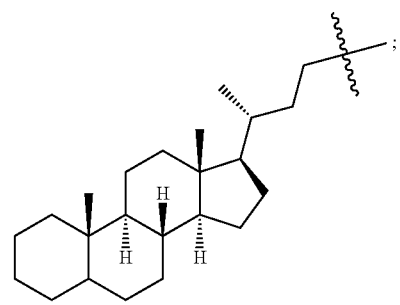

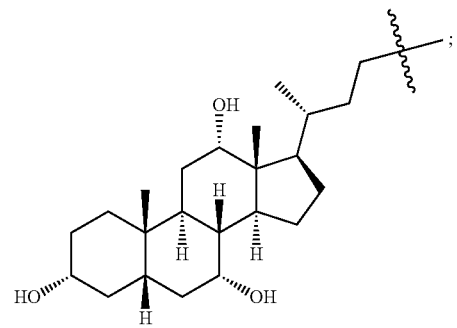

-continued

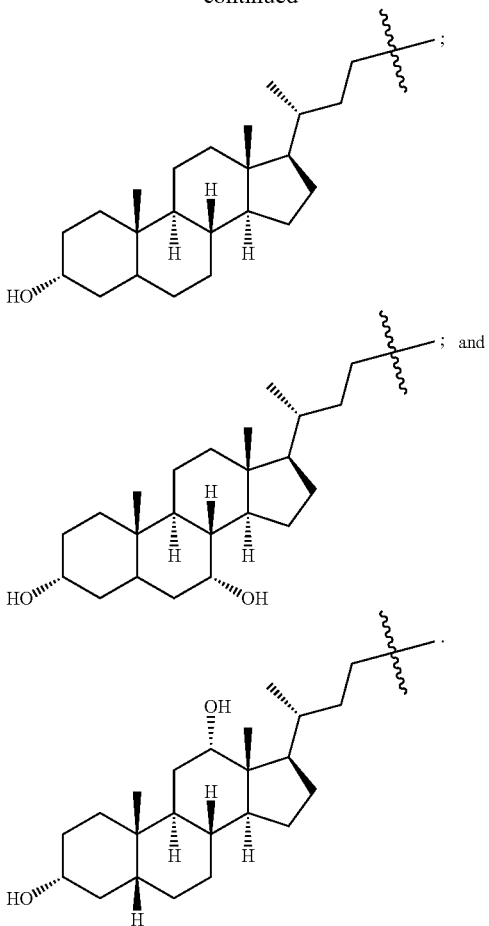

In another further embodiment, T is derived from a bile acid described above that has been modified at other than the acid functional group. For example, T can be derived from any of the bile acids described above, where the hydroxy position has been modified to form an ester or a halo ester. For example, T can be:

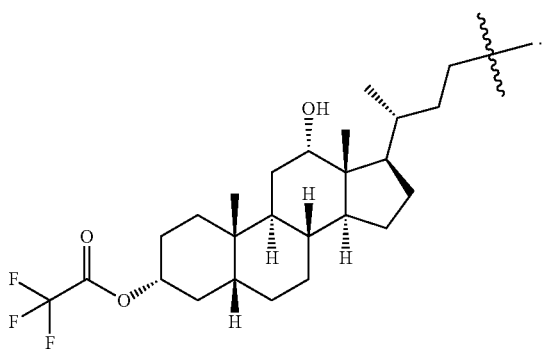

Other lipophilic moieties suitable for use as the lipophilic membrane tether, T, of Formula I, include but are not limited to steroids. Suitable steroids include, but are not limited to, sterols; progestagens; glucocorticoids; mineralcorticoids; androgens; and estrogens. Generally any steroid capable of attachment or which can be modified for incorporation into Formula I can be used. It is understood that the lipophilic membrane tether, T, may be slightly modified from the precursor lipophilic compound as a result of incorporation into Formula I.

Suitable sterols for use in the invention at T, include but are not limited to: cholestanol, coprostanol, cholesterol, epicholesterol, ergosterol, ergocalciferol, and the like. Preferred sterols are those that provide a balance of lipophilicity with water solubility.

Suitable progestagens include, but are not limited to progesterone. Suitable glucocorticoids include, but are not limited to cortisol. Suitable mineralcorticoids include, but are not limited to aldosterone. Suitable androgens include, but are not limited to testosterone and androstenedione. Suitable estrogens include, but are not limited to estrone and estradiol.

In another specific embodiment, T can be derived from 2-tetradecanamideooctadecanoid acid. Similar to the embodiment where T is a fatty acid derivative, it is understood that in accordance with Formula I, when T is derived from 2-tetradecanamideooctadecanoid acid it is attached to L-P at the carbon atom alpha to the carbonyl carbon of the acid functional group in the bile acid from which it is derived. For example, when T is derived from 2-tetradecanamideooctadecanoid acid, the tether is:

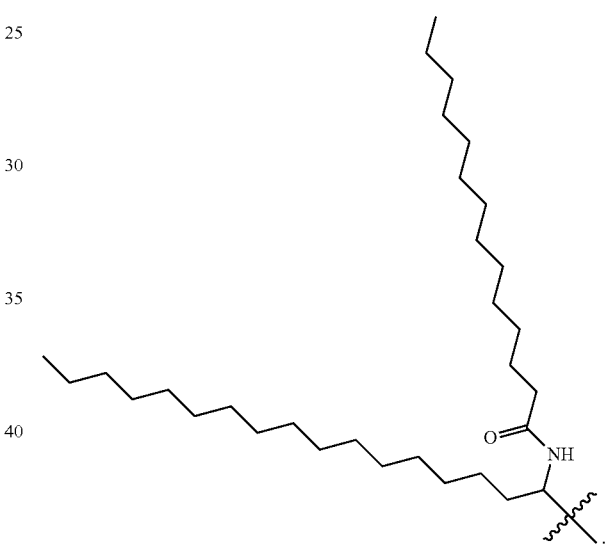

In another embodiment, T of Formula I can be derived from 2-(5-((3aS,4S,6aR)-2-oxohexahydro-1H-thieno[3,4-d]imidazol-4-yl)pentanamido)octadecanoic acid. For example, when T is derived from 2-(5-((3aS,4S,6aR)-2-oxohexahydro-1H-thieno[3,4-d]imidazol-4-yl)pentanamido)octadecanoic acid, the tether is:

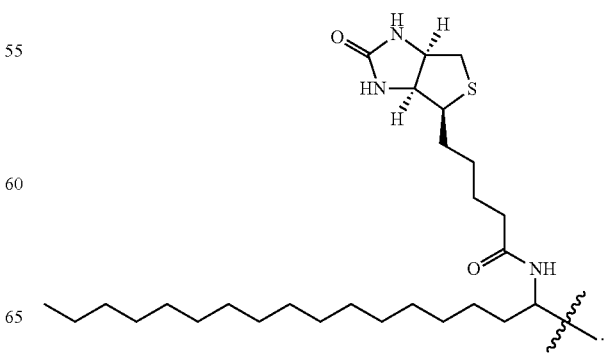

In yet another embodiment, T of Formula I can be:

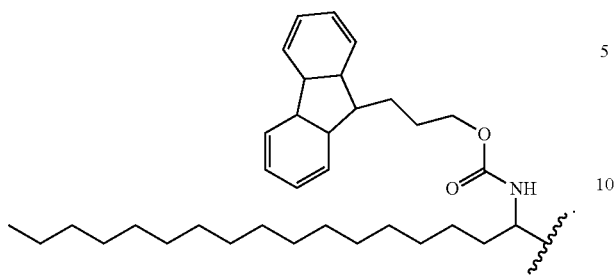

It is understood, that the compounds can contain one of more tether moieties. In certain aspects, the tether moieties are the same. In other embodiments, the tether moieties are different.

Compounds (T-L-P)

In a first aspect, the GPCR Compound of the invention is represented by Formula I:

T-L-P, or a pharmaceutically acceptable salt thereof, wherein:
P is a peptide comprising at least three contiguous amino-acid residues
of an intracellular i1, i2, i3 loop or an intracellular i4 domain of the CXCR4 receptor;
L is a linking moiety represented by C(O) and bonded to P at an N terminal nitrogen of an N-terminal amino-acid residue;
and T is a lipophilic tether moiety bonded to L, wherein the C-terminal amino acid residue of P is optionally functionalized.

In a second aspect, P comprises at least six contiguous amino acid residues.

In a third aspect, P comprises at least 3 contiguous amino acids of the i1 loop.

In a specific embodiment of the third aspect, the i1 loop of the CXCR4 receptor from which P is derived has the following sequence:

MGYQKKLRSMTDKYRLH. (SEQ ID NO: 370)

In another embodiment of the third aspect, P is a sequence selected from:

| CXCR4 i-Loop | Sequence | SEQ ID NO: |
|---|---|---|
| i1 | SGYQKKLRSSTD | 1 |
| i1 | MGYQKKLRSSTD | 2 |
| i1 | SGYQKKLRSMTD | 3 |
| i1 | JGYQKKLRSJTD | 4 |
| i1 | LGYQKKLRSLTD | 5 |
| i1 | IGYQKKLRSITD | 6 |
| i1 | JGYQKKLRSSTD | 7 |
| i1 | JGYQKKLRSMTD | 8 |
| i1 | LGYQKKLRSMTD | 9 |
| i1 | IGYQKKLRSMTD | 10 |
| i1 | AGYQKKLRSMTD | 11 |
| i1 | MAYQKKLRSMTD | 12 |
| i1 | MGAQKKLRSMTD | 13 |
| i1 | MGYAKKLRSMTD | 14 |
| i1 | MGYQKKLRAMTD | 15 |
| i1 | MGYQKKLRSATD | 16 |
| i1 | MGYQKKLRSMAD | 17 |
| i1 | MGYQKKLRSMTA | 18 |
| i1 | MGYQAKLRSMTD | 19 |
| i1 | MGYQKKLASMTD | 20 |
| i1 | MGYQKALRSMTD | 21 |
| i1 | MGYQKKARSMTD | 22 |
| i1 | mGYQKKLRSMTD | 23 |
| i1 | MGyQKKLRSMTD | 24 |
| i1 | MGYqKKLRSMTD | 25 |
| i1 | MGYQkKLRSMTD | 26 |
| i1 | MGYQKkLRSMTD | 27 |
| i1 | MGYQKKlRSMTD | 28 |
| i1 | MGYQKKLrSMTD | 29 |
| i1 | MGYQKKLRsMTD | 30 |
| i1 | MGYQKKLRSmTD | 31 |
| i1 | MGYQKKLRSMtD | 32 |
| i1 | MGYQKKLRSMTd | 33 |
| i1 | GSHYQKKLRSSTD | 34 |
| i1 | GSGYQKKLRSSTD | 35 |
| i1 | YQKKLRSSTD | 36 |
| i1 | GYQKKLRSJTD | 37 |
| i1 | GYQKKLRSLTD | 38 |
| i1 | GYQKKLRSMTDKYRLH | 39 |
| i1 | YQKKLRSMTDKYRLH | 40 |
| i1 | QKKLRSMTDKYRLH | 41 |
| i1 | KKLRSMTDKYRLH | 42 |
| i1 | KLRSMTDKYRLH | 43 |
| i1 | LRSMTDKYRLH | 44 |
| i1 | RSMTDKYRLH | 45 |
| i1 | SMTDKYRLH | 46 |
| i1 | MTDKYRLH | 47 |

-continued

| CXCR4 i-Loop | Sequence | SEQ ID NO: |
| --- | --- | --- |
| i1 | TDKYRLH | 48 |
| i1 | GYQKKLRSMTDKYRL | 49 |
| i1 | GYQKKLRSMTDKYR | 50 |
| i1 | GYQKKLRSMTDKY | 51 |
| i1 | GYQKKLRSMTDK | 52 |
| i1 | GYQKKLRSMTD | 53 |
| i1 | GYQKKLRSITD- | 54 |
| i1 | GYQKKLRSMT | 55 |
| i1 | GYQKKLRSM | 56 |
| i1 | GYQKKLRS | 57 |
| i1 | GYQKKLR | 58 |
| i1 | YQKKLRS | 59 |
| i1 | QKKLRSM | 60 |
| i1 | KKLRSMT | 61 |
| i1 | KLRSMTD | 62 |
| i1 | LRSMTDK | 63 |
| i1 | RSMTDKY | 64 |
| i1 | SMTDKYR | 65 |
| i1 | MTDKYRL | 66 |
| i1 | KRMKTSLYDGRMQYLK | 67 |
| i1 | sGYQKKLRSSTD | 68 |
| i1 | KKLRSMTDKY | 69 |
| i1 | KKLRSMTDKYR | 70 |
| i1 | KKLRSMTDKYRL | 71 |
| i1 | KKLRSXTDKYRLH (X = Norluceine (Nle)) | 72 |
| i1 | KKLRSMTDKYRLHL | 73 |
| i1 | KKLRSMTDKYRLHLSV | 74 |
| i1 | QKKLRSMTDKYRI | 75 |
| i1 | QKKLRSMTDKYRLHL | 76 |
| i1 | YQKKLRSMTDKYRLHLSV | 77 |
| i1 | LVMGYQKKLRSMTD | 78 |
| i1 | MGYQKKLRSMTDK | 79 |
| i1 | MGYQKKLRSMTDKY | 80 |
| i1 | MGYQKKLRSMTDKYRI | 81 |
| i1 | MGYQKKLRSMTDKYRL | 82 |
| i1 | MGYQKKLRSMTDKYRLHL | 83 |
| i1 | MGYQKKLRSMTDKYRLHLSV | 84 |
| i1 | YTKRLDSHRKLKM | 85 |
| i1 | VMGYQKKLRSMTD | 86 |
| i1 | KKLCRSMTDKCYRL | 87 |
| i1 | KKLRCSMTDCKYRL | 88 |
| i1 | kKLRSMTDKYRLH | 89 |
| i1 | KkLRSMTDKYRLH | 90 |
| i1 | KKIRSMTDKYRLH | 91 |
| i1 | KKLrSMTDKYRLH | 92 |
| i1 | KKLRsMTDKYRLH | 93 |
| i1 | KKLRSmTDKYRLH | 94 |
| i1 | AKLRSMTDKYRLH | 95 |
| i1 | KALRSMTDKYRLH | 96 |
| i1 | KKARSMTDKYRLH | 97 |
| i1 | KKLASMTDKYRLH | 98 |
| i1 | KKLRAMTDKYRLH | 99 |
| i1 | KKLRSATDKYRLH | 100 |
| i1 | AGYQKKLRSMTDKYRL | 101 |
| i1 | MAYQKKLRSMTDKYRL | 102 |
| i1 | MGAQKKLRSMTDKYRL | 103 |
| i1 | MGYAKKLRSMTDKYRL | 104 |
| i1 | MGYQAKLRSMTDKYRL | 105 |
| i1 | MGYQKALRSMTDKYRL | 106 |
| i1 | MGYQKKARSMTDKYRL | 107 |
| i1 | MGYQKKLASMTDKYRL | 108 |
| i1 | KKLRSMADKYRLH | 109 |
| i1 | KKLRSMTAKYRLH | 110 |
| i1 | KKLRSMTDAYRLH | 111 |
| i1 | KKLRSMTDKARLH | 112 |
| i1 | KKLRSMTDKYALH | 113 |
| i1 | KKLRSMTDKYRAH | 114 |
| i1 | KKLRSMTDKYRLA | 115 |
| i1 | MGYQKKLRAMTDKYRL | 116 |
| i1 | MGYQKKLRSATDKYRL | 117 |
| i1 | MGYQKKLRSMADKYRL | 118 |
| i1 | MGYQKKLRSMTAKYRL | 119 |
| i1 | MGYQKKLRSMTDAYRL | 120 |
| i1 | MGYQKKLRSMTDKARL | 121 |
| i1 | MGYQKKLRSMTDKYAL | 122 |

-continued

| CXCR4 i-Loop | Sequence | SEQ ID NO: |
|---|---|---|
| i1 | MGYQKKLRSMTDKYRA | 123 |
| i1 | KKLRSMtDKYRLH | 124 |
| i1 | KKLRSMTdKYRLH | 125 |
| i1 | KKLRSMTDKYrLH | 126 |
| i1 | KKLRSMTDKYRlH | 127 |
| i1 | KKLRSMTDKYRLh | 128 |
| i1 | MGYQKKLRSMTDKYrL | 129 |
| i1 | MGYQKKLRSMTDKyRL | 130 |
| i1 | MGYQKKLRSMTDkYRL | 131 |
| i1 | MGYQKKLRSMTdKYRL | 132 |
| i1 | MGYQKKLRSMtDKYRL | 133 |
| i1 | mGYQKKLRSMTDKYRL | 134 |
| i1 | MGyQKKLRSMTDKYRL | 135 |
| i1 | MGYqKKLRSMTDKYRL | 136 |
| i1 | MGYQkKLRSMTDKYRL | 137 |
| i1 | MGYQKkLRSMTDKYRL | 138 |
| i1 | MGYQKKpRSMTDKYRL | 139 |
| i1 | MGYQKKLrSMTDKYRL | 140 |
| i1 | MGYQKKLRsMTDKYRL | 141 |
| i1 | MGYQKKLRSmTDKYRL | 142 |
| i1 | KKLRSMTDKYRlS | 143 |
| i1 | MGYQKKLRSpTDKYRL | 144 |
| i1 | MGYQKKLRpMTDKYRL | 145 |
| i1 | MGYQKKLpSMTDKYRL | 146 |
| i1 | MGYQKKpRSMTDKYRL | 147 |
| i1 | MGYQKKLRSMPDKYRL | 148 |

It is understood that for the embodiments presented herein, that when the amino acid residues of P are represented by X, W, Y or Z that the C-terminal amino acid residue does not include the —OH of the amino acid and that the end group R1 that is bonded to the C-terminal residue includes —OH as well as other moieties defined herein.

In a more specific embodiment, the compounds is represented by Formula A:

$T\text{-}L\text{-}X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-}X_{15}\text{-}X_{16}\text{-}X_{17}\text{-}X_{18}\text{-}X_{19}\text{-}X_{20}\text{-}X_{21}\text{-}X_{22}\text{-}X_{23}\text{-}X_{24}\text{-}R_1$;

or a pharmaceutically acceptable salt thereof, wherein: L is a linking moiety represented by C(O) and bonded to the N terminal nitrogen of $X_1$ or the next present amino acid residue if $X_1$ is absent; T is a lipophilic tether moiety bonded to L; and $R_1$ is $OR_2$ or $N(R_2)_2$, each $R_2$ is independently H or alkyl, wherein at least three contiguous $X_1$-$X_{24}$ amino acid residues are present, and wherein:

$X_1$ is a valine residue or absent $X_2$ is a isoleucine residue or absent, $X_3$ is a leucine residue or absent, $X_4$ is a valine residue, a glycine residue or absent, $X_5$ is a methionine residue, a isoleucine residue, a leucine residue, a norleucine residue, a serine residue, an alanine residue, a d-methionine residue, a d-serine residue, or absent, $X_6$ is a glycine residue, an alanine residue, a histidine residue, a lysine residue or absent, $X_7$ is a tyrosine residue, an alanine residue, a d-tyrosine residue, an arginine residue or absent $X_8$ is a glutamine residue, an alanine residue, a d-glutamine residue, a methionine residue, a threonine residue, or a lysine residue or absent, $X_9$ is a lysine residue, a d-lysine residue, a alanine residue or absent, $X_{10}$ is a lysine residue, a d-lysine residue, a leucine residue, a threonine residue, an alanine residue or absent, $X_{11}$ is a leucine residue, a d-leucine residue, an alanine residue, an isoleucine residue, a serine residue, a cysteine residue, an arginine residue or absent, $X_{12}$ is an arginine residue, a d-arginine residue, an alanine residue, a leucine residue, an aspartic acid residue, a cysteine residue, or absent, $X_{13}$ is a serine residue, a d-serine residue, an alanine residue, a tyrosine residue or absent, $X_{14}$ is a methionine residue, a serine residue, a leucine residue, an isoleucine residue, a norleucine residue, an alanine residue, a d-methionine residue, an aspartic acid residue, or absent, $X_{15}$ is a threonine residue, a d-threonine residue, a arginine residue, a glycine residue, an alanine residue or absent, $X_{16}$ is an aspartic acid residue, and -aspartic acid residue, an alanine residue, an arginine residue, a lysine residue or absent, $X_{17}$ is a methionine residue, a lysine residue, a histidine residue, a leucine residue, a cysteine residue or absent, $X_{18}$ is a tyrosine residue, a glutamine residue, a leucine residue, a lysine residue, a cysteine residue or absent, $X_{19}$ is an arginine residue, a tyrosine residue, a serine residue, a methionine residue or absent, $X_{20}$ is a leucine residue, a isoleucine residue, an arginine residue, or a valine residue or absent, $X_{21}$ is a histidine residue, a lysine residue, a leucine residue or absent, $X_{22}$ is a leucine residue, a tyrosine residue or absent, $X_{23}$ is an arginine residue, a serine residue or absent, and $X_{24}$ is a valine residue, a leucine residue or absent;

wherein when $X_1$-$X_4$ and $X_{17}$-$X_{24}$ are absent and $X_5$ is a methionine residue, then at least one of the amino acids of $X_6$-$X_{16}$ is an alanine residue or a d-amino acid, and wherein when $X_1$-$X_6$ and $X_{17}$-$X_{24}$ are absent and $X_7$ is a tyrosine residue then at least one of the amino acids of $X_8$-$X_{16}$ is an alanine residue, d-amino acid or a serine residue.

In another aspect, the compound is represented wherein, $X_1$-$X_4$ and $X_{17}$-$X_{24}$ are absent and wherein:

$X_5$ is a methionine residue, a d-methionine residue, an isoleucine residue, a leucine residue, a serine residue, an alanine residue, or d-a methionine residue, $X_6$ is a glycine residue or an alanine residue, $X_7$ is a tyrosine residue, an alanine residue, or a d-tyrosine residue, $X_8$ is a glutamine residue, an alanine residue or a d-glutamine residue, $X_9$ is a lysine residue, a d-lysine residue, or an alanine residue, $X_{10}$ is a lysine residue, a d-lysine residue, or an alanine residue, $X_{11}$ is a leucine residue, a d-leucine residue, or an alanine residue, $X_{12}$ is an arginine residue, a d-arginine residue, or an alanine residue, $X_{13}$ is a serine residue, a d-serine residue, or an alanine residue, $X_{14}$ is a methionine residue, a serine residue, a leucine residue, an isoleucine residue, an alanine residue, or a d-methionine residue, $X_{15}$ is a threonine residue, a d-threonine residue, or an alanine residue, and $X_{16}$ is aspartic acid residue, a d-aspartic acid residue, or an alanine residue, or an arginine residue.

In yet another aspect, when $X_1$-$X_4$ and $X_{21}$-$X_{24}$ are absent, and wherein:

$X_5$ is a methionine residue, a d-methionine residue an alanine residue or a glycine residue, $X_6$ is a glycine residue or an alanine residue, $X_7$ is a tyrosine residue, a d-tyrosine residue, or an alanine residue, $X_8$ is a glutamine residue, d-glutamine residue, or an alanine residue, $X_9$ is a lysine residue, a d-lysine residue or an alanine residue, $X_{10}$ is a lysine residue, a d-lysine residue or an alanine residue, $X_{11}$ is a leucine residue, a d-leucine residue, an alanine residue, a proline residue or a d-proline residue, $X_{12}$ is an arginine residue, a d-arginine residue, an alanine residue, a proline residue or d-proline residue, $X_{13}$ is a serine residue, a d-serine residue, an alanine residue, a proline residue or a d-proline residue, $X_{14}$ is a methionine residue, an alanine residue, a d-methionine residue, a d-proline residue, a glycine residue, a histidine residue, or noreleucine residue $X_{15}$ is a threonine residue, a d-threonine residue, a d-proline residue, a proline residue or an alanine residue, $X_{16}$ is an aspartic acid residue, a d-aspartic acid residue, or an alanine residue, $X_{17}$ is a lysine residue, a d-lysine residue or an alanine residue, $X_{18}$ is a tyrosine residue, a d-tyrosine residue, or an alanine residue, $X_{19}$ is an arginine residue, a lysine residue, or a d-arginine residue, and $X_{20}$ is a leucine residue, a d-leucine residue, an alanine residue, a noreleucine residue, an isoleucine residue or a valine residue.

In another aspect, when $X_1$-$X_8$ are absent, and wherein:

$X_9$ is a lysine residue, a d-lysine residue or an alanine residue, $X_{10}$ is a lysine residue, a d-lysine residue or an alanine residue, $X_{11}$ is a leucine residue, a d-leucine residue or an alanine residue, $X_{12}$ is an arginine residue, a d-arginine residue or an alanine residue, $X_{13}$ is a serine residue, a d-serine residue or an alanine residue, $X_{14}$ is a methionine residue, a d-methionine residue, a norleucine residue or an alanine residue, $X_{15}$ is a threonine residue, a d-threonine residue, or an alanine residue, $X_{16}$ is an aspartic acid residue, a d-aspartic acid residue, or an alanine residue, $X_{17}$ is a lysine residue, a d-lysine residue or an alanine residue, $X_{18}$ is a tyrosine residue, a d-tyrosine residue, an alanine residue or absent, $X_{19}$ is an arginine residue, a d-arginine, an alanine residue or absent, $X_{20}$ is leucine residue, a d-leucine, an alanine or absent, $X_{21}$ is a histidine residue, a d-histidine residue, a d-serine residue, an alanine residue or absent, $X_{22}$ is leucine residue, isoleucine residue or absent, $X_{23}$ is a serine residue or absent, and $X_{24}$ is a valine residue or absent. In another embodiment, $X_{22}$, $X_{23}$ and $X_{24}$ are absent.

In yet another specific aspect, $X_1$-$X_5$ and $X_{22}$-$X_{24}$ are absent, and wherein:

$X_6$ is a glycine residue or absent, $X_7$ is a tyrosine residue or absent, $X_8$ is a glutamine residue or absent, $X_9$ is a lysine residue or absent, $X_{10}$ is a lysine residue or absent, $X_{11}$ is a leucine residue or absent, $X_{12}$ is an arginine residue or absent, $X_{13}$ is a serine residue or absent, $X_{14}$ is a methionine residue or absent, $X_{15}$ is a threonine residue, $X_{16}$ is an aspartic acid residue, $X_{17}$ is a lysine residue, $X_{18}$ is a tyrosine residue, $X_{19}$ is an arginine residue, $X_{20}$ is a leucine residue, and $X_{21}$ is a histidine residue.

In another specific aspect, $X_1$-$X_5$ and $X_{22}$-$X_{24}$ are absent, and wherein:

$X_6$ is a glycine residue, $X_7$ is a tyrosine residue, $X_8$ is a glutamine residue, $X_9$ is a lysine residue, $X_{10}$ is a lysine residue, $X_{11}$ is a leucine residue, $X_{12}$ is an arginine residue, $X_{13}$ is a serine residue or absent, $X_{14}$ is a methionine residue or absent, $X_{15}$ is threonine residue or absent, $X_{16}$ is an aspartic acid residue or absent, $X_{17}$ is a lysine residue or absent, $X_{18}$ is a tyrosine residue or absent, $X_{19}$ is an arginine residue or absent, $X_{20}$ is a leucine residue or absent, and $X_{21}$ is a histidine residue or absent.

In another embodiment, compounds wherein $X_1$-$X_5$ and $X_{21}$-$X_{24}$ are absent, wherein at least seven contiguous amino acid residues are present, and wherein:

$X_6$ is a glycine residue or absent, $X_7$ is a tyrosine residue or absent, $X_8$ is a glutamine residue or absent, $X_9$ is a lysine residue or absent, $X_{10}$ is a lysine residue or absent, $X_{11}$ is a leucine residue or absent, $X_{12}$ is a an arginine residue or absent, $X_{13}$ is a serine residue or absent, $X_{14}$ is a methionine residue or absent $X_{15}$ is a threonine residue or absent, $X_{16}$ is an aspartic acid residue or absent, $X_{17}$ is a lysine residue or absent, $X_{18}$ is a tyrosine residue or absent, $X_{19}$ is an arginine residue or absent, and $X_{20}$ is a leucine residue or absent.

In a further embodiment,
X$_3$ is a leucine residue or absent,
X$_4$ is a glycine residue or absent,
X$_5$ is a serine residue, a d-serine residue or absent,
X$_6$ is a glycine residue, a histidine residue, a lysine residue or absent,
X$_7$ is a tyrosine residue or an arginine residue,
X$_8$ is a glutamine residue, or a methionine residue,
X$_9$ is a lysine residue,
X$_{10}$ is a lysine residue or a threonine residue,
X$_{11}$ is a leucine residue or a serine residue,
X$_{12}$ is an arginine residue, or a leucine residue,
X$_{13}$ is a serine residue, or a tyrosine residue,
X$_{14}$ is a serine residue, a leucine residue, an isoleucine residue, or an aspartic acid residue,
X$_{15}$ is a threonine residue or a glycine residue,
X$_{16}$ is an aspartic acid residue or an arginine residue,
X$_{17}$ is a methionine residue or absent,
X$_{18}$ is a glutamine residue or absent,
X$_{19}$ is, a tyrosine residue or absent,
X$_{20}$ is a leucine residue, a isoleucine residue, an arginine residue, a valine residue or absent,
X$_{21}$ is a histidine residue, a lysine residue, or absent,
X$_{22}$ is a leucine residue or absent,
X$_{23}$ is a serine residue or absent, and
X$_{24}$ is a valine residue or absent.

In a more specific embodiment, the compounds are selected from any one of Compound Nos. 1-73 and 117-194 or a pharmaceutically acceptable salt thereof. For example, the compound is selected from any one of Compounds Nos. 1-73 or a pharmaceutically acceptable salt thereof. In another example the compound is selected from any one of Compound Nos. 117-194 or a pharmaceutically acceptable salt thereof.

In a more specific embodiment, the compound is selected from:

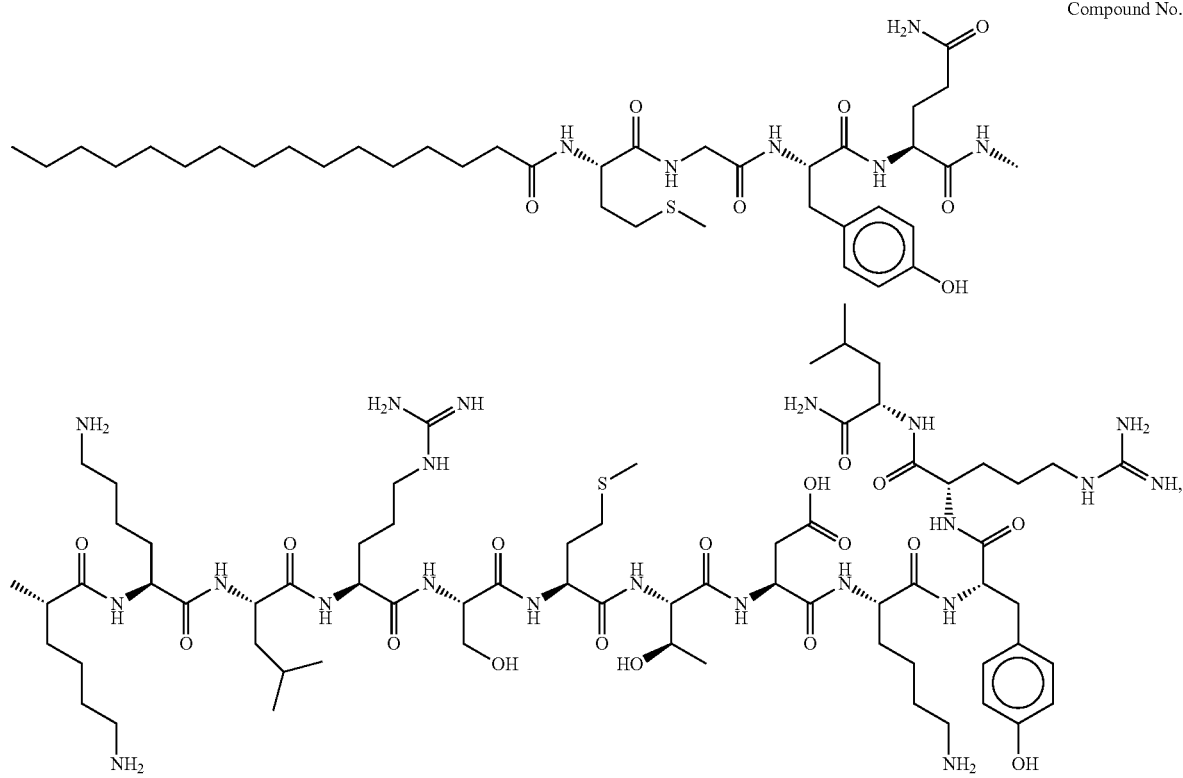

Compound No. 38

Compound No. 43

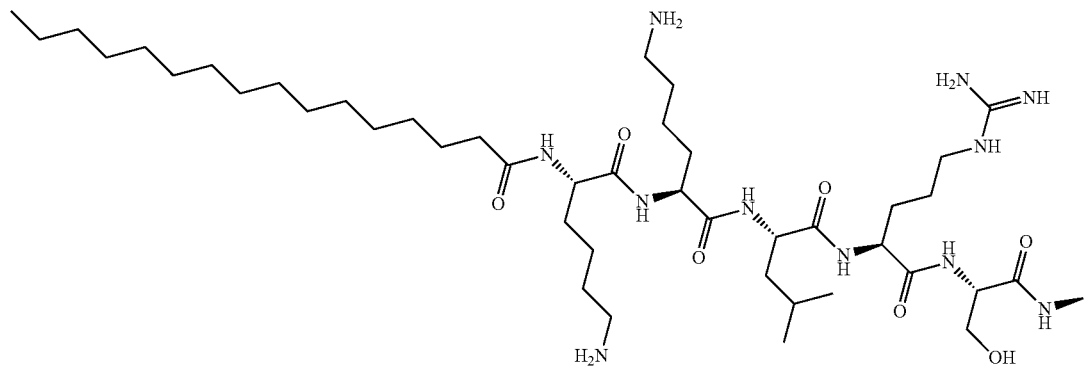

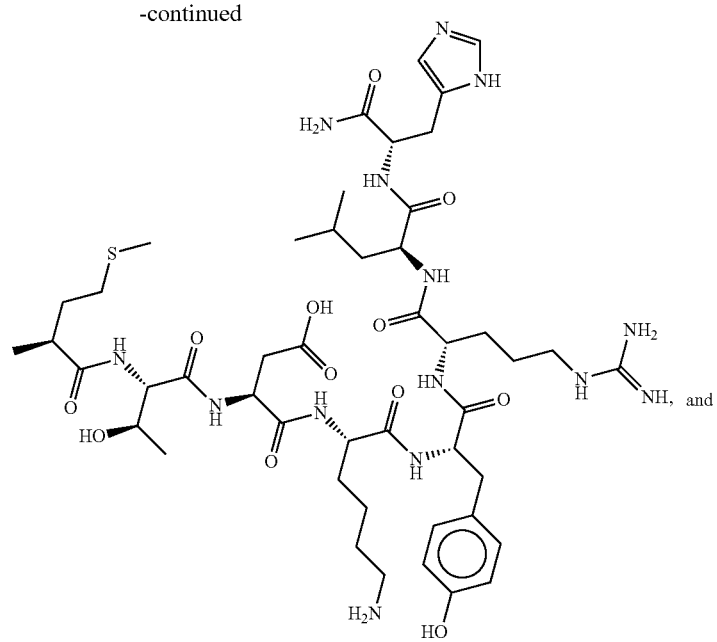
Compound No. 44
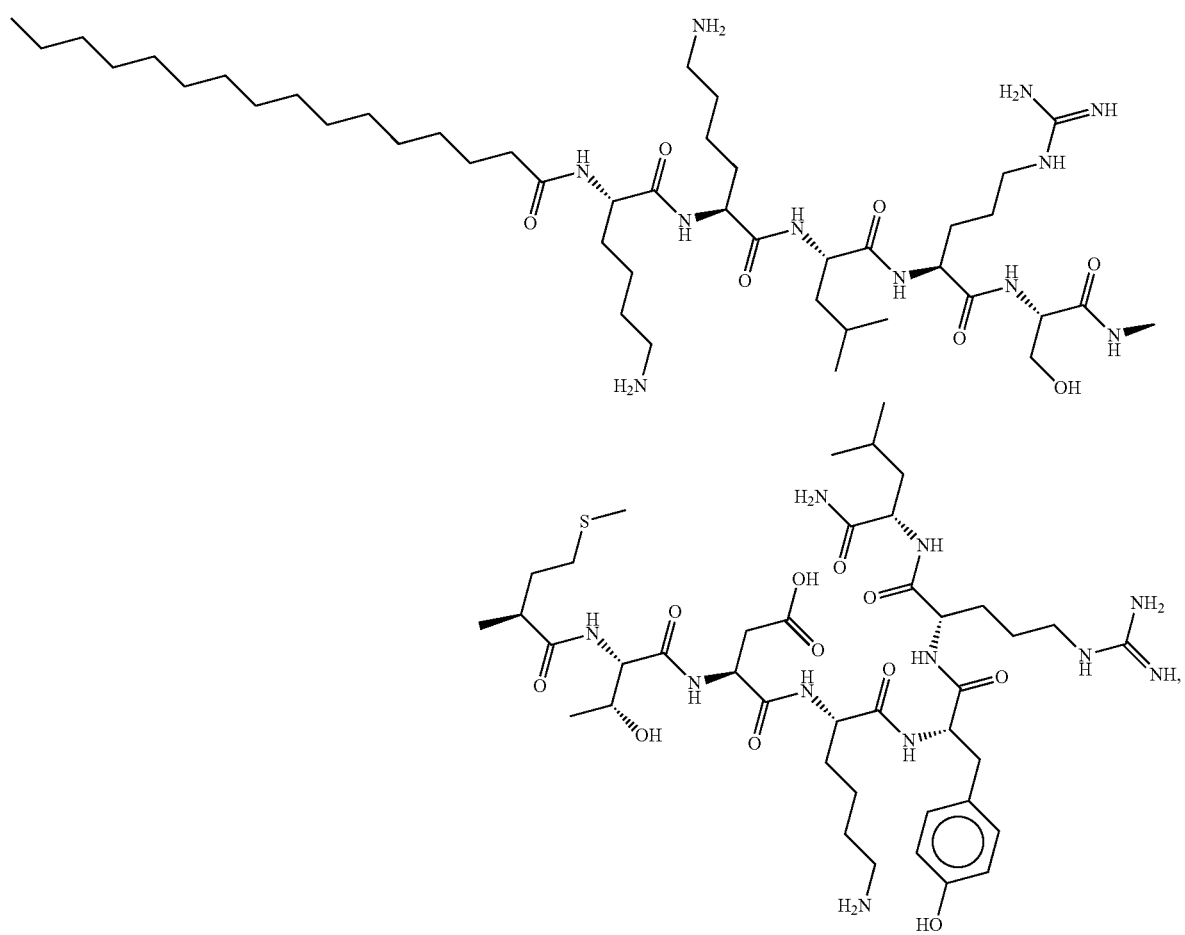
or a pharmaceutically acceptable salt thereof.
In a fourth aspect, P comprises at least 3 contiguous amino acids of the i2 loop.

In a specific embodiment of the fourth aspect, the i2 loop of the CXCR4 receptor from which P is derived has the following sequence:

(SEQ ID NO: 371)
DRYLAIVHATNSQRPRKLLAEK.

In another embodiment of the fourth aspect, P is a sequence selected from SEQ ID NOS:149-199:

| CXCR4 i-Loop | Sequence | SEQ ID NO: |
|---|---|---|
| i2 | DRYLAIVHATNSQRPRKLLAEK | 149 |
| i2 | DRYLAIVHATNSQRPRKLLAE | 150 |
| i2 | DRYLAIVHATNSQRPRKLLA | 151 |
| i2 | DRYLAIVHATNSQRPRKLL | 152 |
| i2 | DRYLAIVHATNSQRPRKL | 153 |
| i2 | DRYLAIVHATNSQRPRK | 154 |
| i2 | DRYLAIVHATNSQRPR | 155 |
| i2 | DRYLAIVHATNSQRP | 156 |
| i2 | DRYLAIVHATNSQR | 157 |
| i2 | DRYLAIVHATNSQ | 158 |
| i2 | DRYLAIVHATNS | 159 |
| i2 | DRYLAIVHATN | 160 |
| i2 | DRYLAIVHAT | 161 |
| i2 | DRYLAIVHA | 162 |
| i2 | DRYLAIVH | 163 |
| i2 | DRYLAIV | 164 |
| i2 | RYLAIVHATNSQRPRKLLAEK | 165 |
| i2 | YLAIVHATNSQRPRKLLAEK | 166 |
| i2 | LAIVHATNSQRPRKLLAEK | 167 |
| i2 | AIVHATNSQRPRKLLAEK | 168 |
| i2 | IVHATNSQRPRKLLAEK | 169 |
| i2 | VHATNSQRPRKLLAEK | 170 |
| i2 | HATNSQRPRKLLAEK- | 171 |
| i2 | ATNSQRPRKLLAEK | 172 |
| i2 | TNSQRPRKLLAEK | 173 |
| i2 | NSQRPRKLLAEK | 174 |
| i2 | SQRPRKLLAEK | 175 |
| i2 | QRPRKLLAEK | 176 |
| i2 | RPRKLLAEK | 177 |
| i2 | PRKLLAEK | 178 |
| i2 | RKLLAEK | 179 |
| i2 | RYLAIVH- | 180 |
| i2 | YLAIVHA | 181 |

-continued

| CXCR4 i-Loop | Sequence | SEQ ID NO: |
|---|---|---|
| i2 | LAIVHAT | 182 |
| i2 | AIVHATN- | 183 |
| i2 | IVHATNS- | 184 |
| i2 | VHATNSQ | 185 |
| i2 | HATNSQR | 186 |
| i2 | ATNSQRP | 187 |
| i2 | TNSQRPR- | 188 |
| i2 | NSQRPRK | 189 |
| i2 | SQRPRKL | 190 |
| i2 | QRPRKLL | 191 |
| i2 | RPRKLLA | 192 |
| i2 | PRKLLAE | 193 |
| i2 | VHATNSQRPRKLLAEKVVY | 194 |
| i2 | VHATNSQRPRKLLA | 195 |
| i2 | HATNSQRPRKL | 196 |
| i2 | HATNSQRPRKLLA | 197 |
| i2 | HATNSQRPRKLLAE | 198 |
| i2 | HATNSQRPRKLLAEKV | 199 |

In a more specific embodiment, a compound of the invention is represented by Formula B or a pharmaceutically acceptable salt thereof: wherein $$T\text{-}L\text{-}Y_1\text{-}Y_2\text{-}Y_3\text{-}Y_4\text{-}Y_5\text{-}Y_6\text{-}Y_7\text{-}Y_8\text{-}Y_9\text{-}Y_{10}\text{-}Y_{11}\text{-}Y_{12}\text{-}Y_{13}\text{-}Y_{14}\text{-}Y_{15}\text{-}Y_{16}\text{-}Y_{17}\text{-}Y_{18}\text{-}Y_{19}\text{-}Y_{20}\text{-}Y_{21}\text{-}Y_{22}\text{-}Y_{23}\text{-}Y_{24}\text{-}Y_{25}\text{-}R_1,$$

wherein L is a linking moiety represented by C(O) and bonded to the N terminal nitrogen of $Y_1$ or the next present amino acid residue if $Y_1$ is absent; T is a lipophilic tether moiety bonded to L; and $R_1$ is $OR_2$ or $N(R_2)_2$, each $R_2$ is independently H or alkyl, wherein at least three contiguous $Y_1$-$Y_{25}$ amino acid residues are present and wherein at least one of $Y_1$-$Y_{22}$ is absent, a d-amino acid residue or an alanine residue, and wherein:

$Y_1$ is an aspartic acid residue, a d-aspartic acid residue, an alanine residue or absent, $Y_2$ is an arginine residue, a d-arginine residue, an alanine residue or absent, $Y_3$ is a tyrosine residue, a d-tyrosine residue, an alanine residue or absent, $Y_4$ is a leucine residue, a d-leucine residue, an alanine residue or absent, $Y_5$ is an alanine residue, a d-alanine residue or absent, $Y_6$ is an isoleucine residue, a d-isoleucine residue, an alanine residue or absent, $Y_7$ is a valine residue, a d-valine acid residue, an alanine residue or absent, $Y_8$ is a histidine residue a d-histidine residue, an alanine residue or absent, $Y_9$ is an alanine residue, a d-alanine residue or absent, $Y_{10}$ is a threonine residue, a d-threonine residue, an alanine residue or absent, $Y_{11}$ is an asparagine residue, a d-asparagine residue, an alanine residue or absent,
$Y_{12}$ is a serine residue, a d-serine residue, an alanine residue or absent,
$Y_{13}$ is a glutamine residue, a d-glutamine residue, an alanine residue or absent,
$Y_{14}$ is an arginine residue, a d-arginine residue, an alanine residue or absent,
$Y_{15}$ is a proline residue, a d-proline residue, an alanine residue or absent,
$Y_{16}$ is an arginine residue, a d-arginine residue, an alanine residue or absent,
$Y_{17}$ is a lysine residue, a d-lysine residue, an alanine residue or absent,
$Y_{18}$ is a leucine residue, a d-leucine residue, an alanine residue or absent,
$Y_{19}$ is a leucine residue, a d-leucine residue, an alanine residue or absent,
$Y_{20}$ is an alanine residue, a d-alanine, an isoleucine residue, a d-isoleucine residue, an arginine residue, a d-arginine residue, a valine residue, a d-valine or absent,
$Y_{21}$ is a glutamic acid residue, a d-glutamic acid residue, an alanine residue, a d-alanine residue or absent,
$Y_{22}$ is a lysine residue, a d-lysine residue, an alanine residue or absent,
$Y_{23}$ is a valine residue, a d-valine residue or absent,
$Y_{24}$ is a valine residue, a d-valine residue or absent, and
$Y_{25}$ is a tyrosine residue, a d-tyrosine residue or absent.

In another embodiment of Formula B, the compound is represented by wherein $Y_{23}$-$Y_{25}$ are absent, and wherein:
$Y_1$ is an aspartic acid residue,
$Y_2$ is an arginine residue,
$Y_3$ is a tyrosine residue,
$Y_4$ is a leucine residue,
$Y_5$ is an alanine,
$Y_6$ is an isoleucine residue,
$Y_7$ is a valine residue,
$Y_8$ is a histidine residue,
$Y_9$ is an alanine or absent,
$Y_{10}$ is a threonine or absent,
$Y_{11}$ is an asparagine or absent,
$Y_{12}$ is a serine residue or absent,
$Y_{13}$ is a glutamine residue or absent,
$Y_{14}$ is an arginine residue or absent,
$Y_{15}$ is a proline residue or absent,
$Y_{16}$ is an arginine residue or absent,
$Y_{17}$ is a lysine residue or absent,
$Y_{18}$ is a leucine residue,
$Y_{19}$ is a leucine residue,
$Y_{20}$ is an alanine residue or absent,
$Y_{21}$ is a glutamic acid residue or absent, and
$Y_{22}$ is a lysine residue or absent.

In yet another aspect, the compound of Formula B comprises, when $Y_1$ and $Y_{23}$-$Y_{25}$ are absent, and wherein:
$Y_2$ is an arginine residue or absent,
$Y_3$ is a tyrosine residue or absent,
$Y_4$ is a leucine residue or absent,
$Y_5$ is an alanine residue or absent,
$Y_6$ is an isoleucine residue or absent,
$Y_7$ is a valine residue or absent,
$Y_8$ is a histidine residue or absent,
$Y_9$ is an alanine or absent,
$Y_{10}$ is a threonine or absent,
$Y_{11}$ is an asparagine or absent,
$Y_{12}$ is a serine residue or absent,
$Y_{13}$ is a glutamine residue or absent,
$Y_{14}$ is an arginine residue or absent,
$Y_{15}$ is a proline residue or absent,
$Y_{16}$ is an arginine residue or absent,
$Y_{17}$ is a lysine residue,
$Y_{18}$ is a leucine residue,
$Y_{19}$ is a leucine residue,
$Y_{20}$ is an alanine residue,
$Y_{21}$ is a glutamic acid residue, and
$Y_{22}$ is a lysine residue.

In another specific embodiment of a compound represented by Formula B, comprises when $Y_{23}$-$Y_{25}$ are absent and wherein seven contiguous $Y_1$-$Y_{22}$ amino acid residues are present, and wherein,
$Y_1$ is an aspartic acid residue or absent,
$Y_2$ is an arginine residue or absent,
$Y_3$ is a tyrosine residue or absent,
$Y_4$ is a leucine residue or absent,
$Y_5$ is an alanine residue or absent,
$Y_6$ is an isoleucine residue or absent,
$Y_7$ is a valine residue or absent,
$Y_8$ is a histidine residue or absent,
$Y_9$ is an alanine residue or absent,
$Y_{10}$ is a threonine residue or absent,
$Y_{11}$ is an asparagine residue or absent,
$Y_{12}$ is a serine residue or absent,
$Y_{13}$ is a glutamine residue or absent,
$Y_{14}$ is an arginine residue or absent;
$Y_{15}$ is a proline residue or absent,
$Y_{16}$ is an arginine residue or absent,
$Y_{17}$ is a lysine residue or absent,
$Y_{18}$ is a isoleucine residue or absent,
$Y_{19}$ is a leucine residue or absent,
$Y_{20}$ is an alanine residue or absent,
$Y_{21}$ is a glutamic acid residue or absent, and
$Y_{22}$ is a lysine residue or absent.

In a more specific embodiment of a compound represented by Formula B, when $Y_1$-$Y_6$ are absent and wherein:
$Y_7$ is a valine residue or absent,
$Y_8$ is a histidine residue,
$Y_9$ is a alanine residue,
$Y_{10}$ is a threonine residue,
$Y_{11}$ is an asparagine residue,
$Y_{12}$ is a serine residue,
$Y_{13}$ is a glutamine residue,
$Y_{14}$ is an arginine residue,
$Y_{15}$ is a proline residue,
$Y_{16}$ is an arginine residue,
$Y_{17}$ is a lysine residue,
$Y_{18}$ is a leucine residue,
$Y_{19}$ is a leucine residue or absent,
$Y_{20}$ is an alanine residue or absent,
$Y_{21}$ is a glutamic acid or absent,
$Y_{22}$ is a lysine residue or absent,
$Y_{23}$ is a valine lysine residue or absent,
$Y_{24}$ is a valine residue or absent, and
$Y_{25}$ is a tyrosine residue or absent.

In a more specific embodiment of Formula B, the CXCR4 compound is selected from any one of the Compound Nos. 74-83 or a pharmaceutically acceptable salt thereof.

In a fifth aspect, P comprises at least 3 contiguous amino acids of the i3 loop.

In a specific embodiment of the fifth aspect, the i3 loop of the CXCR4 receptor from which P is derived has the following sequence:

IIISKLSHSKGHQKRKALKTTVI. (SEQ ID NO: 372)

In another embodiment of the fifth aspect, P is a sequence selected from:

| CXCR4 i-Loop | Sequence | SEQ ID: |
|---|---|---|
| i3 | HSKKGHQKRKALK | 200 |
| i3 | JGYQKKLRSJTD | 201 |
| i3 | IIISKLSHSKGHQKRKALKT | 202 |
| i3 | IIISKLSHSKGHQKRKALK | 203 |
| i3 | IIISKLSHSKGHQKRKAL | 204 |
| i3 | IIISKLSHSKGHQKRKA | 205 |
| i3 | IIISKLSHSKGHQKRK | 206 |
| i3 | IIISKLSHSKGHQKR | 207 |
| i3 | IIISKLSHSKGHQK | 208 |
| i3 | IIISKLSHSKGHQ | 209 |
| i3 | IIISKLSHSKGH | 210 |
| i3 | IIISKLSHSKG | 211 |
| i3 | IIISKLSHSK | 212 |
| i3 | IIISKLSHS | 213 |
| i3 | IIISKLSH | 214 |
| i3 | IIISKLS | 215 |
| i3 | IISKLSHSKGHQKRKALKT | 216 |
| i3 | ISKLSHSKGHQKRKALKT | 217 |
| i3 | SKLSHSKGHQKRKALKT | 218 |
| i3 | KLSHSKGHQKRKALKT | 219 |
| i3 | LSHSKGHQKRKALKT | 220 |
| i3 | SHSKGHQKRKALKT | 221 |
| i3 | HSKGHQKRKALKT | 222 |
| i3 | SKGHQKRKALKT | 223 |
| i3 | KGHQKRKALKT | 224 |
| i3 | GHQKRKALKT | 225 |
| i3 | HQKRKALKT | 226 |
| i3 | QKRKALKT | 227 |
| i3 | KRKALKT | 228 |
| i3 | IISKLSH | 229 |
| i3 | ISKLSHS | 230 |
| i3 | SKLSHSK | 231 |
| i3 | KLSHSKG | 232 |
| i3 | LSHSKGH | 233 |
| i3 | SHSKGHQ | 234 |

| CXCR4 i-Loop | Sequence | SEQ ID: |
|---|---|---|
| i3 | HSKGHQK | 235 |
| i3 | SKGHQKR | 236 |
| i3 | KGHQKRK | 237 |
| i3 | GHQKRKA | 238 |
| i3 | HQKRKAL | 239 |
| i3 | QKRKALK | 240 |
| i3 | HSKGHQKRKALKTT | 241 |
| i3 | HSKGHQKRKALKTTV | 242 |
| i3 | HSKGHQKRKALKTTVI | 243 |
| i3 | HSKGHQKRKQALK | 244 |
| i3 | KLSHSKGHQKRKA | 245 |
| i3 | KLSHSKGHQKRKAL | 246 |
| i3 | KLSHSKGHQKRKALK | 247 |
| i3 | KLSHSKGHQKRKALKTTV | 248 |
| i3 | KLSHSKGHQKRKALKTTVIL | 249 |
| i3 | LSHSKGHQKRKALK | 250 |
| i3 | SHSKGHQKRKALK | 251 |
| i3 | SKLSHSKGHQKRKALK | 252 |
| i3 | SKLSHSKGHQKRKALKTTVIL | 253 |
| i3 | QHLHIALKKSTSRKVKSGTLK | 254 |

In another aspect, a CXCR4 compound of the invention is represented by Formula C or a pharmaceutically acceptable salt thereof:

T-L-$W_1$-$W_2$-$W_3$-$W_4$-$W_5$-$W_6$-$W_7$-$W_8$-$W_9$-$W_{10}$-$W_{11}$-$W_{12}$-$W_{13}$-$W_{14}$-$W_{15}$-$W_{16}$-$W_{17}$-$W_{18}$-$W_{19}$-$W_{20}$-$W_{21}$-$W_{22}$-$W_{23}$-$W_{24}$-$W_{25}$-$W_{26}$-$W_{27}$-$W_{28}$-$W_{29}$-$W_{30}$-$W_{31}$-$W_{32}$-$R_1$;

wherein L is a linking moiety represented by C(O) and bonded to $W_1$ at an N terminal nitrogen of $W_1$ or the next present amino acid residue if $W_1$ is absent; T is a lipophilic tether moiety bonded to L; $R_1$ is $OR_2$ or $N(R_2)_2$, each $R_2$ is independently H or alkyl, wherein at least three contiguous $W_1$-$W_{32}$ are present, and wherein: $W_1$ is an isoleucine residue, a d-isoleucine residue, an alanine residue or absent, $W_2$ is isoleucine residue, a d-isoleucine residue, an alanine residue or absent, $W_3$ is isoleucine residue, a d-isoleucine residue, an alanine residue or absent, $W_4$ is a serine residue, a d-serine residue, an alanine residue or absent, $W_5$ is a lysine residue, a d-lysine residue, an alanine residue or absent, $W_6$ is a leucine residue, a histidine residue, a d-leucine residue, an alanine residue or absent, $W_7$ is a serine residue, a d-serine residue, an alanine residue or absent, $W_8$ is a histidine residue, a d-histidine residue, an alanine residue or absent, $W_9$ is a serine residue, a d-serine residue, an alanine residue a lysine residue, or absent, $W_{10}$ is a lysine residue, a d-lysine residue, an alanine residue, a leucine residue, an isoleucine residue or absent, $W_{11}$ is glycine residue, a d-glycine residue, an alanine residue or absent, $W_{12}$ is a histidine residue, a d-histidine residue, an alanine residue a tyrosine residue or absent, $W_{13}$ is a glutamine residue, a d-glutamine residue, an alanine residue or absent, $W_{14}$ is a lysine residue, a d-lysine residue, an alanine residue or absent; $W_{15}$ is an arginine residue, a d-arginine residue, an alanine residue, a lysine residue or absent, $W_{16}$ is a lysine residue, a d-lysine residue, an alanine residue, a leucine residue or absent, $W_{17}$ is an alanine, d-alanine, an arginine residue or absent, $W_{18}$ is a leucine residue, a d-leucine residue, an alanine residue, a serine residue or absent, $W_{19}$ is a lysine residue, a d-lysine residue, an alanine residue, a leucine residue, an isoleucine residue or absent, $W_{20}$ is threonine, a d-threonine residue, an alanine residue leucine residue or absent, $W_{21}$ is threonine, a d-threonine residue, an alanine residue a lysine residue or aspartic acid or absent, $W_{22}$ is a valine, a d-valine residue, an alanine residue or absent, $W_{23}$ is isoleucine residue, a d-isoleucine residue, an alanine residue a serine residue or absent, $W_{24}$ is leucine residue, a d-leucine residue, an alanine residue an arginine residue or absent, $W_{25}$ is a lysine residue, a d-lysine residue, an alanine residue or absent, $W_{26}$ is a valine residue, a d-valine residue, an alanine residue or absent, $W_{27}$ is a lysine residue, a d-lysine residue, an alanine residue or absent, $W_{28}$ is a serine residue a d-serine residue, an alanine residue or absent, $W_{29}$ is a glycine residue, a d-glycine residue, an alanine residue or absent, $W_{30}$ is a threonine residue, a d-threonine residue, an alanine residue or absent, $W_{31}$ is a leucine residue, a d-leucine residue, an alanine residue or absent, $W_{32}$ is a lysine residue, a d-lysine residue, an alanine residue or absent, wherein when $W_{20}$-$W_{32}$ is absent at least one of $W_1$-$W_{23}$ is also absent and wherein when $W_1$-$W_7$ and $W_{20}$-$W_{32}$ is absent, at least one of $W_8$-$W_{19}$ is absent, a d-amino acid or alanine.

In another aspect, a CXCR4 compound is represented by $W_{24}$-$W_{32}$ are absent and wherein:
$W_1$ is an isoleucine residue,
$W_2$ is an isoleucine residue,
$W_3$ is an isoleucine residue,
$W_4$ is a serine residue,
$W_5$ is a lysine residue,
$W_6$ is a leucine residue,
$W_7$ is a serine residue,
$W_8$ is a histidine residue or absent,
$W_9$ is a serine residue, or absent,
$W_{10}$ is a lysine residue or absent,
$W_{11}$ is a glycine residue or absent,
$W_{12}$ is a histidine residue, or absent,
$W_{13}$ is a glutamine residue or absent,
$W_{14}$ is a lysine residue or absent,
$W_{15}$ is an arginine residue or absent,
$W_{16}$ is a lysine residue or absent,
$W_{17}$ is an alanine residue or absent,
$W_{18}$ is a leucine residue or absent,
$W_{19}$ is a lysine residue or absent,
$W_{20}$ is a threonine residue or absent,
$W_{21}$ is a threonine residue or absent,
$W_{22}$ is a valine residue or absent, and
$W_{23}$ is an isoleucine residue or absent.

In another aspect, the CXCR 4 compounds of the invention are represented when $W_1$, $W_{21}$-$W_{32}$ are absent and wherein:
$W_2$ is an isoleucine residue or absent,
$W_3$ is an isoleucine residue or absent,
$W_4$ is a serine residue or absent,
$W_5$ is a lysine residue or absent,
$W_6$ is a leucine residue or absent,
$W_7$ is a serine residue or absent,
$W_8$ is a histidine residue or absent,
$W_9$ is a serine residue, or absent,
$W_{10}$ is a lysine residue or absent,
$W_{11}$ is a glycine residue or absent,
$W_{12}$ is a histidine residue, or absent,
$W_{13}$ is a glutamine residue or absent,
$W_{14}$ is a lysine residue,
$W_{15}$ is an arginine residue,
$W_{16}$ is a lysine residue,
$W_{17}$ is an alanine residue,
$W_{18}$ is a leucine residue,
$W_{19}$ is a lysine residue, and
$W_{20}$ is a threonine residue.

In yet another embodiment, the CXCR4 compounds of the invention comprise seven contiguous amino acid residues of $W_1$-$W_{19}$ are present and wherein:
$W_1$ is an isoleucine residue or absent,
$W_2$ is an isoleucine residue or absent,
$W_3$ is an isoleucine residue or absent,
$W_4$ is a serine residue or absent,
$W_5$ is a lysine residue or absent,
$W_6$ is a leucine residue or absent,
$W_7$ is a serine residue or absent,
$W_8$ is a histidine residue or absent,
$W_9$ is a serine residue, or absent,
$W_{10}$ is a lysine residue or absent,
$W_{11}$ is a glycine residue or absent,
$W_{12}$ is a histidine residue, or absent,
$W_{13}$ is a glutamine residue or absent,
$W_{14}$ is a lysine residue or absent,
$W_{15}$ is an arginine residue or absent,
$W_{16}$ is a lysine residue or absent,
$W_{17}$ is an alanine residue or absent,
$W_{181}$ is a leucine residue or absent, and
$W_{19}$ is a lysine residue or absent, In yet another embodiment, the CXCR4 compounds are represented when $W_1$. $W_3$ are absent and $W_{25}$-$W_{32}$ are absent, and wherein:
$W_4$ is a serine residue or absent,
$W_5$ is a lysine residue or absent,
$W_6$ is a leucine residue or absent,
$W_7$ is a serine residue or absent,
$W_8$ is a histidine residue,
$W_9$ is a serine residue,
$W_{10}$ is a lysine residue,
$W_{11}$ is a glycine residue,
$W_{12}$ is a histidine residue,
$W_{13}$ is a glutamine residue,
$W_{14}$ is a lysine residue,
$W_{15}$ is an arginine residue,
$W_{16}$ is a lysine residue,
$W_{17}$ is alanine or a glutamine residue,
$W_{18}$ is leucine residue alanine or absent,
$W_{19}$ is a lysine residue, leucine residue or absent,
$W_{20}$ is threonine or absent,
$W_{21}$ is threonine or absent,
$W_{22}$ is a valine residue or absent,
$W_{23}$ is isoleucine residue or absent,
$W_{24}$ is leucine residue or absent.

In a more specific embodiment of Formula C, the compound is selected from any one of the Compound Nos. 84, 87-106 or a pharmaceutically acceptable salt thereof.

In yet another embodiment, a CXCR4 compound of the invention is selected from one of the following compounds or a pharmaceutically acceptable salt thereof:

Compound No. 88
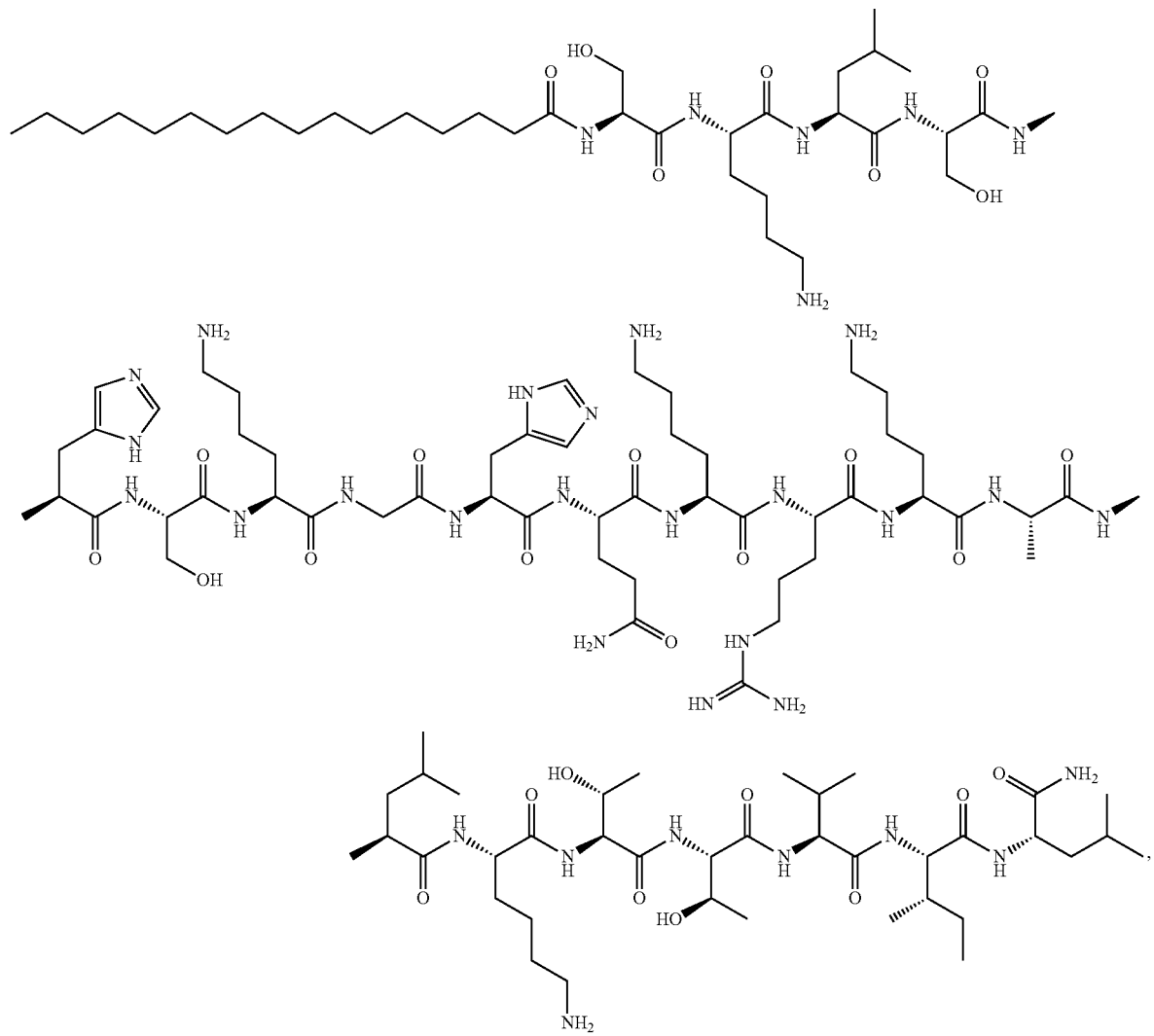
Compound No. 90
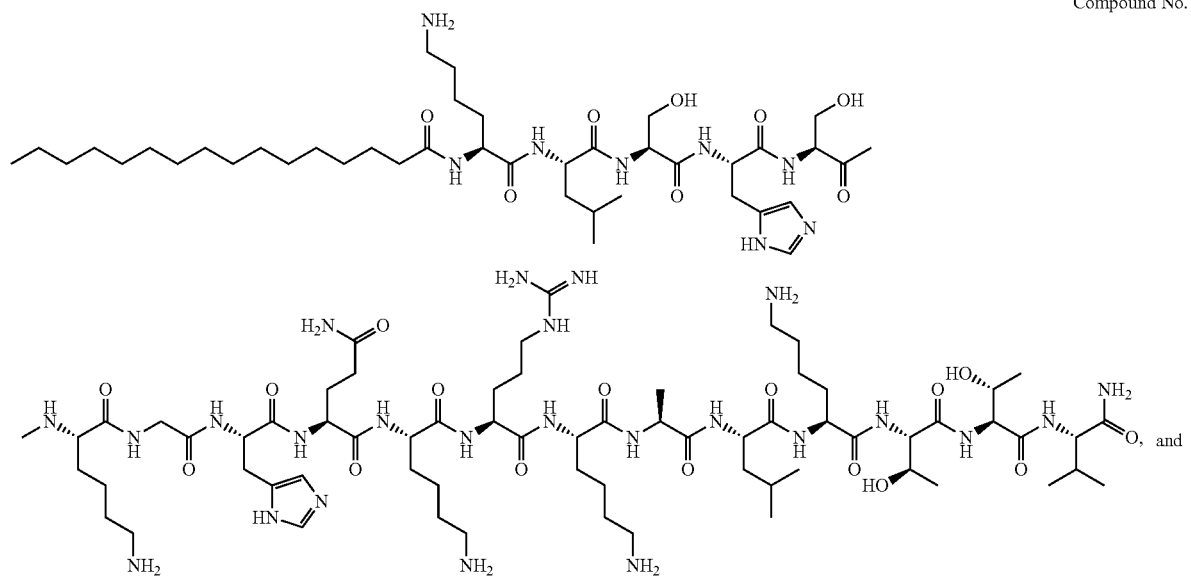
, and

-continued

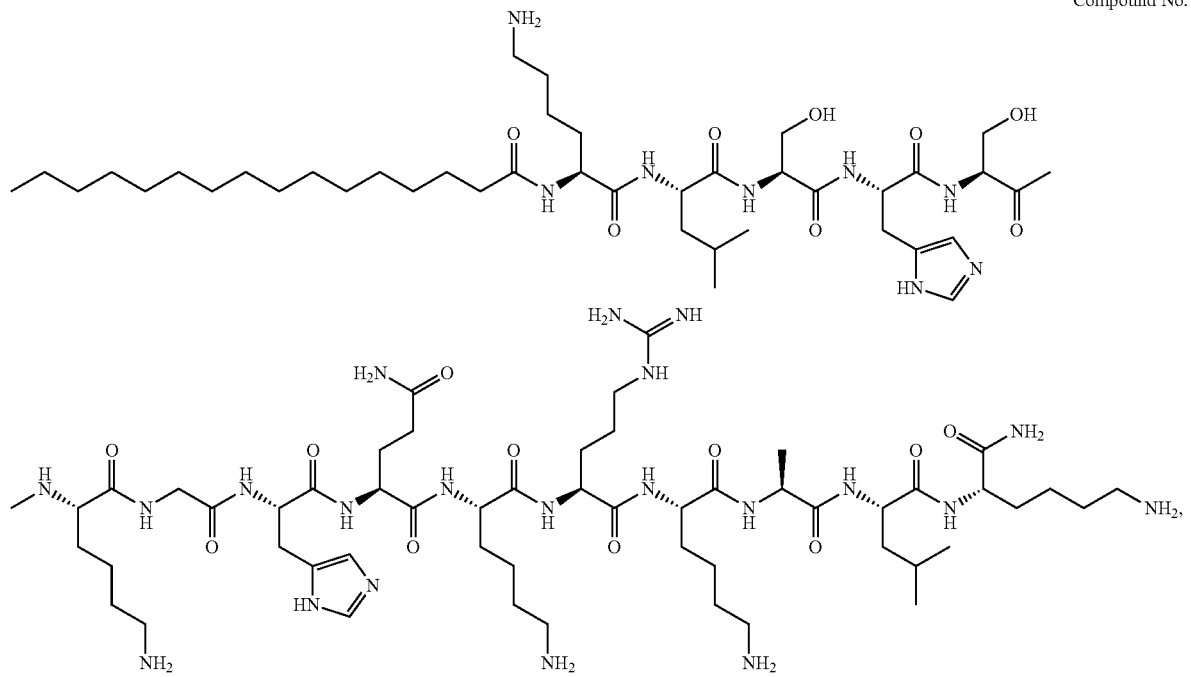

Compound No. 92 or a pharmaceutically acceptable salt thereof.

In a sixth aspect, P comprises at least 3 contiguous amino acids of the i4 domain.

In a specific embodiment of the sixth aspect, the i4 domain of the CXCR4 receptor from which P is derived has the following sequence:

GAKFKTSAQHALTSVSRGSSLKILSKGKRGGHSSVSTESESSSFHSS. (SEQ ID NO: 373)

In another embodiment of the sixth aspect, P is a sequence selected from:

| CXCR4 i-Loop | Sequence | SEQ ID NO: |
|---|---|---|
| i4 | GAKFKTSAQHALTSVSRGSSLKILSKGKRGGHSSVSTESESSSFH | 255 |
| i4 | GAKFKTSAQHALTSVSRGSSLKILSKGKRGGHSSVSTESESSSF | 256 |
| i4 | GAKFKTSAQHALTSVSRGSSLKILSKGKRGGHSSVSTESESSS | 257 |
| i4 | GAKFKTSAQHALTSVSRGSSLKILSKGKRGGHSSVSTESESS | 258 |
| i4 | GAKFKTSAQHALTSVSRGSSLKILSKGKRGGHSSVSTESES | 259 |
| i4 | GAKFKTSAQHALTSVSRGSSLKILSKGKRGGHSSVSTESE | 260 |
| i4 | GAKFKTSAQHALTSVSRGSSLKILSKGKRGGHSSVSTES | 261 |
| i4 | GAKFKTSAQHALTSVSRGSSLKILSKGKRGGHSSVSTE | 262 |
| i4 | GAKFKTSAQHALTSVSRGSSLKILSKGKRGGHSSVST | 263 |
| i4 | GAKFKTSAQHALTSVSRGSSLKILSKGKRGGHSSVS | 264 |
| i4 | GAKFKTSAQHALTSVSRGSSLKILSKGKRGGHSSV | 265 |
| i4 | GAKFKTSAQHALTSVSRGSSLKILSKGKRGGHSS | 266 |
| i4 | GAKFKTSAQHALTSVSRGSSLKILSKGKRGGHS | 267 |
| i4 | GAKFKTSAQHALTSVSRGSSLKILSKGKRGGH | 268 |
| i4 | GAKFKTSAQHALTSVSRGSSLKILSKGKRGG | 269 |
| i4 | GAKFKTSAQHALTSVSRGSSLKILSKGKRG | 270 |
| i4 | GAKFKTSAQHALTSVSRGSSLKILSKGKR | 271 |

-continued

| CXCR4 i-Loop | Sequence | SEQ ID NO: |
|---|---|---|
| i4 | GAKFKTSAQHALTSVSRGSSLKILSKGK | 272 |
| i4 | GAKFKTSAQHALTSVSRGSSLKILSKG | 273 |
| i4 | GAKFKTSAQHALTSVSRGSSLKILSK | 274 |
| i4 | GAKFKTSAQHALTSVSRGSSLKILS | 275 |
| i4 | GAKFKTSAQHALTSVSRGSSLKIL | 276 |
| i4 | GAKFKTSAQHALTSVSRGSSLKI | 277 |
| i4 | GAKFKTSAQHALTSVSRGSSLK | 278 |
| i4 | GAKFKTSAQHALTSVSRGSSL | 279 |
| i4 | GAKFKTSAQHALTSVSRGSS | 280 |
| i4 | GAKFKTSAQHALTSVSRGS | 281 |
| i4 | GAKFKTSAQHALTSVSRG | 282 |
| i4 | GAKFKTSAQHALTSVSR | 283 |
| i4 | GAKFKTSAQHALTSVS | 284 |
| i4 | GAKFKTSAQHALTSV | 285 |
| i4 | GAKFKTSAQHALTS | 286 |
| i4 | GAKFKTSAQHALT | 287 |
| i4 | GAKFKTSAQHAL | 288 |
| i4 | GAKFKTSAQHA | 289 |
| i4 | GAKFKTSAQH | 290 |
| i4 | AKFKTSAQHALTSVSRGSSLKILSKGKRGGHSSVSTESESSSFHSS | 291 |
| i4 | KFKTSAQHALTSVSRGSSLKILSKGKRGGHSSVSTESESSSFHSS | 292 |
| i4 | FKTSAQHALTSVSRGSSLKILSKGKRGGHSSVSTESESSSFHSS | 293 |
| i4 | KTSAQHALTSVSRGSSLKILSKGKRGGHSSVSTESESSSFHSS | 294 |
| i4 | TSAQHALTSVSRGSSLKILSKGKRGGHSSVSTESESSSFHSS | 295 |
| i4 | SAQHALTSVSRGSSLKILSKGKRGGHSSVSTESESSSFHSS | 296 |
| i4 | AQHALTSVSRGSSLKILSKGKRGGHSSVSTESESSSFHSS | 297 |
| i4 | QHALTSVSRGSSLKILSKGKRGGHSSVSTESESSSFHSS | 298 |
| i4 | HALTSVSRGSSLKILSKGKRGGHSSVSTESESSSFHSS | 299 |
| i4 | ALTSVSRGSSLKILSKGKRGGHSSVSTESESSSFHSS | 300 |
| i4 | LTSVSRGSSLKILSKGKRGGHSSVSTESESSSFHSS | 301 |
| i4 | TSVSRGSSLKILSKGKRGGHSSVSTESESSSFHSS | 302 |
| i4 | SVSRGSSLKILSKGKRGGHSSVSTESESSSFHSS | 303 |
| i4 | VSRGSSLKILSKGKRGGHSSVSTESESSSFHSS | 304 |
| i4 | SRGSSLKILSKGKRGGHSSVSTESESSSFHSS | 305 |
| i4 | RGSSLKILSKGKRGGHSSVSTESESSSFHSS | 306 |
| i4 | GSSLKILSKGKRGGHSSVSTESESSSFHSS | 307 |
| i4 | SSLKILSKGKRGGHSSVSTESESSSFHSS | 308 |
| i4 | SLKILSKGKRGGHSSVSTESESSSFHSS | 309 |

| CXCR4 i-Loop | Sequence | SEQ ID NO: |
|---|---|---|
| i4 | LKILSKGKRGGHSSVSTESESSSFHSS | 310 |
| i4 | KILSKGKRGGHSSVSTESESSSFHSS | 311 |
| i4 | ILSKGKRGGHSSVSTESESSSFHSS | 312 |
| i4 | LSKGKRGGHSSVSTESESSSFHSS | 313 |
| i4 | SKGKRGGHSSVSTESESSSFHSS | 314 |
| i4 | KGKRGGHSSVSTESESSSFHSS | 315 |
| i4 | GKRGGHSSVSTESESSSFHSS | 316 |
| i4 | KRGGHSSVSTESESSSFHSS | 317 |
| i4 | RGGHSSVSTESESSSFHSS | 318 |
| i4 | GGHSSVSTESESSSFHSS | 320 |
| i4 | GHSSVSTESESSSFHSS | 321 |
| i4 | HSSVSTESESSSFHSS | 322 |
| i4 | SSVSTESESSSFHSS | 323 |
| i4 | SVSTESESSSFHSS | 324 |
| i4 | VSTESESSSFHSS | 325 |
| i4 | STESESSSFHSS | 326 |
| i4 | TESESSSFHSS | 327 |
| i4 | ESESSSFHSS | 328 |
| i4 | AKFKTSAQHA | 329 |
| i4 | KFKTSAQHAL | 330 |
| i4 | FKTSAQHALT | 331 |
| i4 | KTSAQHALTS | 332 |
| i4 | TSAQHALTSV | 333 |
| i4 | SAQHALTSVS | 334 |
| i4 | AQHALTSVSR | 335 |
| i4 | QHALTSVSRG | 336 |
| i4 | HALTSVSRGS | 337 |
| i4 | ALTSVSRGSS | 338 |
| i4 | LTSVSRGSSL | 339 |
| i4 | TSVSRGSSLK | 340 |
| i4 | SVSRGSSLKI | 341 |
| i4 | VSRGSSLKIL | 342 |
| i4 | SRGSSLKILS | 343 |
| i4 | RGSSLKILSK | 345 |
| i4 | GSSLKILSKG | 346 |
| i4 | SSLKILSKGK | 347 |
| i4 | SLKILSKGKR | 348 |
| i4 | LKILSKGKRG | 349 |

-continued

| CXCR4 i-Loop | Sequence | SEQ ID NO: |
|---|---|---|
| i4 | KILSKGKRGG | 350 |
| i4 | ILSKGKRGGH | 351 |
| i4 | LSKGKRGGHS | 352 |
| i4 | SKGKRGGHSS | 353 |
| i4 | KGKRGGHSSV | 354 |
| i4 | GKRGGHSSVS | 355 |
| i4 | KRGGHSSVST | 356 |
| i4 | RGGHSSVSTE | 357 |
| i4 | GGHSSVSTES | 358 |
| i4 | GHSSVSTESE | 359 |
| i4 | HSSVSTESES | 360 |
| i4 | SSVSTESESS | 361 |
| i4 | SVSTESESSS | 362 |
| i4 | VSTESESSSF | 363 |
| i4 | STESESSSFH | 364 |
| i4 | TESESSSFHS | 365 |
| i4 | ESESSSFHSS | 366 |
| i4 | GAKFKTSAQHALTSVSRGSSLKILSKGKRGGHSSVSTESESSSFHS | 367 |
| i4 | GAKFKTSAQHALTSVSRGSSLKILSKGKRGGHSCFH | 368 |

In a another embodiment, CXCR4 compounds of the invention are represented by Formula D or a pharmaceutically acceptable salt thereof, wherein:

$$T\text{-}L\text{-}Z_1\text{-}Z_2\text{-}Z_3\text{-}Z_4\text{-}Z_5\text{-}Z_6\text{-}Z_7\text{-}Z_8\text{-}Z_9\text{-}Z_{10}\text{-}Z_{11}\text{-}Z_{12}\text{-}Z_{13}\text{-}Z_{14}\text{-}Z_{15}\text{-}Z_{16}\text{-}Z_{17}\text{-}Z_{18}\text{-}Z_{19}\text{-}Z_{20}\text{-}Z_{21}\text{-}Z_{22}\text{-}Z_{23}\text{-}Z_{24}\text{-}Z_{25}\text{-}Z_{26}\text{-}Z_{27}\text{-}Z_{28}\text{-}Z_{29}\text{-}Z_{30}\text{-}Z_{31}\text{-}Z_{32}\text{-}Z_{33}\text{-}Z_{34}\text{-}Z_{35}\text{-}Z_{36}\text{-}Z_{37}\text{-}Z_{38}\text{-}Z_{39}\text{-}Z_{40}\text{-}Z_{41}\text{-}Z_{42}\text{-}Z_{43}\text{-}Z_{44}\text{-}Z_{45}\text{-}Z_{46}\text{-}Z_{47}\text{-}R_1\text{; wherein:}$$

L is a linking moiety represented by C(O) and bonded to the N terminal nitrogen of $Z_1$ or the next present amino acid residue if $Z_1$ is absent;

and T is a lipophilic tether moiety bonded to L; $R_1$ is $OR_2$ or $N(R_2)_2$, each $R_2$ is independently H or alkyl, wherein at least three contiguous $Z_1$-$Z_{32}$ amino acid residues are present, and wherein:

- $Z_1$ is a glycine residue, a d-glycine residue, an alanine residue or absent,
- $Z_2$ is an alanine residue a d-alanine residue or absent,
- $Z_3$ is a lysine residue, a d-lysine residue, an alanine residue or absent,
- $Z_4$ is a phenylalanine residue, a d-phenylalanine residue, an alanine residue or absent,
- $Z_5$ is a lysine residue, a d-lysine residue, an alanine residue or absent,
- $Z_6$ is a threonine residue, a d-threonine residue, an alanine residue or absent,
- $Z_7$ is a serine residue a d-serine residue, an alanine residue or absent,
- $Z_8$ is an alanine residue, a d-alanine residue or absent,
- $Z_9$ is a glutamine residue, a d-glutamine residue, an alanine residue or absent,
- $Z_{10}$ is a histidine residue, a d-histidine residue, an alanine residue or absent,
- $Z_{11}$ is an alanine residue, a d-alanine residue or absent,
- $Z_{12}$ is a leucine residue, a d-leucine residue, an alanine residue or absent,
- $Z_{13}$ is a threonine residue, a d-threonine residue, an alanine residue or absent,
- $Z_{14}$ is a serine residue, a d-serine residue, an alanine residue or absent;
- $Z_{15}$ is a valine residue, a d-valine residue, an alanine residue or absent,
- $Z_{16}$ is a serine residue, a d-serine residue, an alanine residue or absent,
- $Z_{17}$ is an arginine residue, a d-arginine residue, an alanine residue or absent,
- $Z_{18}$ is a glycine residue, a d-glycine residue, an alanine residue or absent,
- $Z_{19}$ is a serine residue, a d-serine residue, an alanine residue or absent,
- $Z_{20}$ is a serine residue, a d-serine residue, an alanine residue absent,
- $Z_{21}$ is a leucine residue, a d-leucine residue, an alanine residue or absent,
- $Z_{22}$ is a lysine residue, a d-lysine residue, an alanine residue or absent,
- $Z_{23}$ is a isoleucine residue, a d-isoleucine residue, an alanine residue a serine residue or absent, $Z_{24}$ is a leucine residue, a d-leucine residue, an alanine residue or absent,
$Z_{25}$ is a serine residue, a d-serine residue, an alanine residue or absent,
$Z_{26}$ is a lysine residue, a d-lysine residue, an alanine residue or absent,
$Z_{27}$ is glycine residue, a d-glycine residue, an alanine residue or absent,
$Z_{28}$ is a lysine residue, a d-lysine residue, an alanine residue or absent,
$Z_{29}$ is an arginine residue, a d-arginine residue, an alanine residue or absent,
$Z_{30}$ is a glycine residue, a d-glycine residue, an alanine residue or absent,
$Z_{31}$ is a glycine residue, a d-glycine residue, an alanine residue or absent,
$Z_{32}$ is a histidine residue, a d-histidine residue, an alanine residue or absent,
$Z_{33}$ is a serine residue, a d-serine residue, an alanine residue or absent,
$Z_{34}$ is a serine residue, a d-serine residue, an alanine residue cysteine, or absent,
$Z_{35}$ is a valine residue, a d-valine residue, an alanine residue a phenylalanine residue, or absent,
$Z_{36}$ is a serine residue, a d-serine residue, an alanine residue a histidine residue or absent,
$Z_{37}$ is a threonine residue, a d-threonine residue, an alanine residue or absent,
$Z_{38}$ is a glutamic acid residue, a d-glutamic acid residue, an alanine residue or absent,
$Z_{39}$ is a serine residue, a d-serine residue, an alanine residue or absent,
$Z_{40}$ is a glutamic acid, a d-glutamine acid residue, an alanine residue or absent
$Z_{41}$ is a serine residue, a d-serine residue, an alanine residue or absent,
$Z_{42}$ is a serine residue, a d-serine residue, an alanine residue or absent,
$Z_{43}$ is a serine residue, a d-serine residue, an alanine residue or absent,
$Z_{44}$ is a phenylalanine residue, a d-phenylalanine residue, an alanine residue or absent,
$Z_{45}$ is a histidine residue, a d-histidine residue, an alanine residue or absent,
$Z_{46}$ is a serine residue, a d-serine residue, an alanine residue or absent,
$Z_{47}$ is a serine residue, a d-serine residue, an alanine residue or absent,
wherein at least one of $Z_1$-$Z_{47}$ is absent.

In a more specific embodiment, the CXCR4 compounds of the invention are represented by the following:
$Z_1$ is a glycine residue,
$Z_2$ is an alanine residue,
$Z_3$ is a lysine residue,
$Z_4$ is a phenylalanine residue,
$Z_5$ is a lysine residue,
$Z_6$ is a threonine residue,
$Z_7$ is a serine residue,
$Z_8$ is an alanine residue,
$Z_9$ is a glutamine residue,
$Z_{10}$ is a histidine residue or absent,
$Z_{11}$ is an alanine residue or absent,
$Z_{12}$ is a leucine residue or absent,
$Z_{13}$ is a threonine residue or absent,
$Z_{14}$ is a serine residue or absent,
$Z_{15}$ is a valine residue or absent,
$Z_{16}$ is a serine residue or absent,
$Z_{17}$ is an arginine residue or absent,
$Z_{18}$ is a glycine residue or absent,
$Z_{19}$ is a serine residue or absent,
$Z_{20}$ is a serine residue or absent,
$Z_{21}$ is a leucine residue or absent,
$Z_{22}$ is a lysine residue or absent,
$Z_{23}$ is an isoleucine residue, a serine residue or absent,
$Z_{24}$ is a leucine residue or absent,
$Z_{25}$ is a serine residue or absent,
$Z_{26}$ is a lysine residue or absent,
$Z_{27}$ is a glycine residue or absent,
$Z_{28}$ is a lysine residue or absent,
$Z_{29}$ is an arginine residue or absent,
$Z_{30}$ is a glycine residue or absent,
$Z_{31}$ is a glycine residue or absent,
$Z_{32}$ is a histidine residue or absent,
$Z_{33}$ is a serine residue or absent,
$Z_{34}$ is a serine residue or absent,
$Z_{35}$ is a valine residue or absent,
$Z_{36}$ is a serine residue or absent,
$Z_{37}$ is a threonine residue or absent,
$Z_{38}$ is a glutamic acid residue or absent,
$Z_{39}$ is a serine residue or absent,
$Z_{40}$ is a glutamic acid residue or absent,
$Z_{41}$ is a serine residue or absent,
$Z_{42}$ is a serine residue or absent,
$Z_{43}$ is a serine residue or absent,
$Z_{44}$ is a phenylalanine residue or absent,
$Z_{45}$ is a histidine residue or absent,
$Z_{46}$ is a serine residue or absent, and
$Z_{47}$ is a serine residue or absent.

In yet another embodiment, the CXCR4 compounds of the invention are represented by:
$Z_1$ is a glycine residue or absent,
$Z_2$ is an alanine residue or absent,
$Z_3$ is a lysine residue or absent,
$Z_4$ is a phenylalanine residue or absent,
$Z_5$ is a lysine residue or absent,
$Z_6$ is a threonine residue or absent,
$Z_7$ is a serine residue or absent,
$Z_8$ is an alanine residue or absent,
$Z_9$ is a glutamine residue or absent,
$Z_{10}$ is a histidine residue or absent,
$Z_{11}$, is an alanine residue or absent,
$Z_{12}$ is a leucine residue or absent,
$Z_{13}$ is a threonine residue or absent,
$Z_{14}$ is a serine residue or absent,
$Z_{15}$ is a valine residue or absent,
$Z_{16}$ is a serine residue or absent,
$Z_{17}$ is an arginine residue or absent,
$Z_{18}$ is a glycine residue or absent,
$Z_{19}$ is a serine residue or absent,
$Z_{20}$ is a serine residue absent,
$Z_{21}$ is a leucine residue or absent,
$Z_{22}$ is a lysine residue or absent,
$Z_{23}$ is an isoleucine residue, or absent,
$Z_{24}$ is a leucine residue or absent,
$Z_{25}$ is a serine residue or absent,
$Z_{26}$ is a lysine residue or absent,
$Z_{27}$ is a glycine residue or absent,
$Z_{28}$ is a lysine residue or absent,
$Z_{29}$ is an arginine residue or absent,
$Z_{30}$ is a glycine residue or absent,
$Z_{31}$ is a glycine residue or absent,
$Z_{32}$ is a histidine residue or absent,
$Z_{33}$ is a serine residue or absent,
$Z_{34}$ is a serine residue or absent, $Z_{35}$ is a valine residue or absent,
$Z_{36}$ is a serine residue or absent,
$Z_{37}$ is a threonine residue or absent,
$Z_{38}$ is a glutamic acid residue,
$Z_{39}$ is a serine residue,
$Z_{40}$ is a glutamic acid residue,
$Z_{41}$ is a serine residue,
$Z_{42}$ is a serine residue,
$Z_{43}$ is a serine residue,
$Z_{44}$ is a phenylalanine residue,
$Z_{45}$ is a histidine residue,
$Z_{46}$ is a serine residue, and
$Z_{47}$ is a serine residue.

In a more specific embodiment, CXCR4 compounds of the invention are represented when $Z_1$ is absent, and 10 consecutive $Z_2$-$Z_{47}$ are present wherein:
$Z_2$ is an alanine residue or absent,
$Z_3$ is a lysine residue or absent,
$Z_4$ is a phenylalanine residue or absent,
$Z_5$ is a lysine residue or absent,
$Z_6$ is a threonine residue or absent,
$Z_7$ is a serine residue or absent,
$Z_8$ is an alanine residue or absent,
$Z_9$ is a glutamine residue or absent,
$Z_{10}$ is a histidine residue or absent,
$Z_{11}$ is an alanine residue or absent,
$Z_{12}$ is a leucine residue or absent,
$Z_{13}$ is a threonine residue or absent,
$Z_{14}$ is a serine residue or absent;
$Z_{15}$ is a valine residue or absent,
$Z_{16}$ is a serine residue or absent,
$Z_{17}$ is an arginine residue or absent,
$Z_{18}$ is a glycine residue or absent,
$Z_{19}$ is a serine residue or absent,
$Z_{20}$ is a serine residue absent,
$Z_{21}$ is leucine residue or absent,
$Z_{22}$ is a lysine residue or absent,
$Z_{23}$ is an isoleucine residue, or absent,
$Z_{24}$ is a leucine residue or absent,
$Z_{25}$ is a serine residue or absent,
$Z_{26}$ is a lysine residue or absent,
$Z_{27}$ is a glycine or absent,
$Z_{28}$ is a lysine residue or absent,
$Z_{29}$ is an arginine residue or absent,
$Z_{30}$ is a glycine residue or absent,
$Z_{31}$ is a glycine residue or absent,
$Z_{32}$ is a histidine residue or absent,
$Z_{33}$ is a serine residue or absent,
$Z_{34}$ is a serine residue or absent,
$Z_{35}$ is a valine residue or absent,
$Z_{36}$ is a serine residue or absent,
$Z_{37}$ is a threonine residue or absent,
$Z_{38}$ is a glutamic acid residue,
$Z_{39}$ is a serine residue,
$Z_{40}$ is glutamic acid residue,
$Z_{41}$ is a serine residue,
$Z_{42}$ is a serine residue,
$Z_{43}$ is a serine residue,
$Z_{44}$ is a phenylalanine residue,
$Z_{45}$ is a histidine residue,
$Z_{46}$ is a serine residue, and
$Z_{47}$ is a serine residue.

In a more specific embodiment of Formula D, the CXCR4 compound is selected from any one of the Compound Nos. 107-116 or a pharmaceutically acceptable salt thereof.

In a seventh aspect, T is an optionally substituted ($C_6$-$C_{30}$) alkyl, ($C_6$-$C_{30}$)alkenyl, ($C_6$-$C_{30}$)alkynyl, wherein 0-3 carbon atoms are replaced with oxygen, sulfur, nitrogen or a combination thereof. This value of T is applicable to the first, second, third, fourth, fifth and sixth aspects and the specific (i.e., specific, more specific and most specific) embodiments of same.

In a specific embodiment of the seventh aspect, T is selected from: $CH_3(CH_2)_{16}$, $CH_3(CH_2)_{15}$, $CH_3(CH_2)_{14}$, $CH_3(CH_2)_{13}$, $CH_3(CH_2)_{12}$, $CH_3(CH_2)_{11}$, $CH_3(CH_2)_{10}$, $CH_3(CH_2)_9$, $CH_3(CH_2)_8$, $CH_3(CH_2)_9OPh$-, $CH_3(CH_2)_6C$=$C(CH_2)_6$, $CH_3(CH_2)_{11}O(CH_2)_3$, and $CH_3(CH_2)_9O(CH_2)_2$.

In another specific embodiment of the seventh aspect, T is a fatty acid derivative.

In a more specific embodiment of the seventh aspect, the fatty acid is selected from the group consisting of: butyric acid, caproic acid, caprylic acid, capric acid, lauric acid, myristic acid, palmitic acid, stearic acid, arachidic acid, behenic acid, lignoceric acid, myristoleic acid, palmitoleic acid, oleic acid, linoleic acid, α-linolenic acid, arachidonic acid, eicosapentaenoic acid, erucic acid, docosahexaenoic acid.

In an eighth aspect, T is a bile acid derivative. This value of T is applicable to the first, second, third, fourth, fifth and sixth aspects and the specific (i.e., specific, more specific and most specific) embodiments of same.

In a specific embodiment of the eighth aspect, the bile acid is selected from the group consisting of: lithocholic acid, chenodeoxycholic acid, deoxycholic acid, cholanic acid, cholic acid, ursocholic acid, ursodeoxycholic acid, isoursodeoxycholic acid, lagodeoxycholic acid, dehydrocholic acid, hyocholic acid, and hyodeoxycholic acid.

In a ninth aspect, T is selected from sterols; progestagens; glucocorticoids; mineralcorticoids; androgens; and estrogens. This value of T is applicable to the first, second, third, fourth, fifth and sixth aspects and the specific (i.e., specific, more specific and most specific) embodiments of same.

In a tenth aspect, T-L of Formula I is represented by a moiety selected from the group consisting of:
$CH_3(CH_2)_{15}$—C(O);
$CH_3(CH_2)_{13}$—C(O);
$CH_3(CH_2)_9O(CH_2)_2C(O)$;
$CH_3(CH_2)_{10}O(CH_2)_2C(O)$;
$CH_3(CH_2)_6C$=$C(CH_2)_6$—C(O);
LCA-C(O); and
$CH_3(CH_2)_9OPh$-C(O) wherein

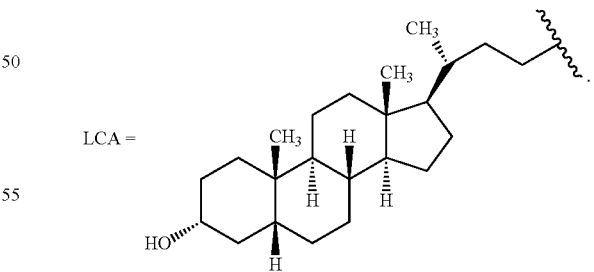

LCA =

In an eleventh aspect, T of Formula I is represented by a moiety selected from the group consisting of:

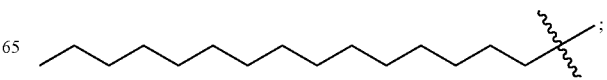

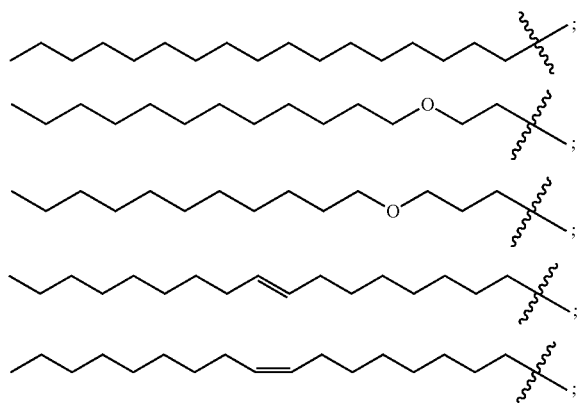

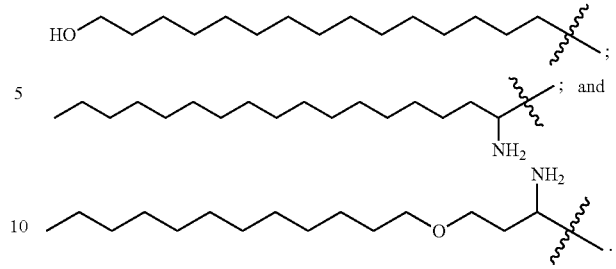

In a twelfth aspect, the CXCR4 receptor compounds are selected from the compounds represented in Tables 6-13, excluding controls and those compounds not with the structure of Formula I or a pharmaceutically acceptable salt thereof.

TABLE 6

CXCR4 i1 loop compounds

| No. | Loop | Sequence | Lipid | Comments | MW |
|---|---|---|---|---|---|
| 1 | i1 | AGYQKKLRSMTD (SEQ ID NO: 11) | Pal | | 1635.024 |
| 2 | i1 | MAYQKKLRSMTD (SEQ ID NO: 12) | Pal | | 1709.168 |
| 3 | i1 | MGAQKKLRSMTD (SEQ ID NO: 13) | Pal | | 1603.046 |
| 4 | i1 | MGYAKKLRSMTD (SEQ ID NO: 14) | Pal | | 1638.09 |
| 5 | i1 | MGYQKKLRAMTD (SEQ ID NO: 15) | Pal | | 1679.142 |
| 6 | i1 | MGYQKKLRSATD (SEQ ID NO: 16) | Pal | | 1635.024 |
| 7 | i1 | MGYQKKLRSMAD (SEQ ID NO: 17) | Pal | | 1665.116 |
| 8 | i1 | MGYQKKLRSMTA (SEQ ID NO: 18) | Pal | | 1651.132 |
| 9 | i1 | MGYQAKLRSMTD (SEQ ID NO: 19) | Pal | | 1638.047 |
| 10 | i1 | MGYQKKLASMTD (SEQ ID NO: 20) | Pal | | 1610.034 |
| 11 | i1 | MGYQKALRSMTD (SEQ ID NO: 21) | Pal | | 1638.047 |
| 12 | i1 | MGYQKKARSMTD (SEQ ID NO: 22) | Pal | | 1653.062 |
| 13 | i1 | mGYQKKLRSMTD (SEQ ID NO: 23) | Pal | D-Methionine | 1695.142 |
| 14 | i1 | MGyQKKLRSMTD (SEQ ID NO: 24) | Pal | D-Tyrosine | 1695.142 |
| 15 | i1 | MGYqKKLRSMTD (SEQ ID NO: 25) | Pal | D-Glutamine | 1695.142 |
| 16 | i1 | MGYQkKLRSMT (SEQ ID NO: 26) | Pal | D-Lysine | 1695.142 |
| 17 | i1 | MGYQKkLRSMTD (SEQ ID NO: 27) | Pal | D-Lysine | 1695.142 |
| 18 | i1 | MGYQKKIRSMTD (SEQ ID NO: 28) | Pal | D-Leucine | 1695.142 |

TABLE 6 -continued

CXCR4 i1 loop compounds

| No. | Loop | Sequence | Lipid | Comments | MW |
|---|---|---|---|---|---|
| 19 | i1 | MGYQKKLrSMTD (SEQ ID NO: 29) | Pal | D-Arginine | 1695.142 |
| 20 | i1 | MGYQKKLRsMTD (SEQ ID NO: 30) | Pal | D-Serine | 1695.142 |
| 21 | i1 | MGYQKKLRSmTD (SEQ ID NO: 31) | Pal | D-Methionine | 1695.142 |
| 22 | i1 | MGYQKKLRSMtD (SEQ ID NO: 32) | Pal | D-Threonine | 1695.142 |
| 23 | i1 | MGYQKKLRSMTd (SEQ ID NO: 33) | Pal | D-Aspartic acid | 1695.142 |
| 24 | i1 | GSHYQKKLRSSTD (SEQ ID NO: 34) | Pal | | 1744.043 |
| 25 | i1 | SGYQKKLRSSTD (SEQ ID NO: 1) | Elaidic | | 1632.942 |
| 26 | i1 | SGYQKKLRSSTD (SEQ ID NO: 1) | Oleic | | 1618.915 |
| 27 | i1 | sGYQKKLRS STD (SEQ ID NO: 68) | Pal | D-Serine | 1606.904 |
| 28 | i1 | GSGYQKKLRSSTD (SEQ ID NO: 35) | Pal | | 1663.955 |
| 29 | i1 | YQKKLRSSTD (SEQ ID NO: 36) | Pal | | 1462.776 |
| 30 | i3 | JGYQKKLRSJTD (SEQ ID NO: 4) | Pal | | 1659.065 |
| 31 | i3 | JGYQKKLRSJTD (SEQ ID NO: 4) | Pal | | 1645.038 |
| 32 (control) | i1 | MGYQKKLRSMTD (SEQ ID NO: 376) | None | capped peptide | 1498.77 |
| 33 | i1 | MGYQKKLRSMTD (SEQ ID NO: 376) | C16H33 backbone | Pentadecyla- lanine with Biotin | 1964.505 |
| 34 | i1 | LVMGYQKKLRSMTD (SEQ ID NO: 78) | Pal | | 1907.43 |
| 35 | i1 | VMGYQKKLRSMTD (SEQ ID NO: 86) | Pal | | 1794.273 |
| 36 | i1 | MGYQKKLRSMTDK (SEQ ID NO: 79) | Pal | | 1823.314 |
| 37 | i1 | MGYQKKLRSMTDKY (SEQ ID NO: 80) | Pal | | 1986.487 |
| 38 | i1 | MGYQKKLRSMTDKYRL (SEQ ID NO: 82) | Pal | | 2255.831 |
| 39 | i1 | MGYQKKLRSMTDKYRLHL (SEQ ID NO: 83) | Pal | | 2506.127 |
| 40 | i1 | YQKKLRSMTDKYRLHLSV (SEQ ID NO: 77) | Pal | | 2504.088 |
| 41 | i1 | KKLRSMTDKYRLHLSV (SEQ ID NO: 74) | Pal | | 2212.786 |
| 42 | i1 | KKLRSMTDKYRLHL (SEQ ID NO: 73) | Pal | | 2026.578 |

TABLE 6 -continued

CXCR4 i1 loop compounds

| No. | Loop | Sequence | Lipid | Comments | MW |
|---|---|---|---|---|---|
| 43 | i1 | KKLRSMTDKYRLH (SEQ ID NO: 42) | Pal | | 1913.42 |
| 44 | i1 | KKLRSMTDKYRL (SEQ ID NO: 71) | Pal | | 1776.281 |
| 45 | i1 | KKLRSMTDKYR (SEQ ID NO: 70) | Pal | | 1663.123 |
| 46 | i1 | KKLRSMTDKY (SEQ ID NO: 69) | Pal | | 1506.937 |
| 47 | i1 | MGYQKKLRSMTDKYRI (SEQ ID NO: 81) | Pal | lipid on both termini | 2480.256 |
| 48 | i1 | MGYQKKLRSMTDKYRI (SEQ ID NO: 81) | Myr | also on backbone | 2509.254 |
| 49 | i1 | MGYQKKLRSMTDKYRI (SEQ ID NO: 81) | Pal | | 2255.831 |
| 50 | i1 | SGYQKKLRSSTD (SEQ ID NO: 1) | Myr | also backbone lipid | 1860.328 |
| 51 | i1 | MGYQKKLRSMTD (SEQ ID NO: 376) | Myr NH(CH2)15- | also backbone lipid | 1948.565 |
| 52 | i1 | QKKLRSMTDKYRI (SEQ ID NO: 75) | CH3 | | 1932.463 |
| 53 | i1 | MGYQKKLRSMTDKYRLHL (SEQ ID NO: 83) | Pal | also C-terminus | 2730.553 |
| 54 | i1 | MGYQKKLRSMTDKYRLHL (SEQ ID NO: 83) | Myr | dual lipid backbone | 2759.551 |
| 55 | i1 | MGYQKKLRSMTDKYRLHLSV (SEQ ID NO: 84) | Pal | | 2692.336 |
| 56 | i1 | MGYQKKLRSMTDKYRLHLSV (SEQ ID NO: 84) | Myr | dual lipid backbone | 2945.759 |
| 58 | i1 | MGYQKKLRSMTDK (SEQ ID NO: 79) | | capped peptide | 1626.942 |
| 59 | i1 | MGYQKKLRSMTDK (SEQ ID NO: 79) | NH(CH$_2$)15-CH3 | | 1851.367 |
| 60 | i1 | MGYQKKLRSMTDK (SEQ ID NO: 79) | Myr | Dual peptide Myr and C16 backbone | 2076.737 |
| 61 | i1 | KKLCRSMTDKCYRL (SEQ ID NO: 87) | Pal | 4, 11 Cys cyclization | 1980.551 |
| 62 | i1 | KKLRCSMTDCKYRL (SEQ ID NO: 88) | Pal | 5, 10 Cys cyclization | 1980.551 |
| 63 | i1 | KKLRSMTDKYRL (SEQ ID NO: 71) | Pal | head to tail cyclized | 1802.318 |
| 64 | i1 | KKLRSMTDKYRL (SEQ ID NO: 71) | Pal | | 1820.333 |
| 65 | i1 | KRMKTSLYDGRMQYLK (SEQ ID NO: 67) | Pal | scrambled No.: 39 | 2255.831 |
| 66 | i1 | YTKRLDSHRKLKM (SEQ ID NO: 85) | Pal | scrambled No. 44 | 1913.42 |
| 67 | i1 | MGYQKKLRSMTDKYRL (SEQ ID NO: 82) | | | 2060:447 |

TABLE 6 -continued

CXCR4 i1 loop compounds

| No. | Loop | Sequence | Lipid | Comments | MW |
|---|---|---|---|---|---|
| 68 | i1 | KKLRSXTDKYRLH (SEQ ID NO: 72) | Pal | X = Norluecine substitution | 1895.382 |
| 69 | i1 | SGYQKKLRSSTD (SEQ ID NO: 1) | Pal | | 1606.904 |
| 70 | i1 | SGYQKKLRSSTD (SEQ ID NO: 1) | Myr | | 1565.852 |
| 71 | i1 | SGYQKKLRSSTD (SEQ ID NO: 1) | Lca | | 1727.053 |
| 72 | i1 | MGYQKKLRSSTD (SEQ ID NO: 2) | Pal | | 1651.023 |
| 73 | i1 | SGYQKKLRSMTD (SEQ ID NO: 3) | Pal | | 1651.023 |
| 117 | i1 | kKLRSMTDKYRLH (SEQ ID NO: 89) | Pal | | |
| 118 | i1 | KkLRSMTDKYRLH (SEQ ID NO: 90) | Pal | | |
| 119 | i1 | KKlRSMTDKYRLH (SEQ ID NO: 91) | Pal | | |
| 120 | i1 | KKLTSMTDKYRLH (SEQ ID NO: 92) | Pal | | |
| 121 | i1 | KKLRsMTDKYRLH (SEQ ID NO: 93) | Pal | | |
| 122 | i1 | KKLRSmTDKYRLH (SEQ ID NO: 94) | Pal | | |
| 123 | i1 | AKLRSMTDKYRLH (SEQ ID NO: 95) | Pal | | |
| 124 | i1 | KALRSMTDKYRLH (SEQ ID NO: 96) | Pal | | |
| 125 | i1 | KKARSMTDKYRLH (SEQ ID NO: 97) | Pal | | |
| 126 | i1 | KKLASMTDKYRLH (SEQ ID NO: 98) | Pal | | |
| 127 | i1 | KKLRAMTDKYRLH (SEQ ID NO: 99) | Pal | | |
| 128 | i1 | KKLRSATDKYRLH (SEQ ID NO: 100) | Pal | | |
| 129 | i1 | AGYQKKLRSMTDKYRL (SEQ ID NO: 101) | Pal | | |
| 130 | i1 | MAYQKKLRSMTDKYRL (SEQ ID NO: 102) | Pal | | |
| 131 | i1 | MGAQKKLRSMTDKYRL (SEQ ID NO: 103) | Pal | | |
| 132 | i1 | MGYAKKLRSMTDKYRL (SEQ ID NO: 104) | Pal | | |
| 133 | i1 | MGYQAKLRSMTDKYRL (SEQ ID NO: 105) | Pal | | |
| 134 | i1 | MGYQKALRSMTDKYRL (SEQ ID NO: 106) | Pal | | |
| 135 | i1 | MGYQKKARSMTDKYRL (SEQ ID NO: 107) | Pal | | |

TABLE 6 -continued

CXCR4 i1 loop compounds

| No. | Loop | Sequence | Lipid | Comments | MW |
|---|---|---|---|---|---|
| 136 | i1 | MGYQKKLASMT DKYRL (SEQ ID NO: 108) | Pal | | |
| 137 | i1 | KKLRSMTDKYR LH (SEQ ID NO: 42) | Myr | | |
| 138 | i1 | KKLRSMTDKYR LH (SEQ ID NO: 42) | Lca | | |
| 139 | i1 | KKLRSMADKYR LH (SEQ ID NO: 109) | Pal | | |
| 140 | i1 | KKLRSMTAKYR LH (SEQ ID NO: 110) | Pal | | |
| 141 | i1 | KKLRSMTDAYR LH (SEQ ID NO: 111) | Pal | | |
| 142 | i1 | KKLRSMTDKAR LH (SEQ ID NO: 112) | Pal | | |
| 143 | i1 | KKLRSMTDKYA LH (SEQ ID NO: 113) | Pal | | |
| 144 | i1 | KKLRSMTDKYR AH (SEQ ID NO: 114) | Pal | | |
| 145 | i1 | KKLRSMTDKYR LA (SEQ ID NO: 115) | Pal | | |
| 146 | i1 | MGYQKKLRAMT DKYRL (SEQ ID NO: 116) | Pal | | |
| 147 | i1 | MGYQKKLRSAT DKYRL (SEQ ID NO: 117) | Pal | | |
| 148 | i1 | MGYQKKLRSMA DKYRL (SEQ ID NO: 118) | Pal | | |
| 149 | i1 | MGYQKKLRSMT AKYRL (SEQ ID NO: 119) | Pal | | |
| 150 | i1 | MGYQKKLRSMT DAYRL (SEQ ID NO: 120) | Pal | | |
| 151 | i1 | MGYQKKLRSMT DKARL(SEQ ID NO: 121) | Pal | | |
| 152 | i1 | MGYQKKLRSMT DKYAL (SEQ ID NO: 122) | Pal | | |
| 153 | i1 | MGYQKKLRSMT DKYRA (SEQ ID NO: 123) | Pal | | |
| 154 | i1 | KKLRSMtDKYRL H (SEQ ID NO: 124) | Pal | | |
| 155 | i1 | KKLRSMTdKYRL H (SEQ ID NO: 125) | Pal | | |
| 156 | i1 | KKLRSMTDKYrL H (SEQ ID NO: 126) | Pal | | |
| 157 | i1 | KKLRSMTDKYRl H (SEQ ID NO: 127) | Pal | | |
| 158 | i1 | KKLRSMTDKYR Lh (SEQ ID NO: 128) | Pal | | |
| 159 | i1 | MGYQKKLRSMT DKYR1 (SEQ ID NO: 381) | Pal | | |
| 160 | i1 | MGYQKKLRSMT DKYrL (SEQ ID NO: 129) | Pal | | |
| 161 | i1 | MGYQKKLRSMT DKyRL (SEQ ID NO: 130) | Pal | | |

TABLE 6 -continued

CXCR4 i1 loop compounds

| No. | Loop | Sequence | Lipid | Comments | MW |
|---|---|---|---|---|---|
| 162 | i1 | MGYQKKLRSMTDkYRL (SEQ ID NO: 131) | Pal | | |
| 163 | i1 | MGYQKKLRSMTdKYRL (SEQ ID NO: 132) | Pal | | |
| 164 | i1 | MGYQKKLRSMtDKYRL (SEQ ID NO: 133) | Pal | | |
| 165 | i1 | mGYQKKLRSMTDKYRL (SEQ ID NO: 134) | Pal | | |
| 166 | i1 | MGyQKKLRSMTDKYRL (SEQ ID NO: 135) | Pal | | |
| 167 | | MGYqKKLRSMTDKYRL (SEQ ID NO: 136) | Pal | | |
| 168 | i1 | MGYQkKLRSMTDKYRL (SEQ ID NO: 137) | Pal | | |
| 169 | i1 | MGYQKkLRSMTDKYRL (SEQ ID NO: 138) | Pal | | |
| 170 | i1 | MGYQKKlRSMTDKYRL (SEQ ID NO: 139) | Pal | | |
| 171 | i1 | MGYQKKLrSMTDKYRL (SEQ ID NO: 140) | Pal | | |
| 172 | | MGYQKKLRsMTDKYRL (SEQ ID NO: 141) | Pal | | |
| 173 | i1 | MGYQKKLRSmTDKYRL (SEQ ID NO: 142) | Pal | | |
| 174 | i1 | KKLRSMTDKYRlS (SEQ ID NO: 143) | Pal | | |
| 175 | i1 | MGYQKKLRSMTDKYRL (SEQ ID NO: 82) | Pal | | |
| 176 | i1 | MGYQKKLRSMTDKYRL (SEQ ID NO: 82) | Elaidic | | |
| 177 | i1 | MGYQKKLRSMTDKYRL (SEQ ID NO: 82) | Oleic | | |
| 178 | i1 | MGYQKKLRSMTDKYRL (SEQ ID NO: 82) | 3-(dodecyloxy) propanoate | | |
| 179 | i1 | MGYQKKLRSMTDKYRL (SEQ ID NO: 82) | 16-hydroxy-Pal | | |
| 180 | i1 | KKLRSMTDKYRLH (SEQ ID NO: 42) | Pal | | |
| 181 | i1 | KKLRSMTDKYRLH (SEQ ID NO: 42) | 3-(dodecyloxy)propanoate | | |
| 182 | i1 | KKLRSMTDKYRLH (SEQ ID NO:42) | 16-hydroxy-Pal | | |
| 183 | i1 | KKLRSMTDKYRLH (SEQ ID NO: 42) | | | |
| 184 | i1 | KKLRSMTDKYRLH (SEQ ID NO: 42) | | | |
| 185 | i1 | KKLRSMTDKYRLH (SEQ ID NO: 42) | | | |

TABLE 6 -continued

CXCR4 i1 loop compounds

| No. | Loop | Sequence | Lipid | Comments | MW |
|---|---|---|---|---|---|
| 186 | i1 | MGYQKKLRSMT DKYRL (SEQ ID NO: 82) | | | |
| 187 | i1 | MGYQKKLRSMT DKYRL (SEQ ID NO: 82) | | | |
| 188 | i1 | MGYQKKLRSMT DKYRL (SEQ ID NO: 82) | | | |
| 189 | i1 | MGYQKKLRSpT DKYRL (SEQ ID NO: 144) | Pal | | |
| 190 | i1 | MGYQKKLRpMT DKYRL (SEQ ID NO: 145) | Pal | | |
| 191 | i1 | MGYQKKLpSMT DKYRL (SEQ ID NO: 146) | Pal | | |
| 192 | i1 | MGYQKKpRSMT DKYRL (SEQ ID NO: 147) | Pal | | |
| 193 | i1 | MGYQKKLRSMP DKYRL (SEQ ID NO: 148) | Pal | | |
| 194 | i1 | XGYQKKRLSXT DKYRL (SEQ ID NO: 382) X = noreleucine | $C_{15}H_{31}(CO)$ | | |

TABLE 7

CXCR4 it loop compound structures

| Comp. # | Structure |
|---|---|
| 1 | 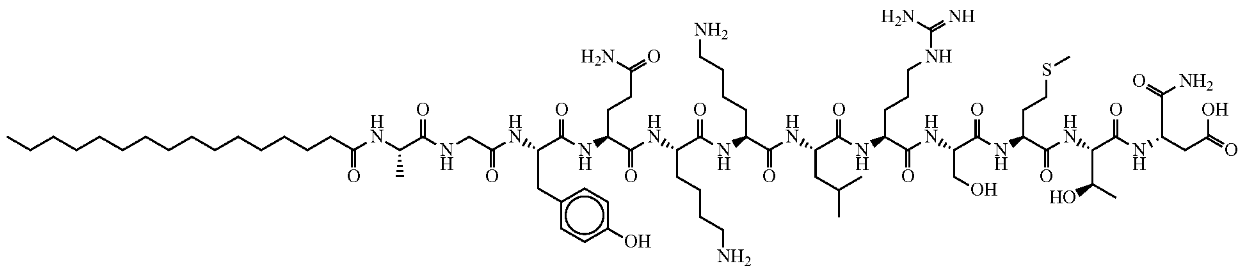 |
| 2 | 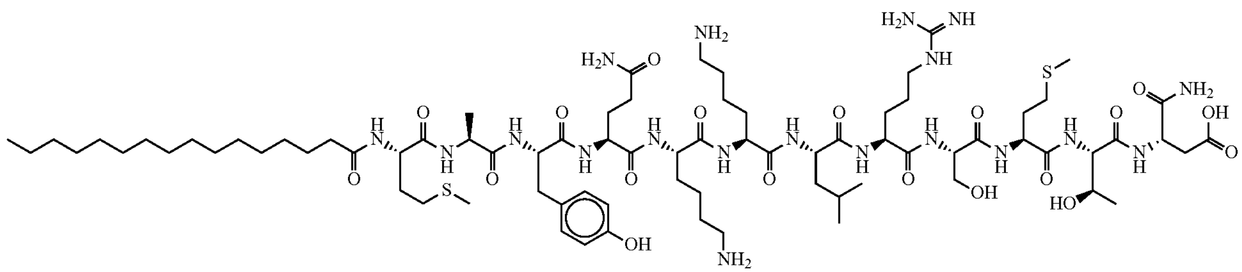 |
| 3 | 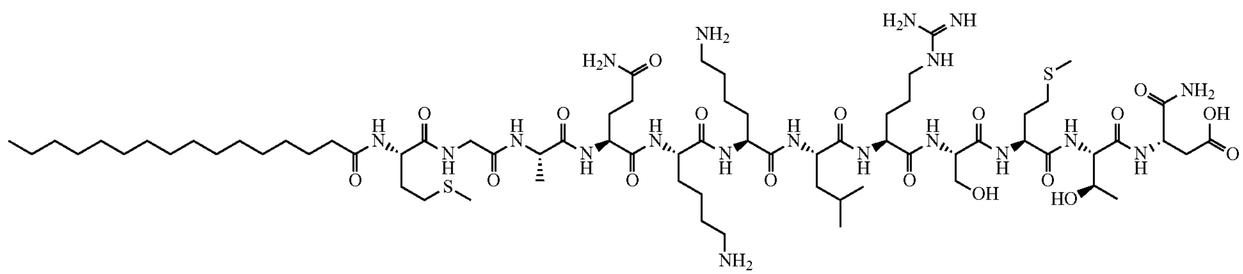 [SMILES: CCCCCCCCCCCCCCCC(=O)N[C@@H](CCSC)C(=O)NCC(=O)N[C@@H](C)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(N)=O)[C@@H](C)O] |

TABLE 7-continued
CXCR4 it loop compound structures
| Comp. # | Structure |
|---|---|
| 4 | 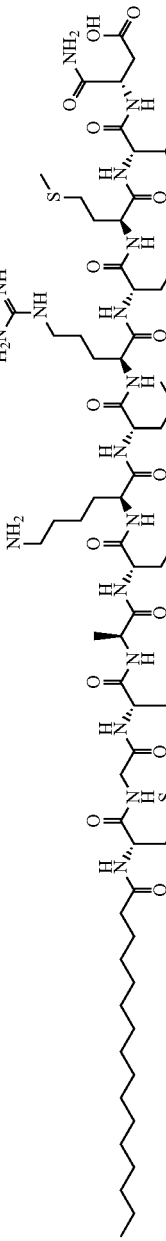 |
| 5 | 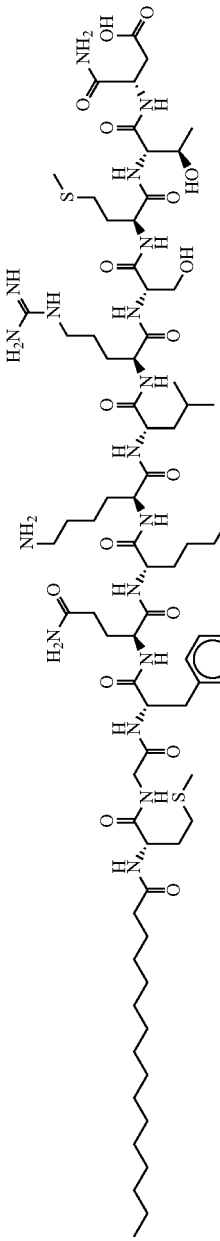 |
| 6 | 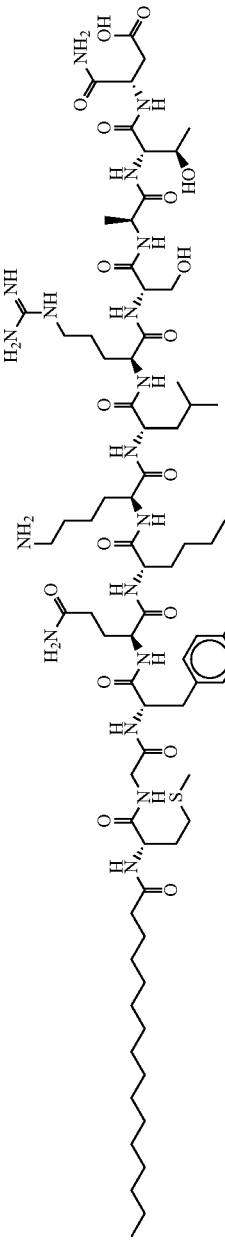 |

TABLE 7-continued

CXCR4 it loop compound structures

| Comp. # | Structure |
|---|---|
| 7 | 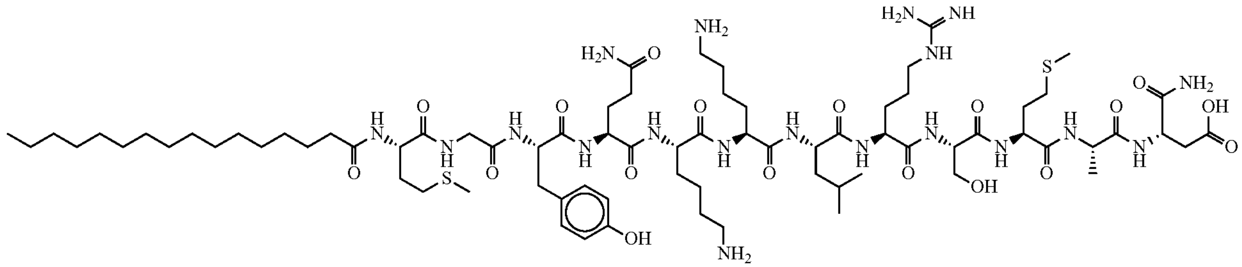 |
| 8 | 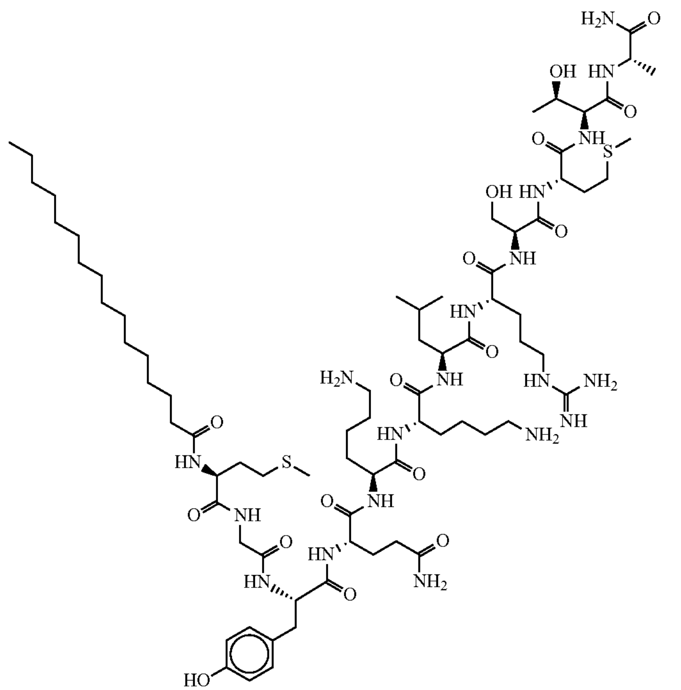 |

TABLE 7-continued

CXCR4 it loop compound structures

| Comp. # | Structure |
|---|---|
| 9 | 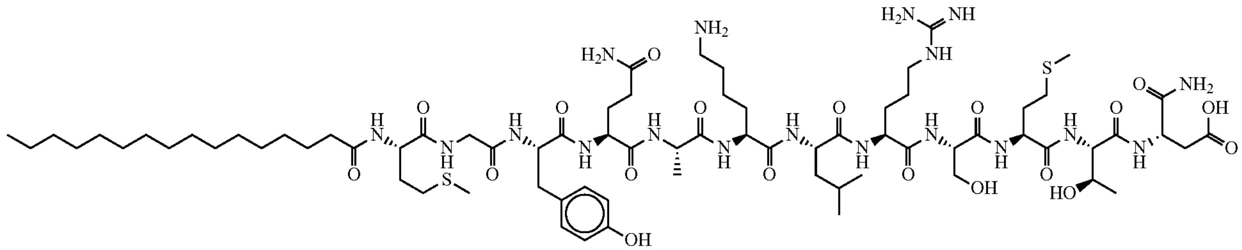 |
| 10 | 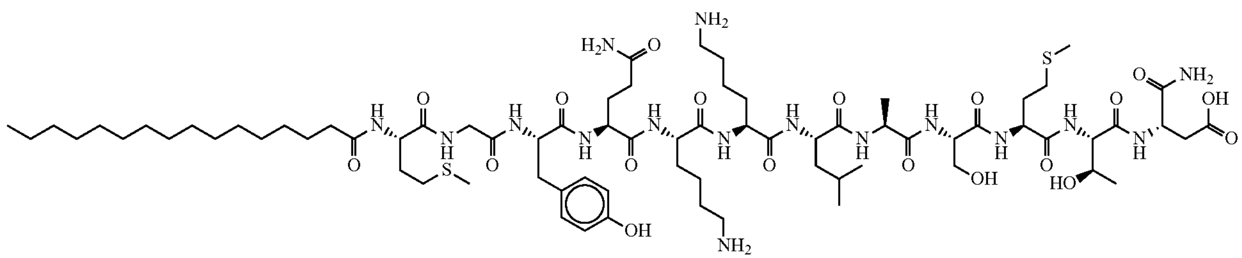 |
| 11 | 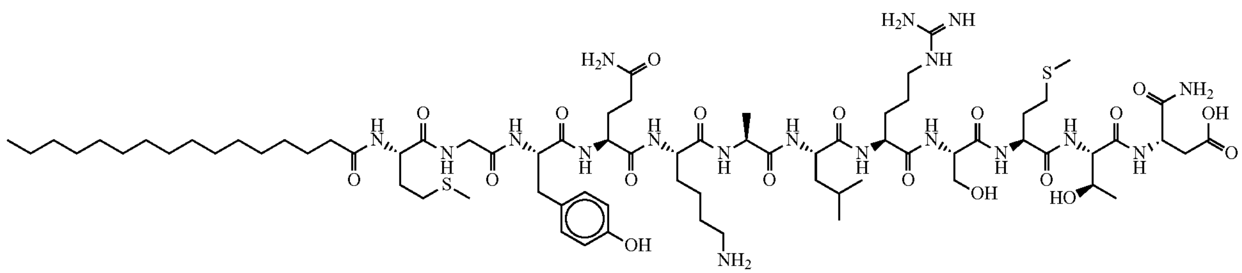 |

TABLE 7-continued

CXCR4 it loop compound structures

| Comp. # | Structure |
|---|---|
| 12 | 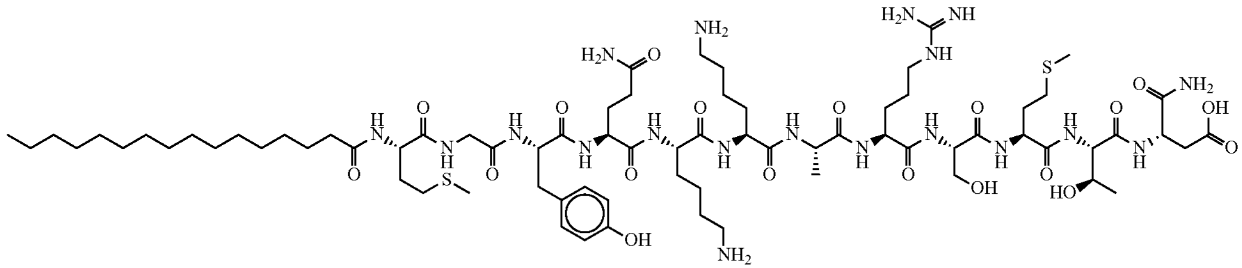 |
| 13 | 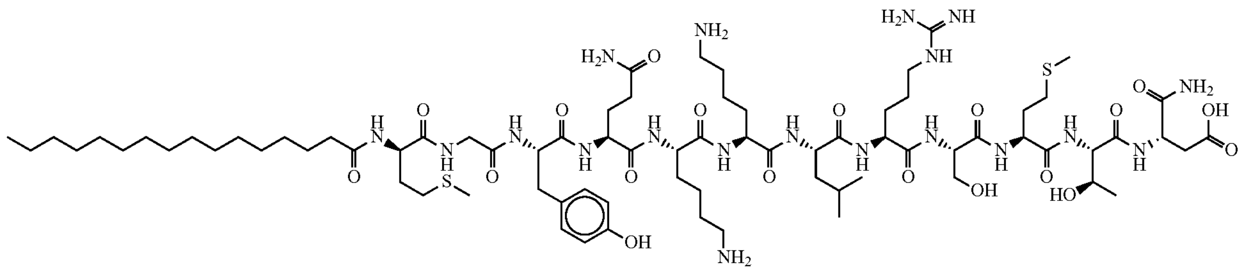 |
| 14 | 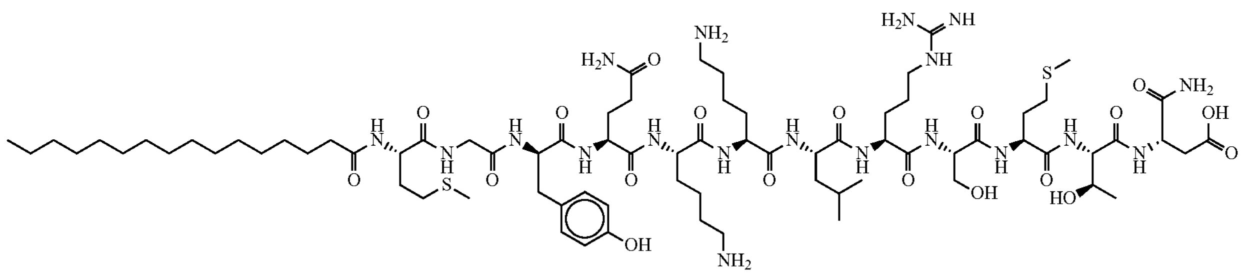 |

TABLE 7-continued

CXCR4 it loop compound structures

| Comp. # | Structure |
|---|---|
| 15 | 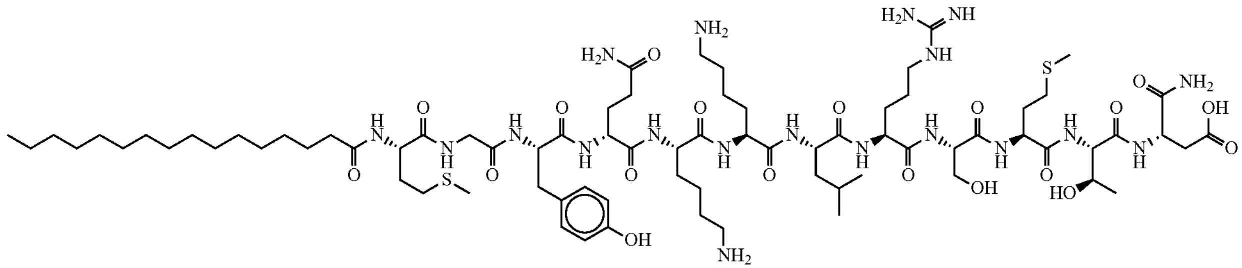 |
| 16 | 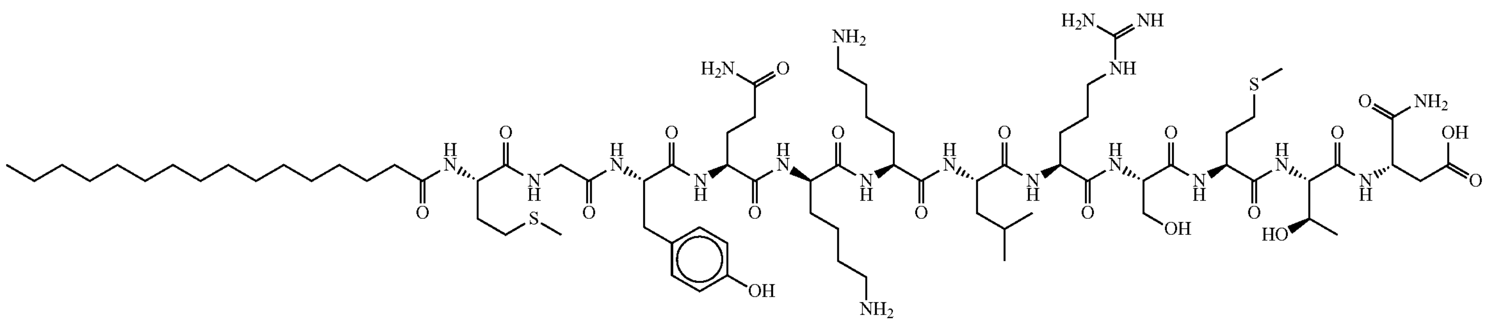 |
| 17 | 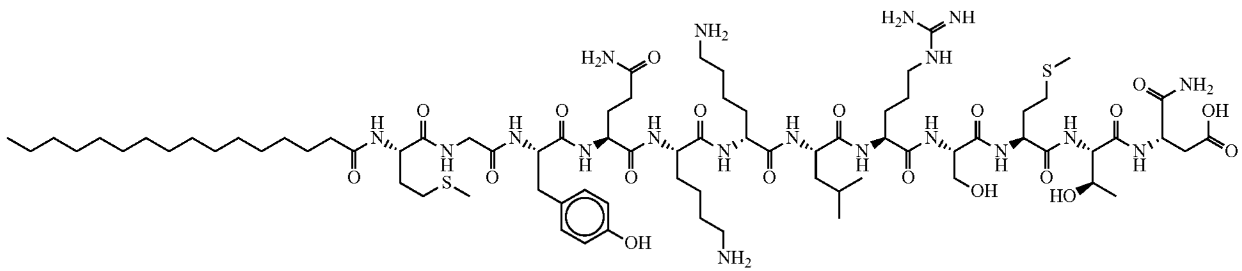 |

TABLE 7-continued

CXCR4 it loop compound structures

| Comp. # | Structure |
|---|---|
| 18 | 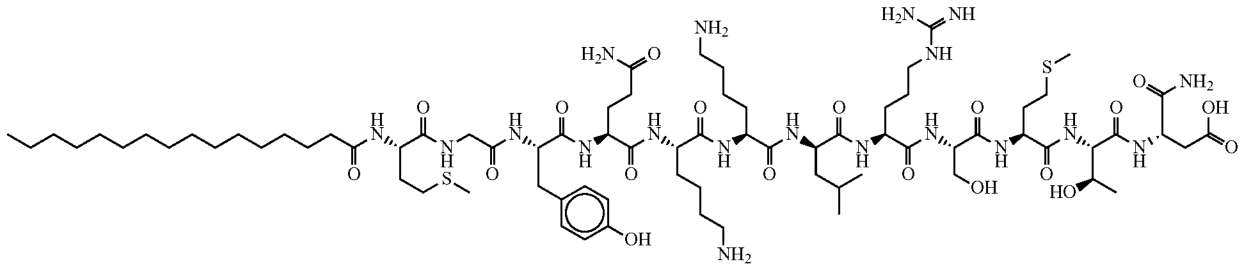 |
| 19 | 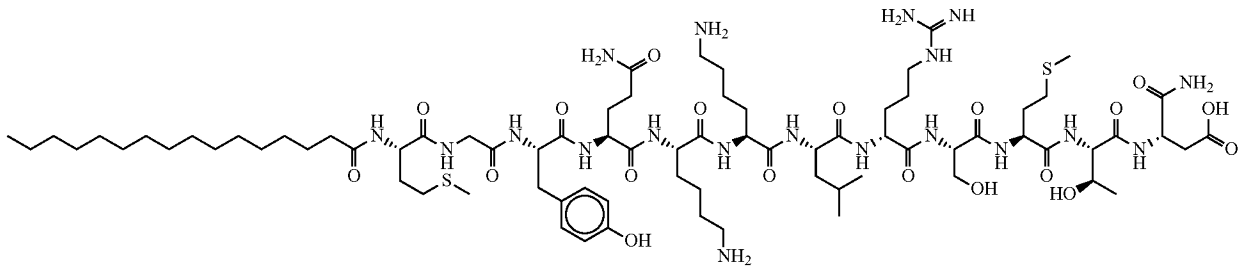 |
| 20 | 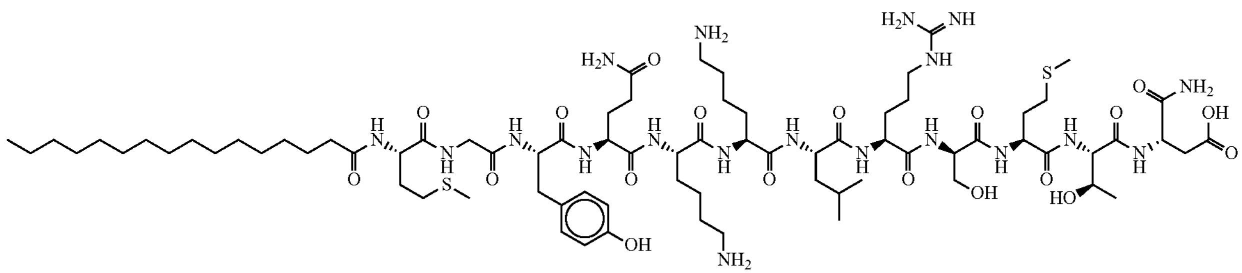 |

TABLE 7-continued

CXCR4 it loop compound structures

| Comp. # | Structure |
|---|---|
| 21 | 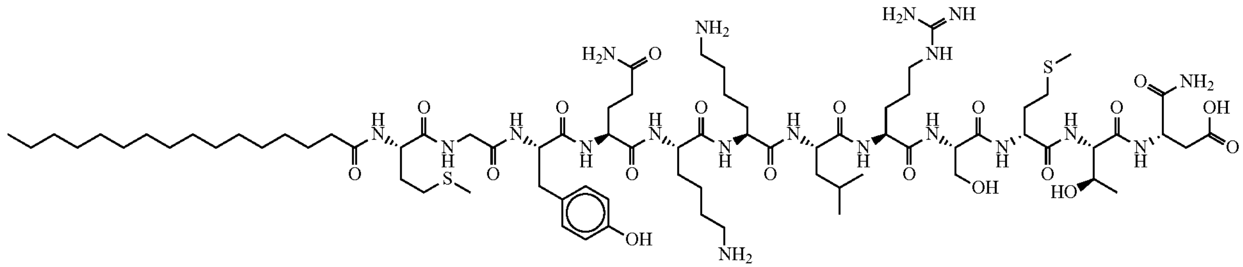 |
| 22 | 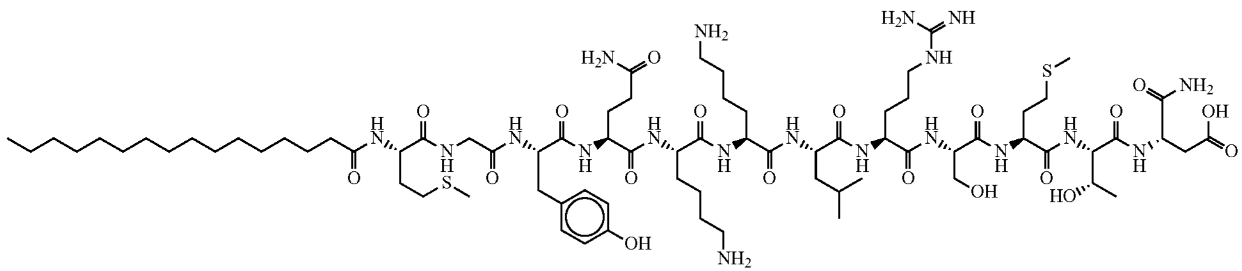 |
| 23 | 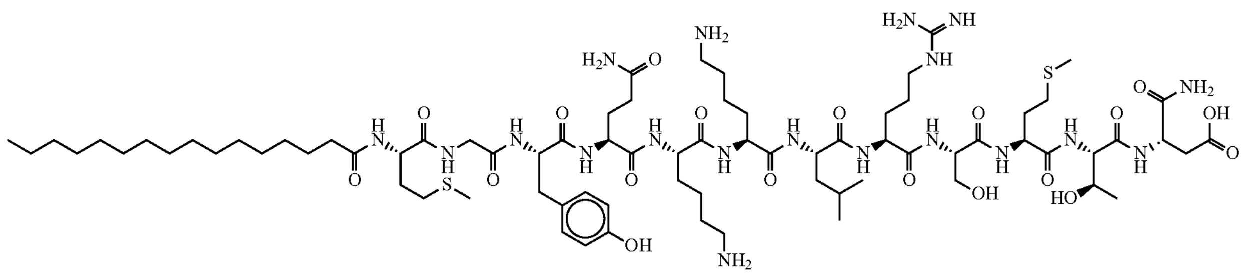 |

TABLE 7-continued

CXCR4 it loop compound structures

| Comp. # | Structure |
|---|---|
| 24 | 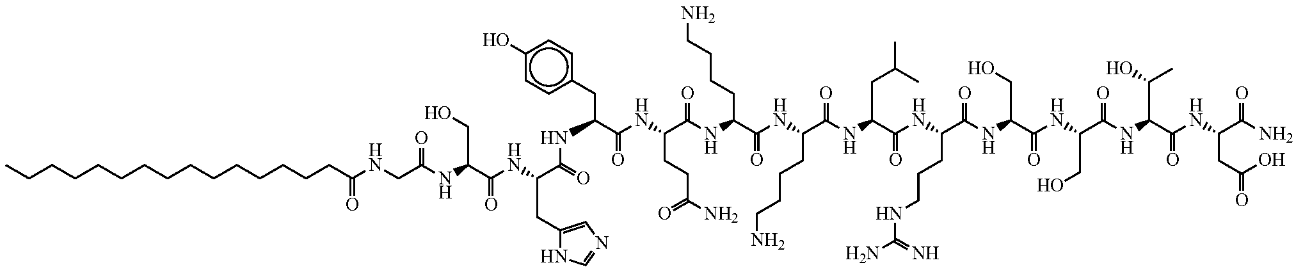 |
| 25 | 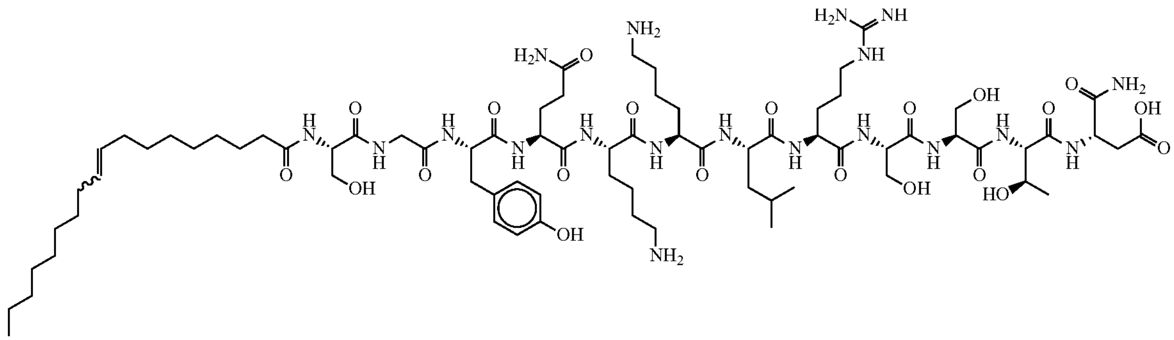 |
| 26 | 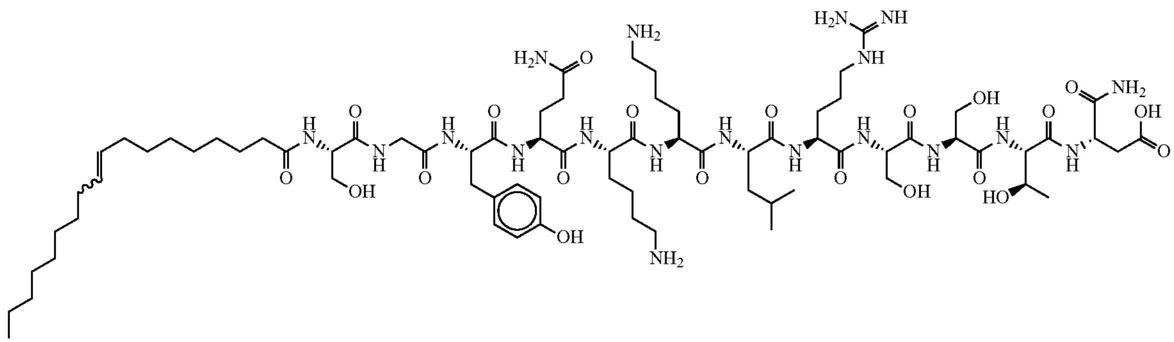 |

TABLE 7-continued

CXCR4 it loop compound structures

| Comp. # | Structure |
|---|---|
| 27 | 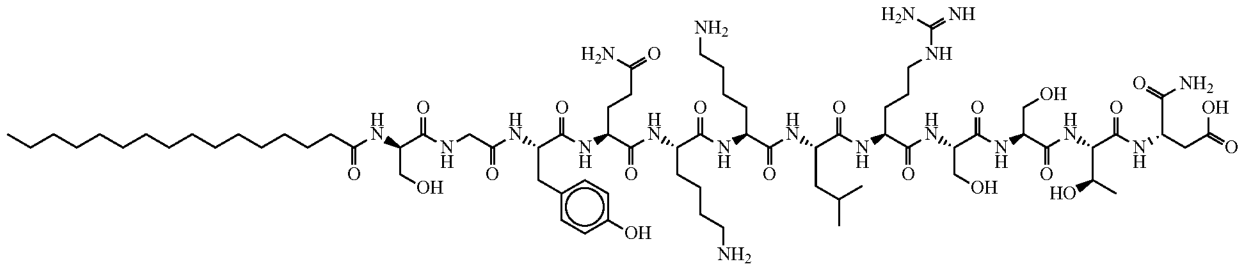 |
| 28 | 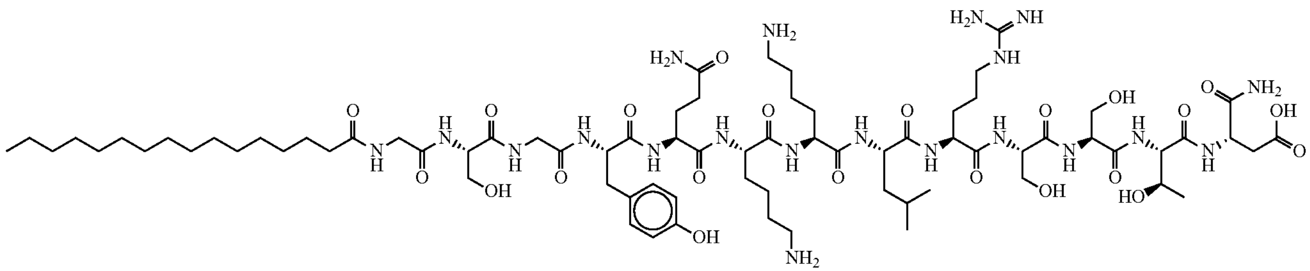 |
| 29 | 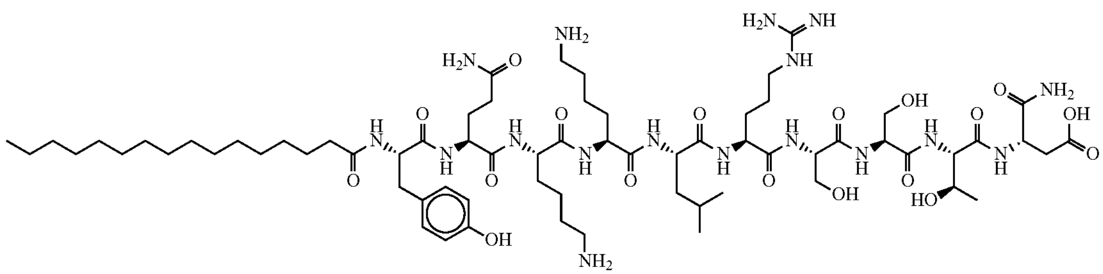 |

TABLE 7-continued

CXCR4 it loop compound structures

| Comp. # | Structure |
|---|---|
| 30 | 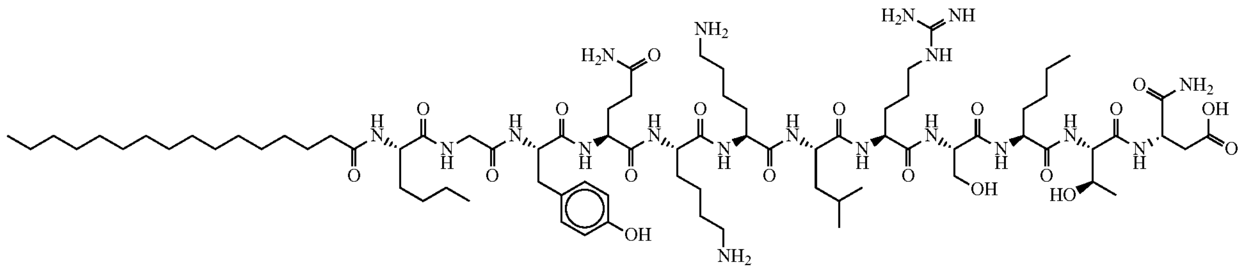 |
| 31 | 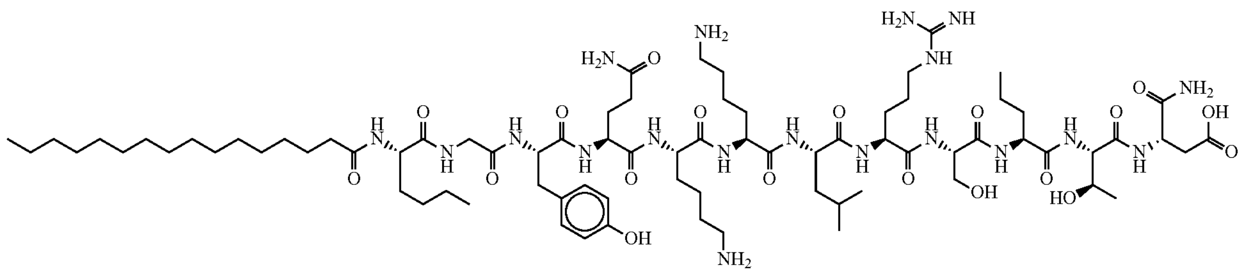 |
| 32 | 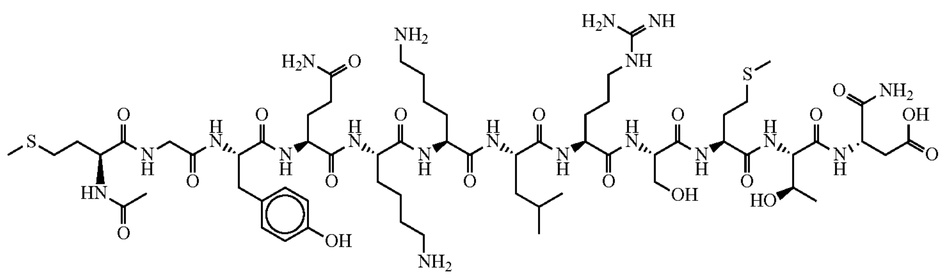 |

TABLE 7-continued

CXCR4 it loop compound structures

| Comp. # | Structure |
|---|---|
| 33 | 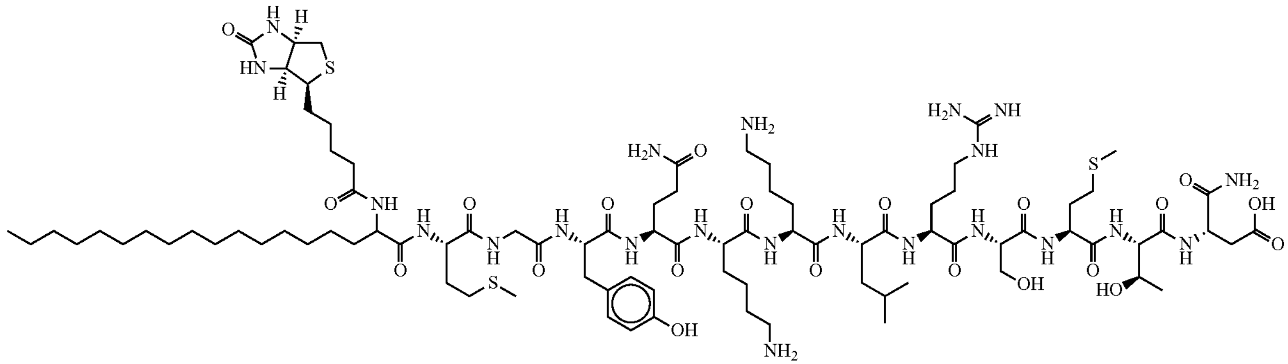 |
| 34 | 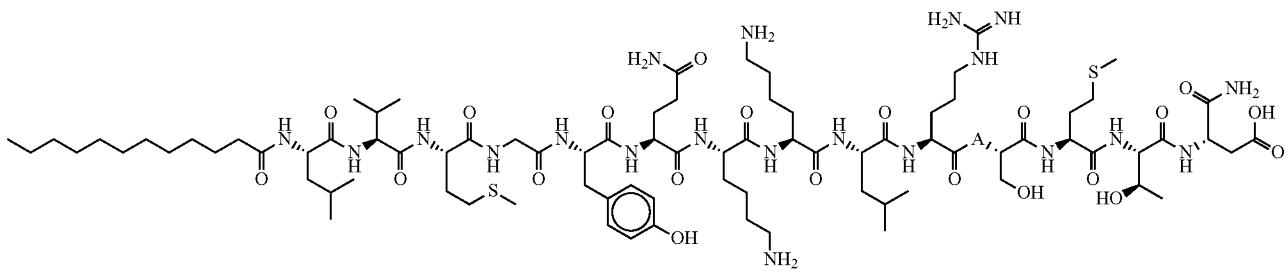 |
| 35 | 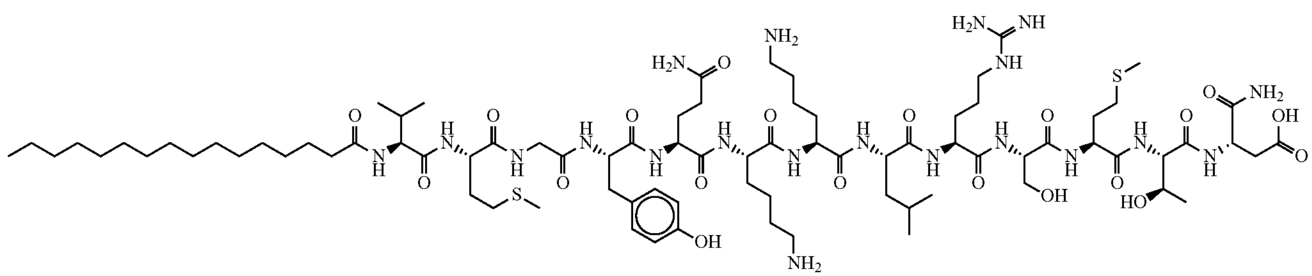 |

TABLE 7-continued
CXCR4 it loop compound structures
| Comp. # | Structure |
|---|---|
| 36 | 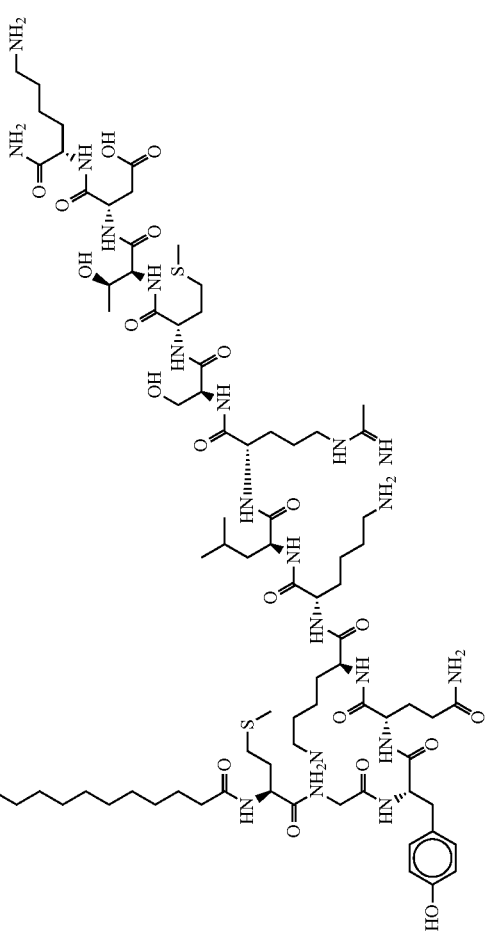 |
| 37 | 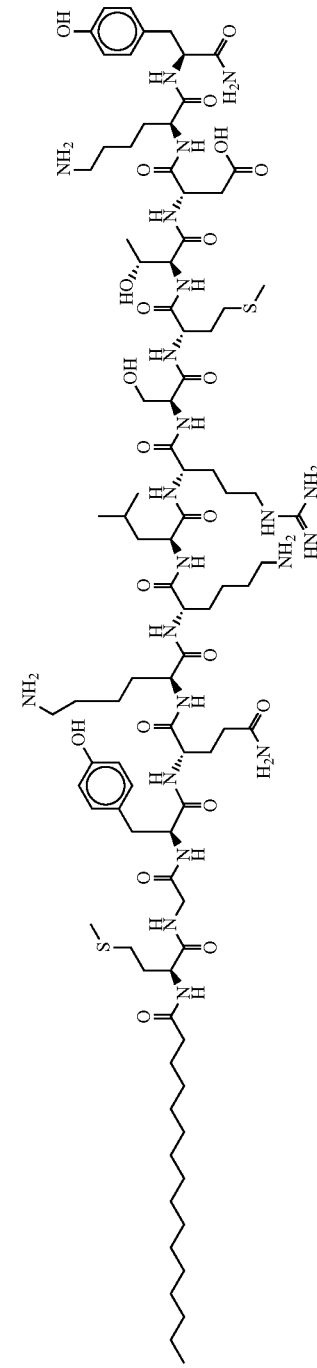 |

TABLE 7-continued

CXCR4 it loop compound structures

| Comp. # | Structure |
|---|---|
| 38 | 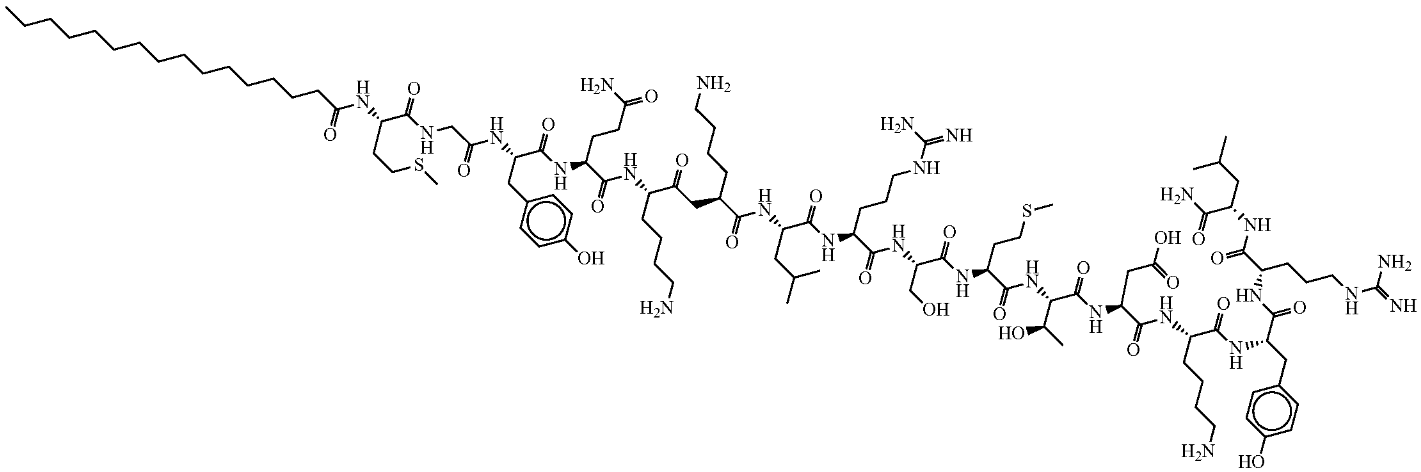 |
| 39 | 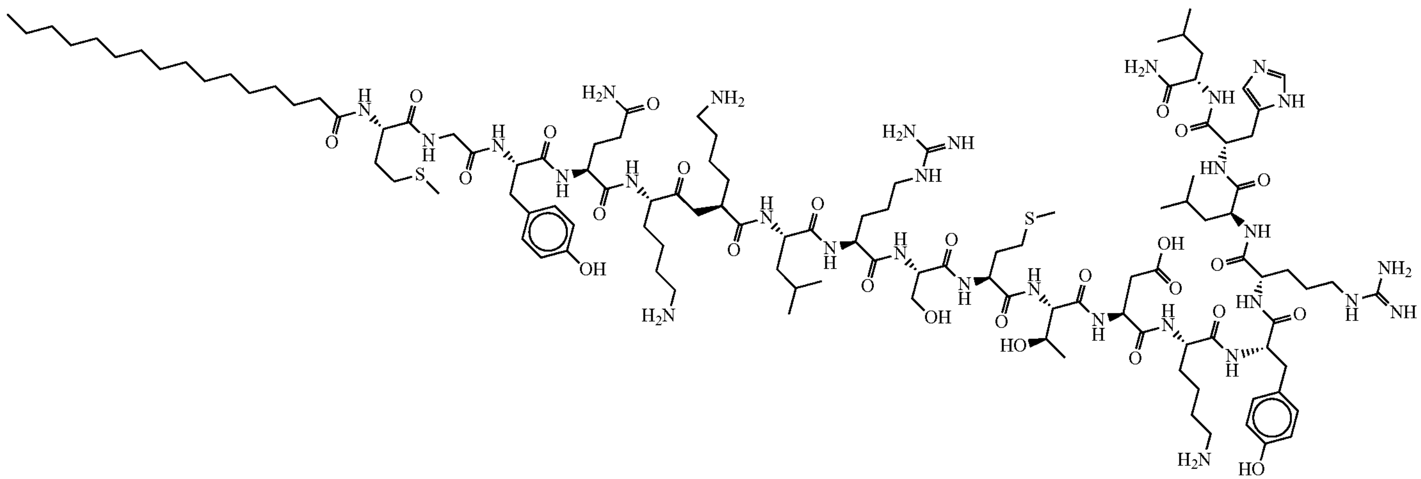 |

TABLE 7-continued
CXCR4 it loop compound structures
| Comp. # | Structure |
|---|---|
| 40 | 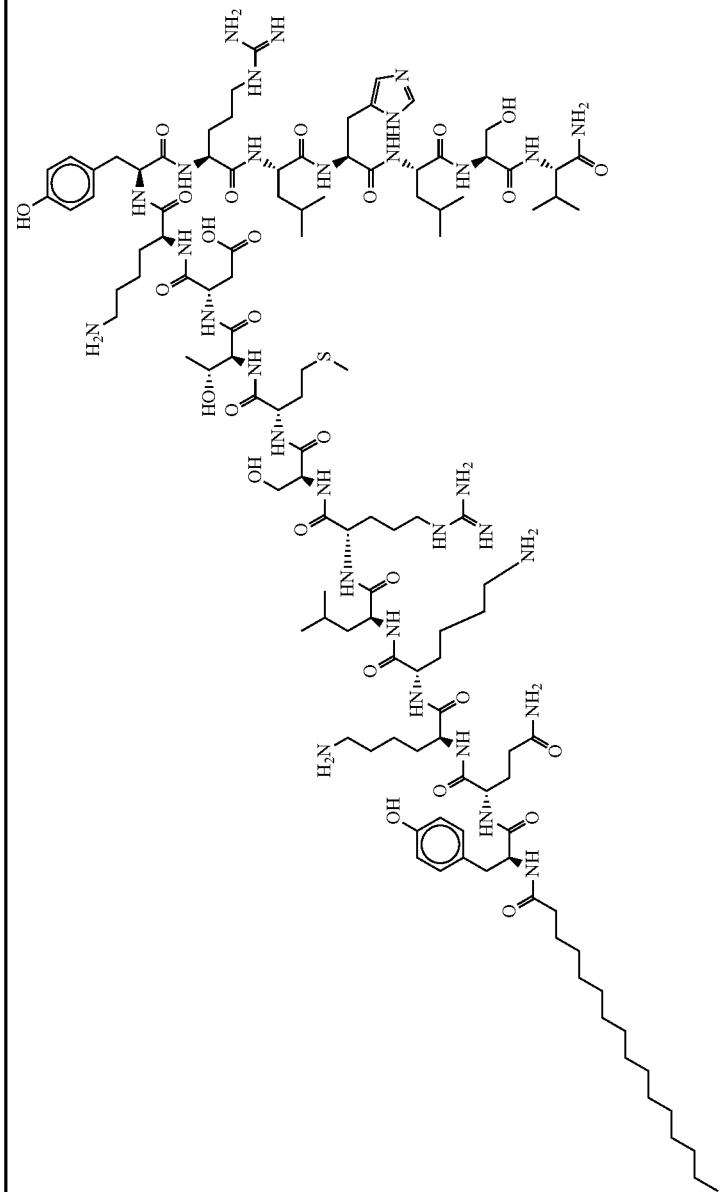 |

TABLE 7-continued
CXCR4 it loop compound structures
| Comp. # | Structure |
|---|---|
| 41 | 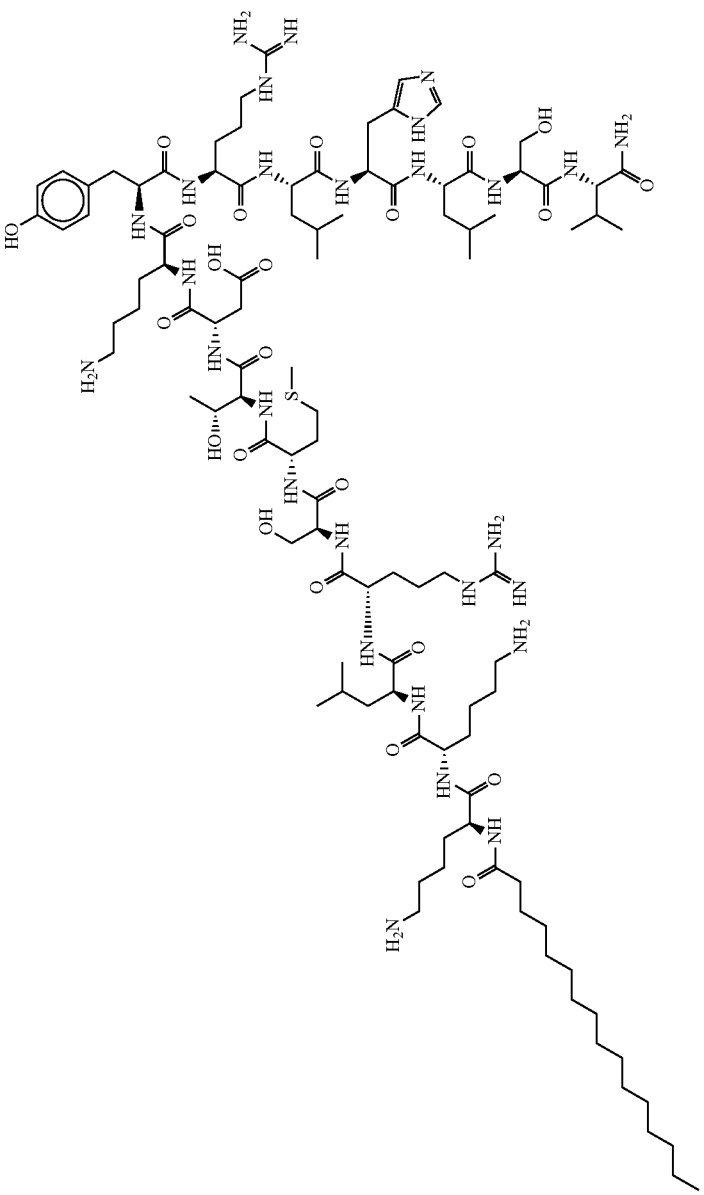 |

TABLE 7-continued
CXCR4 it loop compound structures
| Comp. # | Structure |
|---|---|
| 42 | 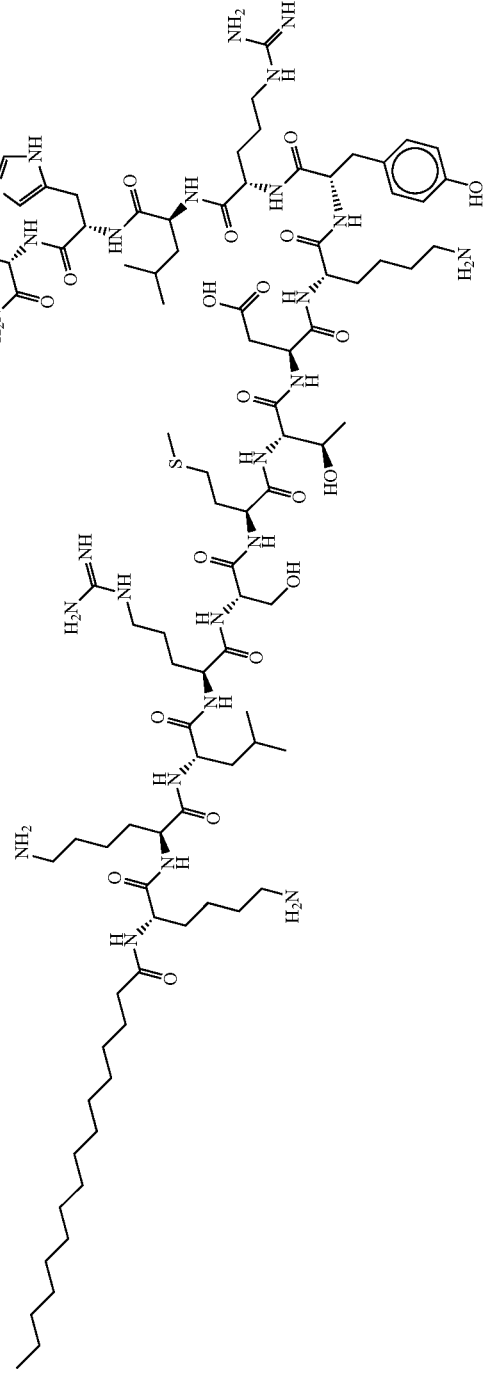 |

TABLE 7-continued

CXCR4 it loop compound structures

| Comp. # | Structure |
|---|---|
| 43 | (structure) |
| 44 | (structure) |

TABLE 7-continued

CXCR4 it loop compound structures

| Comp. # | Structure |
|---|---|
| 45 | 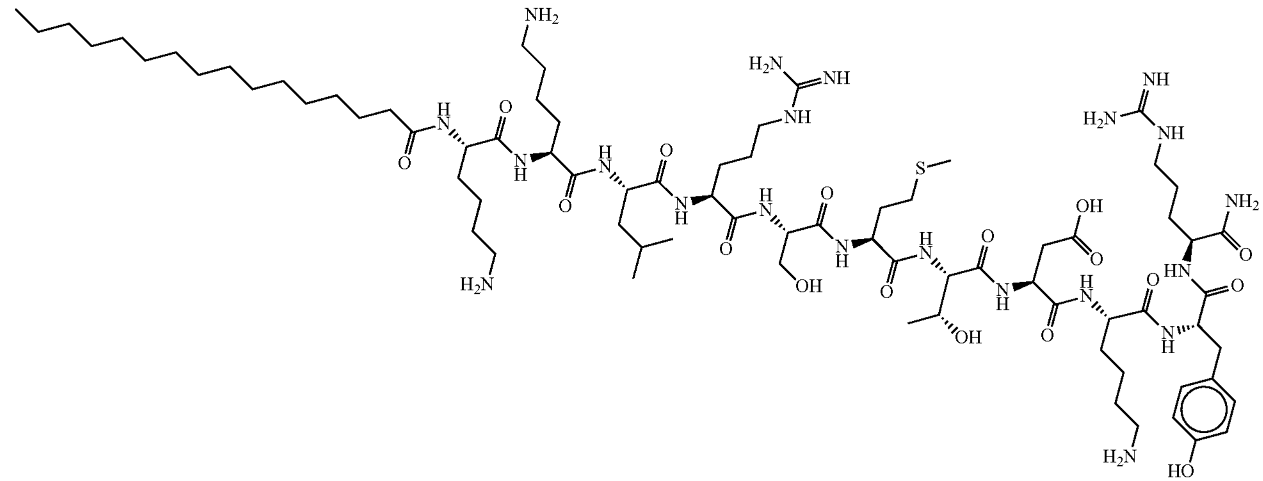 |
| 46 | 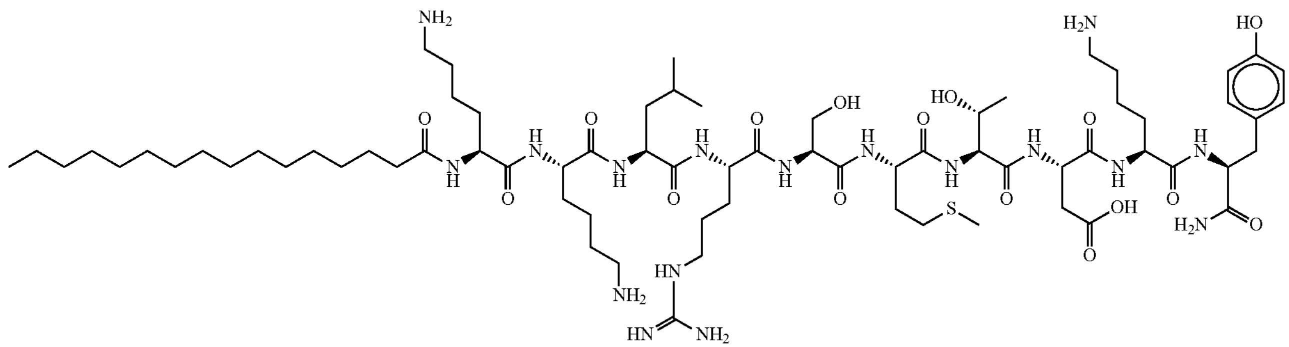 |

TABLE 7-continued
CXCR4 it loop compound structures
| Comp. # | Structure |
|---|---|
| 47 | 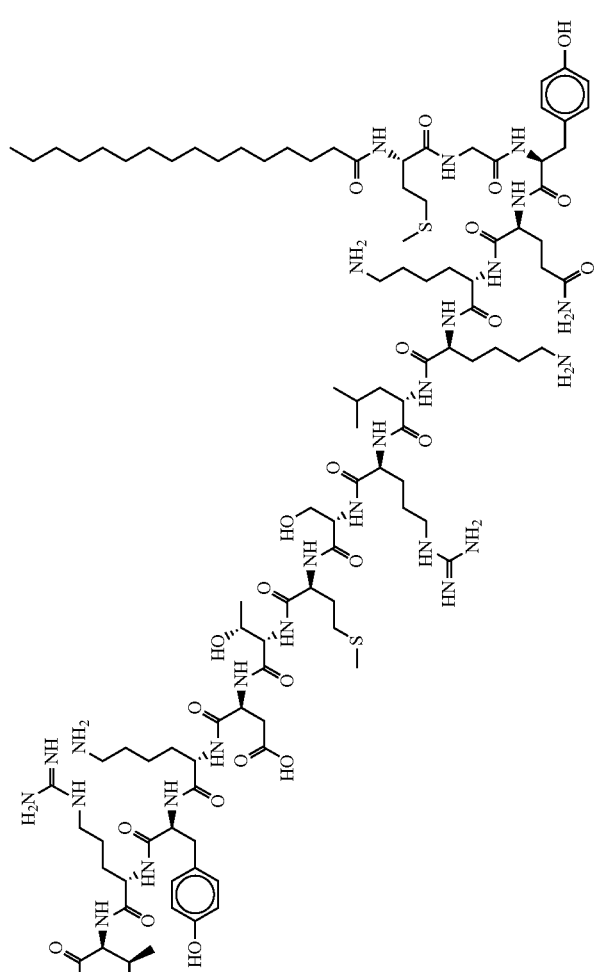 |

TABLE 7-continued

CXCR4 it loop compound structures

| Comp. # | Structure |
|---|---|
| 48 | 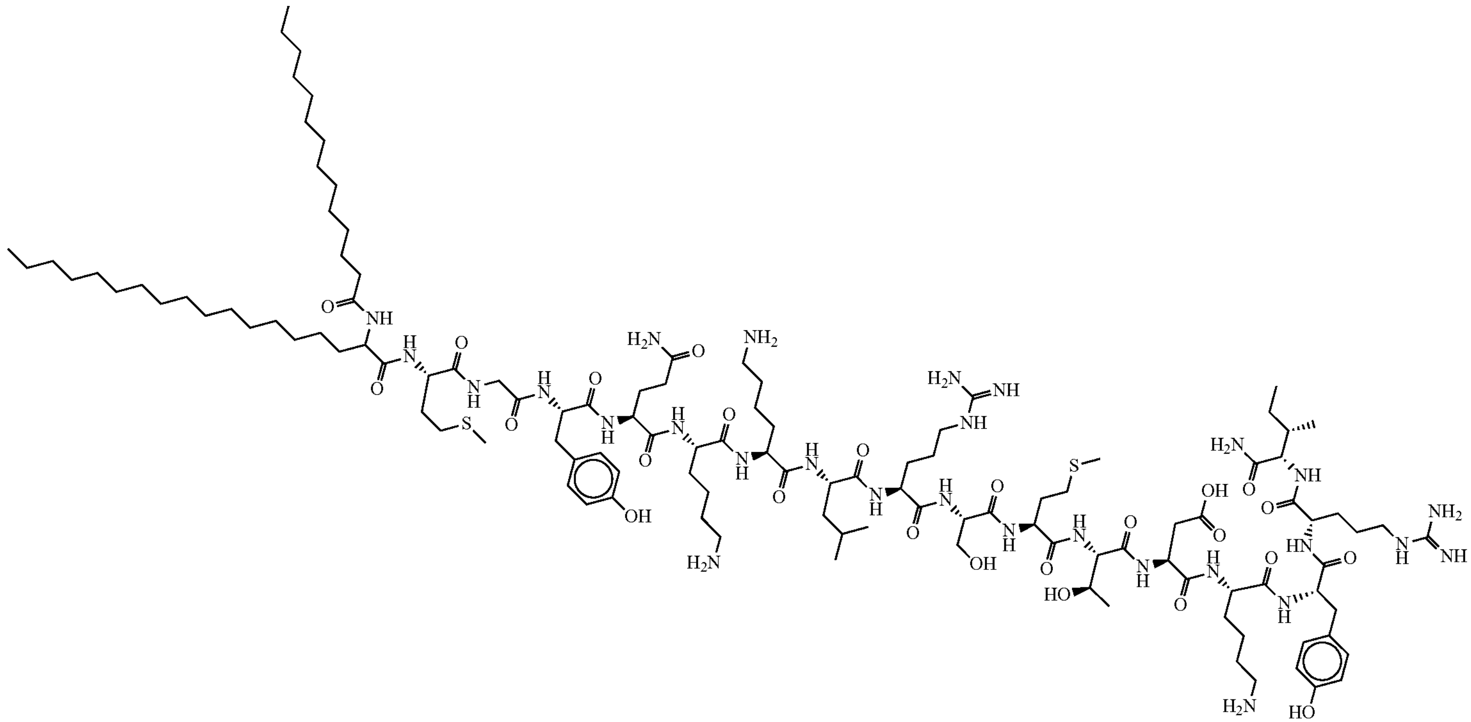 |

TABLE 7-continued

CXCR4 it loop compound structures

| Comp. # | Structure |
|---|---|
| 49 | 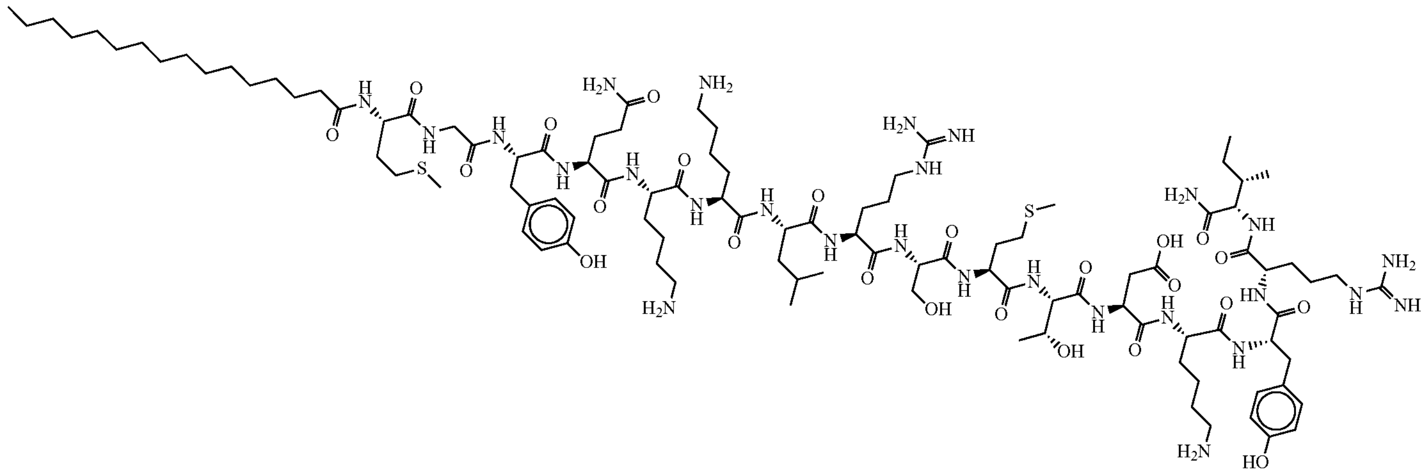 |
| 50 | 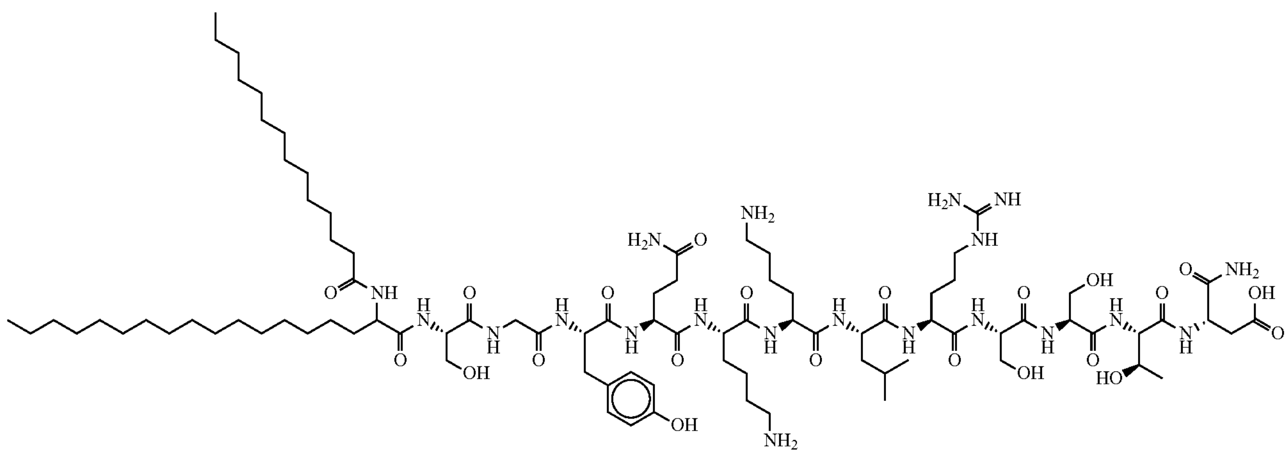 |

TABLE 7-continued
CXCR4 it loop compound structures
| Comp. # | Structure |
|---|---|
| 51 | 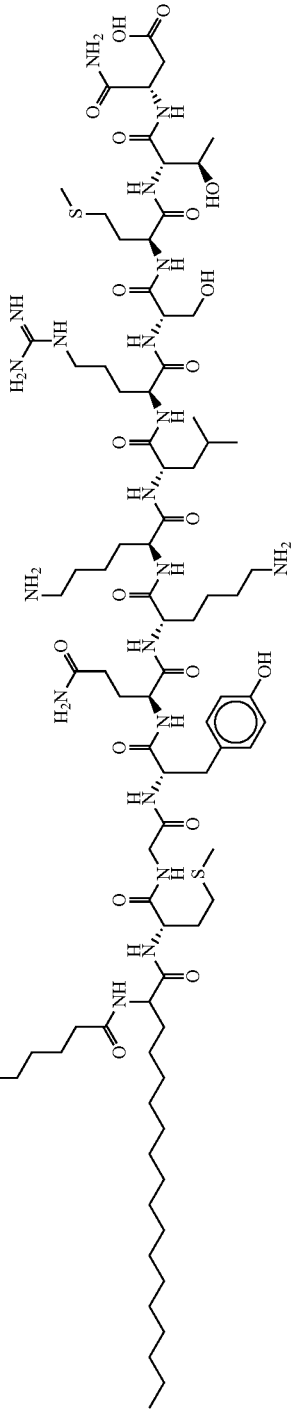 |

TABLE 7-continued

CXCR4 it loop compound structures

| Comp. # | Structure |
|---|---|
| 52 | 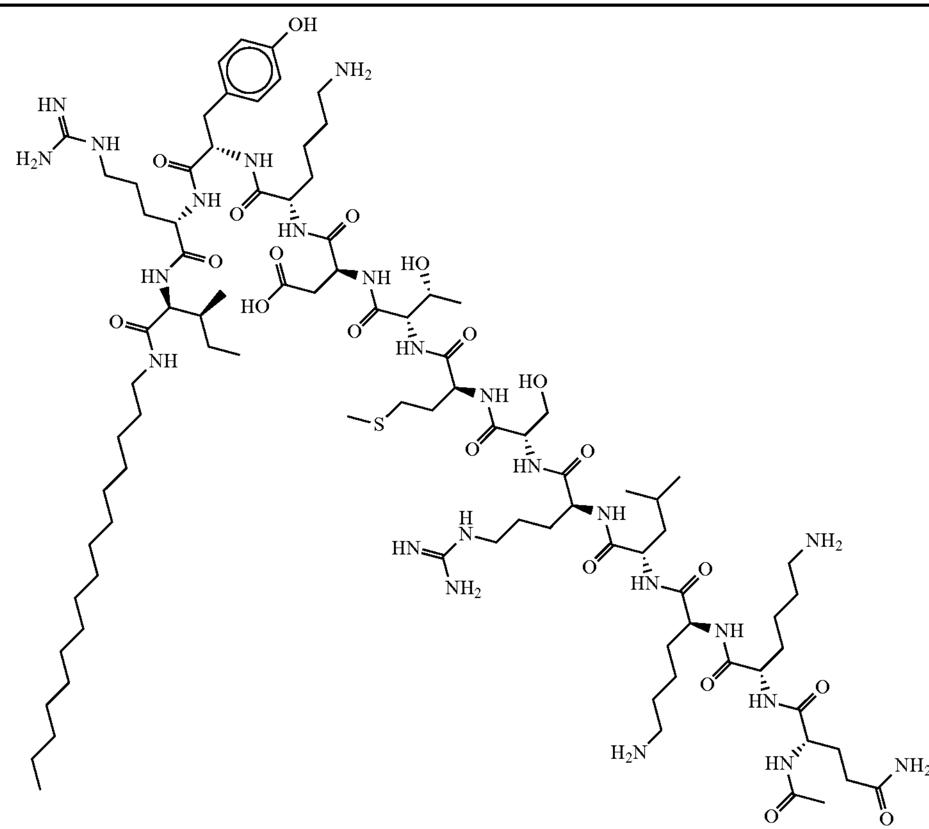 |

TABLE 7-continued
CXCR4 it loop compound structures
| Comp. # | Structure |
|---|---|
| 53 | 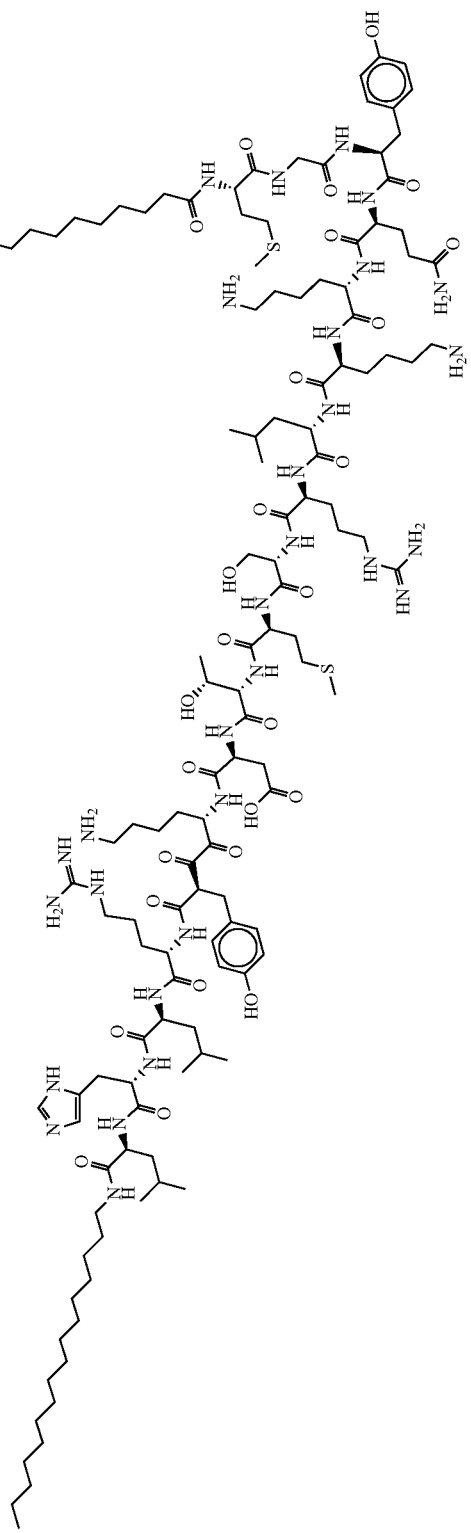 |

TABLE 7-continued
CXCR4 it loop compound structures
| Comp. # | Structure |
|---|---|
| 54 | 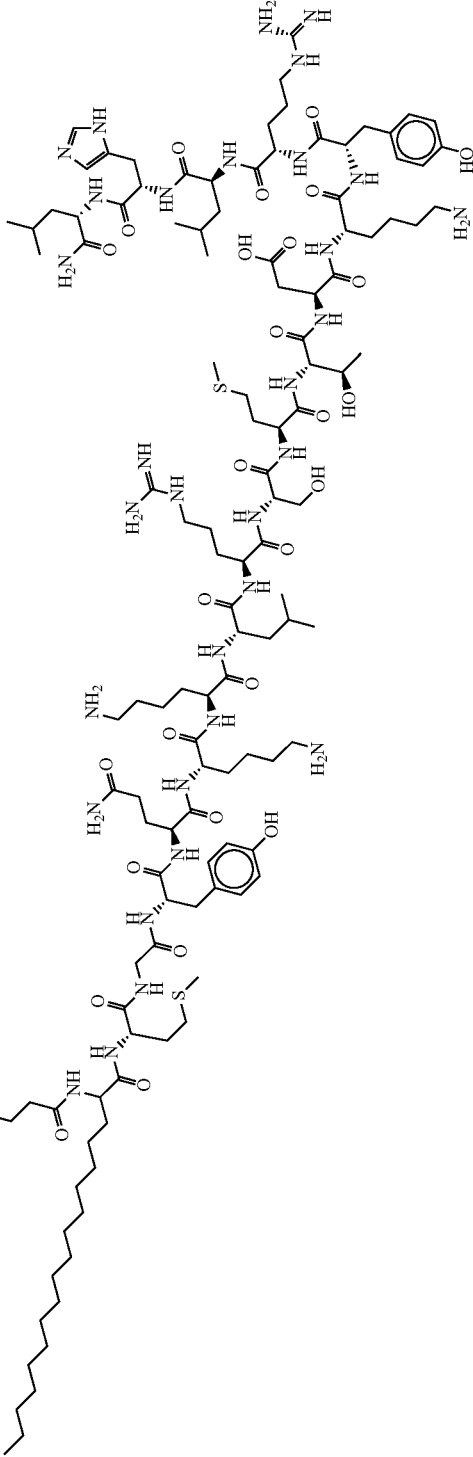 |

TABLE 7-continued
CXCR4 it loop compound structures
| Comp. # | Structure |
|---|---|
| 55 | 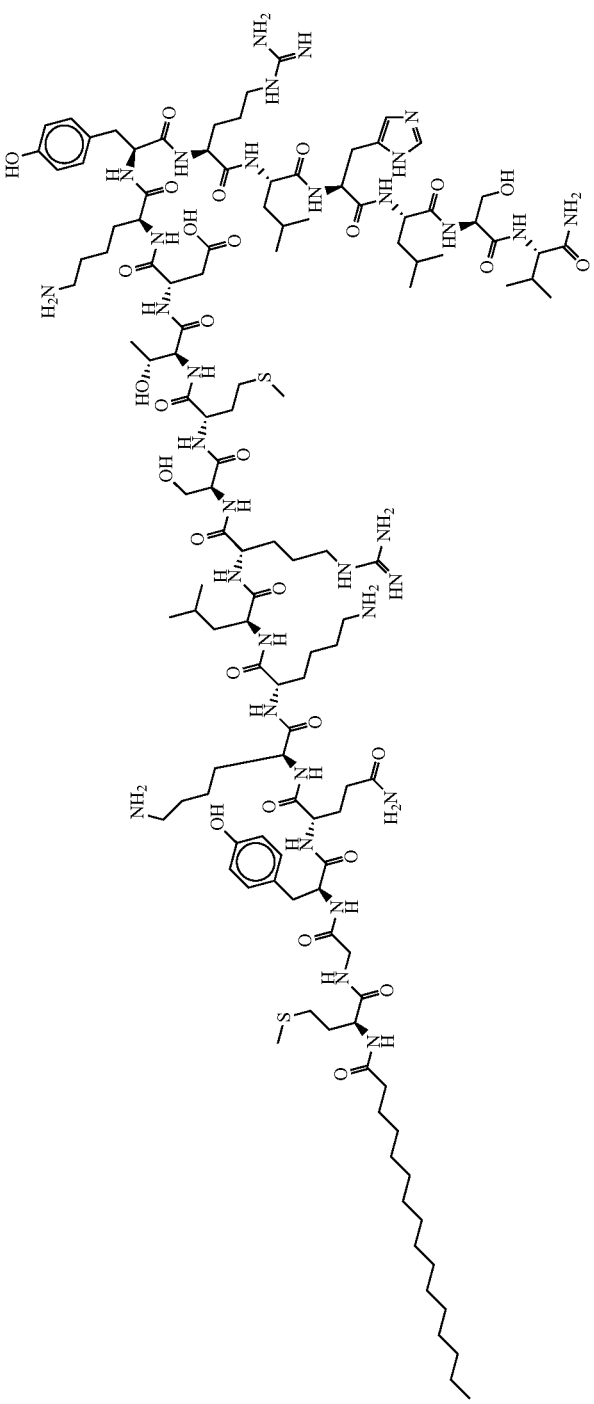 |

TABLE 7-continued
CXCR4 it loop compound structures
| Comp. # | Structure |
|---|---|
| 56 | 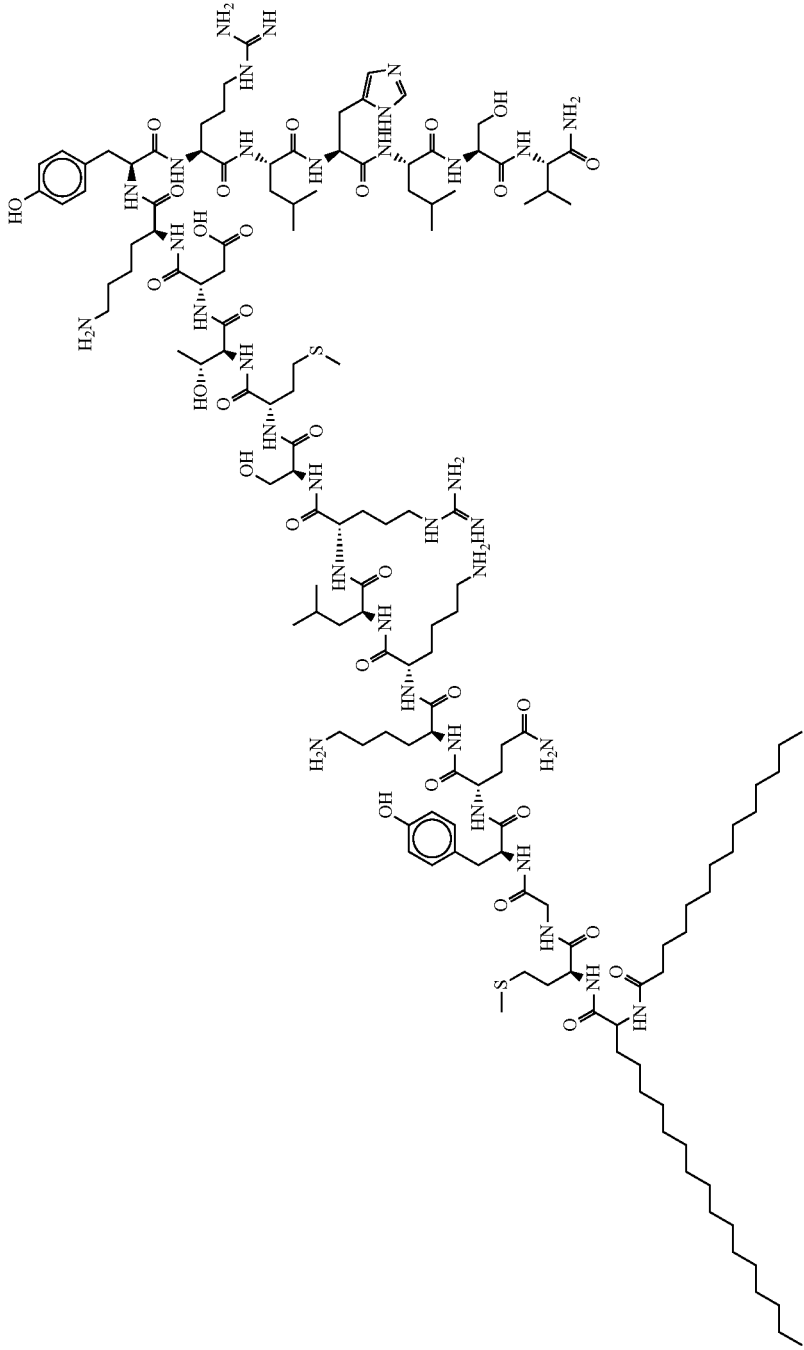 |

TABLE 7-continued

CXCR4 it loop compound structures

| Comp. # | Structure |
|---|---|
| 58 | 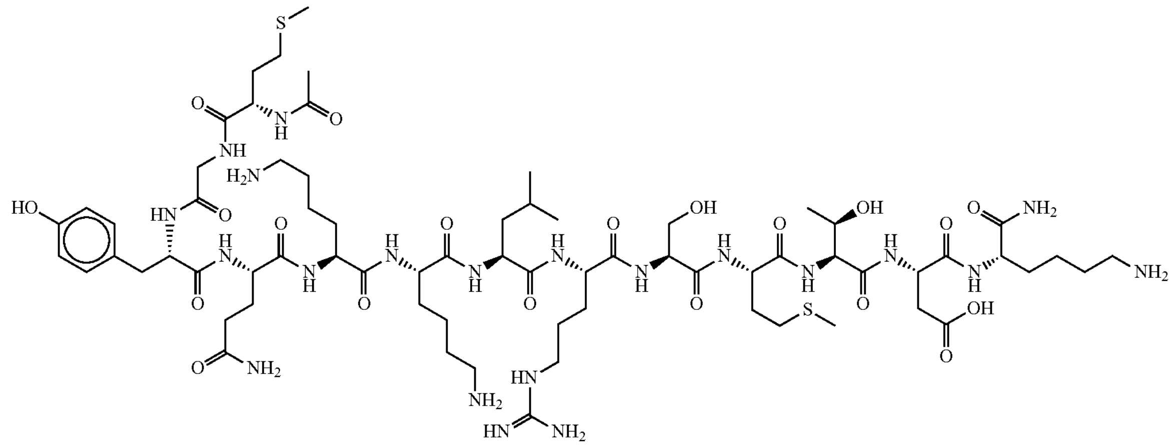 |
| 59 | 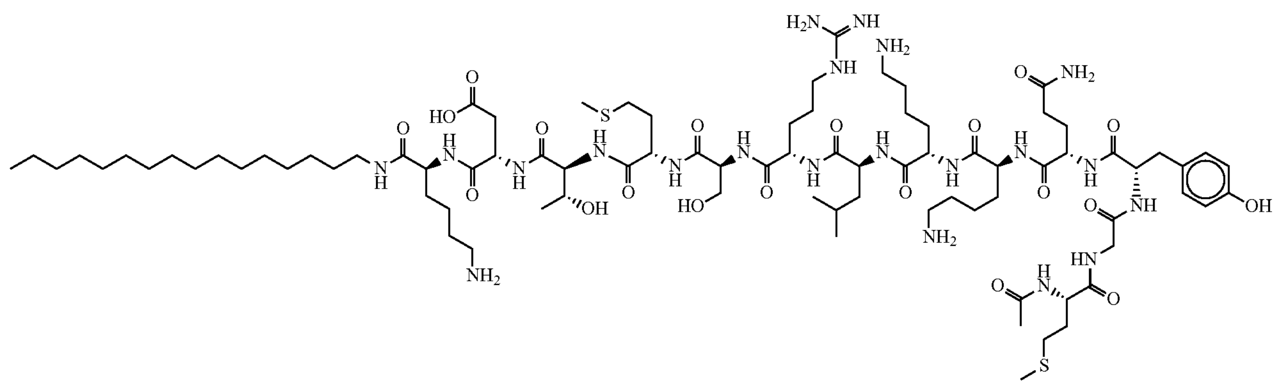 |

TABLE 7-continued
CXCR4 it loop compound structures
| Comp. # | Structure |
|---|---|
| 60 | 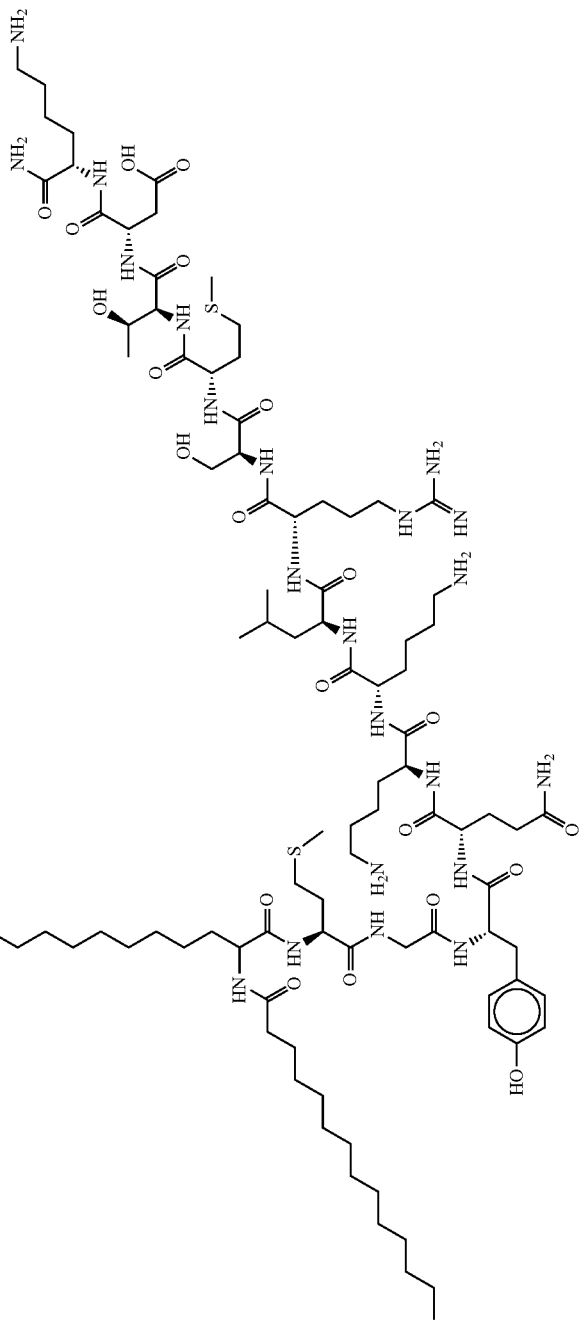 |

TABLE 7-continued
CXCR4 it loop compound structures
| Comp. # | Structure |
|---|---|
| 61 | 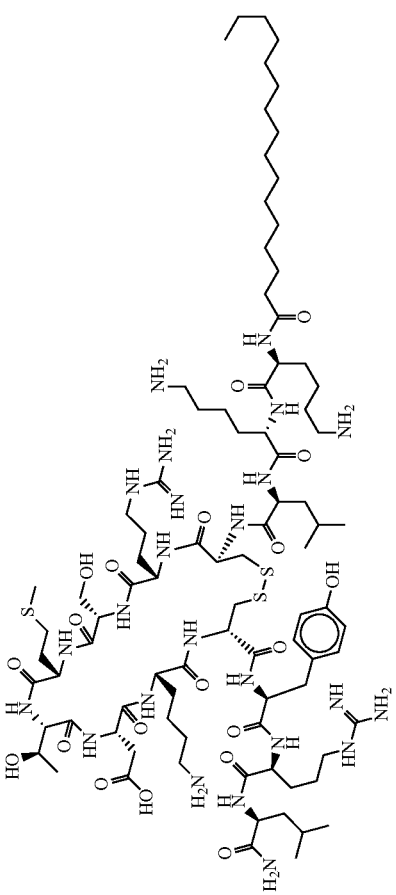 |
| 62 | 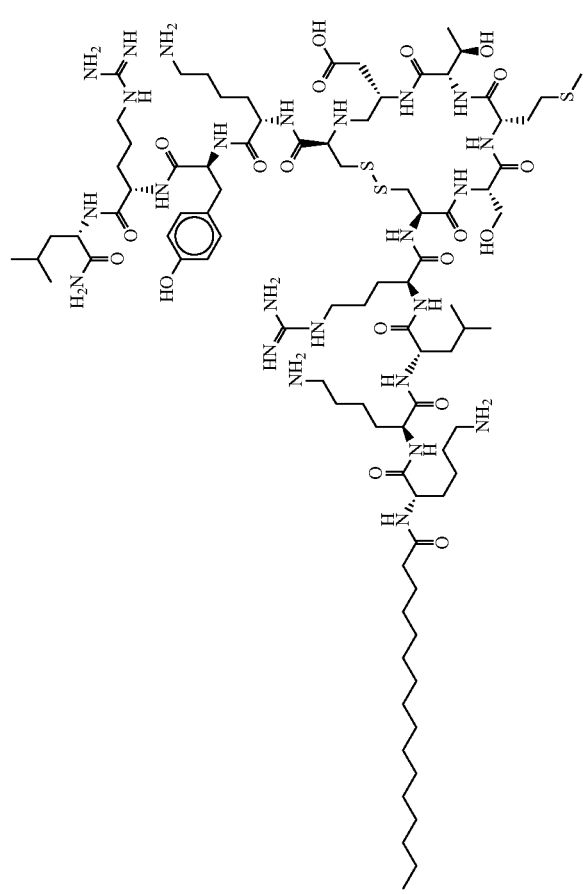 |

TABLE 7-continued

CXCR4 it loop compound structures

| Comp. # | Structure |
|---|---|
| 63 | 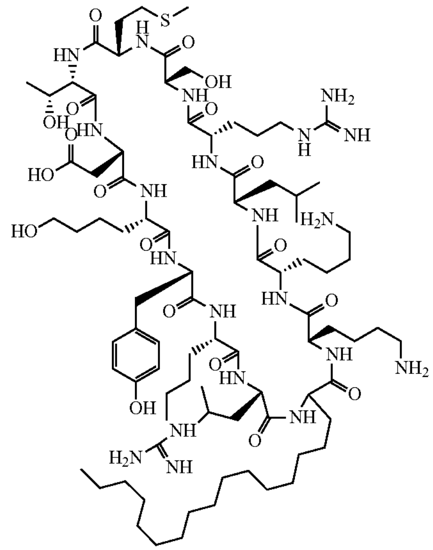 [SMILES: CCCCCCCCCCCCCCCCC1NC(=O)[C@H](CC(C)NC(=N)N)NC(=O)[C@H](CCCC)NC(=O)[C@H](Cc2ccc(O)cc2)NC(=O)[C@H](CCCCO)NC(=O)[C@H](CC(=O)O)NC(=O)[C@H]([C@@H](C)O)NC(=O)[C@H](CCSC)NC(=O)[C@H](CO)NC(=O)[C@H](CCCNC(=N)N)NC(=O)[C@H](CC(C)C)NC(=O)[C@H](CCCCN)NC(=O)[C@H](CCCCN)NC1=O] |
| 64 | 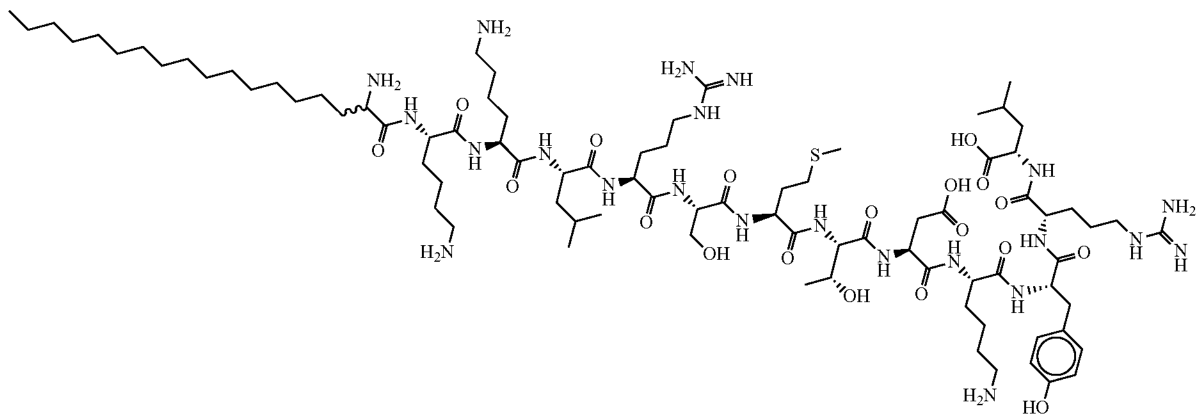 |

TABLE 7-continued
CXCR4 it loop compound structures
| Comp. # | Structure |
|---|---|
| 65 | 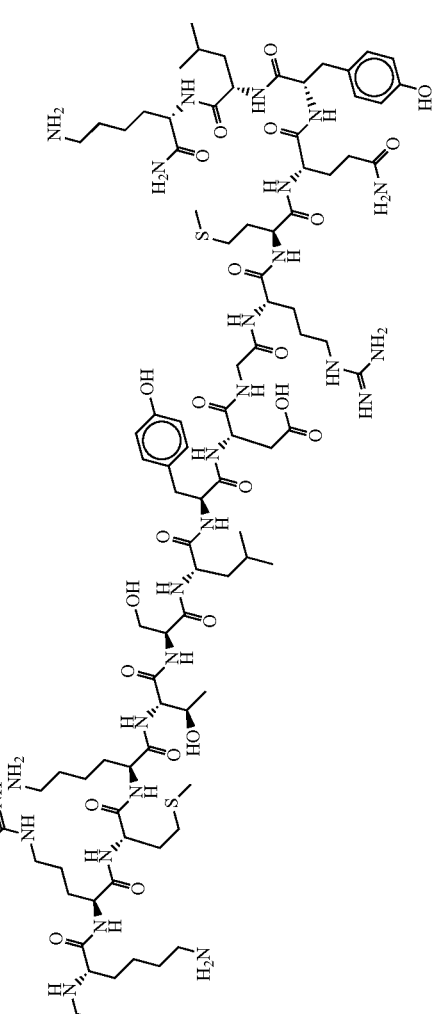 |

TABLE 7-continued

CXCR4 it loop compound structures

| Comp. # | Structure |
|---------|-----------|
| 66 | 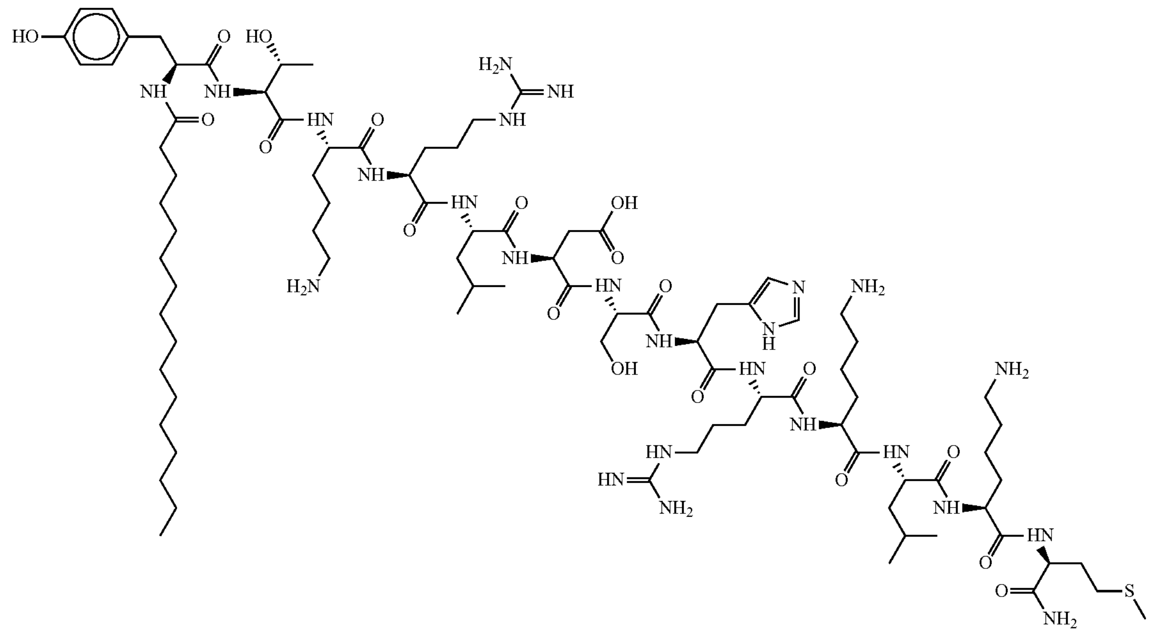 |

TABLE 7-continued
CXCR4 it loop compound structures
| Comp. # | Structure |
|---|---|
| 67 | 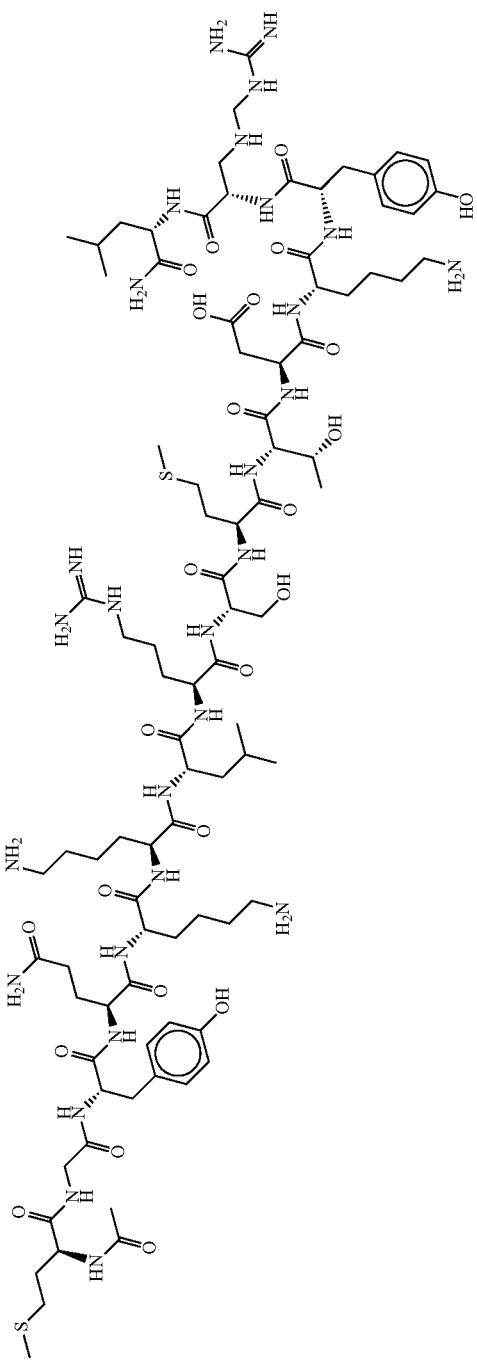 |
| 68 | 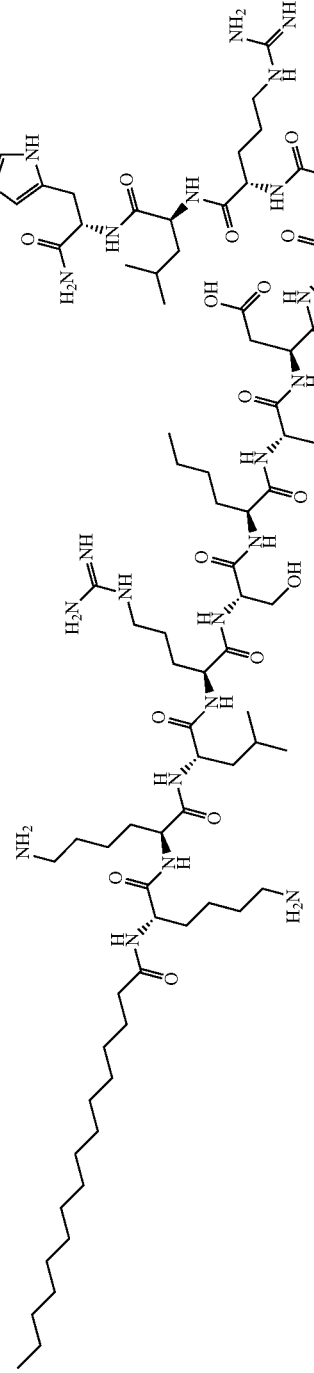 |

TABLE 7-continued

CXCR4 it loop compound structures

| Comp. # | Structure |
|---|---|
| 69 | 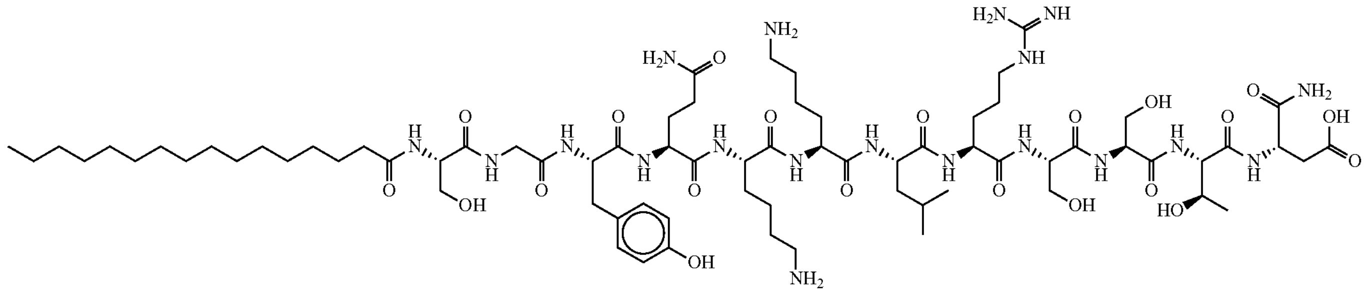 |
| 70 | 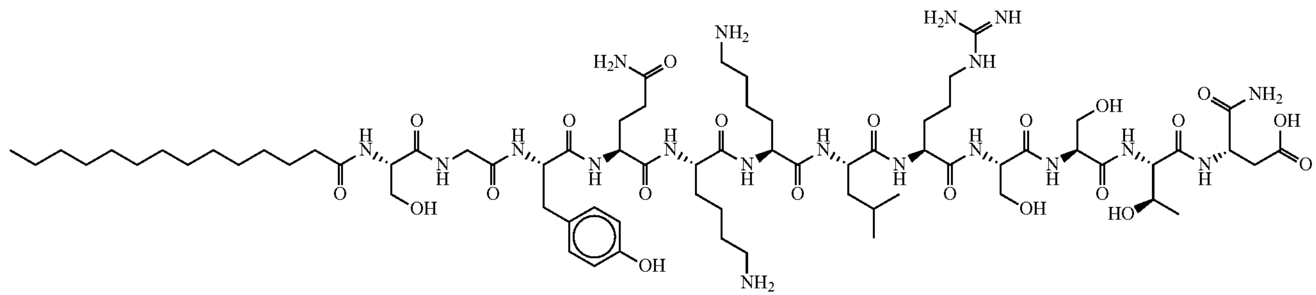 |
| 71 | 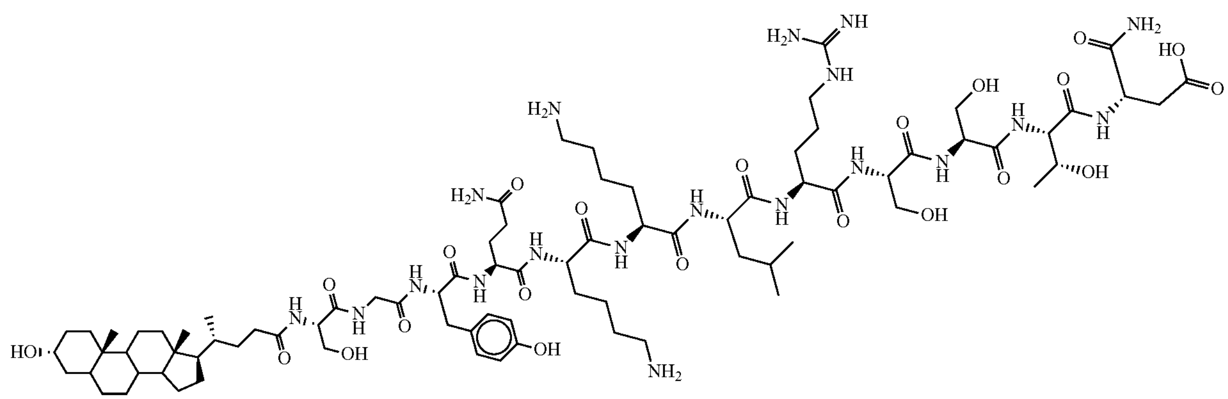 |

TABLE 7-continued
CXCR4 it loop compound structures
| Comp. # | Structure |
|---|---|
| 72 | 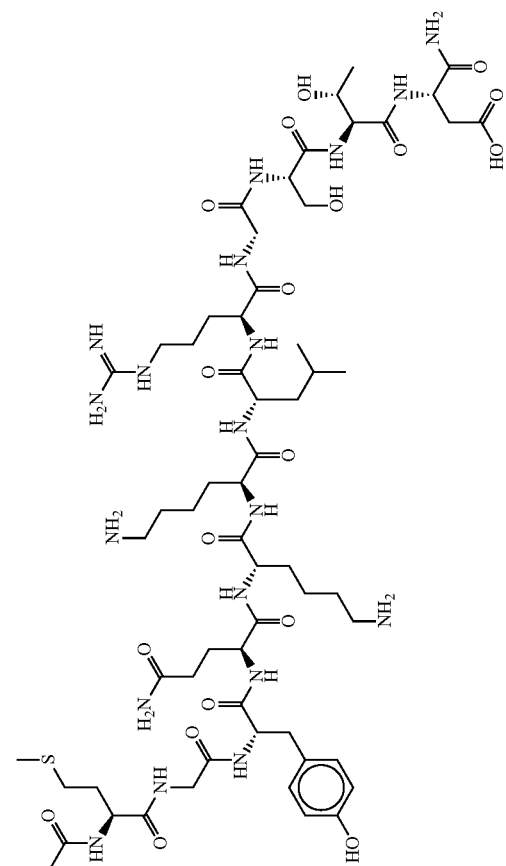 |

TABLE 7-continued

CXCR4 it loop compound structures

| Comp. # | Structure |
|---|---|
| 73 | 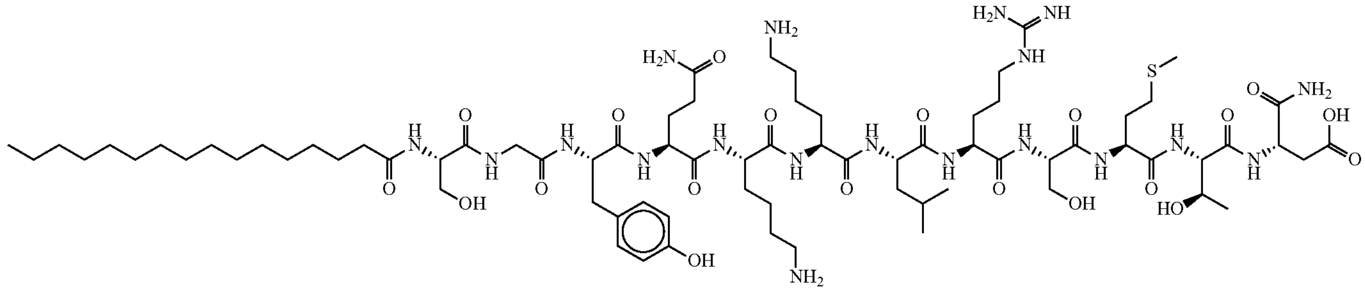 |
| 117 | 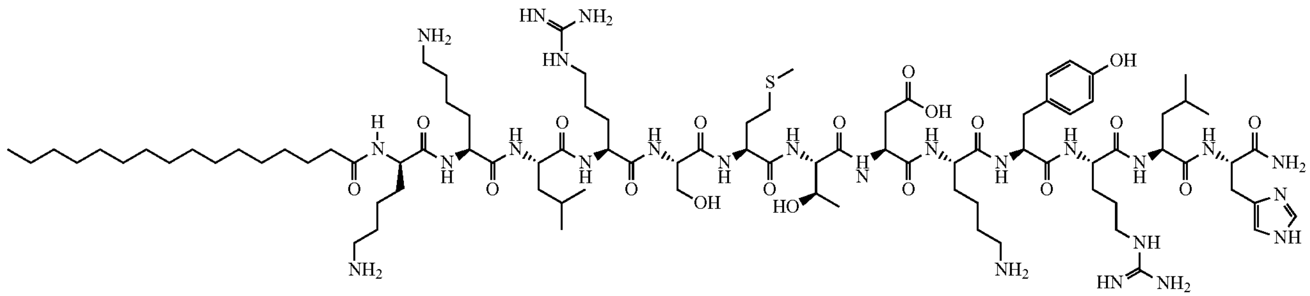 [SMILES: CCCCCCCCCCCCCCCC(=O)N[C@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(=O)N[C@@H](Cc1c[nH]cn1)C(N)=O)[C@@H](C)O] |
| 118 | 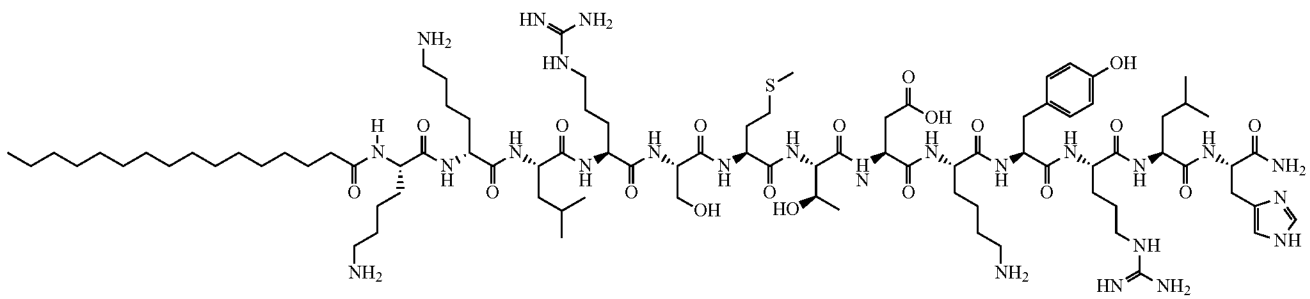 [SMILES: CCCCCCCCCCCCCCCC(=O)N[C@@H](CCCCN)C(=O)N[C@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(=O)N[C@@H](Cc1c[nH]cn1)C(N)=O)[C@@H](C)O] |

TABLE 7-continued
CXCR4 it loop compound structures
| Comp. # | Structure |
|---|---|
| 119 | 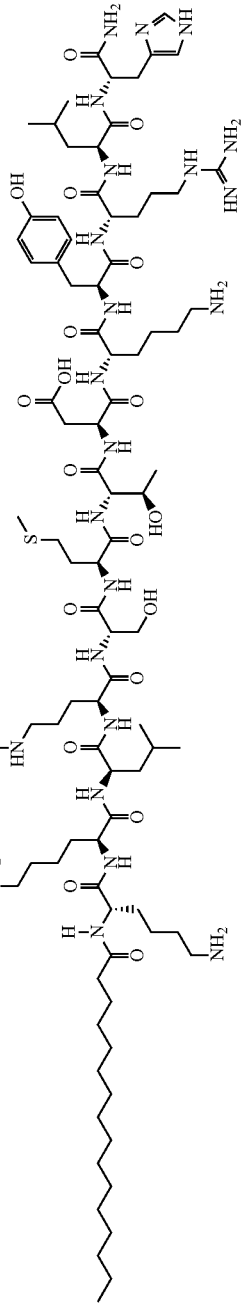 |
| 120 | 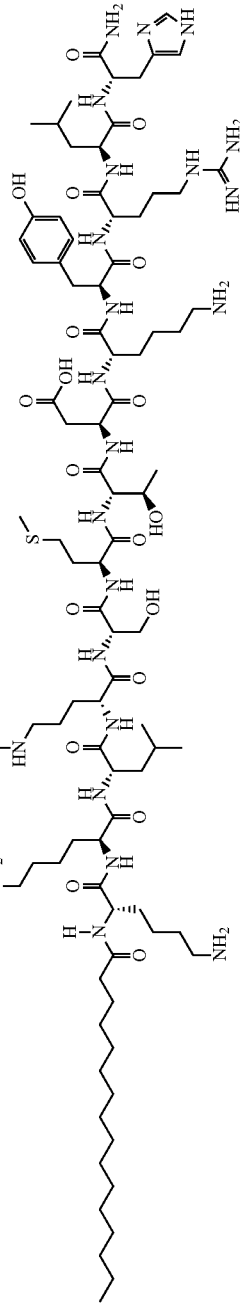 |
| 121 | 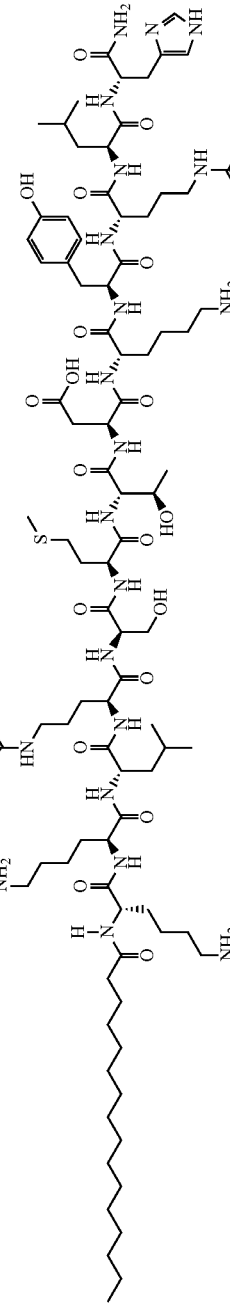 |

TABLE 7-continued

CXCR4 it loop compound structures

| Comp. # | Structure |
|---|---|
| 122 | 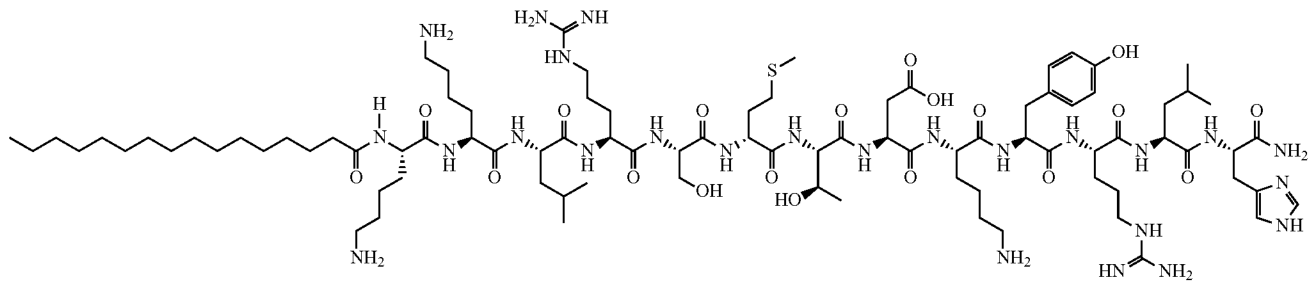 [SMILES: CCCCCCCCCCCCCCCC(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(=O)N[C@@H](Cc1c[nH]cn1)C(N)=O)[C@@H](C)O] |
| 123 | 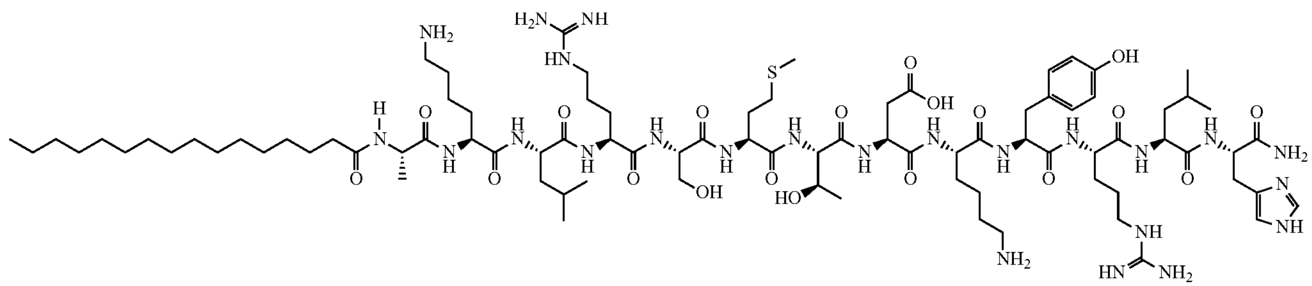 [SMILES: CCCCCCCCCCCCCCCC(=O)N[C@@H](C)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(=O)N[C@@H](Cc1c[nH]cn1)C(N)=O)[C@@H](C)O] |
| 124 | 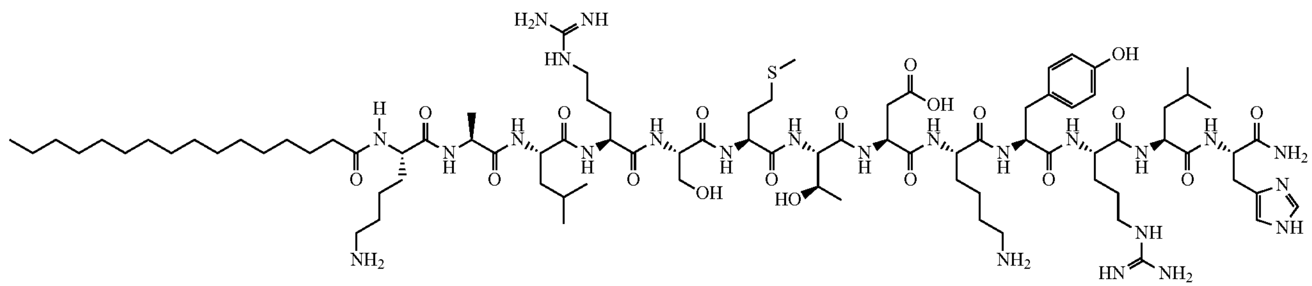 [SMILES: CCCCCCCCCCCCCCCC(=O)N[C@@H](CCCCN)C(=O)N[C@@H](C)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(=O)N[C@@H](Cc1c[nH]cn1)C(N)=O)[C@@H](C)O] |

TABLE 7-continued
CXCR4 it loop compound structures
| Comp. # | Structure |
|---|---|
| 125 | 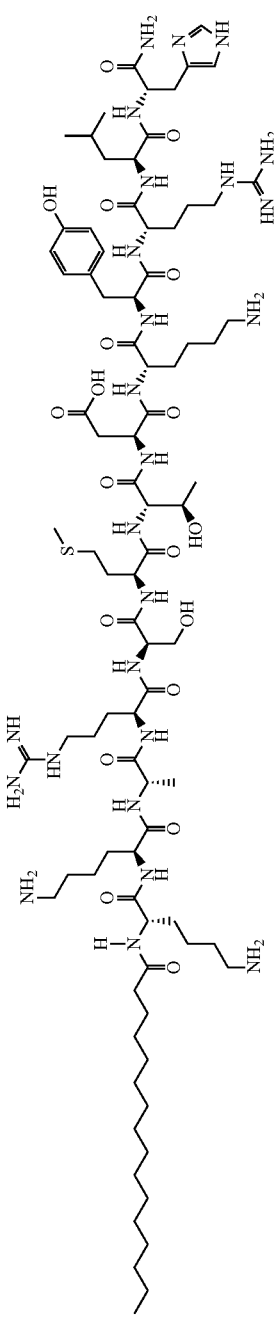 |
| 126 | 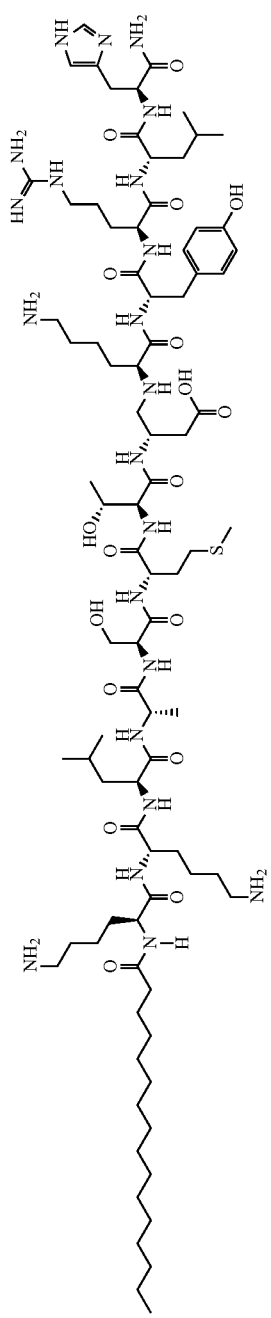 |
| 127 | 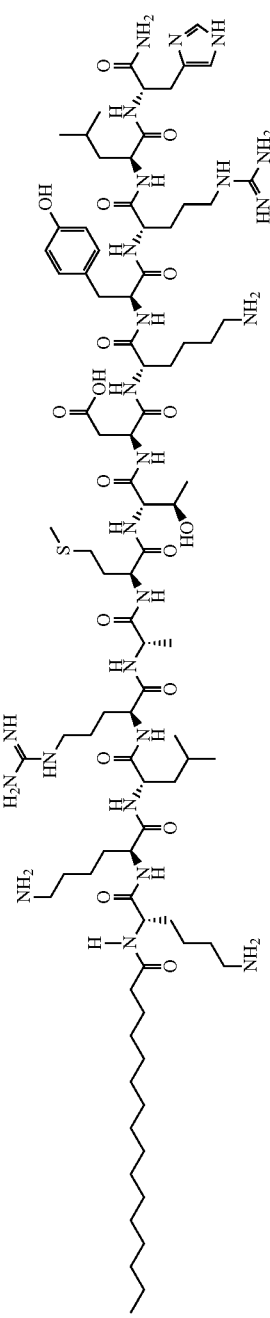 |

TABLE 7-continued

CXCR4 it loop compound structures

| Comp. # | Structure |
|---|---|
| 128 | 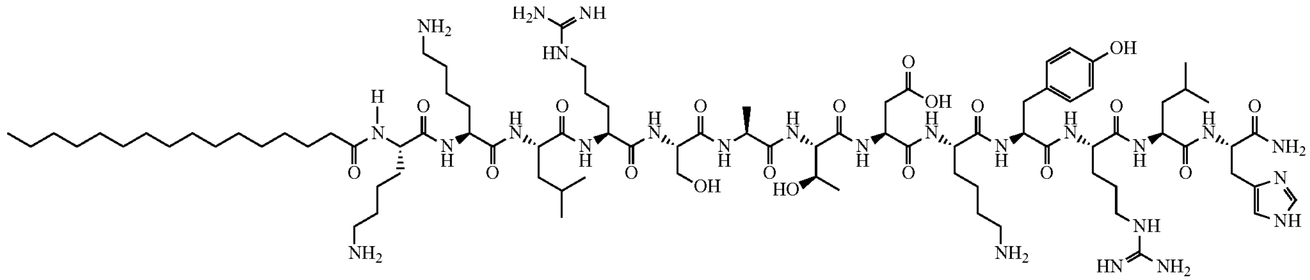 [SMILES: CCCCCCCCCCCCCCCC(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](C)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(=O)N[C@@H](Cc1c[nH]cn1)C(N)=O)[C@@H](C)O] |
| 129 | 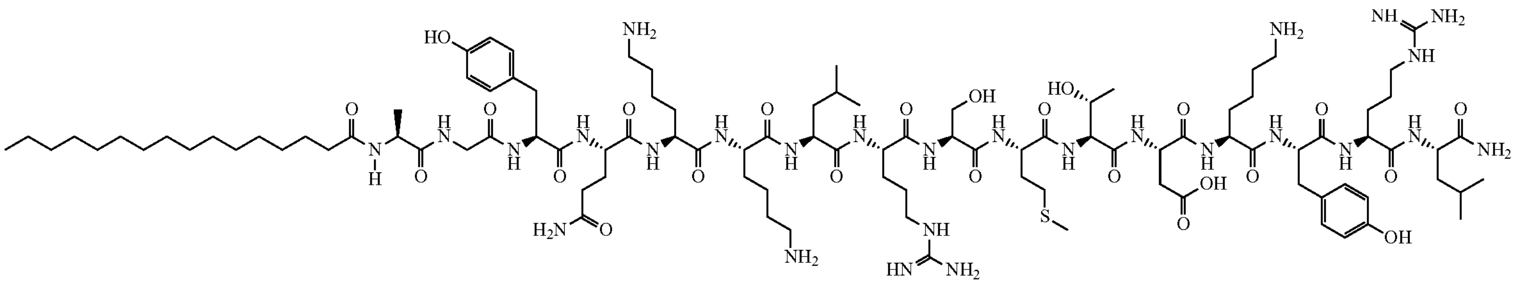 [SMILES: CCCCCCCCCCCCCCCC(=O)N[C@@H](C)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |
| 130 | 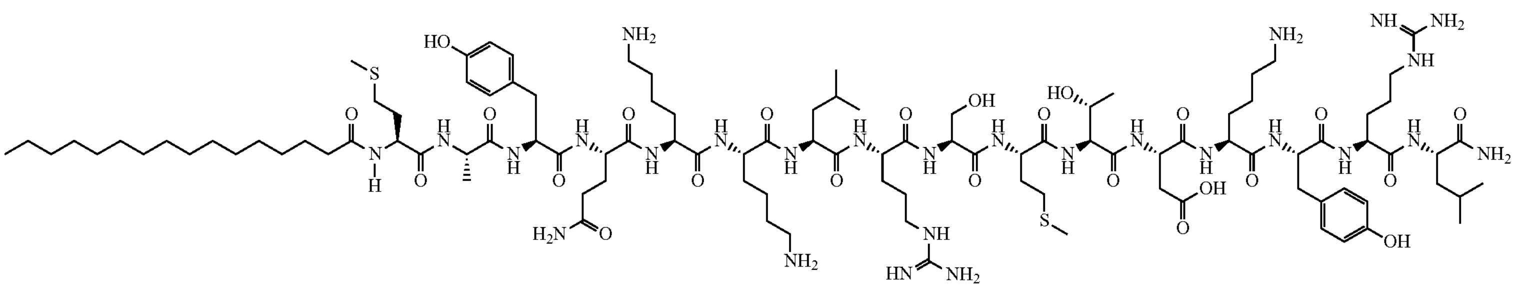 [SMILES: CCCCCCCCCCCCCCCC(=O)N[C@@H](CCSC)C(=O)N[C@@H](C)C(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |

TABLE 7-continued

CXCR4 it loop compound structures

| Comp. # | Structure |
|---------|-----------|
| 131 | 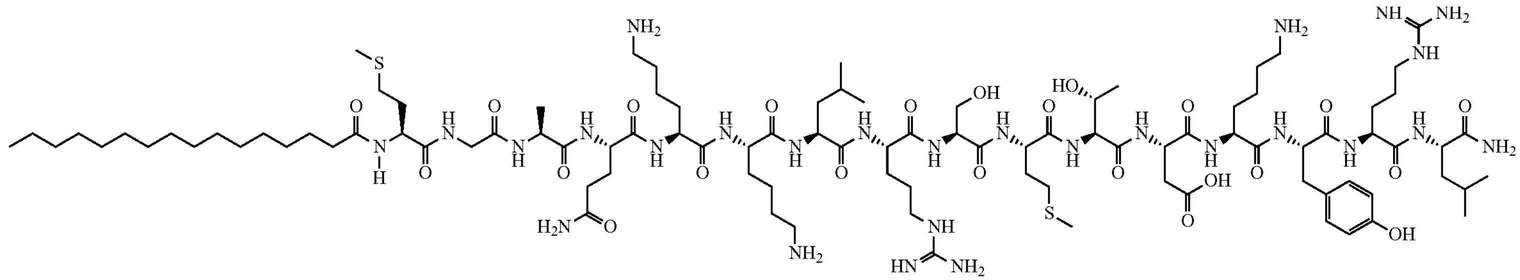 [SMILES: CCCCCCCCCCCCCCCC(=O)N[C@@H](CCSC)C(=O)NCC(=O)N[C@@H](C)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |
| 132 | 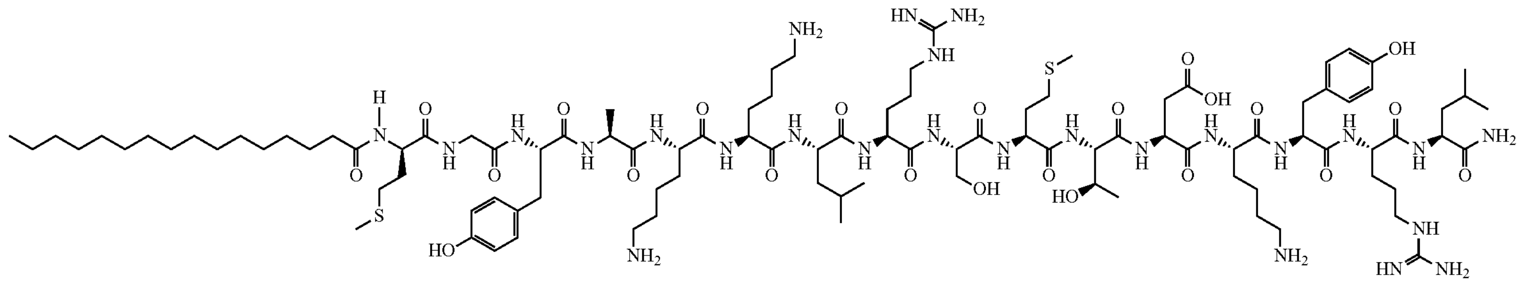 [SMILES: CCCCCCCCCCCCCCCC(=O)N[C@H](CCSC)C(=O)NCC(=O)N[C@@H](Cc1ccc(O)cc1)C(=O)N[C@@H](C)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |
| 133 | 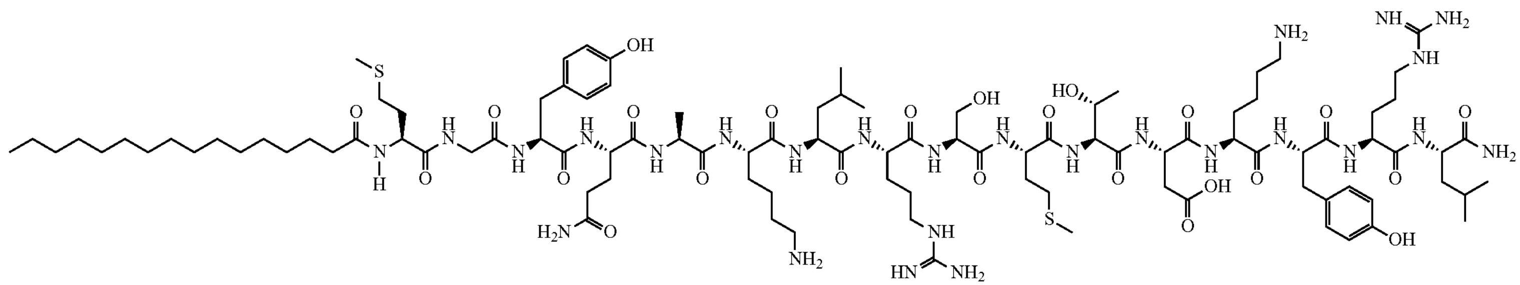 [SMILES: CCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@@H](C)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |

TABLE 7-continued

CXCR4 it loop compound structures

| Comp. # | Structure |
|---|---|
| 134 | 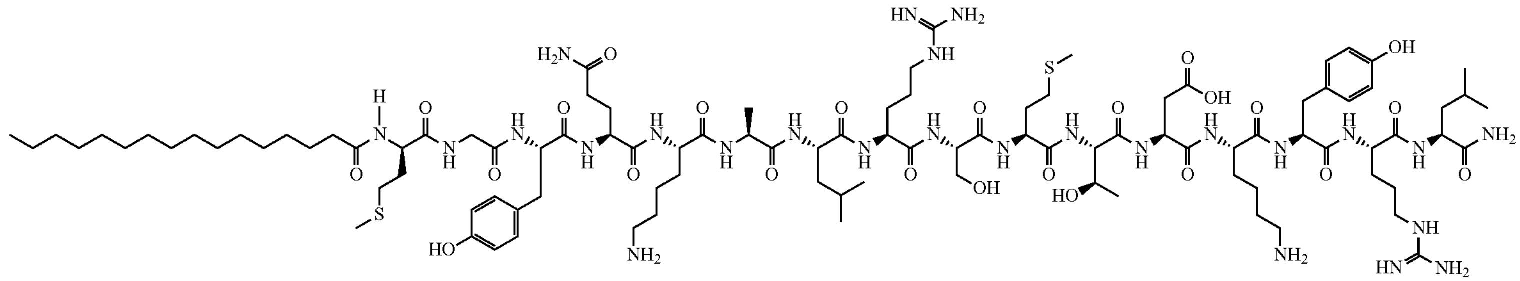 [SMILES: CCCCCCCCCCCCCCCC(=O)N[C@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](C)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |
| 135 | 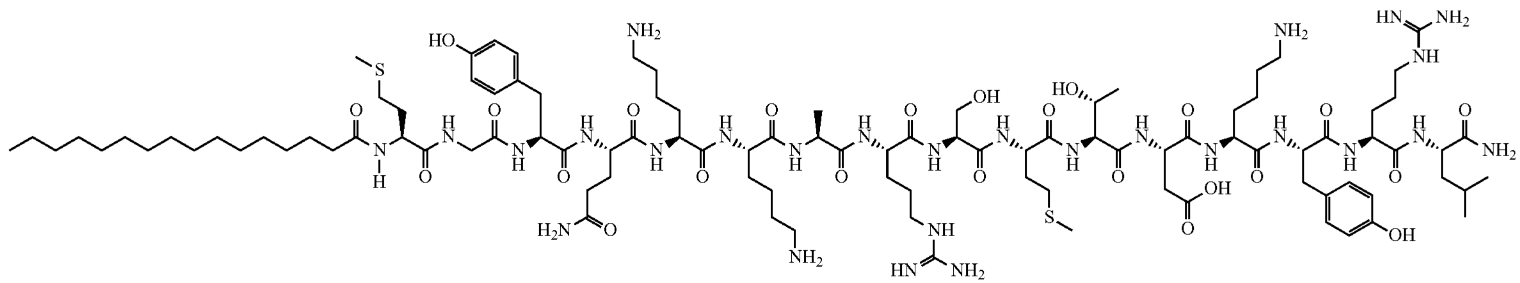 [SMILES: CCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |
| 136 | 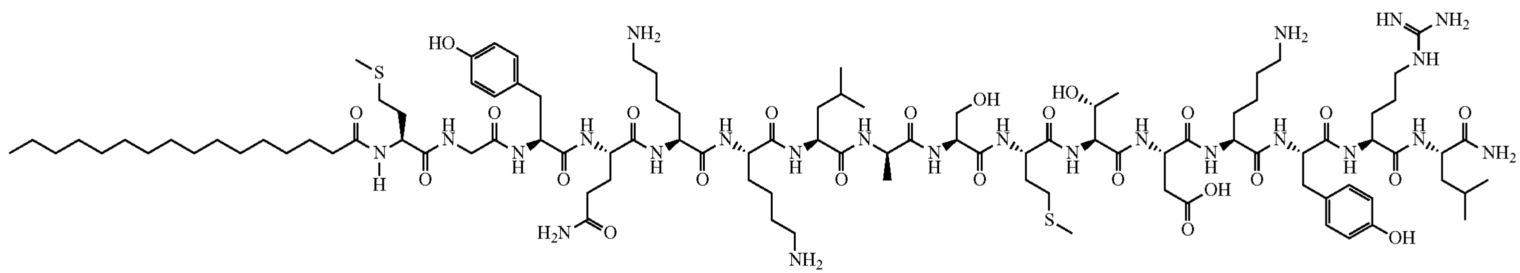 [SMILES: CCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@H](C)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |

TABLE 7-continued

CXCR4 it loop compound structures

| Comp. # | Structure |
|---|---|
| 137 | 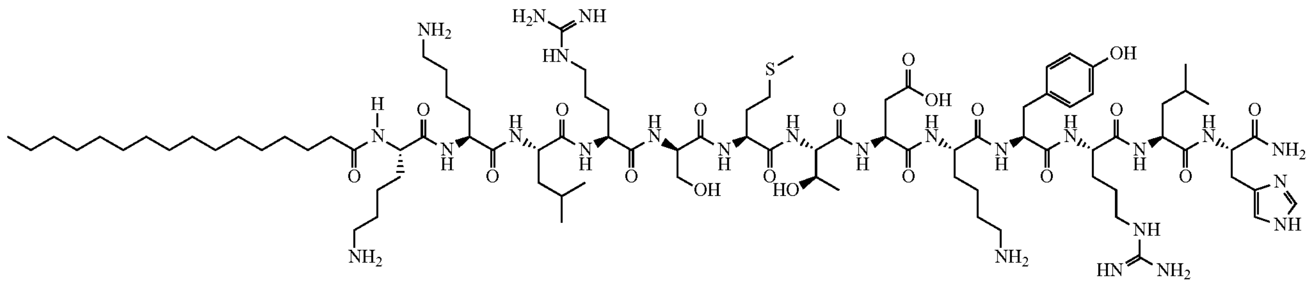 [SMILES: CCCCCCCCCCCCCCCC(=O)N[C@@H](CCCCN)C(=O)N[C@@H](CCCCN)C(=O)N[C@@H](CC(C)C)C(=O)N[C@@H](CCCNC(=N)N)C(=O)N[C@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(=O)N[C@@H](Cc1c[nH]cn1)C(N)=O)[C@@H](C)O] |
| 138 | 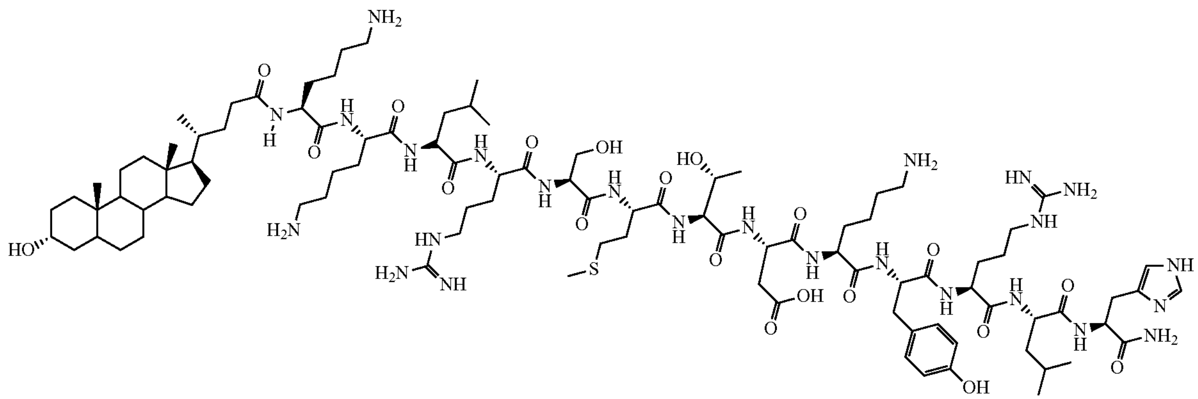 |
| 139 | 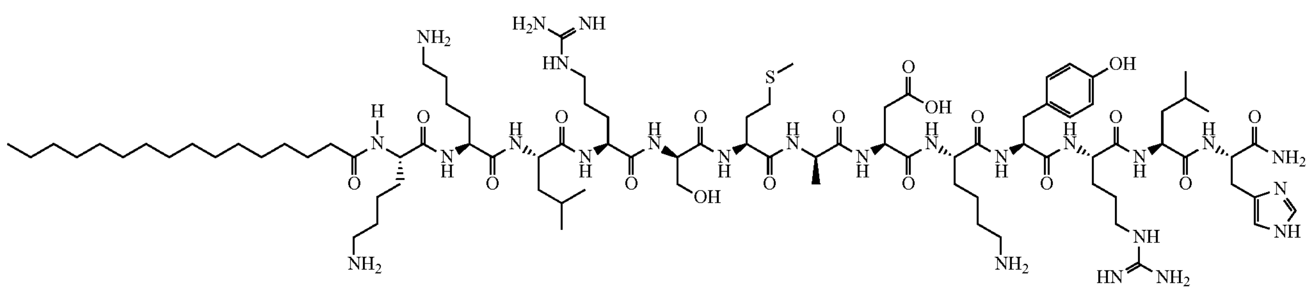 [SMILES: CCCCCCCCCCCCCCCC(=O)N[C@@H](CCCCN)C(=O)N[C@@H](CCCCN)C(=O)N[C@@H](CC(C)C)C(=O)N[C@@H](CCCNC(=N)N)C(=O)N[C@H](CO)C(=O)N[C@@H](CCSC)C(=O)N[C@H](C)C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(=O)N[C@@H](Cc1c[nH]cn1)C(N)=O] |

TABLE 7-continued

CXCR4 it loop compound structures

| Comp. # | Structure |
|---|---|
| 140 | 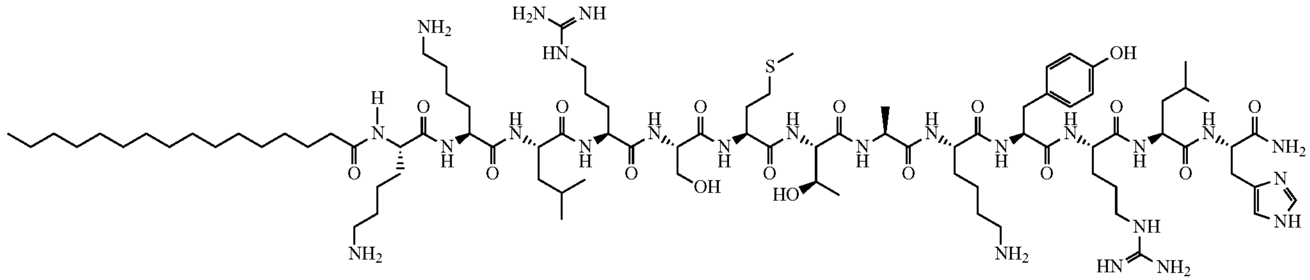 [SMILES: CCCCCCCCCCCCCCCC(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](C)C(=O)N[C@@H](CCCCN)C(=O)N[C@@H](Cc1ccc(O)cc1)C(=O)N[C@@H](CCCNC(=N)N)C(=O)N[C@@H](CC(C)C)C(=O)N[C@@H](Cc1c[nH]cn1)C(N)=O)[C@@H](C)O] |
| 141 | 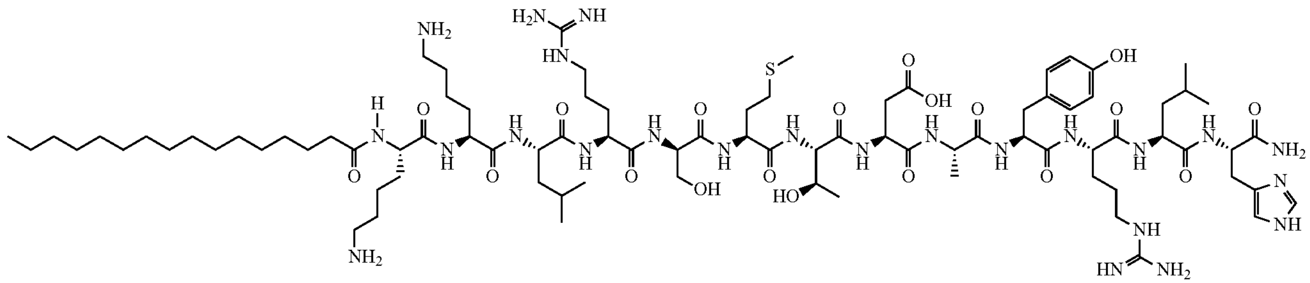 [SMILES: CCCCCCCCCCCCCCCC(=O)N[C@@H](CCCCN)C(=O)N[C@@H](CCCCN)C(=O)N[C@@H](CC(C)C)C(=O)N[C@@H](CCCNC(=N)N)C(=O)N[C@H](CO)C(=O)N[C@@H](CCSC)C(=O)N[C@H](C(=O)N[C@@H](CC(=O)O)C(=O)N[C@@H](C)C(=O)N[C@@H](Cc1ccc(O)cc1)C(=O)N[C@@H](CCCNC(=N)N)C(=O)N[C@@H](CC(C)C)C(=O)N[C@@H](Cc1c[nH]cn1)C(N)=O)[C@@H](C)O] |
| 142 | 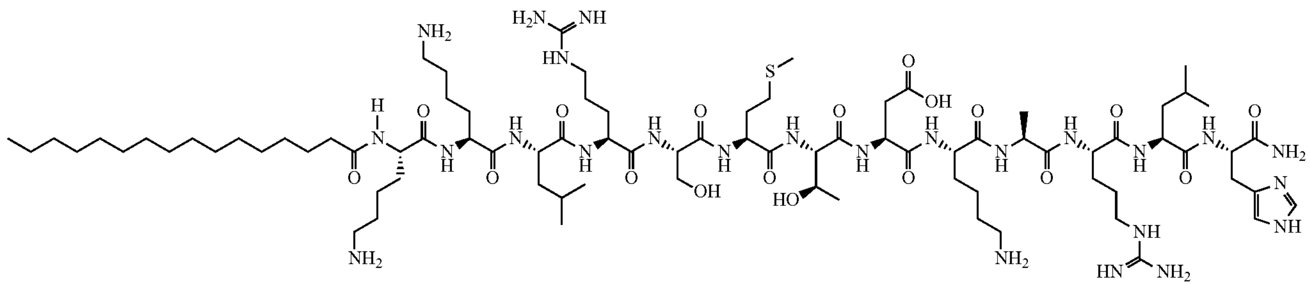 [SMILES: CCCCCCCCCCCCCCCC(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](C)C(=O)N[C@@H](CCCNC(=N)N)C(=O)N[C@@H](CC(C)C)C(=O)N[C@@H](Cc1c[nH]cn1)C(N)=O)[C@@H](C)O] |

TABLE 7-continued

CXCR4 it loop compound structures

| Comp. # | Structure |
|---|---|
| 143 | 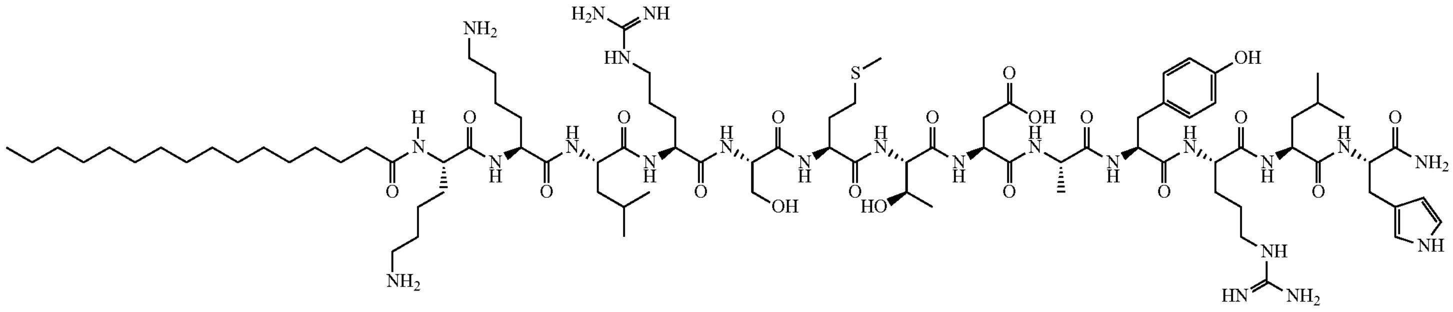 [SMILES: CCCCCCCCCCCCCCCC(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](C)C(=O)N[C@@H](Cc1ccc(O)cc1)C(=O)N[C@@H](CCCNC(=N)N)C(=O)N[C@@H](CC(C)C)C(=O)N[C@@H](Cc1cc[nH]c1)C(N)=O)[C@@H](C)O] |
| 144 | 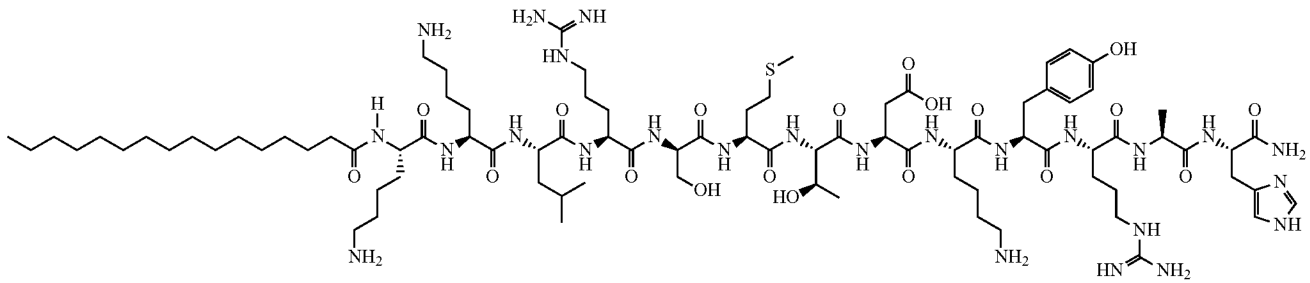 [SMILES: CCCCCCCCCCCCCCCC(=O)N[C@@H](CCCCN)C(=O)N[C@@H](CCCCN)C(=O)N[C@@H](CC(C)C)C(=O)N[C@@H](CCCNC(=N)N)C(=O)N[C@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](C)C(=O)N[C@@H](Cc1c[nH]cn1)C(N)=O)[C@@H](C)O] |
| 145 | 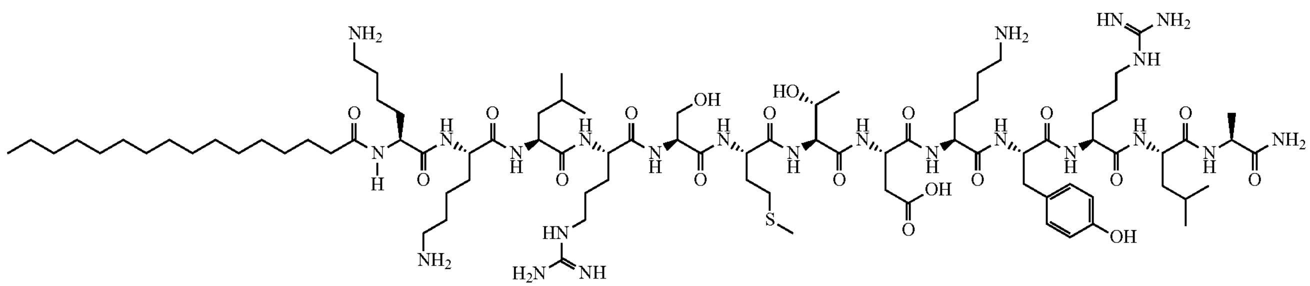 [SMILES: CCCCCCCCCCCCCCCC(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(=O)N[C@@H](C)C(N)=O)[C@@H](C)O] |

TABLE 7-continued

CXCR4 it loop compound structures

| Comp. # | Structure |
|---|---|
| 146 | 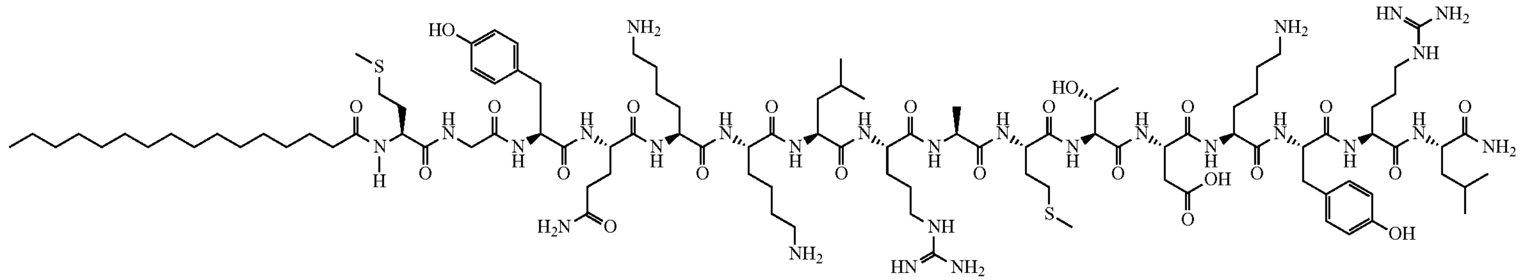 [SMILES: CCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](C)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |
| 147 | 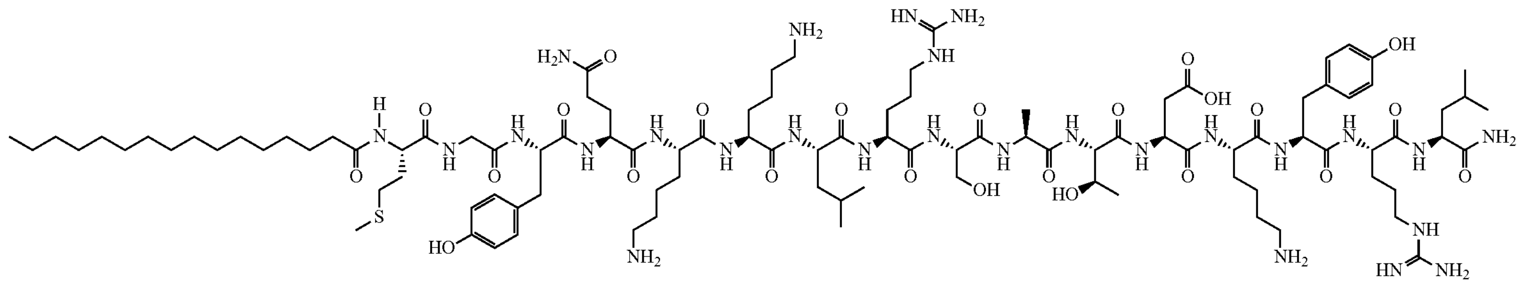 [SMILES: CCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](C)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |
| 148 | 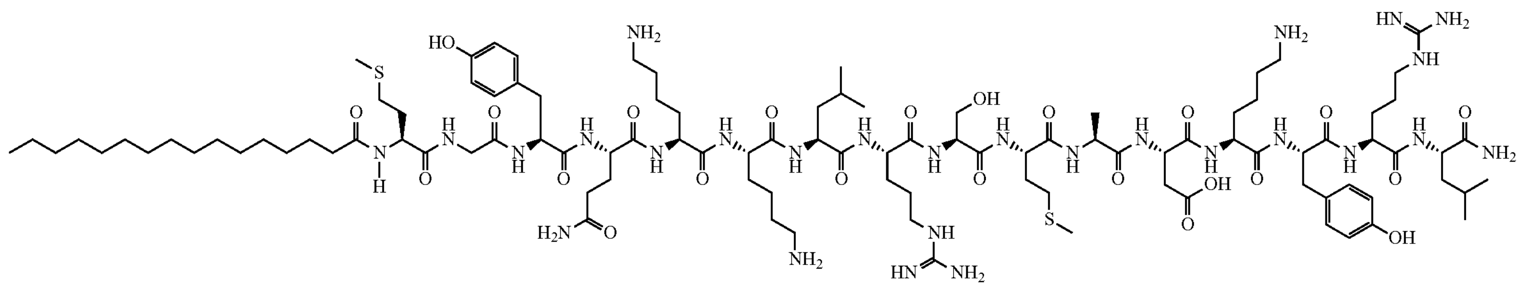 [SMILES: CCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@@H](C)C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O] |

TABLE 7-continued

CXCR4 it loop compound structures

| Comp. # | Structure |
|---|---|
| 149 | 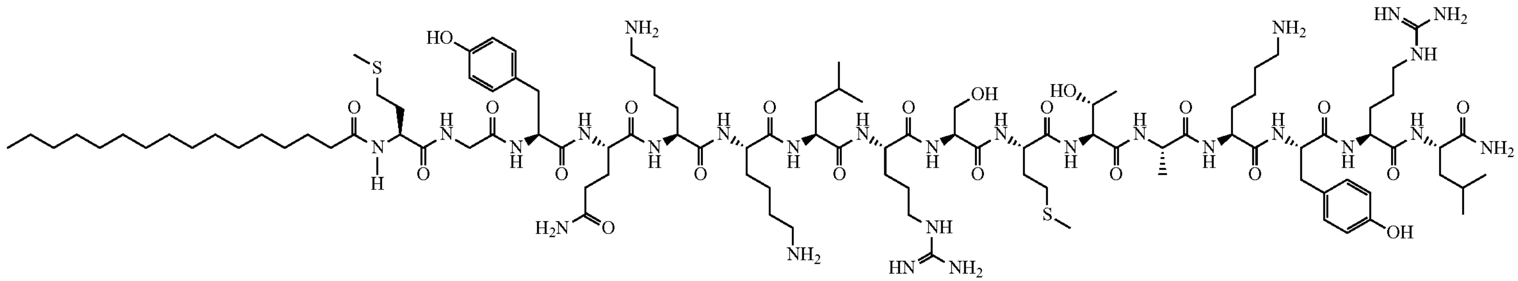 [SMILES: CCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](C)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |
| 150 | 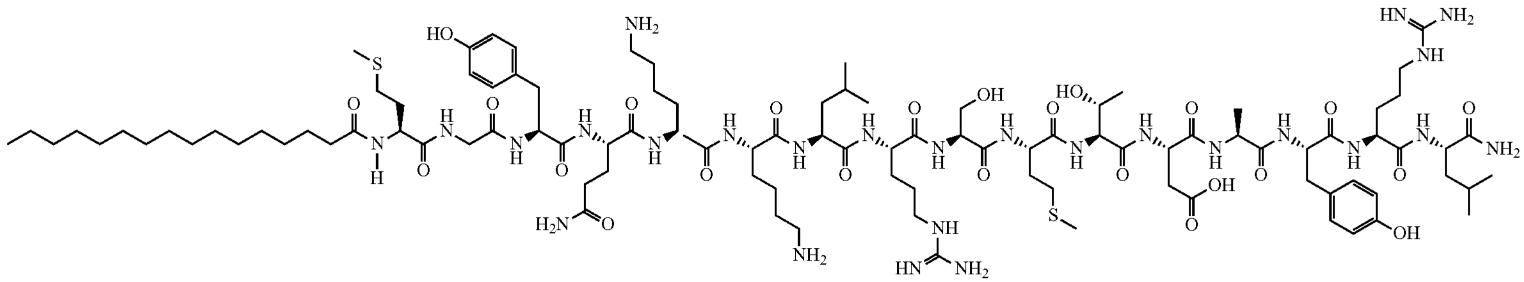 |
| 151 | 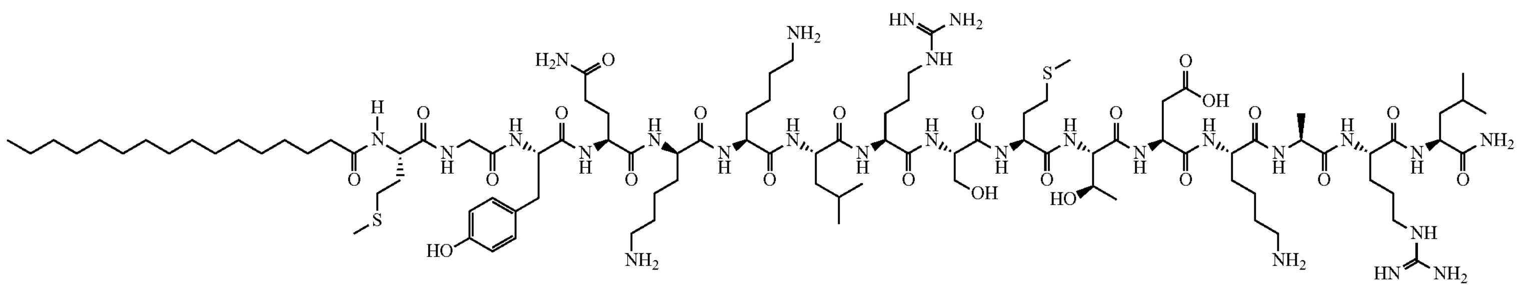 [SMILES: CCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](C)C(=O)N[C@@H](CCCNC(=N)N)C(=O)N[C@@H](CC(C)C)C(N)=O)[C@@H](C)O] |

TABLE 7-continued

CXCR4 it loop compound structures

| Comp. # | Structure |
|---|---|
| 152 | 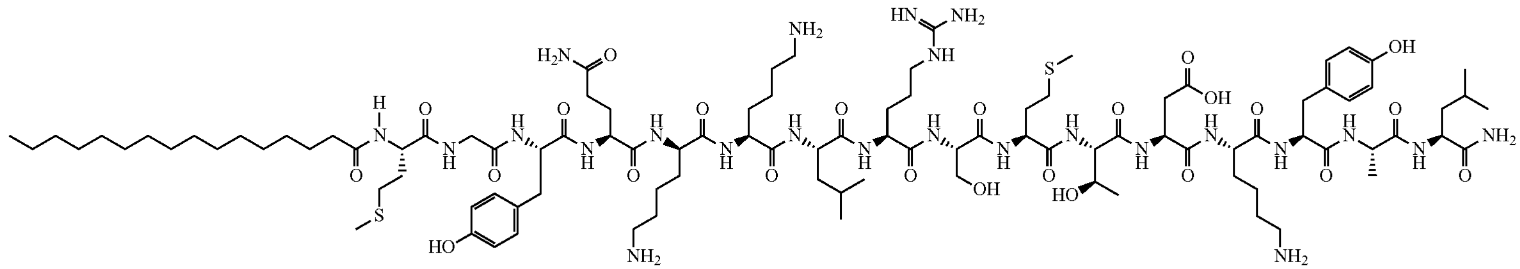 [SMILES: CCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](C)C(=O)N[C@@H](CC(C)C)C(N)=O)[C@@H](C)O] |
| 153 | 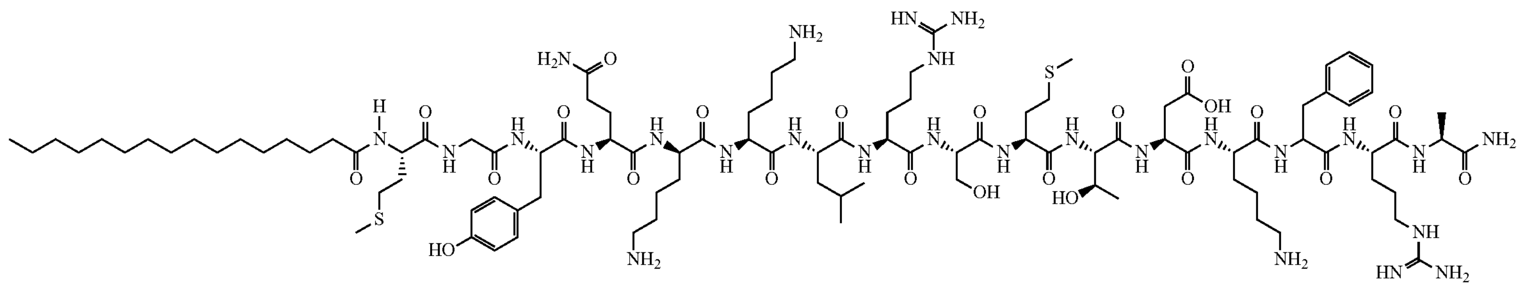 [SMILES: CCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)NC(Cc1ccccc1)C(=O)N[C@@H](CCCNC(=N)N)C(=O)N[C@@H](C)C(N)=O)[C@@H](C)O] |
| 154 | 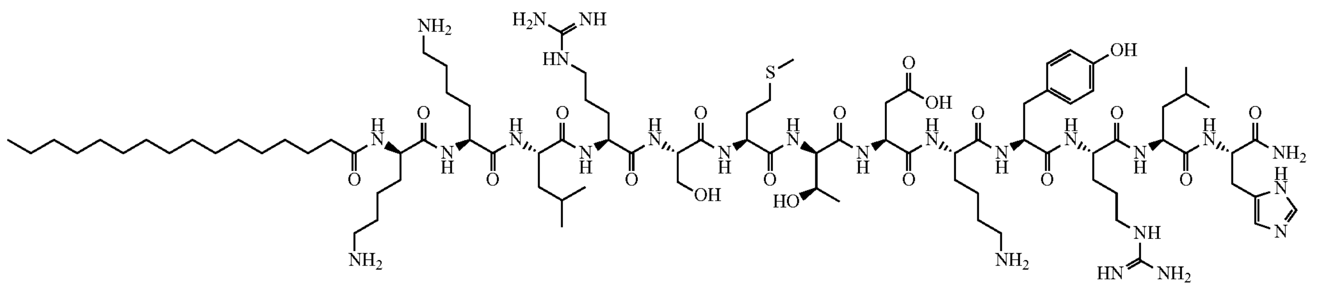 [SMILES: CCCCCCCCCCCCCCCC(=O)N[C@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(=O)N[C@@H](Cc1cnc[nH]1)C(N)=O)[C@@H](C)O] |

TABLE 7-continued
CXCR4 it loop compound structures
| Comp. # | Structure |
|---|---|
| 155 | 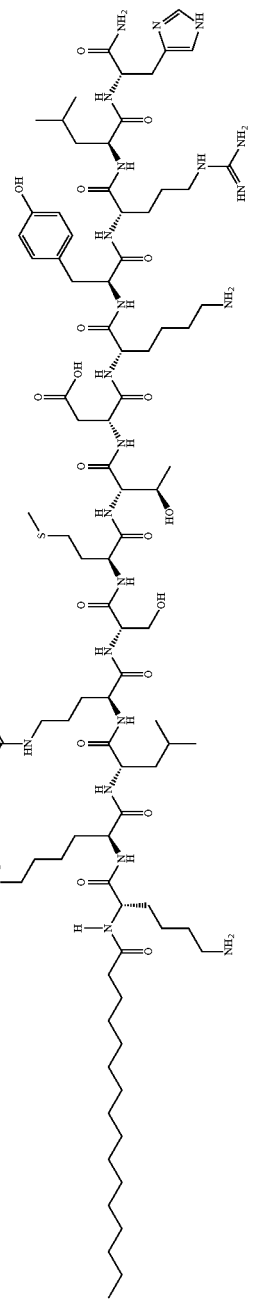 |
| 156 | 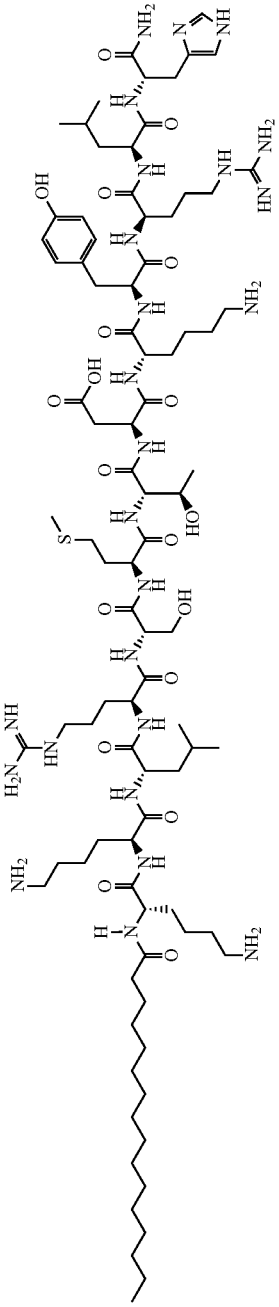 |
| 157 | 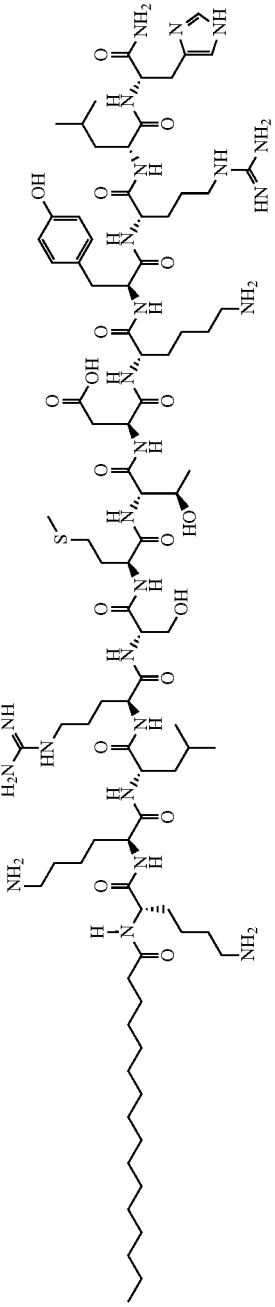 |

TABLE 7-continued

CXCR4 it loop compound structures

| Comp. # | Structure |
|---------|-----------|
| 158 | 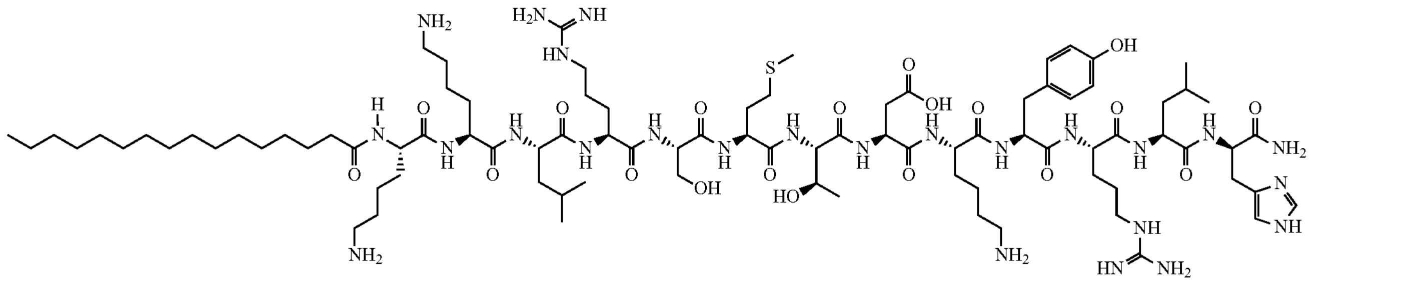 [SMILES: CCCCCCCCCCCCCCCC(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(=O)N[C@H](Cc1c[nH]cn1)C(N)=O)[C@@H](C)O] |
| 159 | 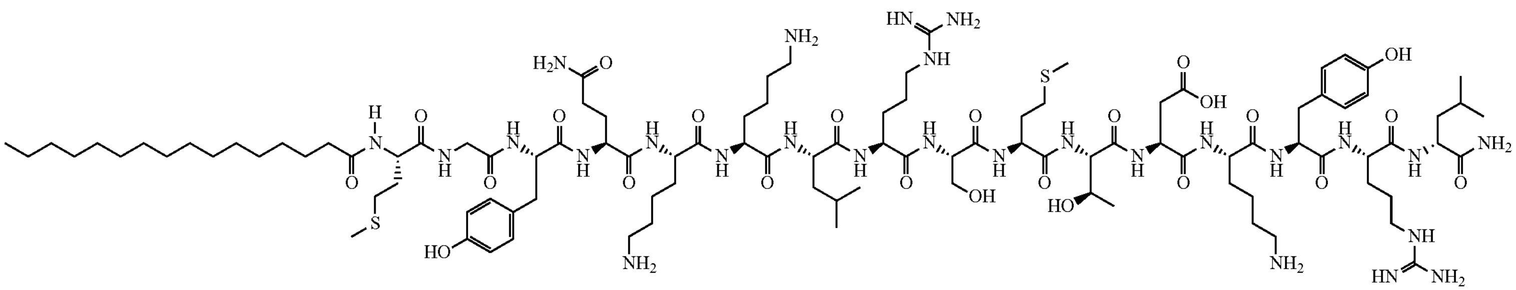 [SMILES: CCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@H](CC(C)C)C(N)=O)[C@@H](C)O] |
| 160 | 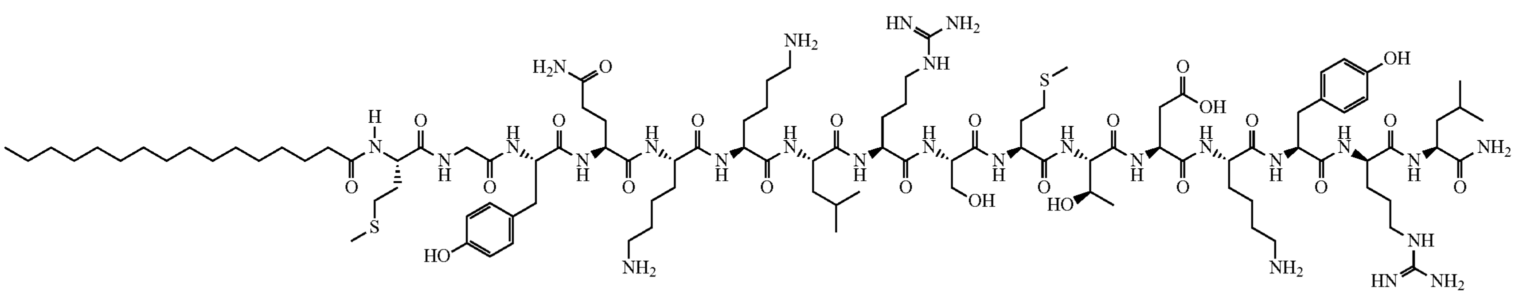 |

TABLE 7-continued
CXCR4 it loop compound structures
| Comp. # | Structure |
|---|---|
| 161 | 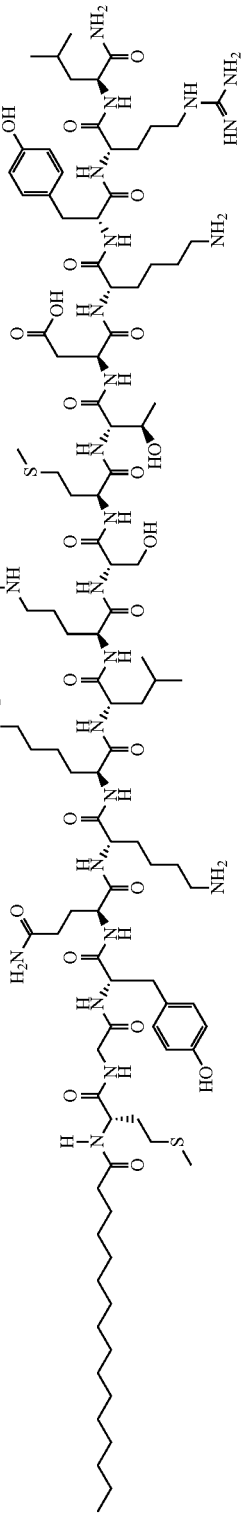 |
| 162 | 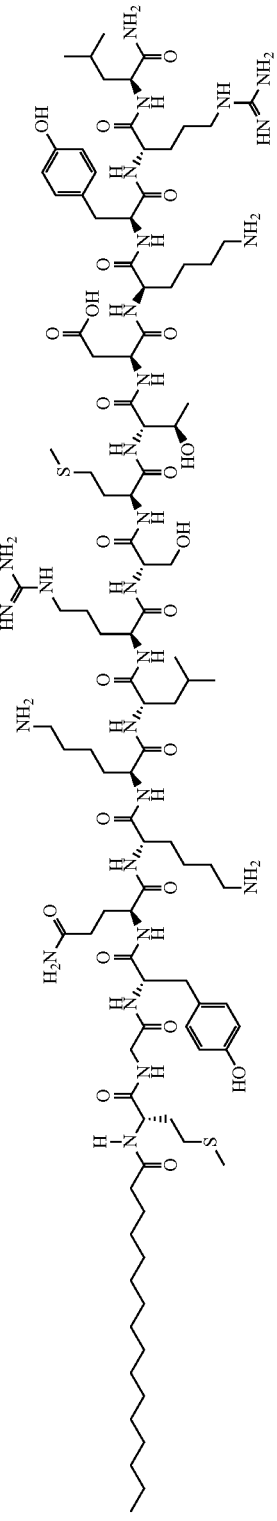 |
| 163 | 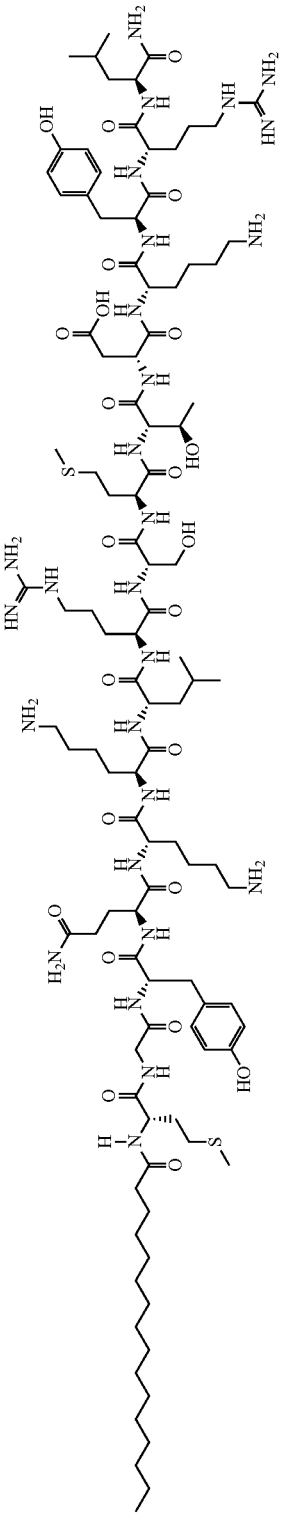 |

TABLE 7-continued

CXCR4 it loop compound structures

| Comp. # | Structure |
|---|---|
| 164 | 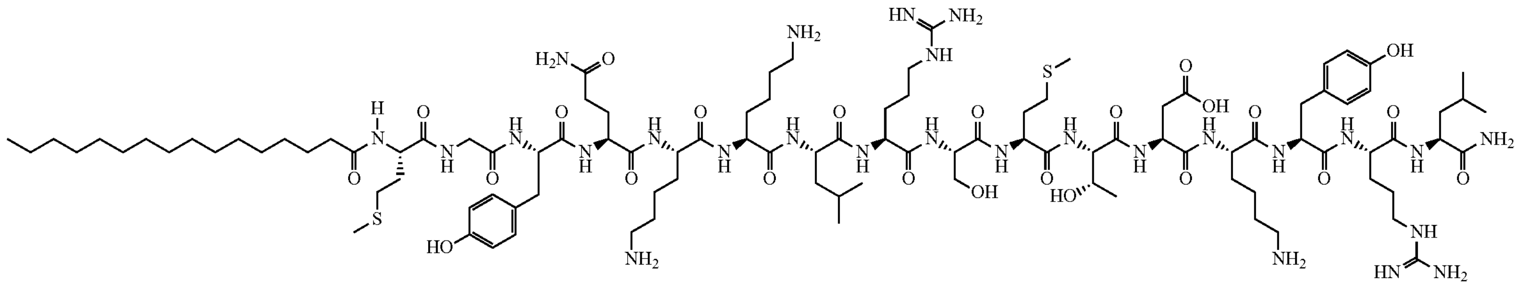 [SMILES: CCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@H](C)O] |
| 165 | 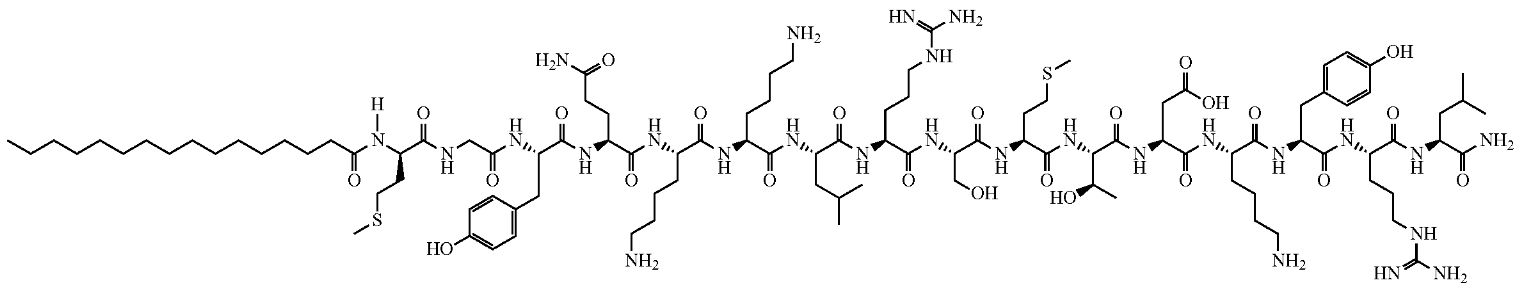 |
| 166 | 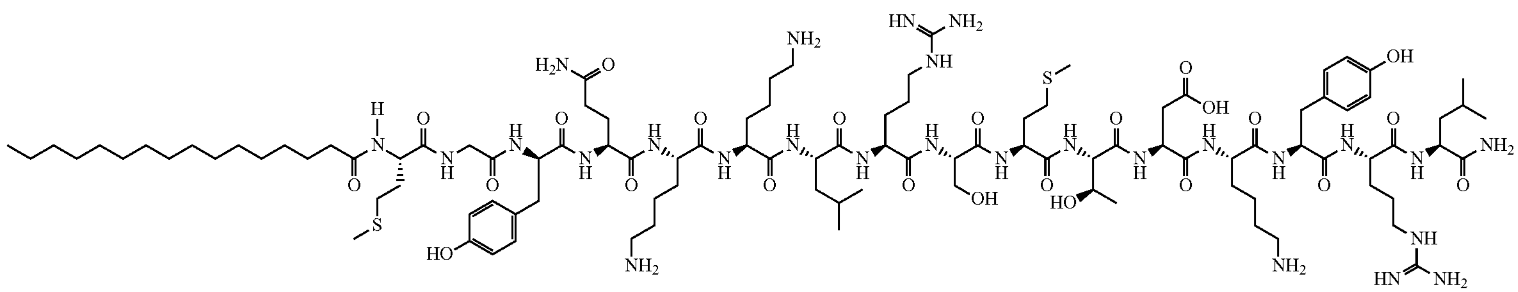 |

TABLE 7-continued

CXCR4 it loop compound structures

| Comp. # | Structure |
|---------|-----------|
| 167 | 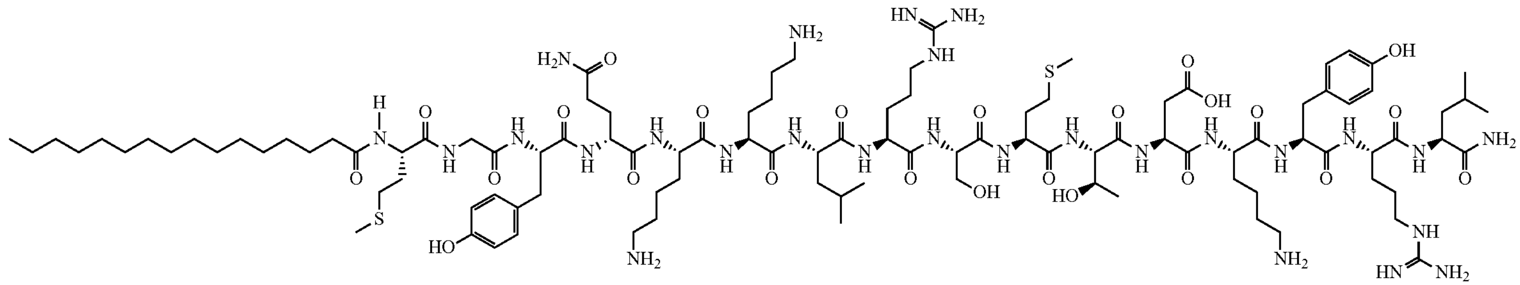 [SMILES: CCCCCCCCCCCCCCCC(=O)N[C@@H](CCSC)C(=O)NCC(=O)N[C@@H](Cc1ccc(O)cc1)C(=O)N[C@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |
| 168 | 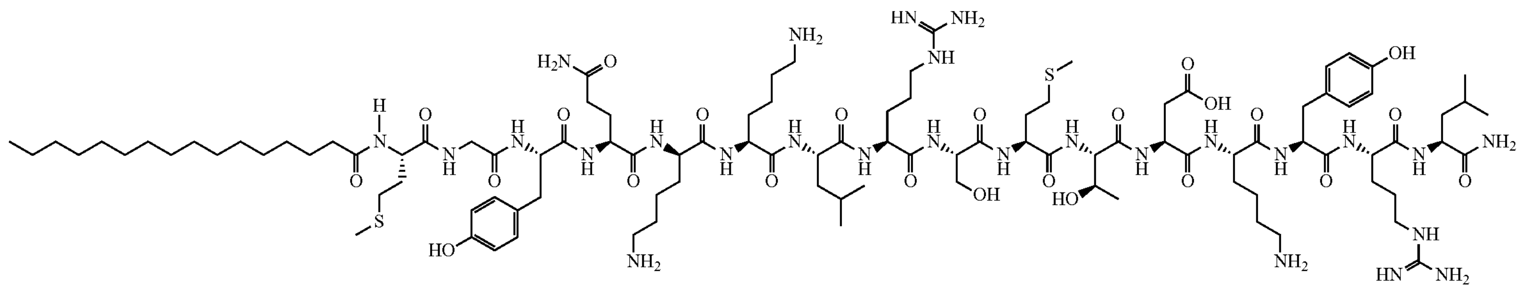 [SMILES: CCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |
| 169 | 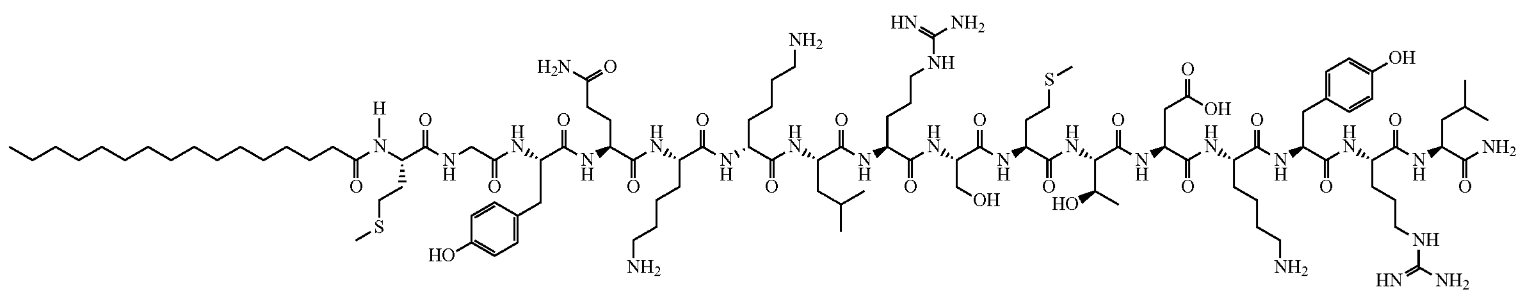 |

TABLE 7-continued

CXCR4 it loop compound structures

| Comp. # | Structure |
|---|---|
| 170 | 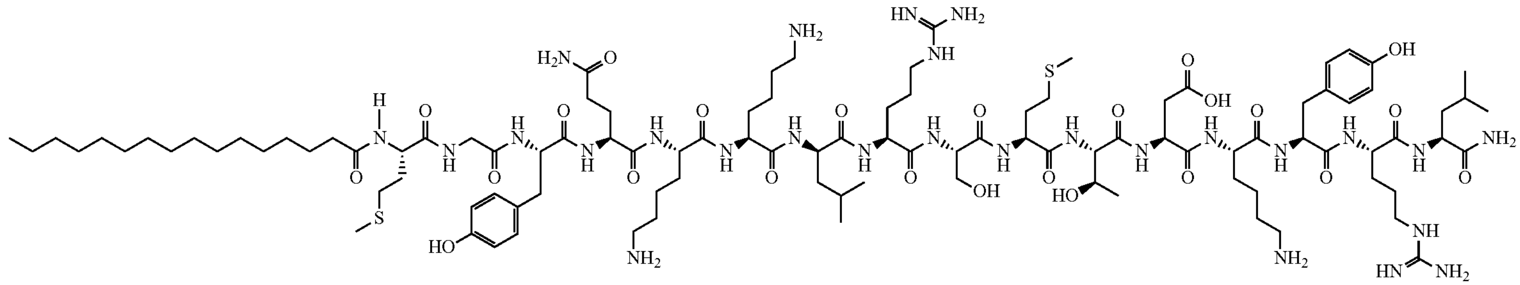 [SMILES: CCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |
| 171 | 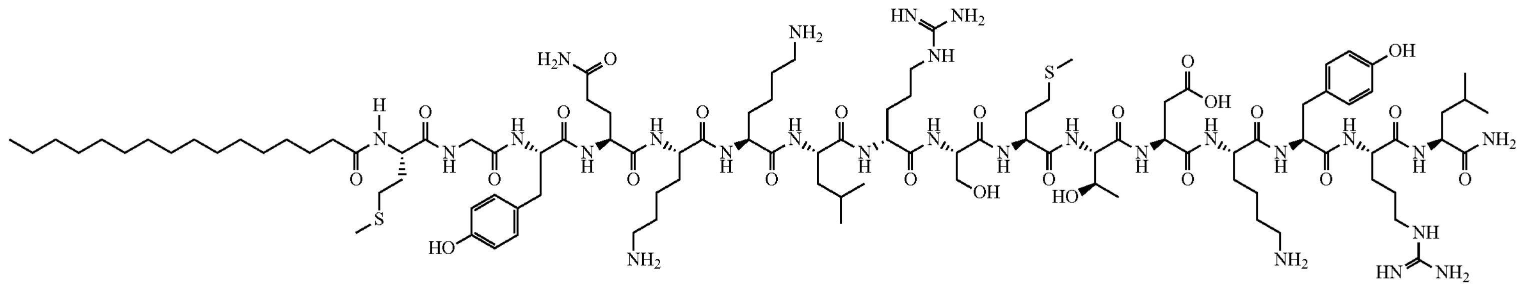 |
| 172 | 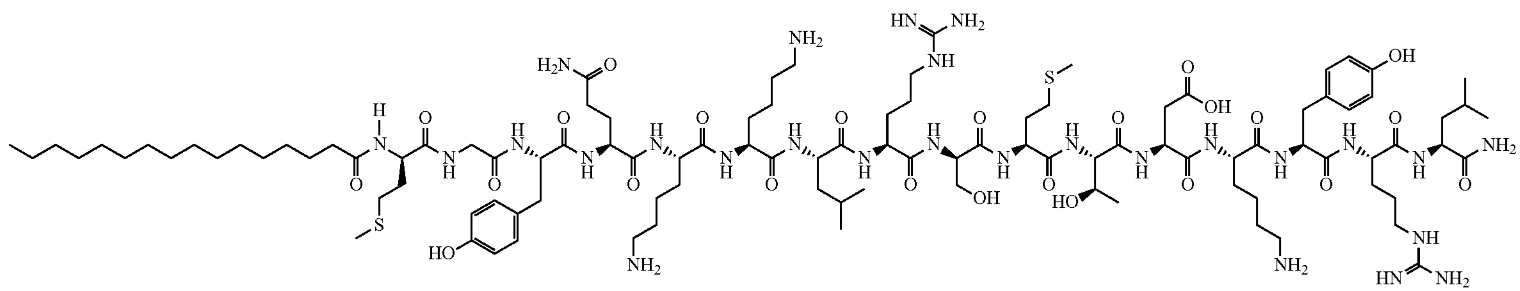 |

TABLE 7-continued

CXCR4 it loop compound structures

| Comp. # | Structure |
|---|---|
| 173 | 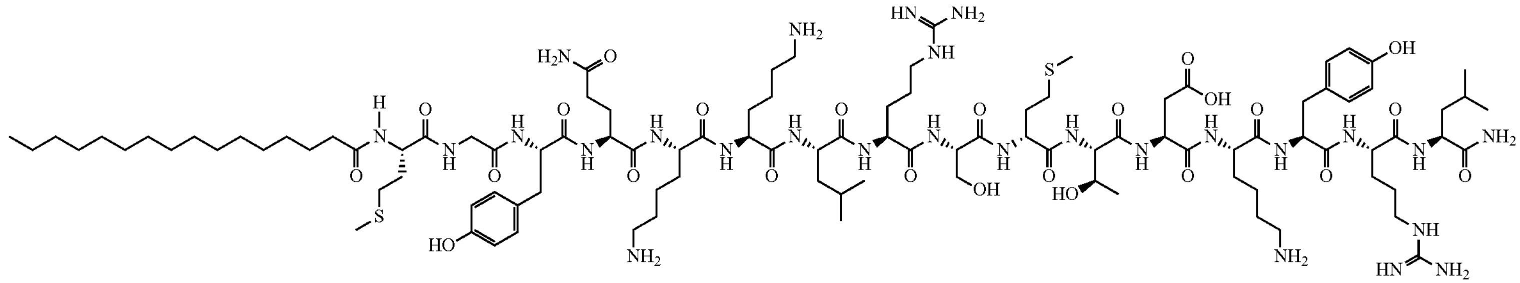 [SMILES: CCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |
| 174 | 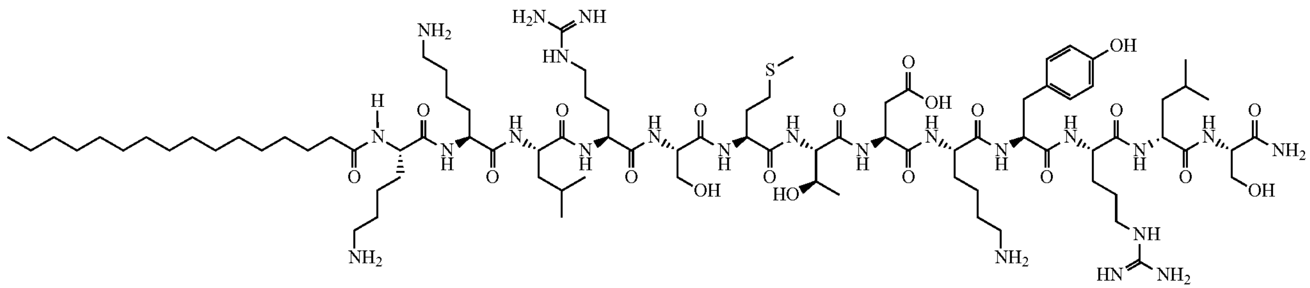 [SMILES: CCCCCCCCCCCCCCCC(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@H](CC(C)C)C(=O)N[C@@H](CO)C(N)=O)[C@@H](C)O] |
| 175 | 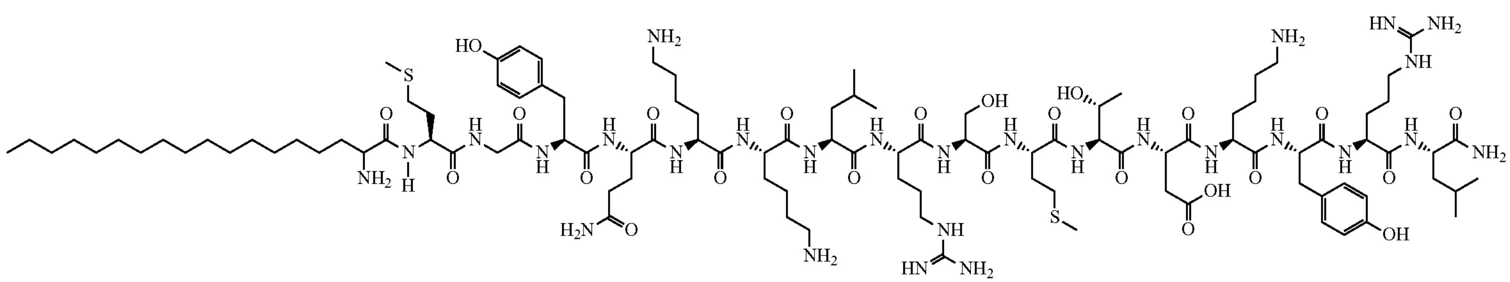 [SMILES: CCCCCCCCCCCCCCCCC(N)C(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |

TABLE 7-continued

CXCR4 it loop compound structures

| Comp. # | Structure |
|---|---|
| 176 | 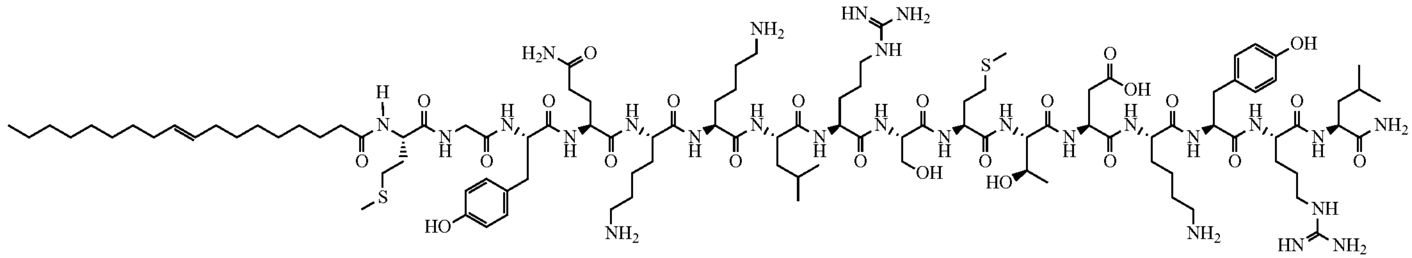 [SMILES: CCCCCCCC/C=C/CCCCCCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |
| 177 | 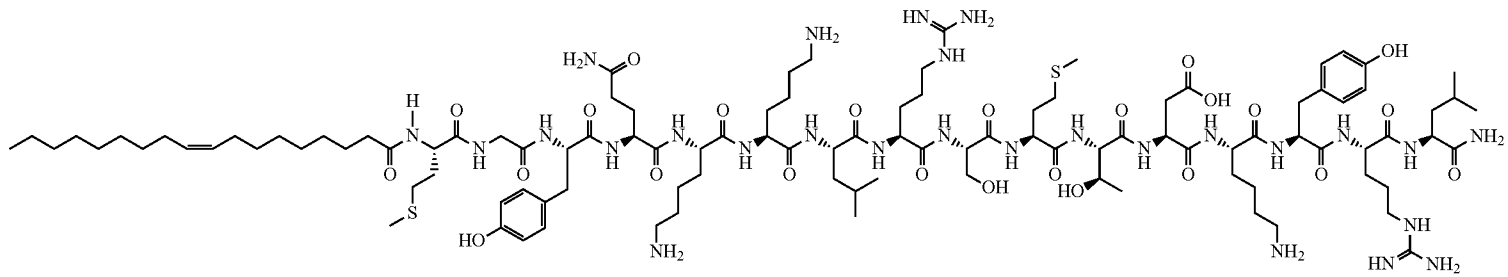 [SMILES: CCCCCCCC/C=C\CCCCCCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |
| 178 | 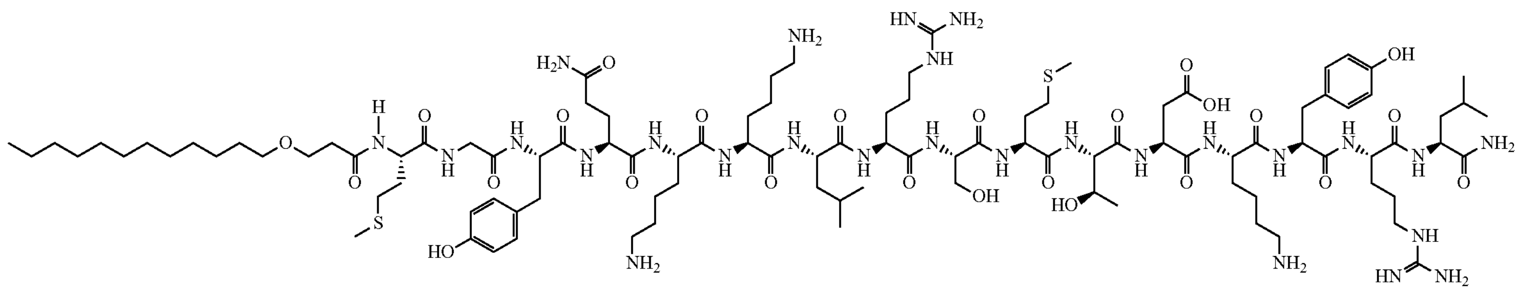 [SMILES: CCCCCCCCCCCCOCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |

TABLE 7-continued

CXCR4 it loop compound structures

| Comp. # | Structure |
|---|---|
| 179 | 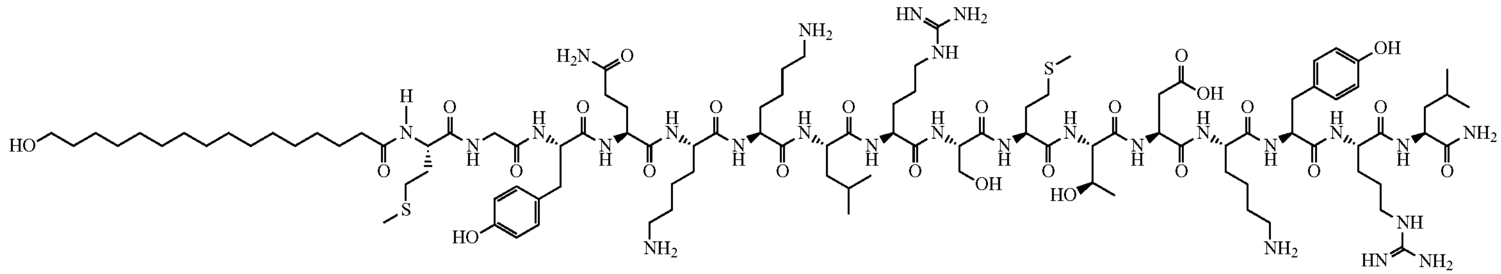 [SMILES: CSCC[C@H](NC(=O)CCCCCCCCCCCCCCCO)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |
| 180 | 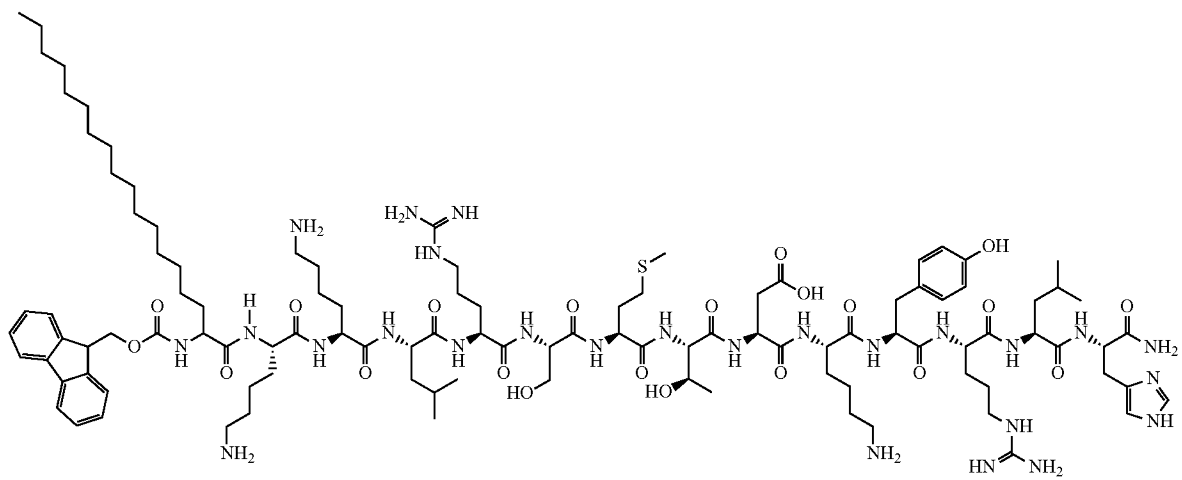 [SMILES: CCCCCCCCCCCCCCCCC(NC(=O)OCC1c2ccccc2-c2ccccc21)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(=O)N[C@@H](Cc1c[nH]cn1)C(N)=O)[C@@H](C)O] |

TABLE 7-continued

CXCR4 it loop compound structures

| Comp. # | Structure |
|---|---|
| 181 | 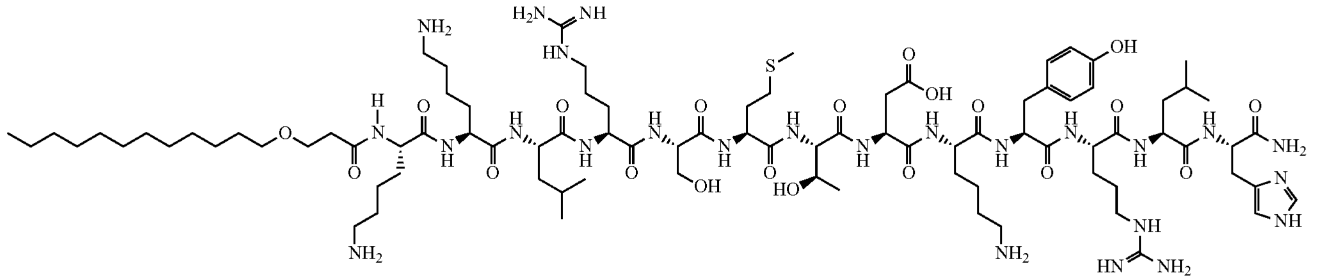 [SMILES: CCCCCCCCCCCCOCCC(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(=O)N[C@@H](Cc1c[nH]cn1)C(N)=O)[C@@H](C)O] |
| 182 | 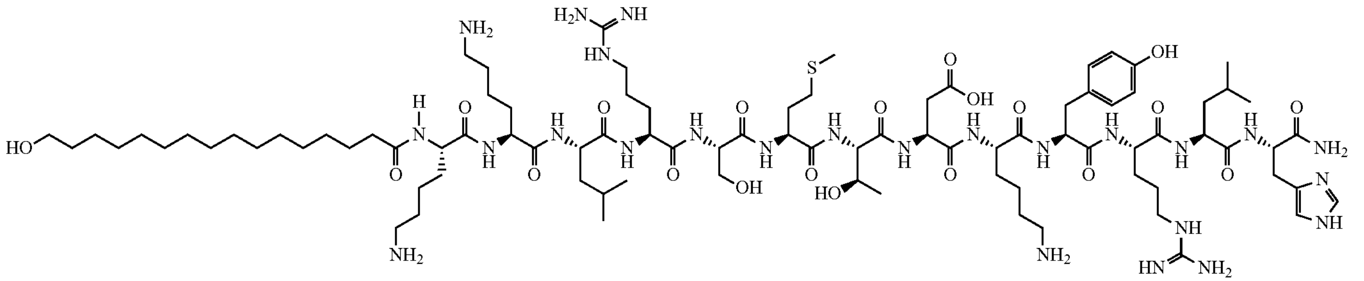 [SMILES: CSCC[C@H](NC(=O)[C@H](CO)NC(=O)[C@H](CCCNC(=N)N)NC(=O)[C@H](CC(C)C)NC(=O)[C@H](CCCCN)NC(=O)[C@H](CCCCN)NC(=O)CCCCCCCCCCCCCCCO)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(=O)N[C@@H](Cc1c[nH]cn1)C(N)=O)[C@@H](C)O] |
| 183 | 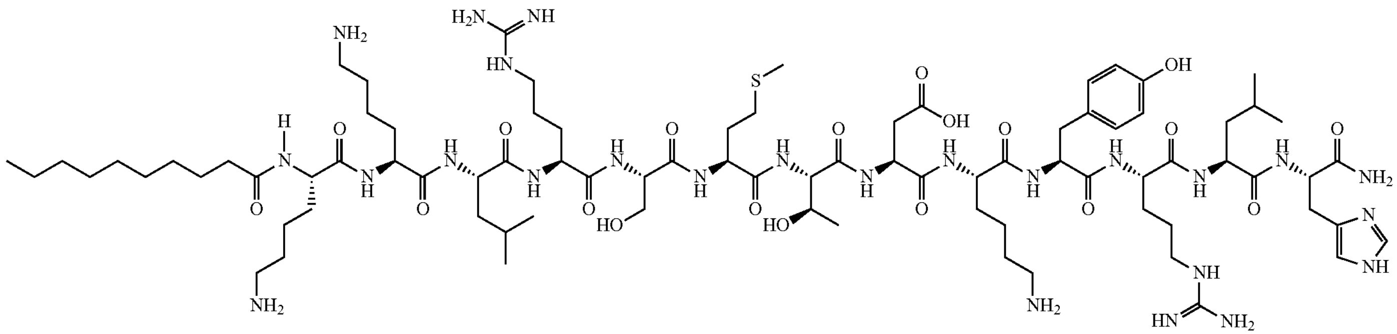 [SMILES: CCCCCCCCCC(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(=O)N[C@@H](Cc1c[nH]cn1)C(N)=O)[C@@H](C)O] |

TABLE 7-continued

CXCR4 it loop compound structures

| Comp. # | Structure |
|---|---|
| 184 | 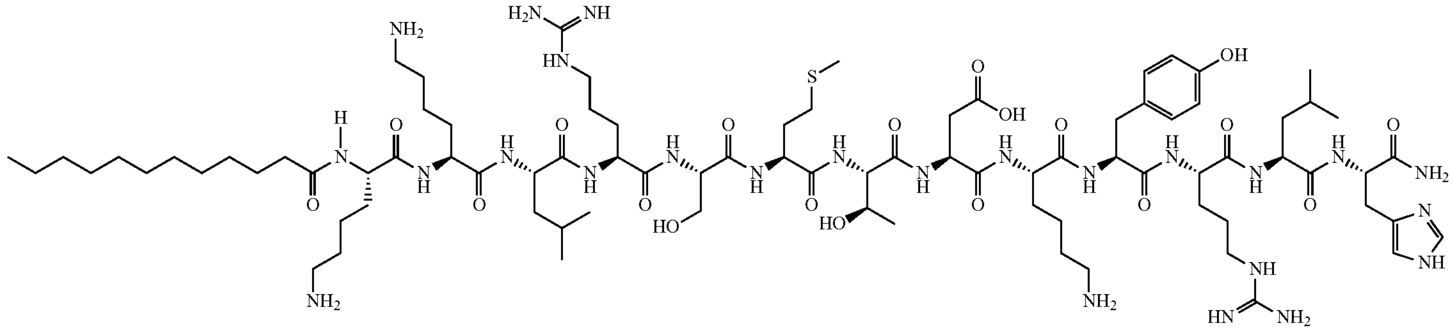 [SMILES: CCCCCCCCCCCC(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(=O)N[C@@H](Cc1c[nH]cn1)C(N)=O)[C@@H](C)O] |
| 185 | 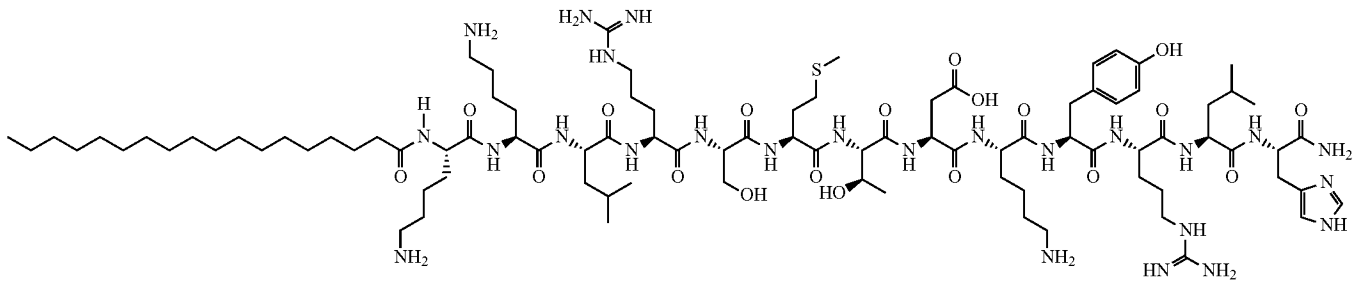 [SMILES: CCCCCCCCCCCCCCCCCC(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(=O)N[C@@H](Cc1c[nH]cn1)C(N)=O)[C@@H](C)O] |
| 186 | 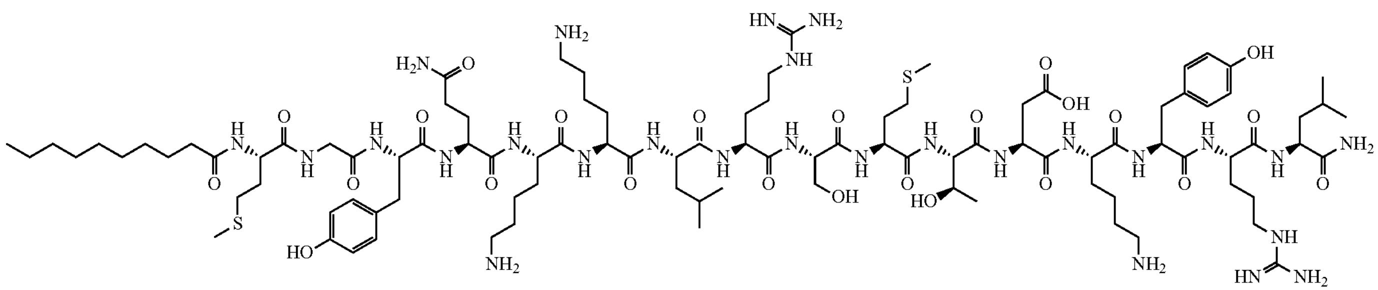 [SMILES: CCCCCCCCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |

TABLE 7-continued

CXCR4 it loop compound structures

| Comp. # | Structure |
|---|---|
| 187 | 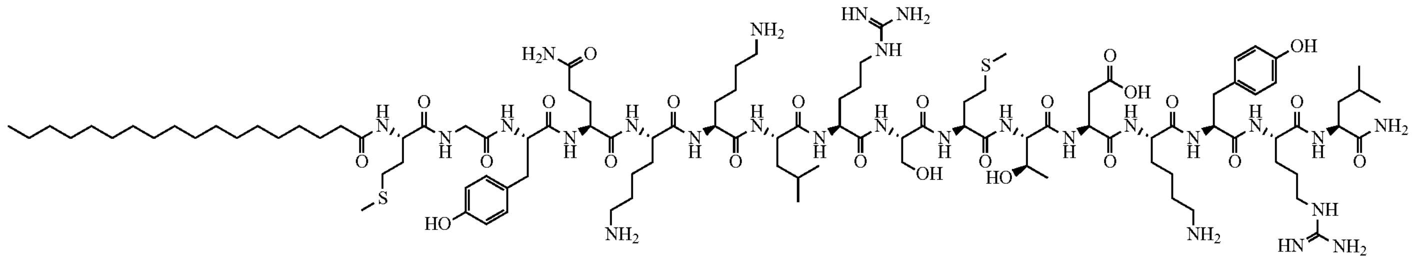 [SMILES: CCCCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |
| 188 | 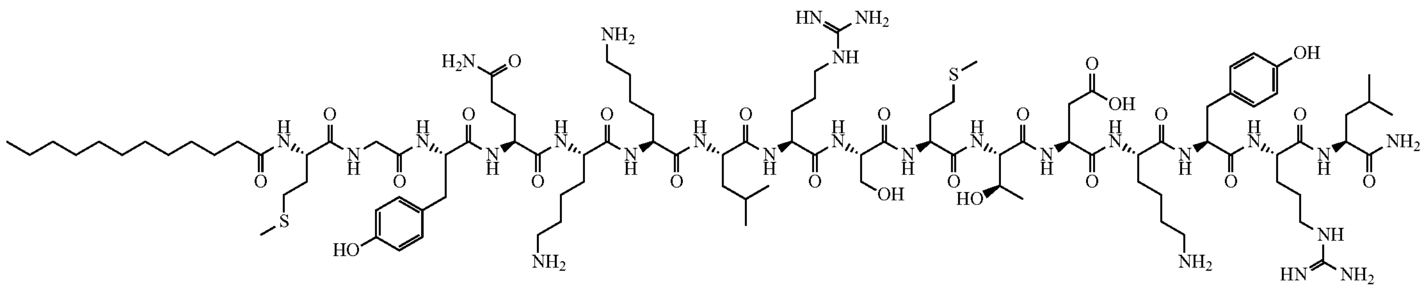 [SMILES: CCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |
| 189 | 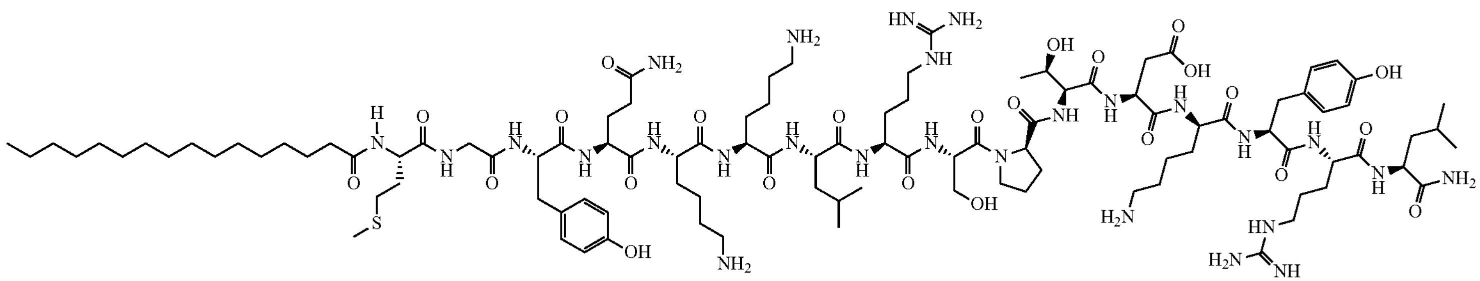 [SMILES: CCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N1CCC[C@@H]1C(=O)N[C@H](C(=O)N[C@@H](CC(=O)O)C(=O)N[C@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |

TABLE 7-continued

CXCR4 it loop compound structures

| Comp. # | Structure |
|---------|-----------|
| 190 | 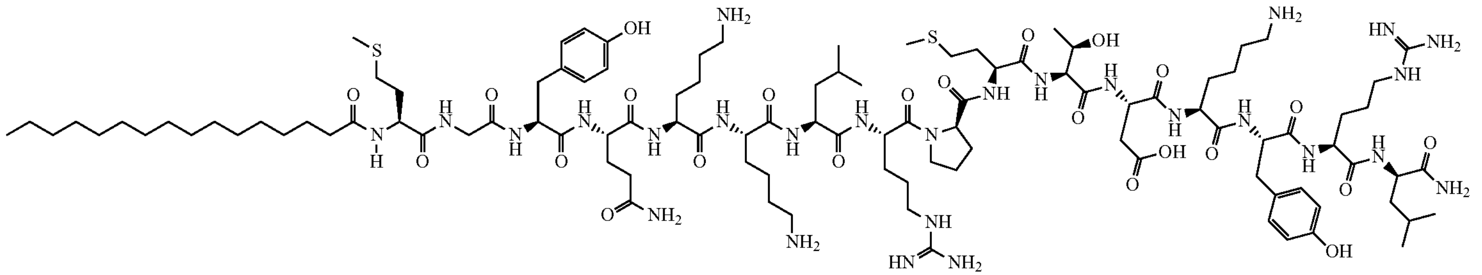 [SMILES: CCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N1CCC[C@@H]1C(=O)N[C@@H](CCSC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@H](CC(C)C)C(N)=O)[C@@H](C)O] |
| 191 | 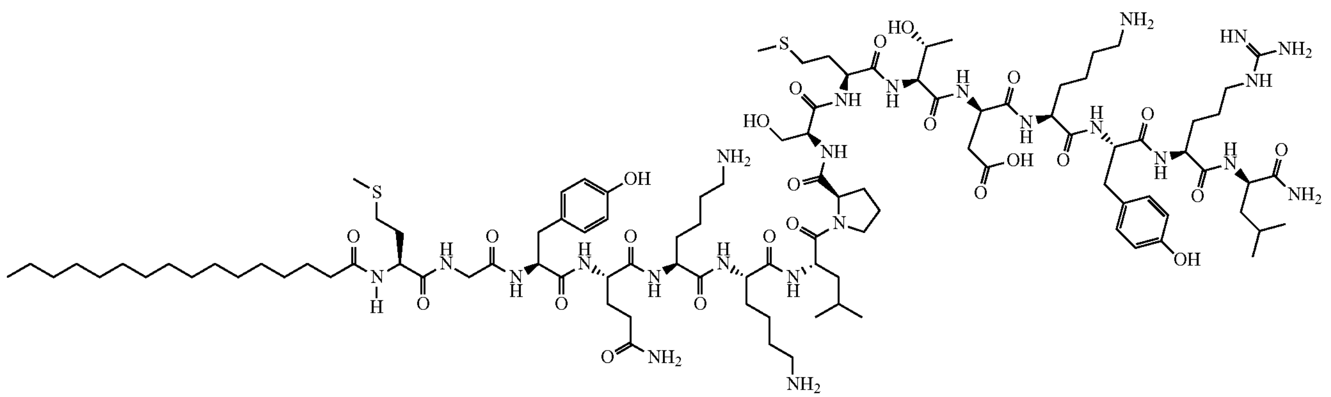 [SMILES: CCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N1CCC[C@@H]1C(=O)N[C@@H](CO)C(=O)N[C@@H](CCSC)C(=O)N[C@H](C(=O)N[C@H](CC(=O)O)C(=O)N[C@@H](CCCCN)C(=O)N[C@@H](Cc1ccc(O)cc1)C(=O)N[C@@H](CCCNC(=N)N)C(=O)N[C@H](CC(C)C)C(N)=O)[C@@H](C)O] |

TABLE 7-continued

CXCR4 it loop compound structures

| Comp. # | Structure |
|---|---|
| 192 | 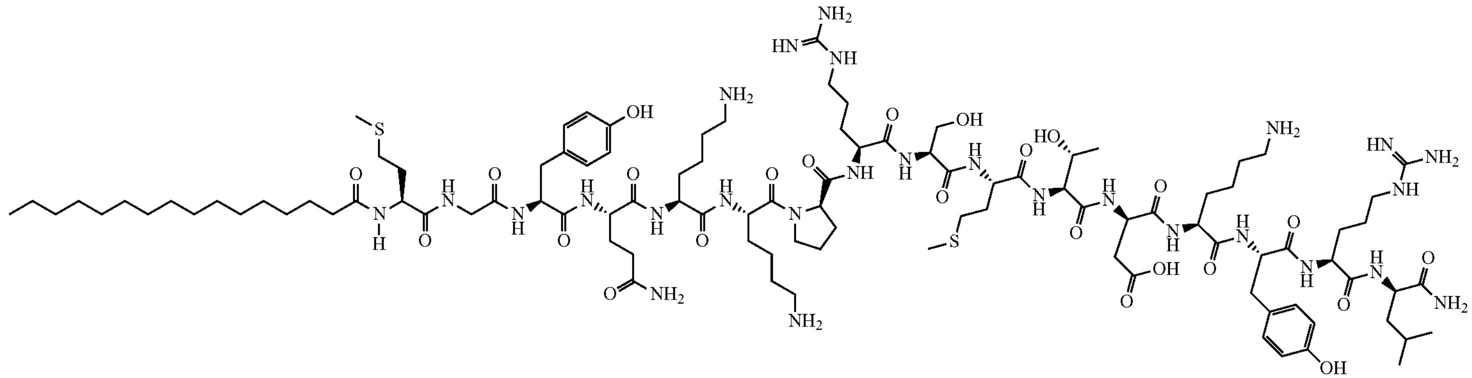 [SMILES: CCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N1CCC[C@@H]1C(=O)N[C@@H](CCCNC(=N)N)C(=O)N[C@@H](CO)C(=O)N[C@@H](CCSC)C(=O)N[C@H](C(=O)N[C@H](CC(=O)O)C(=O)N[C@@H](CCCCN)C(=O)N[C@@H](Cc1ccc(O)cc1)C(=O)N[C@@H](CCCNC(=N)N)C(=O)N[C@H](CC(C)C)C(N)=O)[C@@H](C)O] |
| 193 | 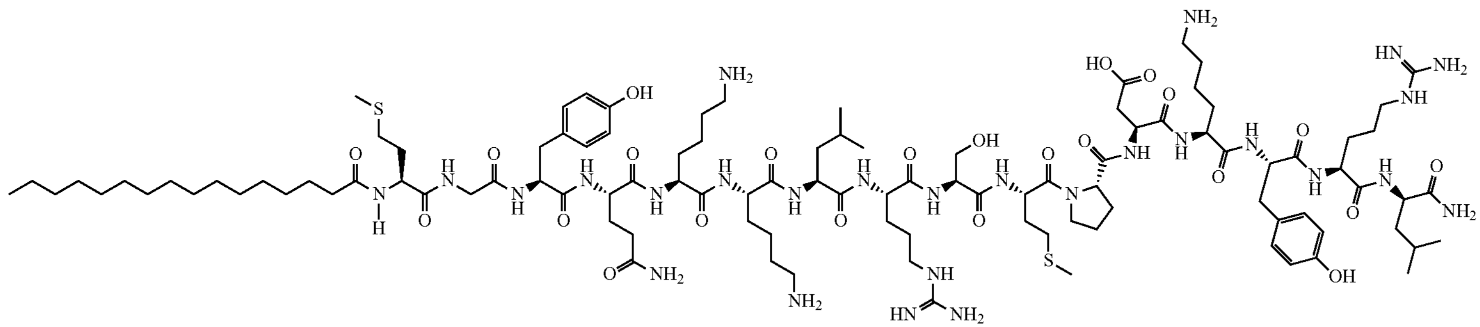 [SMILES: CCCCCCCCCCCCCCCC(=O)N[C@@H](CCSC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CC(C)C)C(=O)N[C@@H](CCCNC(=N)N)C(=O)N[C@@H](CO)C(=O)N[C@@H](CCSC)C(=O)N1CCC[C@H]1C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@H](CC(C)C)C(N)=O] |
| 194 | 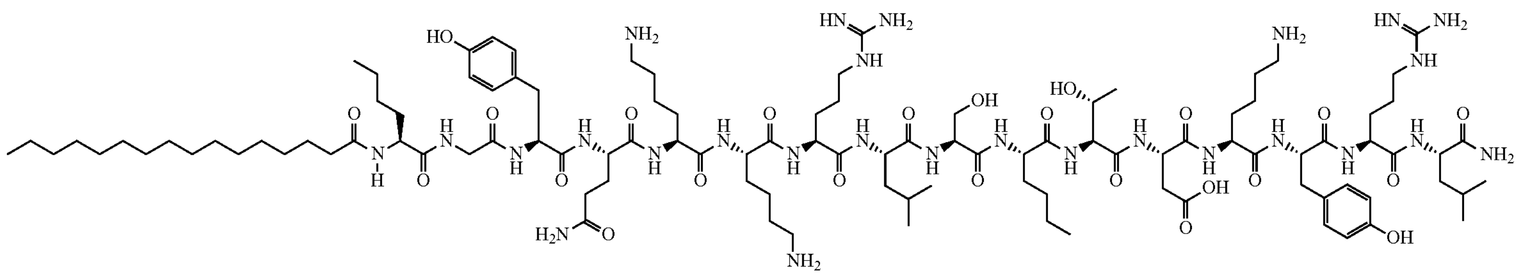 [SMILES: CCCCCCCCCCCCCCCC(=O)N[C@@H](CCCC)C(=O)NCC(=O)N[C@@H](Cc1ccc(O)cc1)C(=O)N[C@@H](CCC(N)=O)C(=O)N[C@@H](CCCCN)C(=O)N[C@@H](CCCCN)C(=O)N[C@@H](CCCNC(=N)N)C(=O)N[C@@H](CC(C)C)C(=O)N[C@@H](CO)C(=O)N[C@@H](CCCC)C(=O)N[C@H](C(=O)N[C@@H](CC(=O)O)C(=O)N[C@@H](CCCCN)C(=O)N[C@@H](Cc1ccc(O)cc1)C(=O)N[C@@H](CCCNC(=N)N)C(=O)N[C@@H](CC(C)C)C(N)=O)[C@@H](C)O] |

TABLE 8

CXCR4 i2 loop compounds

| No. | Loop | Sequence | Lipid | MW | Comments |
|---|---|---|---|---|---|
| 74 | i2 | DRYLAIVHATNSQRPRKLL (SEQ ID NO: 152), | Pal | 2713.439 | Dual-Lipid |
| 75 | i2 | VHATNSQRPRKLLAEKVVY (SEQ ID NO: 194), | Pal | 2446.974 | |
| 76 | i2 | DRYLAIVHATNSQRPRKLL (SEQ ID NO: 152), | Myr | 2742.438 | second lipid on backbone |
| 77 | i2 | DRYLAIVHATNSQRPRKLL (SEQ ID NO: 152), | Pal | 2489.014 | |
| 78 | i2 | VHATNSQRPRKLLA (SEQ ID NO: 195), | Pal | 1828.253 | |
| 79 | i2 | HATNSQRPRKL (SEQ ID NO: 196), | Pal | 1544.886 | |
| 80 | i2 | HATNSQRPRKLLA (SEQ ID NO: 197), | Pal | 1729.121 | |
| 81 | i2 | HATNSQRPRKLLAE (SEQ ID NO: 198), | Pal | 1858.235 | |
| 82 | i2 | HATNSQRPRKLLAEK (SEQ ID NO: 171), | Pal | 1986.408 | |
| 83 | i2 | HATNSQRPRKLLAEKV (SEQ ID NO: 199), | Pal | 2085.539 | |

TABLE 9

CXCR4 i2 loop compound structures

| Comp. # | Structure |
|---|---|
| 74 | 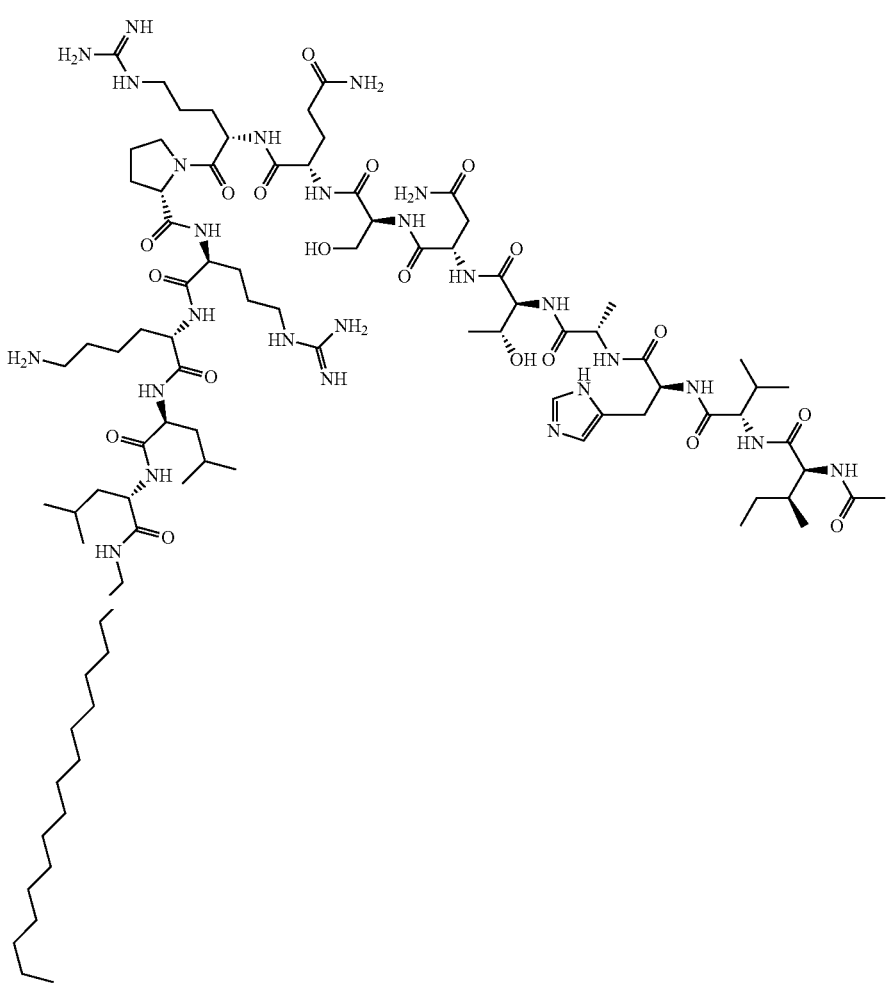 |

TABLE 9-continued
CXCR4 i2 loop compound structures
| Comp. # | Structure |
|---|---|
| | 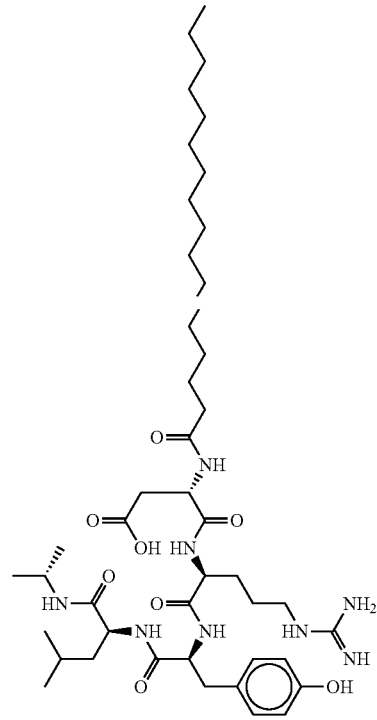 |
| 75 | 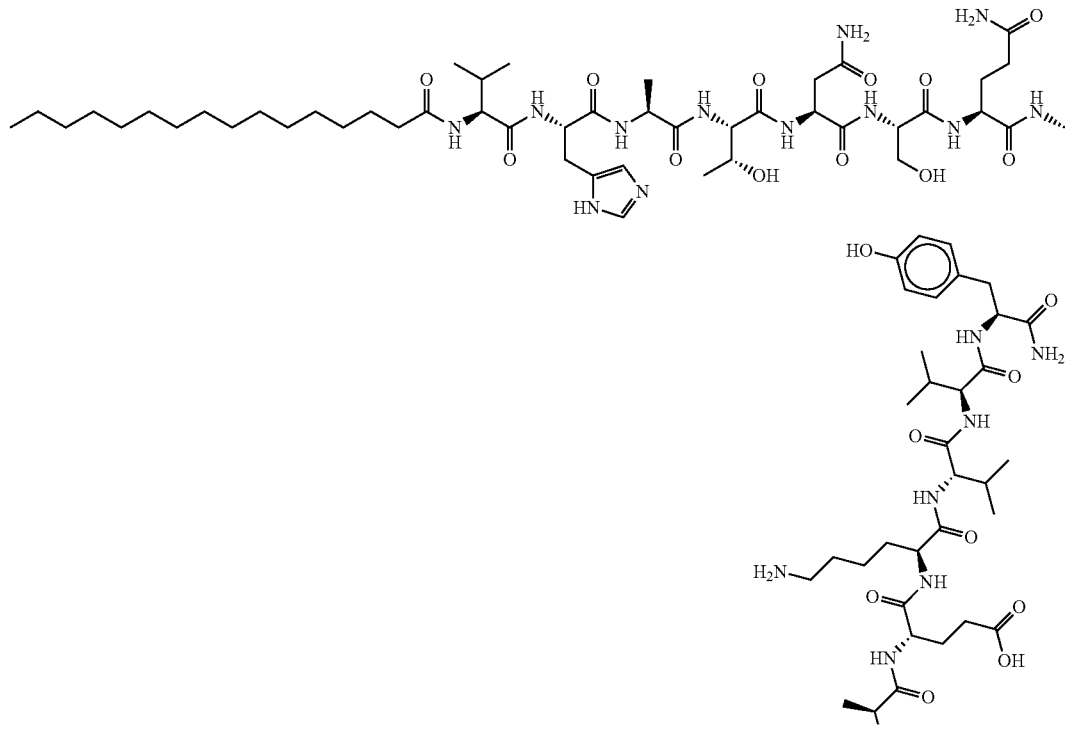 |

TABLE 9-continued
CXCR4 i2 loop compound structures
| Comp. # | Structure |
|---|---|
| | 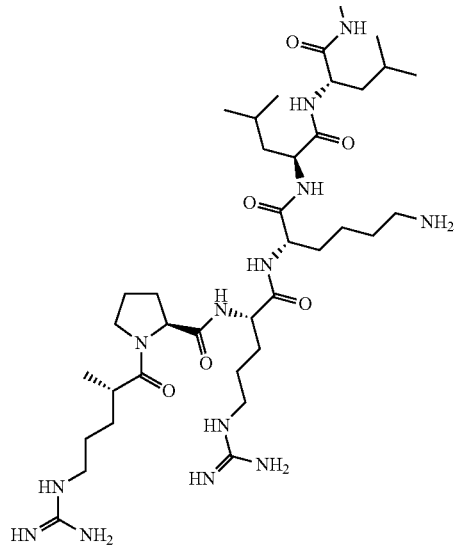 |
| 76 | 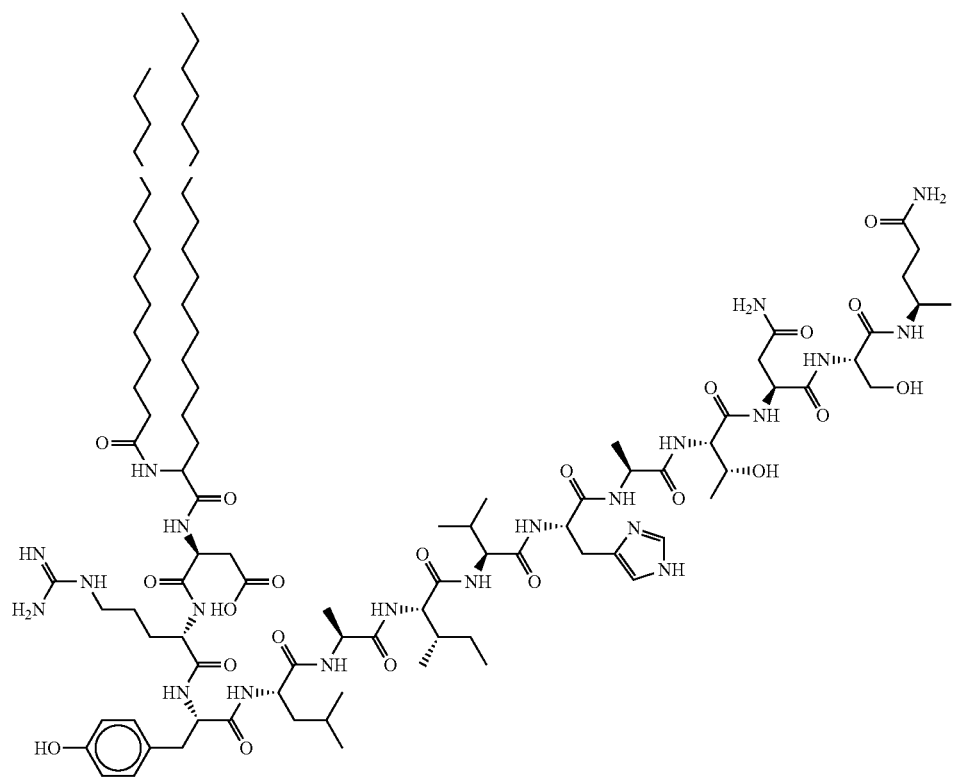 |

TABLE 9-continued
CXCR4 i2 loop compound structures
| Comp. # | Structure |
|---|---|
| | 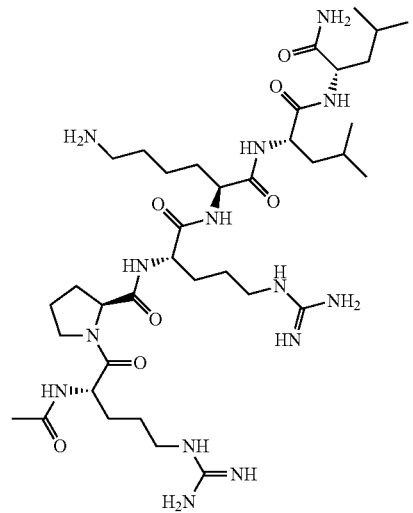 |
| 77 | 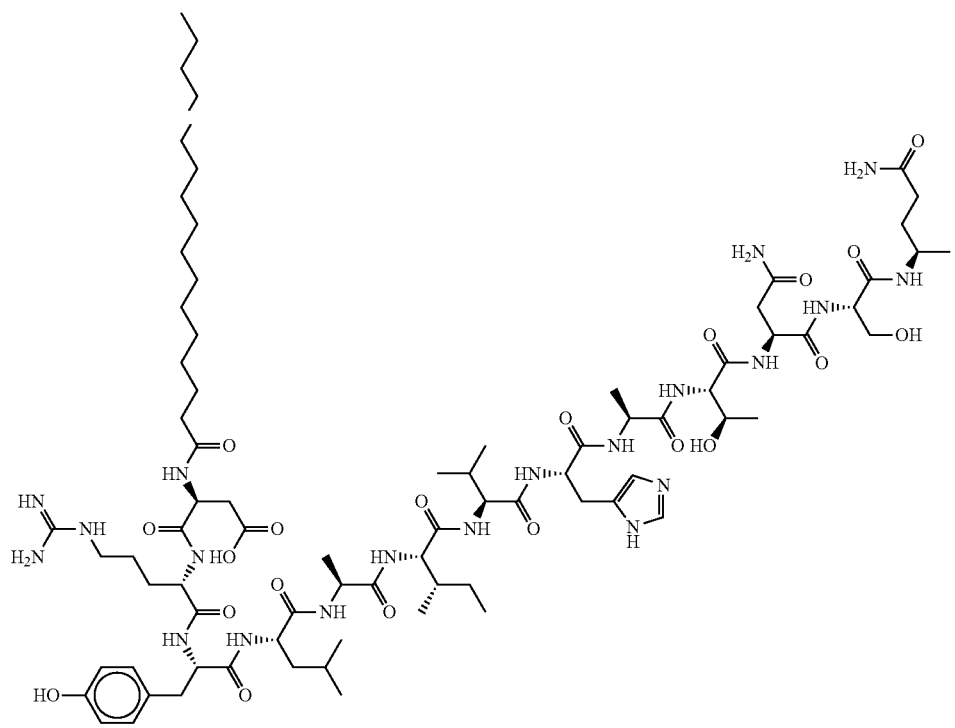 |

TABLE 9-continued
CXCR4 i2 loop compound structures
| Comp. # | Structure |
|---|---|
| 78 | 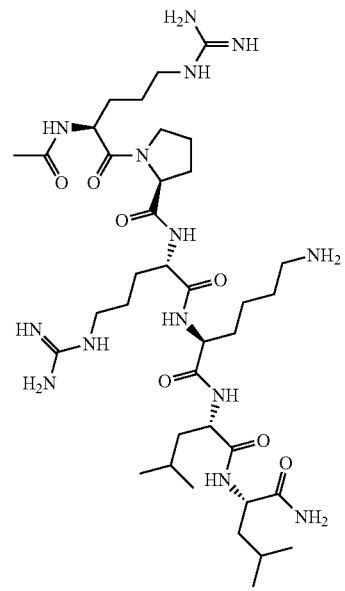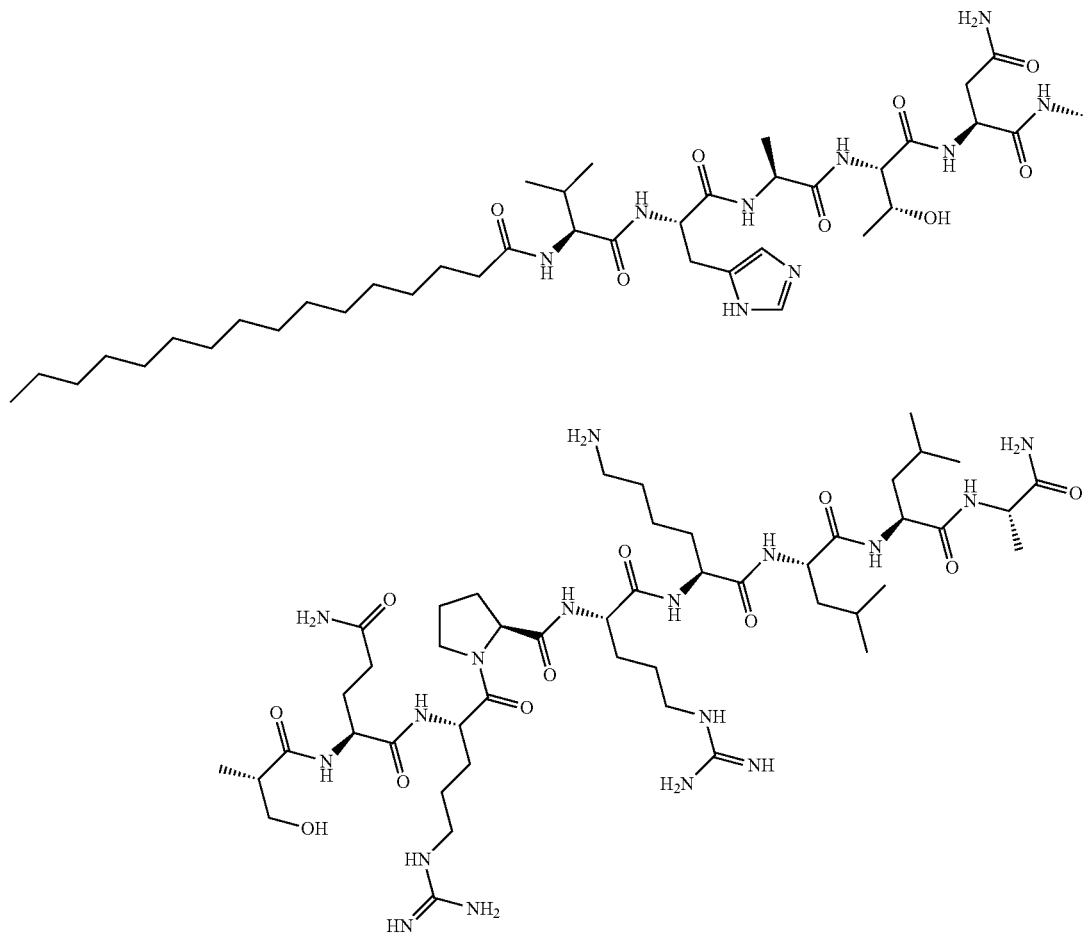 |

TABLE 9-continued
CXCR4 i2 loop compound structures
| Comp. # | Structure |
|---|---|
| 79 | 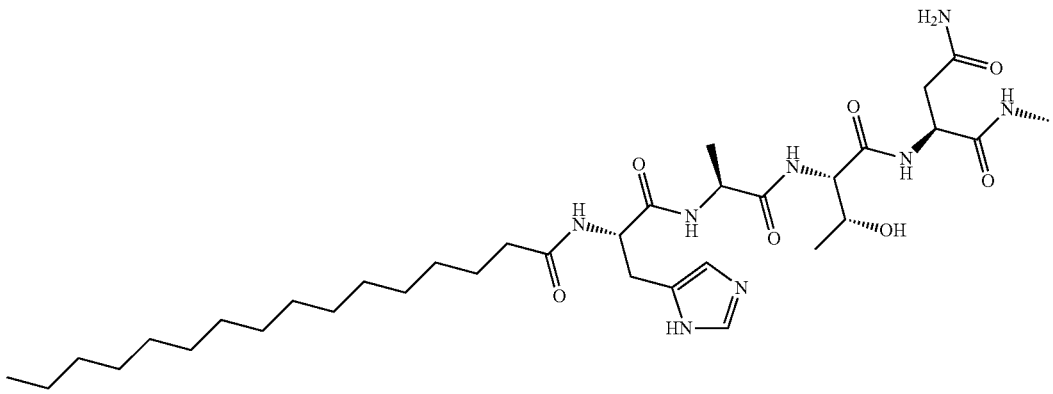 |
| 80 | 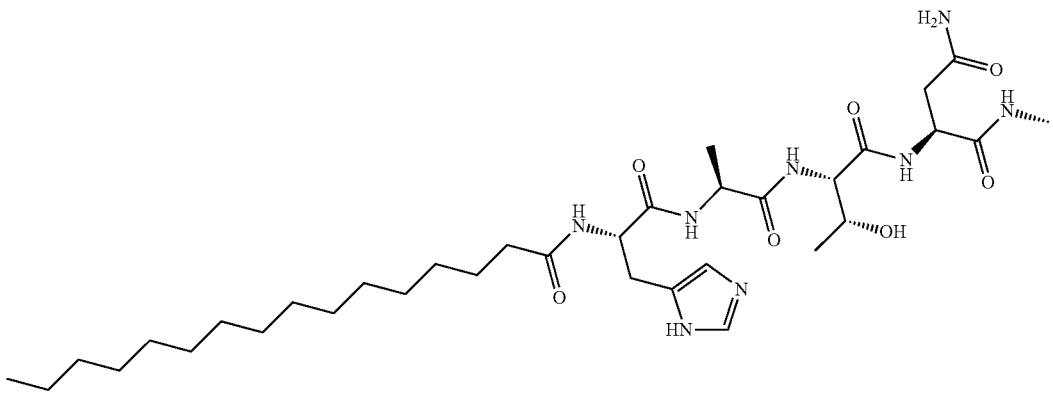 |

TABLE 9-continued
CXCR4 i2 loop compound structures
| Comp. # | Structure |
|---|---|
| | 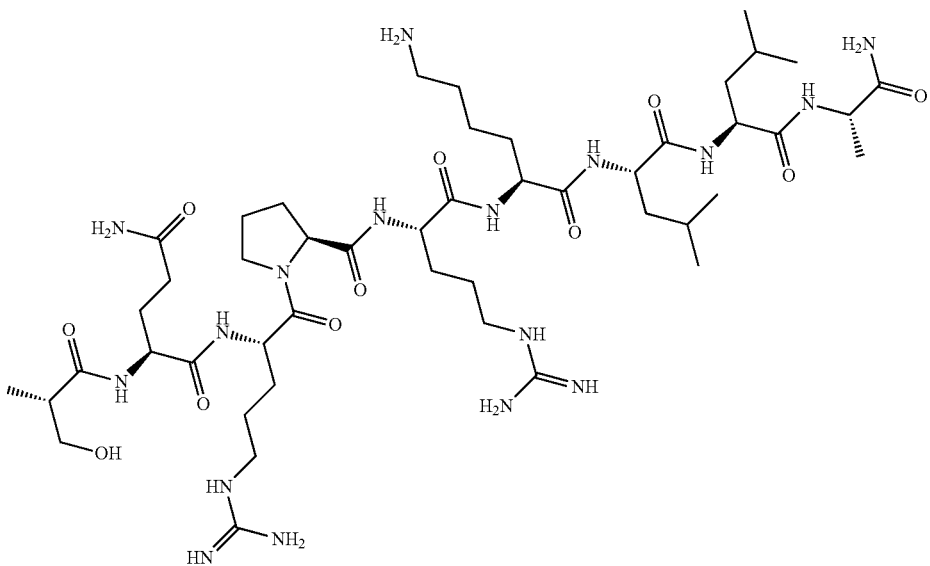 |
| 81 | 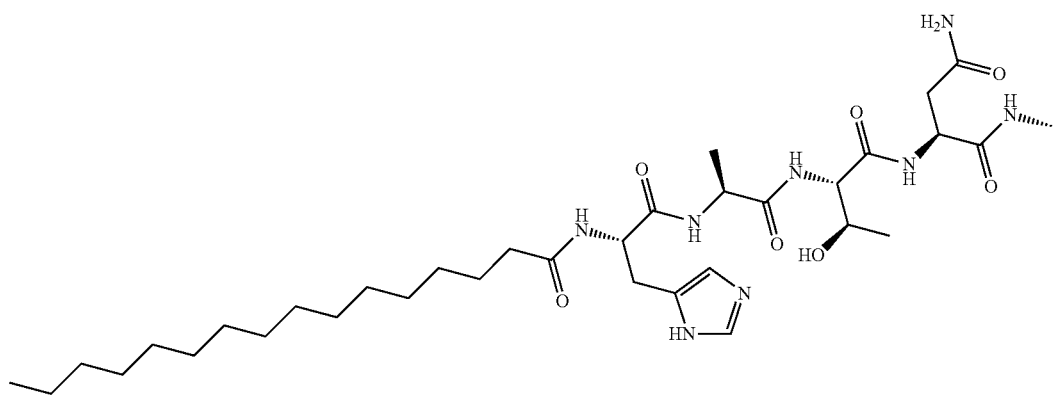 |

TABLE 9-continued
CXCR4 i2 loop compound structures
| Comp. # | Structure |
|---|---|
| | 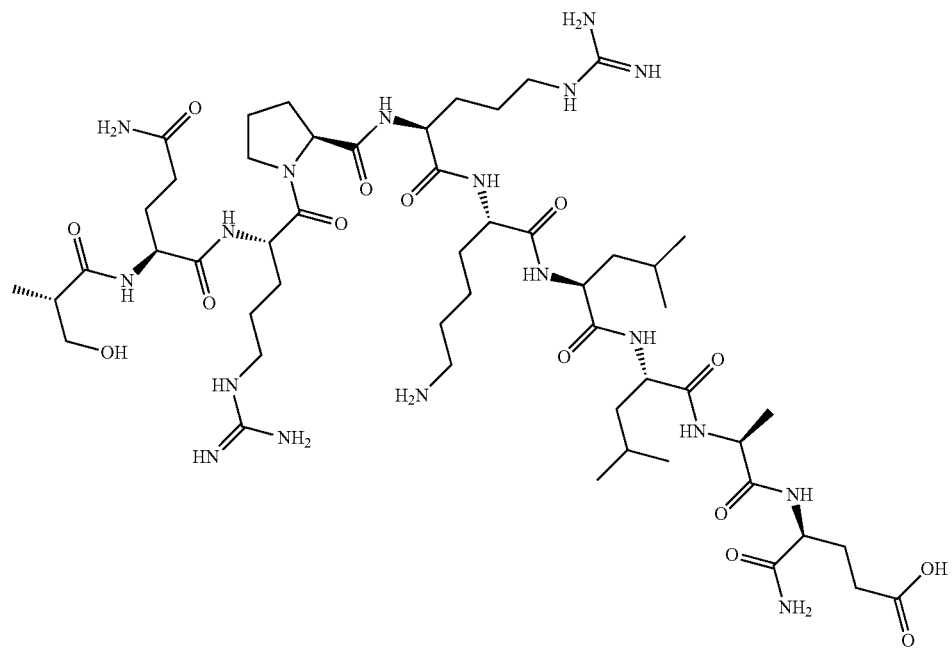 |
| 82 | 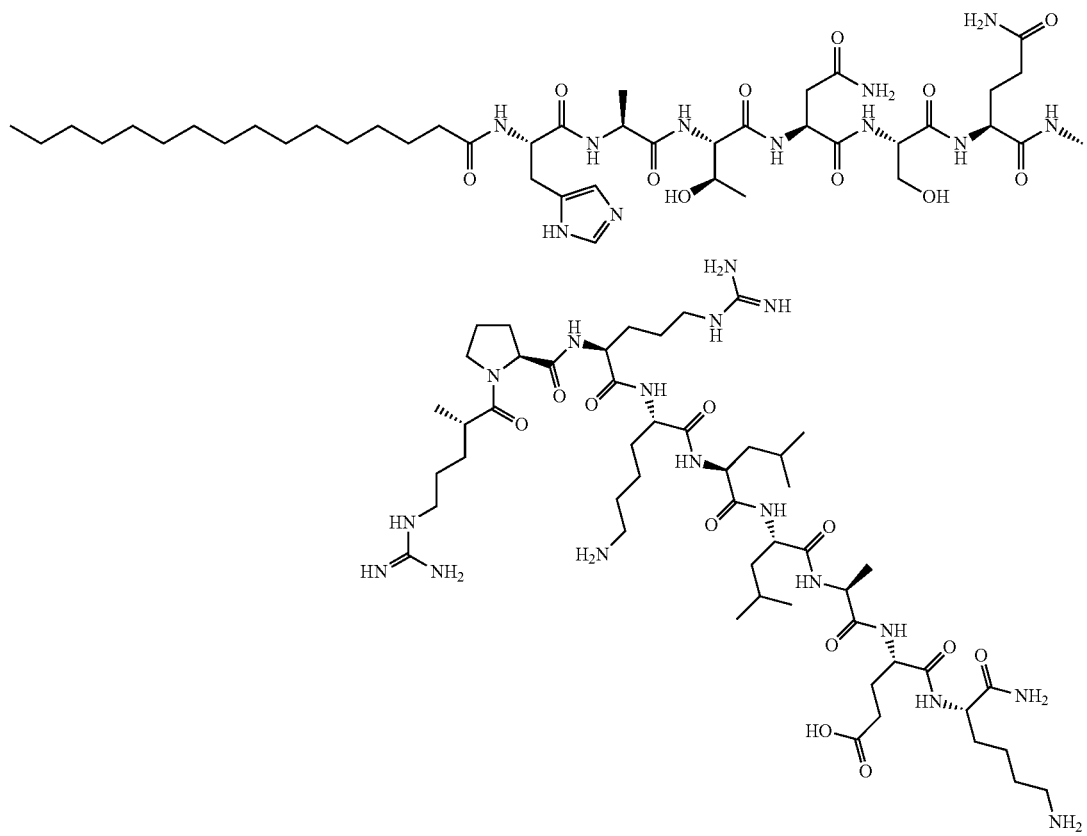 |

TABLE 9-continued

CXCR4 i2 loop compound structures

| Comp. # | Structure |
|---|---|
| 83 | (structure image) |

TABLE 10

CXCR4 i3 loop compounds

| | | Loop Sequence | Lipid | Comments | MW |
|---|---|---|---|---|---|
| 84 | i3 | HSKKGHQKRKALK (SEQ. ID NO: 200) | Pal | | 1783.258 |
| 85 | i3 | HSKGHQKRKALK (SEQ. ID NO: 369) | Pal | | 1655.086 |
| 87 | i3 | HSKGHQKRKQALK (SEQ ID NO: 244) | C16H33 | Pentadecyl-alanine with Biotin | 1924.449 |
| 88 | i3 | SKLSHSKGHQKRKAL KTTVIL (SEQ ID NO: 253) | Pal | | 2598.225 |
| 89 | i3 | KLSHSKGHQKRKALK TTVIL (SEQ ID NO: 249) | Pal | | 2511.147 |
| 90 | i3 | KLSHSKGHQKRKALK TTV (SEQ ID NO: 248) | Pal | | 2284.832 |
| 91 | i3 | KLSHSKGHQKRKALK T(SEQ ID NO: 219) | Pal | | 2084.597 |

TABLE 10 -continued

CXCR4 i3 loop compounds

| | | Loop Sequence | Lipid | Comments | MW |
|---|---|---|---|---|---|
| 92 | i3 | KLSHSKGHQKRKALK (SEQ ID NO: 247) | Pal | | 1983.493 |
| 93 | i3 | KLSHSKGHQKRKAL (SEQ ID NO: 246) | Pal | | 1855.321 |
| 94 | i3 | KLSHSKGHQKRKA (SEQ ID NO: 245) | Pal | | 1742.163 |
| 95 | i3 | LSHSKGHQKRKALK (SEQ ID NO: 250) | Pal | | 1855.321 |
| 96 | i3 | SHSKGHQKRKALK (SEQ ID NO: 251) | Pal | | 1742.163 |
| 97 | i3 | HSKGHQKRKALKT (SEQ ID NO: 222) | Pal | | 1756.19 |
| 98 | i3 | HSKGHQKRKALKTT (SEQ ID NO: 241) | Pal | | 1857.294 |
| 99 | i3 | HSKGHQKRKALKTTV (SEQ ID NO: 242) | Pal | | 1956.425 |
| 100 | i3 | HSKGHQKRKALKTTVI (SEQ ID NO: 243) | Pal | | 2069.583 |
| 101 | i3 | SKLSHSKGHQKRKALK (SEQ ID NO: 252) | Pal | | 2070.571 |
| 102 | i3 | IIISKLSHSKGHQKRKALKT (SEQ ID NO: 202) | Pal | | 2511.147 |
| 103 | i3 | IIISKLSHSKGHQKRKALKT (SEQ ID NO: 202) | myr | dula lipid, backbone | 2765.556 |
| 104 | i3 | IIISKLSHSKGHQKRKALKT (SEQ ID NO: 202) | Pal | dual lipid | 2735.573 |
| 105 | i3 | KLSHSKGHQKRKALKTTVIL (SEQ ID No: 249) | Myr | Dual lipid, backbone | 2764.571 |
| 106 | i3 | QHLHIALKKSTSRKVKSGTLK (SEQ ID No: 254) | Pal | scrambled ATI2357 | 2598.225 |

TABLE 11
CXCR4 i3 loop compound structures
| Comp. # | Structure |
|---|---|
| 106 | 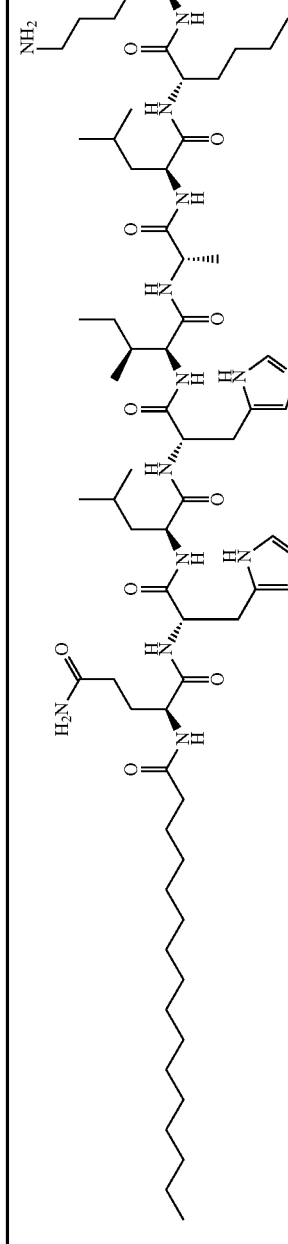 |

TABLE 11-continued
CXCR4 i3 loop compound structures
| Comp. # | Structure |
|---|---|
| 105 | 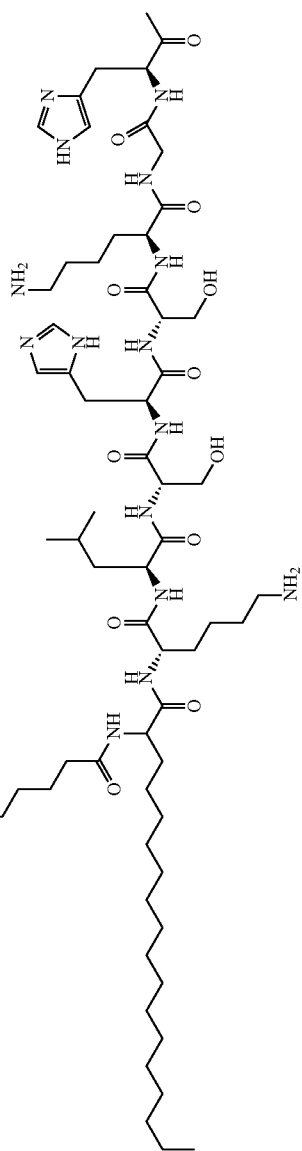 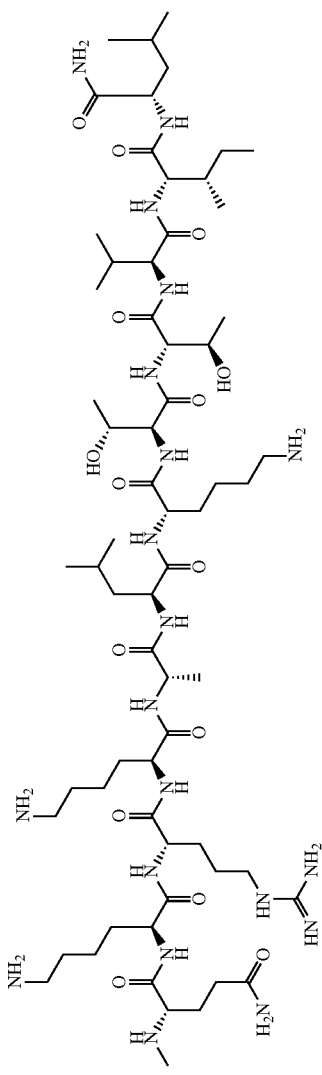 |

TABLE 11-continued
CXCR4 i3 loop compound structures
| Comp. # | Structure |
|---|---|
| 104 | 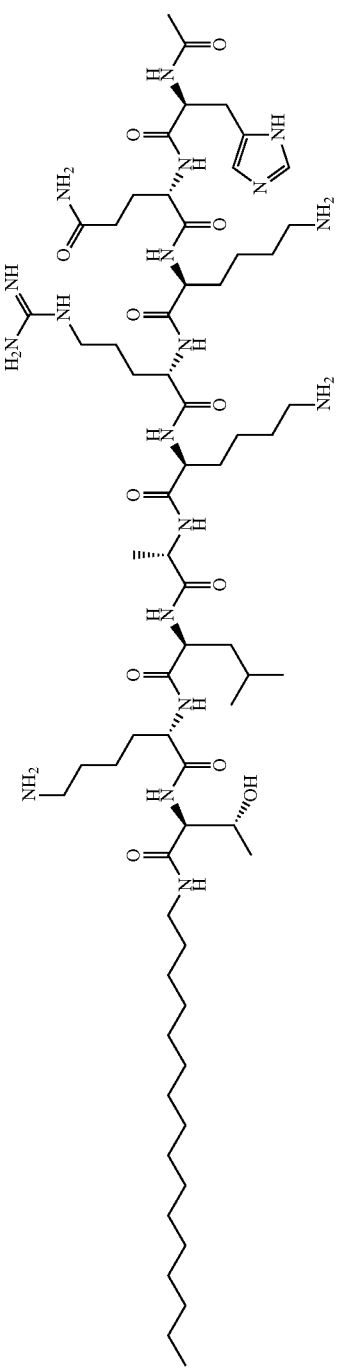 |

TABLE 11-continued

CXCR4 i3 loop compound structures

| Comp. # | Structure |
|---|---|
| 103 | 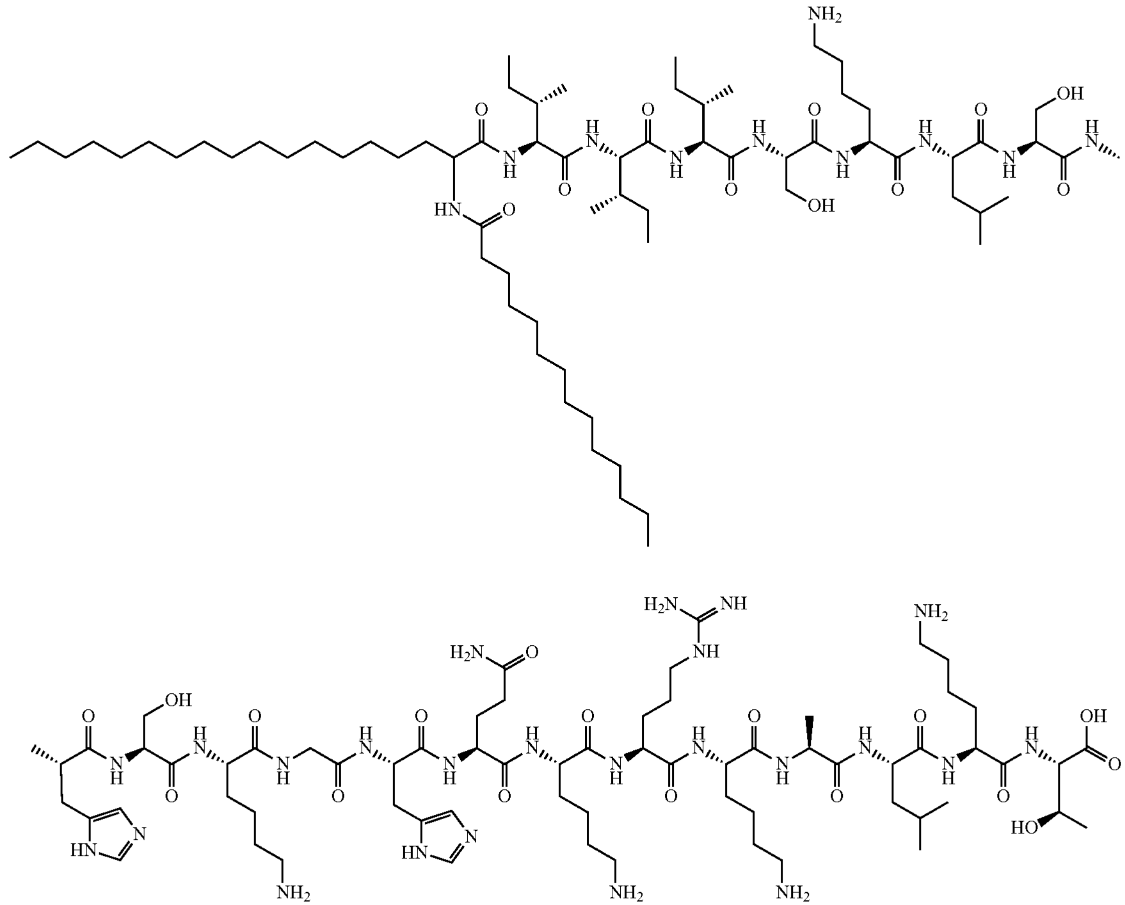 |

TABLE 11-continued

CXCR4 i3 loop compound structures

| Comp. # | Structure |
|---|---|
| 102 | 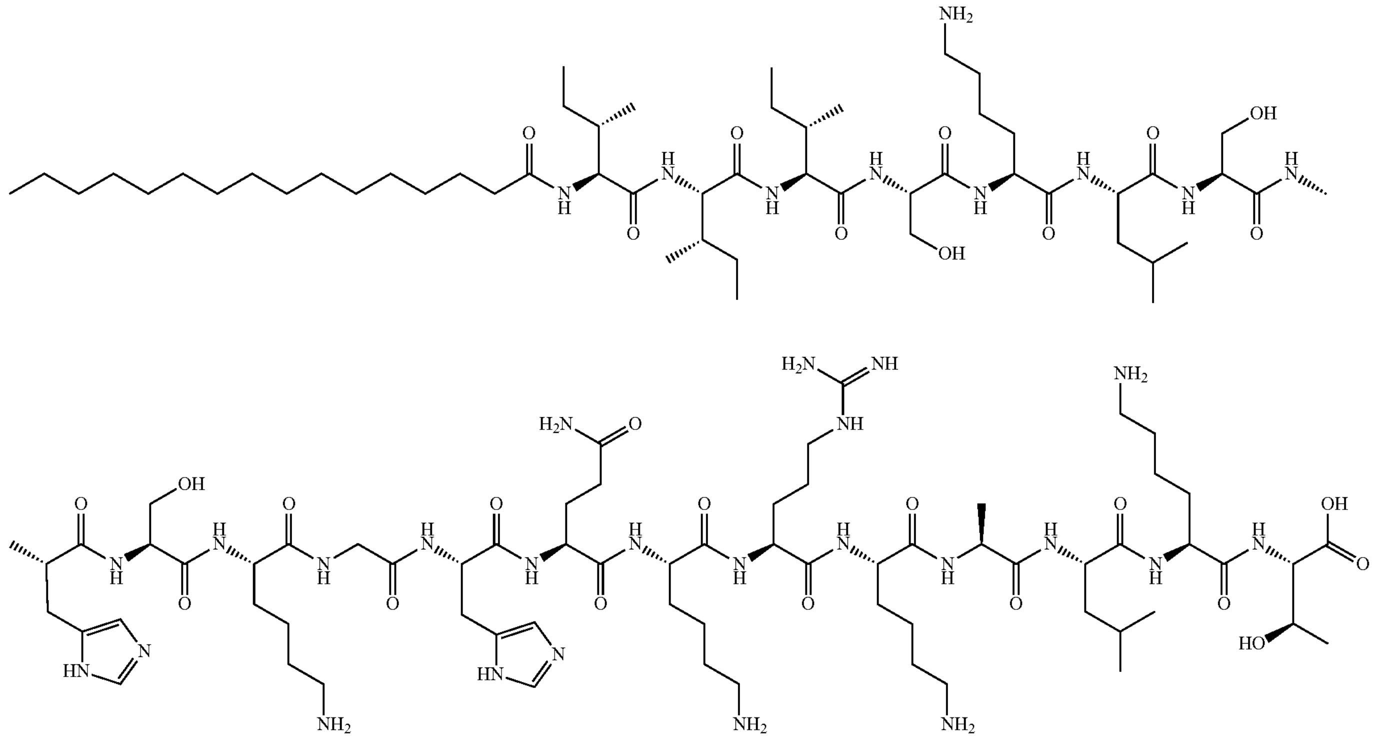 |

TABLE 11-continued

CXCR4 l3 loop compound structures

| Comp. # | Structure |
|---|---|
| 101 | 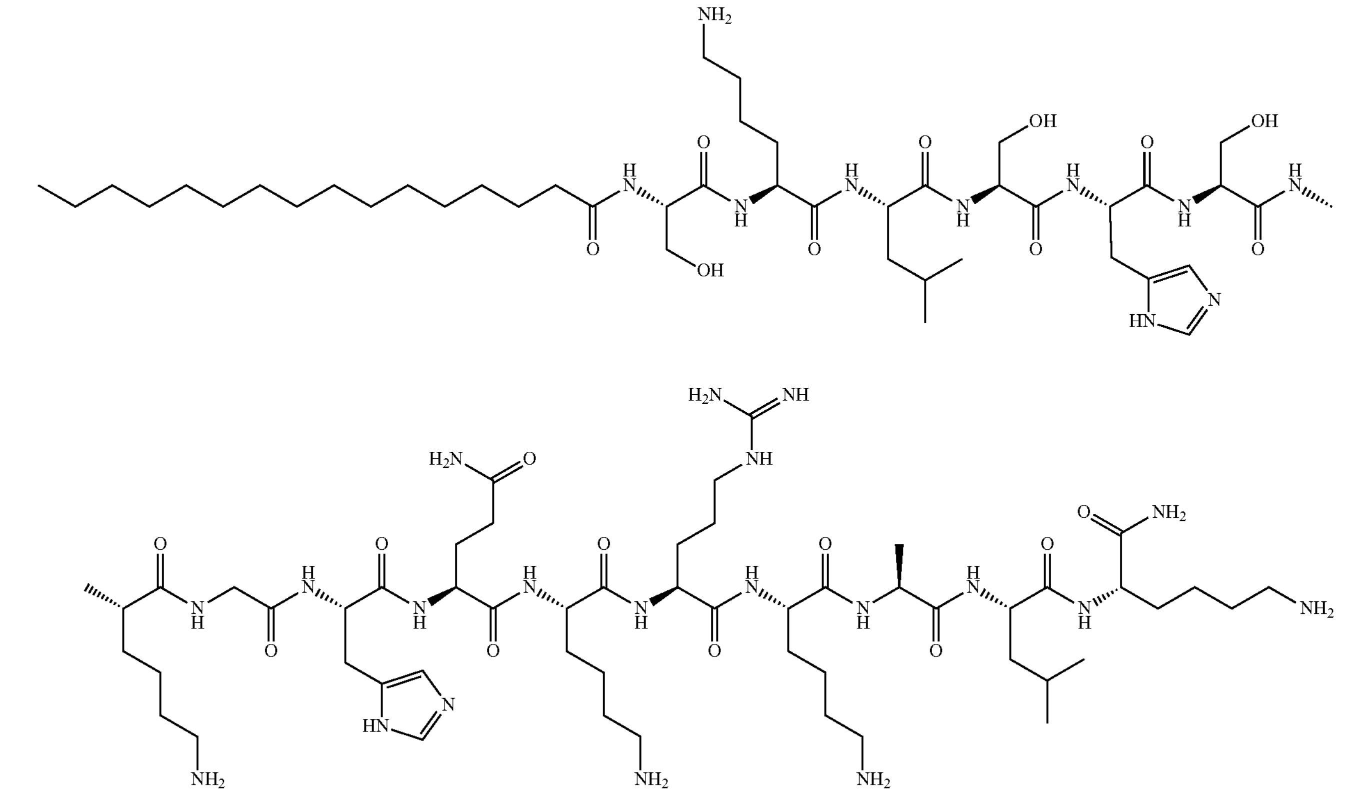 |
| 100 | 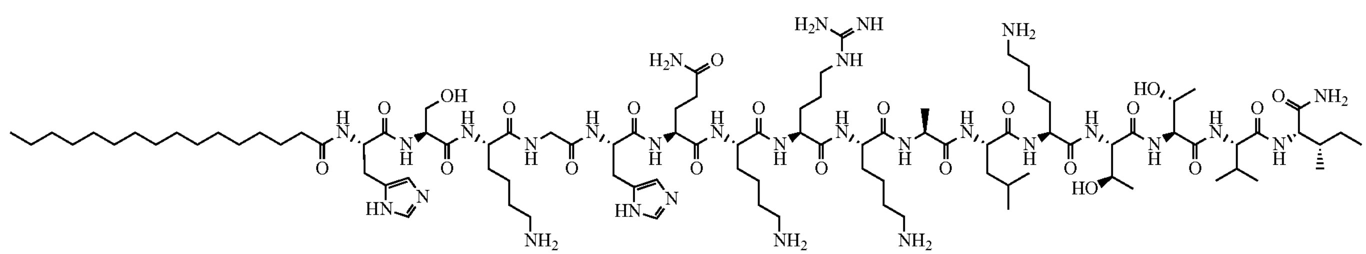 [SMILES: CCCCCCCCCCCCCCCC(=O)N[C@@H](Cc1cnc[nH]1)C(=O)N[C@@H](CO)C(=O)N[C@@H](CCCCN)C(=O)NCC(=O)N[C@@H](Cc1cnc[nH]1)C(=O)N[C@@H](CCC(N)=O)C(=O)N[C@@H](CCCCN)C(=O)N[C@@H](CCCNC(=N)N)C(=O)N[C@@H](CCCCN)C(=O)N[C@@H](C)C(=O)N[C@@H](CC(C)C)C(=O)N[C@@H](CCCCN)C(=O)N[C@H](C(=O)N[C@H](C(=O)N[C@H](C(=O)N[C@H](C(N)=O)[C@@H](C)CC)C(C)C)[C@@H](C)O)[C@@H](C)O] |

TABLE 11-continued

CXCR4 i3 loop compound structures

| Comp. # | Structure |
|---|---|
| 99 | 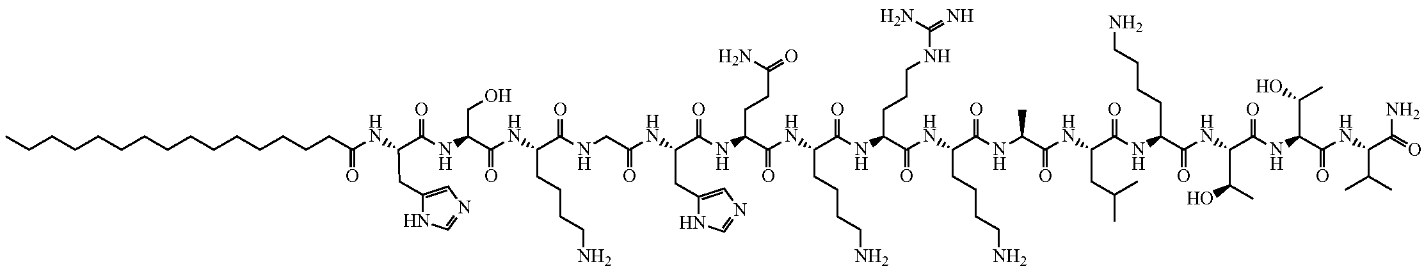 [SMILES: CCCCCCCCCCCCCCCC(=O)N[C@@H](Cc1cnc[nH]1)C(=O)N[C@@H](CO)C(=O)N[C@@H](CCCCN)C(=O)NCC(=O)N[C@@H](Cc1cnc[nH]1)C(=O)N[C@@H](CCC(N)=O)C(=O)N[C@@H](CCCCN)C(=O)N[C@@H](CCCNC(=N)N)C(=O)N[C@@H](CCCCN)C(=O)N[C@@H](C)C(=O)N[C@@H](CC(C)C)C(=O)N[C@@H](CCCCN)C(=O)N[C@H](C(=O)N[C@H](C(=O)N[C@H](C(N)=O)C(C)C)[C@@H](C)O)[C@@H](C)O] |
| 98 | 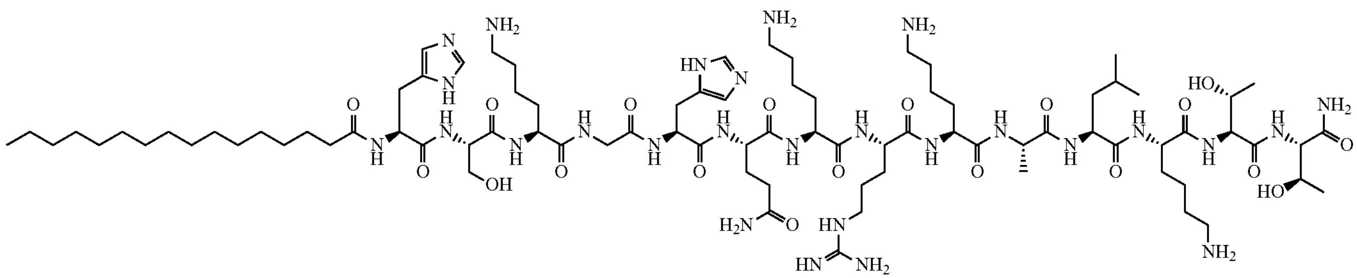 [SMILES: CCCCCCCCCCCCCCCC(=O)N[C@@H](Cc1cnc[nH]1)C(=O)N[C@@H](CO)C(=O)N[C@@H](CCCCN)C(=O)NCC(=O)N[C@@H](Cc1cnc[nH]1)C(=O)N[C@@H](CCC(N)=O)C(=O)N[C@@H](CCCCN)C(=O)N[C@@H](CCCNC(=N)N)C(=O)N[C@@H](CCCCN)C(=O)N[C@@H](C)C(=O)N[C@@H](CC(C)C)C(=O)N[C@@H](CCCCN)C(=O)N[C@H](C(=O)N[C@H](C(N)=O)[C@@H](C)O)[C@@H](C)O] |
| 97 | 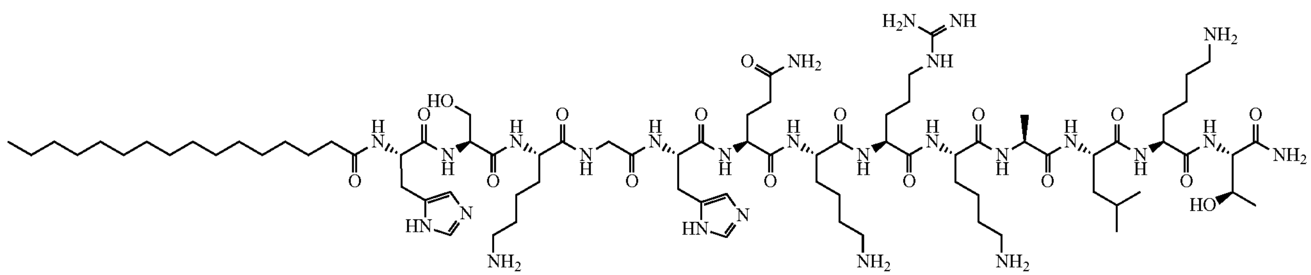 [SMILES: CCCCCCCCCCCCCCCC(=O)N[C@@H](Cc1cnc[nH]1)C(=O)N[C@@H](CO)C(=O)N[C@@H](CCCCN)C(=O)NCC(=O)N[C@@H](Cc1cnc[nH]1)C(=O)N[C@@H](CCC(N)=O)C(=O)N[C@@H](CCCCN)C(=O)N[C@@H](CCCNC(=N)N)C(=O)N[C@@H](CCCCN)C(=O)N[C@@H](C)C(=O)N[C@@H](CC(C)C)C(=O)N[C@@H](CCCCN)C(=O)N[C@H](C(N)=O)[C@@H](C)O] |

TABLE 11-continued
CXCR4 i3 loop compound structures
| Comp. # | Structure |
|---|---|
| 96 | 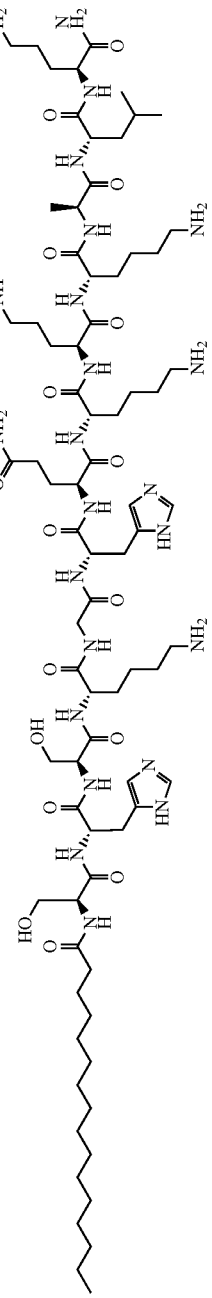 |
| 95 | 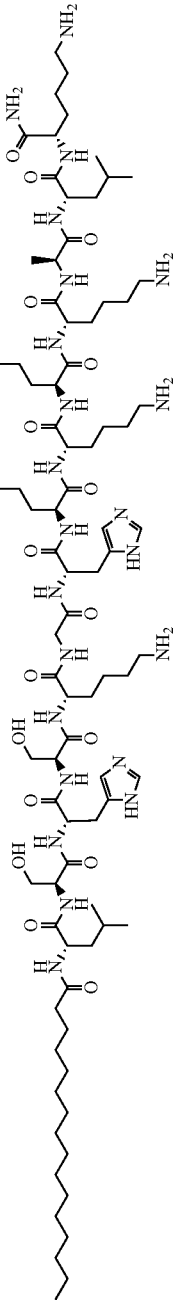 |

TABLE 11-continued
CXCR4 i3 loop compound structures
| Comp. # | Structure |
|---|---|
| 94 | 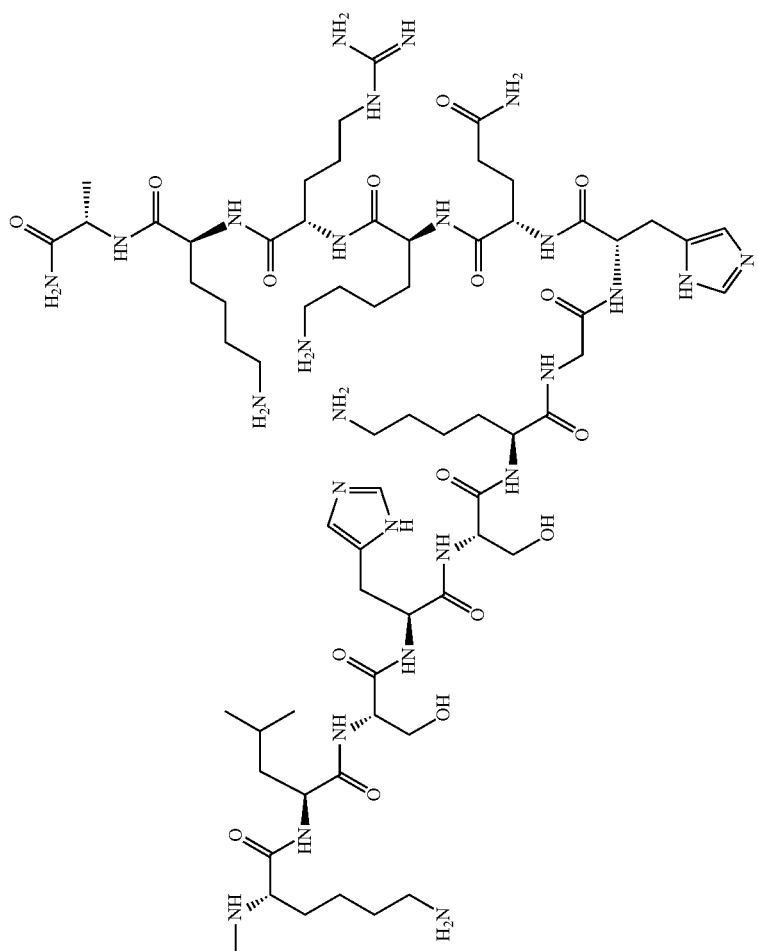 |

TABLE 11-continued

CXCR4 i3 loop compound structures

| Comp. # | Structure |
| --- | --- |
| 93 | 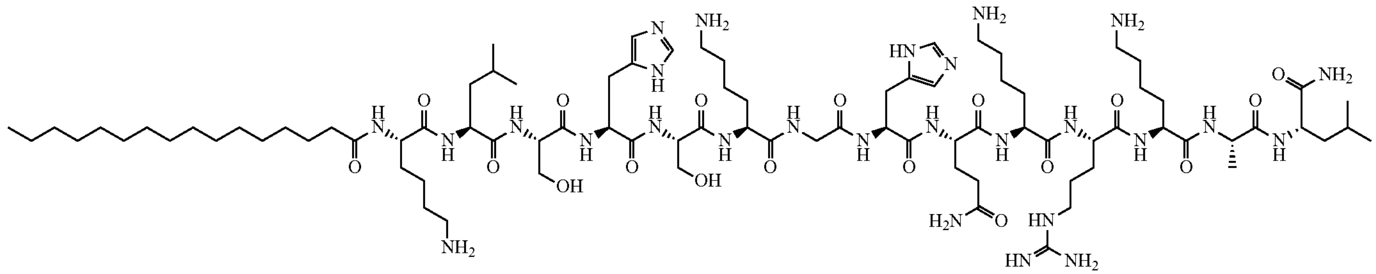 [SMILES: CCCCCCCCCCCCCCCC(=O)N[C@@H](CCCCN)C(=O)N[C@@H](CC(C)C)C(=O)N[C@@H](CO)C(=O)N[C@@H](Cc1cnc[nH]1)C(=O)N[C@@H](CO)C(=O)N[C@@H](CCCCN)C(=O)NCC(=O)N[C@@H](Cc1cnc[nH]1)C(=O)N[C@@H](CCC(N)=O)C(=O)N[C@@H](CCCCN)C(=O)N[C@@H](CCCNC(=N)N)C(=O)N[C@@H](CCCCN)C(=O)N[C@@H](C)C(=O)N[C@@H](CC(C)C)C(N)=O] |
| 92 | 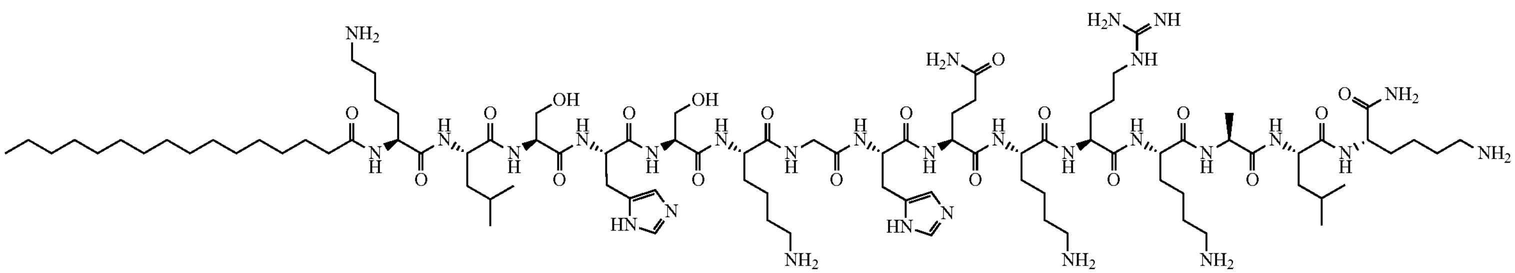 [SMILES: CCCCCCCCCCCCCCCC(=O)N[C@@H](CCCCN)C(=O)N[C@@H](CC(C)C)C(=O)N[C@@H](CO)C(=O)N[C@@H](Cc1cnc[nH]1)C(=O)N[C@@H](CO)C(=O)N[C@@H](CCCCN)C(=O)NCC(=O)N[C@@H](Cc1cnc[nH]1)C(=O)N[C@@H](CCC(N)=O)C(=O)N[C@@H](CCCCN)C(=O)N[C@@H](CCCNC(=N)N)C(=O)N[C@@H](CCCCN)C(=O)N[C@@H](C)C(=O)N[C@@H](CC(C)C)C(=O)N[C@@H](CCCCN)C(N)=O] |
| 91 | 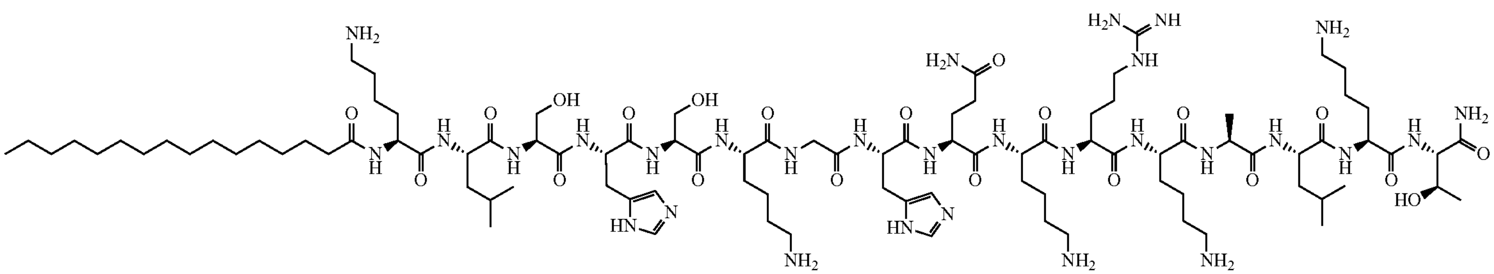 [SMILES: CCCCCCCCCCCCCCCC(=O)N[C@@H](CCCCN)C(=O)N[C@@H](CC(C)C)C(=O)N[C@@H](CO)C(=O)N[C@@H](Cc1cnc[nH]1)C(=O)N[C@@H](CO)C(=O)N[C@@H](CCCCN)C(=O)NCC(=O)N[C@@H](Cc1cnc[nH]1)C(=O)N[C@@H](CCC(N)=O)C(=O)N[C@@H](CCCCN)C(=O)N[C@@H](CCCNC(=N)N)C(=O)N[C@@H](CCCCN)C(=O)N[C@@H](C)C(=O)N[C@@H](CC(C)C)C(=O)N[C@@H](CCCCN)C(=O)N[C@H](C(N)=O)[C@@H](C)O] |

TABLE 11-continued
CXCR4 i3 loop compound structures
| Comp. # | Structure |
|---|---|
| 90 | 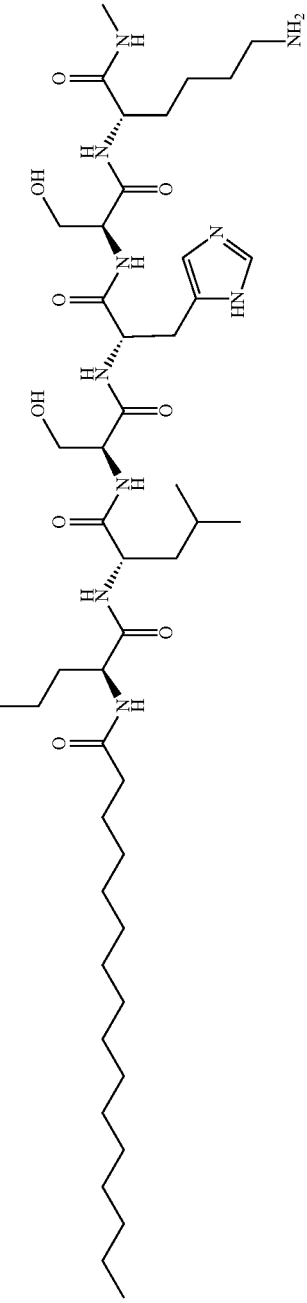 |

TABLE 11-continued
CXCR4 i3 loop compound structures
| Comp. # | Structure |
|---|---|
| 89 | 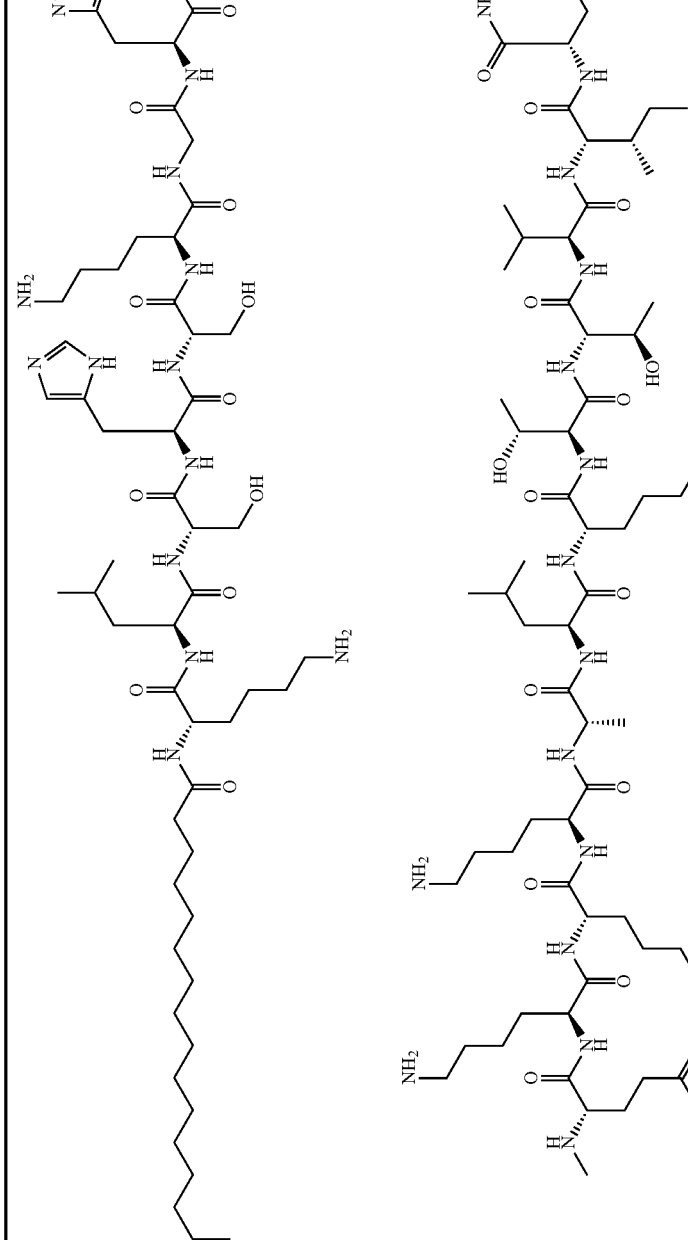 |

TABLE 11-continued
CXCR4 i3 loop compound structures
| Comp. # | Structure |
|---|---|
| 88 | 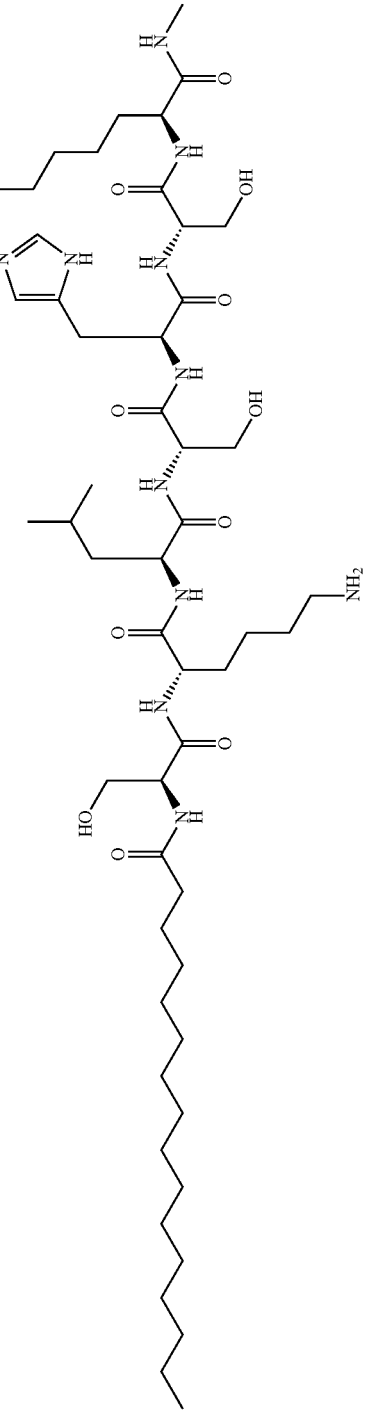 |

TABLE 11-continued
CXCR4 i3 loop compound structures
| Comp. # | Structure |
|---|---|
| 87 | 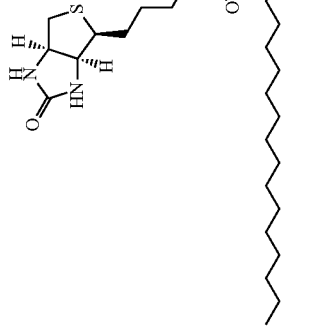 |
| 85 | 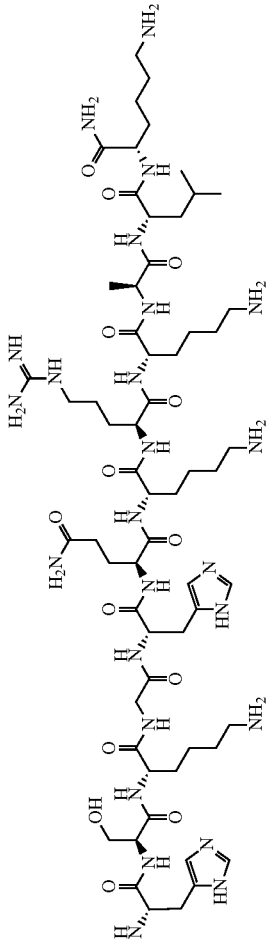 |
| 84 | 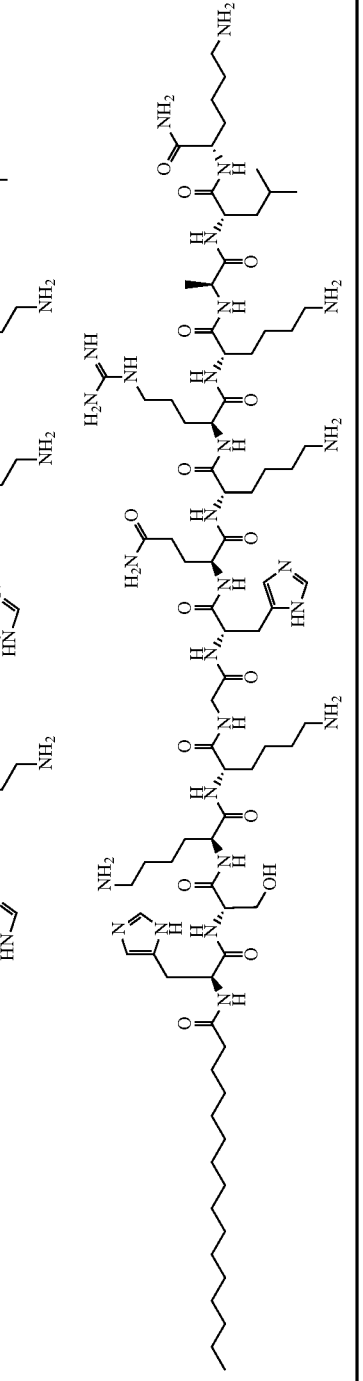 |

TABLE 12

CXCR4 i4 loop compounds

| No. | Loop | Sequence | Lipid | MW | Comments |
|---|---|---|---|---|---|
| 107 | i4 | GAKFKTSAQHALTSVSRGSSLKILSKGKRGGHSSVST (SEQ ID NO.) | Myr | 4248.067 | Backbone lipid-dual lipid |
| 108 | i4 | GAKFKTSAQHALTSVSRGSSLKILSKGKRG (SEQ ID NO.) | Myr | 3592.41 | N-terminus and backbone lipid |
| 109 | i4 | GAKFKTSAQHALTSVSRGSSLKILSKGKRGGHSSVST (SEQ ID NO.) | Pal | 3994.644 | |
| 110 | i4 | GAKFKTSAQHALTSVSRGSSLKILSKGKRGGSCFH (SEQ ID NO.) | Pal | 3870.571 | |
| 111 | i4 | GAKFKTSAQHALTSVSRGSSLKILSKGKRG (SEQ ID NO.) | Pal | 3338.987 | |
| 112 | i4 | GAKFKTSAQHALTSVSRGSSLKILSGGK (SEQ ID NO.) | Pal | 3052.8 | |
| 113 | i4 | GAKFKTSAQHALTSVSRG (SEQ ID NO.) | Pal | 2083.477 | |
| 114 | i4 | GAKFKTSAQHALTSVSRGSSLKILSK (SEQ ID NO.) | Pal | 2940.526 | |
| 115 | i4 | GAKFKTSAQHALTSVSRGSSLK (SEQ ID NO.) | Pal | 2498.961 | |
| 116 | i4 | GAKFKTSAQHALTSVR (SEQ ID NO.) | Pal | 1938.18 | |

TABLE 13
CXCR4 i4 loop compound structures
| Comp. # | Structure |
|---|---|
| 107 | 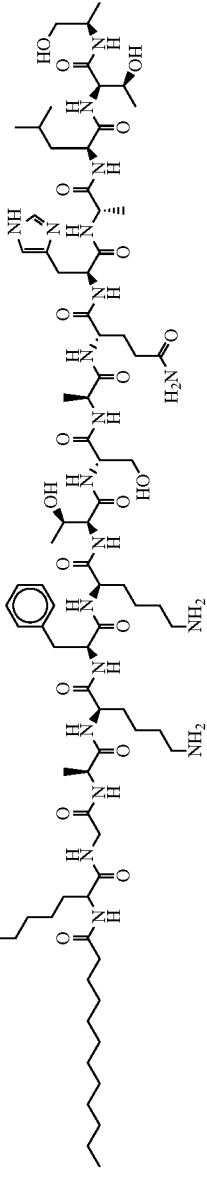 |

TABLE 13-continued
CXCR4 i4 loop compound structures
| Comp. # | Structure |
|---|---|
| 108 | 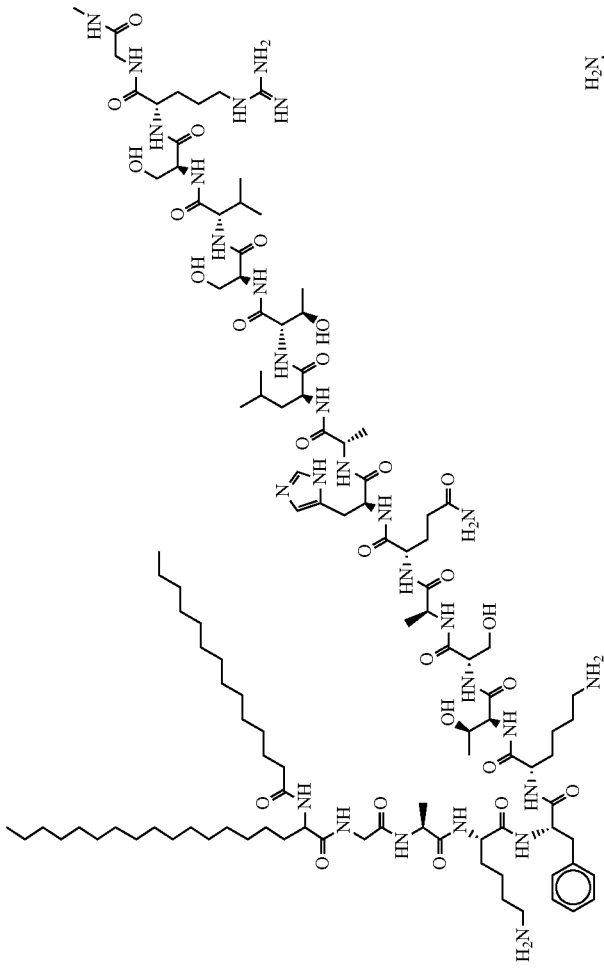 |

TABLE 13-continued
CXCR4 i4 loop compound structures
| Comp. # | Structure |
|---|---|
| 109 | 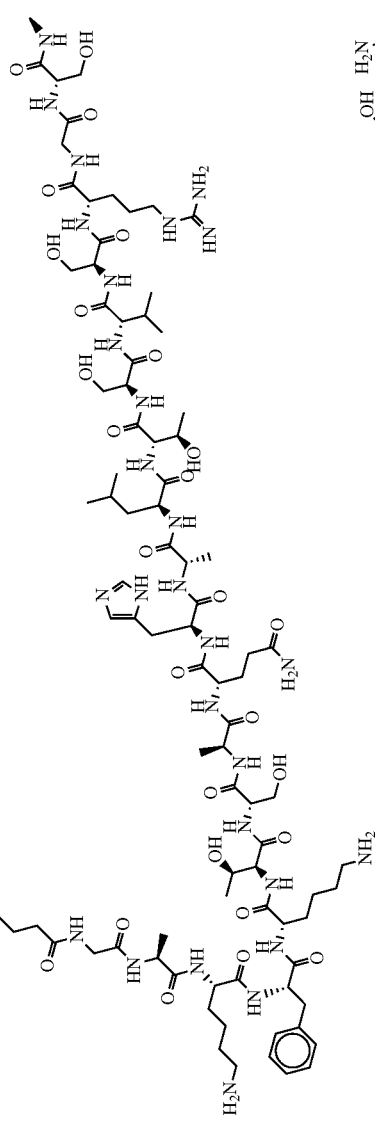 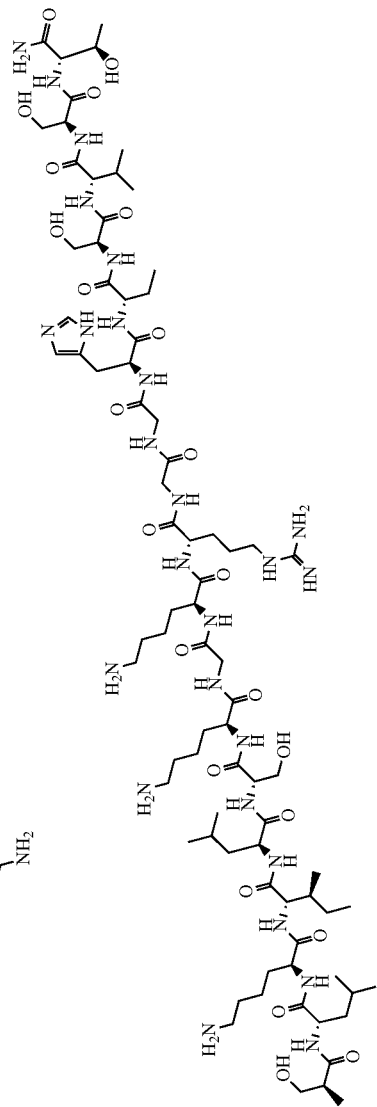 |

TABLE 13-continued

CXCR4 i4 loop compound structures

| Comp. # | Structure |
|---|---|
| 110 | 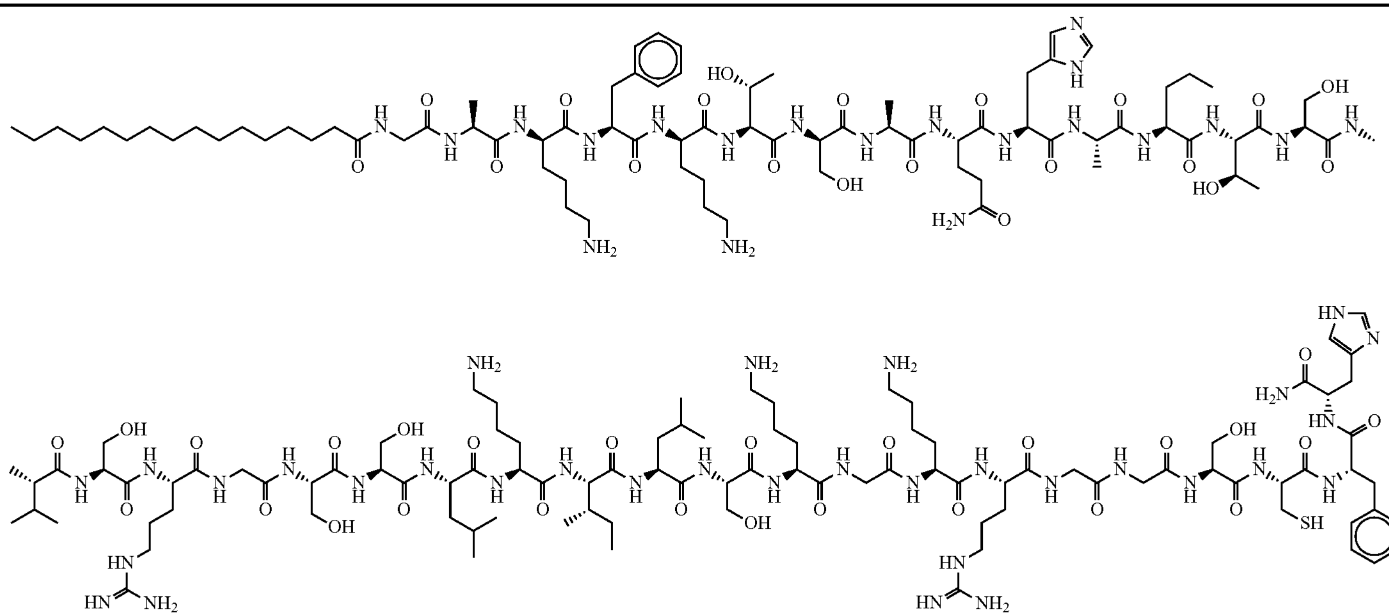 |

TABLE 13-continued
CXCR4 i4 loop compound structures
| Comp. # | Structure |
|---|---|
| 111 | 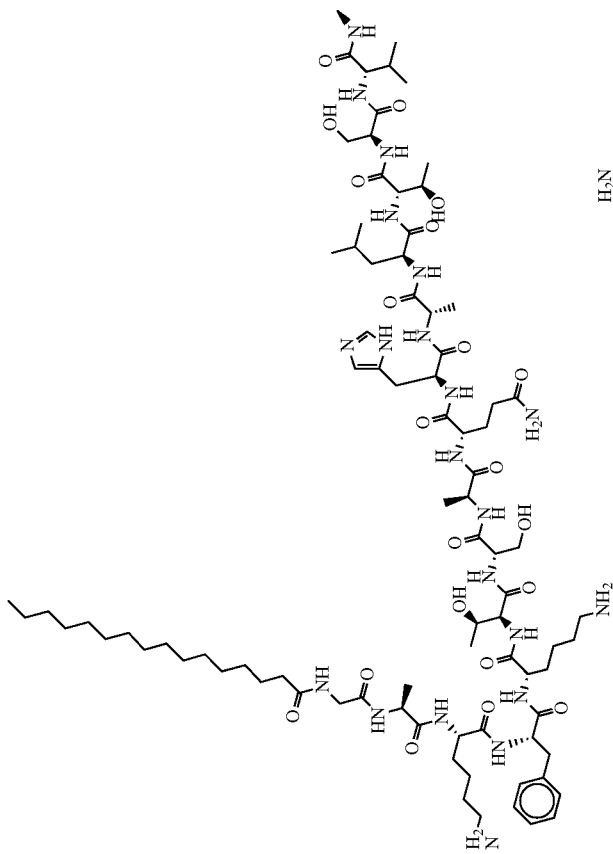 |

TABLE 13-continued
CXCR4 i4 loop compound structures
| Comp. # | Structure |
|---|---|
| 112 | 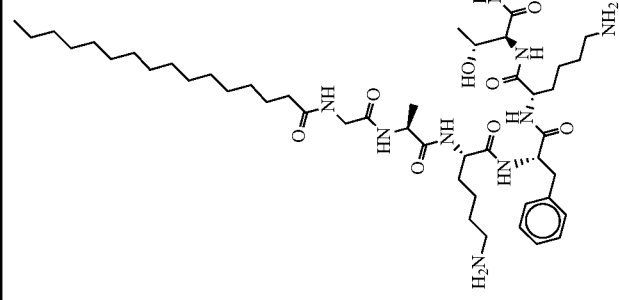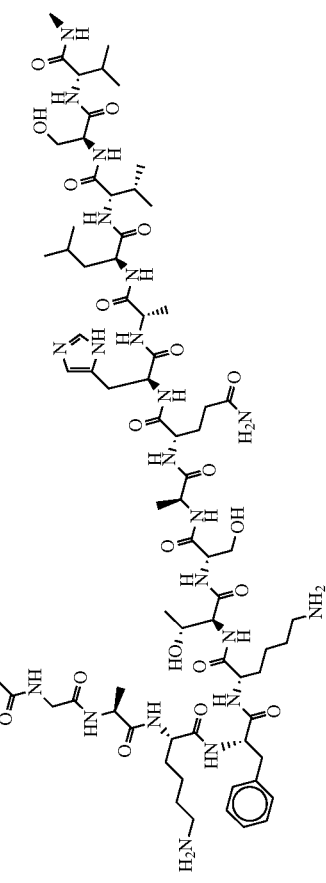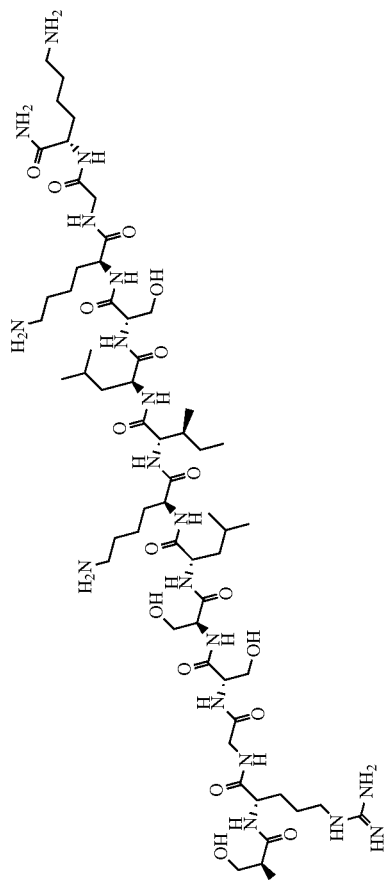 |

TABLE 13-continued
CXCR4 i4 loop compound structures
| Comp. # | Structure |
|---|---|
| 113 | 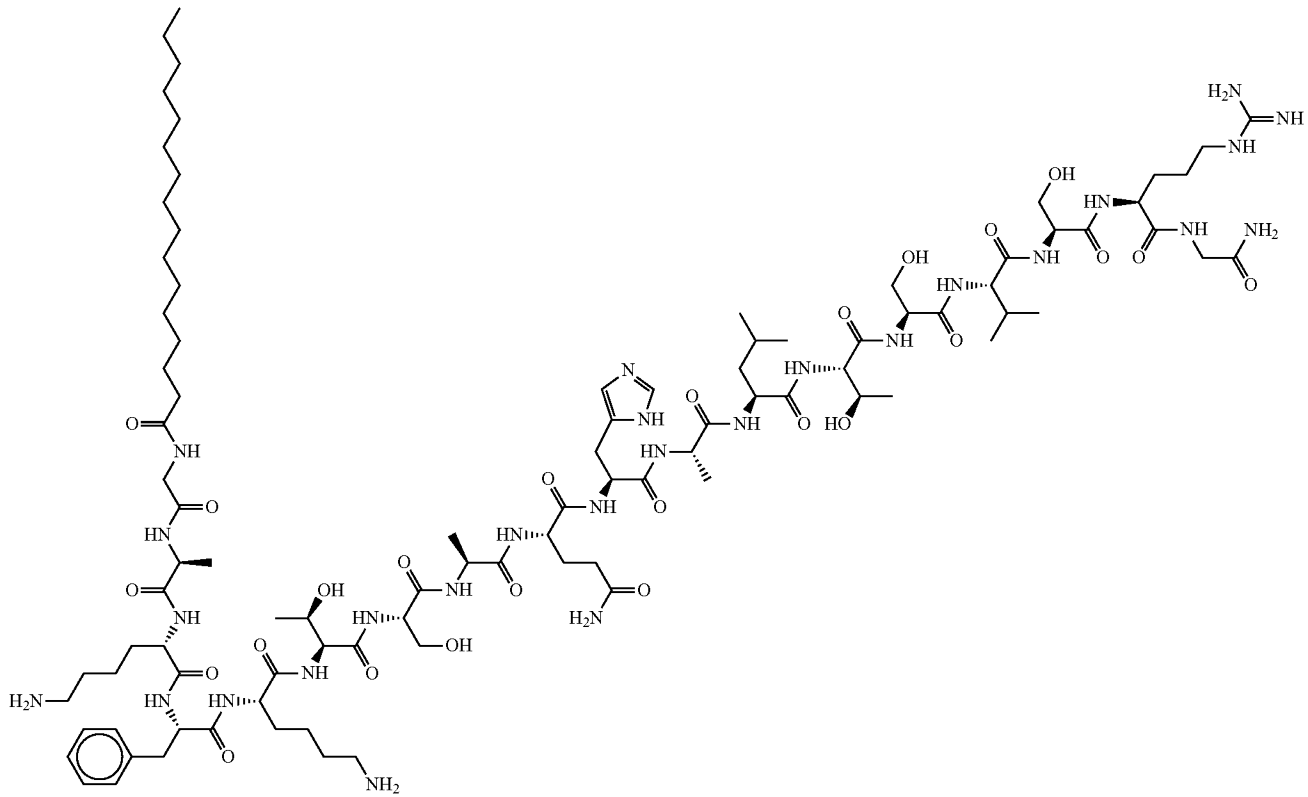 |

TABLE 13-continued

CXCR4 i4 loop compound structures

| Comp. # | Structure |
|---|---|
| 114 | |

TABLE 13-continued

CXCR4 i4 loop compound structures

| Comp. # | Structure |
|---|---|
| 115 | 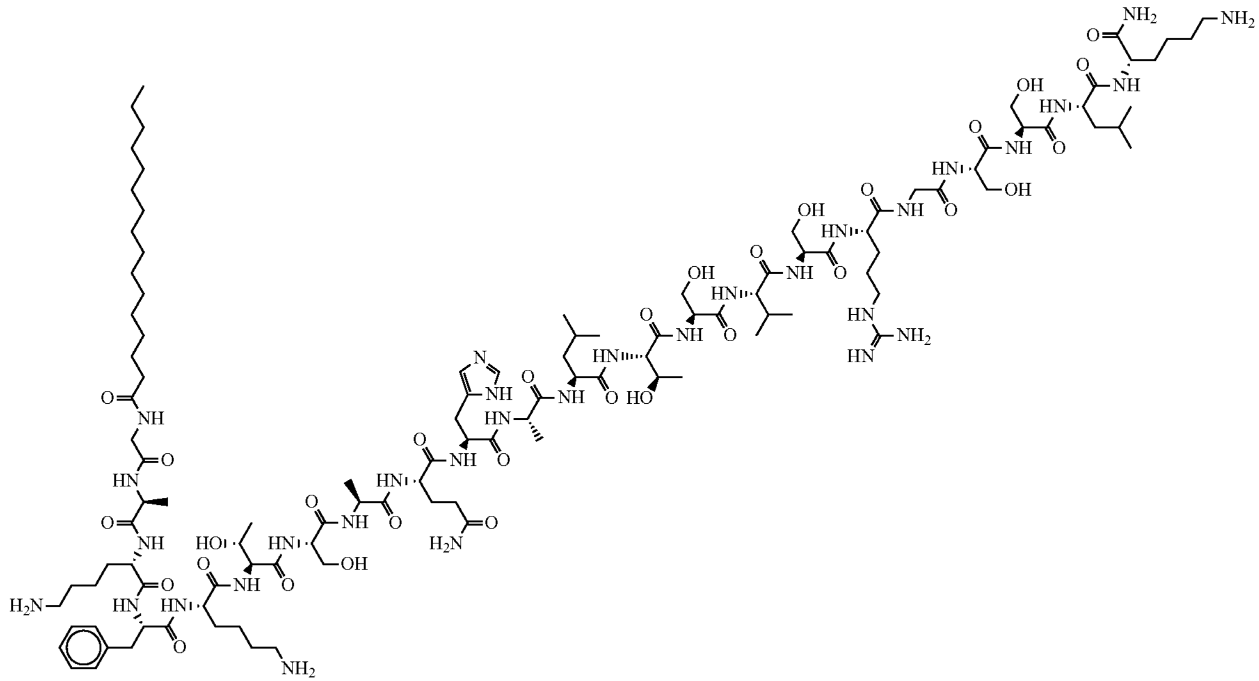 |

TABLE 13-continued
CXCR4 i4 loop compound structures
| Comp. # | Structure |
|---|---|
| 116 | 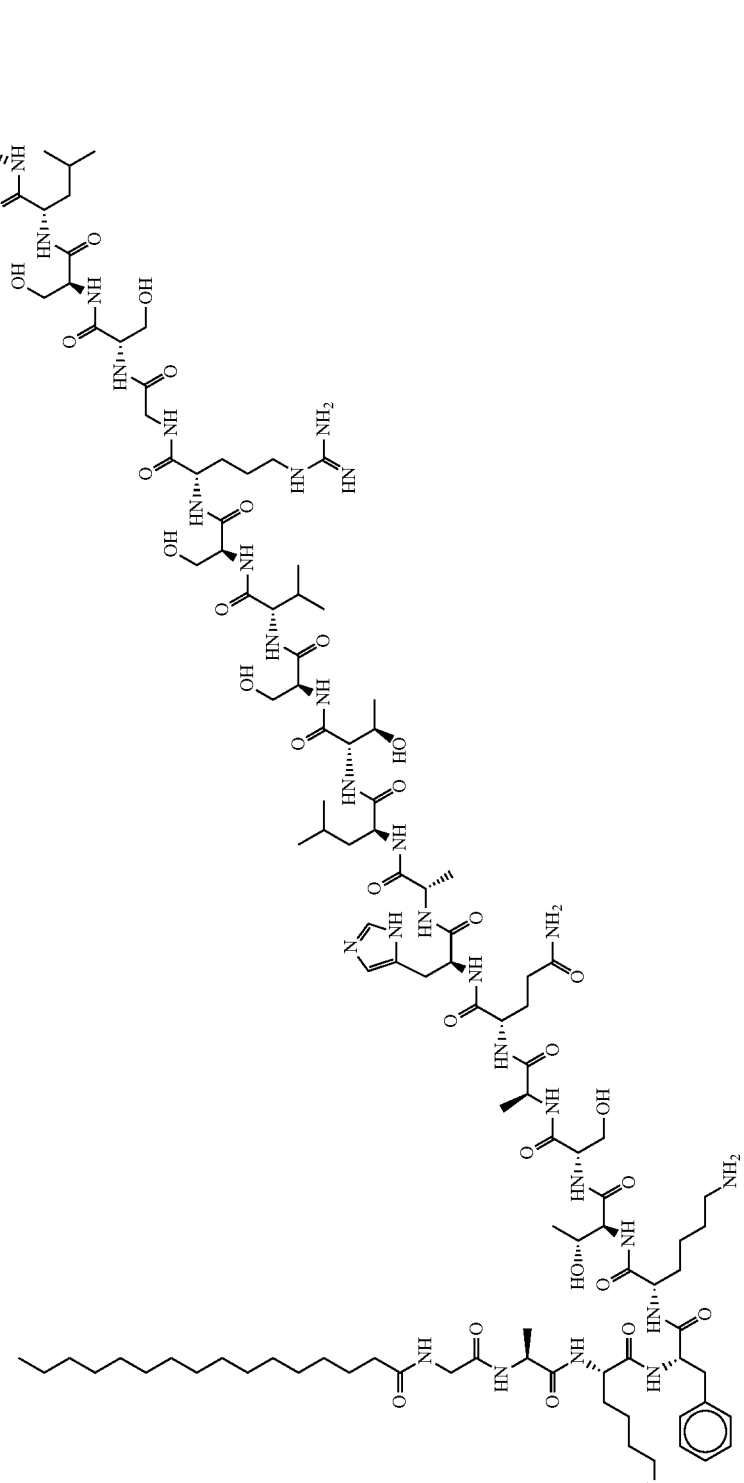 |

In a thirteenth aspect, the compounds are selected from:
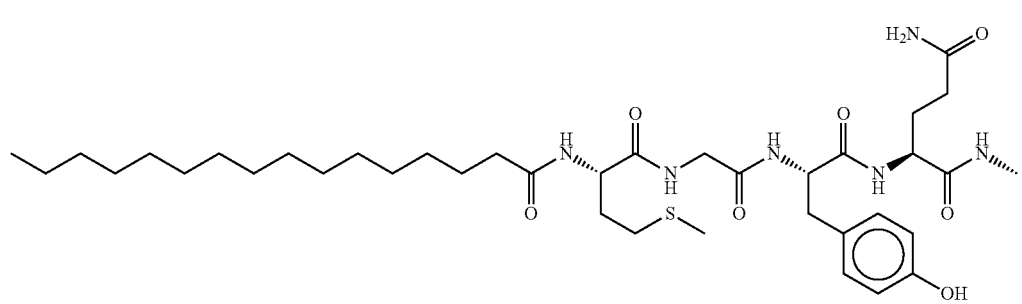
Compound No. 38
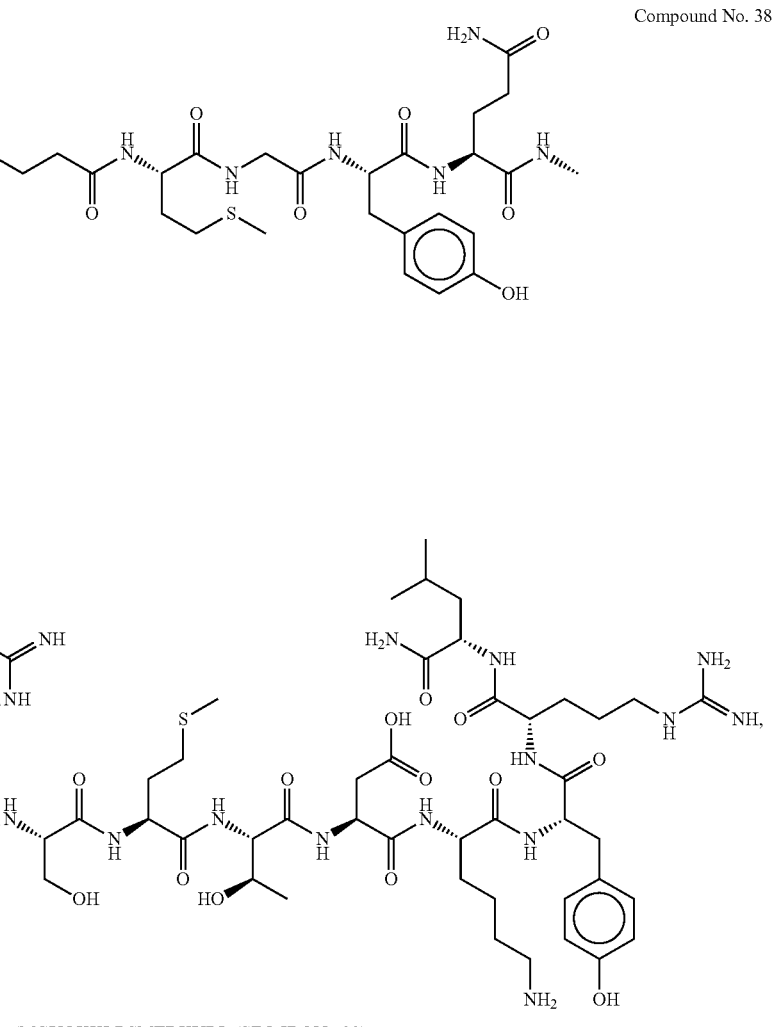
(MGYQKKLRSMTDKYRL (SEQ ID NO: 82)
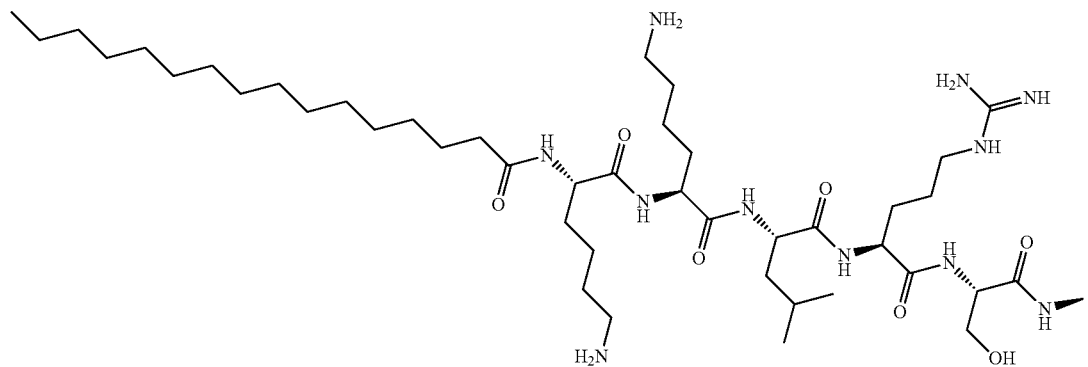
Compound No. 43

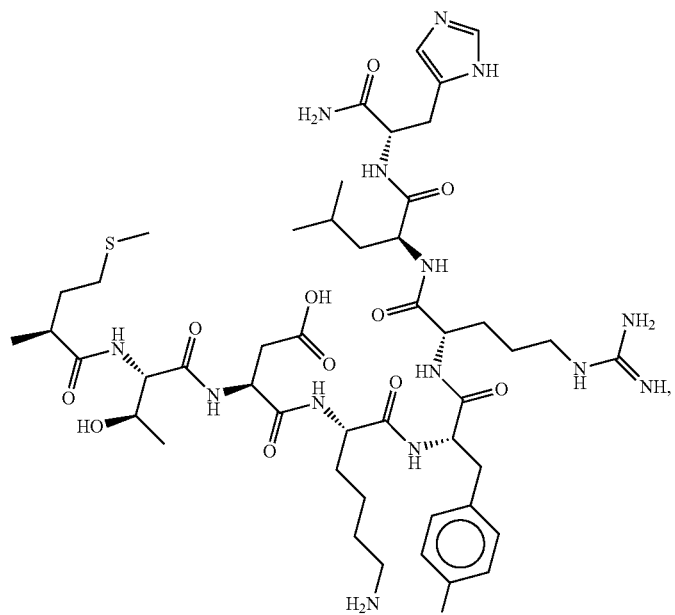
(KKLRSMTDKYRLH (SEQ ID NO. 42))
Compound No. 44
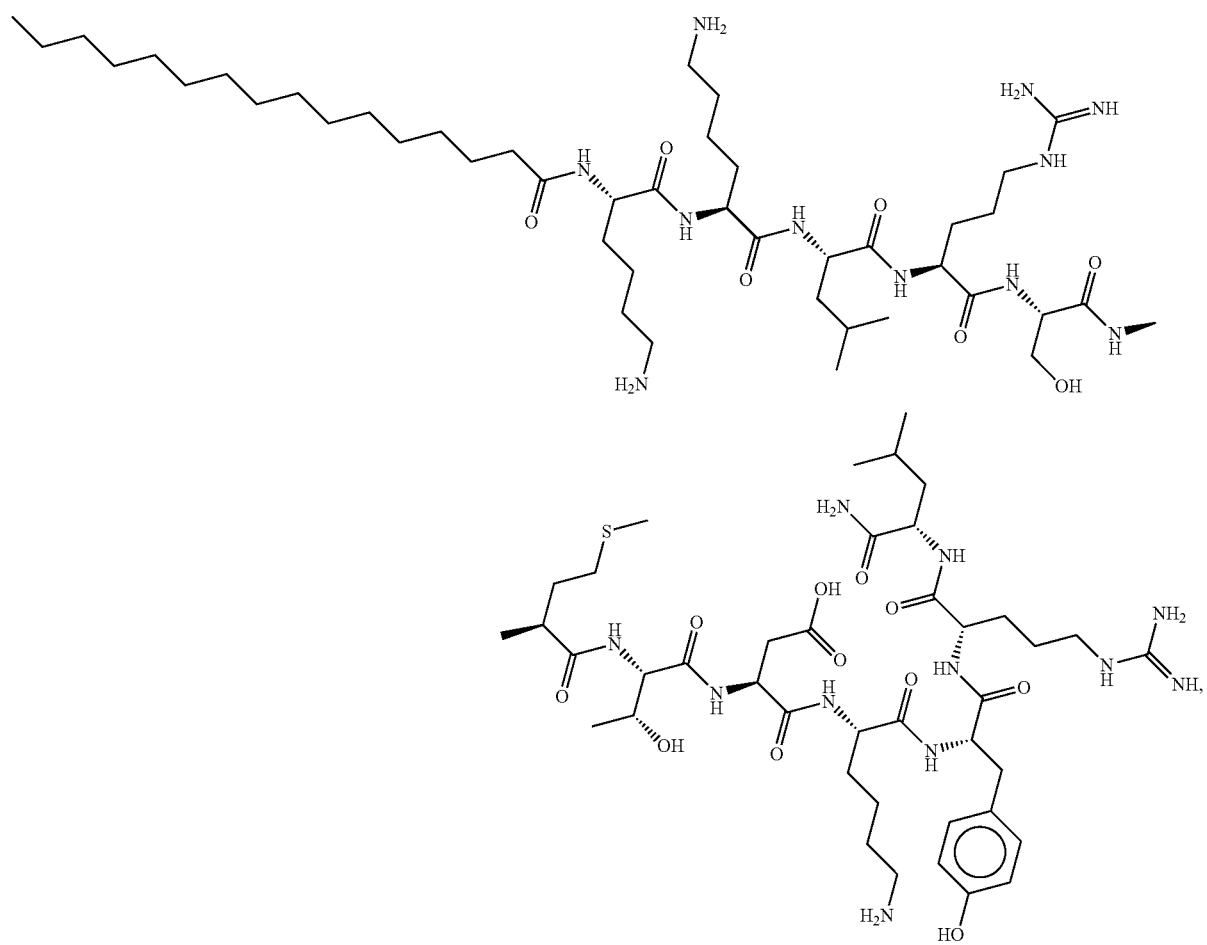
(KKLRSMTDKYR (SEQ ID NO: 71))

-continued
Compound No. 88
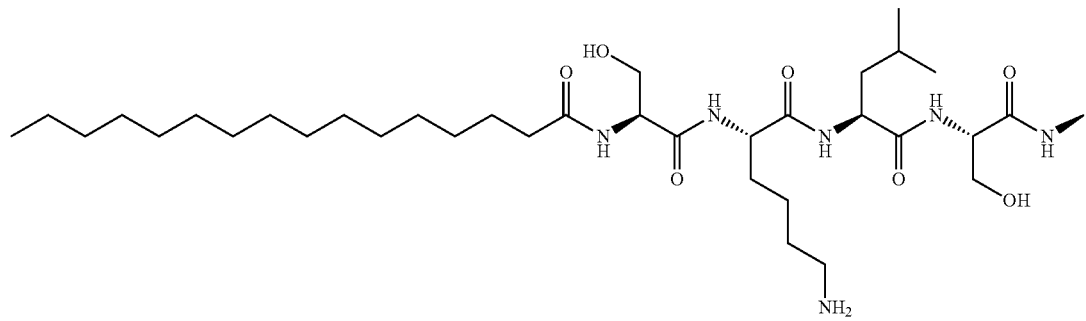
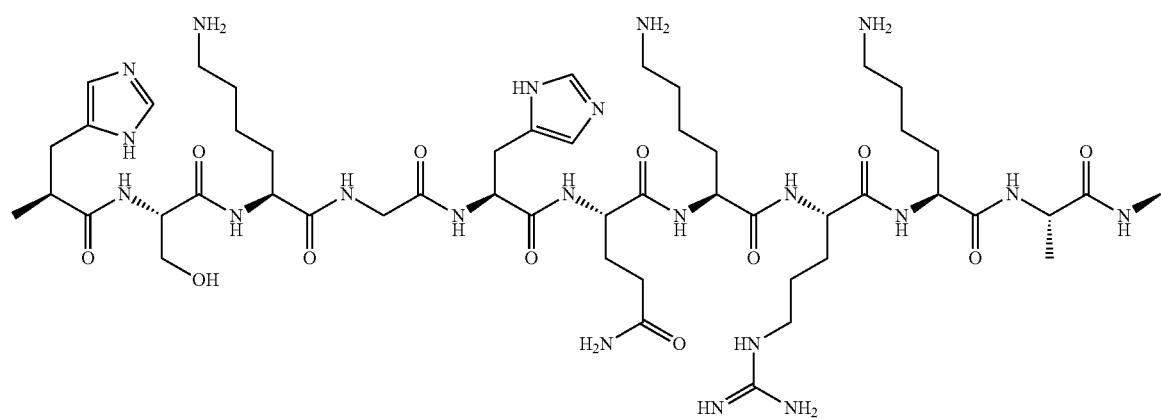
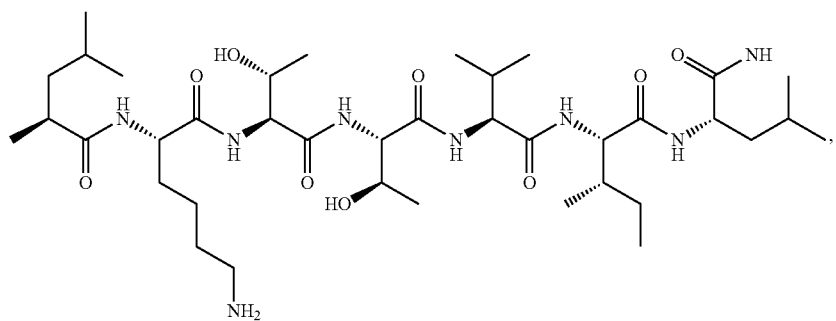
(SKLSHSKGHQKRKALKTTVIL (SEQ ID NO: 253))
Compound No. 90
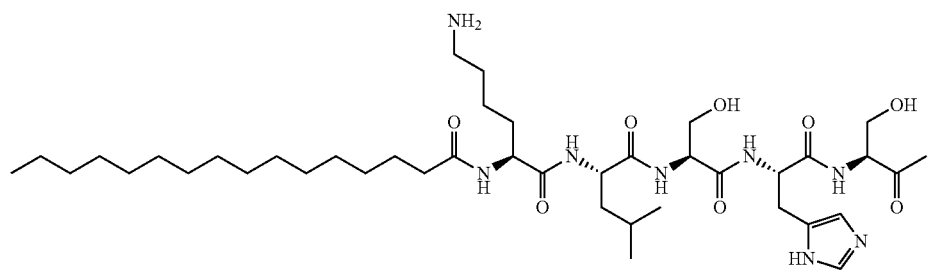

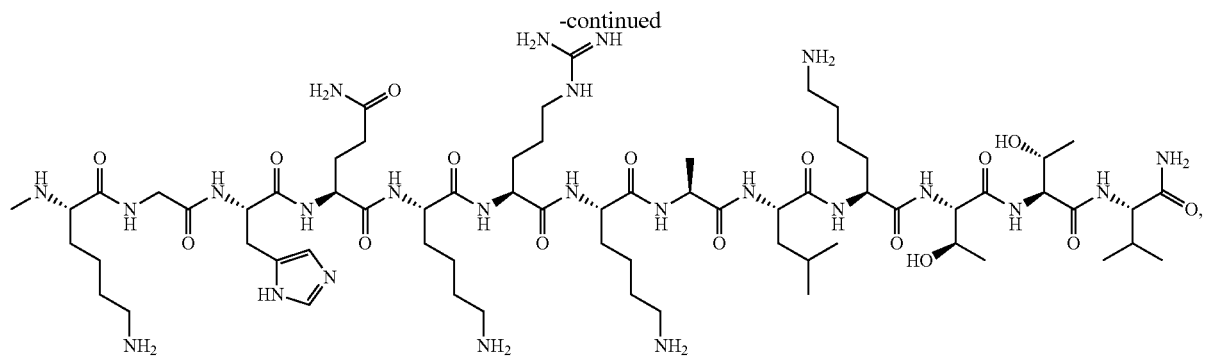

(KLSHSKGHQKRKALKTTV (SEQ ID NO: 248))

Compound No. 92

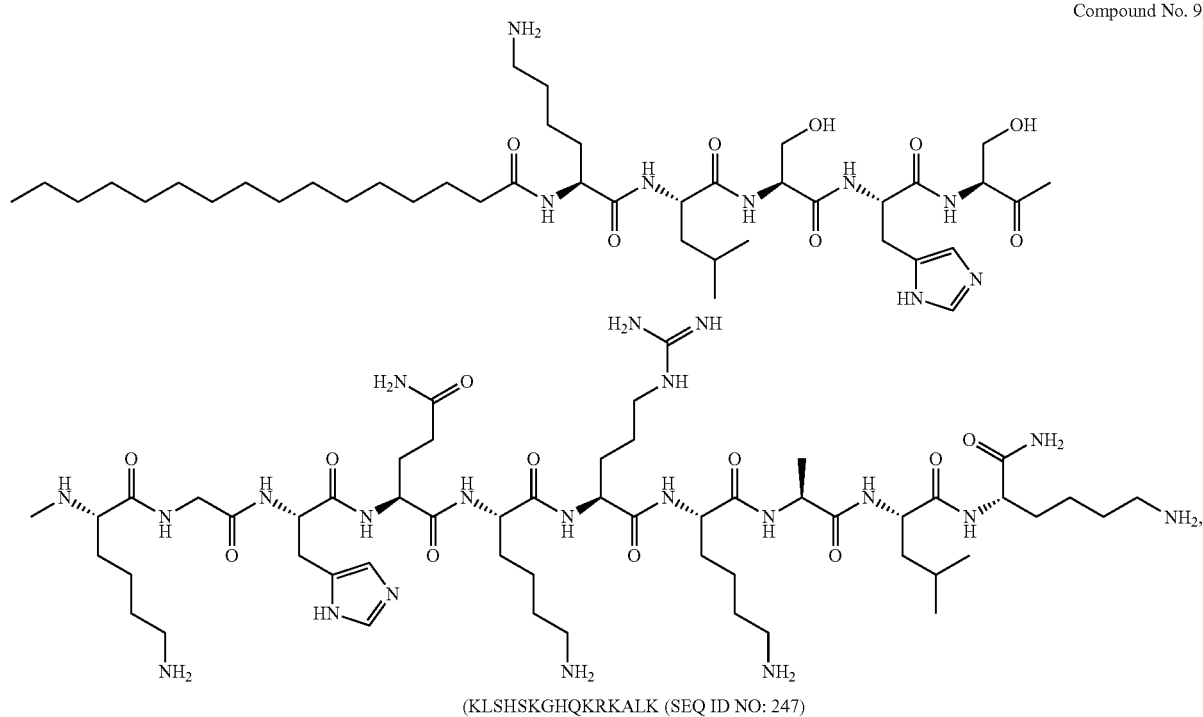

(KLSHSKGHQKRKALK (SEQ ID NO: 247))

or a pharmaceutically acceptable salt of any of the foregoing.

"Cycloalkyl" used alone or as part of a larger moiety such as "cycloalkylalkyl" refers to a monocyclic or polycyclic, non-aromatic ring system of 3 to 20 carbon atoms, 3 to 12 carbon atoms, or 3 to 9 carbon atoms, which may be saturated or unsaturated. Examples of cycloalkyl groups include cyclopropyl, cyclobutyl, cyclopentyl, cyclohexyl, cyclohexenyl, cyclohexa-1,3-dienyl, cyclooctyl, cycloheptanyl, norbornyl, adamantyl, and the like.

"Heterocycloalkyl" refers to a saturated or unsaturated, non-aromatic, monocyclic or polycyclic ring system of 3 to 20 atoms, 3 to 12 atoms, or 3 to 8 atoms, containing one to four ring heteroatoms chosen from O, N and S. Examples of heterocyclyl groups include pyrrolidine, piperidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, morpholine, thiomorpholine, thiomorpholine-1,1-dioxide, tetrahydro-2H-1,2-thiazine-1,1-dioxide, isothiazolidine-1,1-dioxide, pyrrolidin-2-one, piperidin-2-one, piperazin-2-one, and morpholin-2-one, and the like.

"Halogen" and "halo" refer to fluoro, chloro, bromo or iodo.

"Haloalkyl" refers to an alkyl group substituted with one or more halogen atoms. By analogy, "haloalkenyl", "haloalkynyl", etc., refers to the group (for example alkenyl or alkynyl) substituted by one or more halogen atomes.

"Cyano" refers to the group —CN.
"Oxo" refers to a divalent =O group.
"Thioxo" refers to a divalent =S group.
"Ph" refers to a phenyl group.
"Carbonyl" refers to a divalent —C(O)— group.

"Alkyl" used alone or as part of a larger moiety such as "hydroxyalkyl", "alkoxyalkyl", "alkylamine" refers to a straight or branched, saturated aliphatic group having the specified number of carbons, typically having 1 to 12 carbon atoms. More particularly, the aliphatic group may have 1 to 10, 1 to 8, 1 to 6, or 1 to 4 carbon atoms. This term is exemplified by groups such as methyl, ethyl, n-propyl, isopropyl, n-butyl, isobutyl, tert-butyl, n-hexyl, and the like.

"Alkenyl" refers to a straight or branched aliphatic group with at least one double bond. Typically, alkenyl groups have from 2 to 12 carbon atoms, from 2 to 8, from 2 to 6, or from 2 to 4 carbon atoms. Examples of alkenyl groups include ethenyl (—CH=CH$_2$), n-2-propenyl (allyl, —CH$_2$CH=CH$_2$), pentenyl, hexenyl, and the like.

"Alkynyl" refers to a straight or branched aliphatic group having at least 1 site of alkynyl unsaturation. Typically, alkynyl groups contain 2 to 12, 2 to 8, 2 to 6 or 2 to 4 carbon atoms. Examples of alkynyl groups include ethynyl (—C≡CH), propargyl (—CH$_2$C≡CH), pentynyl, hexynyl, and the like.

"Alkylene" refers to a bivalent saturated straight-chained hydrocarbon, e.g., C$_1$-C$_6$ alkylene includes —(CH$_2$)$_6$—, —CH$_2$—CH—(CH$_2$)$_3$CH$_3$, and the like. "Bivalent means that the alkylene group is attached to the remainder of the molecule through two different carbon atoms.

"Alkenylene" refers to an alkylene group with in which one carbon-carbon single bond is replaced with a double bond.

"Alkynylene" refers to an alkylene group with in which one carbon-carbon single bond is replaced with a triple bond.

"Aryl" used alone or as part of a larger moiety as in "aralkyl" refers to an aromatic carbocyclic group of from 6 to 14 carbon atoms having a single ring or multiple condensed rings. The term "aryl" also includes aromatic carbocycle(s) fused to cycloalkyl or heterocycloalkyl groups. Examples of aryl groups include phenyl, benzo[d][1,3]dioxole, naphthyl, phenantrenyl, and the like.

"Aryloxy" refers to an —OAr group, wherein 0 is an oxygen atom and Ar is an aryl group as defined above.

"Aralkyl" refers to an alkyl having at least one alkyl hydrogen atom replaced with an aryl moiety, such as benzyl, —(CH$_2$)$_2$phenyl, —(CH$_2$)$_3$phenyl, —CH(phenyl)$_2$, and the like.

"Alkyl cycloalkyl" refers to an alkyl having at least one alkyl hydrogen atom replaced with a cycloalkyl moiety, such as —CH$_2$-cyclohexyl, —CH$_2$-cyclohexenyl, and the like.

"Heteroaryl" used alone or a part of a larger moiety as in "heteroaralkyl" refers to a 5 to 14 membered monocyclic, bicyclic or tricyclic heteroaromatic ring system, containing one to four ring heteroatoms independently selected from nitrogen, oxygen and sulfur. The term "heteroaryl" also includes heteroaromatic ring(s) fused to cycloalkyl or heterocycloalkyl groups. Particular examples of heteroaryl groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 1,2,3,4-tetrahydroquinolyl, 1,2,3,4-tetrahydroisoquinolyl, purinyl, pteridinyl, carbazolyl, xanthenyl, benzoquinolyl, and the like.

"Heteroaryloxy" refers to an —OHet group, wherein O is an oxygen atom and Het is a heteroaryl group as defined above.

"Heteroaralkyl" refers to an alkyl having at least one alkyl hydrogen atom replaced with a heteroaryl moiety, such as —CH$_2$-pyridinyl, —CH$_2$-pyrimidinyl, and the like.

"Alkoxy" refers to the group —O—R where R is "alkyl", "cycloalkyl", "alkenyl", or "alkynyl". Examples of alkoxy groups include for example, methoxy, ethoxy, ethenoxy, and the like.

"Alkyl heterocycloalkyl" refers to an alkyl having at least one alkyl hydrogen atom replaced with a heterocycloalkyl moiety, such as —CH$_2$-morpholino, —CH$_2$-piperidyl and the like.

"Alkoxycarbonyl" refers to the group —C(O)OR where R is "alkyl", "alkenyl", "alkynyl", "cycloalkyl", "heterocycloalkyl", "aryl", or "heteroaryl".

"Hydroxyalkyl" and "alkoxyalkyl" are alky groups substituted with hydroxyl and alkoxy, respectively.

"Amino" means —NH$_2$; "alkylamine" and "dialkylamine" mean —NHR and —NR$_2$, respectively, wherein R is an alkyl group. "Cycloalkylamine" and "dicycloalkylamine" mean —NHR and —NR$_2$, respectively, wherein R is a cycloalkyl group. "Cycloalkylalkylamine" means —NHR wherein R is a cycloalkylalkyl group. "[Cycloalkylalkyl][alkyl]amine" means —N(R)$_2$ wherein one R is cycloalkylalkyl and the other R is alkyl.

Haloalkyl and halocycloalkyl include mono, poly, and perhaloalkyl groups where the halogens are independently selected from fluorine, chlorine, bromine and iodine.

Suitable substituents for "alkyl", "alkenyl", "alkynyl", "cycloalkyl", "heterocycloalkyl", "aryl", or "heteroaryl", etc., are those which will form a stable compound of the invention. Examples of suitable substituents are those selected from the group consisting of halogen, —CN, —OH, —NH$_2$, (C$_1$-C$_4$)alkyl, (C$_1$-C$_4$)haloalkyl, aryl, heteroaryl, (C$_3$-C$_7$)cycloalkyl, (5-7 membered) heterocycloalkyl, —NH(C$_1$-C$_6$)alkyl, —N((C$_1$-C$_6$)alkyl)$_2$, (C$_1$-C$_6$)alkoxy, (C$_1$-C$_6$)alkoxycarbonyl, —CONH$_2$, —OCONH$_2$, —NHCONH$_2$, —N(C$_1$-C$_6$)alkylCONH$_2$, —N(C$_1$-C$_6$)alkylCONH(C$_1$-C$_6$)alkyl, —NHCONH(C$_1$-C$_6$)alkyl, —NHCON((C$_1$-C$_6$)alkyl)$_2$, —N(C$_1$-C$_6$)alkylCON((C$_1$-C$_6$)alkyl)$_2$, —NHC(S)NH$_2$, —N(C$_1$-C$_6$)alkylC(S)NH$_2$, —N(C$_1$-C$_6$)alkylC(S)NH(C$_1$-C$_6$)alkyl, —NHC(S)NH(C$_1$-C$_6$)alkyl, —NHC(S)N((C$_1$-C$_6$)alkyl)$_2$, —N(C$_1$-C$_6$)alkylC(S)N((C$_1$-C$_6$)alkyl)$_2$, —CONH(C$_1$-C$_6$)alkyl, —OCONH(C$_1$-C$_6$)alkyl —CON((C$_1$-C$_6$)alkyl)$_2$, —C(S)(C$_1$-C$_6$)alkyl, —S(O)$_p$(C$_1$-C$_6$)alkyl, —S(O)$_p$NH$_2$, —S(O)$_p$NH(C$_1$-C$_6$)alkyl, —S(O)$_p$N((C$_1$-C$_6$)alkyl)$_2$, —CO(C$_1$-C$_6$)alkyl, —OCO(C$_1$-C$_6$)alkyl, —C(O)O(C$_1$-C$_6$)alkyl, —OC(O)O(C$_1$-C$_6$)alkyl, —C(O)H or —CO$_2$H. More particularly, the substituents are selected from halogen, —CN, —OH, —NH$_2$, (C$_1$-C$_4$)alkyl, (C$_1$-C$_4$) haloalkyl, (C$_1$-C$_4$)alkoxy, phenyl, and (C$_3$-C$_7$)cycloalkyl. Within the framework of this invention, said "substitution" is also meant to encompass situations where a hydrogen atom is replaced with a deuterium atom. p is an integer with a value of 1 or 2.

Pharmaceutically acceptable salts of the compounds disclosed herein are included in the present invention. For example, an acid salt of a compound containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide salts.

Salts of the compounds containing an acidic functional group can be prepared by reacting with a suitable base. Such a pharmaceutically acceptable salt can be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

Pharmaceutical Compositions

The invention also provides pharmaceutical compositions comprising an effective amount of a compound Formula I (e.g., including any of the formulae herein), or a pharmaceutically acceptable salt of said compound; and a pharmaceutically acceptable carrier. The carrier(s) are "pharmaceutically acceptable" in that they are not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), pulmonary, vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the patient therapeutics may be local, so as to be administered at the site of interest. Various techniques can be used for providing the patient compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. In one embodiment, the second therapeutic agent is one or more additional compounds of the invention.

In another embodiment, the second therapeutic agent may be selected from any compound or therapeutic agent known to have or that demonstrates advantageous properties when administered with a compound having the same mechanism of action as the CXCR4 receptor compound of Formula I.

In a particular embodiment, the second therapeutic is an agent useful in the treatment or prevention of a disease or condition selected from, bone marrow transplantation, chemosensitization, cancer, metastatic disease (e.g., cancer), inflammatory diseases, HIV infection and stem cell-based regenerative medicine, bone marrow transplantation, chemosensitization, cancer, metastatic disease (e.g., cancer), inflammatory diseases, HIV infection and stem cell-based regenerative medicine. For example, the second therapeutic agent is an agent useful in improving the quanity and quality of stem cell harvesting prior to bone marrow ablative cancer therapy.

For example, the second therapeutic agent can be selected from: G-CSF (granulocyte colony-stimulating factor), cyclophosphamide, rituximab and fludaraine. In a particular embodiment, the second therapeutic agent is G-CSF.

In one embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy. Preferably, the compound is present in the composition in an amount of from 0.1 to 50 wt. %, more preferably from 1 to 30 wt. %, most preferably from 5 to 20 wt. %.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

The compounds for use in the method of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily treatment dose or one of multiple daily treatment doses (e.g., about 1 to 4 or more times per day). When multiple daily treatment doses are used, the unit dosage form can be the same or different for each dose.

Methods of Treatment

As used herein the term "subject" and "patient" typically means a human, but can also be an animal in need of treatment, e.g., companion animals (dogs, cats, and the like), farm animals (cows, pigs, horses, sheep, goats, and the like) and laboratory animals (rats, mice, guinea pigs, and the like).

The terms "treat" and "treating" are used interchangeably and include both therapeutic treatment and prophylactic treatment (reducing the likelihood of development). Both terms mean decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The invention also includes methods of treating diseases, disorders or pathological conditions which benefit from modulation of the CXCR4 receptor comprising administering an effective amount of a CXCR4 receptor compound of the invention to a subject in need thereof. Diseases and conditions which can benefit from modulation (inhibition or activation) of the CXCR4 receptor include, but are not limited to, bone marrow transplantation, chemosensitization, cancer, metastatic disease (e.g., cancer), inflammatory diseases, HIV infection and stem cell-based regenerative medicine. For example, improving the quanity and quality of stem cell harvesting prior to bone marrow ablative cancer therapy.

Bone marrow transplantation can be for treatment of hematological and non hematological malignancies, phagocyte disorders, anemias and myeloproliferative disorders, amyloidoses, radiation poisoning, congenital lysosomal storage disorders and congenital immunodeffciencies.

CXCR4 antagonists are useful for autologous and allogeneic hematopoietic stem cell transplantation (HSCT) to treat acquired as well as congenital diseases. CXCR4 antagonist will be injected into the patients (autologous HSCT) or healthy HLA-matched donor (allogeneic HSCT) before the HSCT procedure. Injection the CXCR4 antagonist induces mobilization of hematopoietc stem cells from bone marrow niche into the peripheral blood. Treatment with the novel CXCR4 antagonist will increase the yield of peripheral hematopoietic stem cells in the amount sufficient for their successful reengraftment or long term storage. HSCs collected during the apheresis procedure will be further reinfused into the patient undergoing HSCT.

The CXCR4 receptor compounds of the invention having antagonist activity are also useful for chemosensitization treatment of patients with hematological malignancies. These patients will be treated with CXCR4 antagonist to induce egress of malignant white blood cells from hematopoietic organs into peripheral circulation. As a result, these abnormal cells will be more readily targeted by chemotherapeutic agents administered intravenously.

Accumulated preclinical data suggests that CXCR4 is essential for the development and progression of inflammatory diseases including but not limited to rheumatoid arthritis and inflammatory bowel disease. Therefore antagonism of CXCR4 can be beneficial for the patients suffering from these disorders. CXCR4 is also a coreceptor for the entry of several HIV-1 strains. Pharmacological targeting of CXCR4-dependent can potentially modulate HIV-1 tropism and it's infectivity.

In one embodiment, an effective amount of a compound of this invention can range from about 0.005 mg to about 5000 mg per treatment. In more specific embodiments, the range is from about 0.05 mg to about 1000 mg, or from about 0.5 mg to about 500 mg, or from about 5 mg to about 50 mg. Treatment can be administered one or more times per day (for example, once per day, twice per day, three times per day, four times per day, five times per day, etc.). When multiple treatments are used, the amount can be the same or different.

It is understood that a treatment can be administered every day, every other day, every 2 days, every 3 days, every 4 days, every 5 days, etc. For example, with every other day administration, a treatment dose can be initiated on Monday with a first subsequent treatment administered on Wednesday, a second subsequent treatment administered on Friday, etc. Treatment is typically administered from one to two times daily. Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

Alternatively, the effective amount of a compound of the invention is from about 0.01 mg/kg/day to about 1000 mg/kg/day, from about 0.1 mg/kg/day to about 100 mg/kg/day, from about 0.5 mg/kg/day to about 50 mg/kg/day, or from about 1 mg/kg/day to 10 mg/kg/day.

In another embodiment, any of the above methods of treatment comprises the further step of co-administering to said patient one or more second therapeutic agents. The choice of second therapeutic agent may be made from any second therapeutic agent known to be useful for co-administration with a compound that modulates the CXCR4 receptor. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

Kits

The present invention also provides kits for use to treat the target disease, disorder or condition. These kits comprise (a) a pharmaceutical composition comprising a compound of Formula I, or a salt thereof, wherein said pharmaceutical composition is in a container; and (b) instructions describing a method of using the pharmaceutical composition to treat the target disease, disorder or condition.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

General Methods for Preparing CXCR4 Receptor Compounds

Synthesis of Peptides

The peptide component (P) of the compounds of the invention can be synthesized by incorporating orthogonally protected amino acids in a step-wise fashion. Any suitable synthetic methods can be used. Traditional Fmoc or Boc chemistry can be easily adapted to provide the desired peptide component (P) of the compounds of the invention. Fmoc is generally preferred, because the cleavage of the Fmoc protecting group is milder than the acid deprotection required for Boc cleavage, which requires repetitive acidic deprotections that lead to alteration of sensitive residues, and increase acid catalyzed side reactions. (G. B. FIELDS et al. in *Int. J. Pept. Protein,* 1990, 35, 161).

The peptides can be assembled linearly via Solid Phase Peptide Synthesis (SPPS), can be assembled in solution using modular condensations of protected or unprotected peptide components or a combination of both.

Solid Phase Peptide Synthesis

For SPPS, an appropriate resin is chosen that will afford the desired moiety on the C-terminus upon cleavage. For example upon cleavage of the linear peptide, a Rink amide resin will provide a primary amide on the C-terminus, whereas a Rink acid resin will provide an acid. Rink acid resins are more labile than Rink amide resins and the protected peptide could also be cleaved and subsequently the free acid activated to react with amines or other nucleophiles. Alternatively, other resins could provide attachment of other moieties prior to acylation, leading to cleavage of an alkylated secondary amide, ester or other desired C-terminal modification. A review of commonly used resins and the functional moiety that results after cleavage can be found in manufacturer literature such as NovaBiochem or Advanced Chemtech catalogues.

Typically a resin is chosen such that after cleavage the C-terminus is an amide bond. Rink amide resin is a resin that results in a C-terminal amide during cleavage. The orthogonally protected Fmoc amino acids are added stepwise using methods well known in literature (Bodansky M. Principles of Peptide synthesis (1993) 318 p; Peptide Chemistry, a Practical Textbook (1993); Spinger-Verlag). These procedures could be done manually or by using automated peptide synthesizers.

The process involves activating the acid moiety of a protected amino acid, using activating agents such as HBTU, HATU, PyBop or simple carbodiimides. Often an additive is used to decrease racemization during coupling such as HOBt or HOAt (M. SCHNÖLZER et al., *Int. J. Pept. Protein Res.,* 1992, 40, 180). Manually, the coupling efficiency can be determined photometrically using a ninhydrin assay. If the coupling efficiency is below 98%, a second coupling may be desired. After the second coupling a capping step may be employed to prevent long deletion sequences to form, simplifying the purification of the desired final compound. With automation, second couplings are not commonly required, unless a residue is known to be problematic such as Arginine.

Deprotection of the Fmoc is most commonly accomplished using piperidine (20%) in dimethylformamide (DMF). Alternatively other secondary amines may also be used such as morpholine, diethylamine or piperazine. This reaction is facile and normally is accomplished within 20 minutes using piperidine. After deprotection the resin is washed several times with DMF and DCM prior to coupling with the next residue. This process is repeated, assembling the peptide linearly until the sequence is complete. The final Fmoc is removed, which allows for coupling with the tether moiety.

In a preferred synthesis, the peptide is formed by SPPS accomplished manually or in an automated fashion using a commercially available synthesizer such as the CEM Microwave peptide synthesizer, Rainin Symphony synthesizer, or ABI 433 flow-through synthesizer. Commercially available Rink Amide resin is used for synthesizing the C-terminal amide peptides (Rink, H. *Tetrahedron Lett,* 28, 4645, 1967). Peptide synthesis reagents (coupling, deprotection agents) are commercially available and include HOBT, HBTU (Novabiochem) as well as DMF, DCM, Piperidine, NMP, and DIEA (Sigma-Aldrich). Suitably protected amino acids for use in solid phase peptide synthesis are commercially available from many sources, including Sigma-Aldrich and CEM Corporation.

For example, a convenient preparation of peptides on a 0.1 mmol or 0.25 mmol scale uses Rink amide solid-phase resin with a substitution of about 0.6 mmol/g. Linear attachment of the amino acids is accomplished on a ABI continuous flow automated synthesizer using 5 eq of orthogonally protected amino acid (AA), and using HBTU/HOBt coupling protocol, (5 eq. of each reagent). In another preferred synthesis, peptides can be synthesized using a microwave instrument using 10 eq of reagents. Deprotection of Fmoc can be accomplished with 20% piperidine in DMF followed by washing with DMF and DCM.

In both cases (i.e., Rink acid and Rink amide resins), final Fmoc deprotection of the N-terminus would leave a free amine after cleavage from the resin unless it is modified prior to cleavage. In the compounds of the invention, tether moieties are attached through amide bonds.

Solution Phase Synthesis of Peptides

For solution phase synthesis the desired peptide is generally broken down into peptide fragments in units of 2-4 amino acids. The selected unit is dependent on the sequence, the stability of the fragment to racemization, and the ease of assembly. As each amino acid is added, only 1-1.5 eq of the residue is required, versus the 5-10 equivalents of reagent required for SSPS. Preactivated amino acids such as OSu active ester and acid fluorides also can be used, requiring only a base for completion of the reaction.

Coupling times require 1.5-2 hours for each step. Two fragments are condensed in solution, giving a larger fragment that then can be further condensed with additional fragments until the desired sequence is complete. The solution phase protocol uses only 1 eq of each fragment and will use coupling reagents such as carbodiimides (DIC). For racemized prone fragments, PyBop or HBTU/HOBt can be used. Amino acids with Bsmoc/tBu or Fmoc/tBu and Boc/Benzyl protection are equally suitable for use.

When Fmoc is used, the use of 4-(aminomethyl) piperidine or tris(2-aminoethyl)amine as the deblocking agent can avoid undesired side reactions. The resulting Fmoc adduct can be extracted with a phosphate aqueous buffer of pH 5.5 (Organic Process Research & Development 2003, 7, 2837). If Bsmoc is used, no buffer is required, only aqueous extractions are needed. Deprotections using these reagents occur in 30-60 minutes. Deblocking of the Fmoc group on the N-terminal residue provides a free terminal amine that is used for attachment of the tether moiety. In the compounds of the invention, tether moieties are attached through amide bonds to the N-terminal amine.

One advantage of solution phase synthesis is the ability to monitor the compound after every coupling step by mass spectrometry to see that the product is forming. In addition, a simple TLC system could be used to determine completion of reaction.

Attachment of Tethers

Tethers are attached to the terminal nitrogen of the N-terminal amino acid of the peptide chain using amide bond coupling:

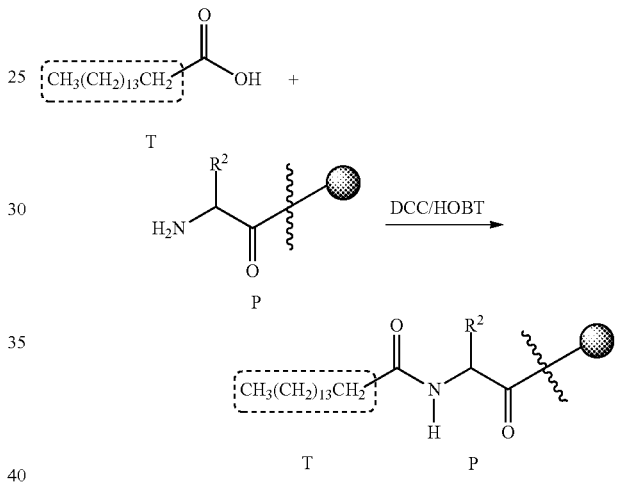

The tether can be attached using solid phase procedures or in solution using an amide bond coupling. After the N-terminus is suitably coupled, the final compound is cleaved from the resin using an acidic cocktail (Peptide Synthesis and Applications, John Howl, Humana Press, 262 p, 2005). Typically these cocktails use concentrated trifluoroacetic acid (80-95%) and various scavengers to trap carbocations and prevent side chain reactions. Typical scavengers include isopropylsilanes, thiols, phenols and water. The cocktail mixture is determined by the residues of the peptide. Special care needs to be taken with sensitive residues, such as methionine, aspartic acid, and cysteine. Typical deprotection occurs over 2-5 hours in the cocktail. A preferred deprotection cocktail include the use of triisopropylsilane (TIS), Phenol, thioanisole, dodecanethiol (DDT) and water. Methane sulfonic acid (MSA) may also be used in the cocktail (4.8%). A more preferred cocktail consists of (TFA:MSA:TIS:DDT:Water 82:4.5:4.5:4.5:4.5; 10 mL/0.1 mmol resin).

After deprotection, the resin is removed via filtration, and the final compound is isolated via precipitation from an organic solvent such as diethyl ether, m-tert-butyl ether, or ethyl acetate and the resulting solid collected via filtration or lyophilized to a powder. Purification of the peptide using reverse phase HPLC may be required to achieve sufficient purity. Generally, a gradient of aqueous solvent with an organic solvent will provide sufficient separation from impurities and deletion sequences. Typically 0.1% TFA is used as the aqueous and organic modifier, however, other modifiers such as ammonium acetate can also be used. After purification, the compound is collected, analyzed and fractions of sufficient purity are combined and lyophilized, providing the compound as a solid.

Amino Acid Reagents

The following commercially available orthogonally protected amino acids used can be used in the synthesis of compounds of the invention: Fmoc-Tyr(tBu)-OH, Fmoc-Ala-OH*H₂O, Fmoc-Arg(Pbf)-OH, Fmoc, Asn(Trt)-OH, Fmoc-Asp(tBu), Fmoc-Cys(tBu)-OH, Fmoc-Glu(tBu)-OH, Fmoc-Glx(Pbf)-OH, Fmoc-Gly-OH, Fmoc-His(Trt)-OH, Fmoc-Leu-OH, Fmoc-Ile-OH, Fmoc, Lys(tBu)-OH, Fmoc-Met-OH, Fmoc-Phe-OH, Fmoc-Ser(tBu)-OH, Fmoc-Thr(tBu)-OH, Fmoc-Typ-OH, and Fmoc-Val-OH. Additional amino acids suitable for incorporation into the compounds of the invention (e.g., D amino acids, substituted amino acids and other protecting group variations) are also commercially available or synthesized by methods known in the art.

Analytical Methods

The compounds of the invention are analyzed for purity by HPLC using the methods listed below. Purification is achieved by preparative HPLC.

Fast LC/MS Method
Column: Phenomenex Luna C-5 20×30 mm
Flow: 1.0 ml/min
Solvent A: 0.1% TFA in Type I water
Solvent B: 0.1% TFA in Acetonitrile
UV 220 nm
Injection: 20 ul
Gradient 5-95% B (7 minutes); 95-5% B (1 minute); 5% B (4 minutes)

Analytical Purity Method
Column: Phenomenex Luna C-5 20×30 mm
Flow: 1.0 ml/min
Solvent A: 0.1% TFA in Type I water
Solvent B: 0.1% TFA in Acetonitrile
UV: 220 nm
Injection: 20 ul
Gradient: 2-95% B (10 minutes); 95-2% B (2 minutes); 2% B (2 minutes)

Preparative LC/MS Method
Column: Phenomenex Luna C-5 250×150 mm
Flow: 5.0 ml/min
Solvent A: 0.1% TFA in Type I water
Solvent B: 0.1% TFA in Acetonitrile
UV: 220 nm
Injection: 900 ul
Gradient: 35% B (5 minutes); 35-85% B (13 minutes); 85-35% B (0.5 minutes); 35% B (1.5 minutes)

The compounds listed in Tables 14-17 or pharmaceutically acceptable salts thereof were prepared according to the methods described herein.

TABLE 14

CXCR4 i1 loop compounds

| No. | Loop | Sequence | N-terminus T-L | MS C-terminus | MS Theoretical | MS Observed Ion |
|---|---|---|---|---|---|---|
| 1 | i1 | AGYQKKLRSMTD (SEQ ID NO: 11) | $C_{15}H_{31}C(O)-$ | $NH_2$ | | |
| 2 | i1 | MAYQKKLRSMTD (SEQ ID NO: 12) | $C_{15}H_{31}C(O)-$ | $NH_2$ | | |
| 3 | i1 | MGAQKKLRSMTD (SEQ ID NO: 13) | $C_{15}H_{31}C(O)-$ | $NH_2$ | | |
| 4 | i1 | MGYAKKLRSMTD (SEQ ID NO: 14) | $C_{15}H_{31}C(O)-$ | $NH_2$ | | |
| 5 | i1 | MGYQKKLRAMTD (SEQ ID NO: 15) | $C_{15}H_{31}C(O)-$ | $NH_2$ | | |
| 6 | i1 | MGYQKKLRSATD (SEQ ID NO: 16) | $C_{15}H_{31}C(O)-$ | $NH_2$ | | |
| 7 | i1 | MGYQKKLRSMAD (SEQ ID NO: 17) | $C_{15}H_{31}C(O)-$ | $NH_2$ | | |
| 8 | i1 | MGYQKKLRSMTA (SEQ ID NO: 18) | $C_{15}H_{31}C(O)-$ | $NH_2$ | | |
| 9 | i1 | MGYQAKLRSMTD (SEQ ID NO: 19) | $C_{15}H_{31}C(O)-$ | $NH_2$ | | |
| 10 | i1 | MGYQKKLASMTD (SEQ ID NO: 20) | $C_{15}H_{31}C(O)-$ | $NH_2$ | | |
| 11 | i1 | MGYQKALRSMTD (SEQ ID NO: 21) | $C_{15}H_{31}C(O)-$ | $NH_2$ | | |
| 12 | i1 | MGYQKKARSMTD (SEQ ID NO: 22) | $C_{15}H_{31}C(O)-$ | $NH_2$ | | |
| 13 | i1 | mGYQKKLRSMTD (SEQ ID NO: 23) | $C_{15}H_{31}C(O)-$ | $NH_2$ | | |

TABLE 14-continued

CXCR4 i1 loop compounds

| No. | Loop | Sequence | N-terminus T-L | C-terminus | MS Theoretical | MS Observed Ion |
|---|---|---|---|---|---|---|
| 14 | i1 | MGyQKKLRSMTD (SEQ ID NO: 24) | $C_{15}H_{31}C(O)-$ | $NH_2$ | | |
| 15 | i1 | MGYqKKLRSMTD (SEQ ID NO: 25) | $C_{15}H_{31}C(O)-$ | $NH_2$ | | |
| 16 | i1 | MGYQkKLRSMTD (SEQ ID NO: 26) | $C_{15}H_{31}C(O)-$ | $NH_2$ | | |
| 17 | i1 | MGYQKkLRSMTD (SEQ ID NO: 27) | $C_{15}H_{31}C(O)-$ | $NH_2$ | | |
| 18 | i1 | MGYQKKlRSMTD (SEQ ID NO: 28) | $C_{15}H_{31}C(O)-$ | $NH_2$ | | |
| 19 | i1 | MGYQKKLrSMTD (SEQ ID NO: 29) | $C_{15}H_{31}C(O)-$ | $NH_2$ | | |
| 20 | i1 | MGYQKKLRsMTD (SEQ ID NO: 30) | $C_{15}H_{31}C(O)-$ | $NH_2$ | | |
| 21 | i1 | MGYQKKLRSmTD (SEQ ID NO: 31) | $C_{15}H_{31}C(O)-$ | $NH_2$ | | |
| 22 | i1 | MGYQKKLRSMtD (SEQ ID NO: 32) | $C_{15}H_{31}C(O)-$ | $NH_2$ | | |
| 23 | i1 | MGYQKKLRSMTd (SEQ ID NO: 33) | $C_{15}H_{31}C(O)-$ | $NH_2$ | | |
| 24 | i1 | GSHYQKKLRSSTD (SEQ ID NO: 34) | $C_{15}H_{31}C(O)-$ | $NH_2$ | | |
| 25 | i1 | SGYQKKLRSSTD (SEQ ID NO: 1) | $C_{17}H_{33}C(O)-$ | $NH_2$ | | |
| 26 | i1 | SGYQKKLRSSTD (SEQ ID NO: 1) | $C_{16}H_{31}C(O)-$ | $NH_2$ | | |
| 27 | i1 | sGYQKKLRSSTD (SEQ ID NO: 68) | $C_{15}H_{31}C(O)-$ | $NH_2$ | | |
| 28 | i1 | GSGYQKKLRSSTD (SEQ ID NO: 35) | $C_{15}H_{31}C(O)-$ | $NH_2$ | | |
| 29 | i1 | YQKKLRSSTD (SEQ ID NO: 36) | $C_{15}H_{31}C(O)-$ | $NH_2$ | | |
| 30 | i3 | JGYQKKLRSJTD (SEQ ID NO: 4) | $C_{15}H_{31}C(O)-$ | $NH_2$ | | |
| 31 | i3 | JGYQKKLRSJTD (SEQ ID NO: 4) | $C_{15}H_{31}C(O)-$ | $NH_2$ | | |
| 32 | i1 | MGYQKKLRSMTD (SEQ ID NO: 376) | $CH_3C(O)-$ | $NH_2$ | | |
| 33 | i1 | MGYQKKLRSMTD (SEQ ID NO: 376) | Footnote: 1 | $NH_2$ | 655.8 | 655.5 |
| 34 | i1 | LVMGYQKKLRSMTD (SEQ ID NO: 78) | $C_{15}H_{31}C(O)-$ | $NH_2$ | 954.7, 636.8 | 954.2, 646.3 |
| 35 | i1 | VMGYQKKLRSMTD (SEQ ID NO: 86) | $C_{15}H_{31}C(O)-$ | $NH_2$ | 898.1 | 897.7 |
| 36 | i1 | MGYQKKLRSMTDK (SEQ ID NO: 79) | $C_{15}H_{31}C(O)-$ | $NH_2$ | 912.7 | 912.2 |
| 37 | i1 | MGYQKKLRSMTDKY (SEQ ID NO: 80) | $C_{15}H_{31}C(O)-$ | $NH_2$ | 994.3 | 993.7 |

TABLE 14-continued

CXCR4 i1 loop compounds

| No. | Loop | Sequence | N-terminus T-L | C-terminus | MS Theoretical | MS Observed Ion |
|---|---|---|---|---|---|---|
| 38 | i1 | MGYQKKLRSMTDKYRL (SEQ ID NO: 82) | $C_{15}H_{31}C(O)-$ | $NH_2$ | 752.9 | 753 |
| 39 | i1 | MGYQKKLRSMTDKYRLHL (SEQ ID NO: 83) | $C_{15}H_{31}C(O)-$ | $NH_2$ | 836.4 | 836 |
| 40 | i1 | YQKKLRSMTDKYRLHLSV (SEQ ID NO: 77) | $C_{15}H_{31}C(O)-$ | $NH_2$ | 1253.0, 835.7, 627.2 | 1254, 836, 627.50 |
| 41 | i1 | KKLRSMTDKYRLHLSV (SEQ ID NO: 74) | $C_{15}H_{31}C(O)-$ | $NH_2$ | 1107.4, 738.6, 554.2 | 1107.0, 738.0, 554 |
| 42 | i1 | KKLRSMTDKYRLHL (SEQ ID NO: 73) | $C_{15}H_{31}C(O)-$ | $NH_2$ | 1014.3, 676.5 | 1014.0, 676.0 |
| 43 | i1 | KKLRSMTDKYRLH (SEQ ID NO: 42) | $C_{15}H_{31}C(O)-$ | $NH_2$ | 957.7, 638.8 | 958.0, 638.0 |
| 44 | i1 | KKLRSMTDKYRL (SEQ ID NO: 71) | $C_{15}H_{31}C(O)-$ | $NH_2$ | 889.2, 592.1 | 888.0, 592.0 |
| 45 | i1 | KKLRSMTDKYR (SEQ ID NO: 70) | $C_{15}H_{31}C(O)-$ | $NH_2$ | 832.6 | 833 |
| 46 | i1 | KKLRSMTDKY (SEQ ID NO: 69) | $C_{15}H_{31}C(O)-$ | $NH_2$ | 754.5 | 754 |
| 47 | i1 | MGYQKKLRSMTDKYRI (SEQ ID NO: 81) | $C_{15}H_{31}C(O)-$ | $NH_2$ | 827.8, 621.0 | 828.0, 621.0 |
| 48 | i1 | MGYQKKLRSMTDKYRI (SEQ ID NO: 81) | Footnote: 2 | $NH_2$ | 837.4 | 837.4 |
| 49 | i1 | MGYQKKLRSMTDKYRI (SEQ ID NO: 81) | $C_{15}H_{31}C(O)-$ | $NH_2$ | 752.9 | 753 |
| 50 | i1 | SGYQKKLRSSTD (SEQ ID NO: 1) | Footnote: 2 | $NH_2$ | 931.2 | 931 |
| 51 | i1 | MGYQKKLRSMTD (SEQ ID NO: 376) | Footnote: 2 | $NH_2$ | 975.3, 650.5 | 975.0, 650.5 |
| 52 | i1 | QKKLRSMTDKYRI (SEQ ID NO: 75) | $CH_3C(O)-$ | $NHC_{16}H_{33}$ | 645.2 | 645 |
| 53 | i1 | MGYQKKLRSMTDKYRLHL (SEQ ID NO: 83) | $C_{15}H_{31}C(O)-$ | $NH_2$ | 683.7 | 684 |
| 54 | i1 | MGYQKKLRSMTDKYRLHL (SEQ ID NO: 83) | Footnote: 2 | $NH_2$ | 920.9, 690.9 | 921.0, 691.0 |
| 55 | i1 | MGYQKKLRSMTDKYRLHLSV (SEQ ID NO: 84) | $C_{15}H_{31}C(O)-$ | $NH_2$ | 898.4 | 898 |
| 56 | i1 | MGYQKKLRSMTDKYRLHLSV (SEQ ID NO: 84) | Footnote: 2 | $NH_2$ | 982.9, 737.5 | 982.0, 737.0 |
| 58 | i1 | MGYQKKLRSMTDK (SEQ ID NO: 79) | $CH_3C(O)-$ | $NH_2$ | 814.5 | 814.5 |

TABLE 14-continued

CXCR4 i1 loop compounds

| No. | Loop | Sequence | N-terminus T-L | C-terminus | MS Theoretical | MS Observed Ion |
|---|---|---|---|---|---|---|
| 59 | i1 | MGYQKKLRSMTDK (SEQ ID NO: 79) | $CH_3C(O)-$ | $NHC_{16}H_{33}$ | 926.7, 618.1 | 926.5, 618 |
| 60 | i1 | MGYQKKLRSMTDK (SEQ ID NO: 79) | Footnote: 2 | $NH_2$ | 693.2 | 693.2 |
| 61 | i1 | KKLCRSMTDKCYRL (SEQ ID NO: 87) | $C_{15}H_{31}C(O)-$ | $NH_2$ | 991.2 | 990 |
| 62 | i1 | KKLRCSMTDCKYRL (SEQ ID NO: 88) | $C_{15}H_{31}C(O)-$ | $NH_2$ | | |
| 63 | i1 | KKLRSMTDKYRL (SEQ ID NO: 71) | $C_{15}H_{31}C(O)-$ | $NH_2$ | 902.2 | 901.7 |
| 64 | i1 | KKLRSMTDKYRL (SEQ ID NO: 71) | $C_{15}H_{31}C(O)-$ | $NH_2$ | 911.2 | 910.5 |
| 65 | i1 | KRMKTSLYDGRMQYLK (SEQ ID NO: 67) | $C_{15}H_{31}C(O)-$ | $NH_2$ | 752.9 | 752.3 |
| 66 | i1 | YTKRLDSHRKLKM (SEQ ID NO: 85) | $C_{15}H_{31}C(O)-$ | $NH_2$ | 957.7 | 956.7 |
| 67 | i1 | MGYQKKLRSMTDKYRL (SEQ ID NO: 82) | $CH3C(O)-$ | $NH_2$ | 687.8 | 687 |
| 68 | i1 | KKLRSXTDKYRLH (SEQ ID NO: 72) | $C_{15}H_{31}C(O)-$ | $NH_2$ | 632.8 | 632.3 |
| 69 | i1 | SGYQKKLRSSTD (SEQ ID NO: 1) | $C_{15}H_{31}C(O)-$ | $NH_2$ | | |
| 70 | i1 | SGYQKKLRSSTD (SEQ ID NO: 1) | $C_{16}H_{33}O_2C(O)-$ | $NH_2$ | | |
| 71 | i1 | SGYQKKLRSSTD (SEQ ID NO: 1) | $C_{23}H_{39}OC(O)-$ | $NH_2$ | | |
| 72 | i1 | MGYQKKLRSSTD (SEQ ID NO: 2) | $C_{15}H_{31}C(O)-$ | $NH_2$ | | |
| 73 | i1 | SGYQKKLRSMTD (SEQ ID NO: 3) | $C_{15}H_{31}C(O)-$ | $NH_2$ | | |
| 117 | i1 | kKLRSMTDKYRLH (SEQ ID NO: 89) | Pal | | | |
| 118 | i1 | KkLRSMTDKYRLH (SEQ ID NO: 90) | Pal | | | |
| 119 | i1 | KKlRSMTDKYRLH (SEQ ID NO: 91) | Pal | | | |
| 120 | i1 | KKLrSMTDKYRLH (SEQ ID NO: 92) | Pal | | | |
| 121 | i1 | KKLRsMTDKYRLH (SEQ ID NO: 93) | Pal | | | |
| 122 | i1 | KKLRSmTDKYRLH (SEQ ID NO: 94) | Pal | | | |
| 123 | i1 | AKLRSMTDKYRLH (SEQ ID NO: 95) | Pal | | | |

TABLE 14-continued

CXCR4 i1 loop compounds

| No. | Loop | Sequence | N-terminus T-L | MS C-terminus Theoretical | MS Observed Ion |
|---|---|---|---|---|---|
| 124 | i1 | KALRSMTDKYR LH (SEQ ID NO: 96) | Pal | | |
| 125 | i1 | KKARSMTDKYR LH (SEQ ID NO: 97) | Pal | | |
| 126 | i1 | KKLASMTDKYR LH (SEQ ID NO: 98) | Pal | | |
| 127 | i1 | KKLRAMTDKYR LH (SEQ ID NO: 99) | Pal | | |
| 128 | i1 | KKLRSATDKYR LH (SEQ ID NO: 100) | Pal | | |
| 129 | i1 | AGYQKKLRSMT DKYRL (SEQ ID NO: 101) | Pal | | |
| 130 | i1 | MAYQKKLRSMT DKYRL (SEQ ID NO: 102) | Pal | | |
| 131 | i1 | MGAQKKLRSMT DKYRL (SEQ ID NO: 103) | Pal | | |
| 132 | i1 | MGYAKKLRSMT DKYRL (SEQ ID NO: 104) | Pal | | |
| 133 | i1 | MGYQAKLRSMT DKYRL (SEQ ID NO: 105) | Pal | | |
| 134 | i1 | MGYQKALRSMT DKYRL (SEQ ID NO: 106) | Pal | | |
| 135 | i1 | MGYQKKARSM TDKYRL (SEQ ID NO: 107) | Pal | | |
| 136 | i1 | MGYQKKLASMT DKYRL (SEQ ID NO: 108) | Pal | | |
| 137 | i1 | KKLRSMTDKYR LH (SEQ ID NO: 42) | Myr | | |
| 138 | i1 | KKLRSMTDKYR LH (SEQ ID NO: 42) | Lca | | |
| 139 | i1 | KKLRSMADKYR LH (SEQ ID NO: 109) | Pal | | |
| 140 | i1 | KKLRSMTAKYR LH (SEQ ID NO: 110) | Pal | | |
| 141 | i1 | KKLRSMTDAYR LH (SEQ ID NO: 111) | Pal | | |
| 142 | i1 | KKLRSMTDKAR LH (SEQ ID NO: 112) | Pal | | |
| 143 | i1 | KKLRSMTDKYA LH (SEQ ID NO: 113) | Pal | | |

TABLE 14-continued

CXCR4 i1 loop compounds

| No. | Loop | Sequence | N-terminus T-L | MS C-terminus Theoretical | MS Observed Ion |
|---|---|---|---|---|---|
| 144 | i1 | KKLRSMTDKYRAH (SEQ ID NO: 114) | Pal | | |
| 145 | i1 | KKLRSMTDKYRLA (SEQ ID NO: 115) | Pal | | |
| 146 | i1 | MGYQKKLRAMTDKYRL (SEQ ID NO: 116) | Pal | | |
| 147 | i1 | MGYQKKLRSATDKYRL (SEQ ID NO: 117) | Pal | | |
| 148 | i1 | MGYQKKLRSMADKYRL (SEQ ID NO: 118) | Pal | | |
| 149 | i1 | MGYQKKLRSMTAKYRL (SEQ ID NO: 119) | Pal | | |
| 150 | i1 | MGYQKKLRSMTDAYRL (SEQ ID NO: 120) | Pal | | |
| 151 | i1 | MGYQKKLRSMTDKARL (SEQ ID NO: 121) | Pal | | |
| 152 | i1 | MGYQKKLRSMTDKYAL (SEQ ID NO: 122) | Pal | | |
| 153 | i1 | MGYQKKLRSMTDKYRA (SEQ ID NO: 123) | Pal | | |
| 154 | i1 | KKLRSMtDKYRLH (SEQ ID NO: 124) | Pal | | |
| 155 | i1 | KKLRSMTdKYRLH (SEQ ID NO: 125) | Pal | | |
| 156 | i1 | KKLRSMTDKYrLH (SEQ ID NO: 126) | Pal | | |
| 157 | i1 | KKLRSMTDKYRlH (SEQ ID NO: 127) | Pal | | |
| 158 | i1 | KKLRSMTDKYRLh (SEQ ID NO: 128) | Pal | | |
| 159 | i1 | MGYQKKLRSMTDKYRl (SEQ ID NO: 381) | Pal | | |
| 160 | i1 | MGYQKKLRSMTDKYrL (SEQ ID NO: 129) | Pal | | |
| 161 | i1 | MGYQKKLRSMTDKyRL (SEQ ID NO: 130) | Pal | | |
| 162 | i1 | MGYQKKLRSMTDkYRL (SEQ ID NO: 131) | Pal | | |
| 163 | i1 | MGYQKKLRSMTdKYRL (SEQ ID NO: 132) | Pal | | |

TABLE 14-continued

CXCR4 i1 loop compounds

| No. | Loop | Sequence | N-terminus T-L | MS C-terminus Theoretical | MS Observed Ion |
|---|---|---|---|---|---|
| 164 | i1 | MGYQKKLRSMtDKYRL (SEQ ID NO: 133) | Pal | | |
| 165 | i1 | mGYQKKLRSMTDKYRL (SEQ ID NO: 134) | Pal | | |
| 166 | i1 | MGyQKKLRSMTDKYRL (SEQ ID NO: 135) | Pal | | |
| 167 | | MGYqKKLRSMTDKYRL (SEQ ID NO: 136) | Pal | | |
| 168 | i1 | MGYQkKLRSMTDKYRL (SEQ ID NO: 137) | Pal | | |
| 169 | i1 | MGYQKkLRSMTDKYRL (SEQ ID NO: 138) | Pal | | |
| 170 | i1 | MGYQKKlRSMTDKYRL (SEQ ID NO: 139) | Pal | | |
| 171 | i1 | MGYQKKLrSMTDKYRL (SEQ ID NO: 140) | Pal | | |
| 172 | | MGYQKKLRsMTDKYRL (SEQ ID NO: 141) | Pal | | |
| 173 | i1 | MGYQKKLRSmTDKYRL (SEQ ID NO: 142) | Pal | | |
| 174 | i1 | KKLRSMTDKYRlS (SEQ ID NO: 143) | Pal | | |
| 175 | i1 | MGYQKKLRSMTDKYRL (SEQ ID NO: 82) | Pal | | |
| 176 | i1 | MGYQKKLRSMTDKYRL (SEQ ID NO: 82) | Elaidic | | |
| 177 | i1 | MGYQKKLRSMTDKYRL (SEQ ID NO: 82) | Oleic | | |
| 178 | i1 | MGYQKKLRSMTDKYRL (SEQ ID NO: 82) | 3-(dodecyloxy) propanoate | | |
| 179 | i1 | MGYQKKLRSMTDKYRL (SEQ ID NO. 82) | | | |
| 180 | i1 | KKLRSMTDKYRLH (SEQ ID NO: 42) | Pal | | |
| 181 | i1 | KKLRSMTDKYRLH (SEQ ID NO: 42) | 3-(dodecyloxy) propanoate | | |
| 182 | i1 | KKLRSMTDKYRLH (SEQ ID NO: 42) | | | |

TABLE 14-continued

CXCR4 i1 loop compounds

| No. | Loop | Sequence | N-terminus T-L | C-terminus | MS Theoretical | MS Observed Ion |
|---|---|---|---|---|---|---|
| 183 | i1 | KKLRSMTDKYRLH (SEQ ID NO: 42) | | | | |
| 184 | i1 | KKLRSMTDKYRLH (SEQ ID NO: 42) | | | | |
| 185 | i1 | KKLRSMTDKYRLH (SEQ ID NO: 42) | | | | |
| 186 | i1 | MGYQKKLRSMTDKYRL (SEQ ID NO: 82) | | | | |
| 187 | i1 | MGYQKKLRSMTDKYRL (SEQ ID NO: 82) | | | | |
| 188 | i3 | MGYQKKLRSMTDKYRL (SEQ ID NO: 82) | | | | |
| 189 | i1 | MGYQKKLRSpTDKYRL (SEQ ID NO: 144) | Pal | | | |
| 190 | i1 | MGYQKKLRpMTDKYRL (SEQ ID NO: 145) | Pal | | | |
| 191 | i1 | MGYQKKLpSMTDKYRL (SEQ ID NO: 146) | Pal | | | |
| 192 | i1 | MGYQKKpRSMTDKYRL (SEQ ID NO: 147) | Pal | | | |
| 193 | i1 | MGYQKKLRSMPDKYRL (SEQ ID NO: 148) | Pal | | | |

TABLE 15

CXCR4 i2 loop compounds

| Sample Lot | Loop | N-terminus T-L | Sequence | C-terminus | MS Theoretical | MS Observed Ion |
|---|---|---|---|---|---|---|
| 74 | i2 | $C_{15}H_{31}C(O)-$ | DRYLAIVHATNSQRPRKLL (SEQ ID NO: 152) | $-(NH)C_{16}H_{33}$ | 679.4, 905.5 | 679.3, 905.0 |
| 75 | i2 | $C_{15}H_{31}C(O)-$ | VHATNSQRPRKLLAEKVVY (SEQ ID NO: 194) | $NH_2$ | 612.8 | 613.0 |
| 76 | i2 | $C_{31}H_{62}NC(O)-$ | DRYLAIVHATNSQRPRKLL (SEQ ID NO: 152 | $NH_2$ | 686.6 | 686.6 |
| 77 | i2 | $C_{15}H_{31}C(O)-$ | DRYLAIVHATNSQRPRKLL (SEQ ID NO: 152) | $NH_2$ | 623.3 | 623.5 |
| 78 | i2 | $C_{15}H_{31}C(O)-$ | VHATNSQRPRKLLA (SEQ ID NO: 195) | $NH_2$ | 915.2 | 915 |
| 79 | i2 | $C_{15}H_{31}C(O)-$ | HATNSQRPRKL (SEQ ID NO: 196) | $NH_2$ | 773.5 | 773.9 |

TABLE 15-continued

CXCR4 i2 loop compounds

| Sample Lot | Loop | N-terminus T-L | Sequence | C-terminus | MS Theoretical | MS Observed Ion |
|---|---|---|---|---|---|---|
| 80 | i2 | $C_{15}H_{31}C(O)-$ | HATNSQRPRKLLA (SEQ ID NO: 197) | $NH_2$ | 865.6 | 865.5 |
| 81 | i2 | $C_{15}H_{31}C(O)-$ | HATNSQRPRKLLAE (SEQ ID NO: 198) | $NH_2$ | 930.2 | 930.5 |
| 82 | i2 | $C_{15}H_{31}C(O)-$ | HATNSQRPRKLLAEK (SEQ ID NO: 171) | $NH_2$ | 663.1 | 663.0 |
| 83 | i2 | $C_{15}H_{31}C(O)-$ | HATNSQRPRKLLAEKV (SEQ ID NO: 199) | $NH_2$ | 696.2 | 696.0 |

TABLE 16

CXCR4 i3 loop compounds

| Sequence | C-terminus | N-terminus | MW | MS Theoretical | MS Observed Ion |
|---|---|---|---|---|---|
| 84 HSKKGHQKRKALK (SEQ ID NO: 200) | $NH_2$ | $C_{15}H_{31}C(O)-$ | 1783.258 | | |
| 85 HSKGHQKRKALK (SEQ ID NO: 369) | $NH_2$ | $C_{15}H_{31}C(O)-$ | 1655.086 | | |
| 87 HSKGHQKRKQALK (SEQ ID NO: 244) | $NH_2$ | C27H50N3O2SC(O)— | 1924.449 | 963.2 | 962.0 |
| 88 SKLSHSKGHQKRKALKTTVIL (SEQ ID NO: 253) | $NH_2$ | $C_{15}H_{31}C(O)-$ | 2598.225 | 867.1, 650.6 | 866.7, 650.0 |
| 89 KLSHSKGHQKRKALKTTVIL (SEQ ID NO: 249) | $NH_2$ | $C_{15}H_{31}C(O)-$ | 2511.147 | 838.0, 1256.6 | 837.5, 1255.8 |
| 90 KLSHSKGHQKRKALKTTV (SEQ ID NO: 248) | $NH_2$ | $C_{15}H_{31}C(O)-$ | 2284.832 | 762.6 | 762.0 |
| 91 KLSHSKGHQKRKALKT (SEQ ID NO: 219) | $NH_2$ | $C_{15}H_{31}C(O)-$ | 2084.597 | 1043.3 | 1043.0 |
| 92 KLSHSKGHQKRKALK (SEQ ID NO: 247) | $NH_2$ | $C_{15}H_{31}C(O)-$ | 1983.493 | 992.7 | 992.0 |
| 93 KLSHSKGHQKRKAL (SEQ ID NO: 246) | $NH_2$ | $C_{15}H_{31}C(O)-$ | 1855.321 | 619.4, 928.7 | 619.3, 929.0 |
| 94 KLSHSKGHQKRKA (SEQ ID NO: 245) | $NH_2$ | $C_{15}H_{31}C(O)-$ | 1742.163 | 581.7, 872.1 | 582.0, 872.0 |
| 95 LSHSKGHQKRKALK (SEQ ID NO: 250) | $NH_2$ | $C_{15}H_{31}C(O)-$ | 1855.321 | 928.7 | 928.0 |
| 96 SHSKGHQKRKALK (SEQ ID NO: 251) | $NH_2$ | $C_{15}H_{31}C(O)-$ | 1742.163 | 581.7 | 585.0 |
| 97 HSKGHQKRKALKT (SEQ ID NO: 222) | $NH_2$ | $C_{15}H_{31}C(O)-$ | 1756.19 | 879.1 | 879.0 |
| 98 HSKGHQKRKALKTT (SEQ ID NO: 241) | $NH_2$ | $C_{15}H_{31}C(O)-$ | 1857.294 | 620.1 | 619.9 |
| 99 HSKGHQKRKALKTTV (SEQ ID NO: 242) | $NH_2$ | $C_{15}H_{31}C(O)-$ | 1956.425 | 653.0 | 653.0 |
| 100 HSKGHQKRKALKTTVI (SEQ ID NO: 243) | $NH_2$ | $C_{15}H_{31}C(O)-$ | 2069.583 | 733.0 | 733.6 |

TABLE 16-continued

| | | CXCR4 i3 loop compounds | | | |
|---|---|---|---|---|---|
| Sequence | C-terminus | N-terminus | MW | MS Theoretical | MS Observed Ion |
| 101 SKLSHSKGHQ KRKALK (SEQ ID NO: 252) | NH$_2$ | C$_{15}$H$_{31}$C(O)— | 2070.571 | 1036.3 | 1036.0 |
| 102 IIISKLSHSKG HQKRKALKT (SEQ ID NO: 202) | NH$_2$ | C$_{15}$H$_{31}$C(O)— | 2511.147 | 628.8 | 628.7 |
| 103 IIISKLSHSKG HQKRKALKT (SEQ ID NO: 202) | NH$_2$ | C$_{31}$H$_{62}$NC(O)— | 2765.556 | 692.4 | 692.4 |
| 104 IIISKLSHSKG HQKRKALKT (SEQ ID NO: 202) | —(NH)C16H33 | C$_{15}$H$_{31}$C(O)— | 2735.573 | 684.9 | 684.7 |
| 105 KLSHSKGHQ KRKALKTTVIL (SEQ ID NO: 249) | NH$_2$ | C$_{31}$H$_{62}$NC(O)— | 2764.571 | 684.9 | 685.0 |
| 106 QHLHIALKKS TSRKVKSGTLK (SEQ ID NO: 254) | NH$_2$ | C$_{15}$H$_{31}$C(O)— | 2598.225 | 650.6 | 650.0 |

Foot Note 1 of Tables is

1. 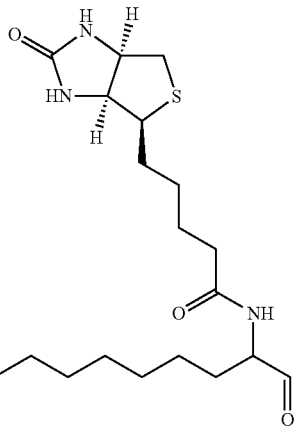

Footnote 2 of the tables is:

2. 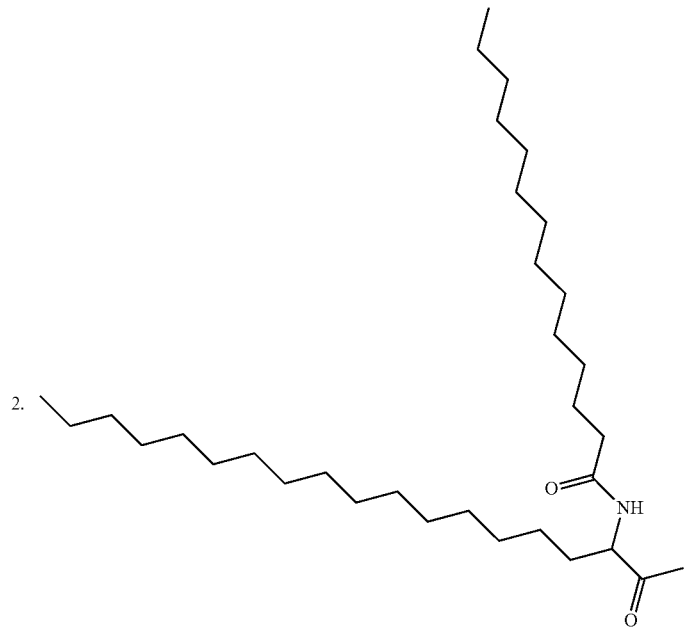 [SMILES: CCCCCCCCCCCCCCCCC(NC(=O)CCCCCCCCCCCCC)C(C)=O]

TABLE 17

CXCR4 i4 loop compounds

| No. | Loop | N-terminus | MW | C-terminus | Sequence | MS Theoretical | MS Observed Ion |
|---|---|---|---|---|---|---|---|
| 107 | i4 | $C_{31}H_{62}NC(O)-$ | 4248.067 | $NH_2$ | GAKFKTSAQHALTS VSRGSSLKILSKGKR GGHSSVST (SEQ ID NO: 263) | 1063.0 | 1063.0 |
| 108 | i4 | $C_{31}H_{62}NC(O)-$ | 3592.41 | $NH_2$ | GAKFKTSAQHALTS VSRGSSLKILSKGKR G (SEQ ID NO: 270) | 1198.5 | 1199 |
| 109 | i4 | $C_{15}H_{31}C(O)-$ | 3994.644 | $NH_2$ | GAKFKTSAQHALTS VSRGSSLKILSKGKR GGHSSVST (SEQ ID NO: 263) | 999.7, 799.2 | 800.0, 1000.0 |
| 110 | i4 | $C_{15}H_{31}C(O)-$ | 3870.571 | $NH_2$ | GAKFKTSAQHALTS VSRGSSLKILSKGKR GGSCFH (SEQ ID NO: 368) | 775.1 | 774.7 |
| 111 | i4 | $C_{15}H_{31}C(O)-$ | 3338.987 | $NH_2$ | GAKFKTSAQHALTS VSRGSSLKILSKGKR G (SEQ ID NO: 270) | 835.8, 1114.0 | 1835.8, 1114.0 |
| 112 | i4 | $C_{15}H_{31}C(O)-$ | 3052.8 | $NH_2$ | GAKFKTSAQHALTS VSRGSSLKILSGGK (SEQ ID NO: 383) | 764.2, 1018.6 | 764.6, 1019.0 |
| 113 | i4 | $C_{15}H_{31}C(O)-$ | 2083.477 | $NH_2$ | GAKFKTSAQHALTS VSRG (SEQ ID NO: 282) | 695.5, 1042.8 | 695.0, 1042.0 |
| 114 | i4 | $C_{15}H_{31}C(O)-$ | 2940.526 | $NH_2$ | GAKFKTSAQHALTS VSRGSSLKILSK (SEQ ID NO: 274) | 736.1, 981.2 | 736.0, 982.0 |
| 115 | i4 | $C_{15}H_{31}C(O)-$ | 2498.961 | $NH_2$ | GAKFKTSAQHALTS VSRGSSLK (SEQ ID NO: 278) | 625.8, 834.0 | 626.0, 834.0 |
| 116 | i4 | $C_{15}H_{31}C(O)-$ | 1938.18 | $NH_2$ | GAKFKTSAQHALTS VR (SEQ ID NO: 384) | 646.7 | 647.3 |

Synthesis of Selected Compounds (SEQ ID NO: 253):
Compound No. 88 (Pal-SKLSHSKGHQKRKALKTTVIL-amide)

Compound 88 was synthesized as described above on Rink amide resin at 0.1 mmol scale. Amino acids were coupled sequentially as described above. Following deprotection of the Fmoc group on the N-terminal residue serine, the N-terminal amine was capped with palmitic acid (10 eq.), HBTU (10 eq.) and DIEA (10 eq.) as described above. The compound was cleaved from the resin by TFA containing MS, TIS, DDT, and water (82: 4.5:4.5:4.5:4.5; 10 mL), filtered through a coarse frit Buchner full, triturated with ether and the resulting precipitate collected by centrifugation. Crude peptide was taken up in minimum amount of DMSO and TFA and purified by RP-HPLC as described previously. Fractions with correct MW were pooled and lyophilized and analyzed for purity using Method A. The yield of representative lots is illustrated in the following table.

| Lot # | Yield (mg) |
|---|---|
| 1 | 4 |
| 2 | 2.7 |
| 3 | 6.9 |

Compound No. 90 (Pal-KLSHSKGHQKRKALKTTV-amide) (SEQ ID NO: 248):

Compound 90 was synthesized as described for Compound 88. The yield of representative lots is illustrated in the following table.

| Lot # | Yield (mg) |
|---|---|
| 1 | 8.6 |

Compound No. 38 (Pal-MGYQKKLRSMTDKYRL-amide) (SEQ ID NO: 82):

Compound No. 38 was synthesized as described for Compound 88. The yield of representative lots is illustrated in the following table.

| Lot # | Yield (mg) |
|---|---|
| 1 | 1.8 |
| 2 | 3.4 |
| 3 | 11.0 |

Compound No. 44 (Pal-KKLRSMTDKYRL-amide) (SEQ ID NO: 71):

Compound No. 44 was synthesized as described for Compound No. 88. The yield of representative lots is illustrated in the following table.

| Lot # | Yield (mg) |
|---|---|
| 1 | 7.9 |
| 2 | 7.3 |
| 3 | 9.7 |

Methods of Screening
Functional Assays

Functional assays suitable for use in detecting and characterizing GPCR signaling include Gene Reporter Assays and Calcium Flux assays, cAMP and kinase activation assays. Several suitable assays are described in detail below.

Gene Reporter Assays

Cells expressing the GPCR of interest can be transiently or stably transfected with a reporter gene plasmid construct containing an enhancer element which responds to activation of a second messenger signaling pathway or pathways, thereby controlling transcription of a cDNA encoding a detectable reporter protein. GPCR expression can be the result of endogenous expression on a cell line or cell type or the result of stable or transient transfection of DNA encoding the receptor of interest into a cell line by means commonly used in the art. Immortalized cell lines or primary cell cultures can be used.

If the activated pathway is stimulatory (e.g., Gs or Gq), agonist activity results in activation of transcription factors, in turn causing an increase in reporter gene transcription, detectable by an increase in reporter activity. To test for agonist or inverse agonist activity, cells expressing the GPCR and the reporter gene construct can be challenged by the test compound for a predetermined period of time (e.g., 2-12 hours, typically 4 hours). Cells can then be assessed for levels of reporter gene product. Inverse agonists will suppress levels of reporter to below basal levels in a dose dependent manner. To test for antagonist or inhibitory activity through a stimulatory pathway, cells expressing both the GPCR and the reporter gene construct can be activated by a receptor agonist to increase gene reporter product levels. Treatment with antagonists will counter the effect of agonist stimulation in a dose- and receptor-dependent manner.

To test for agonist activity on receptor signaling through an inhibitory pathway (e.g., Gi, which couples to CXCR4), cells can be treated with a systematic activator (e.g., forskolin) to increase levels of reporter gene product. Activation of Gi by treatment with receptor agonist will inhibit this expression by inhibiting adenylyl cyclase. To screen for antagonist activity, test compounds can be assessed for the ability to counter agonist inhibition of adenylyl cyclase, resulting in increase reporter transcription.

Alternatively, a plasmid construct expressing the promiscuous G-protein Ga16 can be used to obtain a positive signal from a GPCR which normally couples to an inhibitory G-protein. Co-expression of the chimeric G-protein Gaq/Gai5 (Coward et al. Analytical Biochemistry 270, 242-248 (1999)) allows coupling to Gi-coupled receptors and conversion of second messenger signaling from the inhibitory Gi pathway to the stimulatory Gq pathway. Agonist and antagonist assessment in these systems is the same as the stimulatory pathways. Well-to-well variation caused by such factors as transfection efficiency, unequal plating of cells, and cell survival rates can be normalized in transient transfection assays by co-transfecting a constitutively expressing reporter gene with a non-interfering signal independent of the regulated reporter.

Chemotaxis Assay

Chemotaxis assays were utilized to determine the effect of compound on the directed migration of cells in response to chemokine. Cells that express a receptor of interest were placed in the upper chamber of a Transwell chemotaxis plate (Corning) and allowed to migrate through a polycarbonate membrane to a lower chamber containing the appropriate receptor-specific ligand. To test for antagonist or potentiating activity, cells were mixed with the desired concentration of compound prior to addition to the upper chamber. Conversely, agonist activity was determined by adding compound in the bottom chamber only without endogenous chemokine. The effect of compound is quantified by several parameters, including the extent of maximum response, the shift of agonist dose-response curves, and the area under the curve.

To measure the CXCR4-dependent migration of cells, the appropriate concentration of CXCL12 (SDF1a) or test compound was diluted in phenol red-free RMPI-1640/20 mM HEPES/0.5% BSA buffer and placed in the bottom chamber of a transwell apparatus. CCRF-CEM cells, a human T-cell ALL line that endogenously expresses CXCR4, were washed twice in buffer and resuspended at 133,000 cells/ml. A 75 μl sample of this suspension is mixed with the test compound of interest and placed in the upper chamber of a 5-micron transwell apparatus.

To initiate cell migration, the assembled transwell plate was placed in a 37° C., 0.5% $CO_2$ incubator for a specified time interval, typically between 30 and 120 minutes. After incubation, the unit was disassembled and the lower chamber placed at −80° C. overnight to facilitate lysis of cells. To quantify migrated cells, plates were thawed at 37° C. in a humidified chamber, and then a sample volume was removed from each well and mixed with an equal volume of CyQuant (Invitrogen) working solution in opaque plates. The fluorescence intensity of each well represents the DNA content and is directly proportional to cell number. Each sample was typically run in duplicate or triplicate and each plate included two separate negative controls. The plate background control, which included no cells in the upper chamber, was subtracted from all values. The negative control had no agonist added in the lower chamber, and served to establish the baseline for random migration. A similar procedure was followed for chemotaxis using SUP B-15 cells.

Calcium Flux Assay

Calcium Flux Assay is one of the most popular cell-based GPCR functional assays. It most often uses calcium sensing fluorescent dyes such as fura2 AM, fluo-4 and Calcium-4 to measure changes in intracellular calcium concentration. It is used mainly to detect GPCR signaling via Gaq subunit. Activation of these Gq-coupled GPCRs leads to activation of phospholipase C, which subsequently leads to increase in inositol phosphate production. IP3 receptors on endoplasmic reticulum sense the change then release calcium into cytoplasm. Intracellular calcium binding to the fluorescent dyes can be detected by instruments that quantify fluorescent intensities, such as FLIPR Tetra, Flexstation (MDS) and FDSS (Hamamatsu). In additional to assess Gq-couple receptor signaling, calcium flux assay can also be used to study Gs and Gi couple receptors by co-expressing CNG (cyclic nucleotide gated calcium channel) or chimeric G-proteins (Gqi5, Gsi5 for example). Activation of some Gi-coupled receptors can also be detected by calcium flux assay via Gβγ mediated phospholipase C activation.

CXCR4 Testing

The calcium flux assay was used to assess SDF-1α activation of CXCR4 in CCRF-CEM cells (human T lymphoblasts from acute lymphoblastic leukemia). CCRF-CEM cells were seeded into 96-well black plates with clear bottom at 200K/well in RPMI 1640 media with 20 mM HEPES containing 0.2% BSA. After dye loading by incubating with Calcium-4 dye at 37° C. for 1 hour, cell plates were read at 37° C. using the Flexstation 3 workstation. The addition of test compounds or reference antagonists was accomplished either by manual pipetting or by liquid handling using the Flexstation. The latter allows the assessment of intrinsic agonist activity of the test compounds by measuring initial changes in fluorescent intensity. After incubation of 24 minutes at 37° C., SDF-1α was added and receptor activation was assessed by measuring changes in fluorescent intensity using the Flexstation.

Representative Results

| | | | CXCR4 i1 loop compound Calcium Flux Data | | | |
|---|---|---|---|---|---|---|
| Comp. # | Loop | N-terminus | Sequence | C-terminus | MW | IC50 (nM) |
| 38 | i1 | Pal | MGYQKKLRSMTDKYRL (SEQ ID NO: 82) | Amide | 2255.831 | 98 |
| 129 | i1 | Pal | AGYQKKLRSMTDKYRL (SEQ ID NO: 101) | Amide | 2195.712 | 197 |
| 130 | i1 | Pal | MAYQKKLRSMTDKYRL (SEQ ID NO: 102) | Amide | 2269.857 | 125 |
| 131 | i1 | Pal | MGAQKKLRSMTDKYRL (SEQ ID NO: 103) | Amide | 2163.735 | 147 |
| 132 | i1 | Pal | MGYAKKLRSMTDKYRL (SEQ ID NO: 104) | Amide | 2198.779 | 213 |
| 133 | i1 | Pal | MGYQAKLRSMTDKYRL (SEQ ID NO: 105) | Amide | 2198.736 | 200 |
| 134 | i1 | Pal | MGYQKALRSMTDKYRL (SEQ ID NO: 106) | Amide | 2198.736 | 250 |
| 135 | i1 | Pal | MGYQKKLRSMTDKYRL (SEQ ID NO: 107) | Amide | 2213.751 | 175 |
| 136 | i1 | Pal | MGYQKKLRSMTDKYRL (SEQ ID NO: 108) | Amide | 2170.723 | 302 |
| 146 | i1 | Pal | MGYQKKLRAMTDKYRL (SEQ ID NO: 116) | Amide | 2239.831 | 170 |
| 147 | i1 | Pal | MGYQKKLRSATDKYRL (SEQ ID NO: 117) | Amide | 2195.712 | 54 |
| 148 | i1 | Pal | MGYQKKLRSMADKYRL (SEQ ID NO: 118) | Amide | 2225.805 | 298 |
| 149 | i1 | Pal | MGYQKKLRSMTAKYRL (SEQ ID NO: 119) | Amide | 2211.821 | 126 |
| 150 | i1 | Pal | MGYQKKLRSMTDAYRL (SEQ ID NO: 120) | Amide | 2198.736 | 313 |
| 151 | i1 | Pal | MGYQKKLRSMTDKARL (SEQ ID NO: 121) | Amide | 2163.735 | >10000 |
| 152 | i1 | Pal | MGYQKKLRSMTDKYAL (SEQ ID NO: 122) | Amide | 2170.723 | >10000 |
| 153 | i1 | Pal | MGYQKKLRSMTDKYRA (SEQ ID NO: 123) | Amide | 2213.751 | >10000 |
| 159 | i1 | Pal | MGYQKKLRSMTDKYRL (SEQ ID NO: 831) | Amide | 2255.831 | >10000 |
| 160 | i1 | Pal | MGYQKKLRSMTDKYrL (SEQ ID NO: 129) | Amide | 2255.831 | 5731 |
| 161 | i1 | Pal | MGYQKKLRSMTDKyRL (SEQ ID NO: 130) | Amide | 2255.831 | >10000 |

-continued

| | | | | | | | |
|---|---|---|---|---|---|---|---|
| | | N- | | C- | | | |
| Comp. # | Loop | terminus | Sequence | terminus | MW | IC50 (nM) | |

CXCR4 i1 loop compound Calcium Flux Data

| Comp. # | Loop | N-terminus | Sequence | C-terminus | MW | IC50 (nM) |
|---|---|---|---|---|---|---|
| 162 | i1 | Pal | MGYQKKLRSMTDkYRL (SEQ ID NO: 131) | Amide | 2255.831 | 291 |
| 163 | i1 | Pal | MGYQKKLRSMTdKYRL (SEQ ID NO: 132) | Amide | 2255.831 | 623 |
| 164 | i1 | Pal | MGYQKKLRSMtDKYRL (SEQ ID NO: 133) | Amide | 2255.831 | 322 |
| 165 | i1 | Pal | mGYQKKLRSMTDKYRL (SEQ ID NO: 134) | Amide | 2255.831 | 112 |
| 166 | i1 | Pal | MGyQKKLRSMTDKYRL (SEQ ID NO: 135) | Amide | 2255.831 | 129 |
| 167 | i1 | Pal | MGYqKKLRSMTDKYRL (SEQ ID NO: 136) | Amide | 2255.831 | 116 |
| 168 | i1 | Pal | MGYQkKLRSMTDKYRL (SEQ ID NO: 137) | Amide | 2255.831 | 119 |
| 169 | i1 | Pal | MGYQKkLRSMTDKYRL (SEQ ID NO: 138) | Amide | 2255.831 | 88 |
| 170 | i1 | Pal | MGYQKKlRSMTDKYRL (SEQ ID NO: 139) | Amide | 2255.831 | 72 |
| 171 | i1 | Pal | MGYQKKLrSMTDKYRL (SEQ ID NO: 140) | Amide | 2255.831 | 72 |
| 172 | i1 | Pal | MGYQKKLRsMTDKYRL (SEQ ID NO: 141) | Amide | 2255.831 | 90 |
| 173 | i1 | Pal | MGYQKKLRSmTDKYRL (SEQ ID NO: 142) | Amide | 2255.831 | 97 |

Results

Representative results from the following tables are provided in FIGS. 1-4.

TABLE 18

CXCR4 i1 loop CHTX data
CEM and Sup-B-15 cells

| Comp. # | Sequence | Drug Conc | Cell Type | AUC (% of) | Max (% of) | Peak Test Comp. (nM) | Peak Control (nM) | Peak Ratio |
|---|---|---|---|---|---|---|---|---|
| 33 | MGYQKKLRSMTD (SEQ ID NO: 376) | 1.0 uM | CEM | 68.9 | 68.09 | 1 | 1 | 1 |
| 33 | MGYQKKLRSMTD (SEQ ID NO: 376) | 1.0 uM | CEM | 54.81 | 76.06 | 0.2 | 0.2 | 1 |
| 35 | VMGYQKKLRSMTD (SEQ ID NO: 86) | 1.0 uM | SUP B-15 | 31.7 | 49.27 | 1 | 5 | 0.2 |
| 35 | VMGYQKKLRSMTD (SEQ ID NO: 86) | 1.0 uM | CEM | 57.9 | 56.97 | 5 | 5 | 1 |
| 36 | MGYQKKLRSMTDK (SEQ ID NO: 79) | 1.0 uM | SUP B15 | 49.94 | 54.8 | 1 | 5 | 0.2 |
| 36 | MGYQKKLRSMTDK (SEQ ID NO: 79) | 1.0 uM | CEM | 101.76 | 119.07 | 0.2 | 1 | 0.2 |

TABLE 18-continued

CXCR4 i1 loop CHTX data
CEM and Sup-B-15 cells

| Comp. # | Sequence | Drug Conc | Cell Type | AUC (% of) | Max (% of) | Peak Test Comp. (nM) | Peak Control (nM) | Peak Ratio |
|---|---|---|---|---|---|---|---|---|
| 37 | MGYQKKLRSMTDKY (SEQ ID NO: 80) | 1.0 uM | SUP B-15 | 63.52 | 91.09 | 1 | 5 | 0.2 |
| 37 | MGYQKKLRSMTDKY (SEQ ID NO: 80) | 1.0 uM | CEM | 92.31 | 97.85 | 1 | 25 | 0.04 |
| 38 | MGYQKKLRSMTDKYRL (SEQ ID NO: 82) | 1.0 uM | SUP B-15 | 32.38 | 49.56 | 1 | 5 | 0.2 |
| 38 | MGYQKKLRSMTDKYRL (SEQ ID NO: 82) | 1.0 uM | CEM | 75.53 | 106.96 | 5 | 25 | 0.2 |
| 38 | MGYQKKLRSMTDKYRL (SEQ ID NO: 82) | 1.0 uM | CEM | 46.27 | 71.48 | 0.2 | 1 | 0.2 |
| 39 | MGYQKKLRSMTDKYRLHL (SEQ ID NO: 83) | 1.0 uM | SUP B-15 | 47.43 | 37.65 | 5 | 25 | 0.2 |
| 39 | MGYQKKLRSMTDKYRLHL (SEQ ID NO: 83) | 1.0 uM | CEM | 37.55 | 59.71 | 1 | 25 | 0.04 |
| 40 | YQKKLRSMTDKYRLHLSV (SEQ ID NO: 77) | 1.0 uM | SUP B-15 | 71.92 | 71.22 | 5 | 25 | 0.2 |
| 41 | KKLRSMTDKYRLHLSV (SEQ ID NO: 74) | 1.0 uM | SUP B-15 | 51.69 | 41.71 | 1 | 25 | 0.04 |
| 41 | KKLRSMTDKYRLHLSV (SEQ ID NO: 74) | 1.0 uM | CEM | 66.71 | 76.8 | 0.2 | 25 | 0.01 |
| 42 | KKLRSMTDKYRYRLHL (SEQ ID NO: 73) | 1.0 uM | SUP B-15 | 43.82 | 33.47 | 5 | 25 | 0.2 |
| 46 | KKLRSMTDKYRLHL (SEQ ID NO: 73) | 1.0 uM | CEM | 69.74 | 115.97 | 0.2 | 25 | 0.01 |
| 43 | KKLRSMTDKYRLH (SEQ ID NO: 42) | 1.0 uM | SUP B-15 | 70.8 | 55.84 | 1 | 25 | 0.04 |
| 43 | KKLRSMTDKYRLH (SEQ ID NO: 42) | 1.0 uM | CEM | 32.08 | 77.15 | 0.2 | 1 | 0.2 |
| 43 | KKLRSMTDKYRLH (SEQ ID NO: 42) | 3.0 uM | CEM | 79.43 | 76.32 | 0.2 | 0.2 | 0.2 |
| 43 | KKLRSMTDKYRLH (SEQ ID NO: 42) | 1.0 uM | CEM | 84.82 | 66.81 | 0 | 0 | 0.04 |
| 43 | KKLRSMTDKYRLH (SEQ ID NO: 42) | 0.3 uM | CEM | 92.91 | 80.68 | 0 | 0 | 0.04 |
| 43 | KKLRSMTDKYRLH (SEQ ID NO: 42) | 0.1 uM | CEM | 113.68 | 96.86 | 0.2 | 0.2 | 0.2 |
| 43 | KKLRSMTDKYRLH (SEQ ID NO: 42) | 0.03 uM | CEM | 101.82 | 91.16 | 0.8 | 0.8 | 1 |
| 43 | KKLRSMTDKYRLH (SEQ ID NO: 42) | 0.01 uM | CEM | 98.09 | 93.17 | 0.8 | 0.8 | 1 |
| 43 | KKLRSMTDKYRLH (SEQ ID NO: 42) | 3.0 uM | CEM | 79.17 | 72.73 | 0 | 0.2 | 0.2 |

TABLE 18-continued

CXCR4 i1 loop CHTX data
CEM and Sup-B-15 cells

| Comp. # | Sequence | Drug Conc | Cell Type | AUC (% of) | Max (% of) | Peak Test Comp. (nM) | Peak Control (nM) | Peak Ratio |
|---|---|---|---|---|---|---|---|---|
| 43 | KKLRSMTDKYRLH (SEQ ID NO: 42) | 1.0 uM | CEM | 85.24 | 78.94 | 0 | 0 | 0.04 |
| 43 | KKLRSMTDKYRLH (SEQ ID NO: 42) | 0.3 uM | CEM | 97.93 | 84.51 | 0 | 0 | 0.04 |
| 43 | KKLRSMTDKYRLH (SEQ ID NO: 42) | 0.1 uM | CEM | 108.05 | 93.58 | 0 | 0.2 | 0.2 |
| 43 | KKLRSMTDKYRLH (SEQ ID NO: 42) | 0.03 uM | CEM | 109.76 | 92.65 | 0.8 | 0.8 | 1 |
| 43 | KKLRSMTDKYRLH (SEQ ID NO: 42) | 0.01 uM | CEM | 109.93 | 114.2 | 0.8 | 0.8 | 1 |
| 44 | KKLRSMTDKYRL (SEQ ID NO: 71) | 1.0 uM | SUP B-15 | 25.94 | 31.52 | 1 | 5 | 0.2 |
| 44 | KKLRSMTDKYRL (SEQ ID NO: 71) | 1.0 uM | CEM | 15.86 | 54.8 | 0.2 | 1 | 0.2 |
| 44 | KKLRSMTDKYRL (SEQ ID NO: 71) | 1.0 uM | CEM | 92.31 | 97.85 | 1 | 25 | 0.04 |
| 45 | KKLRSMTDKYR (SEQ ID NO: 70) | 1.0 uM | SUP B-15 | 178.4 | 193.55 | 5 | 5 | 1 |
| 46 | KKLRSMTDKY (SEQ ID NO: 69) | 1.0 uM | SUP B-15 | 87.24 | 82.87 | 1 | 5 | 0.2 |
| 48 | MGYQKKLRSMTDKYRI (SEQ ID NO: 81) | 1.0 uM | CEM | 53.03 | 53.48 | 25 | 5 | 5 |
| 49 | MGYQKKLRSMTDKYRI (SEQ ID NO: 81) | 1.0 uM | CEM | 50.9 | 62.66 | 1 | 5 | 0.2 |
| 50 | SGYQKKLRSSTD (SEQ ID NO: 1) | 1.0 uM | CEM | 102.07 | 121.17 | 0.2 | 1 | 0.2 |
| 50 | SGYQKKLRSSTD (SEQ ID NO: 1) | 1.0 uM | CEM | 52.16 | 59.19 | 1 | 0.2 | 5 |
| 52 | QKKLRSMTDKYRI (SEQ ID NO: 75) | 1.0 uM | CEM | 111.49 | 97.78 | 1 | 5 | 0.2 |
| 52 | QKKLRSMTDKYRI (SEQ ID NO: 75) | 1.0 uM | CEM | 76.62 | 92.8 | 0.2 | 1 | 0.2 |
| 52 | QKKLRSMTDKYRI (SEQ ID NO: 75) | 1.0 uM | CEM | 45.5 | 63.35 | 0.2 | 0.2 | 1 |
| 53 | MGYQKKLRSMTDKYRLHL (SEQ ID NO: 83) | 1.0 uM | CEM | 60.98 | 68.45 | 1 | 0.2 | 5 |
| 53 | MGYQKKLRSMTDKYRLHL (SEQ ID NO: 83) | 1.0 uM | CEM | 91.1 | 89.56 | 1 | 1 | 1 |
| 54 | MGYQKKLRSMTDKYRLHL (SEQ ID NO: 83) | 1.0 uM | CEM | 83.08 | 77.31 | 1 | 1 | 1 |
| 54 | MGYQKKLRSMTDKYRLHL (SEQ ID NO: 83) | 1.0 uM | CEM | 110.43 | 114.34 | 1 | 1 | 1 |

TABLE 18-continued

CXCR4 i1 loop CHTX data
CEM and Sup-B-15 cells

| Comp. # | Sequence | Drug Conc | Cell Type | AUC (% of) | Max (% of) | Peak Test Comp. (nM) | Peak Control (nM) | Peak Ratio |
|---|---|---|---|---|---|---|---|---|
| 55 | MGYQKKLRSM TDKYRLHLSV (SEQ ID NO: 84) | 1.0 uM | CEM | 18.58 | 39.83 | 0.2 | 1 | 0.2 |
| 55 | MGYQKKLRSM TDKYRLHLSV (SEQ ID NO: 84) | 1.0 uM | CEM | 43.3 | 72.73 | 0.2 | 1 | 0.2 |
| 56 | MGYQKKLRSM TDKYRLHLSV (SEQ ID NO: 84) | 1.0 um | CEM | 33.7 | 31.5 | 0.2 | 1 | 0.2 |
| 56 | MGYQKKLRSM TDKYRLHLSV (SEQ ID NO: 84) | 1.0 um | CEM | 64.22 | 70.2 | 1 | 1 | 1 |
| 59 | MGYQKKLRSM TDK (SEQ ID NO: 79) | 1.0 um | CEM | 51.62 | 59.79 | 1 | 1 | 1 |
| 59 | MGYQKKLRSM TDK (SEQ ID NO: 79) | 1.0 uM | CEM | 68.96 | 84.52 | 1 | 1 | 1 |
| 69 | SGYQKKLRSST D (SEQ ID NO: 1) | 1.0 uM | CEM | 100 | 93.13 | 25 | 25 | 1 |

TABLE 19

CXCR4 i2 loop Chemotaxis data
SUPB-15 cells

| Comp. # | Sequence | Conc | AUC (% of vehicle) | Max (% of vehicle) | Peak Test Comp. (nM) | Peak Control (nM) | Peak Ratio |
|---|---|---|---|---|---|---|---|
| 83 | HATNSQRPRK LLAEKV (SEQ ID NO: 199) | 1.0 uM | 126.36 | 110.06 | 5 | 5 | 1 |
| 82 | HATNSQRPRK LLAEK (SEQ ID NO: 171) | 1.0 uM | 124.56 | 126.31 | 1 | 5 | 0.2 |
| 81 | HATNSQRPRK LLAE (SEQ ID NO: 198) | 1.0 uM | 79.85 | 76.46 | 5 | 25 | 0.2 |
| 80 | HATNSQRPRK LLA (SEQ ID NO: 197) | 1.0 uM | 102.2 | 69.02 | 5 | 25 | 0.2 |
| 79 | HATNSQRPRK L (SEQ ID NO: 196) | 1.0 uM | 109.36 | 109.68 | 5 | 25 | 0.2 |
| 78 | VHATNSQRPR KLLA (SEQ ID NO: 195) | 1.0 uM | 71.85 | 72.31 | 5 | 25 | 0.2 |
| 77 | DRYLAIVHAT NSQRPRKLL (SEQ ID NO: 152) | 1.0 uM | 42.24 | 56.21 | 0.2 | 1 | 0.2 |
| 77 | DRYLAIVHAT NSQRPRKLL (SEQ ID NO: 152) | 1.0 uM | 31.64 | 55.59 | 0.2 | 0.2 | 1 |
| 76 | DRYLAIVHAT NSQRPRKLL (SEQ ID NO: 152) | 1.0 uM | 52.16 | 54.04 | 0.2 | 0.2 | 1 |

TABLE 19-continued

CXCR4 i2 loop Chemotaxis data
SUPB-15 cells

| Comp. # | Sequence | Conc | AUC (% of vehicle) | Max (% of vehicle) | Peak Test Comp. (nM) | Peak Control (nM) | Peak Ratio |
|---|---|---|---|---|---|---|---|
| 76 | DRYLAIVHAT NSQRPRKLL (SEQ ID NO: 152) | 1.0 uM | 8.95 | 9.03 | 1 | 1 | 1 |
| 75 | VHATNSQRPR KLLAEKVVY (SEQ ID NO: 194) | 1.0 uM | 46.73 | 52.32 | 1 | 0.2 | 5 |
| 75 | VHATNSQRPR KLLAEKVVY (SEQ ID NO: 194) | 1.0 uM | 47.91 | 64.15 | 0.2 | 1 | 0.2 |
| 74 | DRYLAIVHAT NSQRPRKLL (SEQ ID NO: 152) | 1.0 uM | 90.39 | 91.29 | 5 | 5 | 1 |
| 74 | DRYLAIVHAT NSQRPRKLL (SEQ ID NO: 152) | 1.0 uM | 77.13 | 75.81 | 5 | 1 | 5 |

TABLE 20

CXCR4 i3 loop Chemotaxis data
CEM cells

| Comp. # | Sequence | Conc | AUC (% of vehicle) | Max (% of vehicle) | Peak Test Compound (nM) | Peak Control (nM) | Peak Ratio |
|---|---|---|---|---|---|---|---|
| 87 | HSKGHQKR KQALK (SEQ ID NO: 244) | 1.0 uM | 52.64 | 76.1 | 0.2 | 1 | 0.2 |
| 88 | SKLSHSKGH QKRKALKT TVIL (SEQ ID NO: 253) | 3.0 uM | 116.49 | 114.49 | 0.8 | 0.8 | 1 |
| 88 | SKLSHSKGH QKRKALKT TVIL (SEQ ID NO: 253) | 1.0 uM | 143.61 | 131.59 | 0.8 | 0.8 | 1 |
| 88 | SKLSHSKGH QKRKALKT TVIL (SEQ ID NO: 253) | 0.3 uM | 131.2 | 113.68 | 0.2 | 0.8 | 0.2 |
| 88 | SKLSHSKGH QKRKALKT TVIL (SEQ ID NO: 253) | 0.1 uM | 183.19 | 157.79 | 0.03 | 0.8 | 0.04 |
| 88 | SKLSHSKGH QKRKALKT TVIL (SEQ ID NO: 253) | 0.03 uM | 226.59 | 202.16 | 0.03 | 0.8 | 0.04 |
| 88 | SKLSHSKGH QKRKALKT TVIL (SEQ ID NO: 253) | 0.01 uM | 172.33 | 156.08 | 0.03 | 0.8 | 0.04 |
| 89 | KLSHSKGHQ KRKALKTT VIL (SEQ ID NO: 249) | 1.0 uM | 37.55 | 59.71 | 1 | 25 | 0.04 |

TABLE 20-continued

CXCR4 i3 loop Chemotaxis data CEM cells

| Comp. # | Sequence | Conc | AUC (% of vehicle) | Max (% of vehicle) | Peak Test Compound (nM) | Peak Control (nM) | Peak Ratio |
|---|---|---|---|---|---|---|---|
| 90 | KLSHSKGHQ KRKALKTT V (SEQ ID NO: 248) | 3.0 uM | 152.75 | 114.49 | 0.16 | 0.16 | 1 |
| 90 | KLSHSKGHQ KRKALKTT V (SEQ ID NO: 248) | 1.0 uM | 153.95 | 131.59 | 0.16 | 0.16 | 1 |
| 90 | KLSHSKGHQ KRKALKTT V (SEQ ID NO: 248) | 0.3 uM | 129.83 | 113.68 | 0.16 | 0.16 | 1 |
| 90 | KLSHSKGHQ KRKALKTT V (SEQ ID NO: 248) | 0.1 uM | 175.95 | 157.79 | 0.03 | 0.16 | 0.2 |
| 90 | KLSHSKGHQ KRKALKTT V (SEQ ID NO: 248) | 0.03 uM | 217.53 | 202.16 | 0.16 | 0.16 | 1 |
| 90 | KLSHSKGHQ KRKALKTT V (SEQ ID NO: 248) | 0.01 uM | 171.8 | 156.08 | 0.16 | 0.16 | 1 |
| 90 | KLSHSKGHQ KRKALKTT V (SEQ ID NO: 248) | 1.0 uM | 66.71 | 76.8 | 0.2 | 25 | 0.01 |
| 92 | KLSHSKGHQ KRKALK (SEQ ID NO: 247) | 3.0 uM | 183.65 | 175.7 | 0.8 | 0.8 | 1 |
| 92 | KLSHSKGHQ KRKALK (SEQ ID NO: 247) | 1.0 uM | 196.33 | 163.91 | 0.16 | 0.8 | 0.2 |
| 92 | KLSHSKGHQ KRKALK (SEQ ID NO: 247) | 0.3 uM | 179.77 | 165.35 | 0.16 | 0.8 | 0.2 |
| 92 | KLSHSKGHQ KRKALK (SEQ ID NO: 247) | 0.1 uM | 173.69 | 169.49 | 0.16 | 0.8 | 0.2 |
| 92 | KLSHSKGHQ KRKALK (SEQ ID NO: 247) | 0.03 uM | 200.49 | 198.29 | 0.16 | 0.8 | 0.2 |
| 92 | KLSHSKGHQ KRKALK (SEQ ID NO: 247) | 0.01 uM | 157.79 | 155.72 | 0.16 | 0.8 | 0.2 |
| 92 | KLSHSKGHQ KRKALK (SEQ ID NO: 247) | 1.0 uM | 32.08 | 77.15 | 0.2 | 1 | 0.2 |
| 93 | KLSHSKGHQ KRKAL (SEQ ID NO: 246) | 1.0 uM | 15.86 | 54.8 | 0.2 | 1 | 0.2 |
| 94 | KLSHSKGHQ KRKA (SEQ ID NO: 245) | 1.0 uM | 65.28 | 80.48 | 1 | 1 | 1 |

TABLE 20-continued

CXCR4 i3 loop Chemotaxis data
CEM cells

| Comp. # | Sequence | Conc | AUC (% of vehicle) | Max (% of vehicle) | Peak Test Compound (nM) | Peak Control (nM) | Peak Ratio |
|---|---|---|---|---|---|---|---|
| 95 | LSHSKGHQK RKALK (SEQ ID NO: 250) | 1.0 uM | 77.47 | 92.11 | 1 | 1 | 1 |
| 96 | SHSKGHQK RKALK (SEQ ID NO: 251) | 1.0 uM | 34.22 | 63.12 | 1 | 1 | 1 |
| 97 | HSKGHQKR KALKT (SEQ ID NO: 222) | 1.0 uM | 48.9 | 54.67 | 1 | 5 | 0.2 |
| 99 | HSKGHQKR KALKTTV (SEQ ID NO: 242) | 1.0 uM | 44.95 | 64.52 | 0.2 | 1 | 0.2 |
| 100 | HSKGHQKR KALKKTTVI (SEQ ID NO: 243) | 1.0 uM | 49.31 | 49.84 | 0.2 | 5 | 0.04 |
| 101 | SKLSHSKGH QKRKALK (SEQ ID NO: 252) | 1.0 uM | 75.55 | 74.92 | 1 | 1 | 1 |
| 102 | IIISKLSHSK GHQKRKAL KT (SEQ ID NO: 202) | 1.0 um | 0 | 0.24 |  | 1 |  |
| 103 | IIISKLSHSK GHQKRKAL KT (SEQ ID NO: 202) | 1.0 uM | 26.32 | 24.45 | 1 | 1 | 1 |
| 104 | IIISKLSHSK GHQKRKAL KT (SEQ ID NO: 202) | 1.0 uM | 36.4 | 56.39 | 0.2 | 1 | 0.2 |
| 105 | KLSHSKGHQ KRKALKTT VIL (SEQ ID NO: 249) | 1.0 uM | 23.79 | 42.91 | 0.2 | 1 | 0.2 |

TABLE 21

CXCR4 i4 Loop CHTX data
CEM cells

| Cmpd # | Sequence | Conc | AUC (% of Vehicle) | Max (% of Vehicle) | Peak Test Comp. (nM) | Peak Control (nM) | Peak Ratio |
|---|---|---|---|---|---|---|---|
| 116 | GAKFKTSAQH ALTSVR (SEQ ID NO: 384) | 1.0 uM | 65.28 | 80.48 | 1 | 1 | 1 |
| 115 | GAKFKTSAQH ALTSVSRGSSL K (SEQ ID NO: 278) | 1.0 uM | 77.47 | 92.11 | 1 | 1 | 1 |
| 114 | GAKFKTSAQH ALTSVSRGSSL KILSK (SEQ ID NO: 274) | 1.0 uM | 34.22 | 63.12 | 1 | 1 | 1 |
| 112 | GAKFKTSAQH ALTSVSRGSSL | 1.0 uM | 48.9 | 54.67 | 1 | 5 | 0.2 |

TABLE 21-continued

CXCR4 i4 Loop CHTX data CEM cells

| Cmpd # | Sequence | Conc | AUC (% of Vehicle) | Max (% of Vehicle) | Peak Test Comp. (nM) | Peak Control (nM) | Peak Ratio |
|---|---|---|---|---|---|---|---|
| | KILSGGK (SEQ ID NO: 383) | | | | | | |
| 110 | GAKFKTSAQH ALTSVSRGSSL KILSKGKRGG SCFH (SEQ ID NO: 368) | 1.0 uM | 40.98 | 42.08 | 5 | 5 | 1 |
| 109 | GAKFKTSAQH ALTSVSRGSSL KILSKGKRGG HSSVST (SEQ ID NO: 263) | 1.0 uM | 49.31 | 49.84 | 0.2 | 5 | 0.04 |
| 108 | GAKFKTSAQH ALTSVSRGSSL KILSKGKRG (SEQ ID NO: 270) | 1.0 uM | 89.47 | 83.94 | 25 | 5 | 5 |
| 108 | GAKFKTSAQH ALTSVSRGSSL KILSKGKRG (SEQ ID NO: 270) | 1.0 uM | 89.47 | 83.94 | 25 | 5 | 5 |
| 107 | GAKFKTSAQH ALTSVSRGSSL KILSKGKRGG HSSVST (SEQ ID NO: 263) | 1.0 uM | 57.34 | 49.48 | 25 | 5 | 5 |

Compounds with varying biological activities at the CXCR4 receptor have been identified. These include positive allosteric modulating activity, negative allosteric modulating activity, and allosteric agonists. Compounds exhibiting negative allosteric modulating activity at the CXCR4 receptor are evidenced by their ability to inhibit chemoattraction in response to SDF1-a induced chemoattraction. Compound receptor modulators are capable of modifying CXCR4 dependent activity in several characteristic patterns. In FIGS. 1-4, these activities are present.

One such phenotype is left- or right-shifting of the SDF1-a dependent chemotactic response. An example of this response is shown by Compound 43. In this case, 1 uM of Compound 43 induces a left shift of the SDF1-a mediated chemotactic response.

Another phenotype is positive allosteric modulation of the SDF1-a dependent chemotactic response. An example of this response is shown with Compound No. 44. In this case, 30 nM of Compound 88 induces a positive SDF1-a mediated chemotactic response (i.e., the larger RFU response indicates that a greater number of cells migrate toward SDF1a in the presence of Compound 44).

In another example, Compound 44 negatively modulates the SDF1-a induced chemotactic response in CEM cells as evidenced by the lower raw relative fluorescent units (RFU) which reflects the number of cells migrating toward an SDF1a gradient. The lower RFU response, the fewer migrating cells.

Figure 5:
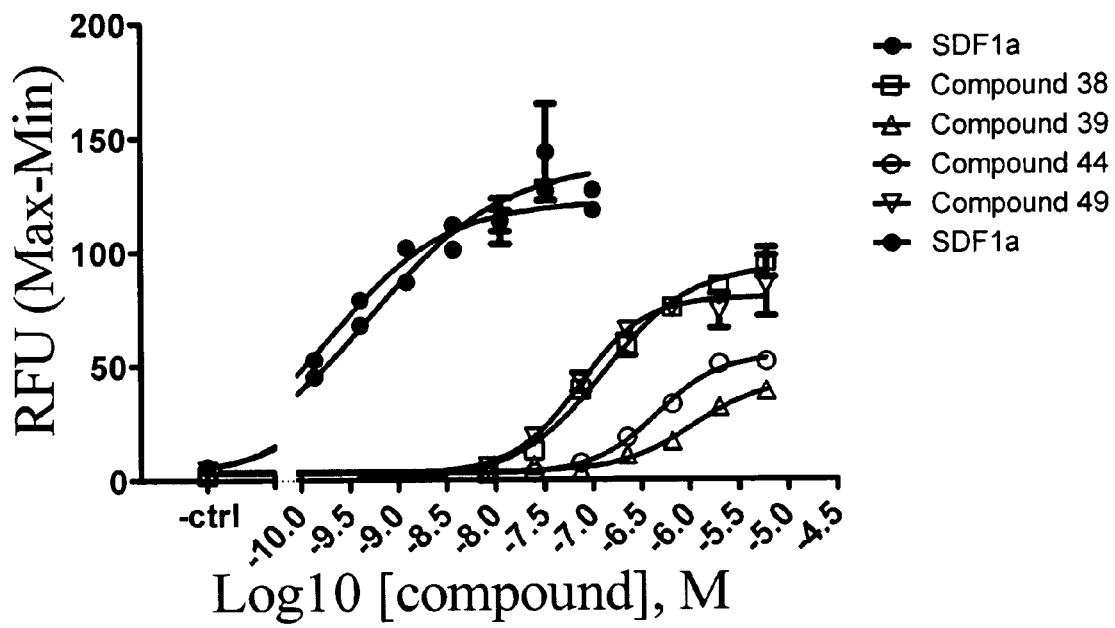
FIG. 5 is a graphical representation of SDF1-a dependent calcium mobilization in CEM cells upon testing with compounds of the invention.
Figure 6:
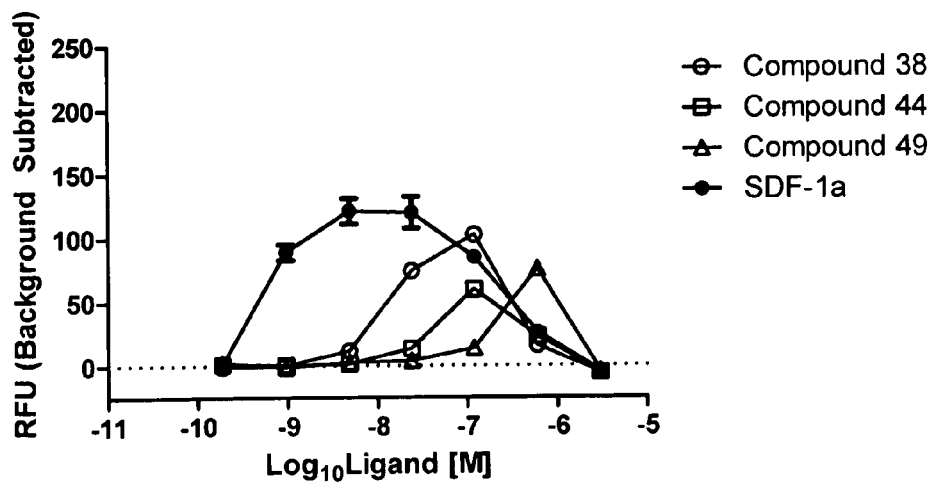
FIG. 6 is a graphical representation of agonist activity of compounds of the invention in a CEM chemotaxis assay.

Compounds with allosteric agonist activity are evidenced by their ability to induce CXCR4 dependent calcium mobilization (FIG. 5) and/or chemoattraction of leukocytes expressing CXCR4 (FIG. 6). Like the endogenous agonist SDF1-a activity, these CXCR4 agonists exhibit a bell-shaped activity curve with respect to chemoattraction.

HTRF cAMP Assay and IP-One Assay (Cisbio)

HTRF (homogeneous time resolved fluorescence) is a technology developed by Cisbio Bioassays based on TR-FRET (time-resolved fluorescence resonance energy transfer). Cisbio Bioassays has developed a wide selection of HTRF-based assays compatible with whole cells, thereby enabling functional assays run under more physiological conditions. cAMP kits are based on a competitive immunoassay using cryptate-labeled anti-cAMP antibody and d2-labeled cAMP. This assay allows the measurement of increase in intracellular cAMP upon Gs-coupled receptor activation as well as decrease in forskolin stimulated increase in cAMP upon Gi-coupled receptor activation. The IP-One assays are competitive immunoassays that use cryptate-labeled anti-IP 1 monoclonal antibody and d2-labeled IP1. IP1 is a relatively stable downstream metabolite of IP3, and accumulates in cells following Gq receptor activation.

AlphaScreen Cellular Kinase Assays.

GPCR activation results in modulation of downstream kinase systems and is often used to probe GPCR function and regulation. TGR Bioscience and PerkinElmer have developed Surefire cellular kinase assay kits that are HTS capable and useful in screening kinase regulation. Such kits enable the monitoring of Gi regulated downstream kinases like ERK1/2. The assay allows the measurement of increases in ERK1/2 kinase phosphorylation upon Gi coupled receptor (e.g., CXCR4) activation and this signal in turn can be used to assay Gi coupled receptor modulator. Similar kits are also available to assay other pathway dependent signaling kinases such as MAP and BAD.

In Vivo Assays

Animal models are currently available for in vivo validation of novel therapeutics targeting the CXCR4/SDF-1 signaling axis include the mouse air pouch WBCs recruitment model, the PMN mobilization model, the HPCs mobilization model and BM transplantation models including NOD/SCID mice repopulation model.

In the mouse air pouch WBCs recruitment model, the air pouch is formed by 2 subcutaneous injections (on day 0 and day 3) of 3 ml of sterile air. On day 6 mice receive an injection of 1 ml of SDF-1 solution into the formed air pouch. Six or 24 hours later WBCs recruited to the air pouch are recovered and WBCs subsets are analyzed using differential cell count and Flow Cytometry. In this model the concentration of SDF-1 in air pouch is controlled by an investigator.

The other animal models that are widely used for the in vivo validation of novel CXCR4 antagonists are PMNs mobilization model and hematopoietic progenitor's cells (HPCs) mobilization models. These two models are very similar and they exploit the fact that bone marrow niche express high level of SDF-1. Bone marrow SDF-1 interacts with the CXCR4 on bone marrow cells and constitutively activates it. This SDF-1/CXCR4 interaction is critical for the retention of HPCs and immature PMNs within the bone marrow. Disruption of this interaction causes release of PMNs and HPCs into peripheral blood where they can be readily detected and counted using differential cell counter (for PMNs), Flow Cytometry and colony forming units assay (for HPCs). In contrast to the air pouch model, in this model the concentration of SDF-1 is physiological. In addition, PMNs/HPCs mobilization models do not require preliminary preparation of animals for actual experiment as is the case in air pouch WBCs recruitment model.

Bone marrow transplantation models allow assessing long term engraftment potential of mobilized into peripheral blood hematopoietic stem cells (HSCs). The donor cells can be of either mouse or human origin like in the NOD/SCID mice repopulation model. In long term repopulation model dilutions of donor blood cells compete with the recipient marrow cells for engraftment in lethally irradiated recipients. This model is relatively long and takes up to 4 months to accomplish.

Recently hematological malignancies such as Acute Myeloid Leukemia (AML) were recognized as potential indications for anti-CXCR4 therapy. Preclinical data suggests that dislodging of malignant cells from bone marrow environment using CXCR4 antagonists significantly improves survival of animals and outcome of chemotherapy. Several animal models of chemosensitization were developed. They are based on the induction of AML following adoptive transfer of malignant cells such APL cells from mCG-PML-PARα mice, A20 cells, or Ba/F3 cells. To facilitate the detection of malignant cells genes encoding fluorescent proteins or luciferase are introduced into them. The progression of AML and efficacy of anti-AML chemotherapy is assessed using FACS analysis of cells from peripheral blood, spleen and bone marrow. In addition, whole body in vivo bioluminescence imaging allows quantitatation of the effect of CXCR4 antagonists on anti-AML therapy in individual animal over time.

Results

Results are shown in FIG. 7-12.

Figure 7A:
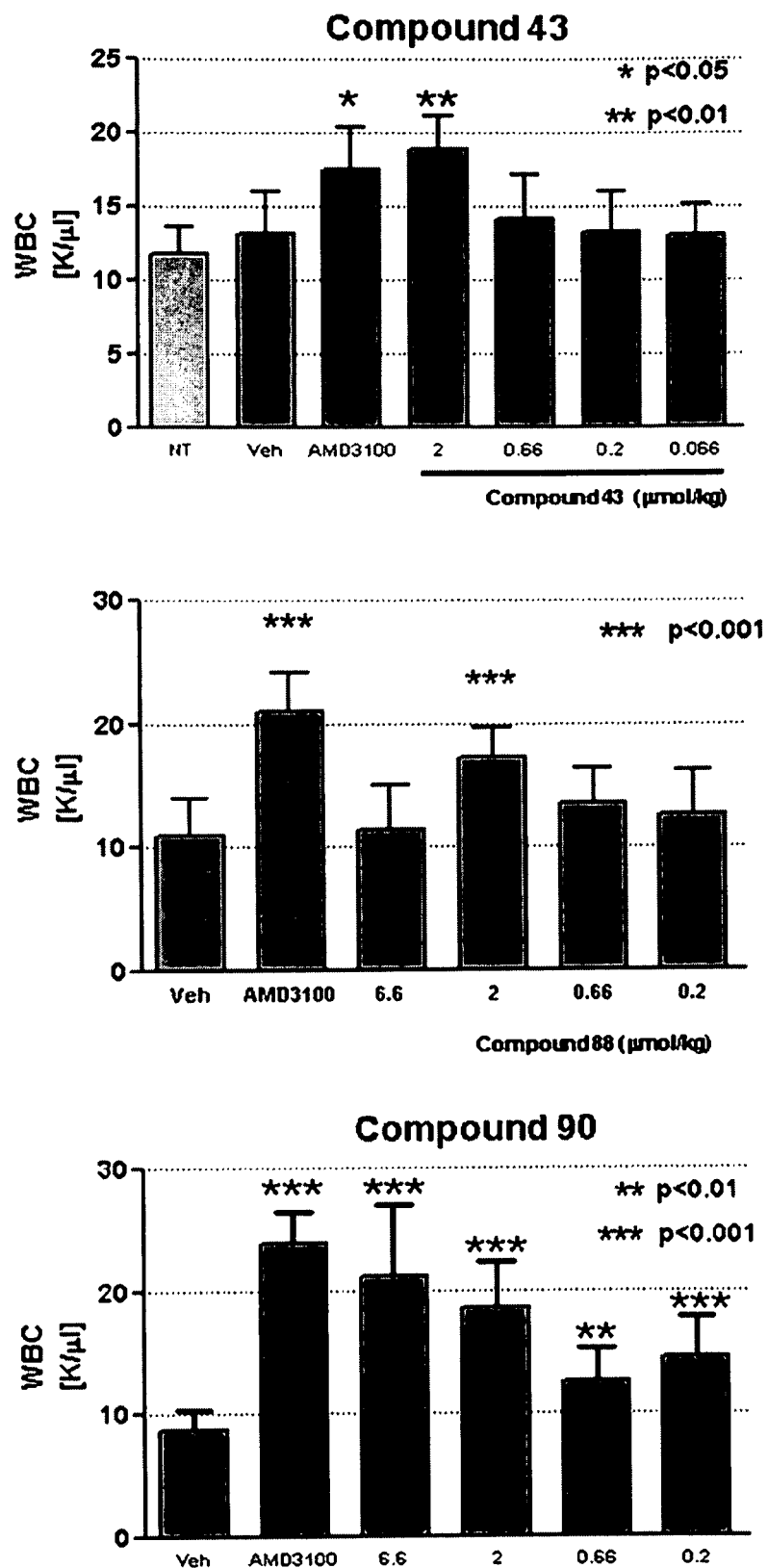
FIGS. 7A-7C is a series of graphs showing WBC mobilization of CXCR4 modulators in response to testing with compounds of the invention.
Figure 7B:
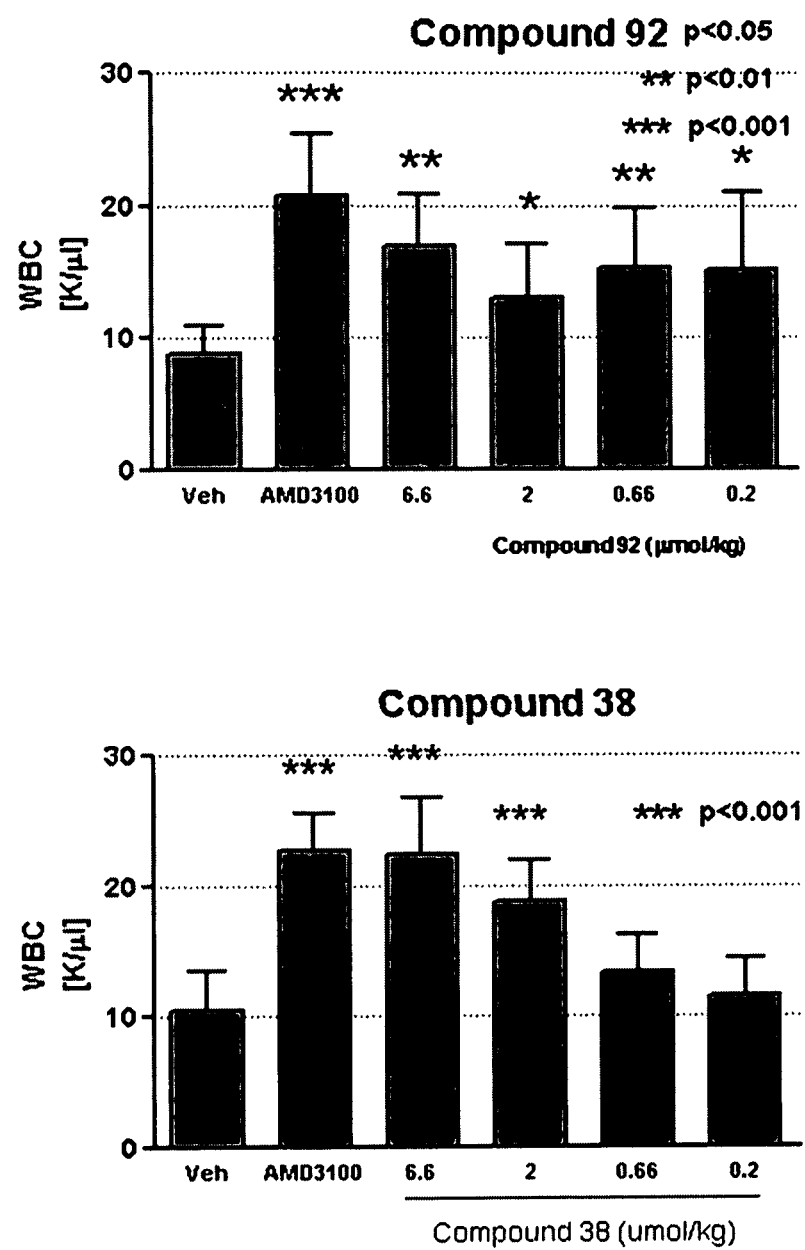
Figure 7C:
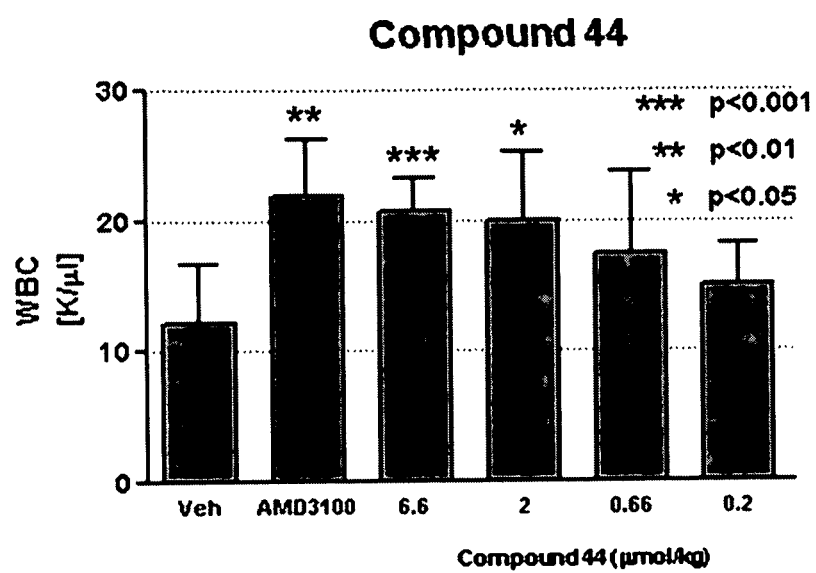
Figure 8A:
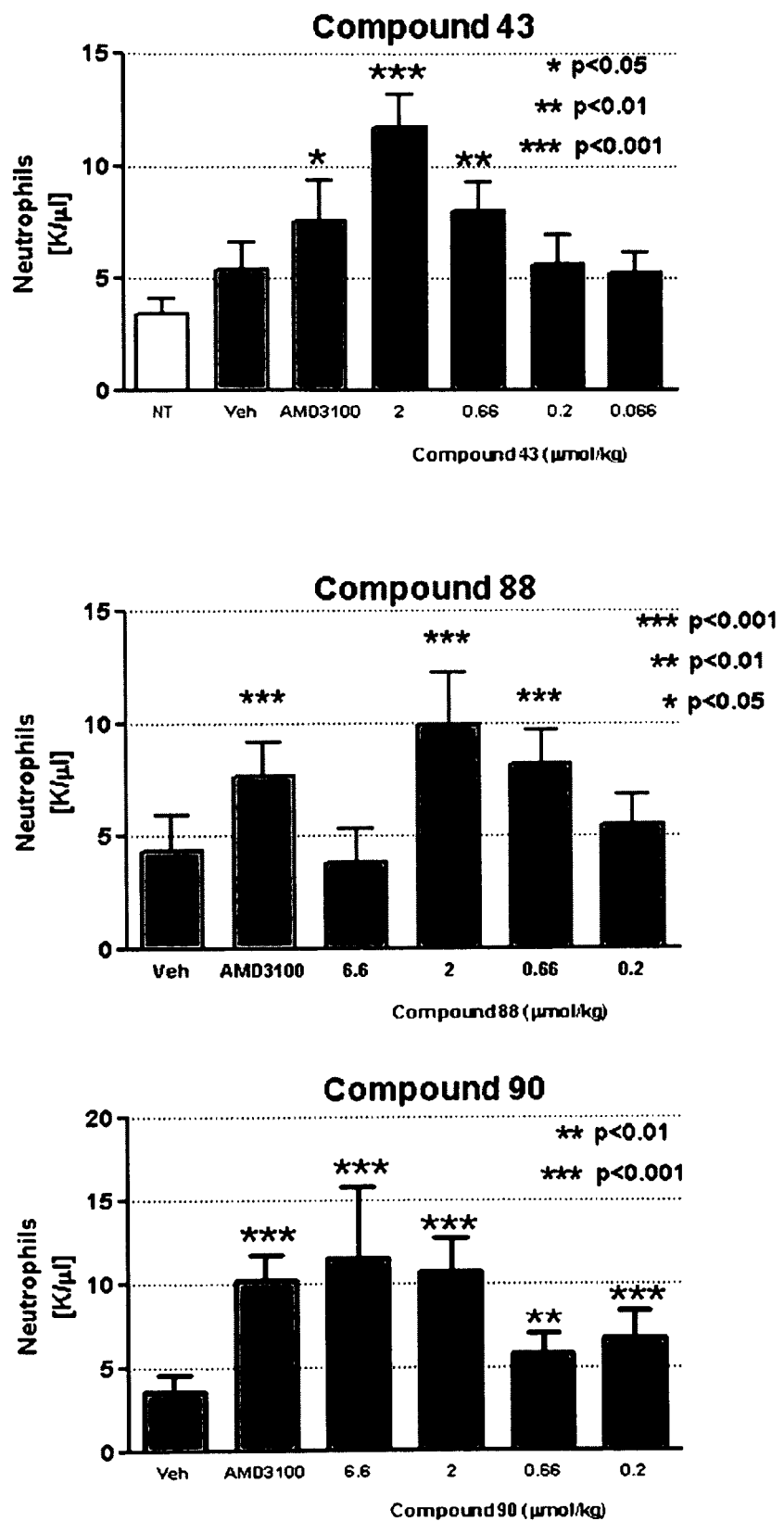
FIGS. 8A-8B is a series of graphs showing results of CXCR4 modulators in a PMN mobilization assay.
Figure 8B:
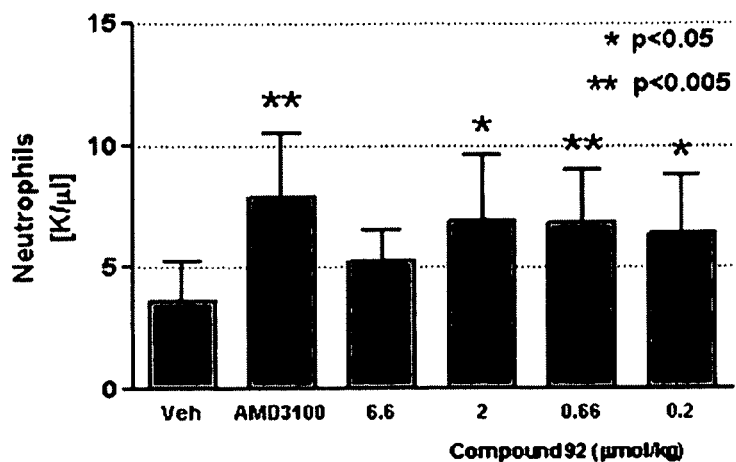
Figure 8B:
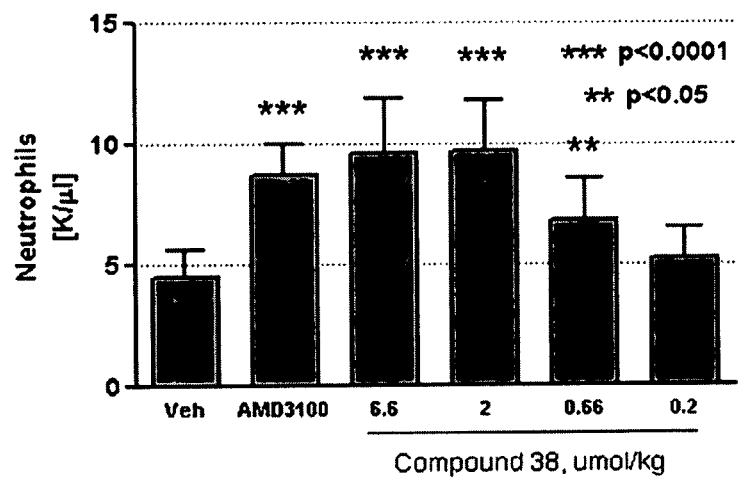
Figure 8B:
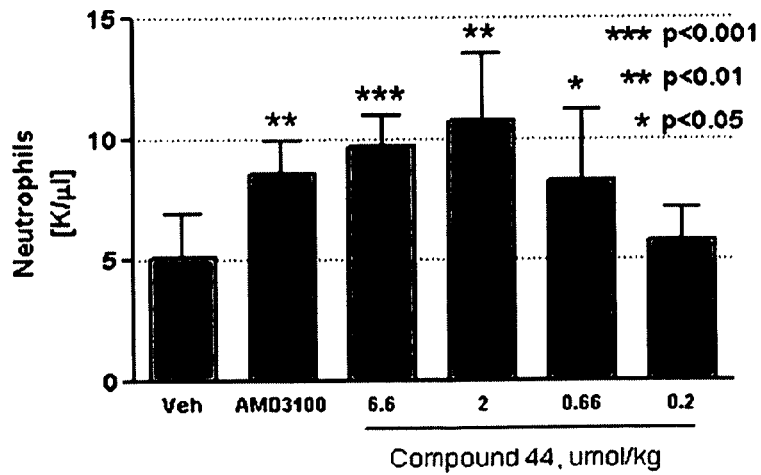
Figure 9A:
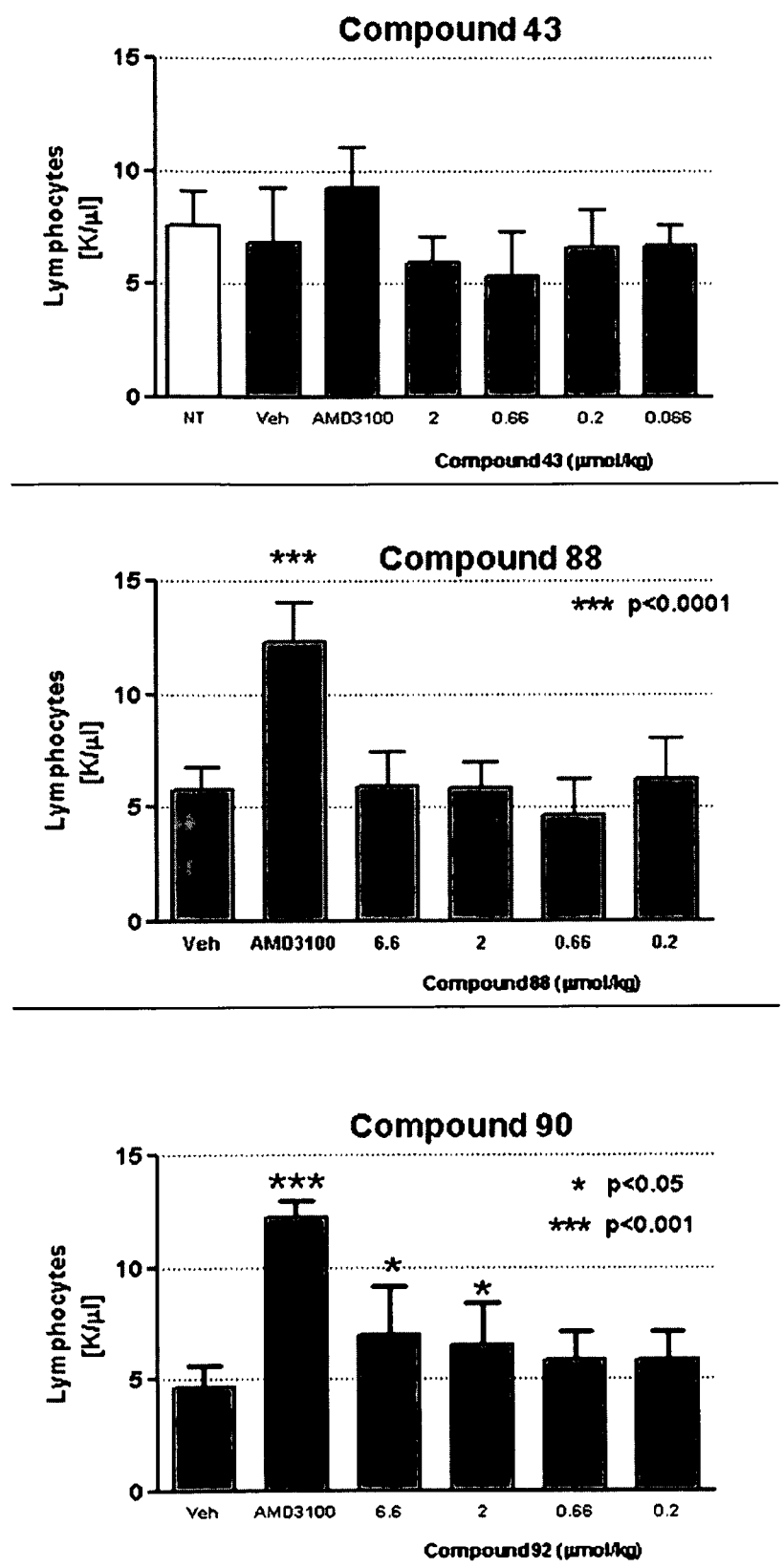
FIGS. 9A-9C is a series of graphs showing results of CXCR4 modulators in a lymphocyte mobilization assay.
Figure 9B:
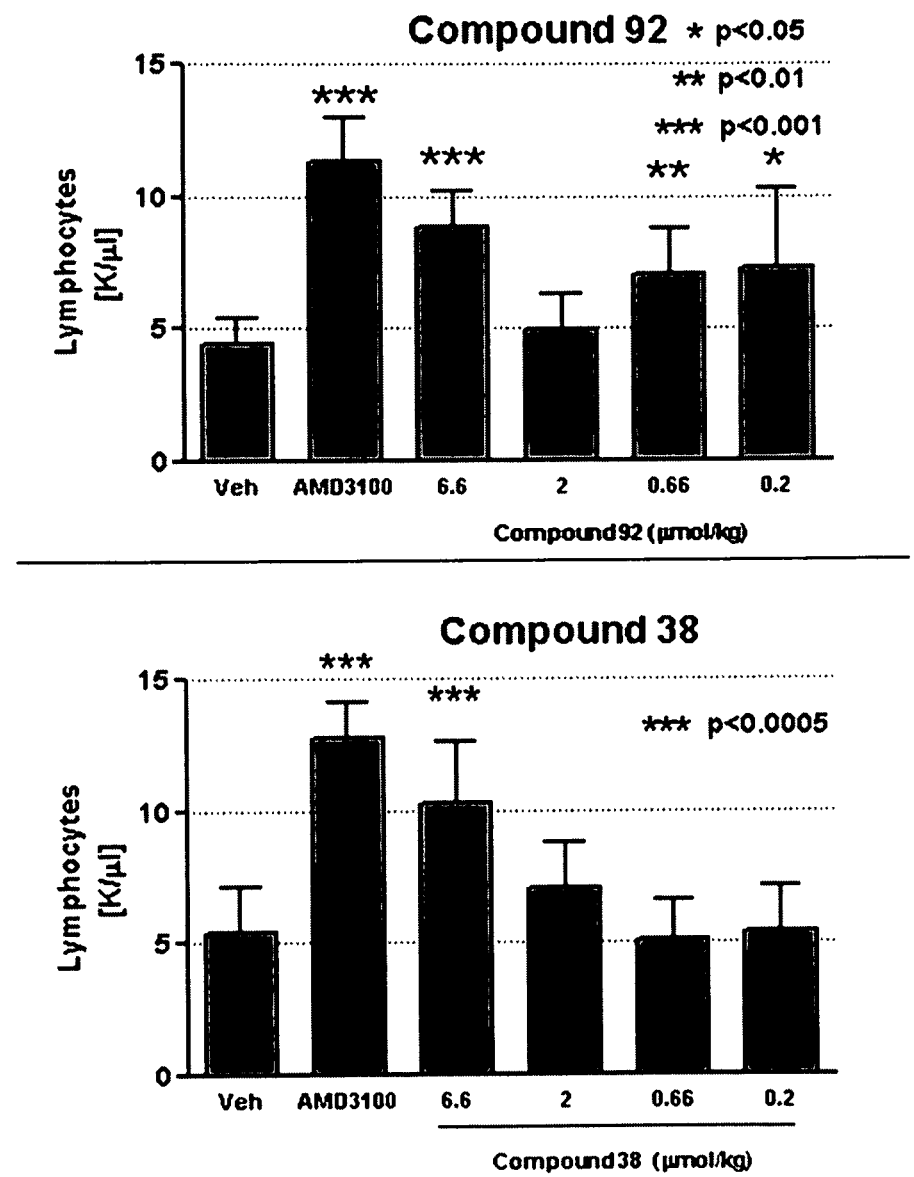
Figure 9C:
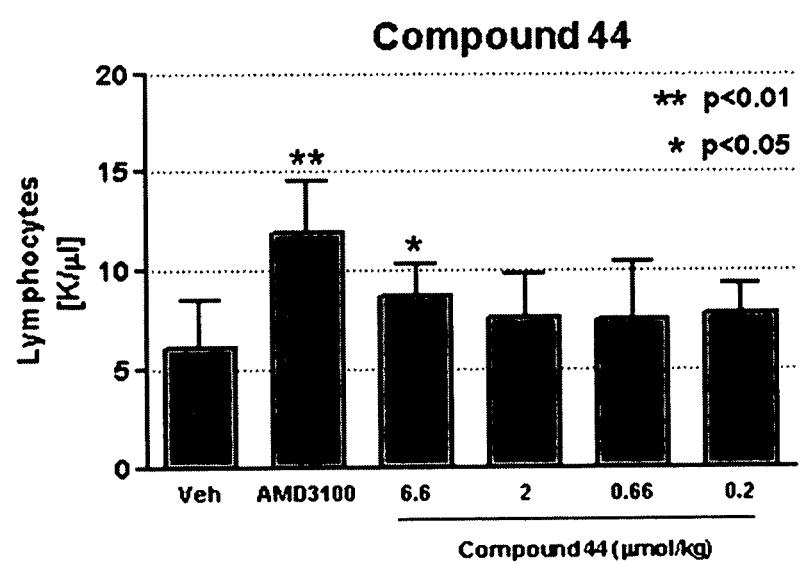
Figure 10:
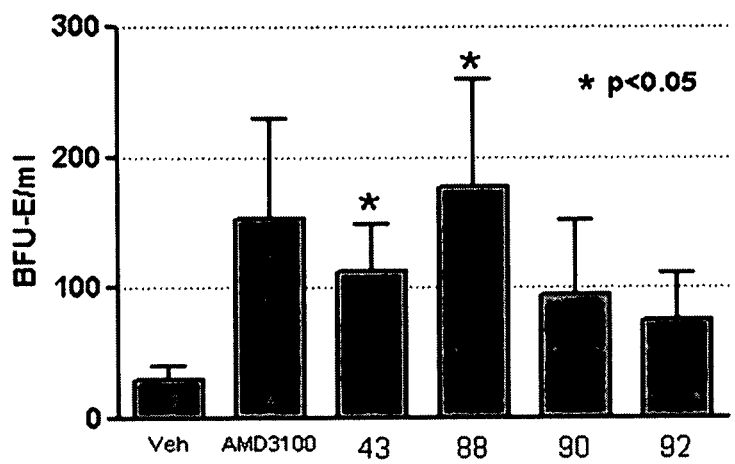
FIG. 10 is a series of graphs showing the effects of CXCR-4 receptor compounds: 43, 88, 90 and 92 on burst forming unit-erythroid cells (BFU-E) and Colonly-forming unit granulocyte macrophages (CFU-GM).
Figure 10:
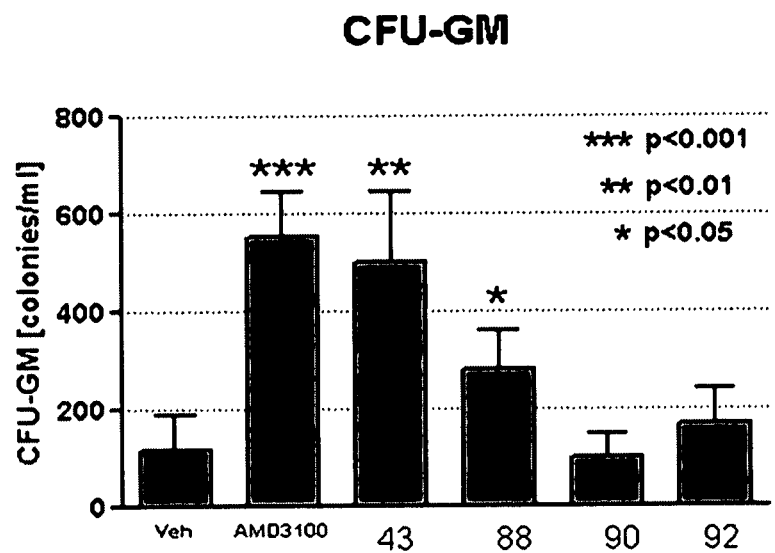

CXCR-4 compound antagonists/modulators mobilize white blood cells in vivo (mouse model) with efficacy similar to AMD3100 (Mozobil) See FIG. 7. Upon analysis of cell types in peripheral blood it was found that CXCR4 receptor compounds are predominately mobilizing polymorphonuclear lymphocytes (See FIG. 9).

CXCR-4 compound antagonists/modulators are active in mobilizing bone marrow progenitor cells with efficacy similar to AMD3100 (Mozobil). This was demonstrated in a mouse model of progenitor cell mobilization. See FIG. 10. In this assay, DBA/2 mice, male, 10 weeks old, n=4/group; vehicle (10% PEG, 0.1 ml; AMD3100 (2 µmol/kg, in PBS); ATI-2346 (2 µmol/kg, 10% PEG, 0.1 ml). WBCs harvested from 150 ml of blood, premixed with 3 ml of Methocult medium. CFU-GM colonies were scored at day 12.

CXCR-4 compound agonists are also active in mobilizing both neutrophils and bone marrow progenitor cells. The CXCR4 agonist SDF1a has similarly been shown to mobilize bone marrow progenitor cells and hypothesized to occur by establishing an additional chemotactant gradient in the blood following intravenous injection to oppose the natural retentive function of SDF1a in the bone marrow. CXCR4 compound agonists also likely function in this way to mobilize BMPC. An example of Compound 38 agonist data are shown in FIG. 8.

Figure 11:
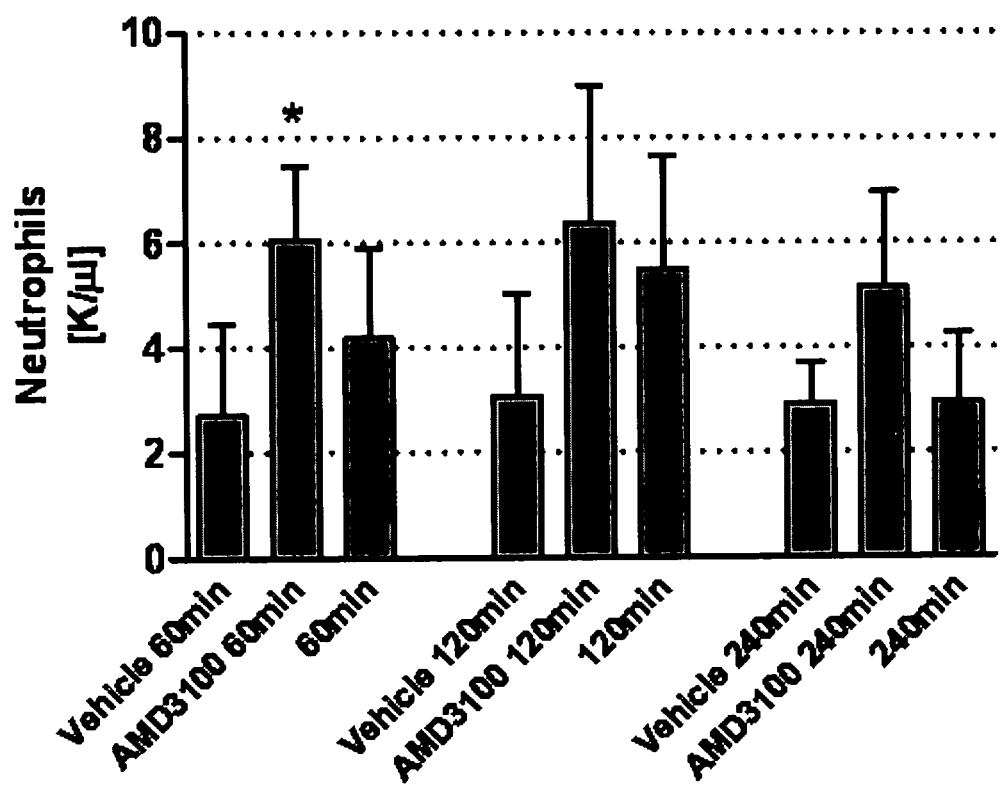
FIG. 11 is a bar graph showing the effects of 10 μmmol/kg CXCR-4 receptor Compound No. 43 and AMD3100 on PMN recruitment in BALB/c mice following subcutaneous injection.

The effects of 10 µmol/kg CXCR-4 receptor compound 43 and CXCR4 compound AMD3100 on PMN recruitment in BALB/c mice following subcutaneous injection are shown in FIG. 11.

Figure 12:
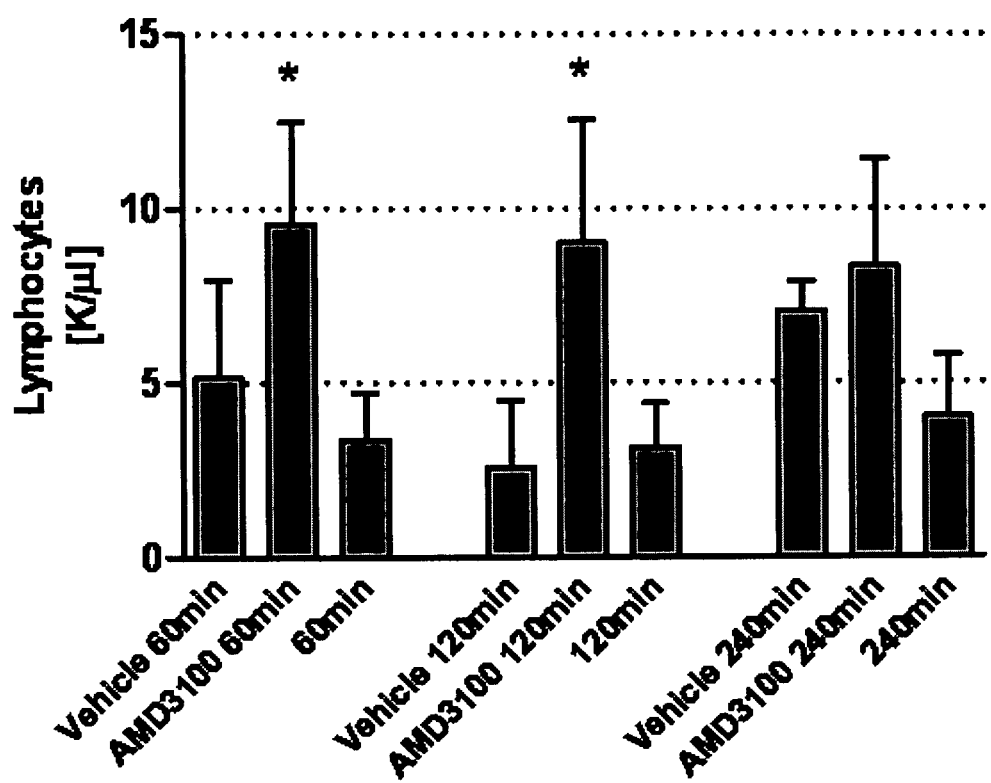
FIG. 12 is a bar graph showing the effects of 10 μmmol/kg CXCR-4 receptor Compound No. 43 and AMD3100 on lymphocyte recruitment in BALB/c mice following subcutaneous injection.

The effects of 10 µmol/kg CXCR-4 receptor compound 43 and CXCR4 compound AMD3100 on lymphocyte recruitment in BALB/c mice following subcutaneous injection are shown in FIG. 12.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by Formula I:

T-L-P, or a pharmaceutically acceptable salt thereof, wherein:
   P is a peptide sequence selected from: SEQ ID NO: 39, 40, 41, 42, 49, 71, 72, 73, 76, 82, 83, 88, 89, 90, 91, 92, 93, 94, 95, 96, 97, 98, 99, 100, 101, 102, 103, 104, 105, 106, 107, 108, 109, 110, 115, 116, 117, 118, 119, 124, 125, 128, 132, 133, 134, 135, 136, 137, 138, 139, 140, 141, 142, 144, 145, 146, 147, or 148;
   L is a linking moiety represented by C(O) and bonded to P at an N terminal nitrogen of an N-terminal amino-acid residue;
   and T is a lipophilic tether moiety bonded to L.

2. The compound of claim 1, wherein the C-terminus of the sequence is functionalized with $NR_1R_2$, wherein $R_1$ and $R_2$ are each independently H or alkyl.

3. The compound of claim 1, wherein the C-terminus of the sequence is functionalized with $NH_2$.

4. The compound of claim 1, further comprising a lipophilic tether moiety bonded on the C-terminus of P.

5. The compound of claim 1, wherein T is an optionally substituted $(C_6-C_{30})$alkyl, $(C_6-C_{30})$alkenyl, $(C_6-C_{30})$alkynyl, wherein 0-3 carbon atoms are replaced with oxygen, sulfur, nitrogen or a combination thereof.

6. The compound of claim 5, wherein T is selected from the group consisting of: $CH_3(CH_2)_{16}$, $CH_3(CH_2)_{15}$, $CH_3(CH_2)_{14}$, $CH_3(CH_2)_{13}$, $CH_3(CH_2)_{12}$, $CH_3(CH_2)_{11}$, $CH_3(CH_2)_{10}$, $CH_3(CH_2)_9$, $CH_3(CH_2)_8$, $CH_3(CH_2)_9OPh$-, $CH_3(CH_2)_6C=C(CH_2)_6$, $CH_3(CH_2)_{11}O(CH_2)_3$, and $CH_3(CH_2)_9O(CH_2)_2$.

7. The compound of claim 1, wherein T is a fatty acid derivative.

8. The compound of claim 7, wherein the fatty acid is selected from the group consisting of: butyric acid, caproic acid, caprylic acid, capric acid, lauric acid, myristic acid, palmitic acid, stearic acid, arachidic acid, behenic acid, lignoceric acid, myristoleic acid, palmitoleic acid, oleic acid, linoleic acid, α-linolenic acid, arachidonic acid, eicosapentaenoic acid, erucic acid, docosahexaenoic acid.

9. The compound of claim 1, wherein T is a bile acid derivative.

10. The compound of claim 9, wherein the bile acid is selected from the group consisting of: lithocholic acid, chenodeoxycholic acid, deoxycholic acid, cholanic acid, cholic acid, ursocholic acid, ursodeoxycholic acid, isoursodeoxycholic acid, lagodeoxycholic acid, dehydrocholic acid, hyocholic acid, and hyodeoxycholic acid.

11. The compound of claim 1, wherein T is selected from sterols; progestagens; glucocorticoids; mineralcorticoids; androgens; and estrogens.

12. The compound of claim 1, wherein TL is selected from:
   $CH_3(CH_2)_{15}$—C(O);
   $CH_3(CH_2)_{13}$—C(O);
   $CH_3(CH_2)_9O(CH_2)_2C(O)$;
   $CH_3(CH_2)_{10}O(CH_2)_2C(O)$;
   $CH_3(CH_2)_6C=C(CH_2)_6$—C(O);
   LCA-C(O); and
   $CH_3(CH_2)_9OPh$-C(O) wherein LCA = 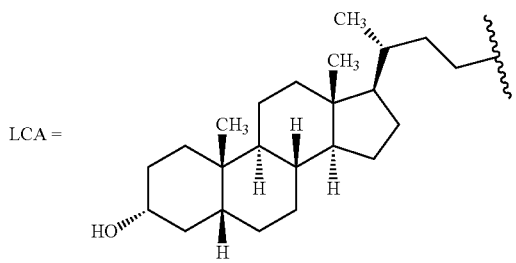

13. The compound of claim 1, wherein T is selected from:

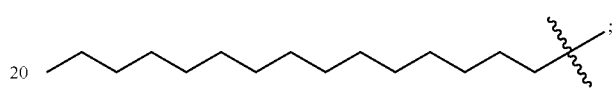

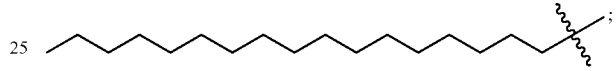

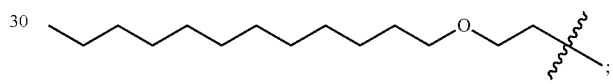

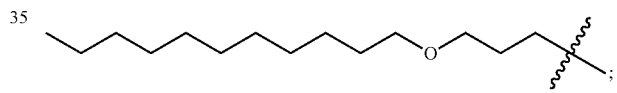

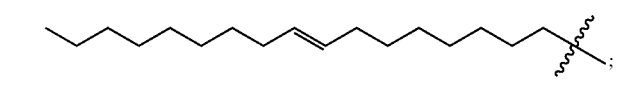

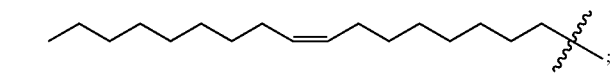

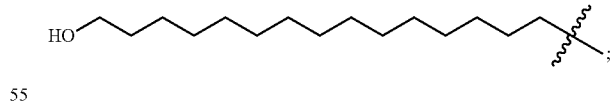

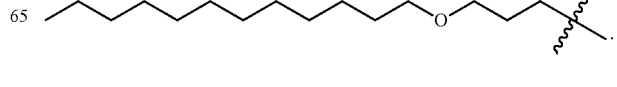

14. The compound of claim 1, selected from:
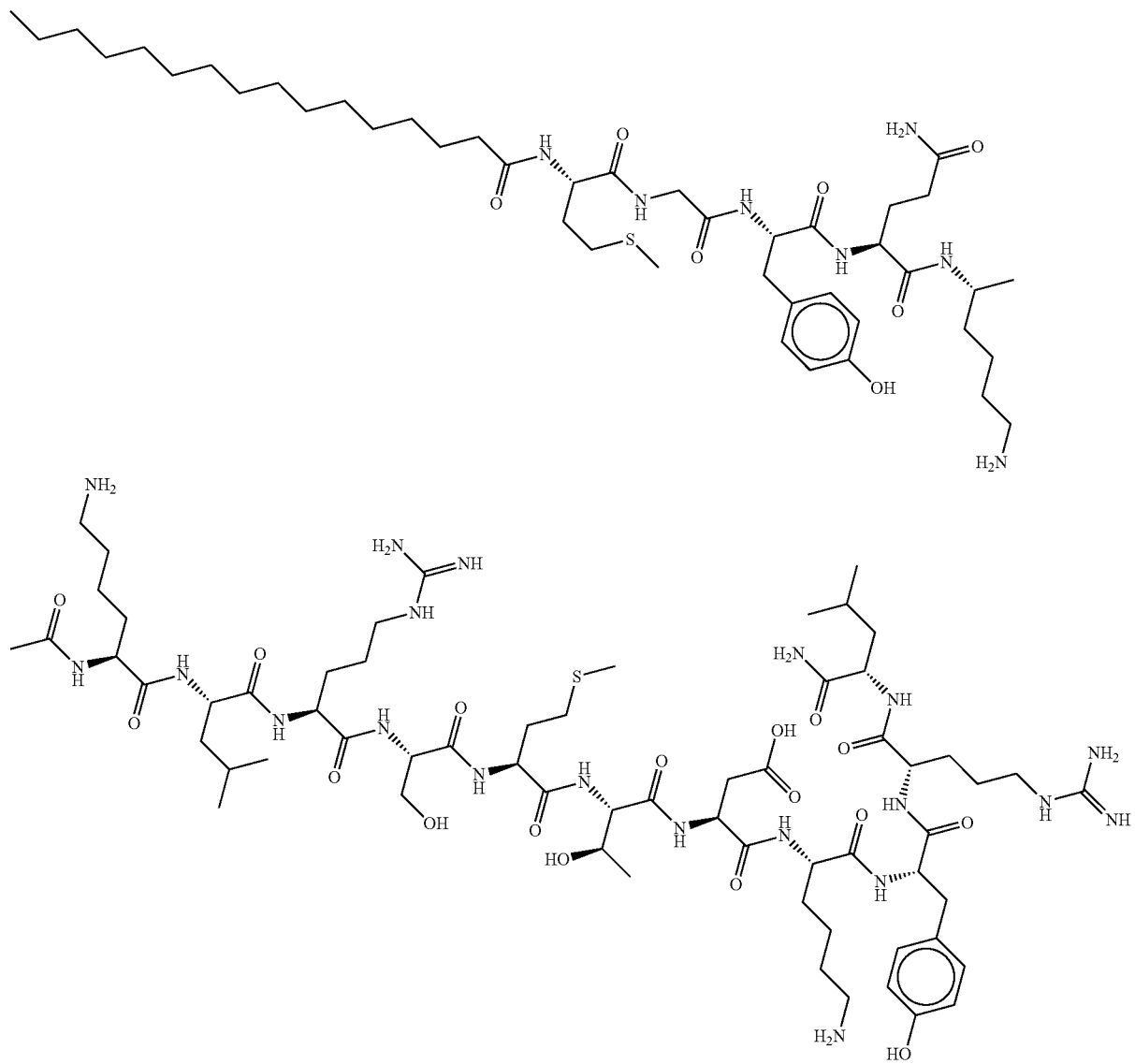
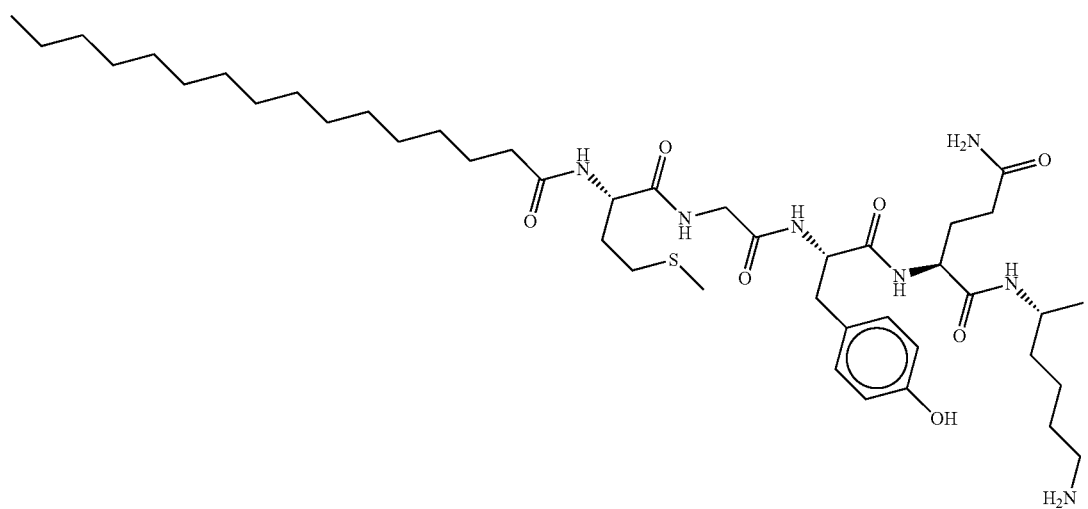

483
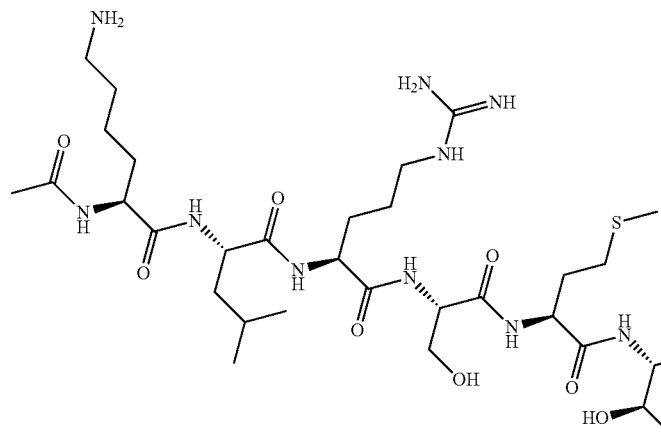
484
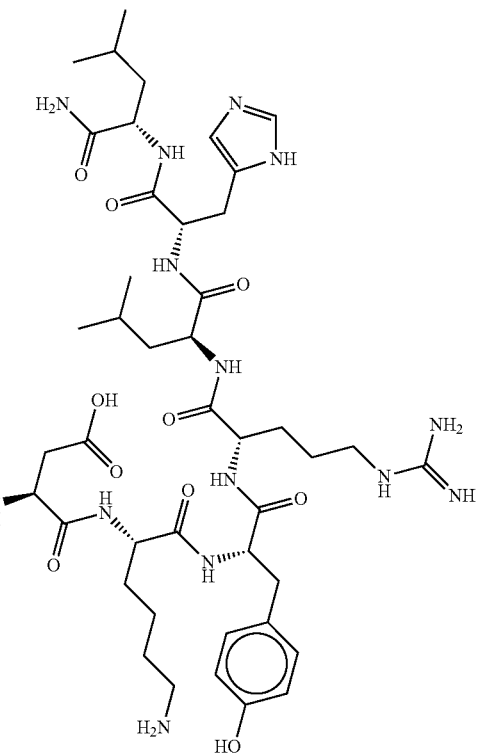
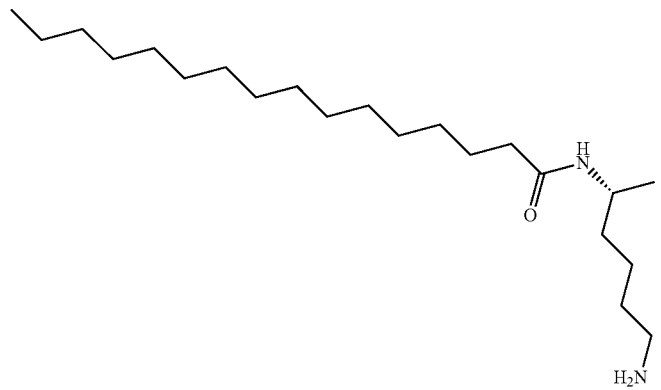

485
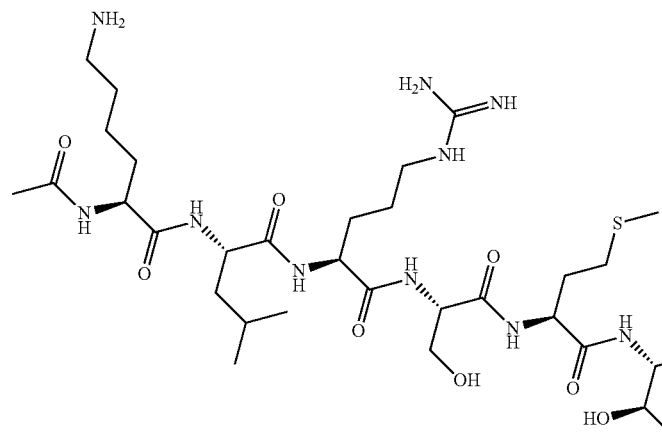
486
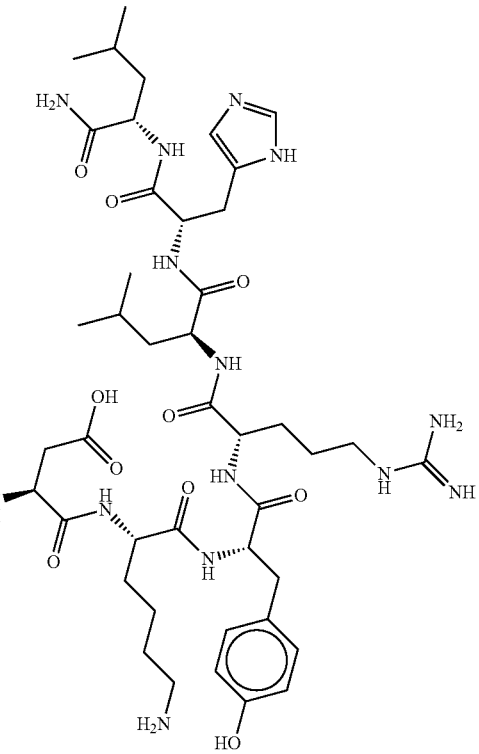
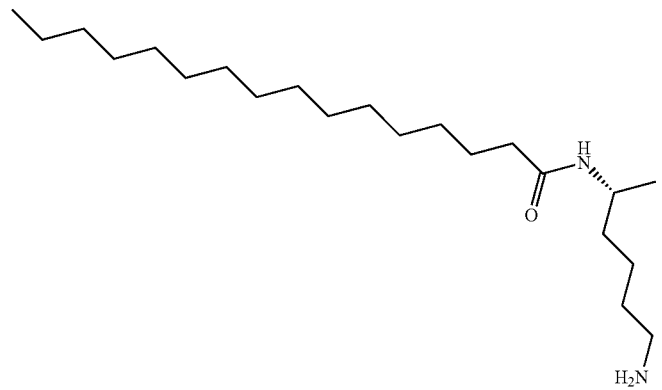

487
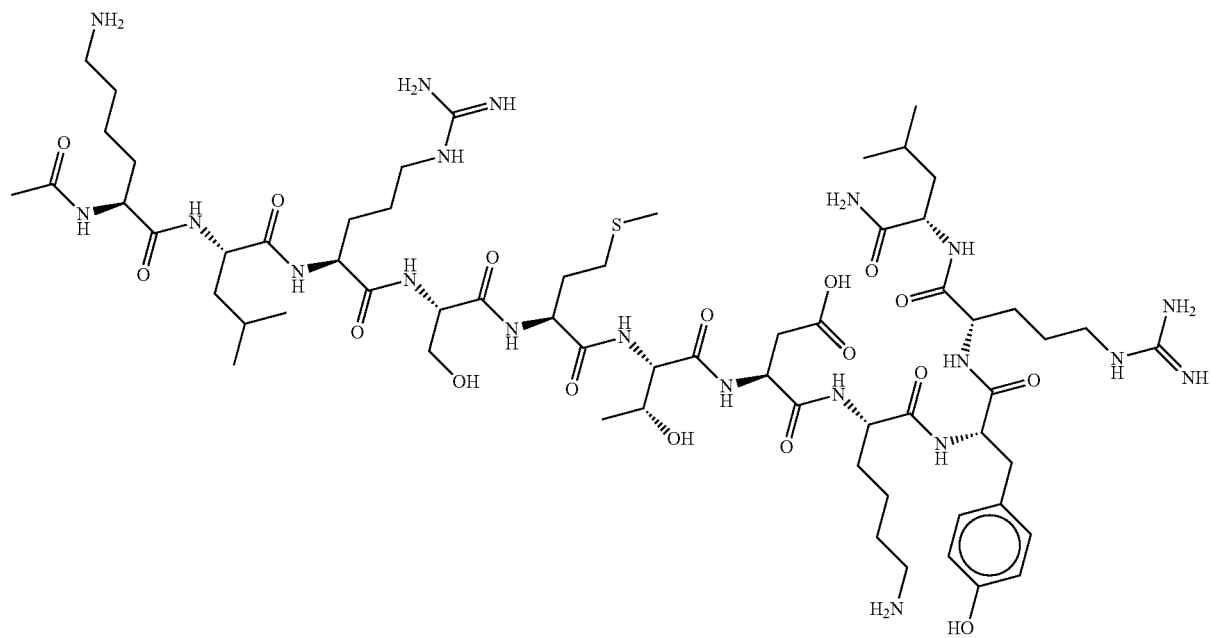
488
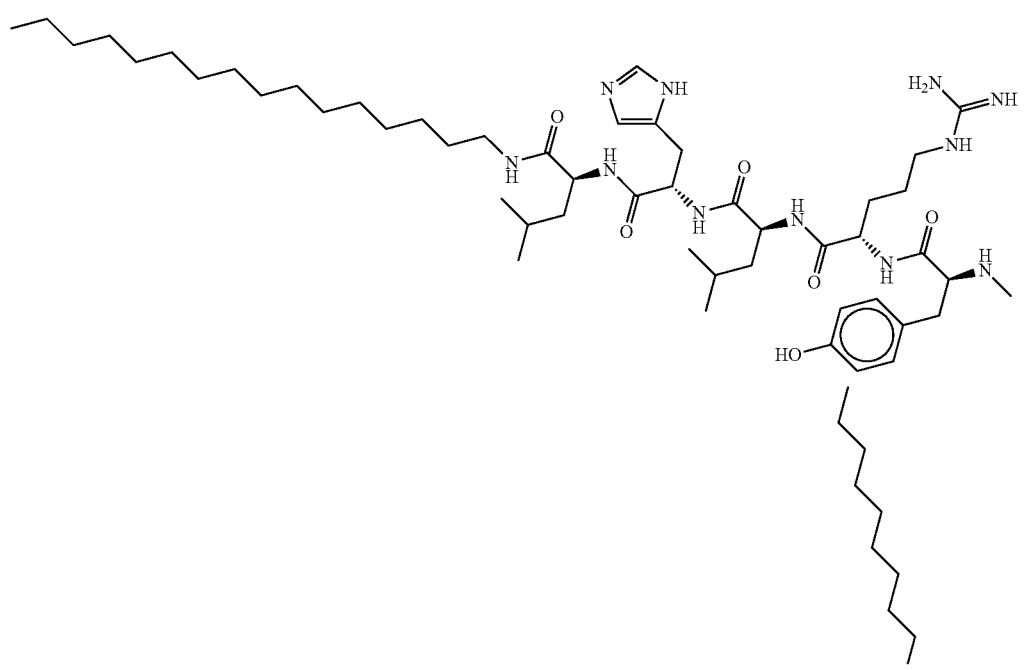

489 490
-continued
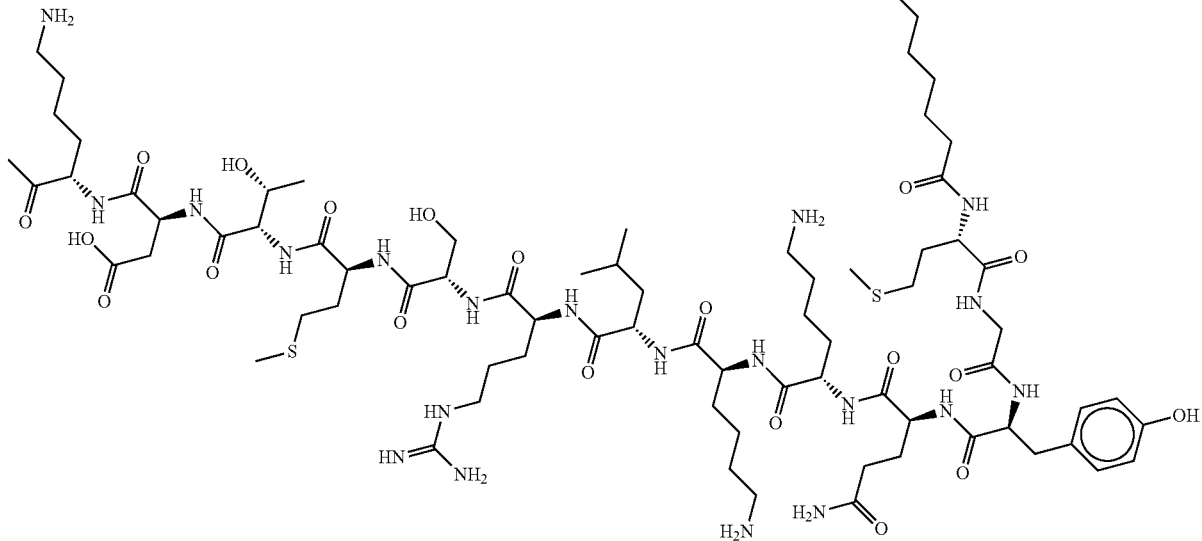
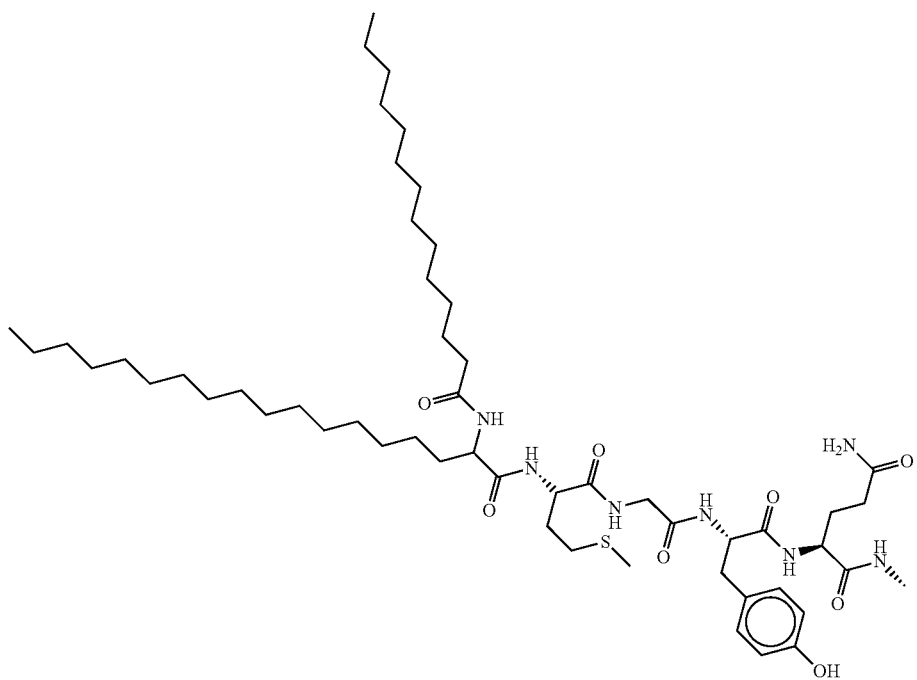

491 492
-continued
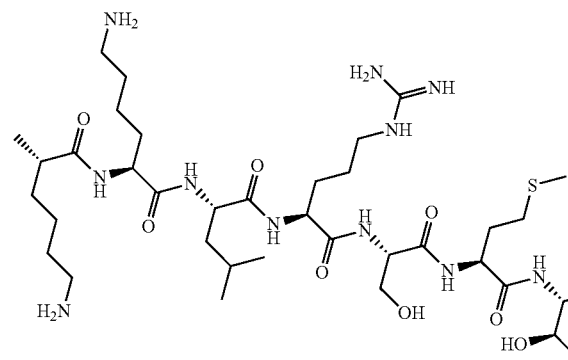
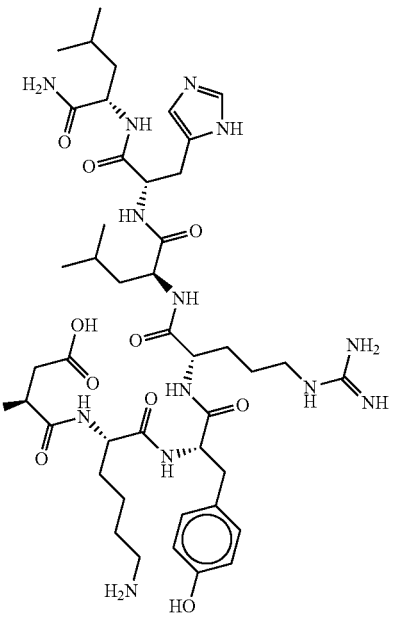
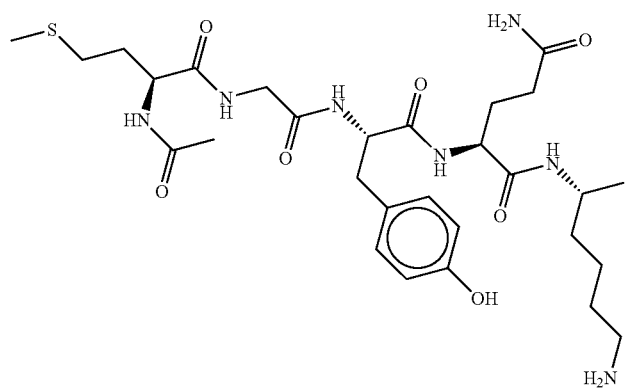
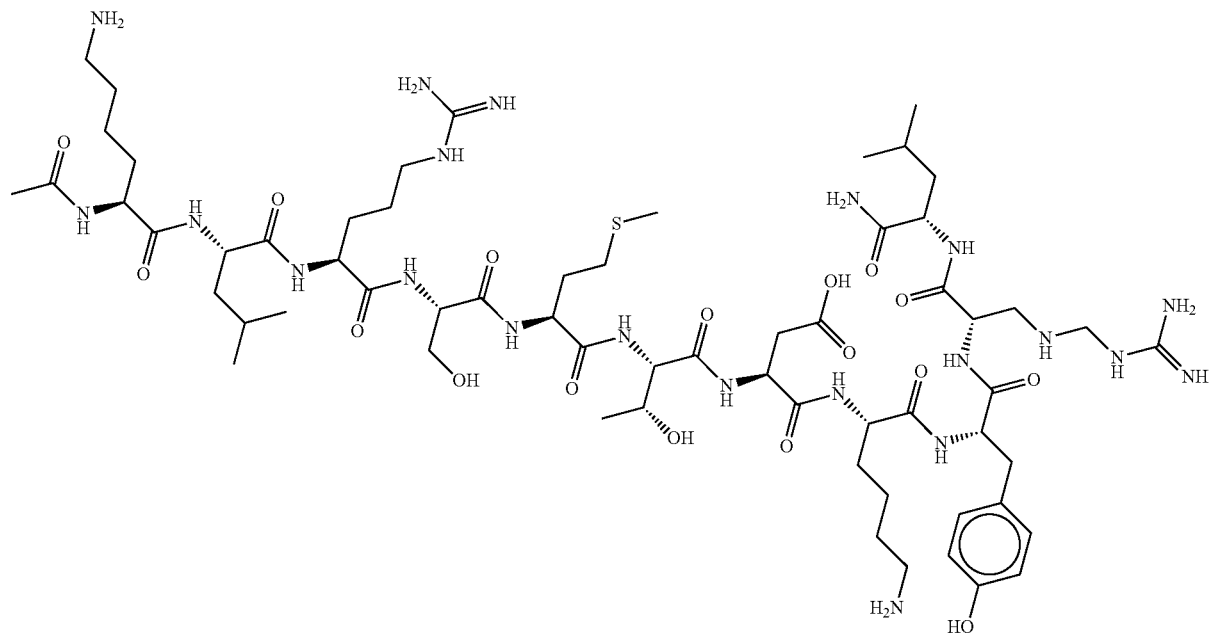

493
494
-continued
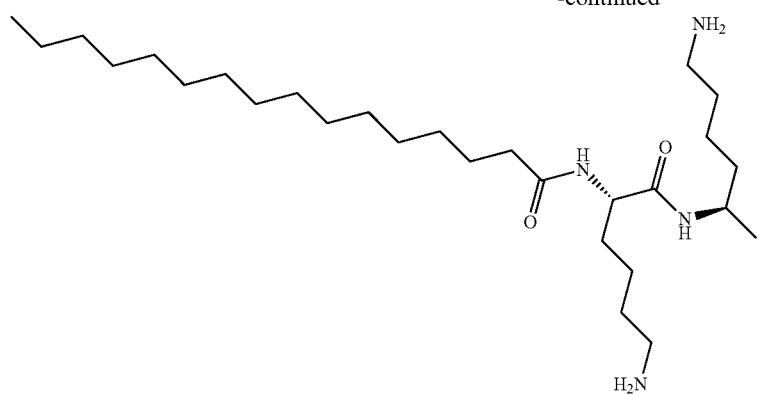
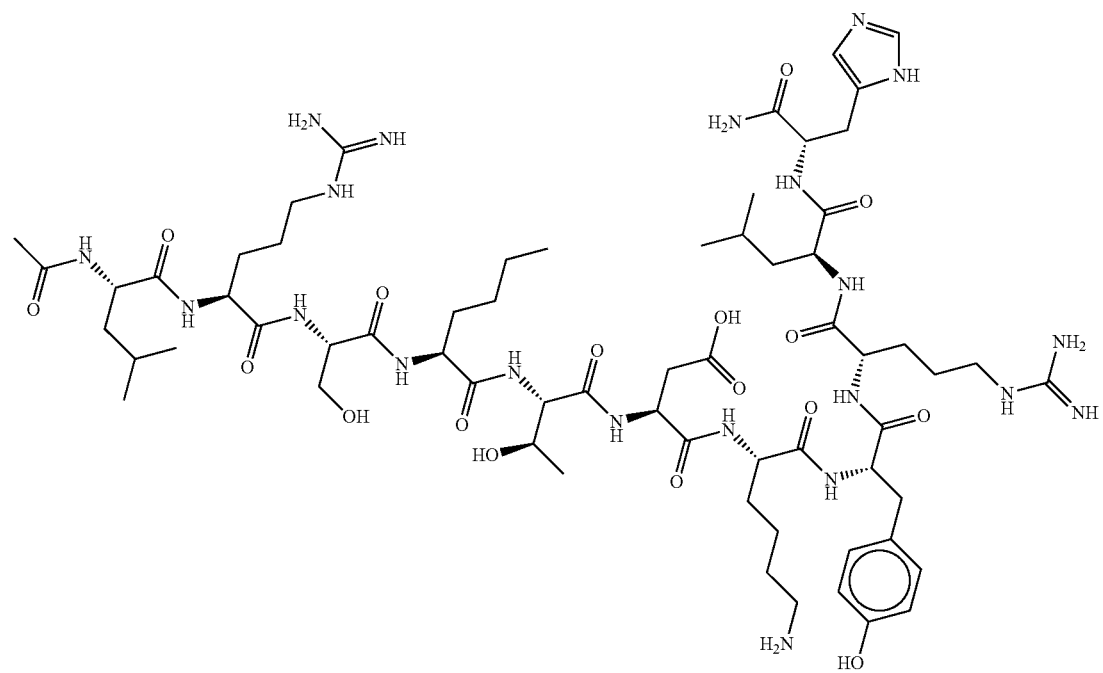
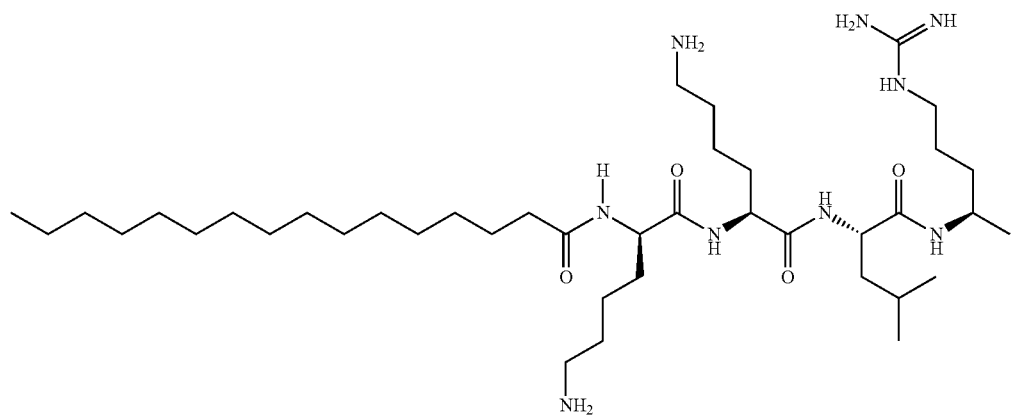

495
496
-continued
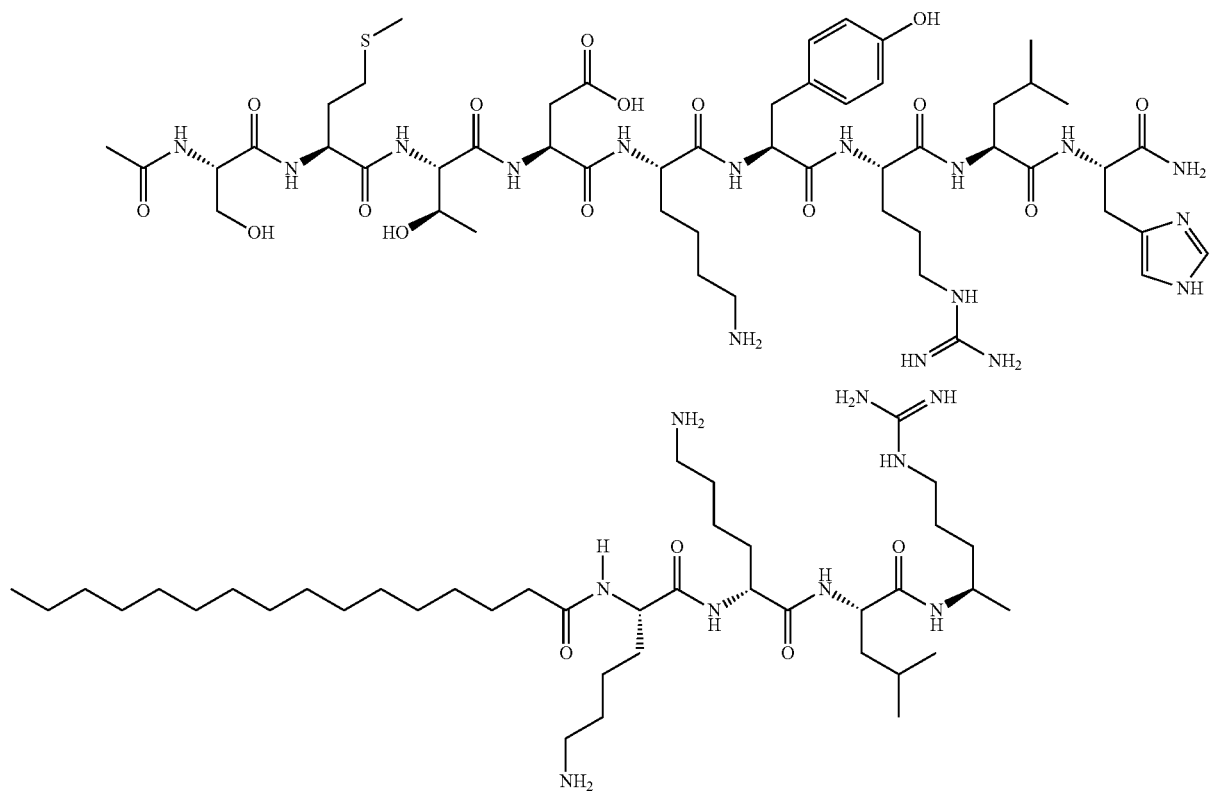
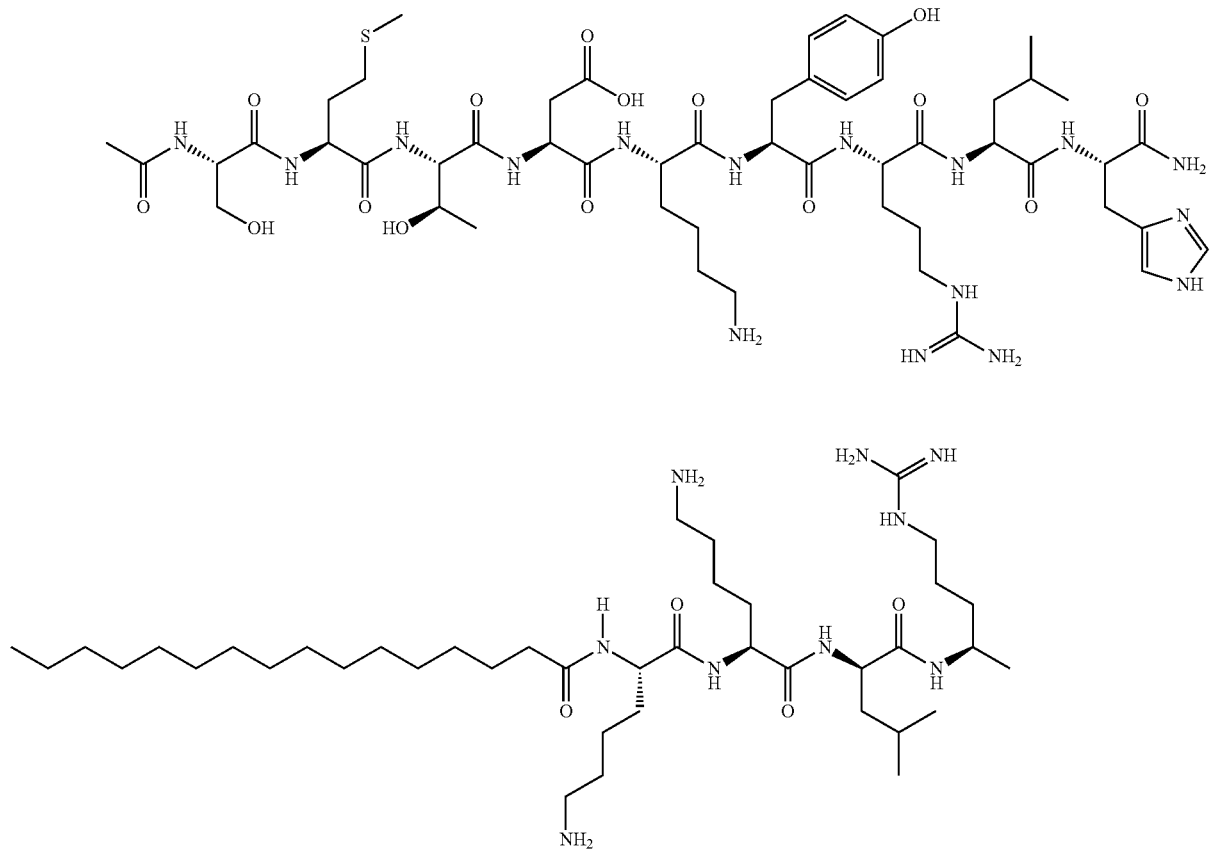

497
-continued
498
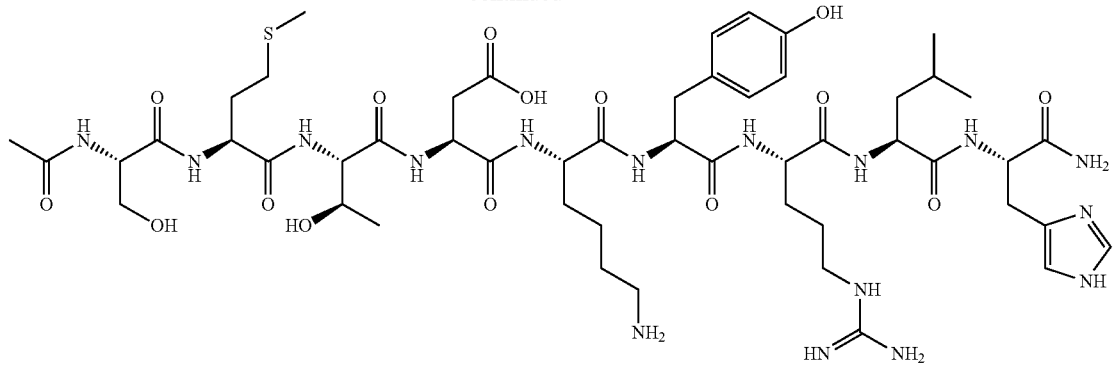
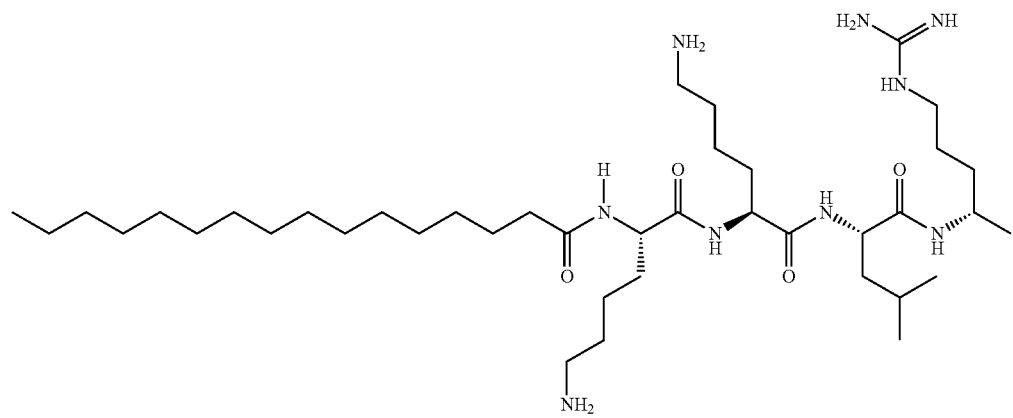
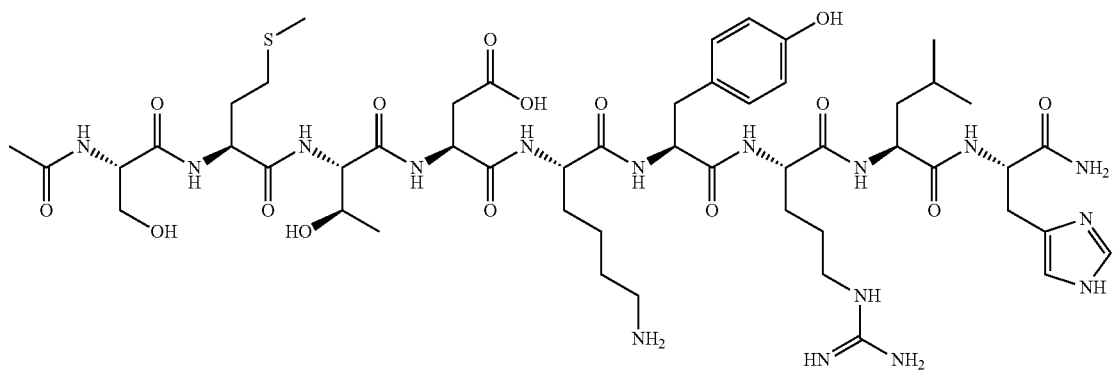
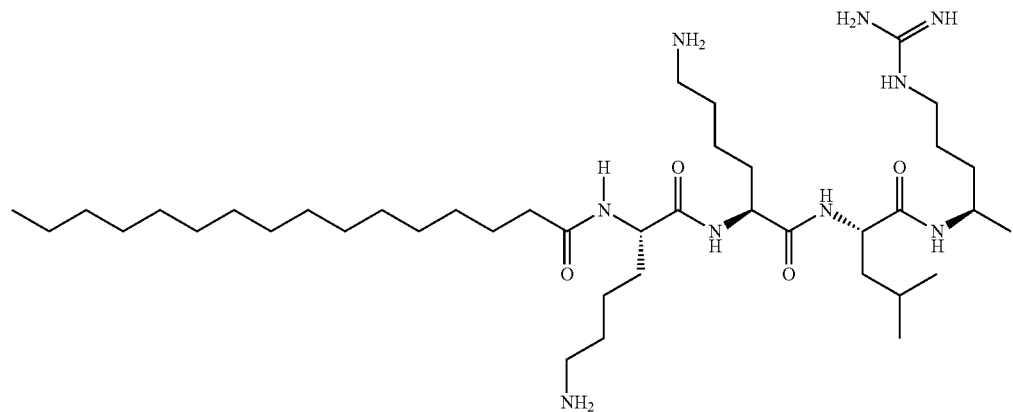

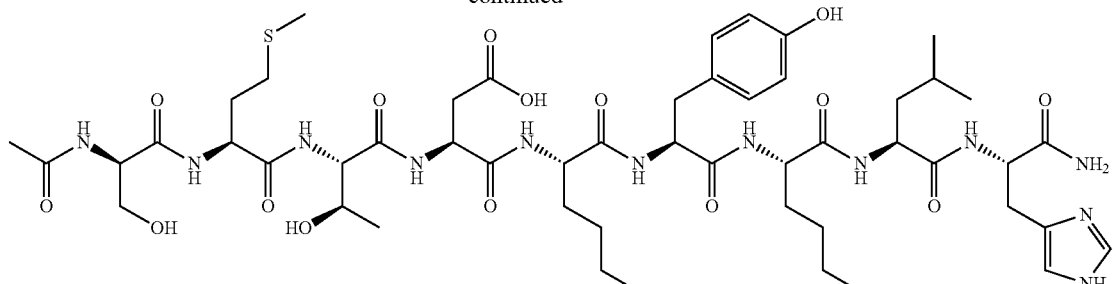
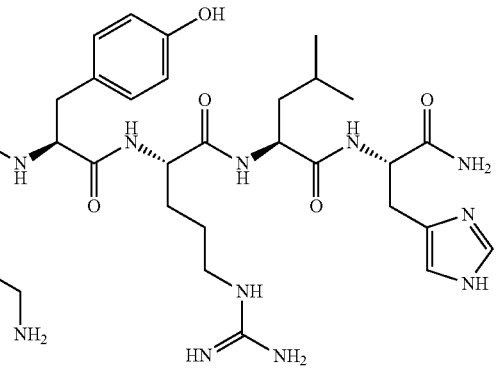
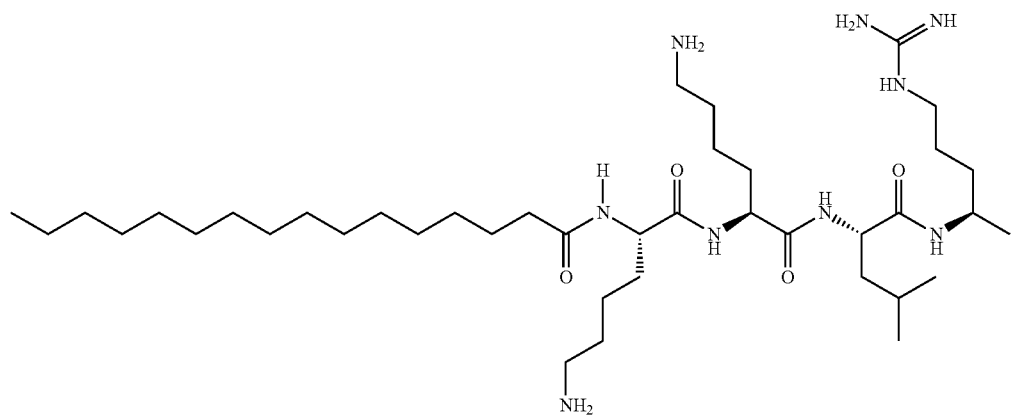
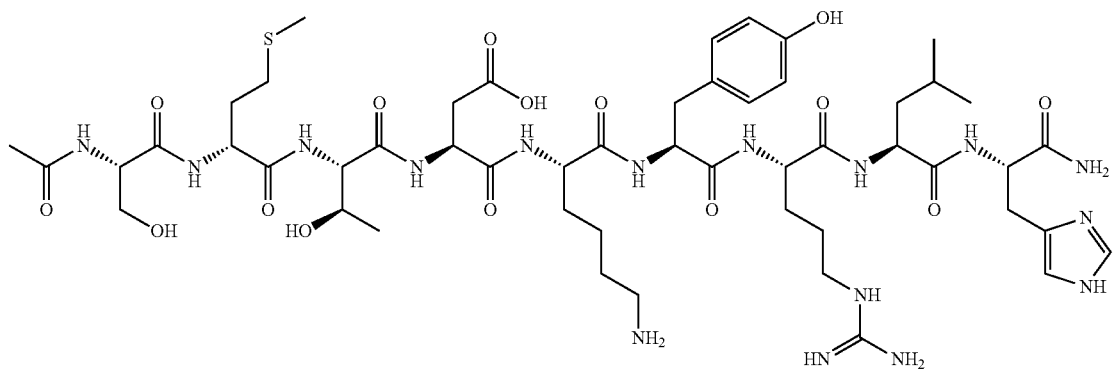
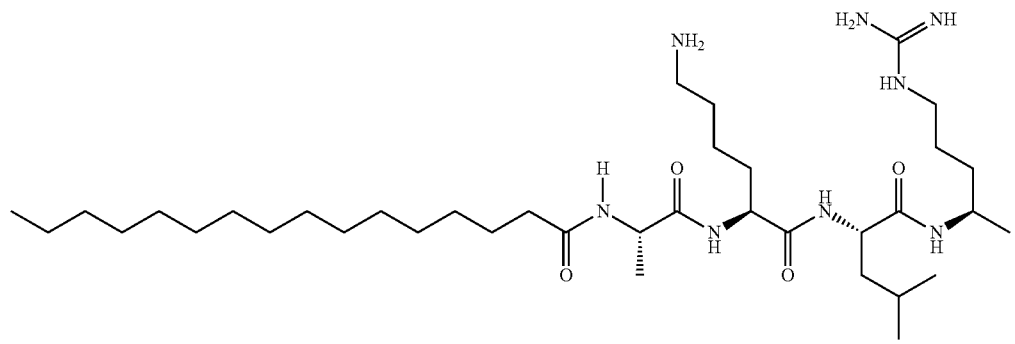

501
502
-continued
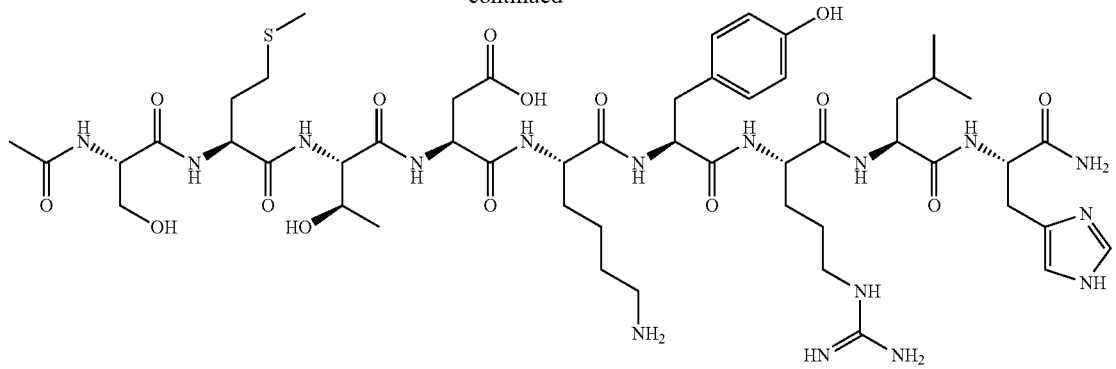
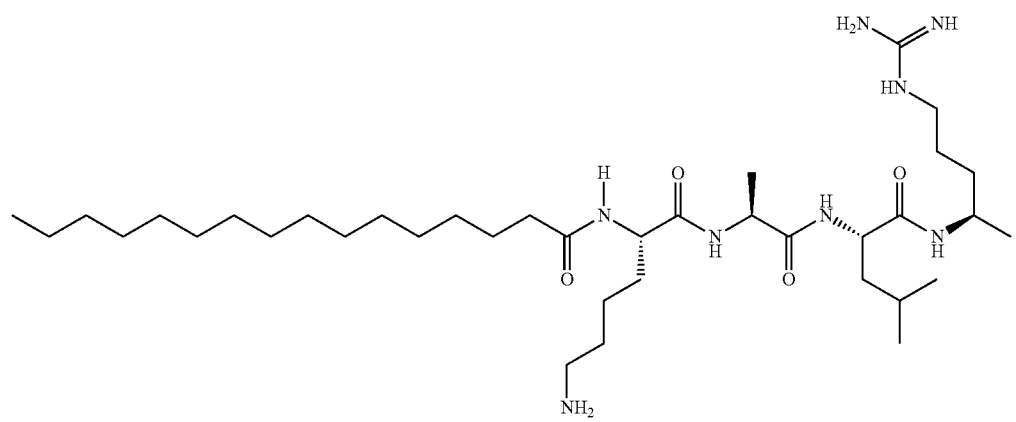
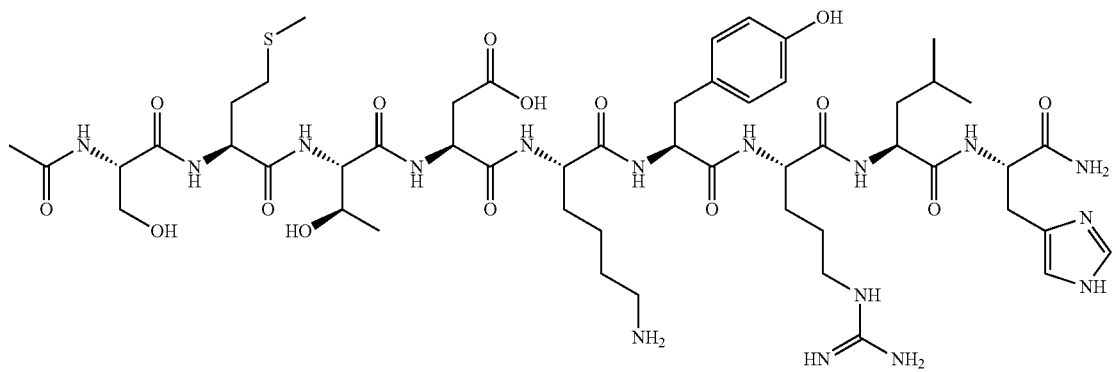
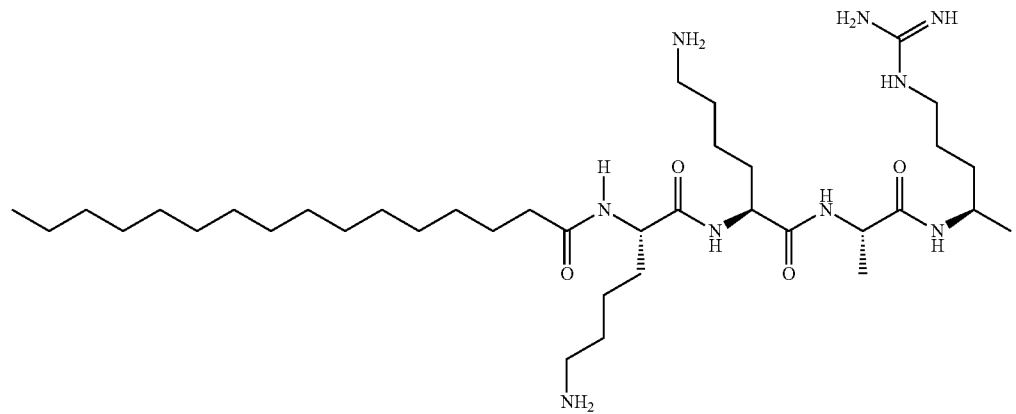

503
504
-continued
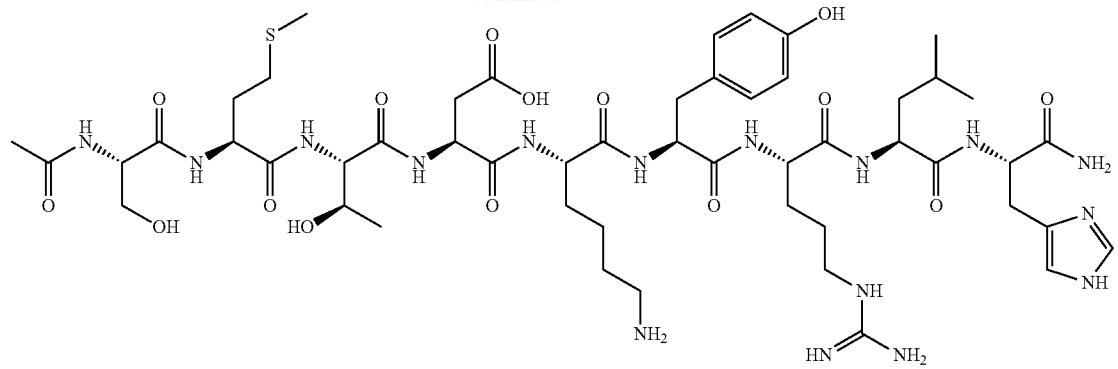
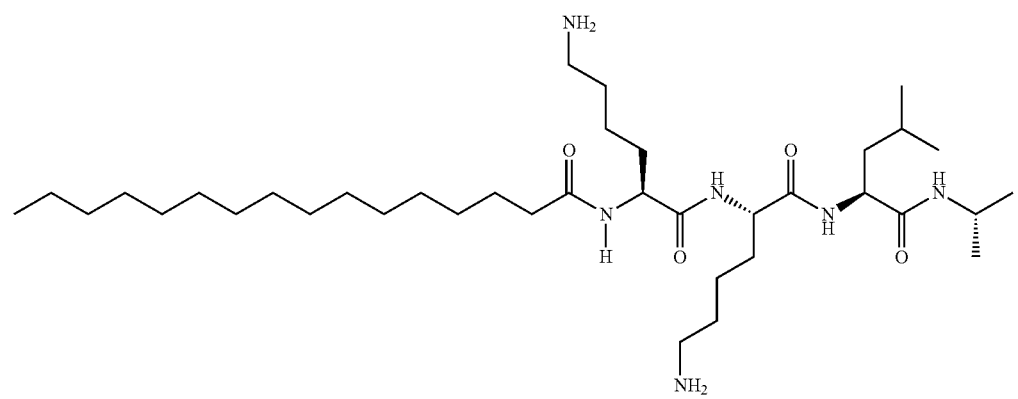
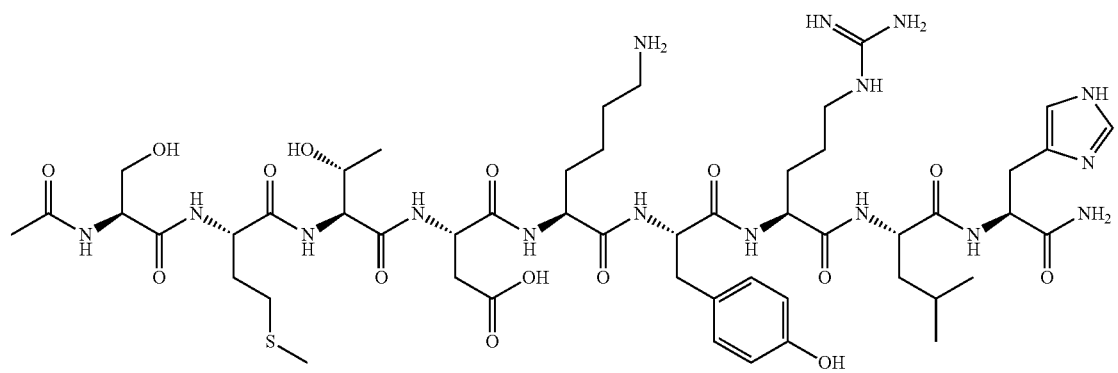
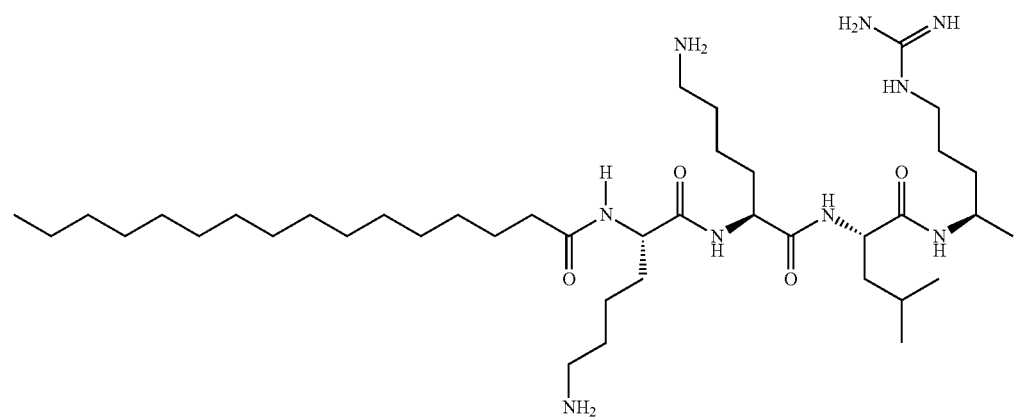

-continued
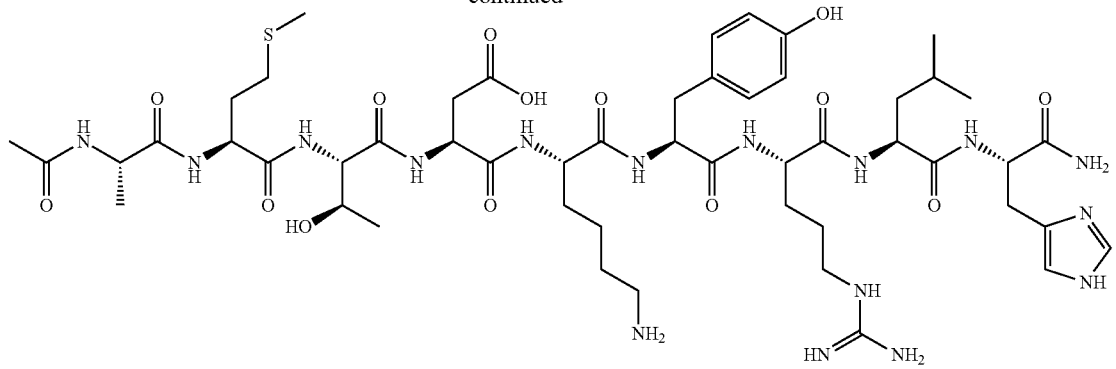
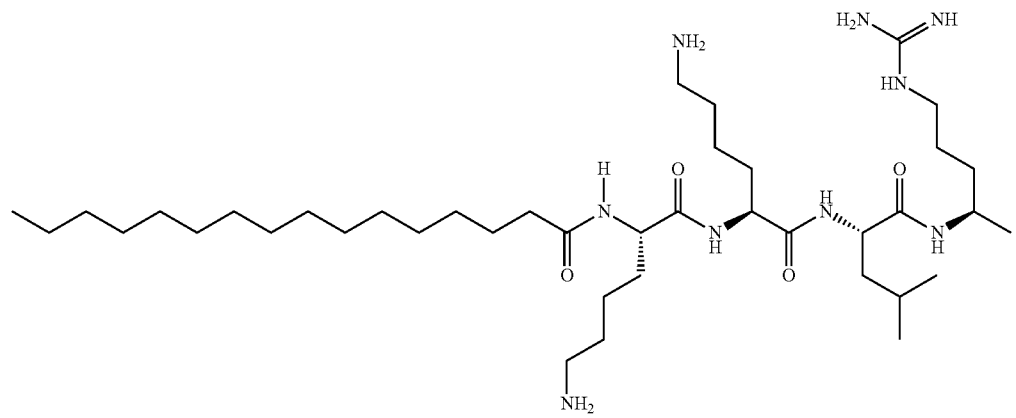
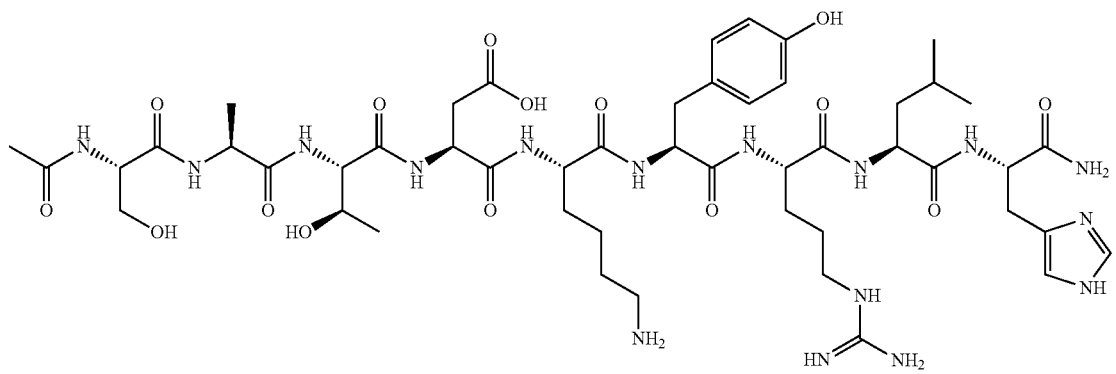
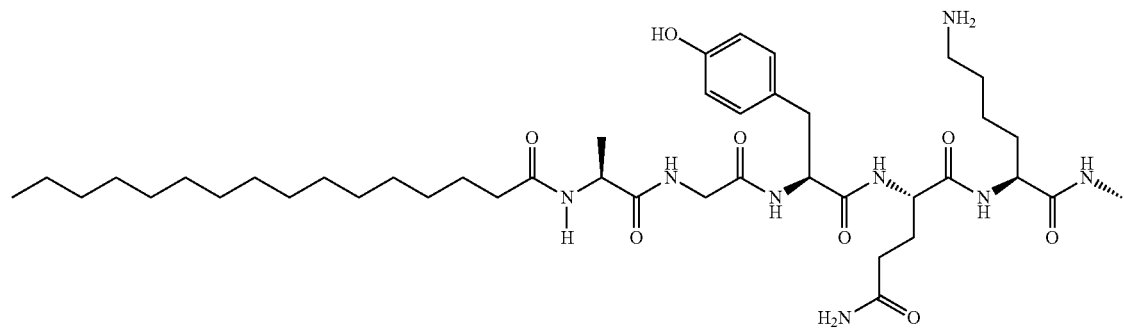

507
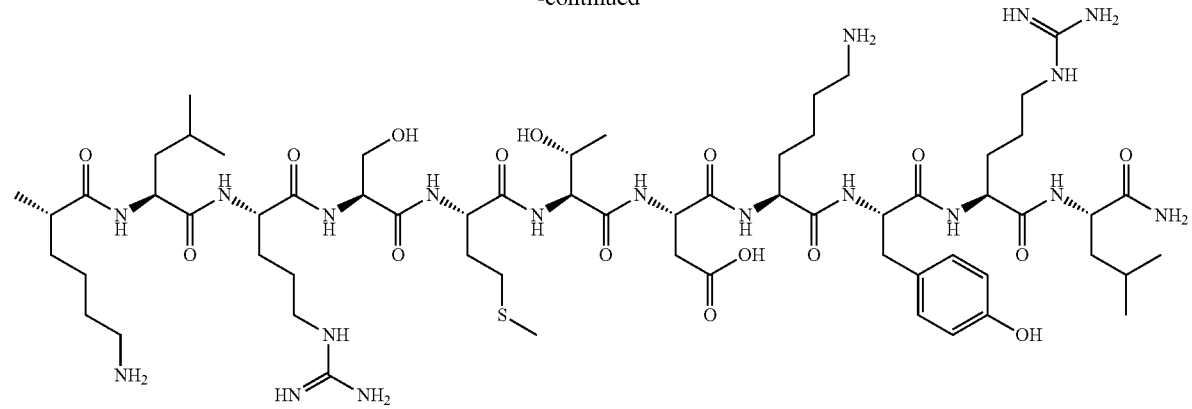
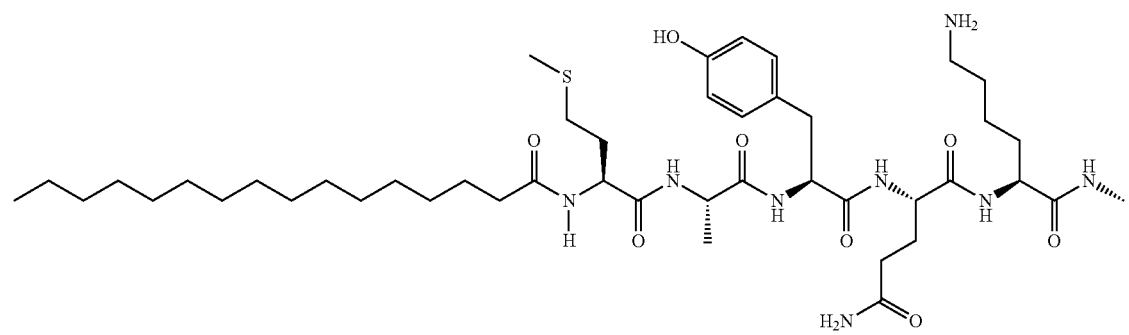
508
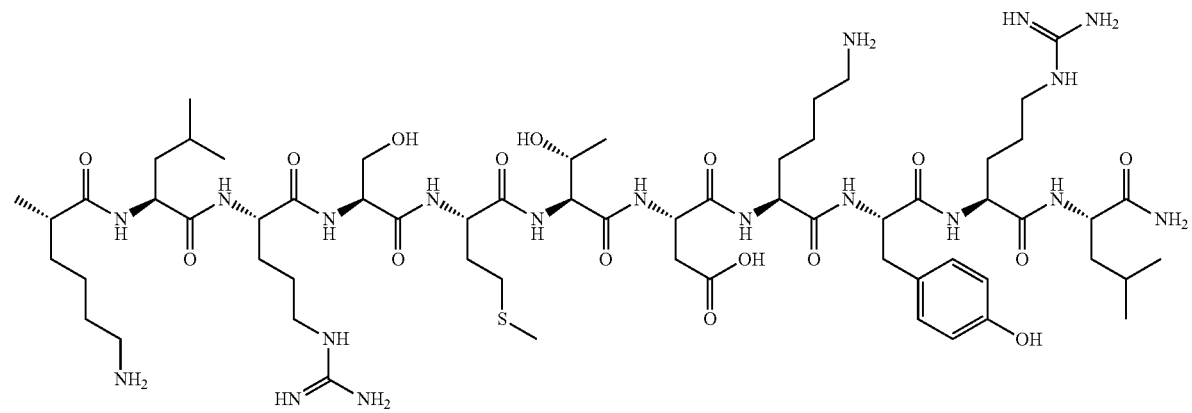
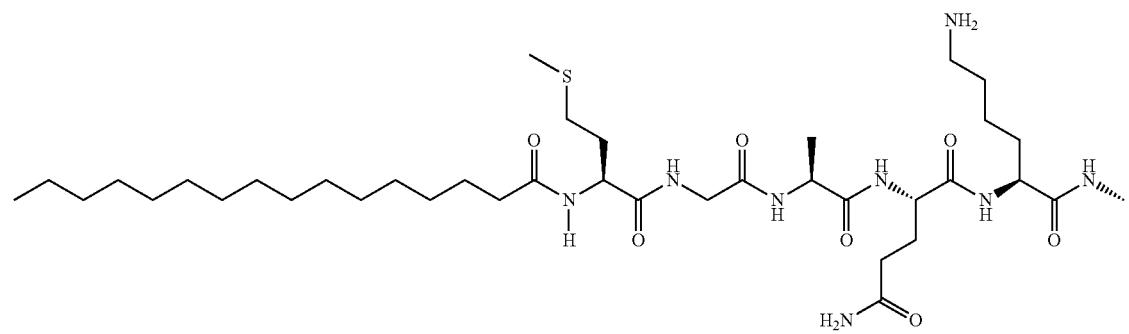

-continued
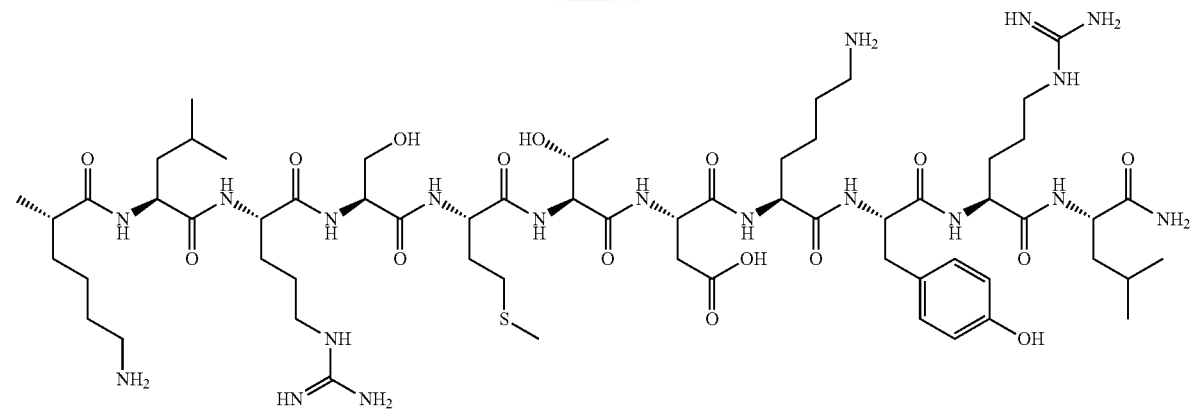
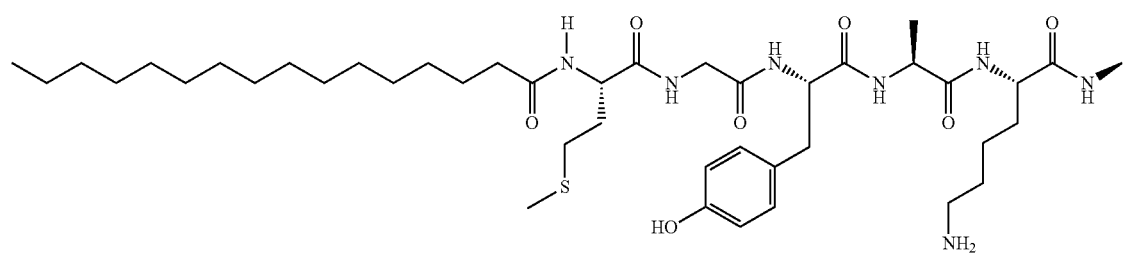
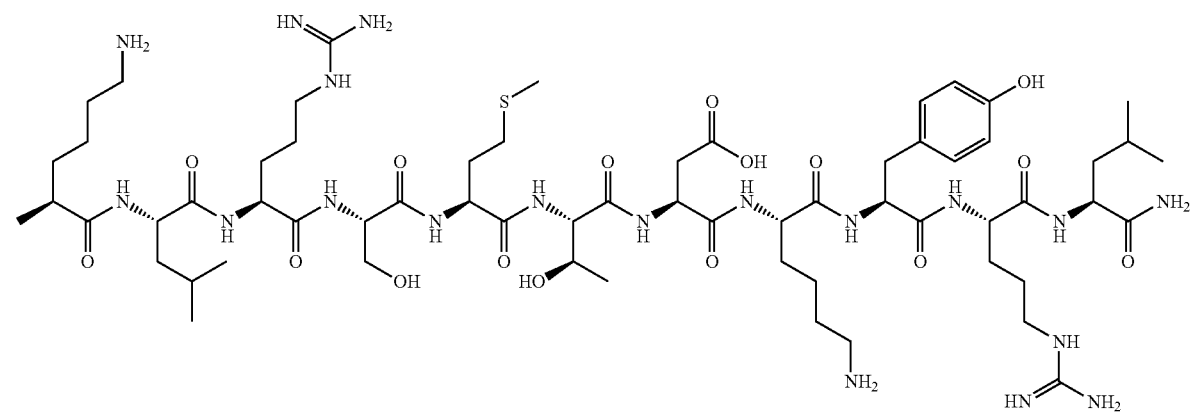
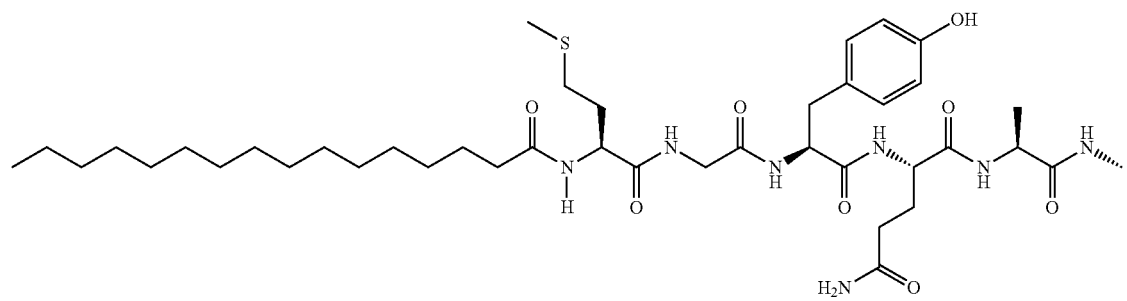

511
512
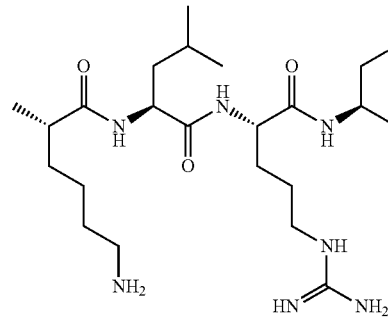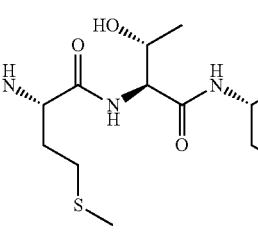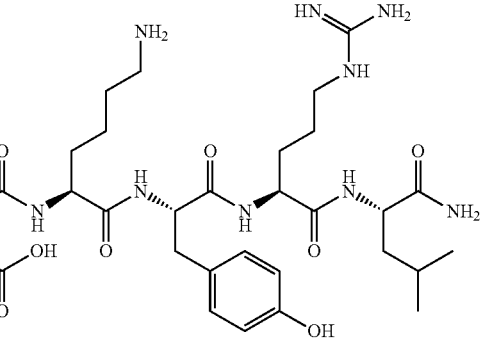
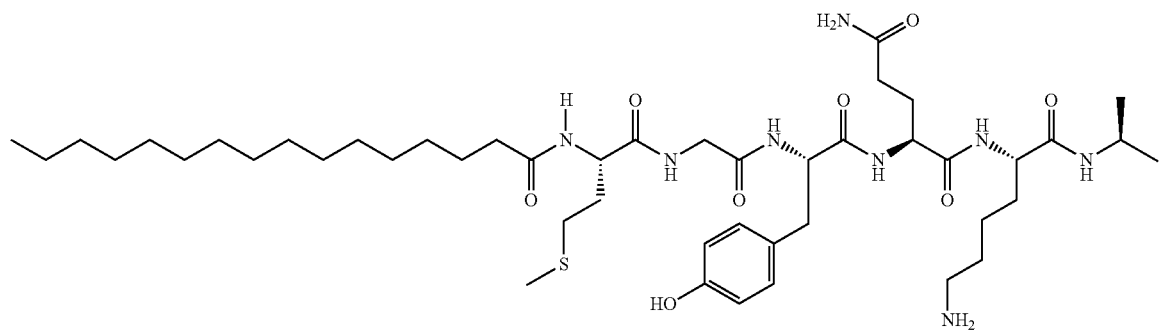
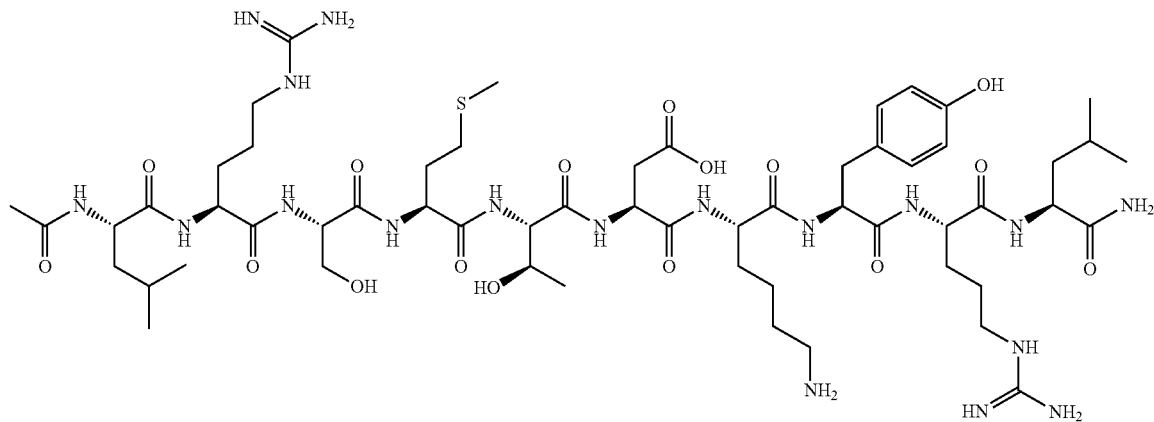
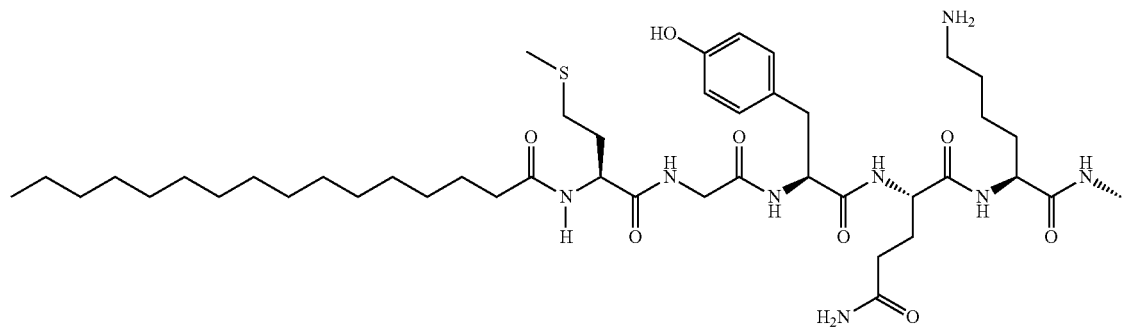

513 514
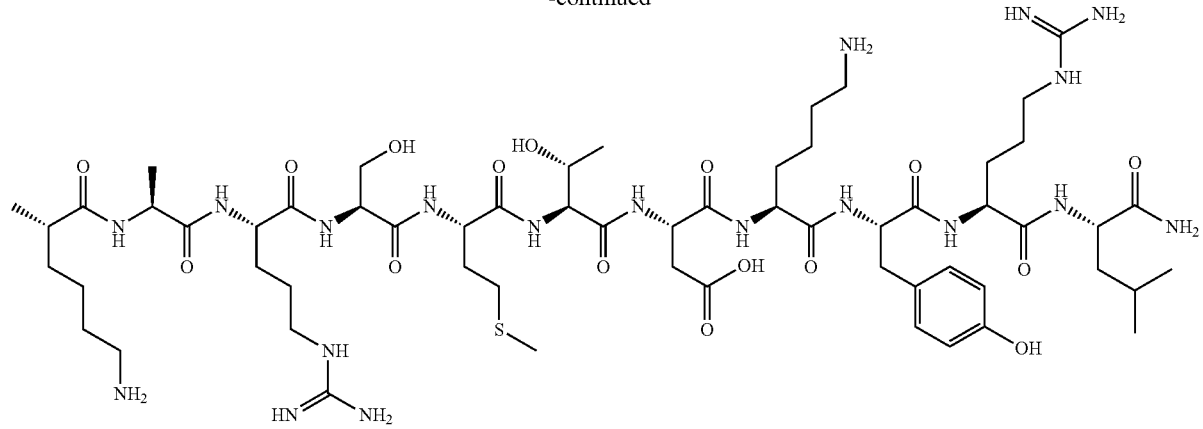
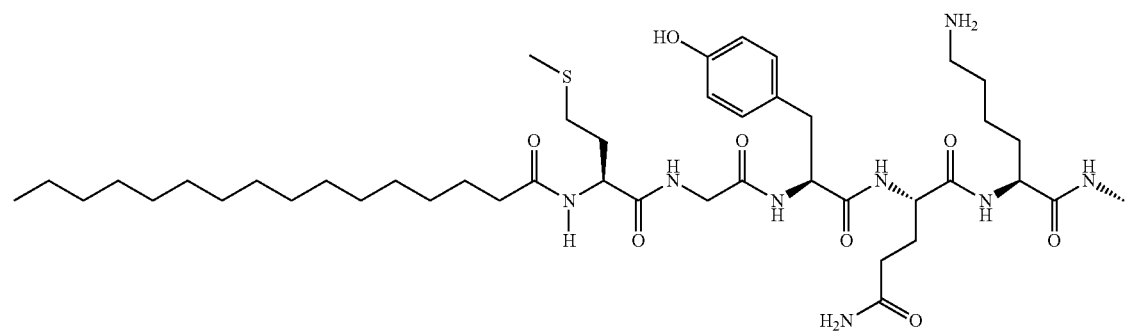
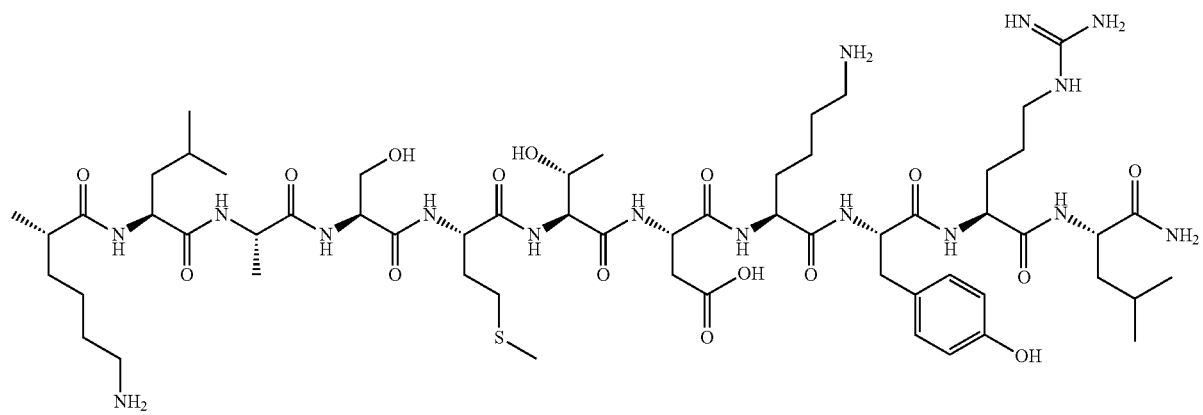
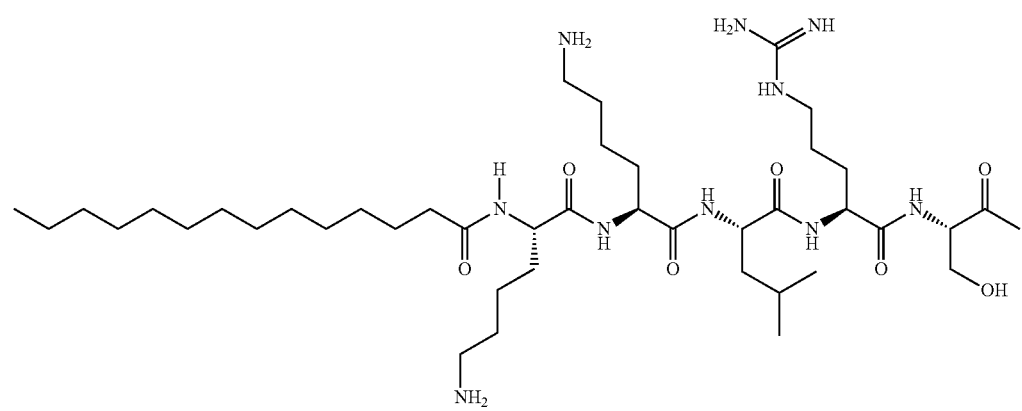

515 516
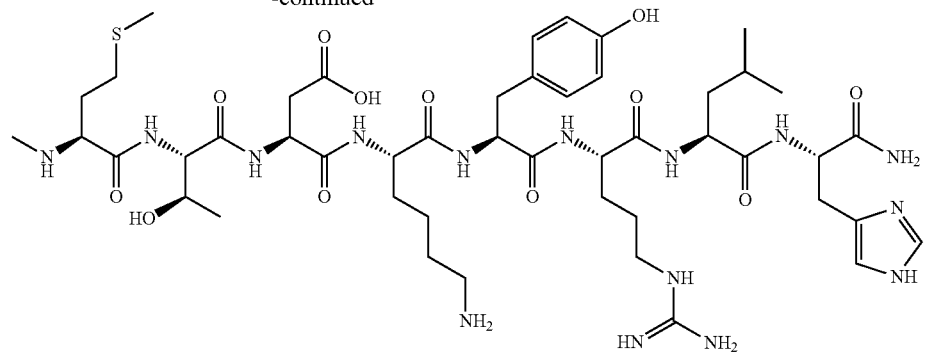
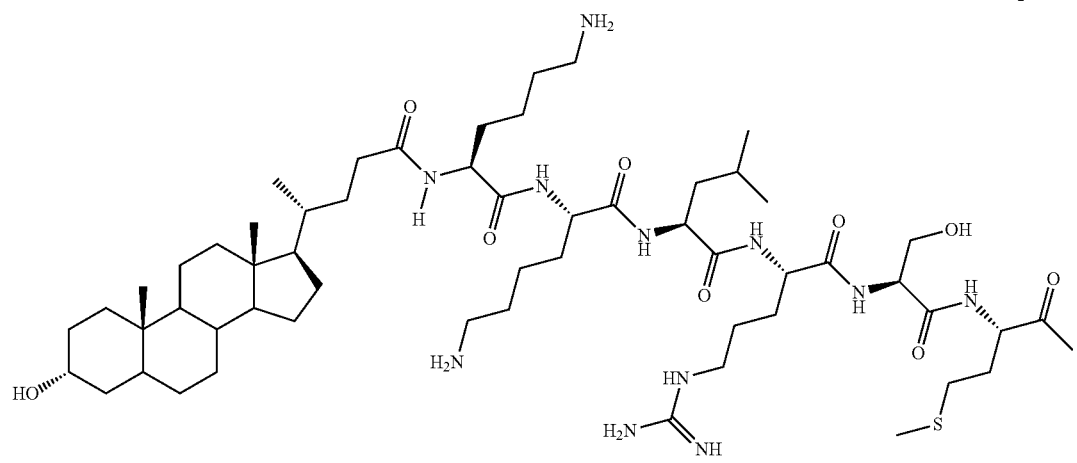
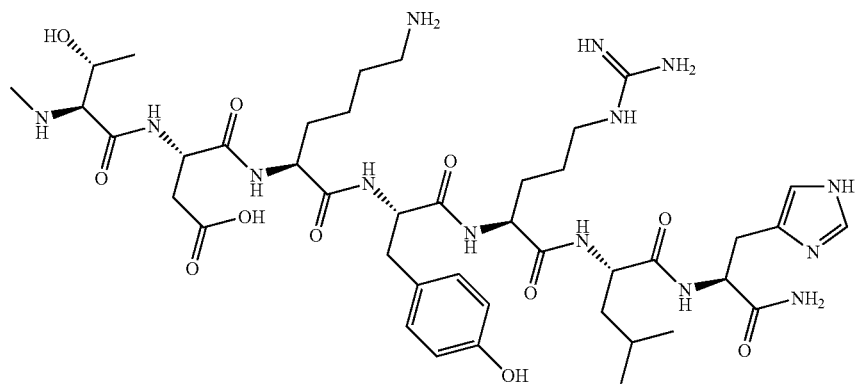
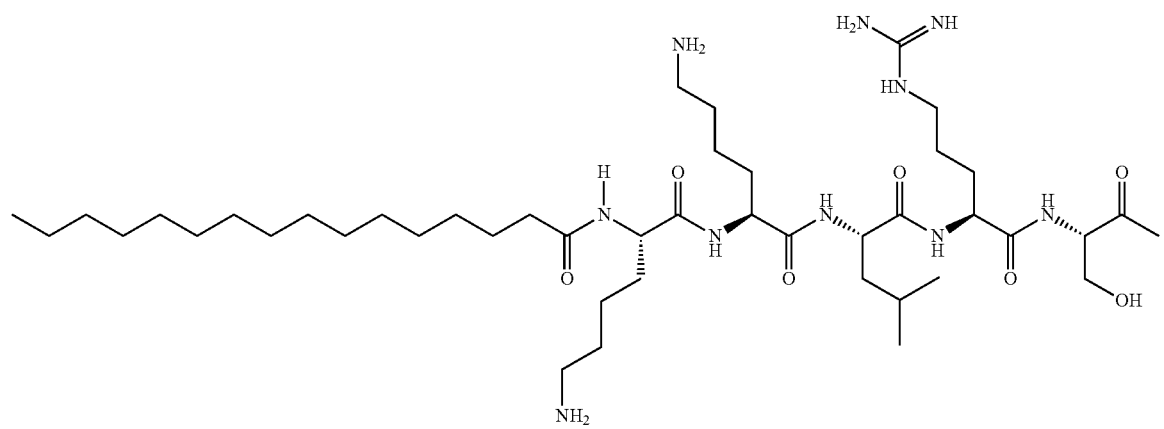

517
-continued
518
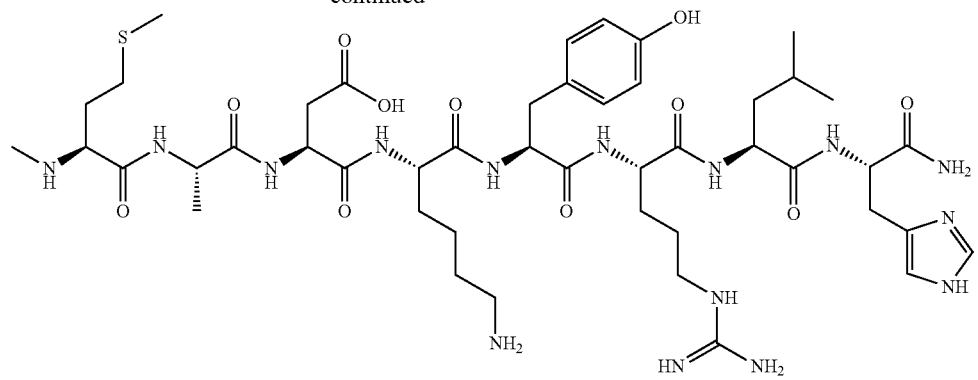
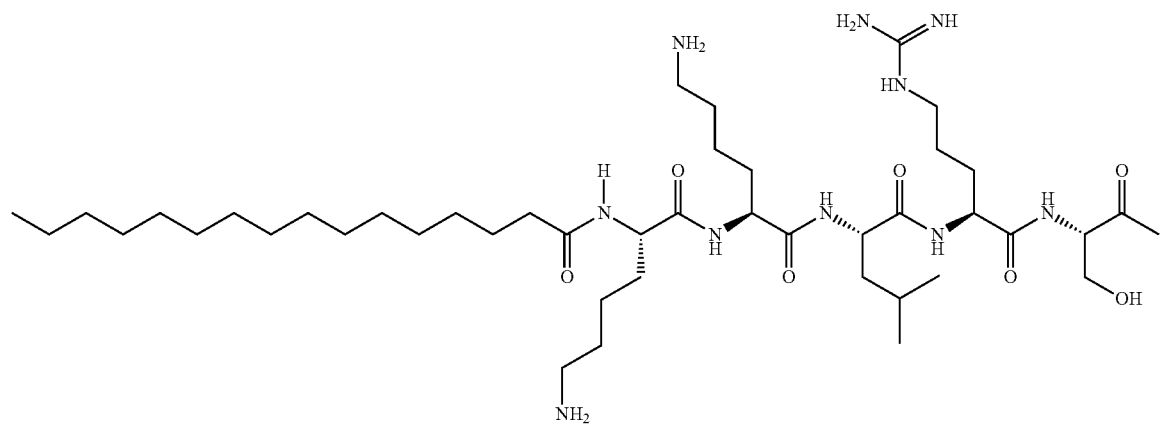
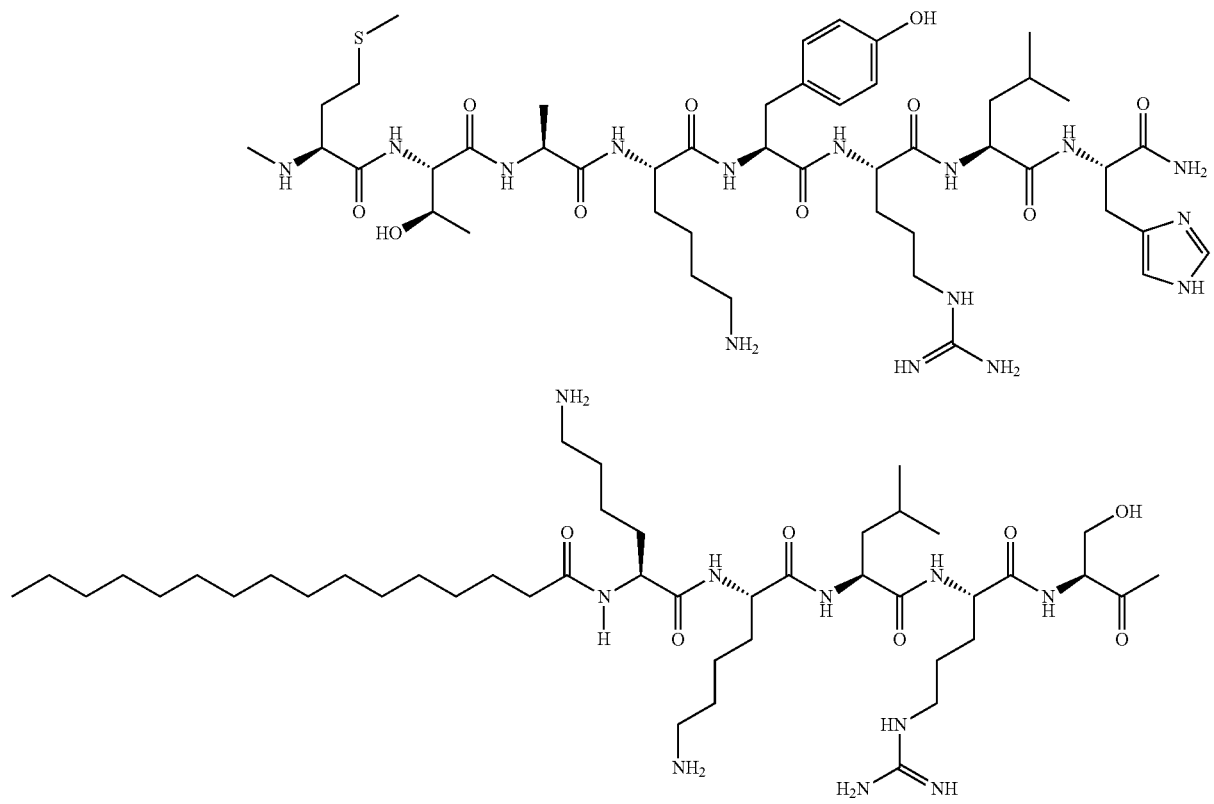

519            520
-continued
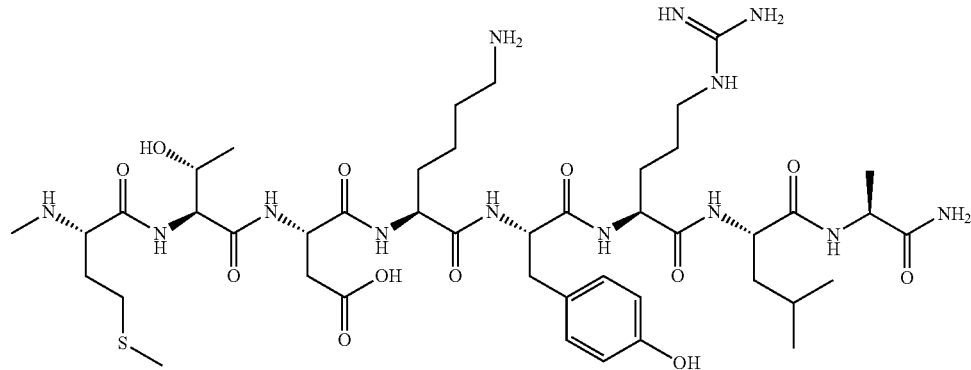
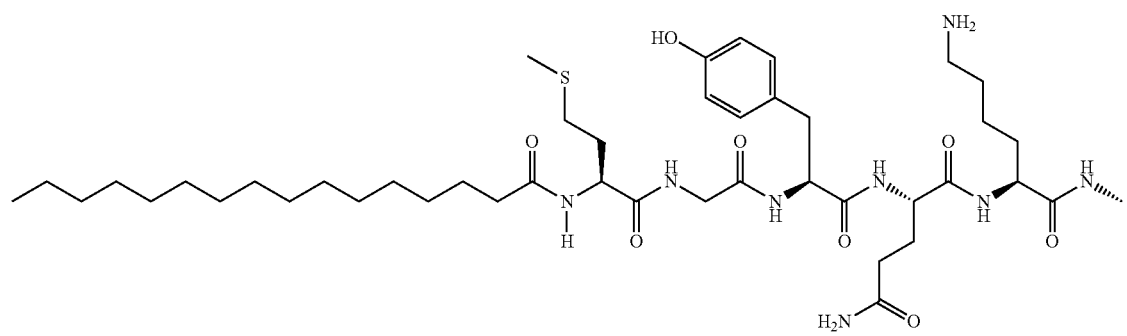
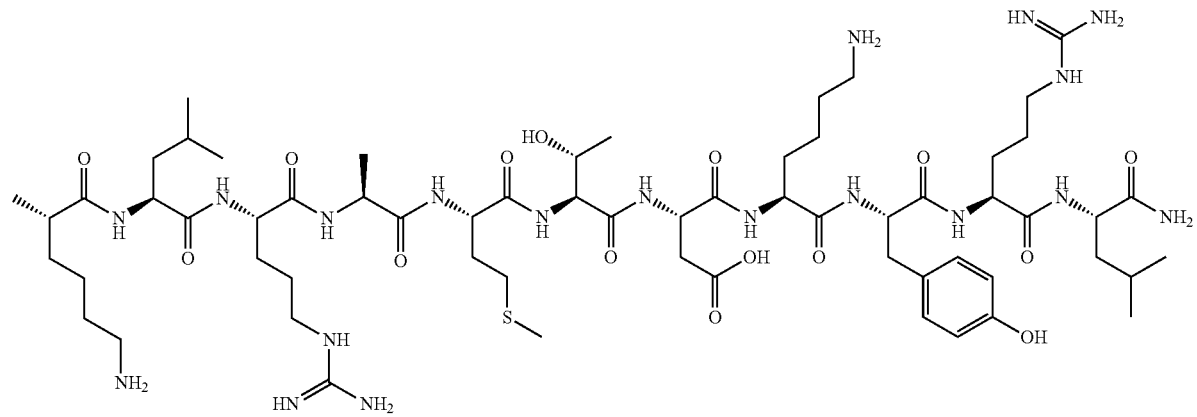
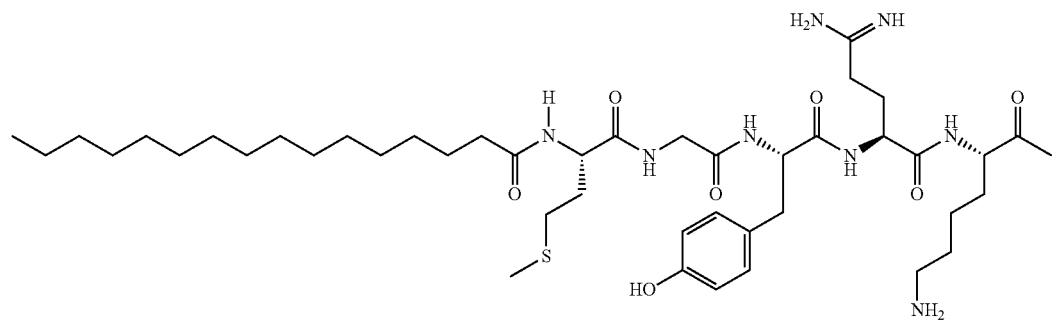

521                                                                    522
-continued
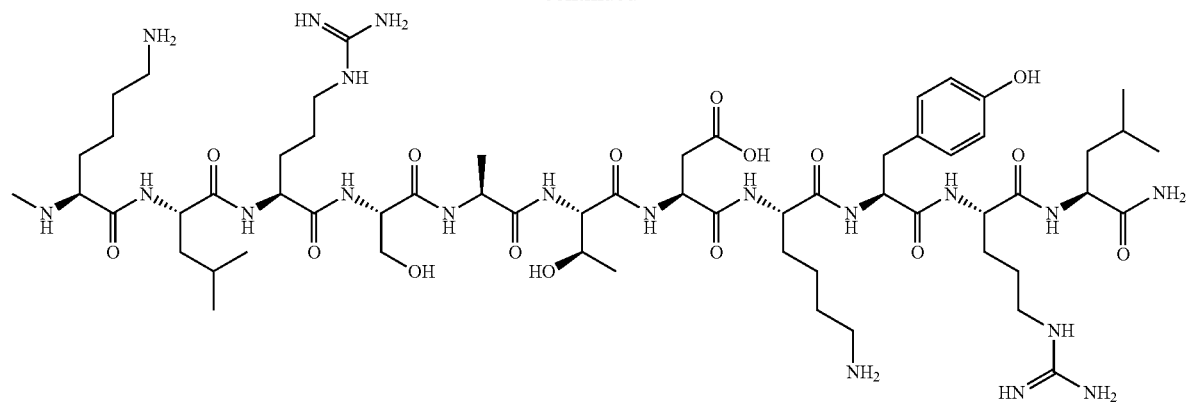
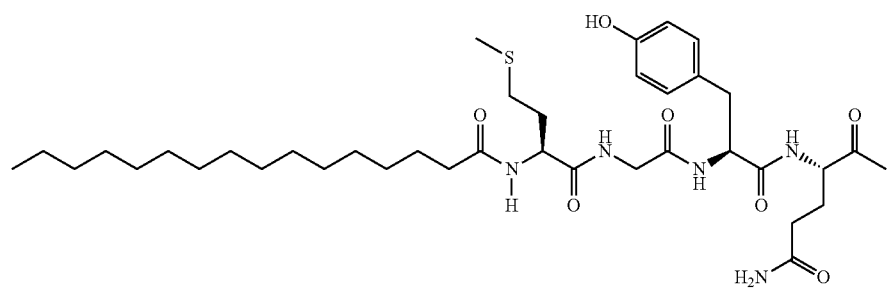
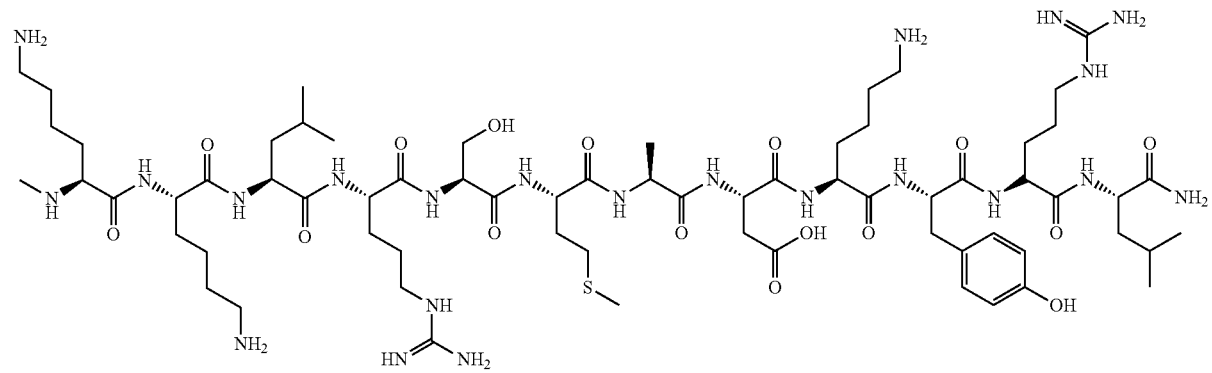
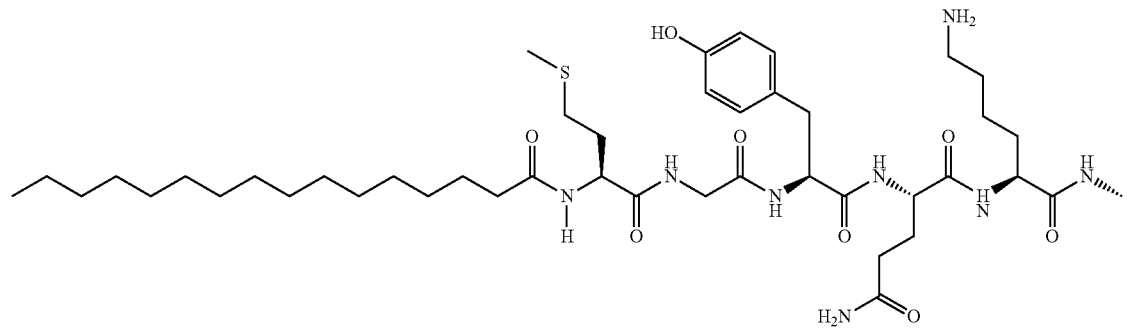

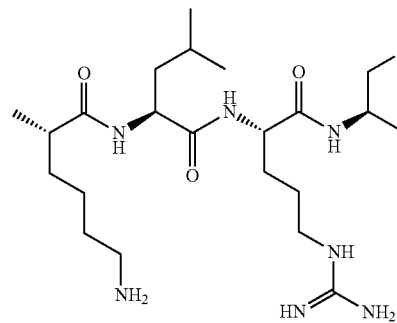
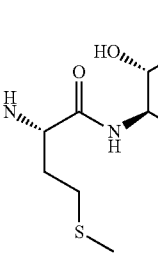
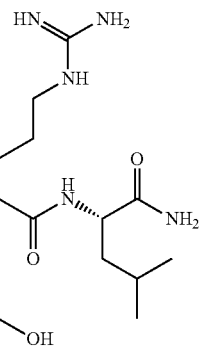
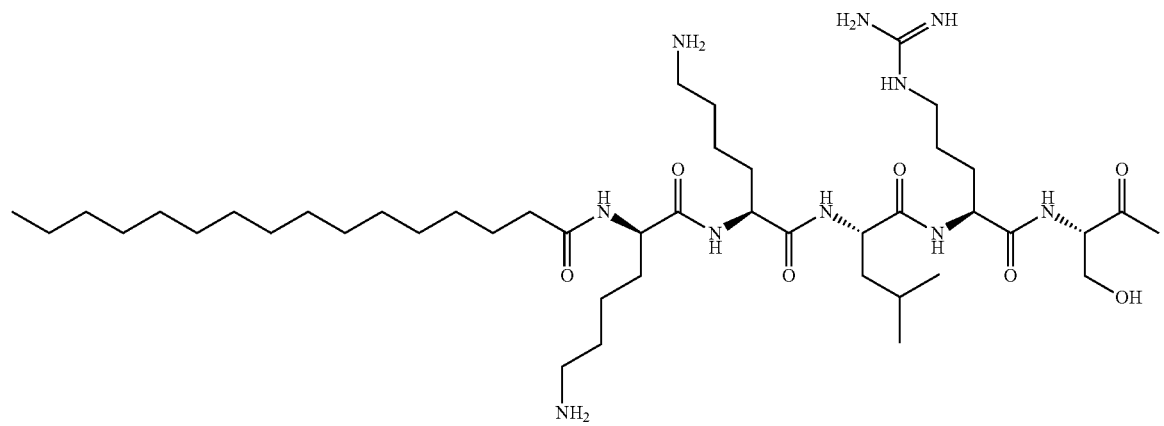
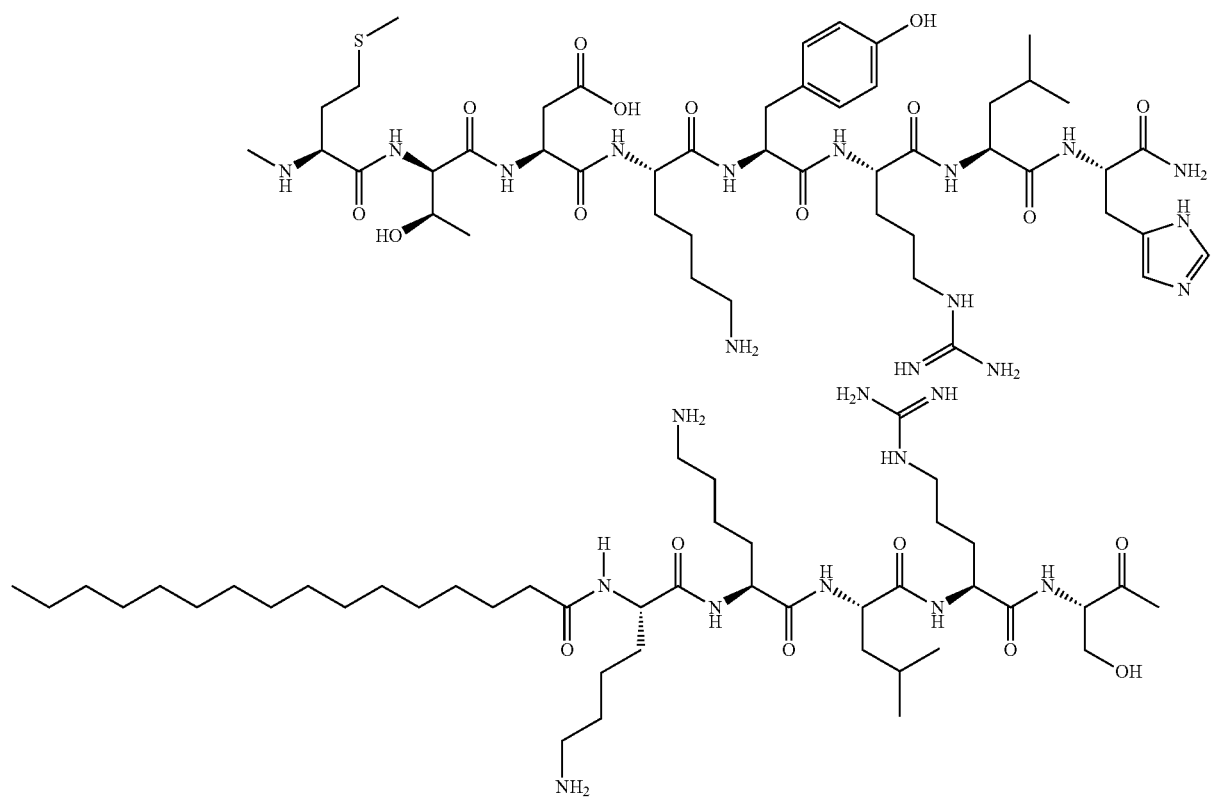

525
526
-continued
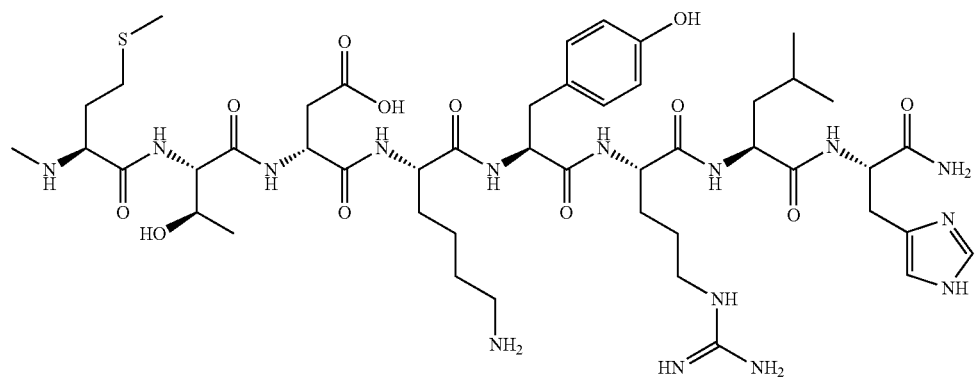
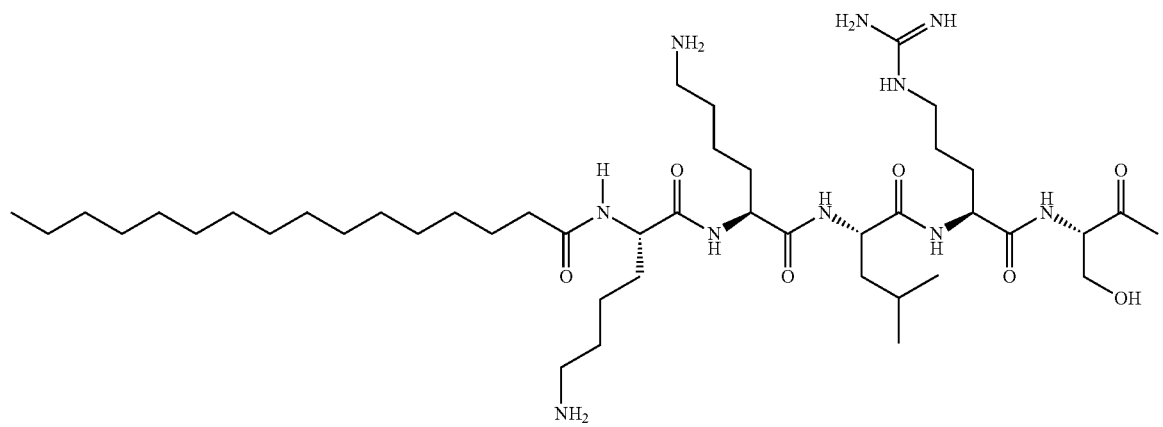
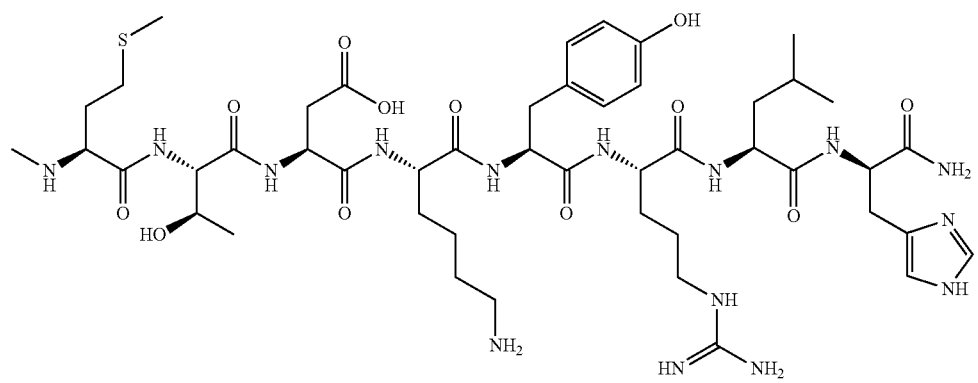
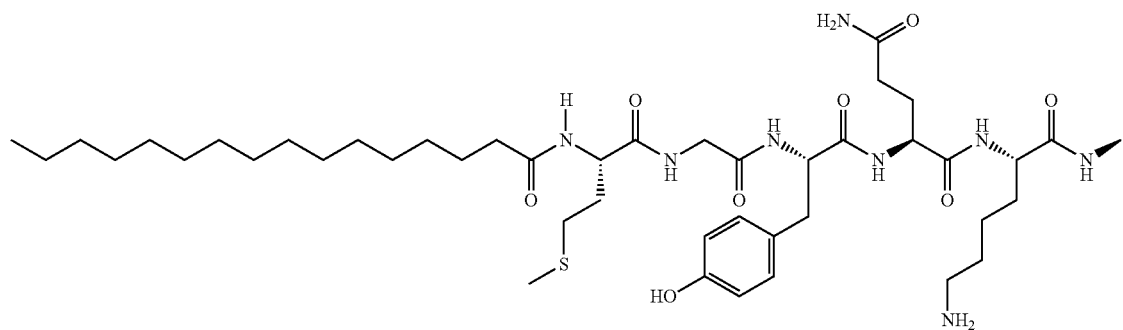

-continued
527
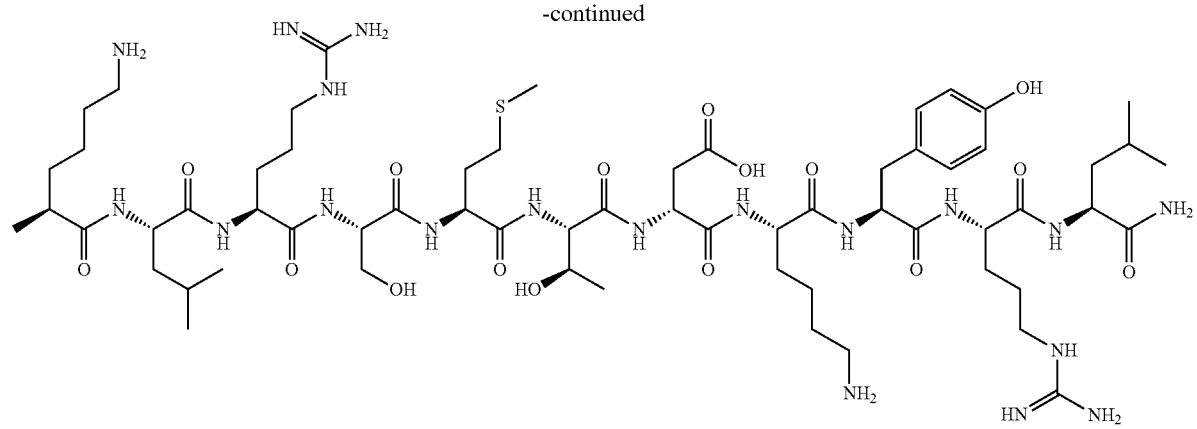
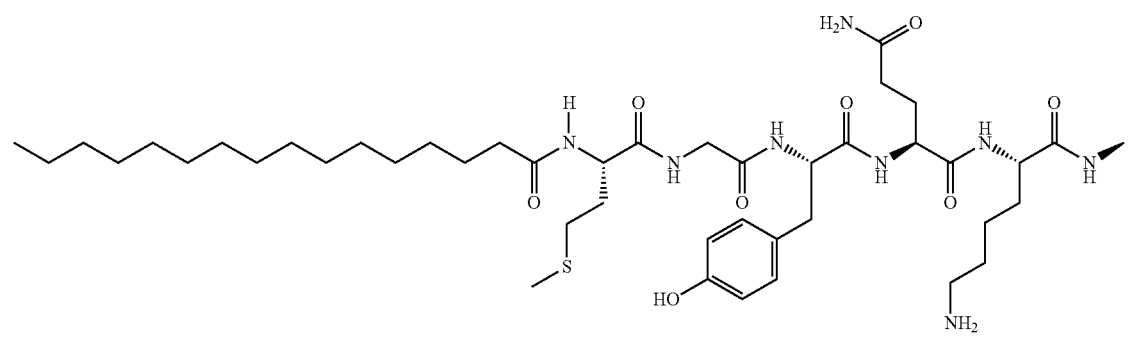
528
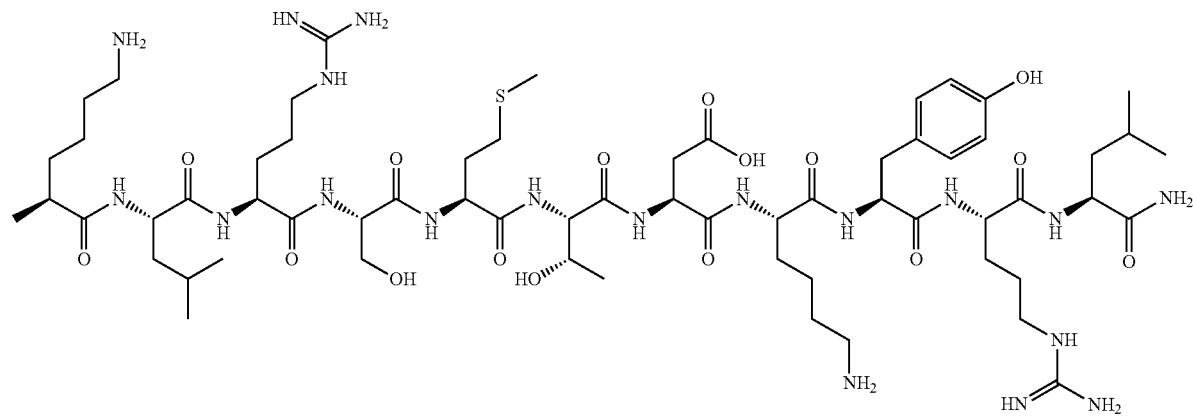
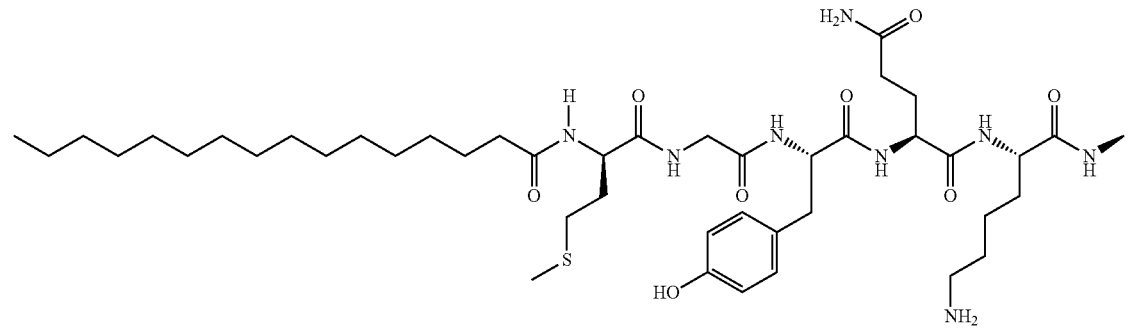

529
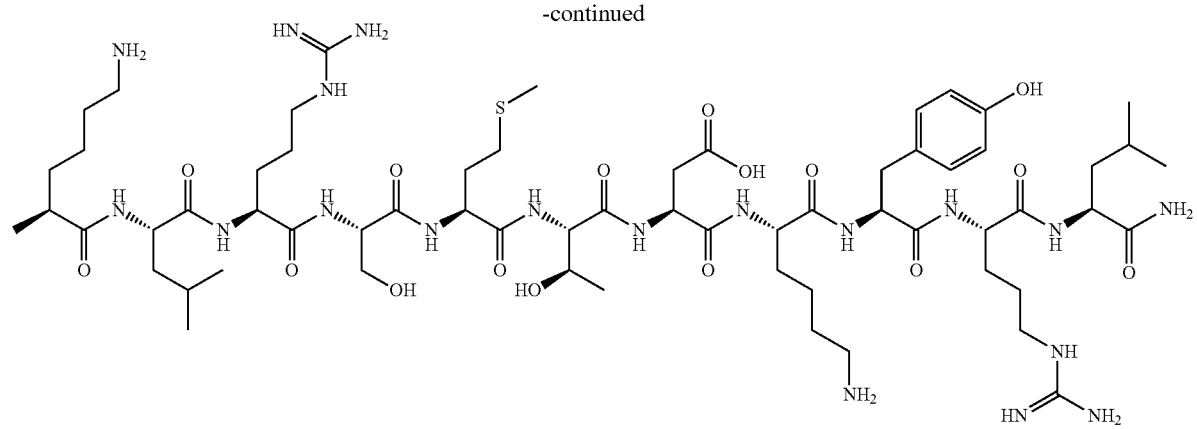
-continued
530
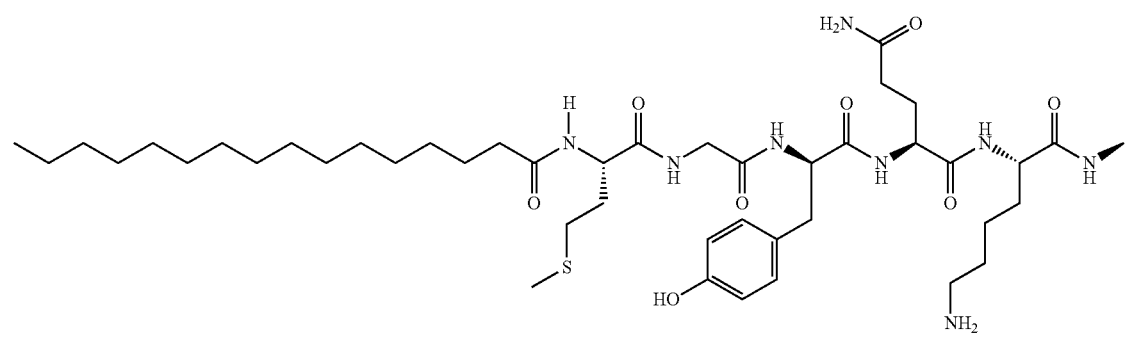
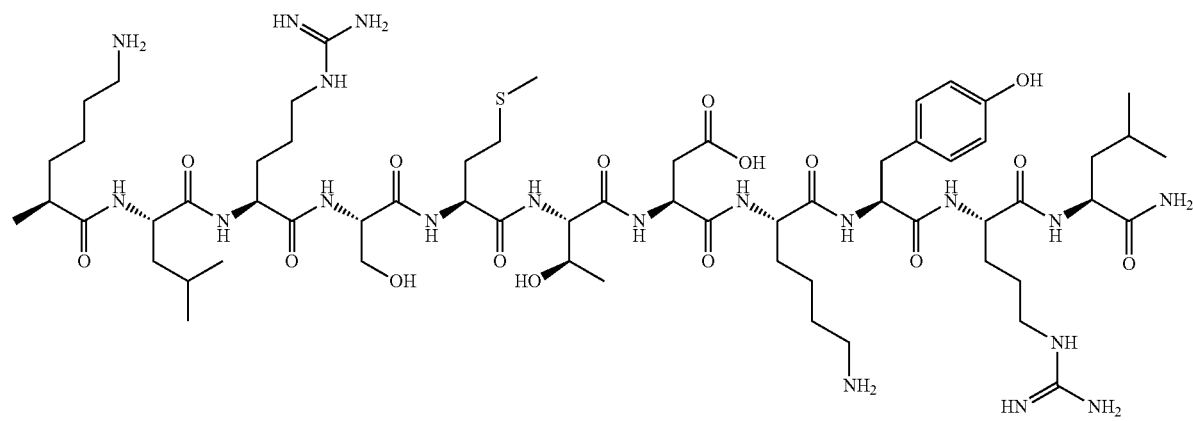
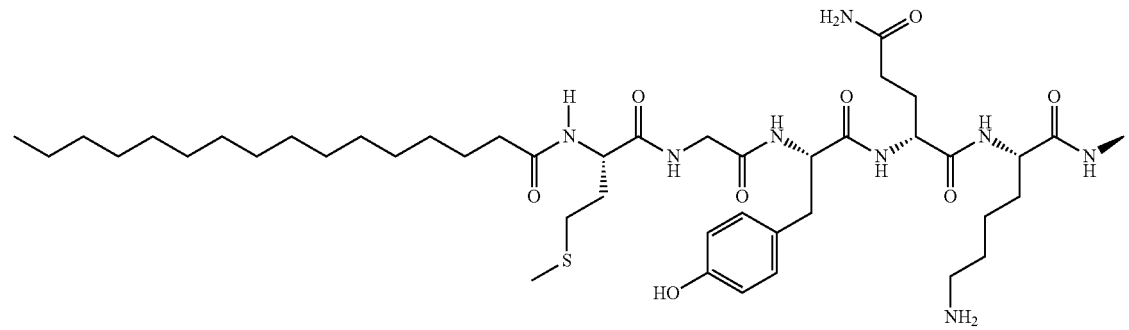

531                                                     532
-continued
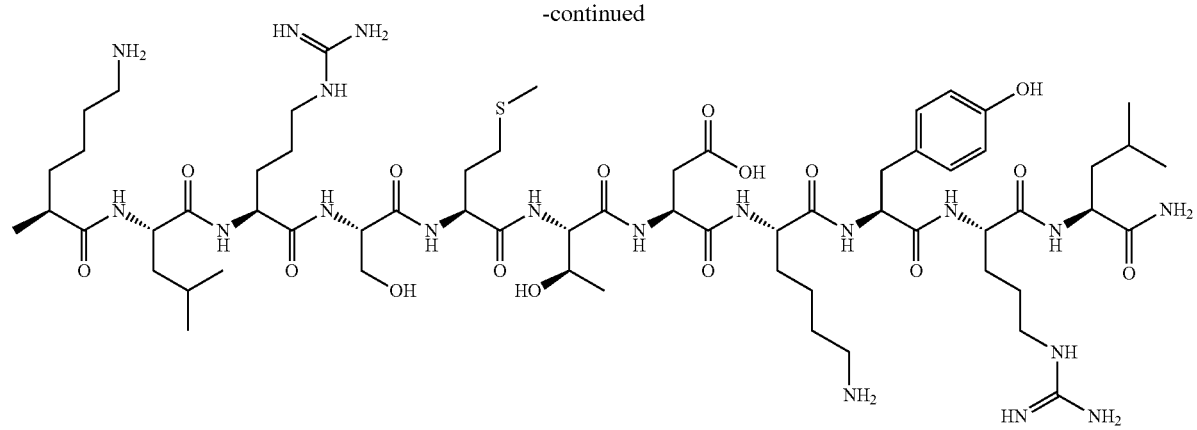
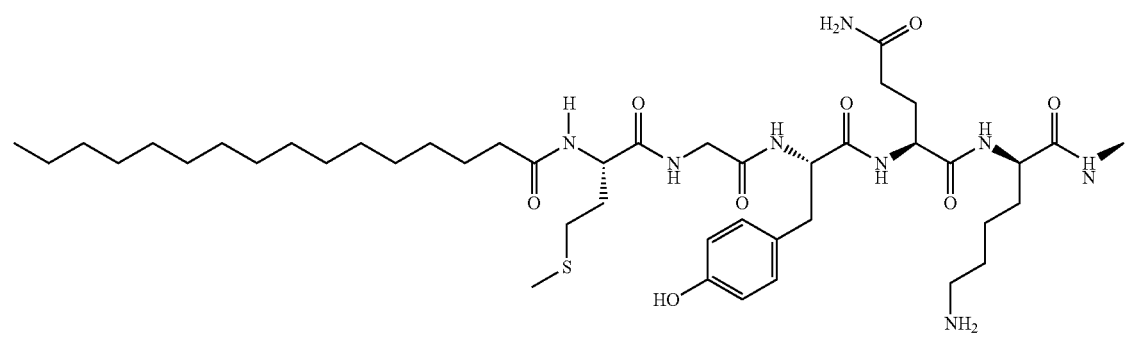
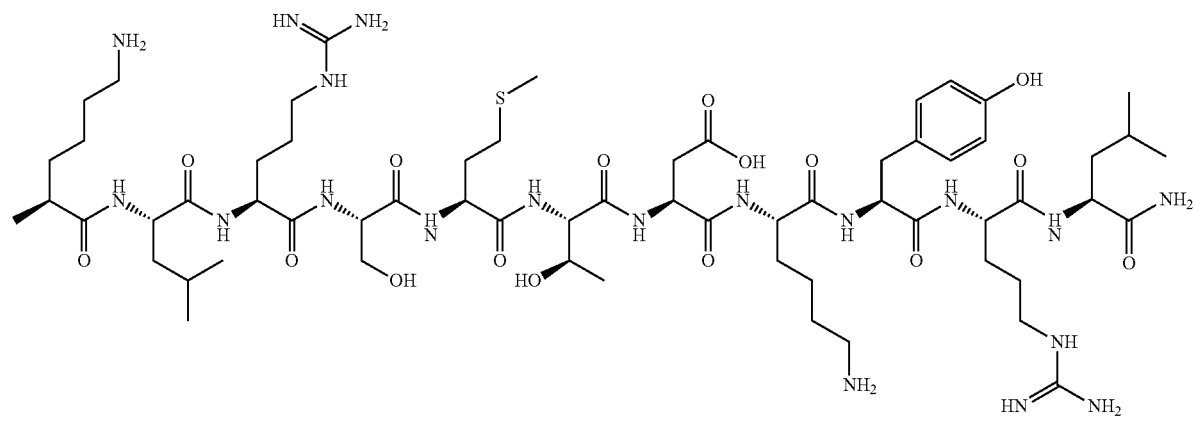
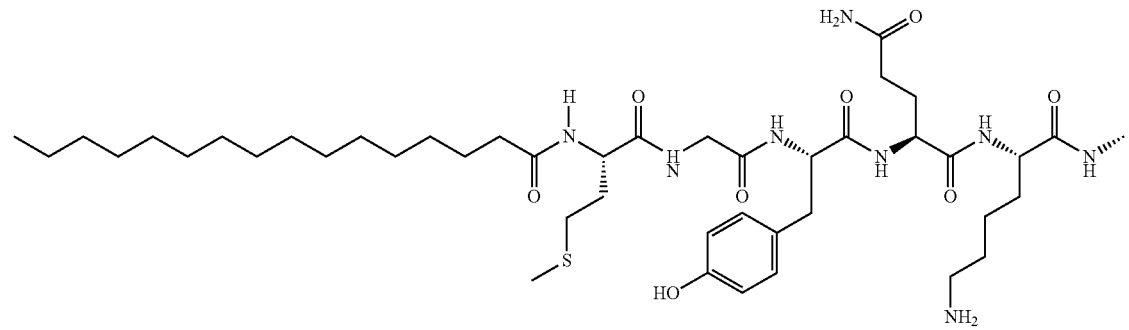

533
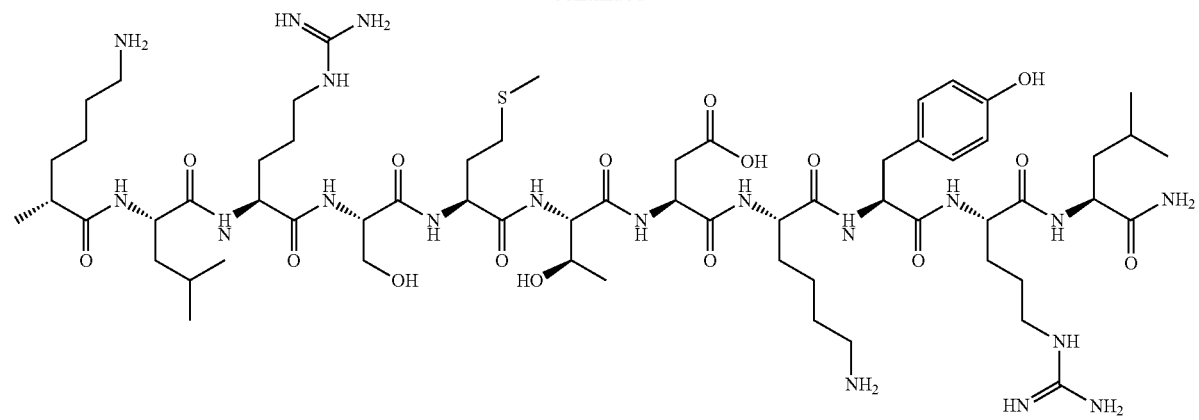
534
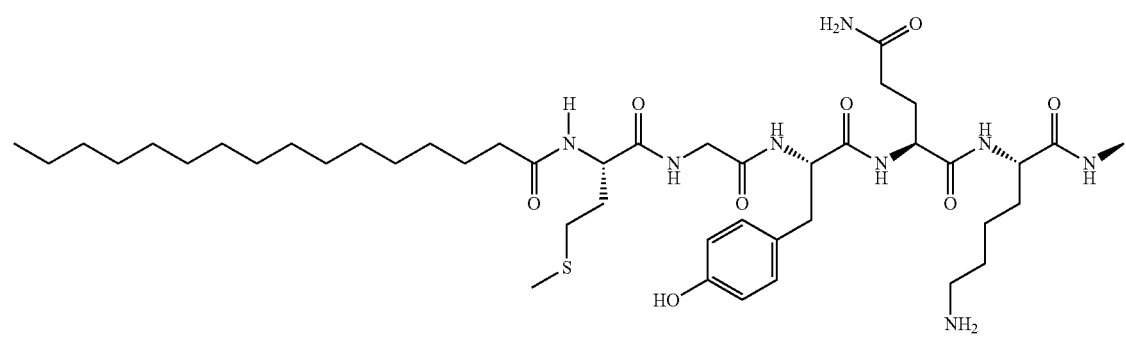
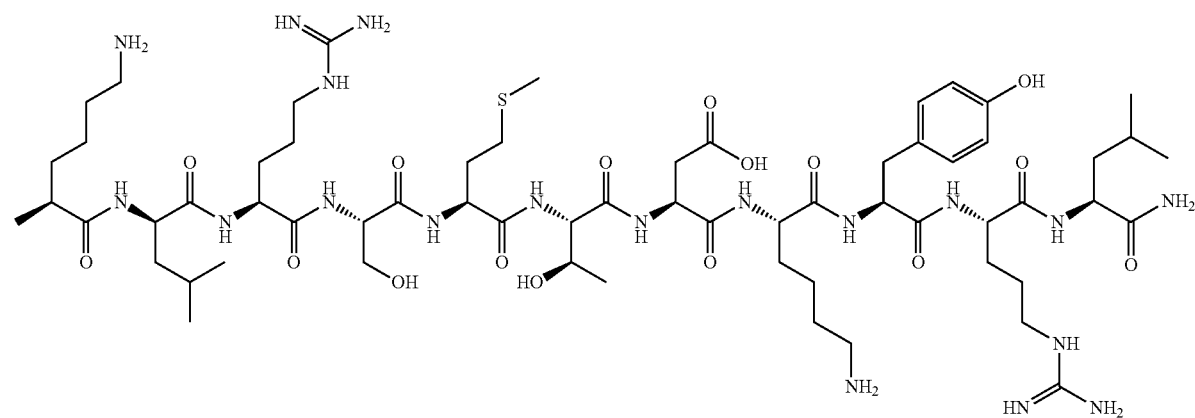

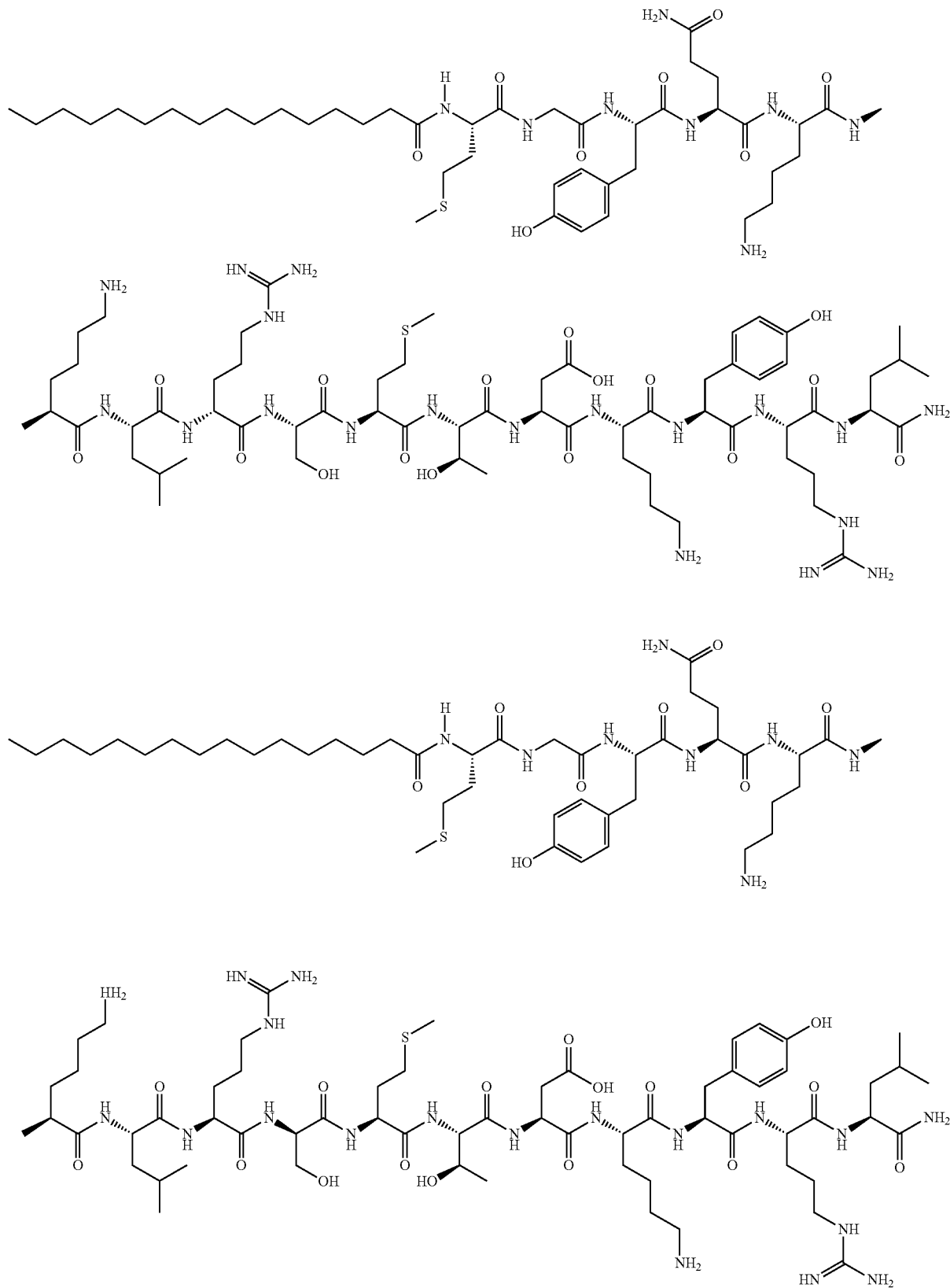

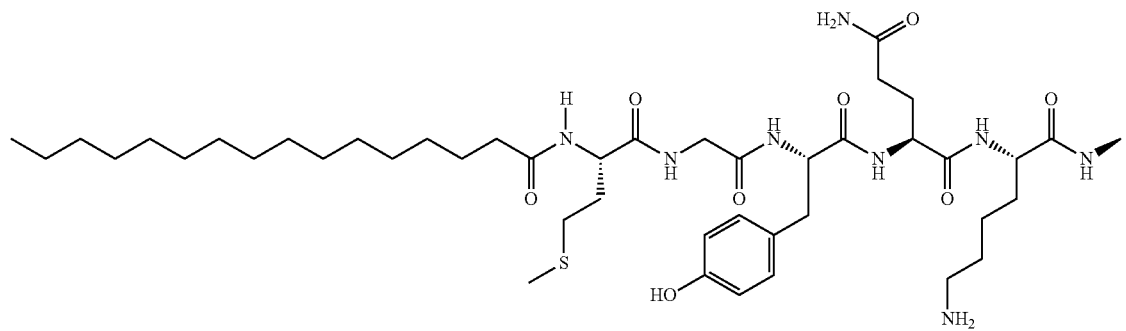
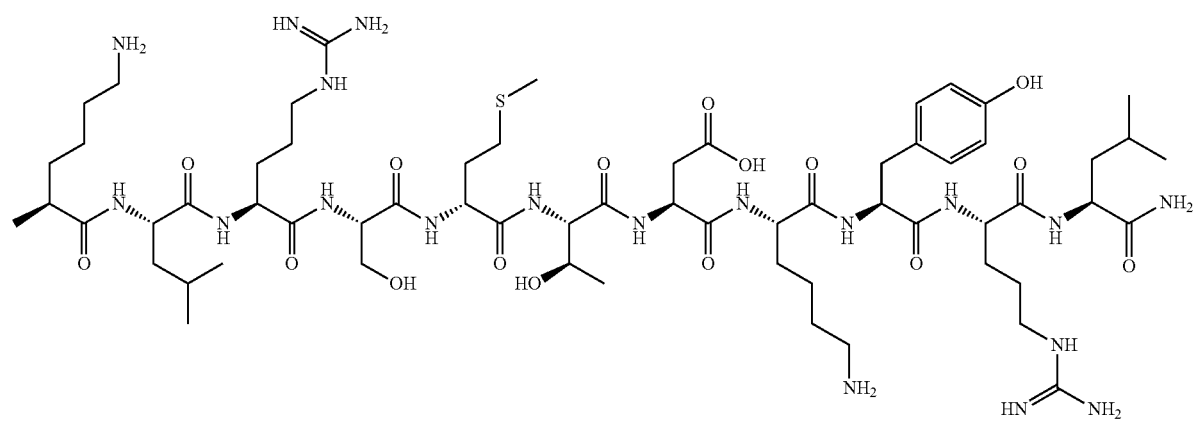
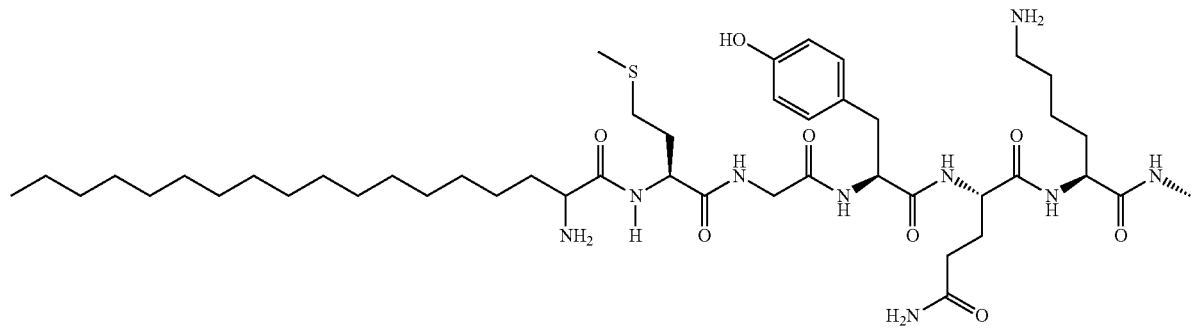

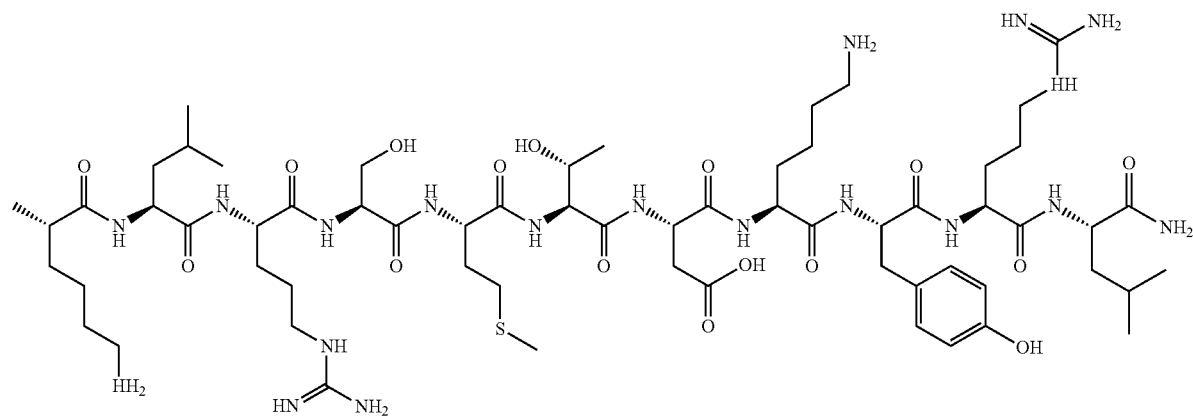
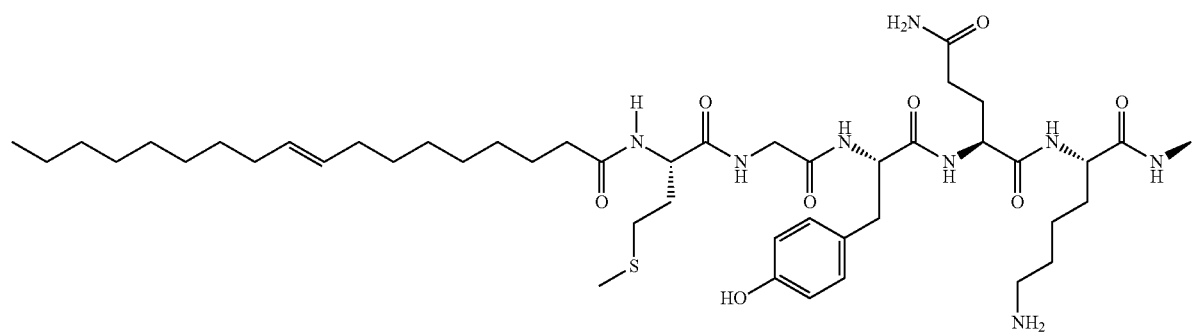
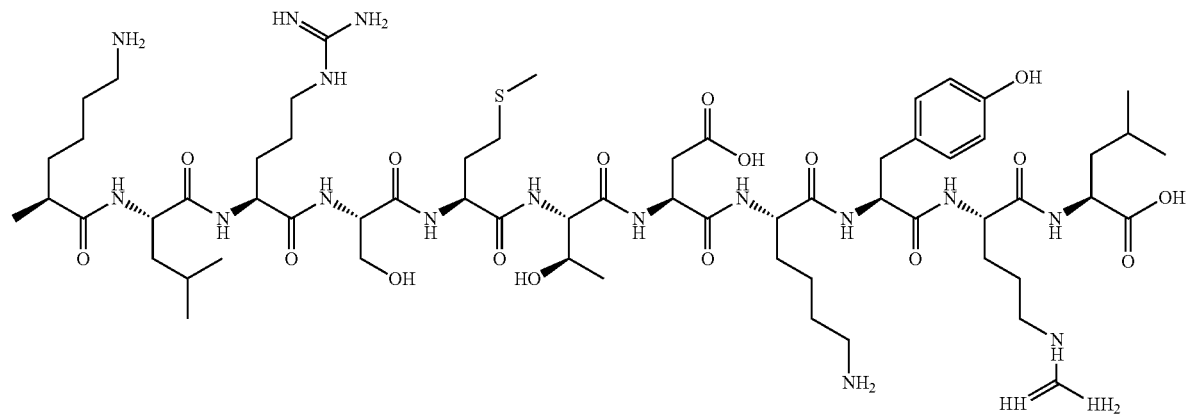

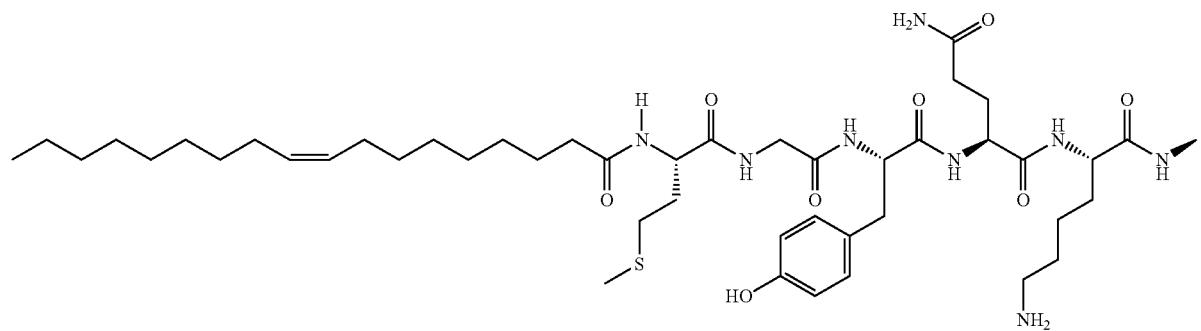
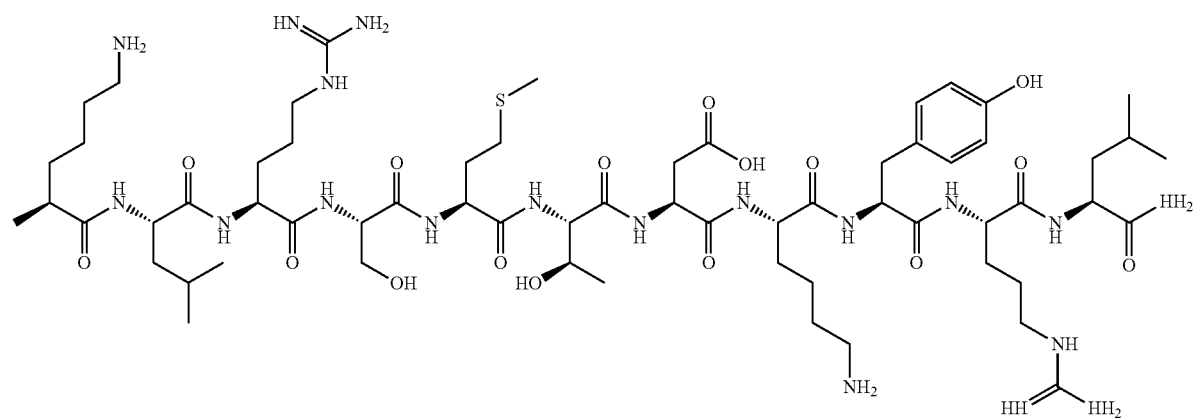
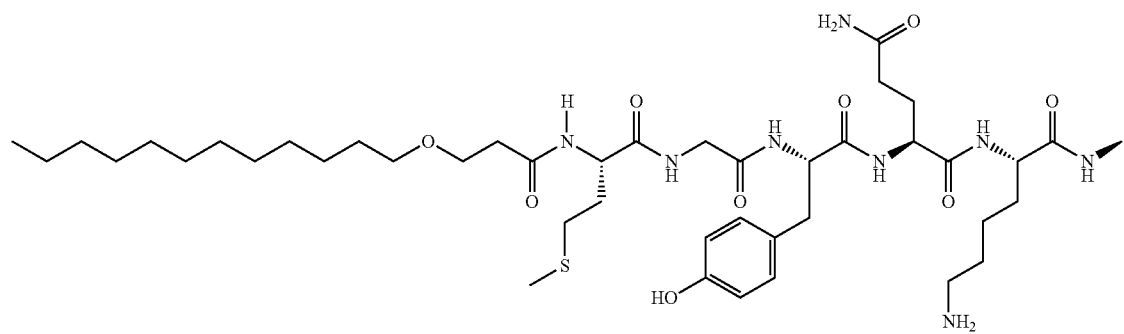

543
544
-continued
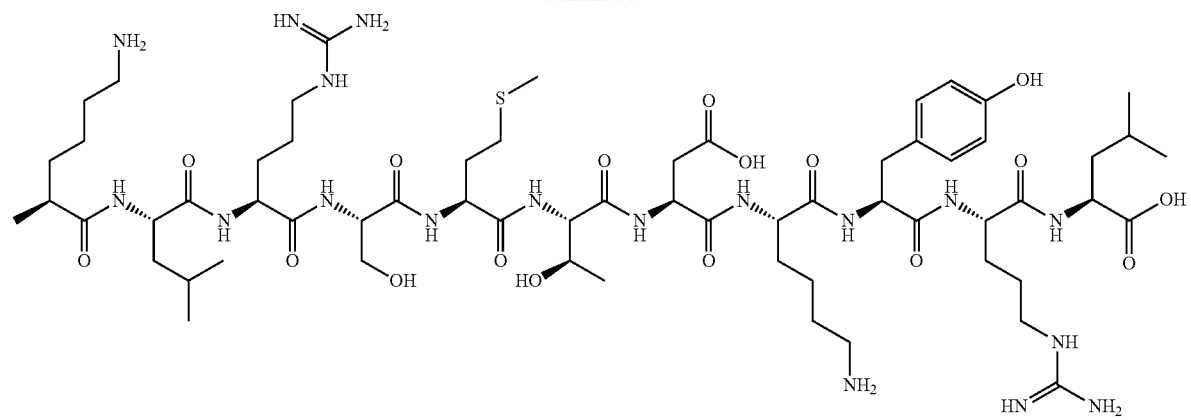
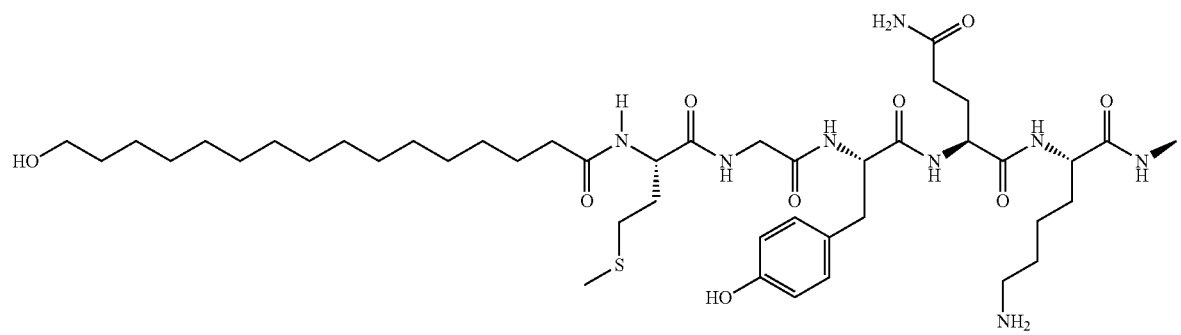
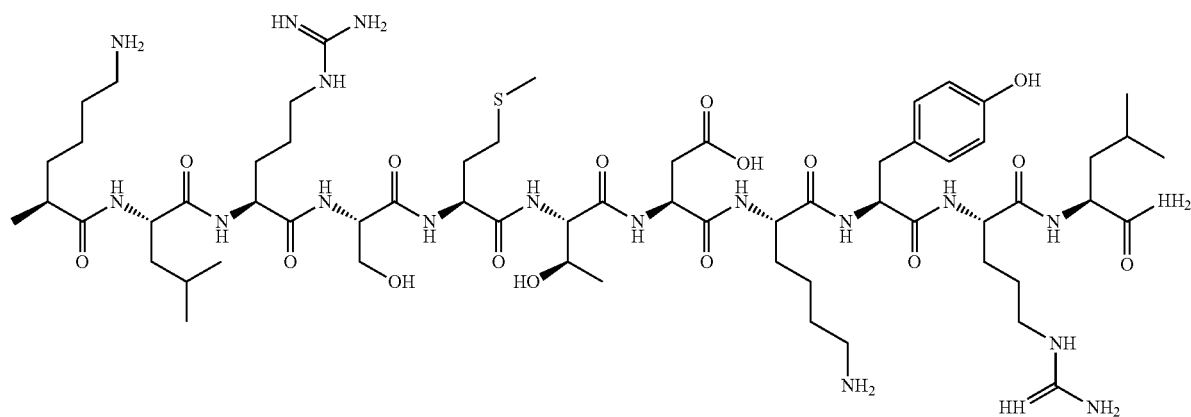

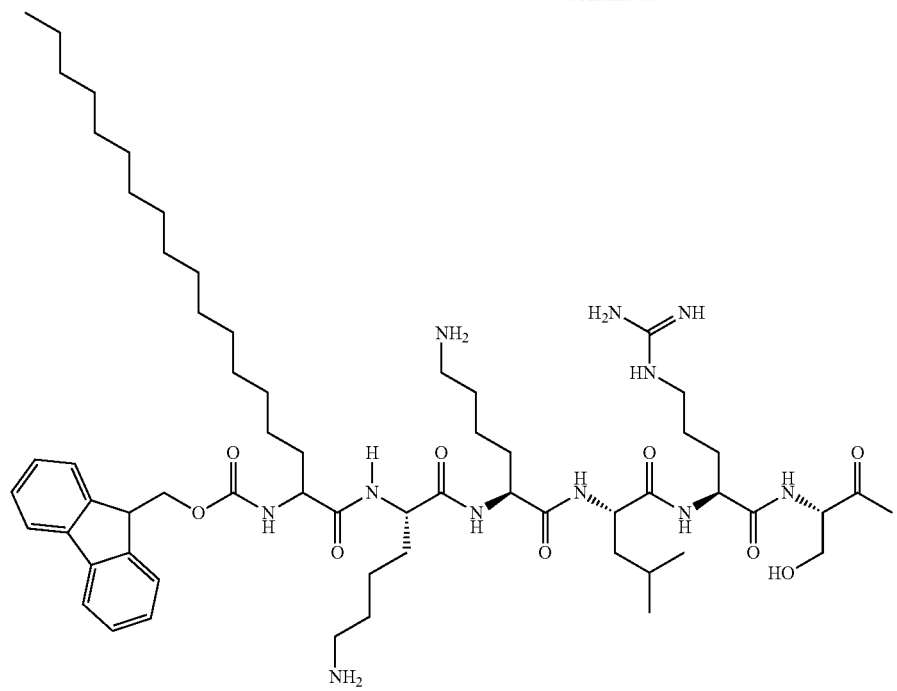
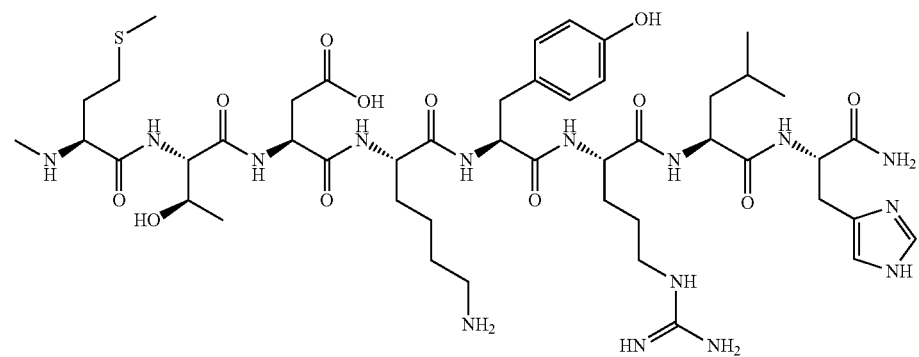
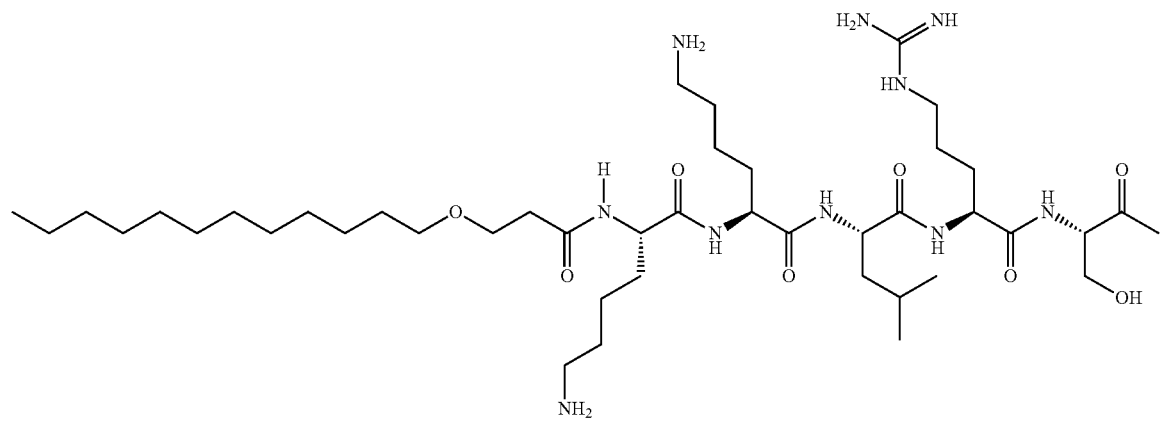

547
-continued
548
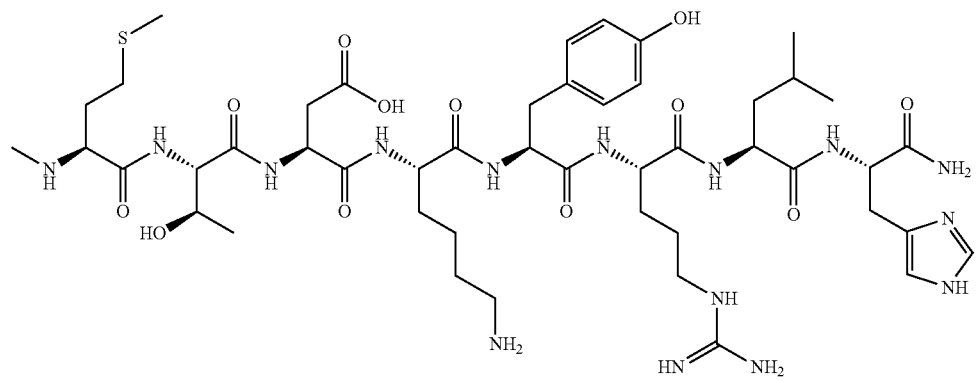
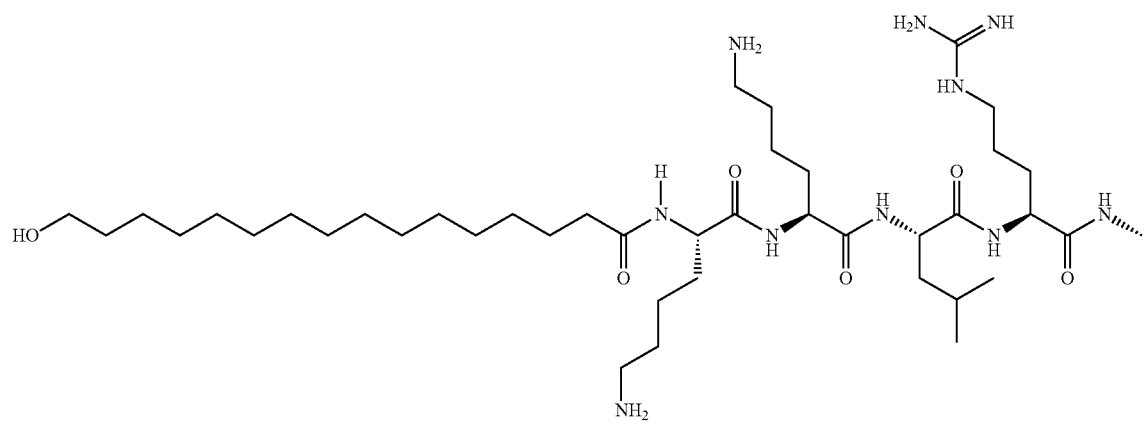
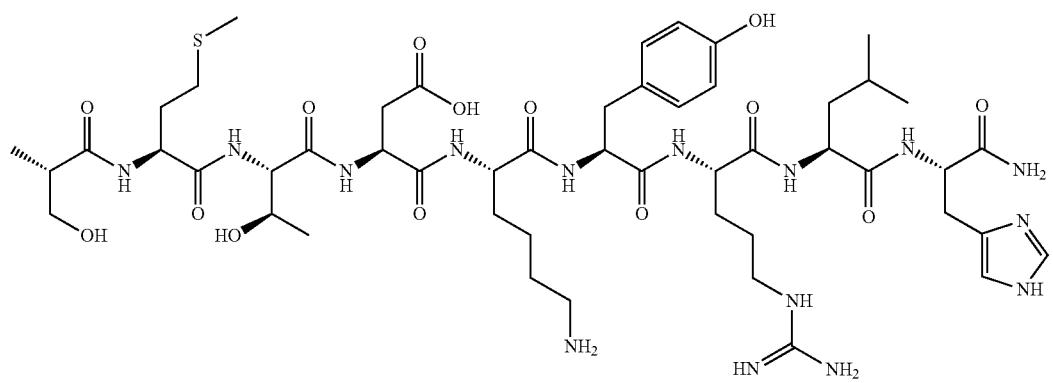

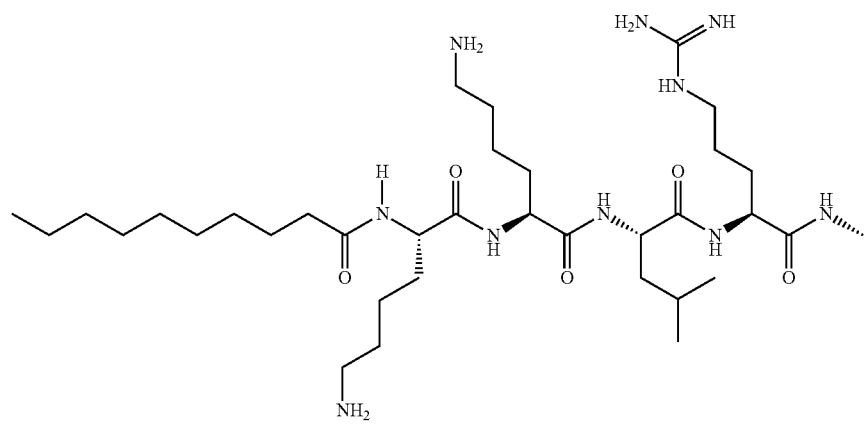
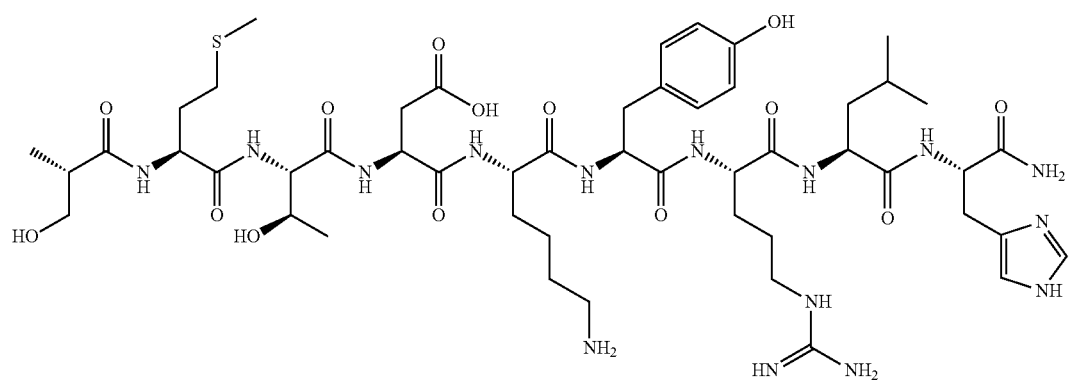
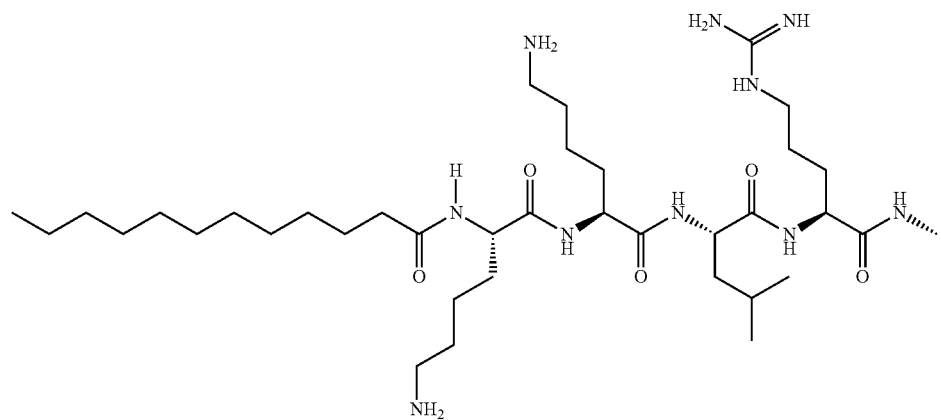

-continued
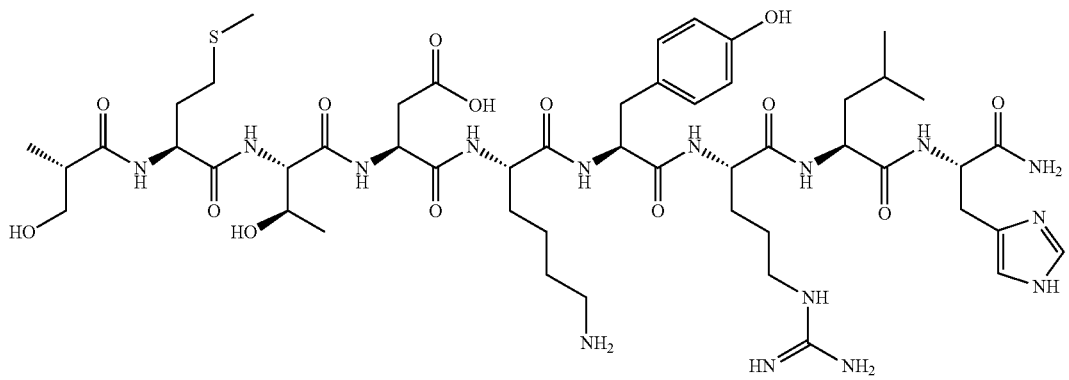
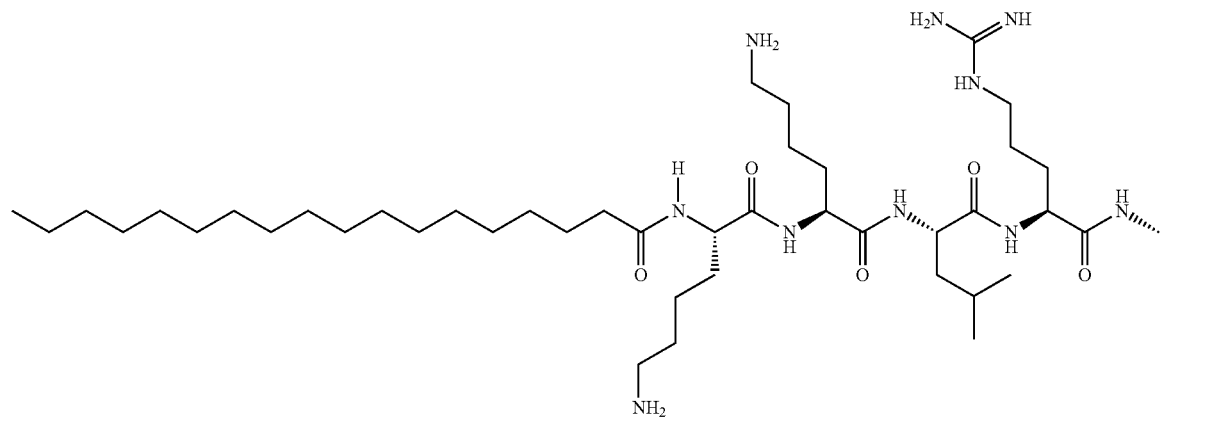
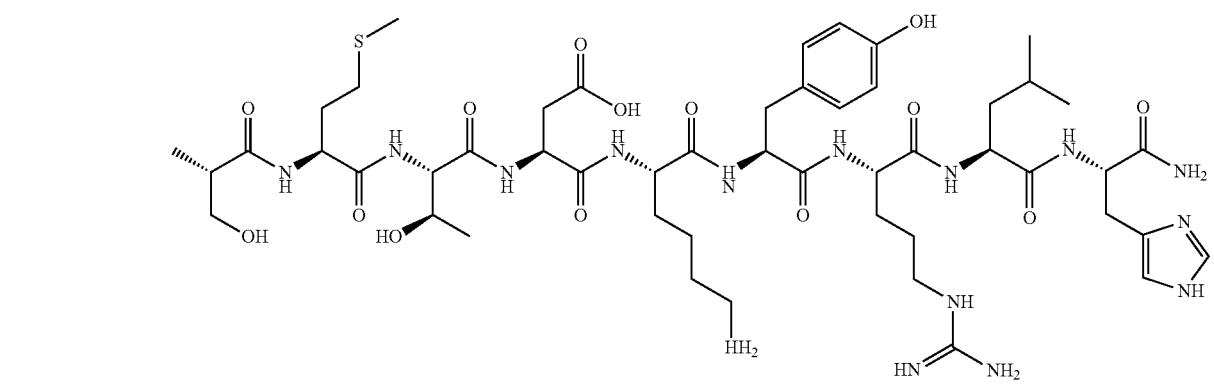
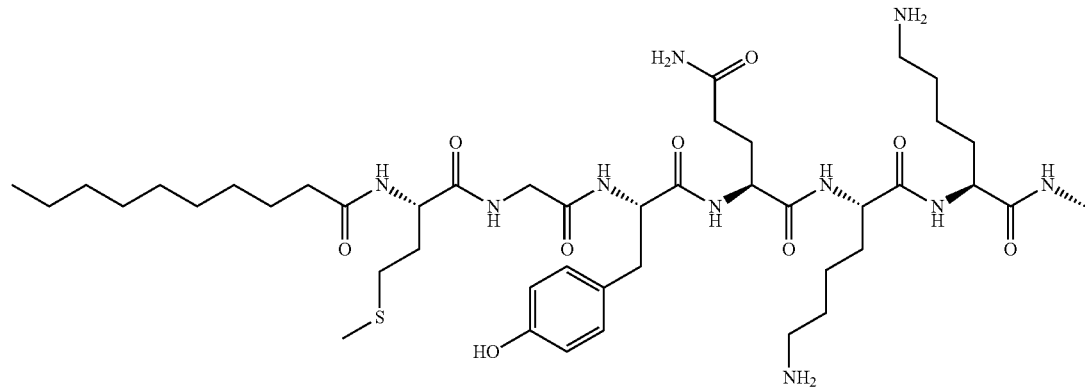

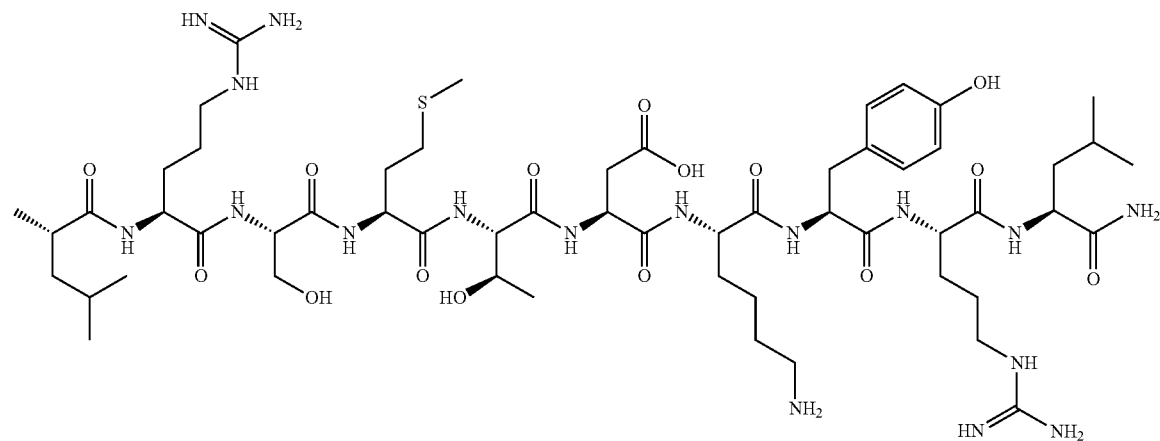
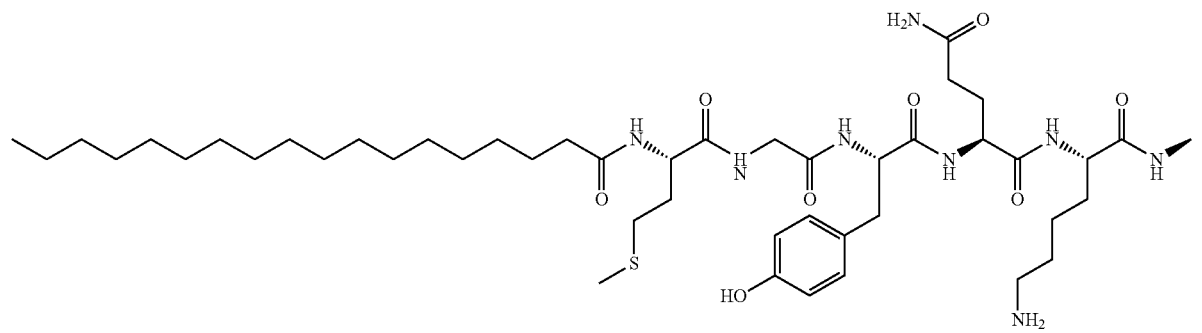
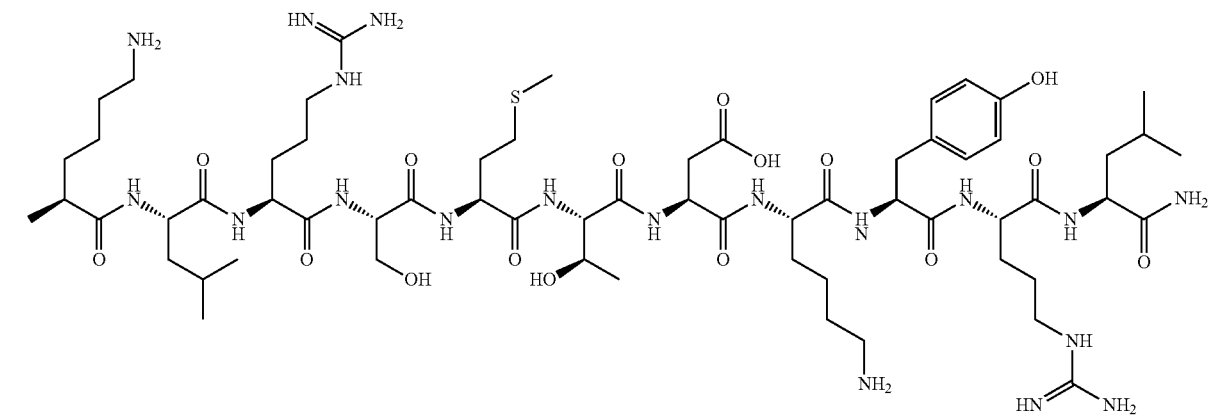
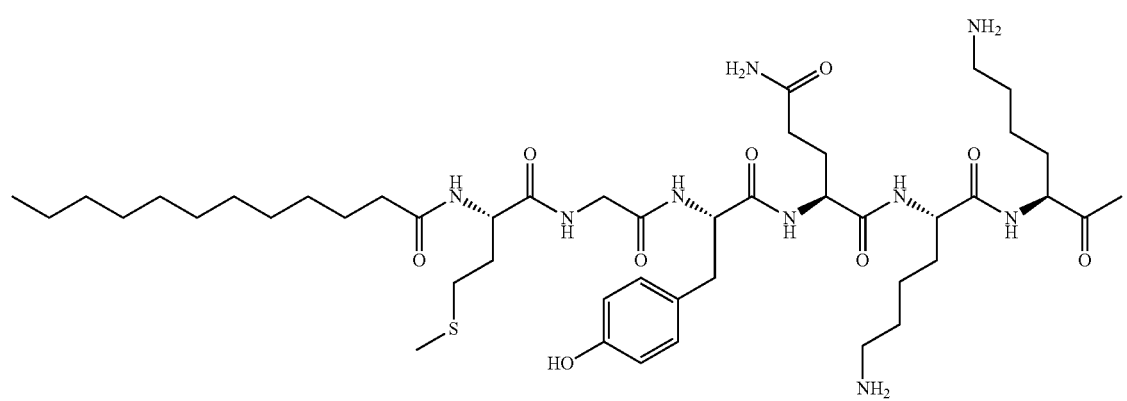

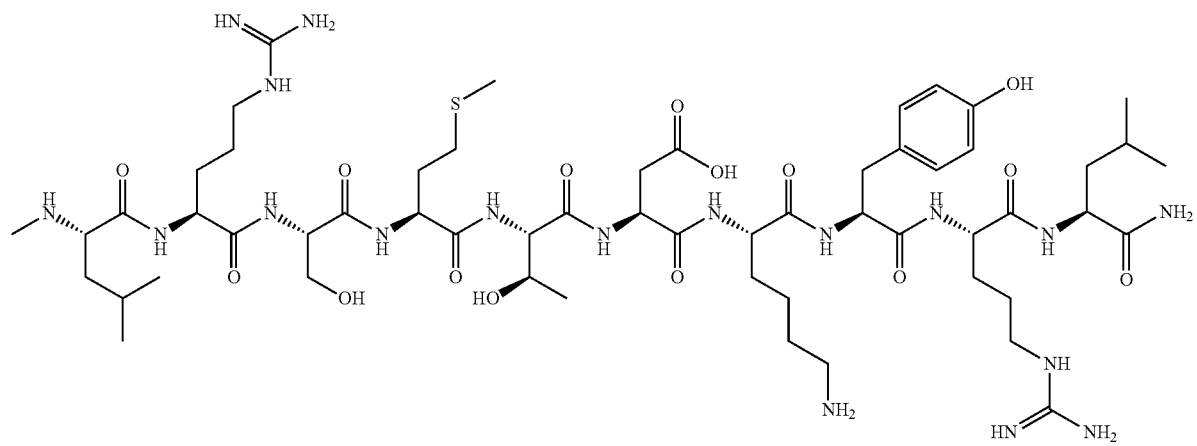
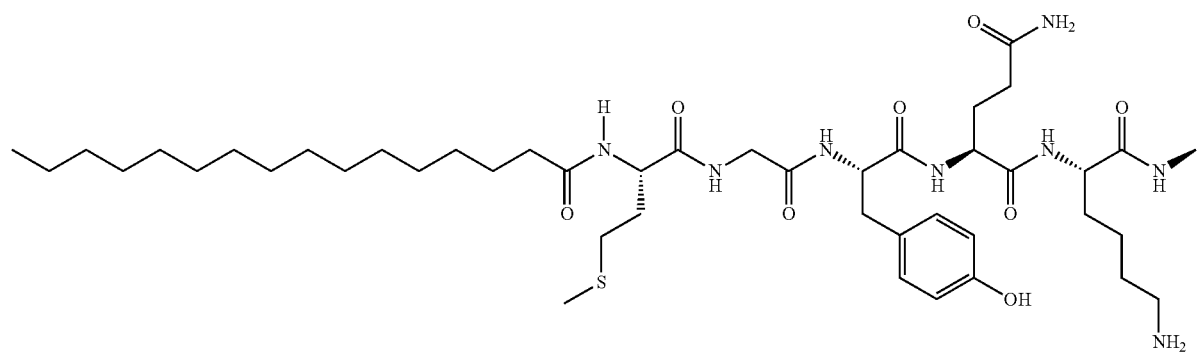
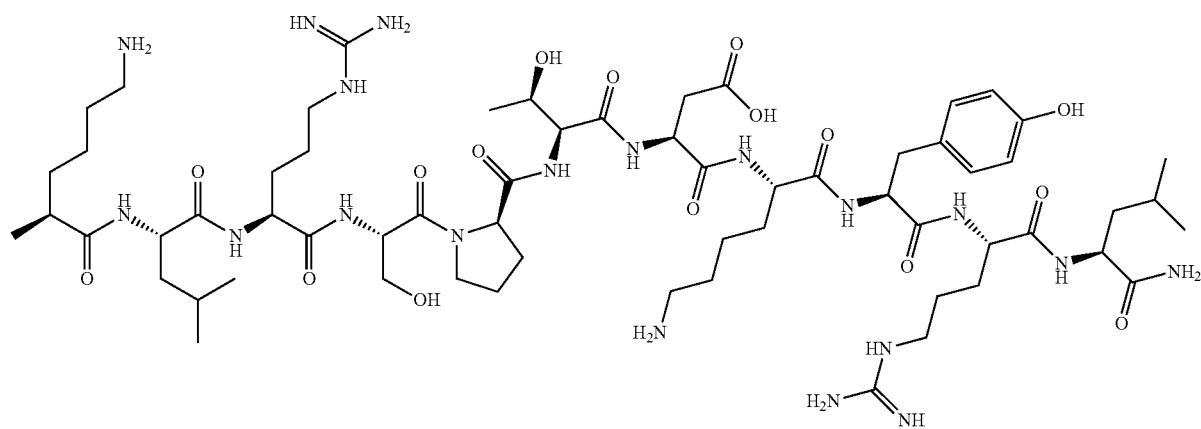

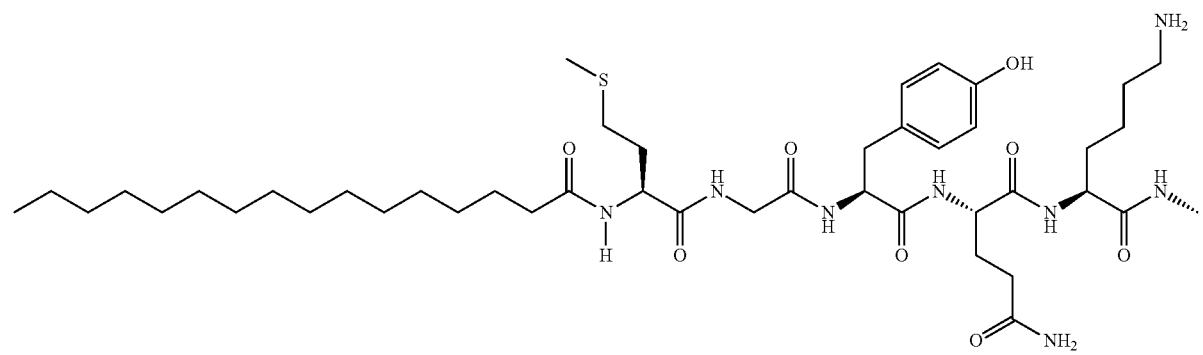
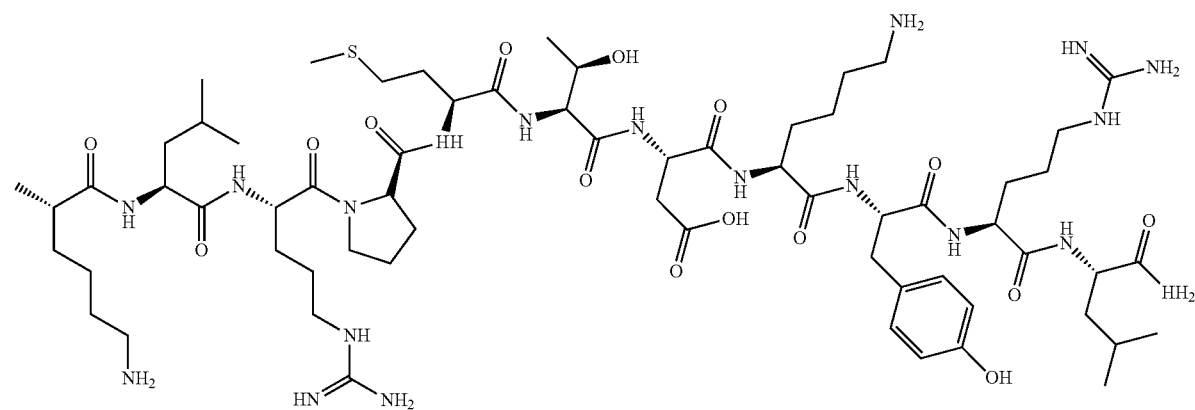
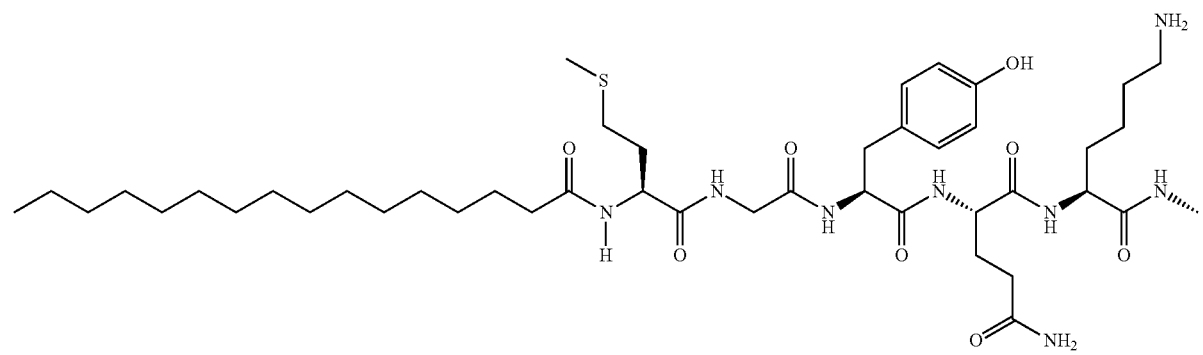

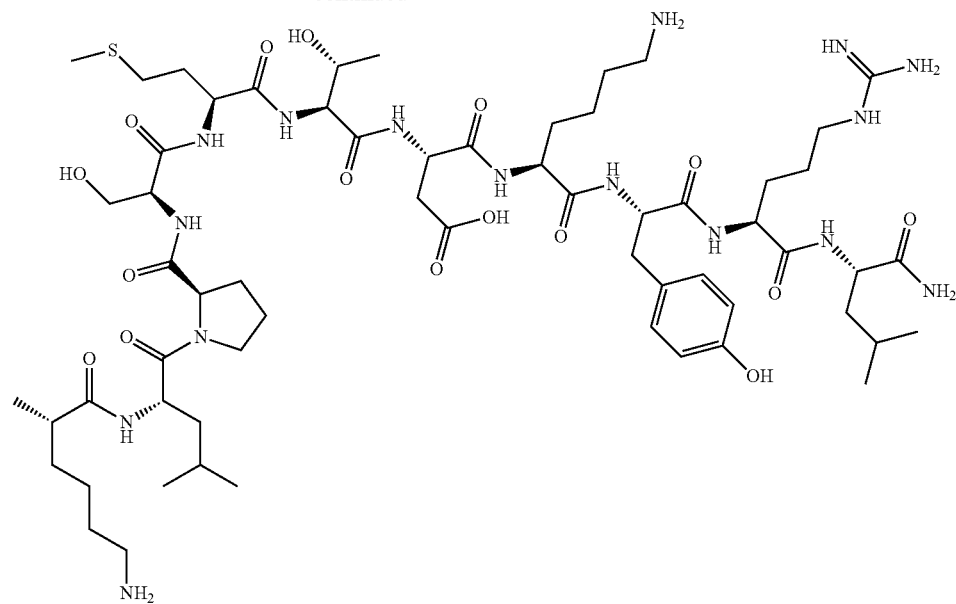
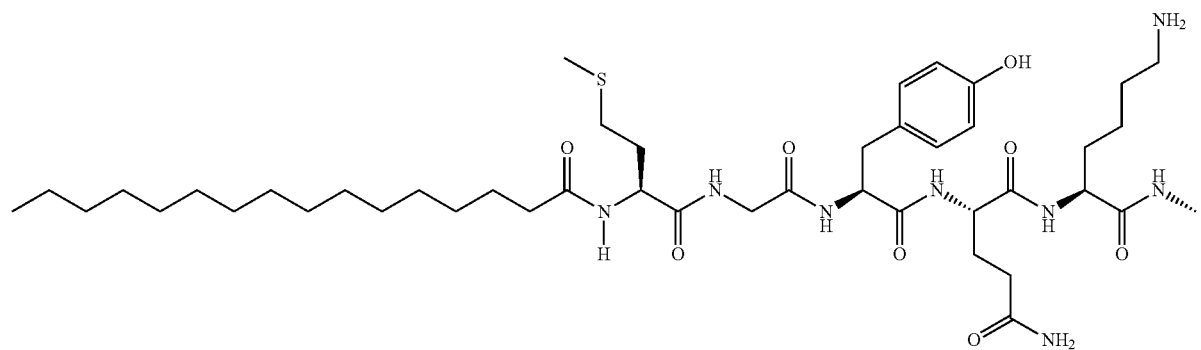
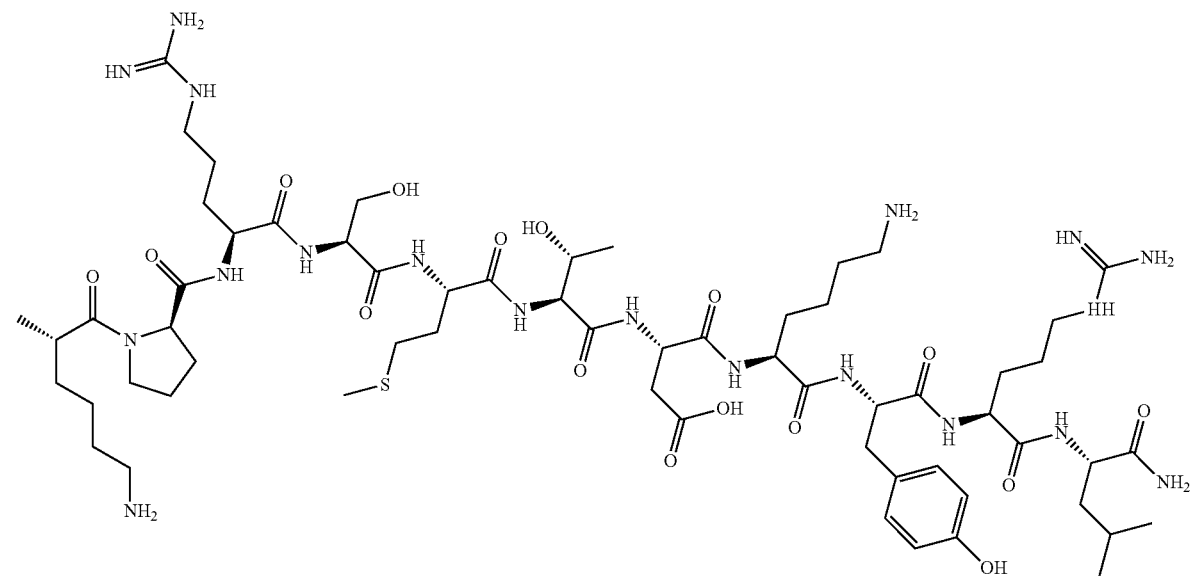

561 562
-continued
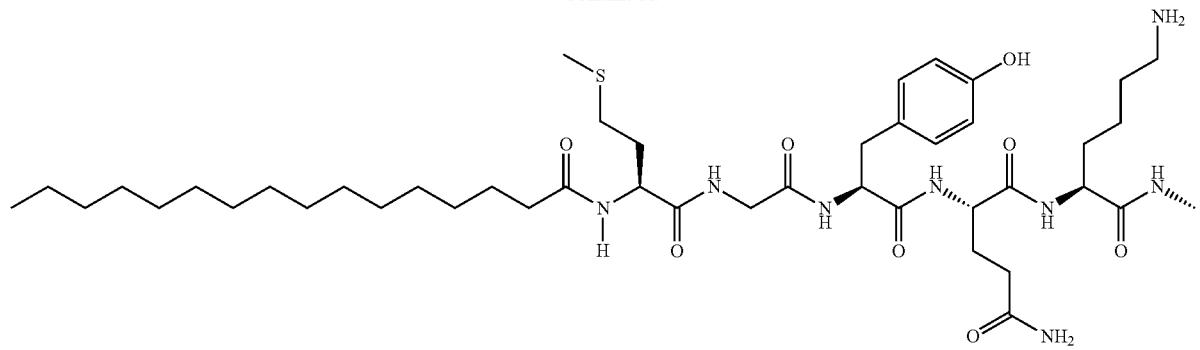
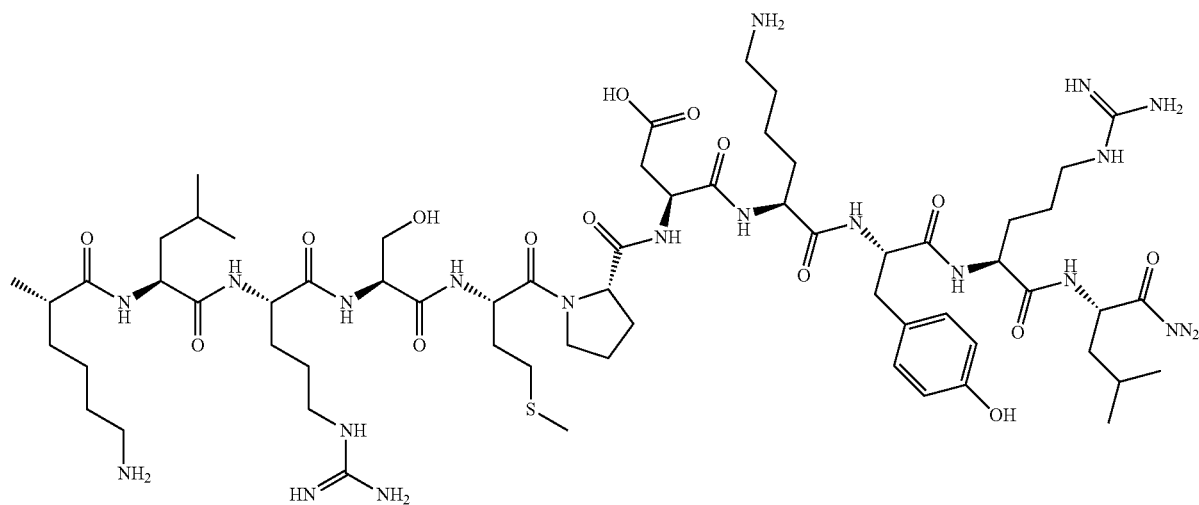
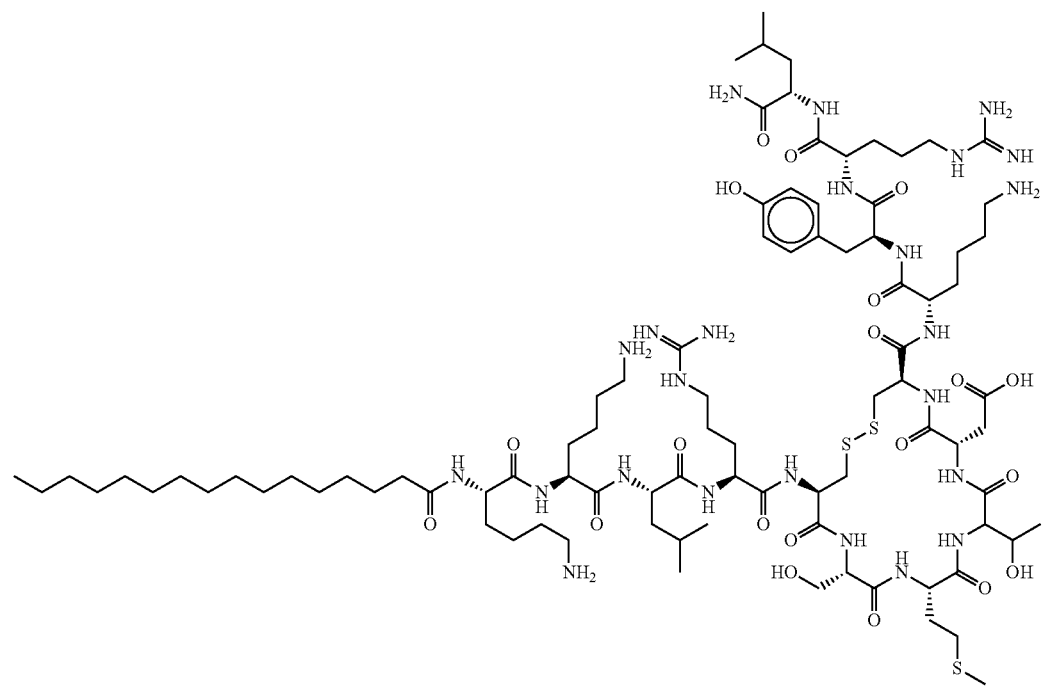

563
564
-continued
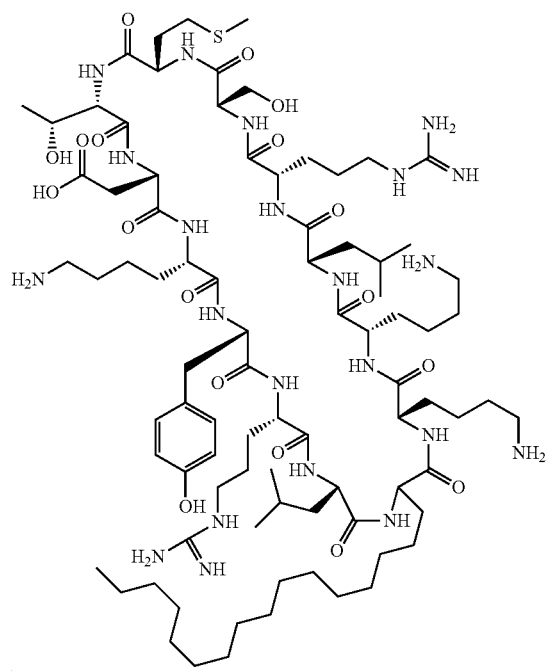
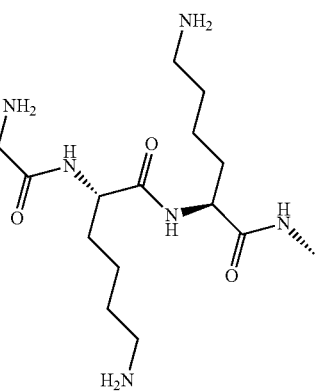
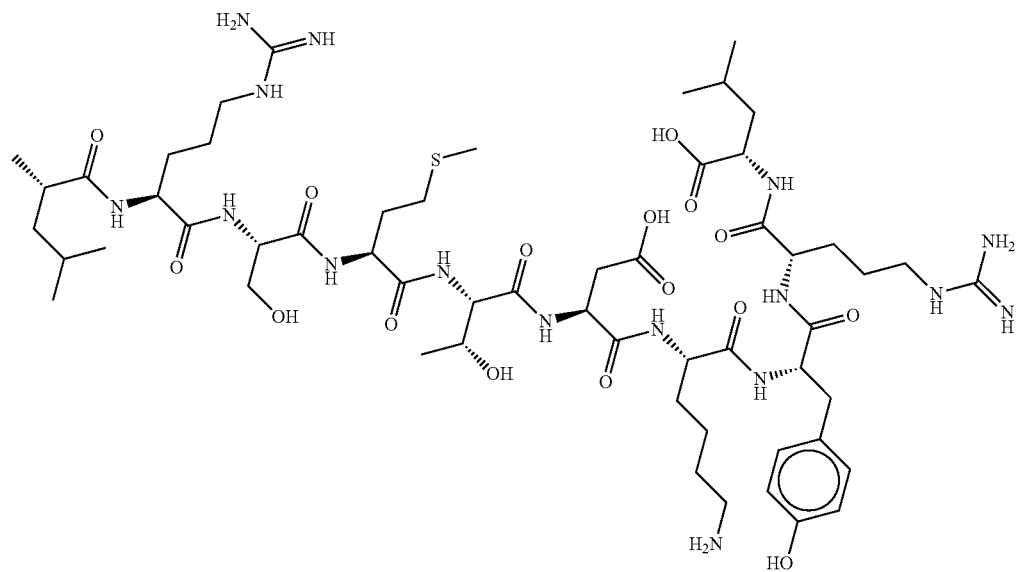

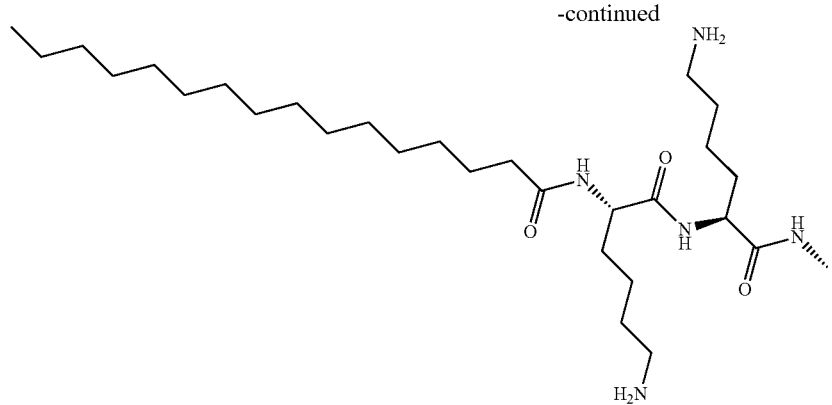
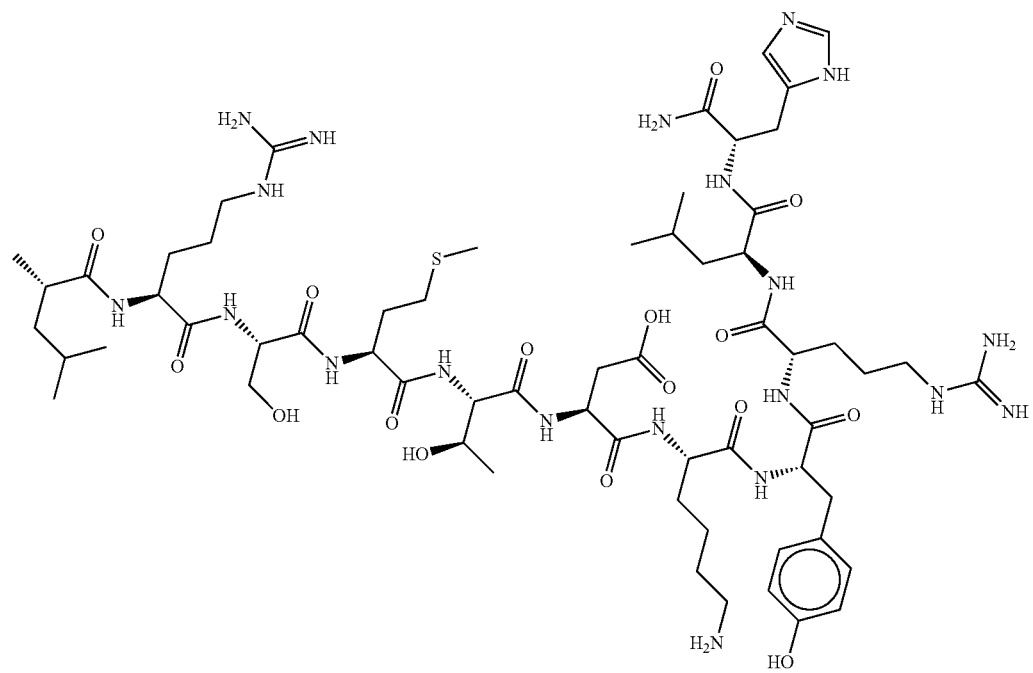
or a pharmaceutically acceptable salt of any of the foregoing.
15. A compound represented by:
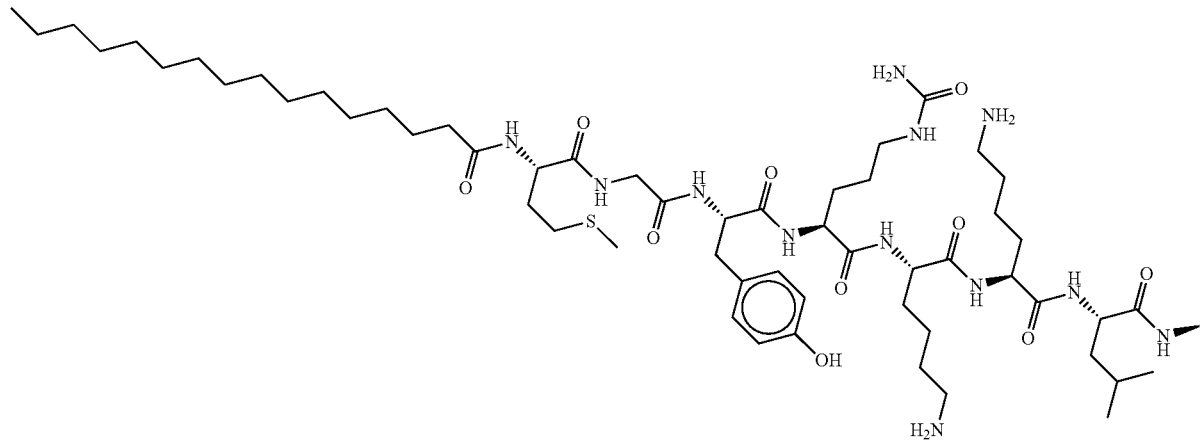

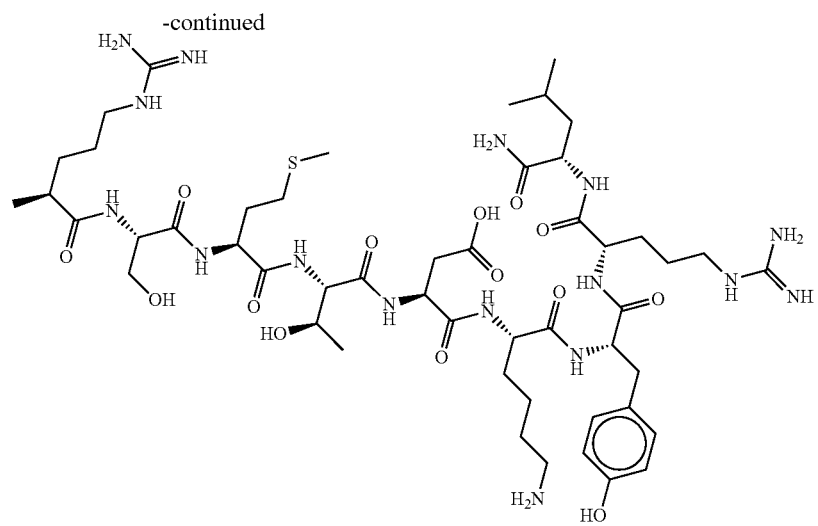
or pharmaceutically acceptable salts thereof.
16. A compound represented by:
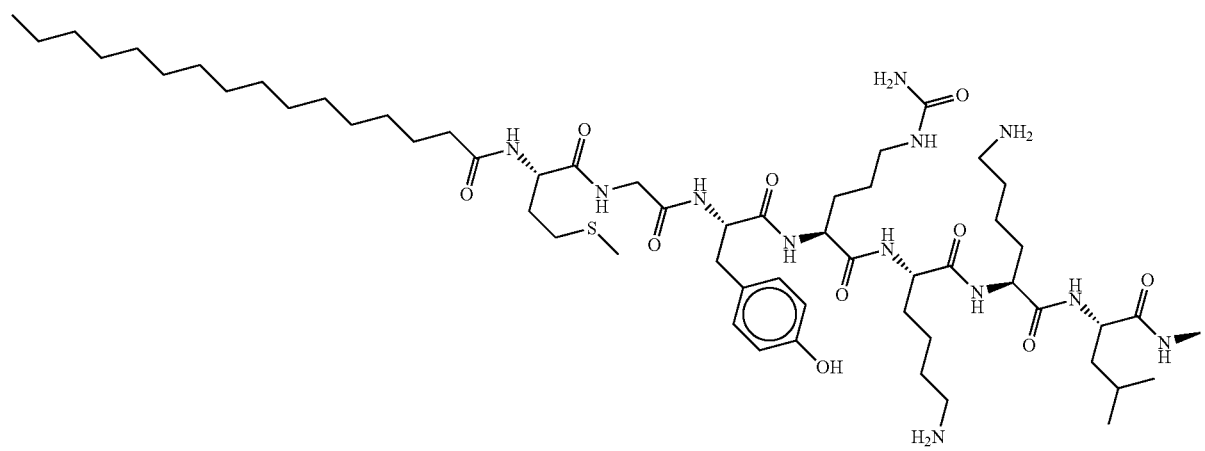

-continued
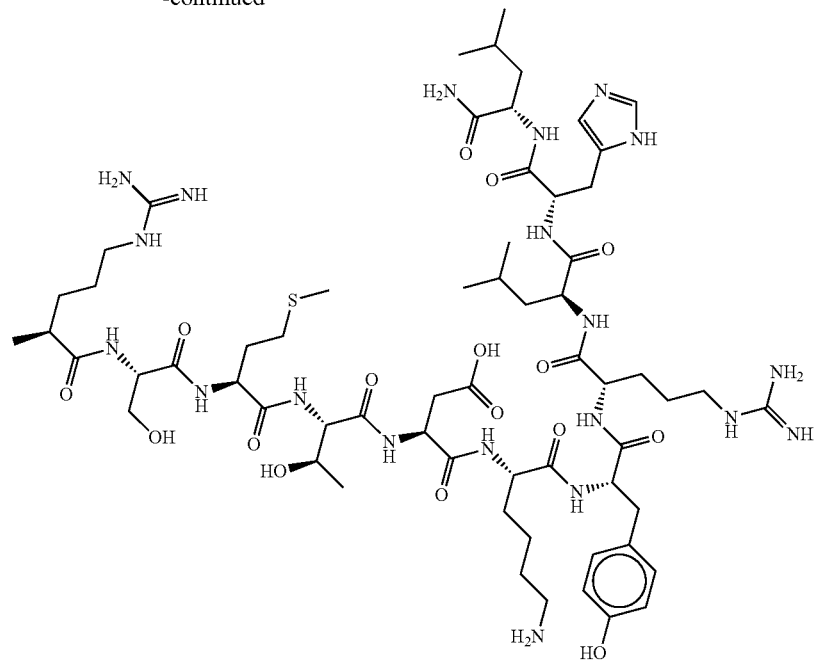
or pharmaceutically acceptable salts thereof.
17. A compound represented by:
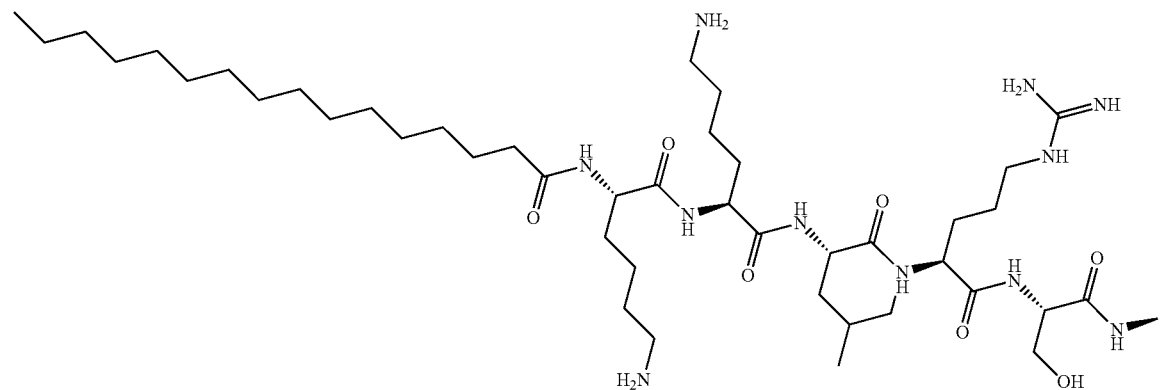

-continued
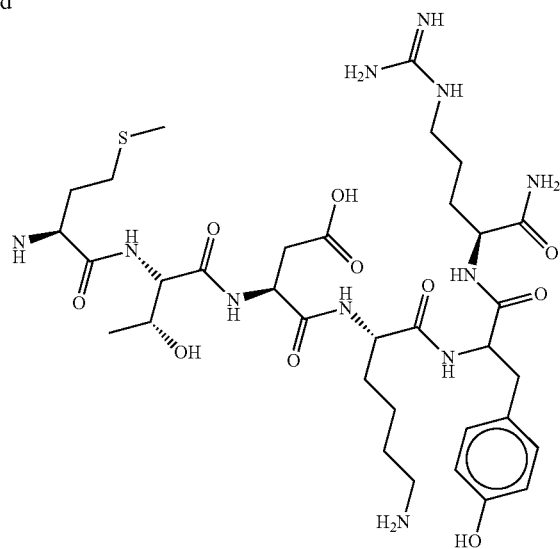
or pharmaceutically acceptable salts thereof.
* * * * *

SEQUENCE LISTING

```
<160> NUMBER OF SEQ ID NOS: 384

<210> SEQ ID NO 1
<211> LENGTH: 12
<212> TYPE: PRT
<213> ORGANISM: Artificial Sequence
<220> FEATURE:
<223> OTHER INFORMATION: Synthetic

<400> SEQUENCE: 1

Ser Gly Tyr Gln Lys Lys Leu Arg Ser Ser Thr Asp
```

```
1               5                  10

<210> SEQ ID NO 2
<211> LENGTH: 12
<212> TYPE: PRT
<213> ORGANISM: Artificial Sequence
<220> FEATURE:
<223> OTHER INFORMATION: Synthetic

<400> SEQUENCE: 2

Met Gly Tyr Gln Lys Lys Leu Arg Ser Ser Thr Asp
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Synthetic

<400> SEQUENCE: 3

Ser Gly Tyr Gln Lys Lys Leu Arg Ser Met Thr Asp
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 1
<223> OTHER INFORMATION: Xaa = Leucine or Isoleucine
<220> FEATURE:
<221> NAME/KEY: MOD_RES
<222> LOCATION: 10
<223> OTHER INFORMATION: Xaa = Leucine or Isoleucine

<400> SEQUENCE: 4

Xaa Gly Tyr Gln Lys Lys Leu Arg Ser Xaa Thr Asp
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: Synthetic

<400> SEQUENCE: 5

Leu Gly Tyr Gln Lys Lys Leu Arg Ser Leu Thr Asp
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Synthetic

<400> SEQUENCE: 6

Ile Gly Tyr Gln Lys Lys Leu Arg Ser Ile Thr Asp
 1               5                  10

<210> SEQ ID NO 7
<211> LENGTH: 12
<212> TYPE: PRT
```

```
<213> ORGANISM: Artificial Sequence
<220> FEATURE:
<223> OTHER INFORMATION: Synthetic
<220> FEATURE:
<221> NAME/KEY: MOD_RES
<222> LOCATION: 1
<223> OTHER INFORMATION: Xaa = Leucine or Isoleucine

<400> SEQUENCE: 7

Xaa Gly Tyr Gln Lys Lys Leu Arg Ser Ser Thr Asp
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 1
<223> OTHER INFORMATION: Xaa = Leucine or Isoleucine

<400> SEQUENCE: 8

Xaa Gly Tyr Gln Lys Lys Leu Arg Ser Met Thr Asp
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic

<400> SEQUENCE: 9

Leu Gly Tyr Gln Lys Lys Leu Arg Ser Met Thr Asp
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic

<400> SEQUENCE: 10

Ile Gly Tyr Gln Lys Lys Leu Arg Ser Met Thr Asp
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic

<400> SEQUENCE: 11

Ala Gly Tyr Gln Lys Lys Leu Arg Ser Met Thr Asp
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic

<400> SEQUENCE: 12
```

Met Ala Tyr Gln Lys Lys Leu Arg Ser Met Thr Asp
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic

<400> SEQUENCE: 13

Met Gly Ala Gln Lys Lys Leu Arg Ser Met Thr Asp
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic

<400> SEQUENCE: 14

Met Gly Tyr Ala Lys Lys Leu Arg Ser Met Thr Asp
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic

<400> SEQUENCE: 15

Met Gly Tyr Gln Lys Lys Leu Arg Ala Met Thr Asp
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic

<400> SEQUENCE: 16

Met Gly Tyr Gln Lys Lys Leu Arg Ser Ala Thr Asp
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic

<400> SEQUENCE: 17

Met Gly Tyr Gln Lys Lys Leu Arg Ser Met Ala Asp
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic

<400> SEQUENCE: 18

Met Gly Tyr Gln Lys Lys Leu Arg Ser Met Thr Ala

```
<210> SEQ ID NO 19
<211> LENGTH: 12
<212> TYPE: PRT
<213> ORGANISM: Artificial Sequence
<220> FEATURE:
<223> OTHER INFORMATION: Synthetic

<400> SEQUENCE: 19

Met Gly Tyr Gln Ala Lys Leu Arg Ser Met Thr Asp
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic

<400> SEQUENCE: 20

Met Gly Tyr Gln Lys Lys Leu Ala Ser Met Thr Asp
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic

<400> SEQUENCE: 21

Met Gly Tyr Gln Lys Ala Leu Arg Ser Met Thr Asp
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic

<400> SEQUENCE: 22

Met Gly Tyr Gln Lys Lys Ala Arg Ser Met Thr Asp
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 1
<223> OTHER INFORMATION: Xaa = D-Methionine

<400> SEQUENCE: 23

Xaa Gly Tyr Gln Lys Lys Leu Arg Ser Met Thr Asp
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic
<220> FEATURE:
```

```
<221> NAME/KEY: MOD_RES
<222> LOCATION: 3
<223> OTHER INFORMATION: Xaa = D-Tyrosine

<400> SEQUENCE: 24

Met Gly Xaa Gln Lys Lys Leu Arg Ser Met Thr Asp
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 4
<223> OTHER INFORMATION: Xaa = D-Glutamine

<400> SEQUENCE: 25

Met Gly Tyr Xaa Lys Lys Leu Arg Ser Met Thr Asp
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 5
<223> OTHER INFORMATION: Xaa = D-Lysine

<400> SEQUENCE: 26

Met Gly Tyr Gln Xaa Lys Leu Arg Ser Met Thr Asp
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 6
<223> OTHER INFORMATION: Xaa = D-Lysine

<400> SEQUENCE: 27

Met Gly Tyr Gln Lys Xaa Leu Arg Ser Met Thr Asp
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 7
<223> OTHER INFORMATION: Xaa = D-Leucine

<400> SEQUENCE: 28

Met Gly Tyr Gln Lys Lys Xaa Arg Ser Met Thr Asp
1               5                   10

<210> SEQ ID NO 29
```

```
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 8
<223> OTHER INFORMATION: Xaa = D-Arginine

<400> SEQUENCE: 29

Met Gly Tyr Gln Lys Lys Leu Xaa Ser Met Thr Asp
 1               5                  10

<210> SEQ ID NO 30
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 9
<223> OTHER INFORMATION: Xaa = D-Serine

<400> SEQUENCE: 30

Met Gly Tyr Gln Lys Lys Leu Arg Xaa Met Thr Asp
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 10
<223> OTHER INFORMATION: Xaa = D-Methionine

<400> SEQUENCE: 31

Met Gly Tyr Gln Lys Lys Leu Arg Ser Xaa Thr Asp
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 11
<223> OTHER INFORMATION: Xaa = D-Threonine

<400> SEQUENCE: 32

Met Gly Tyr Gln Lys Lys Leu Arg Ser Met Xaa Asp
 1               5                  10

<210> SEQ ID NO 33
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 12
<223> OTHER INFORMATION: Xaa = D-Aspartic acid

<400> SEQUENCE: 33
```

```
Met Gly Tyr Gln Lys Lys Leu Arg Ser Met Thr Xaa
 1               5                  10
```

<210> SEQ ID NO 34
<211> LENGTH: 13
<212> TYPE: PRT
<213> ORGANISM: Artificial Sequence
<220> FEATURE:
<223> OTHER INFORMATION: Synthetic

<400> SEQUENCE: 34

```
Gly Ser His Tyr Gln Lys Lys Leu Arg Ser Ser Thr Asp
 1               5                  10
```

<210> SEQ ID NO 35
<211> LENGTH: 13
<212> TYPE: PRT
<213> ORGANISM: Artificial Sequence
<220> FEATURE:
<223> OTHER INFORMATION: Synthetic

<400> SEQUENCE: 35

```
Gly Ser Gly Tyr Gln Lys Lys Leu Arg Ser Ser Thr Asp
 1               5                  10
```

<210> SEQ ID NO 36
<211> LENGTH: 10
<212> TYPE: PRT
<213> ORGANISM: Artificial Sequence
<220> FEATURE:
<223> OTHER INFORMATION: Synthetic

<400> SEQUENCE: 36

```
Tyr Gln Lys Lys Leu Arg Ser Ser Thr Asp
 1               5                  10
```

<210> SEQ ID NO 37
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 9
<223> OTHER INFORMATION: Xaa = Leucine or Isoleucine

<400> SEQUENCE: 37

```
Gly Tyr Gln Lys Lys Leu Arg Ser Xaa Thr Asp
 1               5                  10
```

<210> SEQ ID NO 38
<211> LENGTH: 11
<212> TYPE: PRT
<213> ORGANISM: Artificial Sequence
<220> FEATURE:
<223> OTHER INFORMATION: Synthetic

<400> SEQUENCE: 38

```
Gly Tyr Gln Lys Lys Leu Arg Ser Leu Thr Asp
 1               5                  10
```

<210> SEQ ID NO 39
<211> LENGTH: 16
<212> TYPE: PRT
<213> ORGANISM: Artificial Sequence
<220> FEATURE:

<223> OTHER INFORMATION: Synthetic

<400> SEQUENCE: 39

Gly Tyr Gln Lys Lys Leu Arg Ser Met Thr Asp Lys Tyr Arg Leu His
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Synthetic

<400> SEQUENCE: 40

Tyr Gln Lys Lys Leu Arg Ser Met Thr Asp Lys Tyr Arg Leu His
1               5                   10                  15

<210> SEQ ID NO 41
<211> LENGTH: 14
<212> TYPE: PRT
<213> ORGANISM: Artificial Sequence
<220> FEATURE:
<223> OTHER INFORMATION: Synthetic

<400> SEQUENCE: 41

Gln Lys Lys Leu Arg Ser Met Thr Asp Lys Tyr Arg Leu His
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Synthetic

<400> SEQUENCE: 42

Lys Lys Leu Arg Ser Met Thr Asp Lys Tyr Arg Leu His
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Synthetic

<400> SEQUENCE: 43

Lys Leu Arg Ser Met Thr Asp Lys Tyr Arg Leu His
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic

<400> SEQUENCE: 44

Leu Arg Ser Met Thr Asp Lys Tyr Arg Leu His
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic

<400> SEQUENCE: 45

Arg Ser Met Thr Asp Lys Tyr Arg Leu His
1               5                   10

<210> SEQ ID NO 46
<211> LENGTH: 9
<212> TYPE: PRT
<213> ORGANISM: Artificial Sequence
<220> FEATURE:
<223> OTHER INFORMATION: Synthetic

<400> SEQUENCE: 46

Ser Met Thr Asp Lys Tyr Arg Leu His
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic

<400> SEQUENCE: 47

Met Thr Asp Lys Tyr Arg Leu His
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic

<400> SEQUENCE: 48

Thr Asp Lys Tyr Arg Leu His
1               5

<210> SEQ ID NO 49
<211> LENGTH: 15
<212> TYPE: PRT
<213> ORGANISM: Artificial Sequence
<220> FEATURE:
<223> OTHER INFORMATION: Synthetic

<400> SEQUENCE: 49

Gly Tyr Gln Lys Lys Leu Arg Ser Met Thr Asp Lys Tyr Arg Leu
1               5                   10                  15

<210> SEQ ID NO 50
<211> LENGTH: 14
<212> TYPE: PRT
<213> ORGANISM: Artificial Sequence
<220> FEATURE:
<223> OTHER INFORMATION: Synthetic

<400> SEQUENCE: 50

Gly Tyr Gln Lys Lys Leu Arg Ser Met Thr Asp Lys Tyr Arg
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Synthetic

```
<400> SEQUENCE: 51

Gly Tyr Gln Lys Lys Leu Arg Ser Met Thr Asp Lys Tyr
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic

<400> SEQUENCE: 52

Gly Tyr Gln Lys Lys Leu Arg Ser Met Thr Asp Lys
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Synthetic

<400> SEQUENCE: 53

Gly Tyr Gln Lys Lys Leu Arg Ser Met Thr Asp
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthetic

<400> SEQUENCE: 54

Gly Tyr Gln Lys Lys Leu Arg Ser Ile Thr Asp
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic

<400> SEQUENCE: 55

Gly Tyr Gln Lys Lys Leu Arg Ser Met Thr
1               5                   10

<210> SEQ ID NO 56
<211> LENGTH: 9
<212> TYPE: PRT
<213> ORGANISM: Artificial Sequence
<220> FEATURE:
<223> OTHER INFORMATION: Synthetic

<400> SEQUENCE: 56

Gly Tyr Gln Lys Lys Leu Arg Ser Met
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic

<400> SEQUENCE: 57
```

```
Gly Tyr Gln Lys Lys Leu Arg Ser
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic

<400> SEQUENCE: 58

Gly Tyr Gln Lys Lys Leu Arg
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic

<400> SEQUENCE: 59

Tyr Gln Lys Lys Leu Arg Ser
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic

<400> SEQUENCE: 60

Gln Lys Lys Leu Arg Ser Met
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic

<400> SEQUENCE: 61

Lys Lys Leu Arg Ser Met Thr
1               5

<210> SEQ ID NO 62
<211> LENGTH: 7
<212> TYPE: PRT
<213> ORGANISM: Artificial Sequence
<220> FEATURE:
<223> OTHER INFORMATION: Synthetic

<400> SEQUENCE: 62

Lys Leu Arg Ser Met Thr Asp
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic

<400> SEQUENCE: 63
```

```
Leu Arg Ser Met Thr Asp Lys
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic

<400> SEQUENCE: 64

Arg Ser Met Thr Asp Lys Tyr
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic

<400> SEQUENCE: 65

Ser Met Thr Asp Lys Tyr Arg
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic

<400> SEQUENCE: 66

Met Thr Asp Lys Tyr Arg Leu
1               5

<210> SEQ ID NO 67
<211> LENGTH: 16
<212> TYPE: PRT
<213> ORGANISM: Artificial Sequence
<220> FEATURE:
<223> OTHER INFORMATION: Synthetic

<400> SEQUENCE: 67

Lys Arg Met Lys Thr Ser Leu Tyr Asp Gly Arg Met Gln Tyr Leu Lys
1               5                   10                  15

<210> SEQ ID NO 68
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 1
<223> OTHER INFORMATION: Xaa = D-Serine

<400> SEQUENCE: 68

Xaa Gly Tyr Gln Lys Lys Leu Arg Ser Ser Thr Asp
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthetic
```

<400> SEQUENCE: 69

Lys Lys Leu Arg Ser Met Thr Asp Lys Tyr
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Synthetic

<400> SEQUENCE: 70

Lys Lys Leu Arg Ser Met Thr Asp Lys Tyr Arg
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Synthetic

<400> SEQUENCE: 71

Lys Lys Leu Arg Ser Met Thr Asp Lys Tyr Arg Leu
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 6
<223> OTHER INFORMATION: Xaa = Nle

<400> SEQUENCE: 72

Lys Lys Leu Arg Ser Xaa Thr Asp Lys Tyr Arg Leu His
1               5                   10

<210> SEQ ID NO 73
<211> LENGTH: 14
<212> TYPE: PRT
<213> ORGANISM: Artificial Sequence
<220> FEATURE:
<223> OTHER INFORMATION: Synthetic

<400> SEQUENCE: 73

Lys Lys Leu Arg Ser Met Thr Asp Lys Tyr Arg Leu His Leu
1               5                   10

<210> SEQ ID NO 74
<211> LENGTH: 16
<212> TYPE: PRT
<213> ORGANISM: Artificial Sequence
<220> FEATURE:
<223> OTHER INFORMATION: Synthetic

<400> SEQUENCE: 74

Lys Lys Leu Arg Ser Met Thr Asp Lys Tyr Arg Leu His Leu Ser Val
1               5                   10                  15

<210> SEQ ID NO 75
<211> LENGTH: 13
<212> TYPE: PRT

```
<213> ORGANISM: Artificial Sequence
<220> FEATURE:
<223> OTHER INFORMATION: Synthetic

<400> SEQUENCE: 75

Gln Lys Lys Leu Arg Ser Met Thr Asp Lys Tyr Arg Ile
1               5                   10

<210> SEQ ID NO 76
<211> LENGTH: 15
<212> TYPE: PRT
<213> ORGANISM: Artificial Sequence
<220> FEATURE:
<223> OTHER INFORMATION: Synthetic

<400> SEQUENCE: 76

Gln Lys Lys Leu Arg Ser Met Thr Asp Lys Tyr Arg Leu His Leu
1               5                   10                  15

<210> SEQ ID NO 77
<211> LENGTH: 18
<212> TYPE: PRT
<213> ORGANISM: Artificial Sequence
<220> FEATURE:
<223> OTHER INFORMATION: Synthetic

<400> SEQUENCE: 77

Tyr Gln Lys Lys Leu Arg Ser Met Thr Asp Lys Tyr Arg Leu His Leu
1               5                   10                  15

Ser Val

<210> SEQ ID NO 78
<211> LENGTH: 14
<212> TYPE: PRT
<213> ORGANISM: Artificial Sequence
<220> FEATURE:
<223> OTHER INFORMATION: Synthetic

<400> SEQUENCE: 78

Leu Val Met Gly Tyr Gln Lys Lys Leu Arg Ser Met Thr Asp
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Synthetic

<400> SEQUENCE: 79

Met Gly Tyr Gln Lys Lys Leu Arg Ser Met Thr Asp Lys
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Synthetic

<400> SEQUENCE: 80

Met Gly Tyr Gln Lys Lys Leu Arg Ser Met Thr Asp Lys Tyr
1               5                   10

<210> SEQ ID NO 81
<211> LENGTH: 16
```

```
<212> TYPE: PRT
<213> ORGANISM: Artificial Sequence
<220> FEATURE:
<223> OTHER INFORMATION: Synthetic

<400> SEQUENCE: 81

Met Gly Tyr Gln Lys Lys Leu Arg Ser Met Thr Asp Lys Tyr Arg Ile
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: Synthetic

<400> SEQUENCE: 82

Met Gly Tyr Gln Lys Lys Leu Arg Ser Met Thr Asp Lys Tyr Arg Leu
1               5                   10                  15

<210> SEQ ID NO 83
<211> LENGTH: 18
<212> TYPE: PRT
<213> ORGANISM: Artificial Sequence
<220> FEATURE:
<223> OTHER INFORMATION: Synthetic

<400> SEQUENCE: 83

Met Gly Tyr Gln Lys Lys Leu Arg Ser Met Thr Asp Lys Tyr Arg Leu
1               5                   10                  15

His Leu

<210> SEQ ID NO 84
<211> LENGTH: 20
<212> TYPE: PRT
<213> ORGANISM: Artificial Sequence
<220> FEATURE:
<223> OTHER INFORMATION: Synthetic

<400> SEQUENCE: 84

Met Gly Tyr Gln Lys Lys Leu Arg Ser Met Thr Asp Lys Tyr Arg Leu
1               5                   10                  15

His Leu Ser Val
            20

<210> SEQ ID NO 85
<211> LENGTH: 13
<212> TYPE: PRT
<213> ORGANISM: Artificial Sequence
<220> FEATURE:
<223> OTHER INFORMATION: Synthetic

<400> SEQUENCE: 85

Tyr Thr Lys Arg Leu Asp Ser His Arg Lys Leu Lys Met
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Synthetic

<400> SEQUENCE: 86

Val Met Gly Tyr Gln Lys Lys Leu Arg Ser Met Thr Asp
1               5                   10
```

```
<210> SEQ ID NO 87
<211> LENGTH: 14
<212> TYPE: PRT
<213> ORGANISM: Artificial Sequence
<220> FEATURE:
<223> OTHER INFORMATION: Synthetic

<400> SEQUENCE: 87

Lys Lys Leu Cys Arg Ser Met Thr Asp Lys Cys Tyr Arg Leu
1               5                   10

<210> SEQ ID NO 88
<211> LENGTH: 14
<212> TYPE: PRT
<213> ORGANISM: Artificial Sequence
<220> FEATURE:
<223> OTHER INFORMATION: Synthetic

<400> SEQUENCE: 88

Lys Lys Leu Arg Cys Ser Met Thr Asp Cys Lys Tyr Arg Leu
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 1
<223> OTHER INFORMATION: Xaa = D-Lysine

<400> SEQUENCE: 89

Xaa Lys Leu Arg Ser Met Thr Asp Lys Tyr Arg Leu His
1               5                   10

<210> SEQ ID NO 90
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 2
<223> OTHER INFORMATION: Xaa = D-Lysine

<400> SEQUENCE: 90

Lys Xaa Leu Arg Ser Met Thr Asp Lys Tyr Arg Leu His
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3
<223> OTHER INFORMATION: Xaa = D-Leucine

<400> SEQUENCE: 91

Lys Lys Xaa Arg Ser Met Thr Asp Lys Tyr Arg Leu His
1               5                   10
```

```
<210> SEQ ID NO 92
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 4
<223> OTHER INFORMATION: Xaa = D-Arginine

<400> SEQUENCE: 92

Lys Lys Leu Xaa Ser Met Thr Asp Lys Tyr Arg Leu His
 1               5                  10

<210> SEQ ID NO 93
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 5
<223> OTHER INFORMATION: Xaa = D-Serine

<400> SEQUENCE: 93

Lys Lys Leu Arg Xaa Met Thr Asp Lys Tyr Arg Leu His
 1               5                  10

<210> SEQ ID NO 94
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 6
<223> OTHER INFORMATION: Xaa = D-Methionine

<400> SEQUENCE: 94

Lys Lys Leu Arg Ser Xaa Thr Asp Lys Tyr Arg Leu His
 1               5                  10

<210> SEQ ID NO 95
<211> LENGTH: 13
<212> TYPE: PRT
<213> ORGANISM: Artificial Sequence
<220> FEATURE:
<223> OTHER INFORMATION: Synthetic

<400> SEQUENCE: 95

Ala Lys Leu Arg Ser Met Thr Asp Lys Tyr Arg Leu His
 1               5                  10

<210> SEQ ID NO 96
<211> LENGTH: 13
<212> TYPE: PRT
<213> ORGANISM: Artificial Sequence
<220> FEATURE:
<223> OTHER INFORMATION: Synthetic

<400> SEQUENCE: 96

Lys Ala Leu Arg Ser Met Thr Asp Lys Tyr Arg Leu His
 1               5                  10

<210> SEQ ID NO 97
<211> LENGTH: 13
```

```
<212> TYPE: PRT
<213> ORGANISM: Artificial Sequence
<220> FEATURE:
<223> OTHER INFORMATION: Synthetic

<400> SEQUENCE: 97

Lys Lys Ala Arg Ser Met Thr Asp Lys Tyr Arg Leu His
 1               5                  10

<210> SEQ ID NO 98
<211> LENGTH: 13
<212> TYPE: PRT
<213> ORGANISM: Artificial Sequence
<220> FEATURE:
<223> OTHER INFORMATION: Synthetic

<400> SEQUENCE: 98

Lys Lys Leu Ala Ser Met Thr Asp Lys Tyr Arg Leu His
 1               5                  10

<210> SEQ ID NO 99
<211> LENGTH: 13
<212> TYPE: PRT
<213> ORGANISM: Artificial Sequence
<220> FEATURE:
<223> OTHER INFORMATION: Synthetic

<400> SEQUENCE: 99

Lys Lys Leu Arg Ala Met Thr Asp Lys Tyr Arg Leu His
 1               5                  10

<210> SEQ ID NO 100
<211> LENGTH: 13
<212> TYPE: PRT
<213> ORGANISM: Artificial Sequence
<220> FEATURE:
<223> OTHER INFORMATION: Synthetic

<400> SEQUENCE: 100

Lys Lys Leu Arg Ser Ala Thr Asp Lys Tyr Arg Leu His
 1               5                  10

<210> SEQ ID NO 101
<211> LENGTH: 16
<212> TYPE: PRT
<213> ORGANISM: Artificial Sequence
<220> FEATURE:
<223> OTHER INFORMATION: Synthetic

<400> SEQUENCE: 101

Ala Gly Tyr Gln Lys Lys Leu Arg Ser Met Thr Asp Lys Tyr Arg Leu
 1               5                  10                  15

<210> SEQ ID NO 102
<211> LENGTH: 16
<212> TYPE: PRT
<213> ORGANISM: Artificial Sequence
<220> FEATURE:
<223> OTHER INFORMATION: Synthetic

<400> SEQUENCE: 102

Met Ala Tyr Gln Lys Lys Leu Arg Ser Met Thr Asp Lys Tyr Arg Leu
 1               5                  10                  15

<210> SEQ ID NO 103
<211> LENGTH: 16
<212> TYPE: PRT
```

```
<213> ORGANISM: Artificial Sequence
<220> FEATURE:
<223> OTHER INFORMATION: Synthetic

<400> SEQUENCE: 103

Met Gly Ala Gln Lys Lys Leu Arg Ser Met Thr Asp Lys Tyr Arg Leu
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: Synthetic

<400> SEQUENCE: 104

Met Gly Tyr Ala Lys Lys Leu Arg Ser Met Thr Asp Lys Tyr Arg Leu
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: Synthetic

<400> SEQUENCE: 105

Met Gly Tyr Gln Ala Lys Leu Arg Ser Met Thr Asp Lys Tyr Arg Leu
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: Synthetic

<400> SEQUENCE: 106

Met Gly Tyr Gln Lys Ala Leu Arg Ser Met Thr Asp Lys Tyr Arg Leu
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: Synthetic

<400> SEQUENCE: 107

Met Gly Tyr Gln Lys Lys Ala Arg Ser Met Thr Asp Lys Tyr Arg Leu
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Synthetic

<400> SEQUENCE: 108

Met Gly Tyr Gln Lys Lys Leu Ala Ser Met Thr Asp Lys Tyr Arg Leu
1               5                   10                  15

<210> SEQ ID NO 109
<211> LENGTH: 13
<212> TYPE: PRT
<213> ORGANISM: Artificial Sequence
<220> FEATURE:
<223> OTHER INFORMATION: Synthetic
```

<400> SEQUENCE: 109

Lys Lys Leu Arg Ser Met Ala Asp Lys Tyr Arg Leu His
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Synthetic

<400> SEQUENCE: 110

Lys Lys Leu Arg Ser Met Thr Ala Lys Tyr Arg Leu His
1               5                   10

<210> SEQ ID NO 111
<211> LENGTH: 13
<212> TYPE: PRT
<213> ORGANISM: Artificial Sequence
<220> FEATURE:
<223> OTHER INFORMATION: Synthetic

<400> SEQUENCE: 111

Lys Lys Leu Arg Ser Met Thr Asp Ala Tyr Arg Leu His
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Synthetic

<400> SEQUENCE: 112

Lys Lys Leu Arg Ser Met Thr Asp Lys Ala Arg Leu His
1               5                   10

<210> SEQ ID NO 113
<211> LENGTH: 13
<212> TYPE: PRT
<213> ORGANISM: Artificial Sequence
<220> FEATURE:
<223> OTHER INFORMATION: Synthetic

<400> SEQUENCE: 113

Lys Lys Leu Arg Ser Met Thr Asp Lys Tyr Ala Leu His
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Synthetic

<400> SEQUENCE: 114

Lys Lys Leu Arg Ser Met Thr Asp Lys Tyr Arg Ala His
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Synthetic

```
<400> SEQUENCE: 115

Lys Lys Leu Arg Ser Met Thr Asp Lys Tyr Arg Leu Ala
1               5                   10

<210> SEQ ID NO 116
<211> LENGTH: 16
<212> TYPE: PRT
<213> ORGANISM: Artificial Sequence
<220> FEATURE:
<223> OTHER INFORMATION: Synthetic

<400> SEQUENCE: 116

Met Gly Tyr Gln Lys Lys Leu Arg Ala Met Thr Asp Lys Tyr Arg Leu
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Synthetic

<400> SEQUENCE: 117

Met Gly Tyr Gln Lys Lys Leu Arg Ser Ala Thr Asp Lys Tyr Arg Leu
1               5                   10                  15

<210> SEQ ID NO 118
<211> LENGTH: 16
<212> TYPE: PRT
<213> ORGANISM: Artificial Sequence
<220> FEATURE:
<223> OTHER INFORMATION: Synthetic

<400> SEQUENCE: 118

Met Gly Tyr Gln Lys Lys Leu Arg Ser Met Ala Asp Lys Tyr Arg Leu
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Synthetic

<400> SEQUENCE: 119

Met Gly Tyr Gln Lys Lys Leu Arg Ser Met Thr Ala Lys Tyr Arg Leu
1               5                   10                  15

<210> SEQ ID NO 120
<211> LENGTH: 16
<212> TYPE: PRT
<213> ORGANISM: Artificial Sequence
<220> FEATURE:
<223> OTHER INFORMATION: Synthetic

<400> SEQUENCE: 120

Met Gly Tyr Gln Lys Lys Leu Arg Ser Met Thr Asp Ala Tyr Arg Leu
1               5                   10                  15

<210> SEQ ID NO 121
<211> LENGTH: 16
<212> TYPE: PRT
<213> ORGANISM: Artificial Sequence
<220> FEATURE:
<223> OTHER INFORMATION: Synthetic

<400> SEQUENCE: 121
```

```
Met Gly Tyr Gln Lys Lys Leu Arg Ser Met Thr Asp Lys Ala Arg Leu
 1               5                  10                  15
```

<210> SEQ ID NO 122
<211> LENGTH: 16
<212> TYPE: PRT
<213> ORGANISM: Artificial Sequence
<220> FEATURE:
<223> OTHER INFORMATION: Synthetic

<400> SEQUENCE: 122

```
Met Gly Tyr Gln Lys Lys Leu Arg Ser Met Thr Asp Lys Tyr Ala Leu
 1               5                  10                  15
```

<210> SEQ ID NO 123
<211> LENGTH: 16
<212> TYPE: PRT
<213> ORGANISM: Artificial Sequence
<220> FEATURE:
<223> OTHER INFORMATION: Synthetic

<400> SEQUENCE: 123

```
Met Gly Tyr Gln Lys Lys Leu Arg Ser Met Thr Asp Lys Tyr Arg Ala
 1               5                  10                  15
```

<210> SEQ ID NO 124
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 7
<223> OTHER INFORMATION: Xaa = D-Threonine

<400> SEQUENCE: 124

```
Lys Lys Leu Arg Ser Met Xaa Asp Lys Tyr Arg Leu His
 1               5                  10
```

<210> SEQ ID NO 125
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 8
<223> OTHER INFORMATION: Xaa = D-Aspartic acid

<400> SEQUENCE: 125

```
Lys Lys Leu Arg Ser Met Thr Xaa Lys Tyr Arg Leu His
 1               5                  10
```

<210> SEQ ID NO 126
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 11
<223> OTHER INFORMATION: Xaa = D-Arginine

<400> SEQUENCE: 126

```
Lys Lys Leu Arg Ser Met Thr Asp Lys Tyr Xaa Leu His
```

```
1               5                   10
```

<210> SEQ ID NO 127
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 12
<223> OTHER INFORMATION: Xaa = D-Leucine

<400> SEQUENCE: 127

```
Lys Lys Leu Arg Ser Met Thr Asp Lys Tyr Arg Xaa His
1               5                   10
```

<210> SEQ ID NO 128
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 13
<223> OTHER INFORMATION: Xaa = D-Histidine

<400> SEQUENCE: 128

```
Lys Lys Leu Arg Ser Met Thr Asp Lys Tyr Arg Leu Xaa
1               5                   10
```

<210> SEQ ID NO 129
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 15
<223> OTHER INFORMATION: Xaa = D-Arginine

<400> SEQUENCE: 129

```
Met Gly Tyr Gln Lys Lys Leu Arg Ser Met Thr Asp Lys Tyr Xaa Leu
1               5                   10                  15
```

<210> SEQ ID NO 130
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 14
<223> OTHER INFORMATION: Xaa = D-Tyrosine

<400> SEQUENCE: 130

```
Met Gly Tyr Gln Lys Lys Leu Arg Ser Met Thr Asp Lys Xaa Arg Leu
1               5                   10                  15
```

<210> SEQ ID NO 131
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MOD_RES

```
<222> LOCATION: 13
<223> OTHER INFORMATION: Xaa = D-Lysine

<400> SEQUENCE: 131

Met Gly Tyr Gln Lys Lys Leu Arg Ser Met Thr Asp Xaa Tyr Arg Leu
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 12
<223> OTHER INFORMATION: Xaa = D-Aspartic acid

<400> SEQUENCE: 132

Met Gly Tyr Gln Lys Lys Leu Arg Ser Met Thr Xaa Lys Tyr Arg Leu
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 11
<223> OTHER INFORMATION: Xaa = D-Threonine

<400> SEQUENCE: 133

Met Gly Tyr Gln Lys Lys Leu Arg Ser Met Xaa Asp Lys Tyr Arg Leu
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 1
<223> OTHER INFORMATION: Xaa = D-Methionine

<400> SEQUENCE: 134

Xaa Gly Tyr Gln Lys Lys Leu Arg Ser Met Thr Asp Lys Tyr Arg Leu
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3
<223> OTHER INFORMATION: Xaa = D-Tyrosine

<400> SEQUENCE: 135

Met Gly Xaa Gln Lys Lys Leu Arg Ser Met Thr Asp Lys Tyr Arg Leu
1               5                   10                  15

<210> SEQ ID NO 136
<211> LENGTH: 16
```

```
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 4
<223> OTHER INFORMATION: Xaa = D-Glutamine

<400> SEQUENCE: 136

Met Gly Tyr Xaa Lys Lys Leu Arg Ser Met Thr Asp Lys Tyr Arg Leu
 1               5                  10                  15

<210> SEQ ID NO 137
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 5
<223> OTHER INFORMATION: Xaa = D-Lysine

<400> SEQUENCE: 137

Met Gly Tyr Gln Xaa Lys Leu Arg Ser Met Thr Asp Lys Tyr Arg Leu
 1               5                  10                  15

<210> SEQ ID NO 138
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 6
<223> OTHER INFORMATION: Xaa = D-Lysine

<400> SEQUENCE: 138

Met Gly Tyr Gln Lys Xaa Leu Arg Ser Met Thr Asp Lys Tyr Arg Leu
 1               5                  10                  15

<210> SEQ ID NO 139
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 7
<223> OTHER INFORMATION: Xaa = D-Leucine

<400> SEQUENCE: 139

Met Gly Tyr Gln Lys Lys Xaa Arg Ser Met Thr Asp Lys Tyr Arg Leu
 1               5                  10                  15

<210> SEQ ID NO 140
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 8
<223> OTHER INFORMATION: Xaa = D-Arginine

<400> SEQUENCE: 140
```

```
Met Gly Tyr Gln Lys Lys Leu Xaa Ser Met Thr Asp Lys Tyr Arg Leu
1               5                   10                  15
```

<210> SEQ ID NO 141
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 9
<223> OTHER INFORMATION: Xaa = D-Serine

<400> SEQUENCE: 141

```
Met Gly Tyr Gln Lys Lys Leu Arg Xaa Met Thr Asp Lys Tyr Arg Leu
1               5                   10                  15
```

<210> SEQ ID NO 142
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 10
<223> OTHER INFORMATION: Xaa = D-Methionine

<400> SEQUENCE: 142

```
Met Gly Tyr Gln Lys Lys Leu Arg Ser Xaa Thr Asp Lys Tyr Arg Leu
1               5                   10                  15
```

<210> SEQ ID NO 143
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 12
<223> OTHER INFORMATION: Xaa = D-Leucine

<400> SEQUENCE: 143

```
Lys Lys Leu Arg Ser Met Thr Asp Lys Tyr Arg Xaa Ser
1               5                   10
```

<210> SEQ ID NO 144
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 10
<223> OTHER INFORMATION: Xaa = D-Proline

<400> SEQUENCE: 144

```
Met Gly Tyr Gln Lys Lys Leu Arg Ser Xaa Thr Asp Lys Tyr Arg Leu
1               5                   10                  15
```

<210> SEQ ID NO 145
<211> LENGTH: 16
<212> TYPE: PRT
<213> ORGANISM: Artificial Sequence
<220> FEATURE:
<223> OTHER INFORMATION: Synthetic
<220> FEATURE:

```
<221> NAME/KEY: MOD_RES
<222> LOCATION: 9
<223> OTHER INFORMATION: Xaa = D-Proline

<400> SEQUENCE: 145

Met Gly Tyr Gln Lys Lys Leu Arg Xaa Met Thr Asp Lys Tyr Arg Leu
 1               5                  10                  15

<210> SEQ ID NO 146
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 8
<223> OTHER INFORMATION: Xaa = D-Proline

<400> SEQUENCE: 146

Met Gly Tyr Gln Lys Lys Leu Xaa Ser Met Thr Asp Lys Tyr Arg Leu
 1               5                  10                  15

<210> SEQ ID NO 147
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 7
<223> OTHER INFORMATION: Xaa = D-Proline

<400> SEQUENCE: 147

Met Gly Tyr Gln Lys Lys Xaa Arg Ser Met Thr Asp Lys Tyr Arg Leu
 1               5                  10                  15

<210> SEQ ID NO 148
<211> LENGTH: 16
<212> TYPE: PRT
<213> ORGANISM: Artificial Sequence
<220> FEATURE:
<223> OTHER INFORMATION: Synthetic

<400> SEQUENCE: 148

Met Gly Tyr Gln Lys Lys Leu Arg Ser Met Pro Asp Lys Tyr Arg Leu
 1               5                  10                  15

<210> SEQ ID NO 149
<211> LENGTH: 22
<212> TYPE: PRT
<213> ORGANISM: Artificial Sequence
<220> FEATURE:
<223> OTHER INFORMATION: Synthetic

<400> SEQUENCE: 149

Asp Arg Tyr Leu Ala Ile Val His Ala Thr Asn Ser Gln Arg Pro Arg
 1               5                  10                  15

Lys Leu Leu Ala Glu Lys
            20

<210> SEQ ID NO 150
<211> LENGTH: 21
<212> TYPE: PRT
<213> ORGANISM: Artificial Sequence
<220> FEATURE:
<223> OTHER INFORMATION: Synthetic
```

```
<400> SEQUENCE: 150

Asp Arg Tyr Leu Ala Ile Val His Ala Thr Asn Ser Gln Arg Pro Arg
1               5                   10                  15

Lys Leu Leu Ala Glu
            20

<210> SEQ ID NO 151
<211> LENGTH: 20
<212> TYPE: PRT
<213> ORGANISM: Artificial Sequence
<220> FEATURE:
<223> OTHER INFORMATION: Synthetic

<400> SEQUENCE: 151

Asp Arg Tyr Leu Ala Ile Val His Ala Thr Asn Ser Gln Arg Pro Arg
1               5                   10                  15

Lys Leu Leu Ala
            20

<210> SEQ ID NO 152
<211> LENGTH: 19
<212> TYPE: PRT
<213> ORGANISM: Artificial Sequence
<220> FEATURE:
<223> OTHER INFORMATION: Synthetic

<400> SEQUENCE: 152

Asp Arg Tyr Leu Ala Ile Val His Ala Thr Asn Ser Gln Arg Pro Arg
1               5                   10                  15

Lys Leu Leu

<210> SEQ ID NO 153
<211> LENGTH: 18
<212> TYPE: PRT
<213> ORGANISM: Artificial Sequence
<220> FEATURE:
<223> OTHER INFORMATION: Synthetic

<400> SEQUENCE: 153

Asp Arg Tyr Leu Ala Ile Val His Ala Thr Asn Ser Gln Arg Pro Arg
1               5                   10                  15

Lys Leu

<210> SEQ ID NO 154
<211> LENGTH: 17
<212> TYPE: PRT
<213> ORGANISM: Artificial Sequence
<220> FEATURE:
<223> OTHER INFORMATION: Synthetic

<400> SEQUENCE: 154

Asp Arg Tyr Leu Ala Ile Val His Ala Thr Asn Ser Gln Arg Pro Arg
1               5                   10                  15

Lys

<210> SEQ ID NO 155
<211> LENGTH: 16
<212> TYPE: PRT
<213> ORGANISM: Artificial Sequence
<220> FEATURE:
<223> OTHER INFORMATION: Synthetic

<400> SEQUENCE: 155
```

Asp Arg Tyr Leu Ala Ile Val His Ala Thr Asn Ser Gln Arg Pro Arg
1               5                   10                  15

<210> SEQ ID NO 156
<211> LENGTH: 15
<212> TYPE: PRT
<213> ORGANISM: Artificial Sequence
<220> FEATURE:
<223> OTHER INFORMATION: Synthetic

<400> SEQUENCE: 156

Asp Arg Tyr Leu Ala Ile Val His Ala Thr Asn Ser Gln Arg Pro
1               5                   10                  15

<210> SEQ ID NO 157
<211> LENGTH: 14
<212> TYPE: PRT
<213> ORGANISM: Artificial Sequence
<220> FEATURE:
<223> OTHER INFORMATION: Synthetic

<400> SEQUENCE: 157

Asp Arg Tyr Leu Ala Ile Val His Ala Thr Asn Ser Gln Arg
1               5                   10

<210> SEQ ID NO 158
<211> LENGTH: 13
<212> TYPE: PRT
<213> ORGANISM: Artificial Sequence
<220> FEATURE:
<223> OTHER INFORMATION: Synthetic

<400> SEQUENCE: 158

Asp Arg Tyr Leu Ala Ile Val His Ala Thr Asn Ser Gln
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Synthetic

<400> SEQUENCE: 159

Asp Arg Tyr Leu Ala Ile Val His Ala Thr Asn Ser
1               5                   10

<210> SEQ ID NO 160
<211> LENGTH: 11
<212> TYPE: PRT
<213> ORGANISM: Artificial Sequence
<220> FEATURE:
<223> OTHER INFORMATION: Synthetic

<400> SEQUENCE: 160

Asp Arg Tyr Leu Ala Ile Val His Ala Thr Asn
1               5                   10

<210> SEQ ID NO 161
<211> LENGTH: 10
<212> TYPE: PRT
<213> ORGANISM: Artificial Sequence
<220> FEATURE:
<223> OTHER INFORMATION: Synthetic

<400> SEQUENCE: 161

Asp Arg Tyr Leu Ala Ile Val His Ala Thr
1               5                   10

<210> SEQ ID NO 162
<211> LENGTH: 9
<212> TYPE: PRT
<213> ORGANISM: Artificial Sequence
<220> FEATURE:
<223> OTHER INFORMATION: Synthetic

<400> SEQUENCE: 162

Asp Arg Tyr Leu Ala Ile Val His Ala
1               5

<210> SEQ ID NO 163
<211> LENGTH: 8
<212> TYPE: PRT
<213> ORGANISM: Artificial Sequence
<220> FEATURE:
<223> OTHER INFORMATION: Synthetic

<400> SEQUENCE: 163

Asp Arg Tyr Leu Ala Ile Val His
1               5

<210> SEQ ID NO 164
<211> LENGTH: 7
<212> TYPE: PRT
<213> ORGANISM: Artificial Sequence
<220> FEATURE:
<223> OTHER INFORMATION: Synthetic

<400> SEQUENCE: 164

Asp Arg Tyr Leu Ala Ile Val
1               5

<210> SEQ ID NO 165
<211> LENGTH: 21
<212> TYPE: PRT
<213> ORGANISM: Artificial Sequence
<220> FEATURE:
<223> OTHER INFORMATION: Synthetic

<400> SEQUENCE: 165

Arg Tyr Leu Ala Ile Val His Ala Thr Asn Ser Gln Arg Pro Arg Lys
1               5                   10                  15

Leu Leu Ala Glu Lys
            20

<210> SEQ ID NO 166
<211> LENGTH: 20
<212> TYPE: PRT
<213> ORGANISM: Artificial Sequence
<220> FEATURE:
<223> OTHER INFORMATION: Synthetic

<400> SEQUENCE: 166

Tyr Leu Ala Ile Val His Ala Thr Asn Ser Gln Arg Pro Arg Lys Leu
1               5                   10                  15

Leu Ala Glu Lys
            20

<210> SEQ ID NO 167
<211> LENGTH: 19
<212> TYPE: PRT
<213> ORGANISM: Artificial Sequence

```
<220> FEATURE:
<223> OTHER INFORMATION: Synthetic

<400> SEQUENCE: 167

Leu Ala Ile Val His Ala Thr Asn Ser Gln Arg Pro Arg Lys Leu Leu
1               5                   10                  15

Ala Glu Lys

<210> SEQ ID NO 168
<211> LENGTH: 18
<212> TYPE: PRT
<213> ORGANISM: Artificial Sequence
<220> FEATURE:
<223> OTHER INFORMATION: Synthetic

<400> SEQUENCE: 168

Ala Ile Val His Ala Thr Asn Ser Gln Arg Pro Arg Lys Leu Leu Ala
1               5                   10                  15

Glu Lys

<210> SEQ ID NO 169
<211> LENGTH: 17
<212> TYPE: PRT
<213> ORGANISM: Artificial Sequence
<220> FEATURE:
<223> OTHER INFORMATION: Synthetic

<400> SEQUENCE: 169

Ile Val His Ala Thr Asn Ser Gln Arg Pro Arg Lys Leu Leu Ala Glu
1               5                   10                  15

Lys

<210> SEQ ID NO 170
<211> LENGTH: 16
<212> TYPE: PRT
<213> ORGANISM: Artificial Sequence
<220> FEATURE:
<223> OTHER INFORMATION: Synthetic

<400> SEQUENCE: 170

Val His Ala Thr Asn Ser Gln Arg Pro Arg Lys Leu Leu Ala Glu Lys
1               5                   10                  15

<210> SEQ ID NO 171
<211> LENGTH: 15
<212> TYPE: PRT
<213> ORGANISM: Artificial Sequence
<220> FEATURE:
<223> OTHER INFORMATION: Synthetic

<400> SEQUENCE: 171

His Ala Thr Asn Ser Gln Arg Pro Arg Lys Leu Leu Ala Glu Lys
1               5                   10                  15

<210> SEQ ID NO 172
<211> LENGTH: 14
<212> TYPE: PRT
<213> ORGANISM: Artificial Sequence
<220> FEATURE:
<223> OTHER INFORMATION: Synthetic

<400> SEQUENCE: 172

Ala Thr Asn Ser Gln Arg Pro Arg Lys Leu Leu Ala Glu Lys
1               5                   10
```

<210> SEQ ID NO 173
<211> LENGTH: 13
<212> TYPE: PRT
<213> ORGANISM: Artificial Sequence
<220> FEATURE:
<223> OTHER INFORMATION: Synthetic

<400> SEQUENCE: 173

Thr Asn Ser Gln Arg Pro Arg Lys Leu Leu Ala Glu Lys
1               5                   10

<210> SEQ ID NO 174
<211> LENGTH: 12
<212> TYPE: PRT
<213> ORGANISM: Artificial Sequence
<220> FEATURE:
<223> OTHER INFORMATION: Synthetic

<400> SEQUENCE: 174

Asn Ser Gln Arg Pro Arg Lys Leu Leu Ala Glu Lys
1               5                   10

<210> SEQ ID NO 175
<211> LENGTH: 11
<212> TYPE: PRT
<213> ORGANISM: Artificial Sequence
<220> FEATURE:
<223> OTHER INFORMATION: Synthetic

<400> SEQUENCE: 175

Ser Gln Arg Pro Arg Lys Leu Leu Ala Glu Lys
1               5                   10

<210> SEQ ID NO 176
<211> LENGTH: 10
<212> TYPE: PRT
<213> ORGANISM: Artificial Sequence
<220> FEATURE:
<223> OTHER INFORMATION: Synthetic

<400> SEQUENCE: 176

Gln Arg Pro Arg Lys Leu Leu Ala Glu Lys
1               5                   10

<210> SEQ ID NO 177
<211> LENGTH: 9
<212> TYPE: PRT
<213> ORGANISM: Artificial Sequence
<220> FEATURE:
<223> OTHER INFORMATION: Synthetic

<400> SEQUENCE: 177

Arg Pro Arg Lys Leu Leu Ala Glu Lys
1               5

<210> SEQ ID NO 178
<211> LENGTH: 8
<212> TYPE: PRT
<213> ORGANISM: Artificial Sequence
<220> FEATURE:
<223> OTHER INFORMATION: Synthetic

<400> SEQUENCE: 178

Pro Arg Lys Leu Leu Ala Glu Lys
1               5

```
<210> SEQ ID NO 179
<211> LENGTH: 7
<212> TYPE: PRT
<213> ORGANISM: Artificial Sequence
<220> FEATURE:
<223> OTHER INFORMATION: Synthetic

<400> SEQUENCE: 179

Arg Lys Leu Leu Ala Glu Lys
1               5

<210> SEQ ID NO 180
<211> LENGTH: 7
<212> TYPE: PRT
<213> ORGANISM: Artificial Sequence
<220> FEATURE:
<223> OTHER INFORMATION: Synthetic

<400> SEQUENCE: 180

Arg Tyr Leu Ala Ile Val His
1               5

<210> SEQ ID NO 181
<211> LENGTH: 7
<212> TYPE: PRT
<213> ORGANISM: Artificial Sequence
<220> FEATURE:
<223> OTHER INFORMATION: Synthetic

<400> SEQUENCE: 181

Tyr Leu Ala Ile Val His Ala
1               5

<210> SEQ ID NO 182
<211> LENGTH: 7
<212> TYPE: PRT
<213> ORGANISM: Artificial Sequence
<220> FEATURE:
<223> OTHER INFORMATION: Synthetic

<400> SEQUENCE: 182

Leu Ala Ile Val His Ala Thr
1               5

<210> SEQ ID NO 183
<211> LENGTH: 7
<212> TYPE: PRT
<213> ORGANISM: Artificial Sequence
<220> FEATURE:
<223> OTHER INFORMATION: Synthetic

<400> SEQUENCE: 183

Ala Ile Val His Ala Thr Asn
1               5

<210> SEQ ID NO 184
<211> LENGTH: 7
<212> TYPE: PRT
<213> ORGANISM: Artificial Sequence
<220> FEATURE:
<223> OTHER INFORMATION: Synthetic

<400> SEQUENCE: 184

Ile Val His Ala Thr Asn Ser
1               5

<210> SEQ ID NO 185
```

```
<211> LENGTH: 7
<212> TYPE: PRT
<213> ORGANISM: Artificial Sequence
<220> FEATURE:
<223> OTHER INFORMATION: Synthetic

<400> SEQUENCE: 185

Val His Ala Thr Asn Ser Gln
 1               5

<210> SEQ ID NO 186
<211> LENGTH: 7
<212> TYPE: PRT
<213> ORGANISM: Artificial Sequence
<220> FEATURE:
<223> OTHER INFORMATION: Synthetic

<400> SEQUENCE: 186

His Ala Thr Asn Ser Gln Arg
 1               5

<210> SEQ ID NO 187
<211> LENGTH: 7
<212> TYPE: PRT
<213> ORGANISM: Artificial Sequence
<220> FEATURE:
<223> OTHER INFORMATION: Synthetic

<400> SEQUENCE: 187

Ala Thr Asn Ser Gln Arg Pro
 1               5

<210> SEQ ID NO 188
<211> LENGTH: 7
<212> TYPE: PRT
<213> ORGANISM: Artificial Sequence
<220> FEATURE:
<223> OTHER INFORMATION: Synthetic

<400> SEQUENCE: 188

Thr Asn Ser Gln Arg Pro Arg
 1               5

<210> SEQ ID NO 189
<211> LENGTH: 7
<212> TYPE: PRT
<213> ORGANISM: Artificial Sequence
<220> FEATURE:
<223> OTHER INFORMATION: Synthetic

<400> SEQUENCE: 189

Asn Ser Gln Arg Pro Arg Lys
 1               5

<210> SEQ ID NO 190
<211> LENGTH: 7
<212> TYPE: PRT
<213> ORGANISM: Artificial Sequence
<220> FEATURE:
<223> OTHER INFORMATION: Synthetic

<400> SEQUENCE: 190

Ser Gln Arg Pro Arg Lys Leu
 1               5

<210> SEQ ID NO 191
<211> LENGTH: 7
```

```
<212> TYPE: PRT
<213> ORGANISM: Artificial Sequence
<220> FEATURE:
<223> OTHER INFORMATION: Synthetic

<400> SEQUENCE: 191

Gln Arg Pro Arg Lys Leu Leu
1               5

<210> SEQ ID NO 192
<211> LENGTH: 7
<212> TYPE: PRT
<213> ORGANISM: Artificial Sequence
<220> FEATURE:
<223> OTHER INFORMATION: Synthetic

<400> SEQUENCE: 192

Arg Pro Arg Lys Leu Leu Ala
1               5

<210> SEQ ID NO 193
<211> LENGTH: 7
<212> TYPE: PRT
<213> ORGANISM: Artificial Sequence
<220> FEATURE:
<223> OTHER INFORMATION: Synthetic

<400> SEQUENCE: 193

Pro Arg Lys Leu Leu Ala Glu
1               5

<210> SEQ ID NO 194
<211> LENGTH: 19
<212> TYPE: PRT
<213> ORGANISM: Artificial Sequence
<220> FEATURE:
<223> OTHER INFORMATION: Synthetic

<400> SEQUENCE: 194

Val His Ala Thr Asn Ser Gln Arg Pro Arg Lys Leu Leu Ala Glu Lys
1               5                   10                  15

Val Val Tyr

<210> SEQ ID NO 195
<211> LENGTH: 14
<212> TYPE: PRT
<213> ORGANISM: Artificial Sequence
<220> FEATURE:
<223> OTHER INFORMATION: Synthetic

<400> SEQUENCE: 195

Val His Ala Thr Asn Ser Gln Arg Pro Arg Lys Leu Leu Ala
1               5                   10

<210> SEQ ID NO 196
<211> LENGTH: 11
<212> TYPE: PRT
<213> ORGANISM: Artificial Sequence
<220> FEATURE:
<223> OTHER INFORMATION: Synthetic

<400> SEQUENCE: 196

His Ala Thr Asn Ser Gln Arg Pro Arg Lys Leu
1               5                   10

<210> SEQ ID NO 197
```

```
<211> LENGTH: 13
<212> TYPE: PRT
<213> ORGANISM: Artificial Sequence
<220> FEATURE:
<223> OTHER INFORMATION: Synthetic

<400> SEQUENCE: 197

His Ala Thr Asn Ser Gln Arg Pro Arg Lys Leu Leu Ala
 1               5                  10

<210> SEQ ID NO 198
<211> LENGTH: 14
<212> TYPE: PRT
<213> ORGANISM: Artificial Sequence
<220> FEATURE:
<223> OTHER INFORMATION: Synthetic

<400> SEQUENCE: 198

His Ala Thr Asn Ser Gln Arg Pro Arg Lys Leu Leu Ala Glu
 1               5                  10

<210> SEQ ID NO 199
<211> LENGTH: 16
<212> TYPE: PRT
<213> ORGANISM: Artificial Sequence
<220> FEATURE:
<223> OTHER INFORMATION: Synthetic

<400> SEQUENCE: 199

His Ala Thr Asn Ser Gln Arg Pro Arg Lys Leu Leu Ala Glu Lys Val
 1               5                  10                  15

<210> SEQ ID NO 200
<211> LENGTH: 13
<212> TYPE: PRT
<213> ORGANISM: Artificial Sequence
<220> FEATURE:
<223> OTHER INFORMATION: Synthetic

<400> SEQUENCE: 200

His Ser Lys Lys Gly His Gln Lys Arg Lys Ala Leu Lys
 1               5                  10

<210> SEQ ID NO 201
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 1
<223> OTHER INFORMATION: Xaa = Leucine or Isoleucine
<220> FEATURE:
<221> NAME/KEY: MOD_RES
<222> LOCATION: 10
<223> OTHER INFORMATION: Xaa = Leucine or Isoleucine

<400> SEQUENCE: 201

Xaa Gly Tyr Gln Lys Lys Leu Arg Ser Xaa Thr Asp
 1               5                  10

<210> SEQ ID NO 202
<211> LENGTH: 20
<212> TYPE: PRT
<213> ORGANISM: Artificial Sequence
<220> FEATURE:
<223> OTHER INFORMATION: Synthetic
```

<400> SEQUENCE: 202

Ile Ile Ile Ser Lys Leu Ser His Ser Lys Gly His Gln Lys Arg Lys
1               5                   10                  15

Ala Leu Lys Thr
            20

<210> SEQ ID NO 203
<211> LENGTH: 19
<212> TYPE: PRT
<213> ORGANISM: Artificial Sequence
<220> FEATURE:
<223> OTHER INFORMATION: Synthetic

<400> SEQUENCE: 203

Ile Ile Ile Ser Lys Leu Ser His Ser Lys Gly His Gln Lys Arg Lys
1               5                   10                  15

Ala Leu Lys

<210> SEQ ID NO 204
<211> LENGTH: 18
<212> TYPE: PRT
<213> ORGANISM: Artificial Sequence
<220> FEATURE:
<223> OTHER INFORMATION: Synthetic

<400> SEQUENCE: 204

Ile Ile Ile Ser Lys Leu Ser His Ser Lys Gly His Gln Lys Arg Lys
1               5                   10                  15

Ala Leu

<210> SEQ ID NO 205
<211> LENGTH: 17
<212> TYPE: PRT
<213> ORGANISM: Artificial Sequence
<220> FEATURE:
<223> OTHER INFORMATION: Synthetic

<400> SEQUENCE: 205

Ile Ile Ile Ser Lys Leu Ser His Ser Lys Gly His Gln Lys Arg Lys
1               5                   10                  15

Ala

<210> SEQ ID NO 206
<211> LENGTH: 16
<212> TYPE: PRT
<213> ORGANISM: Artificial Sequence
<220> FEATURE:
<223> OTHER INFORMATION: Synthetic

<400> SEQUENCE: 206

Ile Ile Ile Ser Lys Leu Ser His Ser Lys Gly His Gln Lys Arg Lys
1               5                   10                  15

<210> SEQ ID NO 207
<211> LENGTH: 15
<212> TYPE: PRT
<213> ORGANISM: Artificial Sequence
<220> FEATURE:
<223> OTHER INFORMATION: Synthetic

<400> SEQUENCE: 207

Ile Ile Ile Ser Lys Leu Ser His Ser Lys Gly His Gln Lys Arg
1               5                   10                  15

```
<210> SEQ ID NO 208
<211> LENGTH: 14
<212> TYPE: PRT
<213> ORGANISM: Artificial Sequence
<220> FEATURE:
<223> OTHER INFORMATION: Synthetic

<400> SEQUENCE: 208

Ile Ile Ile Ser Lys Leu Ser His Ser Lys Gly His Gln Lys
1               5                   10

<210> SEQ ID NO 209
<211> LENGTH: 13
<212> TYPE: PRT
<213> ORGANISM: Artificial Sequence
<220> FEATURE:
<223> OTHER INFORMATION: Synthetic

<400> SEQUENCE: 209

Ile Ile Ile Ser Lys Leu Ser His Ser Lys Gly His Gln
1               5                   10

<210> SEQ ID NO 210
<211> LENGTH: 12
<212> TYPE: PRT
<213> ORGANISM: Artificial Sequence
<220> FEATURE:
<223> OTHER INFORMATION: Synthetic

<400> SEQUENCE: 210

Ile Ile Ile Ser Lys Leu Ser His Ser Lys Gly His
1               5                   10

<210> SEQ ID NO 211
<211> LENGTH: 11
<212> TYPE: PRT
<213> ORGANISM: Artificial Sequence
<220> FEATURE:
<223> OTHER INFORMATION: Synthetic

<400> SEQUENCE: 211

Ile Ile Ile Ser Lys Leu Ser His Ser Lys Gly
1               5                   10

<210> SEQ ID NO 212
<211> LENGTH: 10
<212> TYPE: PRT
<213> ORGANISM: Artificial Sequence
<220> FEATURE:
<223> OTHER INFORMATION: Synthetic

<400> SEQUENCE: 212

Ile Ile Ile Ser Lys Leu Ser His Ser Lys
1               5                   10

<210> SEQ ID NO 213
<211> LENGTH: 9
<212> TYPE: PRT
<213> ORGANISM: Artificial Sequence
<220> FEATURE:
<223> OTHER INFORMATION: Synthetic

<400> SEQUENCE: 213

Ile Ile Ile Ser Lys Leu Ser His Ser
1               5
```

```
<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

Ile Ile Ile Ser Lys Leu Ser His
1               5

<210> SEQ ID NO 215
<211> LENGTH: 7
<212> TYPE: PRT
<213> ORGANISM: Artificial Sequence
<220> FEATURE:
<223> OTHER INFORMATION: Synthetic

<400> SEQUENCE: 215

Ile Ile Ile Ser Lys Leu Ser
1               5

<210> SEQ ID NO 216
<211> LENGTH: 19
<212> TYPE: PRT
<213> ORGANISM: Artificial Sequence
<220> FEATURE:
<223> OTHER INFORMATION: Synthetic

<400> SEQUENCE: 216

Ile Ile Ser Lys Leu Ser His Ser Lys Gly His Gln Lys Arg Lys Ala
1               5                   10                  15

Leu Lys Thr

<210> SEQ ID NO 217
<211> LENGTH: 18
<212> TYPE: PRT
<213> ORGANISM: Artificial Sequence
<220> FEATURE:
<223> OTHER INFORMATION: Synthetic

<400> SEQUENCE: 217

Ile Ser Lys Leu Ser His Ser Lys Gly His Gln Lys Arg Lys Ala Leu
1               5                   10                  15

Lys Thr

<210> SEQ ID NO 218
<211> LENGTH: 17
<212> TYPE: PRT
<213> ORGANISM: Artificial Sequence
<220> FEATURE:
<223> OTHER INFORMATION: Synthetic

<400> SEQUENCE: 218

Ser Lys Leu Ser His Ser Lys Gly His Gln Lys Arg Lys Ala Leu Lys
1               5                   10                  15

Thr

<210> SEQ ID NO 219
<211> LENGTH: 16
<212> TYPE: PRT
<213> ORGANISM: Artificial Sequence
<220> FEATURE:
<223> OTHER INFORMATION: Synthetic

<400> SEQUENCE: 219
```

Lys Leu Ser His Ser Lys Gly His Gln Lys Arg Lys Ala Leu Lys Thr
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: Synthetic

<400> SEQUENCE: 220

Leu Ser His Ser Lys Gly His Gln Lys Arg Lys Ala Leu Lys Thr
1               5                   10                  15

<210> SEQ ID NO 221
<211> LENGTH: 14
<212> TYPE: PRT
<213> ORGANISM: Artificial Sequence
<220> FEATURE:
<223> OTHER INFORMATION: Synthetic

<400> SEQUENCE: 221

Ser His Ser Lys Gly His Gln Lys Arg Lys Ala Leu Lys Thr
1               5                   10

<210> SEQ ID NO 222
<211> LENGTH: 13
<212> TYPE: PRT
<213> ORGANISM: Artificial Sequence
<220> FEATURE:
<223> OTHER INFORMATION: Synthetic

<400> SEQUENCE: 222

His Ser Lys Gly His Gln Lys Arg Lys Ala Leu Lys Thr
1               5                   10

<210> SEQ ID NO 223
<211> LENGTH: 12
<212> TYPE: PRT
<213> ORGANISM: Artificial Sequence
<220> FEATURE:
<223> OTHER INFORMATION: Synthetic

<400> SEQUENCE: 223

Ser Lys Gly His Gln Lys Arg Lys Ala Leu Lys Thr
1               5                   10

<210> SEQ ID NO 224
<211> LENGTH: 11
<212> TYPE: PRT
<213> ORGANISM: Artificial Sequence
<220> FEATURE:
<223> OTHER INFORMATION: Synthetic

<400> SEQUENCE: 224

Lys Gly His Gln Lys Arg Lys Ala Leu Lys Thr
1               5                   10

<210> SEQ ID NO 225
<211> LENGTH: 10
<212> TYPE: PRT
<213> ORGANISM: Artificial Sequence
<220> FEATURE:
<223> OTHER INFORMATION: Synthetic

<400> SEQUENCE: 225

Gly His Gln Lys Arg Lys Ala Leu Lys Thr
1               5                   10

<210> SEQ ID NO 226
<211> LENGTH: 9
<212> TYPE: PRT
<213> ORGANISM: Artificial Sequence
<220> FEATURE:
<223> OTHER INFORMATION: Synthetic

<400> SEQUENCE: 226

His Gln Lys Arg Lys Ala Leu Lys Thr
1               5

<210> SEQ ID NO 227
<211> LENGTH: 8
<212> TYPE: PRT
<213> ORGANISM: Artificial Sequence
<220> FEATURE:
<223> OTHER INFORMATION: Synthetic

<400> SEQUENCE: 227

Gln Lys Arg Lys Ala Leu Lys Thr
1               5

<210> SEQ ID NO 228
<211> LENGTH: 7
<212> TYPE: PRT
<213> ORGANISM: Artificial Sequence
<220> FEATURE:
<223> OTHER INFORMATION: Synthetic

<400> SEQUENCE: 228

Lys Arg Lys Ala Leu Lys Thr
1               5

<210> SEQ ID NO 229
<211> LENGTH: 7
<212> TYPE: PRT
<213> ORGANISM: Artificial Sequence
<220> FEATURE:
<223> OTHER INFORMATION: Synthetic

<400> SEQUENCE: 229

Ile Ile Ser Lys Leu Ser His
1               5

<210> SEQ ID NO 230
<211> LENGTH: 7
<212> TYPE: PRT
<213> ORGANISM: Artificial Sequence
<220> FEATURE:
<223> OTHER INFORMATION: Synthetic

<400> SEQUENCE: 230

Ile Ser Lys Leu Ser His Ser
1               5

<210> SEQ ID NO 231
<211> LENGTH: 7
<212> TYPE: PRT
<213> ORGANISM: Artificial Sequence
<220> FEATURE:
<223> OTHER INFORMATION: Synthetic

<400> SEQUENCE: 231

Ser Lys Leu Ser His Ser Lys

```
                1               5

<210> SEQ ID NO 232
<211> LENGTH: 7
<212> TYPE: PRT
<213> ORGANISM: Artificial Sequence
<220> FEATURE:
<223> OTHER INFORMATION: Synthetic

<400> SEQUENCE: 232

Lys Leu Ser His Ser Lys Gly
1               5

<210> SEQ ID NO 233
<211> LENGTH: 7
<212> TYPE: PRT
<213> ORGANISM: Artificial Sequence
<220> FEATURE:
<223> OTHER INFORMATION: Synthetic

<400> SEQUENCE: 233

Leu Ser His Ser Lys Gly His
1               5

<210> SEQ ID NO 234
<211> LENGTH: 7
<212> TYPE: PRT
<213> ORGANISM: Artificial Sequence
<220> FEATURE:
<223> OTHER INFORMATION: Synthetic

<400> SEQUENCE: 234

Ser His Ser Lys Gly His Gln
1               5

<210> SEQ ID NO 235
<211> LENGTH: 7
<212> TYPE: PRT
<213> ORGANISM: Artificial Sequence
<220> FEATURE:
<223> OTHER INFORMATION: Synthetic

<400> SEQUENCE: 235

His Ser Lys Gly His Gln Lys
1               5

<210> SEQ ID NO 236
<211> LENGTH: 7
<212> TYPE: PRT
<213> ORGANISM: Artificial Sequence
<220> FEATURE:
<223> OTHER INFORMATION: Synthetic

<400> SEQUENCE: 236

Ser Lys Gly His Gln Lys Arg
1               5

<210> SEQ ID NO 237
<211> LENGTH: 7
<212> TYPE: PRT
<213> ORGANISM: Artificial Sequence
<220> FEATURE:
<223> OTHER INFORMATION: Synthetic

<400> SEQUENCE: 237

Lys Gly His Gln Lys Arg Lys
1               5
```

```
<210> SEQ ID NO 238
<211> LENGTH: 7
<212> TYPE: PRT
<213> ORGANISM: Artificial Sequence
<220> FEATURE:
<223> OTHER INFORMATION: Synthetic

<400> SEQUENCE: 238

Gly His Gln Lys Arg Lys Ala
1               5

<210> SEQ ID NO 239
<211> LENGTH: 7
<212> TYPE: PRT
<213> ORGANISM: Artificial Sequence
<220> FEATURE:
<223> OTHER INFORMATION: Synthetic

<400> SEQUENCE: 239

His Gln Lys Arg Lys Ala Leu
1               5

<210> SEQ ID NO 240
<211> LENGTH: 7
<212> TYPE: PRT
<213> ORGANISM: Artificial Sequence
<220> FEATURE:
<223> OTHER INFORMATION: Synthetic

<400> SEQUENCE: 240

Gln Lys Arg Lys Ala Leu Lys
1               5

<210> SEQ ID NO 241
<211> LENGTH: 14
<212> TYPE: PRT
<213> ORGANISM: Artificial Sequence
<220> FEATURE:
<223> OTHER INFORMATION: Synthetic

<400> SEQUENCE: 241

His Ser Lys Gly His Gln Lys Arg Lys Ala Leu Lys Thr Thr
1               5                   10

<210> SEQ ID NO 242
<211> LENGTH: 15
<212> TYPE: PRT
<213> ORGANISM: Artificial Sequence
<220> FEATURE:
<223> OTHER INFORMATION: Synthetic

<400> SEQUENCE: 242

His Ser Lys Gly His Gln Lys Arg Lys Ala Leu Lys Thr Thr Val
1               5                   10                  15

<210> SEQ ID NO 243
<211> LENGTH: 16
<212> TYPE: PRT
<213> ORGANISM: Artificial Sequence
<220> FEATURE:
<223> OTHER INFORMATION: Synthetic

<400> SEQUENCE: 243

His Ser Lys Gly His Gln Lys Arg Lys Ala Leu Lys Thr Thr Val Ile
1               5                   10                  15
```

```
<210> SEQ ID NO 244
<211> LENGTH: 13
<212> TYPE: PRT
<213> ORGANISM: Artificial Sequence
<220> FEATURE:
<223> OTHER INFORMATION: Synthetic

<400> SEQUENCE: 244

His Ser Lys Gly His Gln Lys Arg Lys Gln Ala Leu Lys
 1               5                  10

<210> SEQ ID NO 245
<211> LENGTH: 13
<212> TYPE: PRT
<213> ORGANISM: Artificial Sequence
<220> FEATURE:
<223> OTHER INFORMATION: Synthetic

<400> SEQUENCE: 245

Lys Leu Ser His Ser Lys Gly His Gln Lys Arg Lys Ala
 1               5                  10

<210> SEQ ID NO 246
<211> LENGTH: 14
<212> TYPE: PRT
<213> ORGANISM: Artificial Sequence
<220> FEATURE:
<223> OTHER INFORMATION: Synthetic

<400> SEQUENCE: 246

Lys Leu Ser His Ser Lys Gly His Gln Lys Arg Lys Ala Leu
 1               5                  10

<210> SEQ ID NO 247
<211> LENGTH: 15
<212> TYPE: PRT
<213> ORGANISM: Artificial Sequence
<220> FEATURE:
<223> OTHER INFORMATION: Synthetic

<400> SEQUENCE: 247

Lys Leu Ser His Ser Lys Gly His Gln Lys Arg Lys Ala Leu Lys
 1               5                  10                  15

<210> SEQ ID NO 248
<211> LENGTH: 18
<212> TYPE: PRT
<213> ORGANISM: Artificial Sequence
<220> FEATURE:
<223> OTHER INFORMATION: Synthetic

<400> SEQUENCE: 248

Lys Leu Ser His Ser Lys Gly His Gln Lys Arg Lys Ala Leu Lys Thr
 1               5                  10                  15

Thr Val

<210> SEQ ID NO 249
<211> LENGTH: 20
<212> TYPE: PRT
<213> ORGANISM: Artificial Sequence
<220> FEATURE:
<223> OTHER INFORMATION: Synthetic

<400> SEQUENCE: 249

Lys Leu Ser His Ser Lys Gly His Gln Lys Arg Lys Ala Leu Lys Thr
 1               5                  10                  15
```

Thr Val Ile Leu
        20

<210> SEQ ID NO 250
<211> LENGTH: 14
<212> TYPE: PRT
<213> ORGANISM: Artificial Sequence
<220> FEATURE:
<223> OTHER INFORMATION: Synthetic

<400> SEQUENCE: 250

Leu Ser His Ser Lys Gly His Gln Lys Arg Lys Ala Leu Lys
1               5                   10

<210> SEQ ID NO 251
<211> LENGTH: 13
<212> TYPE: PRT
<213> ORGANISM: Artificial Sequence
<220> FEATURE:
<223> OTHER INFORMATION: Synthetic

<400> SEQUENCE: 251

Ser His Ser Lys Gly His Gln Lys Arg Lys Ala Leu Lys
1               5                   10

<210> SEQ ID NO 252
<211> LENGTH: 16
<212> TYPE: PRT
<213> ORGANISM: Artificial Sequence
<220> FEATURE:
<223> OTHER INFORMATION: Synthetic

<400> SEQUENCE: 252

Ser Lys Leu Ser His Ser Lys Gly His Gln Lys Arg Lys Ala Leu Lys
1               5                   10                  15

<210> SEQ ID NO 253
<211> LENGTH: 21
<212> TYPE: PRT
<213> ORGANISM: Artificial Sequence
<220> FEATURE:
<223> OTHER INFORMATION: Synthetic

<400> SEQUENCE: 253

Ser Lys Leu Ser His Ser Lys Gly His Gln Lys Arg Lys Ala Leu Lys
1               5                   10                  15

Thr Thr Val Ile Leu
            20

<210> SEQ ID NO 254
<211> LENGTH: 21
<212> TYPE: PRT
<213> ORGANISM: Artificial Sequence
<220> FEATURE:
<223> OTHER INFORMATION: Synthetic

<400> SEQUENCE: 254

Gln His Leu His Ile Ala Leu Lys Lys Ser Thr Ser Arg Lys Val Lys
1               5                   10                  15

Ser Gly Thr Leu Lys
            20

<210> SEQ ID NO 255
<211> LENGTH: 45
<212> TYPE: PRT

```
<213> ORGANISM: Artificial Sequence
<220> FEATURE:
<223> OTHER INFORMATION: Synthetic

<400> SEQUENCE: 255

Gly Ala Lys Phe Lys Thr Ser Ala Gln His Ala Leu Thr Ser Val Ser
1               5                   10                  15

Arg Gly Ser Ser Leu Lys Ile Leu Ser Lys Gly Lys Arg Gly Gly His
            20                  25                  30

Ser Ser Val Ser Thr Glu Ser Glu Ser Ser Ser Phe His
        35                  40                  45

<210> SEQ ID NO 256
<211> LENGTH: 44
<212> TYPE: PRT
<213> ORGANISM: Artificial Sequence
<220> FEATURE:
<223> OTHER INFORMATION: Synthetic

<400> SEQUENCE: 256

Gly Ala Lys Phe Lys Thr Ser Ala Gln His Ala Leu Thr Ser Val Ser
1               5                   10                  15

Arg Gly Ser Ser Leu Lys Ile Leu Ser Lys Gly Lys Arg Gly Gly His
            20                  25                  30

Ser Ser Val Ser Thr Glu Ser Glu Ser Ser Ser Phe
        35                  40

<210> SEQ ID NO 257
<211> LENGTH: 43
<212> TYPE: PRT
<213> ORGANISM: Artificial Sequence
<220> FEATURE:
<223> OTHER INFORMATION: Synthetic

<400> SEQUENCE: 257

Gly Ala Lys Phe Lys Thr Ser Ala Gln His Ala Leu Thr Ser Val Ser
1               5                   10                  15

Arg Gly Ser Ser Leu Lys Ile Leu Ser Lys Gly Lys Arg Gly Gly His
            20                  25                  30

Ser Ser Val Ser Thr Glu Ser Glu Ser Ser Ser
        35                  40

<210> SEQ ID NO 258
<211> LENGTH: 42
<212> TYPE: PRT
<213> ORGANISM: Artificial Sequence
<220> FEATURE:
<223> OTHER INFORMATION: Synthetic

<400> SEQUENCE: 258

Gly Ala Lys Phe Lys Thr Ser Ala Gln His Ala Leu Thr Ser Val Ser
1               5                   10                  15

Arg Gly Ser Ser Leu Lys Ile Leu Ser Lys Gly Lys Arg Gly Gly His
            20                  25                  30

Ser Ser Val Ser Thr Glu Ser Glu Ser Ser
        35                  40

<210> SEQ ID NO 259
<211> LENGTH: 41
<212> TYPE: PRT
<213> ORGANISM: Artificial Sequence
<220> FEATURE:
<223> OTHER INFORMATION: Synthetic
```

<400> SEQUENCE: 259

Gly Ala Lys Phe Lys Thr Ser Ala Gln His Ala Leu Thr Ser Val Ser
1               5                   10                  15

Arg Gly Ser Ser Leu Lys Ile Leu Ser Lys Gly Lys Arg Gly Gly His
            20                  25                  30

Ser Ser Val Ser Thr Glu Ser Glu Ser
        35                  40

<210> SEQ ID NO 260
<211> LENGTH: 40
<212> TYPE: PRT
<213> ORGANISM: Artificial Sequence
<220> FEATURE:
<223> OTHER INFORMATION: Synthetic

<400> SEQUENCE: 260

Gly Ala Lys Phe Lys Thr Ser Ala Gln His Ala Leu Thr Ser Val Ser
1               5                   10                  15

Arg Gly Ser Ser Leu Lys Ile Leu Ser Lys Gly Lys Arg Gly Gly His
            20                  25                  30

Ser Ser Val Ser Thr Glu Ser Glu
        35                  40

<210> SEQ ID NO 261
<211> LENGTH: 39
<212> TYPE: PRT
<213> ORGANISM: Artificial Sequence
<220> FEATURE:
<223> OTHER INFORMATION: Synthetic

<400> SEQUENCE: 261

Gly Ala Lys Phe Lys Thr Ser Ala Gln His Ala Leu Thr Ser Val Ser
1               5                   10                  15

Arg Gly Ser Ser Leu Lys Ile Leu Ser Lys Gly Lys Arg Gly Gly His
            20                  25                  30

Ser Ser Val Ser Thr Glu Ser
        35

<210> SEQ ID NO 262
<211> LENGTH: 38
<212> TYPE: PRT
<213> ORGANISM: Artificial Sequence
<220> FEATURE:
<223> OTHER INFORMATION: Synthetic

<400> SEQUENCE: 262

Gly Ala Lys Phe Lys Thr Ser Ala Gln His Ala Leu Thr Ser Val Ser
1               5                   10                  15

Arg Gly Ser Ser Leu Lys Ile Leu Ser Lys Gly Lys Arg Gly Gly His
            20                  25                  30

Ser Ser Val Ser Thr Glu
        35

<210> SEQ ID NO 263
<211> LENGTH: 37
<212> TYPE: PRT
<213> ORGANISM: Artificial Sequence
<220> FEATURE:
<223> OTHER INFORMATION: Synthetic

<400> SEQUENCE: 263

```
Gly Ala Lys Phe Lys Thr Ser Ala Gln His Ala Leu Thr Ser Val Ser
1               5                   10                  15

Arg Gly Ser Ser Leu Lys Ile Leu Ser Lys Gly Lys Arg Gly Gly His
            20                  25                  30

Ser Ser Val Ser Thr
            35
```

<210> SEQ ID NO 264
<211> LENGTH: 36
<212> TYPE: PRT
<213> ORGANISM: Artificial Sequence
<220> FEATURE:
<223> OTHER INFORMATION: Synthetic

<400> SEQUENCE: 264

```
Gly Ala Lys Phe Lys Thr Ser Ala Gln His Ala Leu Thr Ser Val Ser
1               5                   10                  15

Arg Gly Ser Ser Leu Lys Ile Leu Ser Lys Gly Lys Arg Gly Gly His
            20                  25                  30

Ser Ser Val Ser
            35
```

<210> SEQ ID NO 265
<211> LENGTH: 35
<212> TYPE: PRT
<213> ORGANISM: Artificial Sequence
<220> FEATURE:
<223> OTHER INFORMATION: Synthetic

<400> SEQUENCE: 265

```
Gly Ala Lys Phe Lys Thr Ser Ala Gln His Ala Leu Thr Ser Val Ser
1               5                   10                  15

Arg Gly Ser Ser Leu Lys Ile Leu Ser Lys Gly Lys Arg Gly Gly His
            20                  25                  30

Ser Ser Val
        35
```

<210> SEQ ID NO 266
<211> LENGTH: 34
<212> TYPE: PRT
<213> ORGANISM: Artificial Sequence
<220> FEATURE:
<223> OTHER INFORMATION: Synthetic

<400> SEQUENCE: 266

```
Gly Ala Lys Phe Lys Thr Ser Ala Gln His Ala Leu Thr Ser Val Ser
1               5                   10                  15

Arg Gly Ser Ser Leu Lys Ile Leu Ser Lys Gly Lys Arg Gly Gly His
            20                  25                  30

Ser Ser
```

<210> SEQ ID NO 267
<211> LENGTH: 33
<212> TYPE: PRT
<213> ORGANISM: Artificial Sequence
<220> FEATURE:
<223> OTHER INFORMATION: Synthetic

<400> SEQUENCE: 267

```
Gly Ala Lys Phe Lys Thr Ser Ala Gln His Ala Leu Thr Ser Val Ser
1               5                   10                  15

Arg Gly Ser Ser Leu Lys Ile Leu Ser Lys Gly Lys Arg Gly Gly His
```

Ser

<210> SEQ ID NO 268
<211> LENGTH: 32
<212> TYPE: PRT
<213> ORGANISM: Artificial Sequence
<220> FEATURE:
<223> OTHER INFORMATION: Synthetic

<400> SEQUENCE: 268

Gly Ala Lys Phe Lys Thr Ser Ala Gln His Ala Leu Thr Ser Val Ser
1               5                   10                  15

Arg Gly Ser Ser Leu Lys Ile Leu Ser Lys Gly Lys Arg Gly Gly His
            20                  25                  30

<210> SEQ ID NO 269
<211> LENGTH: 31
<212> TYPE: PRT
<213> ORGANISM: Artificial Sequence
<220> FEATURE:
<223> OTHER INFORMATION: Synthetic

<400> SEQUENCE: 269

Gly Ala Lys Phe Lys Thr Ser Ala Gln His Ala Leu Thr Ser Val Ser
1               5                   10                  15

Arg Gly Ser Ser Leu Lys Ile Leu Ser Lys Gly Lys Arg Gly Gly
            20                  25                  30

<210> SEQ ID NO 270
<211> LENGTH: 30
<212> TYPE: PRT
<213> ORGANISM: Artificial Sequence
<220> FEATURE:
<223> OTHER INFORMATION: Synthetic

<400> SEQUENCE: 270

Gly Ala Lys Phe Lys Thr Ser Ala Gln His Ala Leu Thr Ser Val Ser
1               5                   10                  15

Arg Gly Ser Ser Leu Lys Ile Leu Ser Lys Gly Lys Arg Gly
            20                  25                  30

<210> SEQ ID NO 271
<211> LENGTH: 29
<212> TYPE: PRT
<213> ORGANISM: Artificial Sequence
<220> FEATURE:
<223> OTHER INFORMATION: Synthetic

<400> SEQUENCE: 271

Gly Ala Lys Phe Lys Thr Ser Ala Gln His Ala Leu Thr Ser Val Ser
1               5                   10                  15

Arg Gly Ser Ser Leu Lys Ile Leu Ser Lys Gly Lys Arg
            20                  25

<210> SEQ ID NO 272
<211> LENGTH: 28
<212> TYPE: PRT
<213> ORGANISM: Artificial Sequence
<220> FEATURE:
<223> OTHER INFORMATION: Synthetic

<400> SEQUENCE: 272

Gly Ala Lys Phe Lys Thr Ser Ala Gln His Ala Leu Thr Ser Val Ser

```
                1               5                   10                  15
Arg Gly Ser Ser Leu Lys Ile Leu Ser Lys Gly Lys
            20                  25

<210> SEQ ID NO 273
<211> LENGTH: 27
<212> TYPE: PRT
<213> ORGANISM: Artificial Sequence
<220> FEATURE:
<223> OTHER INFORMATION: Synthetic

<400> SEQUENCE: 273

Gly Ala Lys Phe Lys Thr Ser Ala Gln His Ala Leu Thr Ser Val Ser
1               5                   10                  15

Arg Gly Ser Ser Leu Lys Ile Leu Ser Lys Gly
            20                  25

<210> SEQ ID NO 274
<211> LENGTH: 26
<212> TYPE: PRT
<213> ORGANISM: Artificial Sequence
<220> FEATURE:
<223> OTHER INFORMATION: Synthetic

<400> SEQUENCE: 274

Gly Ala Lys Phe Lys Thr Ser Ala Gln His Ala Leu Thr Ser Val Ser
1               5                   10                  15

Arg Gly Ser Ser Leu Lys Ile Leu Ser Lys
            20                  25

<210> SEQ ID NO 275
<211> LENGTH: 25
<212> TYPE: PRT
<213> ORGANISM: Artificial Sequence
<220> FEATURE:
<223> OTHER INFORMATION: Synthetic

<400> SEQUENCE: 275

Gly Ala Lys Phe Lys Thr Ser Ala Gln His Ala Leu Thr Ser Val Ser
1               5                   10                  15

Arg Gly Ser Ser Leu Lys Ile Leu Ser
            20                  25

<210> SEQ ID NO 276
<211> LENGTH: 24
<212> TYPE: PRT
<213> ORGANISM: Artificial Sequence
<220> FEATURE:
<223> OTHER INFORMATION: Synthetic

<400> SEQUENCE: 276

Gly Ala Lys Phe Lys Thr Ser Ala Gln His Ala Leu Thr Ser Val Ser
1               5                   10                  15

Arg Gly Ser Ser Leu Lys Ile Leu
            20

<210> SEQ ID NO 277
<211> LENGTH: 23
<212> TYPE: PRT
<213> ORGANISM: Artificial Sequence
<220> FEATURE:
<223> OTHER INFORMATION: Synthetic

<400> SEQUENCE: 277
```

Gly Ala Lys Phe Lys Thr Ser Ala Gln His Ala Leu Thr Ser Val Ser
1               5                   10                  15

Arg Gly Ser Ser Leu Lys Ile
            20

<210> SEQ ID NO 278
<211> LENGTH: 22
<212> TYPE: PRT
<213> ORGANISM: Artificial Sequence
<220> FEATURE:
<223> OTHER INFORMATION: Synthetic

<400> SEQUENCE: 278

Gly Ala Lys Phe Lys Thr Ser Ala Gln His Ala Leu Thr Ser Val Ser
1               5                   10                  15

Arg Gly Ser Ser Leu Lys
            20

<210> SEQ ID NO 279
<211> LENGTH: 21
<212> TYPE: PRT
<213> ORGANISM: Artificial Sequence
<220> FEATURE:
<223> OTHER INFORMATION: Synthetic

<400> SEQUENCE: 279

Gly Ala Lys Phe Lys Thr Ser Ala Gln His Ala Leu Thr Ser Val Ser
1               5                   10                  15

Arg Gly Ser Ser Leu
            20

<210> SEQ ID NO 280
<211> LENGTH: 20
<212> TYPE: PRT
<213> ORGANISM: Artificial Sequence
<220> FEATURE:
<223> OTHER INFORMATION: Synthetic

<400> SEQUENCE: 280

Gly Ala Lys Phe Lys Thr Ser Ala Gln His Ala Leu Thr Ser Val Ser
1               5                   10                  15

Arg Gly Ser Ser
            20

<210> SEQ ID NO 281
<211> LENGTH: 19
<212> TYPE: PRT
<213> ORGANISM: Artificial Sequence
<220> FEATURE:
<223> OTHER INFORMATION: Synthetic

<400> SEQUENCE: 281

Gly Ala Lys Phe Lys Thr Ser Ala Gln His Ala Leu Thr Ser Val Ser
1               5                   10                  15

Arg Gly Ser

<210> SEQ ID NO 282
<211> LENGTH: 18
<212> TYPE: PRT
<213> ORGANISM: Artificial Sequence
<220> FEATURE:
<223> OTHER INFORMATION: Synthetic

<400> SEQUENCE: 282

```
Gly Ala Lys Phe Lys Thr Ser Ala Gln His Ala Leu Thr Ser Val Ser
1               5                   10                  15

Arg Gly
```

<210> SEQ ID NO 283
<211> LENGTH: 17
<212> TYPE: PRT
<213> ORGANISM: Artificial Sequence
<220> FEATURE:
<223> OTHER INFORMATION: Synthetic

<400> SEQUENCE: 283

```
Gly Ala Lys Phe Lys Thr Ser Ala Gln His Ala Leu Thr Ser Val Ser
1               5                   10                  15

Arg
```

<210> SEQ ID NO 284
<211> LENGTH: 16
<212> TYPE: PRT
<213> ORGANISM: Artificial Sequence
<220> FEATURE:
<223> OTHER INFORMATION: Synthetic

<400> SEQUENCE: 284

```
Gly Ala Lys Phe Lys Thr Ser Ala Gln His Ala Leu Thr Ser Val Ser
1               5                   10                  15
```

<210> SEQ ID NO 285
<211> LENGTH: 15
<212> TYPE: PRT
<213> ORGANISM: Artificial Sequence
<220> FEATURE:
<223> OTHER INFORMATION: Synthetic

<400> SEQUENCE: 285

```
Gly Ala Lys Phe Lys Thr Ser Ala Gln His Ala Leu Thr Ser Val
1               5                   10                  15
```

<210> SEQ ID NO 286
<211> LENGTH: 14
<212> TYPE: PRT
<213> ORGANISM: Artificial Sequence
<220> FEATURE:
<223> OTHER INFORMATION: Synthetic

<400> SEQUENCE: 286

```
Gly Ala Lys Phe Lys Thr Ser Ala Gln His Ala Leu Thr Ser
1               5                   10
```

<210> SEQ ID NO 287
<211> LENGTH: 13
<212> TYPE: PRT
<213> ORGANISM: Artificial Sequence
<220> FEATURE:
<223> OTHER INFORMATION: Synthetic

<400> SEQUENCE: 287

```
Gly Ala Lys Phe Lys Thr Ser Ala Gln His Ala Leu Thr
1               5                   10
```

<210> SEQ ID NO 288
<211> LENGTH: 12
<212> TYPE: PRT
<213> ORGANISM: Artificial Sequence
<220> FEATURE:
<223> OTHER INFORMATION: Synthetic

<400> SEQUENCE: 288

Gly Ala Lys Phe Lys Thr Ser Ala Gln His Ala Leu
1               5                   10

<210> SEQ ID NO 289
<211> LENGTH: 11
<212> TYPE: PRT
<213> ORGANISM: Artificial Sequence
<220> FEATURE:
<223> OTHER INFORMATION: Synthetic

<400> SEQUENCE: 289

Gly Ala Lys Phe Lys Thr Ser Ala Gln His Ala
1               5                   10

<210> SEQ ID NO 290
<211> LENGTH: 10
<212> TYPE: PRT
<213> ORGANISM: Artificial Sequence
<220> FEATURE:
<223> OTHER INFORMATION: Synthetic

<400> SEQUENCE: 290

Gly Ala Lys Phe Lys Thr Ser Ala Gln His
1               5                   10

<210> SEQ ID NO 291
<211> LENGTH: 46
<212> TYPE: PRT
<213> ORGANISM: Artificial Sequence
<220> FEATURE:
<223> OTHER INFORMATION: Synthetic

<400> SEQUENCE: 291

Ala Lys Phe Lys Thr Ser Ala Gln His Ala Leu Thr Ser Val Ser Arg
1               5                   10                  15

Gly Ser Ser Leu Lys Ile Leu Ser Lys Gly Lys Arg Gly Gly His Ser
            20                  25                  30

Ser Val Ser Thr Glu Ser Glu Ser Ser Ser Phe His Ser Ser
        35                  40                  45

<210> SEQ ID NO 292
<211> LENGTH: 45
<212> TYPE: PRT
<213> ORGANISM: Artificial Sequence
<220> FEATURE:
<223> OTHER INFORMATION: Synthetic

<400> SEQUENCE: 292

Lys Phe Lys Thr Ser Ala Gln His Ala Leu Thr Ser Val Ser Arg Gly
1               5                   10                  15

Ser Ser Leu Lys Ile Leu Ser Lys Gly Lys Arg Gly Gly His Ser Ser
            20                  25                  30

Val Ser Thr Glu Ser Glu Ser Ser Ser Phe His Ser Ser
        35                  40                  45

<210> SEQ ID NO 293
<211> LENGTH: 44
<212> TYPE: PRT
<213> ORGANISM: Artificial Sequence
<220> FEATURE:
<223> OTHER INFORMATION: Synthetic

<400> SEQUENCE: 293

```
Phe Lys Thr Ser Ala Gln His Ala Leu Thr Ser Val Ser Arg Gly Ser
 1               5                   10                  15

Ser Leu Lys Ile Leu Ser Lys Gly Lys Arg Gly Gly His Ser Ser Val
                20                  25                  30

Ser Thr Glu Ser Glu Ser Ser Ser Phe His Ser Ser
            35                  40
```

<210> SEQ ID NO 294
<211> LENGTH: 43
<212> TYPE: PRT
<213> ORGANISM: Artificial Sequence
<220> FEATURE:
<223> OTHER INFORMATION: Synthetic

<400> SEQUENCE: 294

```
Lys Thr Ser Ala Gln His Ala Leu Thr Ser Val Ser Arg Gly Ser Ser
 1               5                   10                  15

Leu Lys Ile Leu Ser Lys Gly Lys Arg Gly Gly His Ser Ser Val Ser
                20                  25                  30

Thr Glu Ser Glu Ser Ser Ser Phe His Ser Ser
            35                  40
```

<210> SEQ ID NO 295
<211> LENGTH: 42
<212> TYPE: PRT
<213> ORGANISM: Artificial Sequence
<220> FEATURE:
<223> OTHER INFORMATION: Synthetic

<400> SEQUENCE: 295

```
Thr Ser Ala Gln His Ala Leu Thr Ser Val Ser Arg Gly Ser Ser Leu
 1               5                   10                  15

Lys Ile Leu Ser Lys Gly Lys Arg Gly Gly His Ser Ser Val Ser Thr
                20                  25                  30

Glu Ser Glu Ser Ser Ser Phe His Ser Ser
            35                  40
```

<210> SEQ ID NO 296
<211> LENGTH: 41
<212> TYPE: PRT
<213> ORGANISM: Artificial Sequence
<220> FEATURE:
<223> OTHER INFORMATION: Synthetic

<400> SEQUENCE: 296

```
Ser Ala Gln His Ala Leu Thr Ser Val Ser Arg Gly Ser Ser Leu Lys
 1               5                   10                  15

Ile Leu Ser Lys Gly Lys Arg Gly Gly His Ser Ser Val Ser Thr Glu
                20                  25                  30

Ser Glu Ser Ser Ser Phe His Ser Ser
            35                  40
```

<210> SEQ ID NO 297
<211> LENGTH: 40
<212> TYPE: PRT
<213> ORGANISM: Artificial Sequence
<220> FEATURE:
<223> OTHER INFORMATION: Synthetic

<400> SEQUENCE: 297

```
Ala Gln His Ala Leu Thr Ser Val Ser Arg Gly Ser Ser Leu Lys Ile
 1               5                   10                  15
```

Leu Ser Lys Gly Lys Arg Gly Gly His Ser Ser Val Ser Thr Glu Ser
            20                  25                  30

Glu Ser Ser Ser Phe His Ser Ser
        35                  40

<210> SEQ ID NO 298
<211> LENGTH: 39
<212> TYPE: PRT
<213> ORGANISM: Artificial Sequence
<220> FEATURE:
<223> OTHER INFORMATION: Synthetic

<400> SEQUENCE: 298

Gln His Ala Leu Thr Ser Val Ser Arg Gly Ser Ser Leu Lys Ile Leu
1               5                   10                  15

Ser Lys Gly Lys Arg Gly Gly His Ser Ser Val Ser Thr Glu Ser Glu
            20                  25                  30

Ser Ser Ser Phe His Ser Ser
        35

<210> SEQ ID NO 299
<211> LENGTH: 38
<212> TYPE: PRT
<213> ORGANISM: Artificial Sequence
<220> FEATURE:
<223> OTHER INFORMATION: Synthetic

<400> SEQUENCE: 299

His Ala Leu Thr Ser Val Ser Arg Gly Ser Ser Leu Lys Ile Leu Ser
1               5                   10                  15

Lys Gly Lys Arg Gly Gly His Ser Ser Val Ser Thr Glu Ser Glu Ser
            20                  25                  30

Ser Ser Phe His Ser Ser
        35

<210> SEQ ID NO 300
<211> LENGTH: 37
<212> TYPE: PRT
<213> ORGANISM: Artificial Sequence
<220> FEATURE:
<223> OTHER INFORMATION: Synthetic

<400> SEQUENCE: 300

Ala Leu Thr Ser Val Ser Arg Gly Ser Ser Leu Lys Ile Leu Ser Lys
1               5                   10                  15

Gly Lys Arg Gly Gly His Ser Ser Val Ser Thr Glu Ser Glu Ser Ser
            20                  25                  30

Ser Phe His Ser Ser
        35

<210> SEQ ID NO 301
<211> LENGTH: 36
<212> TYPE: PRT
<213> ORGANISM: Artificial Sequence
<220> FEATURE:
<223> OTHER INFORMATION: Synthetic

<400> SEQUENCE: 301

Leu Thr Ser Val Ser Arg Gly Ser Ser Leu Lys Ile Leu Ser Lys Gly
1               5                   10                  15

Lys Arg Gly Gly His Ser Ser Val Ser Thr Glu Ser Glu Ser Ser Ser
            20                  25                  30

Phe His Ser Ser
            35

<210> SEQ ID NO 302
<211> LENGTH: 35
<212> TYPE: PRT
<213> ORGANISM: Artificial Sequence
<220> FEATURE:
<223> OTHER INFORMATION: Synthetic

<400> SEQUENCE: 302

Thr Ser Val Ser Arg Gly Ser Ser Leu Lys Ile Leu Ser Lys Gly Lys
1               5                   10                  15

Arg Gly Gly His Ser Ser Val Ser Thr Glu Ser Glu Ser Ser Ser Phe
            20                  25                  30

His Ser Ser
         35

<210> SEQ ID NO 303
<211> LENGTH: 34
<212> TYPE: PRT
<213> ORGANISM: Artificial Sequence
<220> FEATURE:
<223> OTHER INFORMATION: Synthetic

<400> SEQUENCE: 303

Ser Val Ser Arg Gly Ser Ser Leu Lys Ile Leu Ser Lys Gly Lys Arg
1               5                   10                  15

Gly Gly His Ser Ser Val Ser Thr Glu Ser Glu Ser Ser Ser Phe His
            20                  25                  30

Ser Ser

<210> SEQ ID NO 304
<211> LENGTH: 33
<212> TYPE: PRT
<213> ORGANISM: Artificial Sequence
<220> FEATURE:
<223> OTHER INFORMATION: Synthetic

<400> SEQUENCE: 304

Val Ser Arg Gly Ser Ser Leu Lys Ile Leu Ser Lys Gly Lys Arg Gly
1               5                   10                  15

Gly His Ser Ser Val Ser Thr Glu Ser Glu Ser Ser Ser Phe His Ser
            20                  25                  30

Ser

<210> SEQ ID NO 305
<211> LENGTH: 32
<212> TYPE: PRT
<213> ORGANISM: Artificial Sequence
<220> FEATURE:
<223> OTHER INFORMATION: Synthetic

<400> SEQUENCE: 305

Ser Arg Gly Ser Ser Leu Lys Ile Leu Ser Lys Gly Lys Arg Gly Gly
1               5                   10                  15

His Ser Ser Val Ser Thr Glu Ser Glu Ser Ser Ser Phe His Ser Ser
            20                  25                  30

<210> SEQ ID NO 306
<211> LENGTH: 31
<212> TYPE: PRT

```
<213> ORGANISM: Artificial Sequence
<220> FEATURE:
<223> OTHER INFORMATION: Synthetic

<400> SEQUENCE: 306

Arg Gly Ser Ser Leu Lys Ile Leu Ser Lys Gly Lys Arg Gly Gly His
 1               5                  10                  15

Ser Ser Val Ser Thr Glu Ser Glu Ser Ser Ser Phe His Ser Ser
            20                  25                  30

<210> SEQ ID NO 307
<211> LENGTH: 30
<212> TYPE: PRT
<213> ORGANISM: Artificial Sequence
<220> FEATURE:
<223> OTHER INFORMATION: Synthetic

<400> SEQUENCE: 307

Gly Ser Ser Leu Lys Ile Leu Ser Lys Gly Lys Arg Gly Gly His Ser
 1               5                  10                  15

Ser Val Ser Thr Glu Ser Glu Ser Ser Ser Phe His Ser Ser
            20                  25                  30

<210> SEQ ID NO 308
<211> LENGTH: 29
<212> TYPE: PRT
<213> ORGANISM: Artificial Sequence
<220> FEATURE:
<223> OTHER INFORMATION: Synthetic

<400> SEQUENCE: 308

Ser Ser Leu Lys Ile Leu Ser Lys Gly Lys Arg Gly Gly His Ser Ser
 1               5                  10                  15

Val Ser Thr Glu Ser Glu Ser Ser Ser Phe His Ser Ser
            20                  25

<210> SEQ ID NO 309
<211> LENGTH: 28
<212> TYPE: PRT
<213> ORGANISM: Artificial Sequence
<220> FEATURE:
<223> OTHER INFORMATION: Synthetic

<400> SEQUENCE: 309

Ser Leu Lys Ile Leu Ser Lys Gly Lys Arg Gly Gly His Ser Ser Val
 1               5                  10                  15

Ser Thr Glu Ser Glu Ser Ser Ser Phe His Ser Ser
            20                  25

<210> SEQ ID NO 310
<211> LENGTH: 27
<212> TYPE: PRT
<213> ORGANISM: Artificial Sequence
<220> FEATURE:
<223> OTHER INFORMATION: Synthetic

<400> SEQUENCE: 310

Leu Lys Ile Leu Ser Lys Gly Lys Arg Gly Gly His Ser Ser Val Ser
 1               5                  10                  15

Thr Glu Ser Glu Ser Ser Ser Phe His Ser Ser
            20                  25

<210> SEQ ID NO 311
<211> LENGTH: 26
```

<212> TYPE: PRT
<213> ORGANISM: Artificial Sequence
<220> FEATURE:
<223> OTHER INFORMATION: Synthetic

<400> SEQUENCE: 311

Lys Ile Leu Ser Lys Gly Lys Arg Gly Gly His Ser Ser Val Ser Thr
1               5                   10                  15

Glu Ser Glu Ser Ser Ser Phe His Ser Ser
            20                  25

<210> SEQ ID NO 312
<211> LENGTH: 25
<212> TYPE: PRT
<213> ORGANISM: Artificial Sequence
<220> FEATURE:
<223> OTHER INFORMATION: Synthetic

<400> SEQUENCE: 312

Ile Leu Ser Lys Gly Lys Arg Gly Gly His Ser Ser Val Ser Thr Glu
1               5                   10                  15

Ser Glu Ser Ser Ser Phe His Ser Ser
            20                  25

<210> SEQ ID NO 313
<211> LENGTH: 24
<212> TYPE: PRT
<213> ORGANISM: Artificial Sequence
<220> FEATURE:
<223> OTHER INFORMATION: Synthetic

<400> SEQUENCE: 313

Leu Ser Lys Gly Lys Arg Gly Gly His Ser Ser Val Ser Thr Glu Ser
1               5                   10                  15

Glu Ser Ser Ser Phe His Ser Ser
            20

<210> SEQ ID NO 314
<211> LENGTH: 23
<212> TYPE: PRT
<213> ORGANISM: Artificial Sequence
<220> FEATURE:
<223> OTHER INFORMATION: Synthetic

<400> SEQUENCE: 314

Ser Lys Gly Lys Arg Gly Gly His Ser Ser Val Ser Thr Glu Ser Glu
1               5                   10                  15

Ser Ser Ser Phe His Ser Ser
            20

<210> SEQ ID NO 315
<211> LENGTH: 22
<212> TYPE: PRT
<213> ORGANISM: Artificial Sequence
<220> FEATURE:
<223> OTHER INFORMATION: Synthetic

<400> SEQUENCE: 315

Lys Gly Lys Arg Gly Gly His Ser Ser Val Ser Thr Glu Ser Glu Ser
1               5                   10                  15

Ser Ser Phe His Ser Ser
            20

<210> SEQ ID NO 316

```
<211> LENGTH: 21
<212> TYPE: PRT
<213> ORGANISM: Artificial Sequence
<220> FEATURE:
<223> OTHER INFORMATION: Synthetic

<400> SEQUENCE: 316

Gly Lys Arg Gly Gly His Ser Ser Val Ser Thr Glu Ser Glu Ser Ser
1               5                   10                  15

Ser Phe His Ser Ser
            20

<210> SEQ ID NO 317
<211> LENGTH: 20
<212> TYPE: PRT
<213> ORGANISM: Artificial Sequence
<220> FEATURE:
<223> OTHER INFORMATION: Synthetic

<400> SEQUENCE: 317

Lys Arg Gly Gly His Ser Ser Val Ser Thr Glu Ser Glu Ser Ser Ser
1               5                   10                  15

Phe His Ser Ser
            20

<210> SEQ ID NO 318
<211> LENGTH: 19
<212> TYPE: PRT
<213> ORGANISM: Artificial Sequence
<220> FEATURE:
<223> OTHER INFORMATION: Synthetic

<400> SEQUENCE: 318

Arg Gly Gly His Ser Ser Val Ser Thr Glu Ser Glu Ser Ser Ser Phe
1               5                   10                  15

His Ser Ser

<210> SEQ ID NO 319

<400> SEQUENCE: 319

000

<210> SEQ ID NO 320
<211> LENGTH: 18
<212> TYPE: PRT
<213> ORGANISM: Artificial Sequence
<220> FEATURE:
<223> OTHER INFORMATION: Synthetic

<400> SEQUENCE: 320

Gly Gly His Ser Ser Val Ser Thr Glu Ser Glu Ser Ser Ser Phe His
1               5                   10                  15

Ser Ser

<210> SEQ ID NO 321
<211> LENGTH: 17
<212> TYPE: PRT
<213> ORGANISM: Artificial Sequence
<220> FEATURE:
<223> OTHER INFORMATION: Synthetic

<400> SEQUENCE: 321

Gly His Ser Ser Val Ser Thr Glu Ser Glu Ser Ser Ser Phe His Ser
1               5                   10                  15
```

Ser

<210> SEQ ID NO 322
<211> LENGTH: 16
<212> TYPE: PRT
<213> ORGANISM: Artificial Sequence
<220> FEATURE:
<223> OTHER INFORMATION: Synthetic

<400> SEQUENCE: 322

His Ser Ser Val Ser Thr Glu Ser Glu Ser Ser Ser Phe His Ser Ser
 1               5                  10                  15

<210> SEQ ID NO 323
<211> LENGTH: 15
<212> TYPE: PRT
<213> ORGANISM: Artificial Sequence
<220> FEATURE:
<223> OTHER INFORMATION: Synthetic

<400> SEQUENCE: 323

Ser Ser Val Ser Thr Glu Ser Glu Ser Ser Phe His Ser Ser
 1               5                  10                  15

<210> SEQ ID NO 324
<211> LENGTH: 14
<212> TYPE: PRT
<213> ORGANISM: Artificial Sequence
<220> FEATURE:
<223> OTHER INFORMATION: Synthetic

<400> SEQUENCE: 324

Ser Val Ser Thr Glu Ser Glu Ser Ser Ser Phe His Ser Ser
 1               5                  10

<210> SEQ ID NO 325
<211> LENGTH: 13
<212> TYPE: PRT
<213> ORGANISM: Artificial Sequence
<220> FEATURE:
<223> OTHER INFORMATION: Synthetic

<400> SEQUENCE: 325

Val Ser Thr Glu Ser Glu Ser Ser Ser Phe His Ser Ser
 1               5                  10

<210> SEQ ID NO 326
<211> LENGTH: 12
<212> TYPE: PRT
<213> ORGANISM: Artificial Sequence
<220> FEATURE:
<223> OTHER INFORMATION: Synthetic

<400> SEQUENCE: 326

Ser Thr Glu Ser Glu Ser Ser Ser Phe His Ser Ser
 1               5                  10

<210> SEQ ID NO 327
<211> LENGTH: 11
<212> TYPE: PRT
<213> ORGANISM: Artificial Sequence
<220> FEATURE:
<223> OTHER INFORMATION: Synthetic

<400> SEQUENCE: 327

Thr Glu Ser Glu Ser Ser Ser Phe His Ser Ser

```
<210> SEQ ID NO 328
<211> LENGTH: 10
<212> TYPE: PRT
<213> ORGANISM: Artificial Sequence
<220> FEATURE:
<223> OTHER INFORMATION: Synthetic

<400> SEQUENCE: 328

Glu Ser Glu Ser Ser Ser Phe His Ser Ser
1               5                   10

<210> SEQ ID NO 329
<211> LENGTH: 10
<212> TYPE: PRT
<213> ORGANISM: Artificial Sequence
<220> FEATURE:
<223> OTHER INFORMATION: Synthetic

<400> SEQUENCE: 329

Ala Lys Phe Lys Thr Ser Ala Gln His Ala
1               5                   10

<210> SEQ ID NO 330
<211> LENGTH: 10
<212> TYPE: PRT
<213> ORGANISM: Artificial Sequence
<220> FEATURE:
<223> OTHER INFORMATION: Synthetic

<400> SEQUENCE: 330

Lys Phe Lys Thr Ser Ala Gln His Ala Leu
1               5                   10

<210> SEQ ID NO 331
<211> LENGTH: 10
<212> TYPE: PRT
<213> ORGANISM: Artificial Sequence
<220> FEATURE:
<223> OTHER INFORMATION: Synthetic

<400> SEQUENCE: 331

Phe Lys Thr Ser Ala Gln His Ala Leu Thr
1               5                   10

<210> SEQ ID NO 332
<211> LENGTH: 10
<212> TYPE: PRT
<213> ORGANISM: Artificial Sequence
<220> FEATURE:
<223> OTHER INFORMATION: Synthetic

<400> SEQUENCE: 332

Lys Thr Ser Ala Gln His Ala Leu Thr Ser
1               5                   10

<210> SEQ ID NO 333
<211> LENGTH: 10
<212> TYPE: PRT
<213> ORGANISM: Artificial Sequence
<220> FEATURE:
<223> OTHER INFORMATION: Synthetic

<400> SEQUENCE: 333

Thr Ser Ala Gln His Ala Leu Thr Ser Val
1               5                   10
```

```
<210> SEQ ID NO 334
<211> LENGTH: 10
<212> TYPE: PRT
<213> ORGANISM: Artificial Sequence
<220> FEATURE:
<223> OTHER INFORMATION: Synthetic

<400> SEQUENCE: 334

Ser Ala Gln His Ala Leu Thr Ser Val Ser
1               5                   10

<210> SEQ ID NO 335
<211> LENGTH: 10
<212> TYPE: PRT
<213> ORGANISM: Artificial Sequence
<220> FEATURE:
<223> OTHER INFORMATION: Synthetic

<400> SEQUENCE: 335

Ala Gln His Ala Leu Thr Ser Val Ser Arg
1               5                   10

<210> SEQ ID NO 336
<211> LENGTH: 10
<212> TYPE: PRT
<213> ORGANISM: Artificial Sequence
<220> FEATURE:
<223> OTHER INFORMATION: Synthetic

<400> SEQUENCE: 336

Gln His Ala Leu Thr Ser Val Ser Arg Gly
1               5                   10

<210> SEQ ID NO 337
<211> LENGTH: 10
<212> TYPE: PRT
<213> ORGANISM: Artificial Sequence
<220> FEATURE:
<223> OTHER INFORMATION: Synthetic

<400> SEQUENCE: 337

His Ala Leu Thr Ser Val Ser Arg Gly Ser
1               5                   10

<210> SEQ ID NO 338
<211> LENGTH: 10
<212> TYPE: PRT
<213> ORGANISM: Artificial Sequence
<220> FEATURE:
<223> OTHER INFORMATION: Synthetic

<400> SEQUENCE: 338

Ala Leu Thr Ser Val Ser Arg Gly Ser Ser
1               5                   10

<210> SEQ ID NO 339
<211> LENGTH: 10
<212> TYPE: PRT
<213> ORGANISM: Artificial Sequence
<220> FEATURE:
<223> OTHER INFORMATION: Synthetic

<400> SEQUENCE: 339

Leu Thr Ser Val Ser Arg Gly Ser Ser Leu
1               5                   10
```

```
<210> SEQ ID NO 340
<211> LENGTH: 10
<212> TYPE: PRT
<213> ORGANISM: Artificial Sequence
<220> FEATURE:
<223> OTHER INFORMATION: Synthetic

<400> SEQUENCE: 340

Thr Ser Val Ser Arg Gly Ser Ser Leu Lys
1               5                   10

<210> SEQ ID NO 341
<211> LENGTH: 10
<212> TYPE: PRT
<213> ORGANISM: Artificial Sequence
<220> FEATURE:
<223> OTHER INFORMATION: Synthetic

<400> SEQUENCE: 341

Ser Val Ser Arg Gly Ser Ser Leu Lys Ile
1               5                   10

<210> SEQ ID NO 342
<211> LENGTH: 10
<212> TYPE: PRT
<213> ORGANISM: Artificial Sequence
<220> FEATURE:
<223> OTHER INFORMATION: Synthetic

<400> SEQUENCE: 342

Val Ser Arg Gly Ser Ser Leu Lys Ile Leu
1               5                   10

<210> SEQ ID NO 343
<211> LENGTH: 10
<212> TYPE: PRT
<213> ORGANISM: Artificial Sequence
<220> FEATURE:
<223> OTHER INFORMATION: Synthetic

<400> SEQUENCE: 343

Ser Arg Gly Ser Ser Leu Lys Ile Leu Ser
1               5                   10

<210> SEQ ID NO 344

<400> SEQUENCE: 344

000

<210> SEQ ID NO 345
<211> LENGTH: 10
<212> TYPE: PRT
<213> ORGANISM: Artificial Sequence
<220> FEATURE:
<223> OTHER INFORMATION: Synthetic

<400> SEQUENCE: 345

Arg Gly Ser Ser Leu Lys Ile Leu Ser Lys
1               5                   10

<210> SEQ ID NO 346
<211> LENGTH: 10
<212> TYPE: PRT
<213> ORGANISM: Artificial Sequence
<220> FEATURE:
<223> OTHER INFORMATION: Synthetic
```

<400> SEQUENCE: 346

Gly Ser Ser Leu Lys Ile Leu Ser Lys Gly
1               5                   10

<210> SEQ ID NO 347
<211> LENGTH: 10
<212> TYPE: PRT
<213> ORGANISM: Artificial Sequence
<220> FEATURE:
<223> OTHER INFORMATION: Synthetic

<400> SEQUENCE: 347

Ser Ser Leu Lys Ile Leu Ser Lys Gly Lys
1               5                   10

<210> SEQ ID NO 348
<211> LENGTH: 10
<212> TYPE: PRT
<213> ORGANISM: Artificial Sequence
<220> FEATURE:
<223> OTHER INFORMATION: Synthetic

<400> SEQUENCE: 348

Ser Leu Lys Ile Leu Ser Lys Gly Lys Arg
1               5                   10

<210> SEQ ID NO 349
<211> LENGTH: 10
<212> TYPE: PRT
<213> ORGANISM: Artificial Sequence
<220> FEATURE:
<223> OTHER INFORMATION: Synthetic

<400> SEQUENCE: 349

Leu Lys Ile Leu Ser Lys Gly Lys Arg Gly
1               5                   10

<210> SEQ ID NO 350
<211> LENGTH: 10
<212> TYPE: PRT
<213> ORGANISM: Artificial Sequence
<220> FEATURE:
<223> OTHER INFORMATION: Synthetic

<400> SEQUENCE: 350

Lys Ile Leu Ser Lys Gly Lys Arg Gly Gly
1               5                   10

<210> SEQ ID NO 351
<211> LENGTH: 10
<212> TYPE: PRT
<213> ORGANISM: Artificial Sequence
<220> FEATURE:
<223> OTHER INFORMATION: Synthetic

<400> SEQUENCE: 351

Ile Leu Ser Lys Gly Lys Arg Gly Gly His
1               5                   10

<210> SEQ ID NO 352
<211> LENGTH: 10
<212> TYPE: PRT
<213> ORGANISM: Artificial Sequence
<220> FEATURE:
<223> OTHER INFORMATION: Synthetic

<400> SEQUENCE: 352

Leu Ser Lys Gly Lys Arg Gly Gly His Ser
1               5                   10

<210> SEQ ID NO 353
<211> LENGTH: 10
<212> TYPE: PRT
<213> ORGANISM: Artificial Sequence
<220> FEATURE:
<223> OTHER INFORMATION: Synthetic

<400> SEQUENCE: 353

Ser Lys Gly Lys Arg Gly Gly His Ser Ser
1               5                   10

<210> SEQ ID NO 354
<211> LENGTH: 10
<212> TYPE: PRT
<213> ORGANISM: Artificial Sequence
<220> FEATURE:
<223> OTHER INFORMATION: Synthetic

<400> SEQUENCE: 354

Lys Gly Lys Arg Gly Gly His Ser Ser Val
1               5                   10

<210> SEQ ID NO 355
<211> LENGTH: 10
<212> TYPE: PRT
<213> ORGANISM: Artificial Sequence
<220> FEATURE:
<223> OTHER INFORMATION: Synthetic

<400> SEQUENCE: 355

Gly Lys Arg Gly Gly His Ser Ser Val Ser
1               5                   10

<210> SEQ ID NO 356
<211> LENGTH: 10
<212> TYPE: PRT
<213> ORGANISM: Artificial Sequence
<220> FEATURE:
<223> OTHER INFORMATION: Synthetic

<400> SEQUENCE: 356

Lys Arg Gly Gly His Ser Ser Val Ser Thr
1               5                   10

<210> SEQ ID NO 357
<211> LENGTH: 10
<212> TYPE: PRT
<213> ORGANISM: Artificial Sequence
<220> FEATURE:
<223> OTHER INFORMATION: Synthetic

<400> SEQUENCE: 357

Arg Gly Gly His Ser Ser Val Ser Thr Glu
1               5                   10

<210> SEQ ID NO 358
<211> LENGTH: 10
<212> TYPE: PRT
<213> ORGANISM: Artificial Sequence
<220> FEATURE:
<223> OTHER INFORMATION: Synthetic

<400> SEQUENCE: 358

Gly Gly His Ser Ser Val Ser Thr Glu Ser
1               5                   10

<210> SEQ ID NO 359
<211> LENGTH: 10
<212> TYPE: PRT
<213> ORGANISM: Artificial Sequence
<220> FEATURE:
<223> OTHER INFORMATION: Synthetic

<400> SEQUENCE: 359

Gly His Ser Ser Val Ser Thr Glu Ser Glu
1               5                   10

<210> SEQ ID NO 360
<211> LENGTH: 10
<212> TYPE: PRT
<213> ORGANISM: Artificial Sequence
<220> FEATURE:
<223> OTHER INFORMATION: Synthetic

<400> SEQUENCE: 360

His Ser Ser Val Ser Thr Glu Ser Glu Ser
1               5                   10

<210> SEQ ID NO 361
<211> LENGTH: 10
<212> TYPE: PRT
<213> ORGANISM: Artificial Sequence
<220> FEATURE:
<223> OTHER INFORMATION: Synthetic

<400> SEQUENCE: 361

Ser Ser Val Ser Thr Glu Ser Glu Ser Ser
1               5                   10

<210> SEQ ID NO 362
<211> LENGTH: 10
<212> TYPE: PRT
<213> ORGANISM: Artificial Sequence
<220> FEATURE:
<223> OTHER INFORMATION: Synthetic

<400> SEQUENCE: 362

Ser Val Ser Thr Glu Ser Glu Ser Ser Ser
1               5                   10

<210> SEQ ID NO 363
<211> LENGTH: 10
<212> TYPE: PRT
<213> ORGANISM: Artificial Sequence
<220> FEATURE:
<223> OTHER INFORMATION: Synthetic

<400> SEQUENCE: 363

Val Ser Thr Glu Ser Glu Ser Ser Ser Phe
1               5                   10

<210> SEQ ID NO 364
<211> LENGTH: 10
<212> TYPE: PRT
<213> ORGANISM: Artificial Sequence
<220> FEATURE:
<223> OTHER INFORMATION: Synthetic

<400> SEQUENCE: 364

```
Ser Thr Glu Ser Glu Ser Ser Ser Phe His
  1               5                  10
```

<210> SEQ ID NO 365
<211> LENGTH: 10
<212> TYPE: PRT
<213> ORGANISM: Artificial Sequence
<220> FEATURE:
<223> OTHER INFORMATION: Synthetic

<400> SEQUENCE: 365

```
Thr Glu Ser Glu Ser Ser Ser Phe His Ser
  1               5                  10
```

<210> SEQ ID NO 366
<211> LENGTH: 10
<212> TYPE: PRT
<213> ORGANISM: Artificial Sequence
<220> FEATURE:
<223> OTHER INFORMATION: Synthetic

<400> SEQUENCE: 366

```
Glu Ser Glu Ser Ser Ser Phe His Ser Ser
  1               5                  10
```

<210> SEQ ID NO 367
<211> LENGTH: 46
<212> TYPE: PRT
<213> ORGANISM: Artificial Sequence
<220> FEATURE:
<223> OTHER INFORMATION: Synthetic

<400> SEQUENCE: 367

```
Gly Ala Lys Phe Lys Thr Ser Ala Gln His Ala Leu Thr Ser Val Ser
  1               5                  10                  15

Arg Gly Ser Ser Leu Lys Ile Leu Ser Lys Gly Lys Arg Gly Gly His
                 20                  25                  30

Ser Ser Val Ser Thr Glu Ser Glu Ser Ser Ser Phe His Ser
             35                  40                  45
```

<210> SEQ ID NO 368
<211> LENGTH: 36
<212> TYPE: PRT
<213> ORGANISM: Artificial Sequence
<220> FEATURE:
<223> OTHER INFORMATION: Synthetic

<400> SEQUENCE: 368

```
Gly Ala Lys Phe Lys Thr Ser Ala Gln His Ala Leu Thr Ser Val Ser
  1               5                  10                  15

Arg Gly Ser Ser Leu Lys Ile Leu Ser Lys Gly Lys Arg Gly Gly His
                 20                  25                  30

Ser Cys Phe His
         35
```

<210> SEQ ID NO 369
<211> LENGTH: 12
<212> TYPE: PRT
<213> ORGANISM: Artificial Sequence
<220> FEATURE:
<223> OTHER INFORMATION: Synthetic

<400> SEQUENCE: 369

```
His Ser Lys Gly His Gln Lys Arg Lys Ala Leu Lys
  1               5                  10
```

<210> SEQ ID NO 370
<211> LENGTH: 17
<212> TYPE: PRT
<213> ORGANISM: Homo Sapiens

<400> SEQUENCE: 370

Met Gly Tyr Gln Lys Lys Leu Arg Ser Met Thr Asp Lys Tyr Arg Leu
1               5                   10                  15

His

<210> SEQ ID NO 371
<211> LENGTH: 22
<212> TYPE: PRT
<213> ORGANISM: Homo Sapiens

<400> SEQUENCE: 371

Asp Arg Tyr Leu Ala Ile Val His Ala Thr Asn Ser Gln Arg Pro Arg
1               5                   10                  15

Lys Leu Leu Ala Glu Lys
            20

<210> SEQ ID NO 372
<211> LENGTH: 23
<212> TYPE: PRT
<213> ORGANISM: Homo Sapiens

<400> SEQUENCE: 372

Ile Ile Ile Ser Lys Leu Ser His Ser Lys Gly His Gln Lys Arg Lys
1               5                   10                  15

Ala Leu Lys Thr Thr Val Ile
            20

<210> SEQ ID NO 373
<211> LENGTH: 47
<212> TYPE: PRT
<213> ORGANISM: Homo Sapiens

<400> SEQUENCE: 373

Gly Ala Lys Phe Lys Thr Ser Ala Gln His Ala Leu Thr Ser Val Ser
1               5                   10                  15

Arg Gly Ser Ser Leu Lys Ile Leu Ser Lys Gly Lys Arg Gly Gly His
            20                  25                  30

Ser Ser Val Ser Thr Glu Ser Glu Ser Ser Phe His Ser Ser
        35                  40                  45

<210> SEQ ID NO 374
<211> LENGTH: 18
<212> TYPE: PRT
<213> ORGANISM: Artificial Sequence
<220> FEATURE:
<223> OTHER INFORMATION: Synthetic

<400> SEQUENCE: 374

Met Gly Tyr Gln Lys Lys Leu Arg Ser Met Thr Asp Lys Tyr Arg Leu
1               5                   10                  15

His Ser

<210> SEQ ID NO 375
<211> LENGTH: 19
<212> TYPE: PRT
<213> ORGANISM: Artificial Sequence
<220> FEATURE:
<223> OTHER INFORMATION: Synthetic

<400> SEQUENCE: 375

Met Gly Tyr Gln Lys Lys Leu Arg Ser Met Thr Asp Lys Tyr Arg Leu
1               5                   10                  15

His Ser Ala

<210> SEQ ID NO 376
<211> LENGTH: 12
<212> TYPE: PRT
<213> ORGANISM: Artificial Sequence
<220> FEATURE:
<223> OTHER INFORMATION: Synthetic

<400> SEQUENCE: 376

Met Gly Tyr Gln Lys Lys Leu Arg Ser Met Thr Asp
1               5                   10

<210> SEQ ID NO 377
<211> LENGTH: 18
<212> TYPE: PRT
<213> ORGANISM: Artificial Sequence
<220> FEATURE:
<223> OTHER INFORMATION: Synthetic

<400> SEQUENCE: 377

Val Met Gly Tyr Gln Lys Lys Leu Arg Ser Met Thr Asp Lys Tyr Arg
1               5                   10                  15

Leu His

<210> SEQ ID NO 378
<211> LENGTH: 19
<212> TYPE: PRT
<213> ORGANISM: Artificial Sequence
<220> FEATURE:
<223> OTHER INFORMATION: Synthetic

<400> SEQUENCE: 378

Leu Val Met Gly Tyr Gln Lys Lys Leu Arg Ser Met Thr Asp Lys Tyr
1               5                   10                  15

Arg Leu His

<210> SEQ ID NO 379
<211> LENGTH: 20
<212> TYPE: PRT
<213> ORGANISM: Artificial Sequence
<220> FEATURE:
<223> OTHER INFORMATION: Synthetic

<400> SEQUENCE: 379

Ile Leu Val Met Gly Tyr Gln Lys Lys Leu Arg Ser Met Thr Asp Lys
1               5                   10                  15

Tyr Arg Leu His
            20

<210> SEQ ID NO 380
<211> LENGTH: 21
<212> TYPE: PRT
<213> ORGANISM: Artificial Sequence
<220> FEATURE:
<223> OTHER INFORMATION: Synthetic

<400> SEQUENCE: 380

-continued

```
Val Ile Leu Val Met Gly Tyr Gln Lys Lys Leu Arg Ser Met Thr Asp
1               5                   10                  15

Lys Tyr Arg Leu His
            20

<210> SEQ ID NO 381
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 16
<223> OTHER INFORMATION: Xaa = D-Leucine

<400> SEQUENCE: 381

Met Gly Tyr Gln Lys Lys Leu Arg Ser Met Thr Asp Lys Tyr Arg Xaa
1               5                   10                  15

<210> SEQ ID NO 382
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 1
<223> OTHER INFORMATION: Xaa = Nle
<220> FEATURE:
<221> NAME/KEY: MOD_RES
<222> LOCATION: 10
<223> OTHER INFORMATION: Xaa = Nle

<400> SEQUENCE: 382

Xaa Gly Tyr Gln Lys Lys Arg Leu Ser Xaa Thr Asp Lys Tyr Arg Leu
1               5                   10                  15

<210> SEQ ID NO 383
<211> LENGTH: 28
<212> TYPE: PRT
<213> ORGANISM: Artificial Sequence
<220> FEATURE:
<223> OTHER INFORMATION: Synthetic

<400> SEQUENCE: 383

Gly Ala Lys Phe Lys Thr Ser Ala Gln His Ala Leu Thr Ser Val Ser
1               5                   10                  15

Arg Gly Ser Ser Leu Lys Ile Leu Ser Gly Gly Lys
            20                  25

<210> SEQ ID NO 384
<211> LENGTH: 16
<212> TYPE: PRT
<213> ORGANISM: Artificial Sequence
<220> FEATURE:
<223> OTHER INFORMATION: Synthetic

<400> SEQUENCE: 384

Gly Ala Lys Phe Lys Thr Ser Ala Gln His Ala Leu Thr Ser Val Arg
1               5                   10                  15
```